United States Patent
Shalek et al.

(10) Patent No.: US 11,781,193 B2
(45) Date of Patent: Oct. 10, 2023

(54) MARKERS OF ACTIVE HIV RESERVOIR

(71) Applicant: Massachusetts Institute of Technology, Cambridge, MA (US)

(72) Inventors: Alexander K. Shalek, Cambridge, MA (US); Carly Ziegler, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 178 days.

(21) Appl. No.: 16/756,573

(22) PCT Filed: Oct. 16, 2018

(86) PCT No.: PCT/US2018/056167
§ 371 (c)(1),
(2) Date: Apr. 16, 2020

(87) PCT Pub. No.: WO2019/079361
PCT Pub. Date: Apr. 25, 2019

(65) Prior Publication Data
US 2020/0263264 A1  Aug. 20, 2020

Related U.S. Application Data

(60) Provisional application No. 62/573,025, filed on Oct. 16, 2017.

(51) Int. Cl.
C12Q 1/70 (2006.01)
(52) U.S. Cl.
CPC ....... *C12Q 1/703* (2013.01); *C12Q 2600/158* (2013.01); *G01N 2800/52* (2013.01)
(58) Field of Classification Search
None
See application file for complete search history.

(56) References Cited

U.S. PATENT DOCUMENTS

| | | | |
|---|---|---|---|
| 5,030,015 | A | 7/1991 | Baker et al. |
| 2013/0005792 | A1 | 1/2013 | Haining et al. |

FOREIGN PATENT DOCUMENTS

| | | | | |
|---|---|---|---|---|
| WO | 2016/183276 A1 | 11/2016 | | |
| WO | 2017/147196 A1 | 8/2017 | | |
| WO | WO-2017147196 A1 * | 8/2017 | ............. | A61K 35/15 |
| WO | 2019/079361 A1 | 4/2019 | | |

OTHER PUBLICATIONS

Lacap et al., Canadian Journal of Infectious Diseases and Medical Microbiology, 2011, suppl. SB22: 50B. (Year: 2011).*
Massachusetts Institute of Technology, International Preliminary Report on Patentability issued in International Application No. PCT/US2018/056167, dated Apr. 30, 2020, 10 pages.
Amir et al., "ViSNE Enables Visualization of High Dimensional Single-Cell Data and Reveals Phenotypic Heterogeneity of Leukemia", Nature Biotechnology, vol. 31, No. 6, Jun. 2013, 25 pages.
Heinz et al., "The Selection and Function of Cell Type-Specific Enhancers", Nature Reviews Molecular Cell Biology, vol. 16, No. 3, Mar. 2015, 28 pages.
Lamb Justin, "The Connectivity Map: A New Tool for Biomedical Research", Nature Reviews Cancer, vol. 7, No. 1, Jan. 2007, 54-60.
Lamb et al., "The Connectivity Map: Using Gene-Expression Signatures to Connect Small Molecules, Genes, and Disease", Science, vol. 313, No. 5795, Sep. 29, 2006, 1929-1935.
Shekhar et al., "Comprehensive Classification of Retinal Bipolar Neurons by Single-Cell Transcriptomics", Cell, vol. 166, No. 5, Aug. 25, 2016, 57 pages.
Stegmaier et al., "Gene Expression-Based High-Throughput Screening(GE-HTS) and Application to Leukemia Differentiation", Nature Genetics, vol. 36, No. 3, Mar. 2004, 257-263.
Van Der Maaten et al., "Visualizing Data Using t-SNE", Journal of Machine Learning Research, vol. 9, 2008, 2579-2605.
WHO, "Global Action Plan on HIV Drug Resistance 2017-2021", ISBN: ISBN 978-92-4-151284-8, Jul. 2017, 40 pages.
Massachusetts Institute of Technology, "Notification of Transmittal of the International Search Report and the Written Opinion of the International Searching Authority, or the Declaration", dated Dec. 26, 2018, 12 pages.

* cited by examiner

*Primary Examiner* — Nicole Kinsey White
(74) *Attorney, Agent, or Firm* — F. Brent Nix, Esq.; Johnson, Marcou, Isaacs & Nix, LLC

(57) ABSTRACT

Embodiments disclosed herein provide a pan-tissue cell atlas of healthy and diseased subjects obtained by single cell sequencing. The present invention discloses novel markers for cell types. Moreover, genes associated with disease, including HIV infection and tuberculosis are identified. The invention provides for diagnostic assays based on gene markers and cell composition, as well as therapeutic targets for controlling immune regulations and cell-cell communication of the cell types disclosed herein. In addition, novel cell types and methods of quantitating, detecting and isolating the cell types are disclosed.

11 Claims, 33 Drawing Sheets
Specification includes a Sequence Listing.

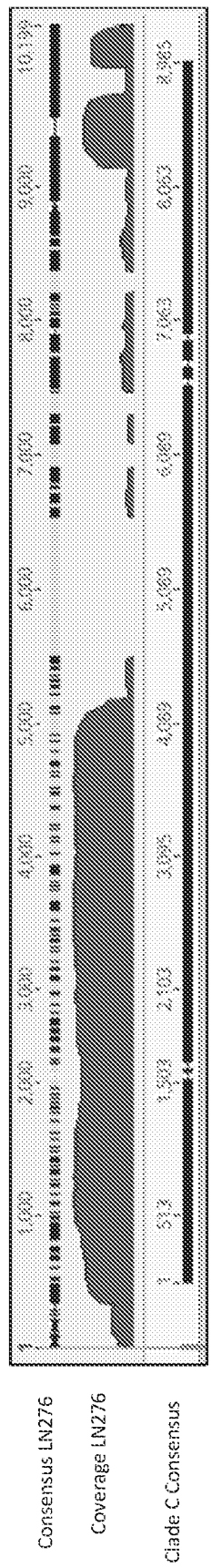
* LN276, SE-300 on MiSeq, alignment to HIV-1 consensus clade C virus
Fig.

SEQUENCE LISTING

```
<160> NUMBER OF SEQ ID NOS: 18

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
```

```
<223> OTHER INFORMATION: Synthetic

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Pro Ala Ala Lys Arg Val Lys Leu Asp
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Arg Gln Arg Arg Asn Glu Leu Lys Arg Ser Pro
1               5                   10

<210> SEQ ID NO 5
<211> LENGTH: 38
<212> TYPE: PRT
<213> ORGANISM: Artificial Sequence
<220> FEATURE:
<223> OTHER INFORMATION: Synthetic

<400> SEQUENCE: 5

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 6
<211> LENGTH: 42
<212> TYPE: PRT
<213> ORGANISM: Artificial Sequence
<220> FEATURE:
<223> OTHER INFORMATION: Synthetic

<400> SEQUENCE: 6

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 7
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 7

Val Ser Arg Lys Arg Pro Arg Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic

<400> SEQUENCE: 8

Pro Pro Lys Lys Ala Arg Glu Asp
1               5

<210> SEQ ID NO 9
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa a position 2 represents pyrrolysine

<400> SEQUENCE: 9

Pro Xaa Pro Lys Lys Lys Pro Leu
1               5

<210> SEQ ID NO 10
<211> LENGTH: 12
<212> TYPE: PRT
<213> ORGANISM: Mus sp.

<400> SEQUENCE: 10

Ser Ala Leu Ile Lys Lys Lys Lys Lys Met Ala Pro
1               5                   10

<210> SEQ ID NO 11
<211> LENGTH: 5
<212> TYPE: PRT
<213> ORGANISM: Influenza virus

<400> SEQUENCE: 11

Asp Arg Leu Arg Arg
1               5

<210> SEQ ID NO 12
<211> LENGTH: 7
<212> TYPE: PRT
<213> ORGANISM: Influenza virus

<400> SEQUENCE: 12

Pro Lys Gln Lys Lys Arg Lys
1               5

<210> SEQ ID NO 13
<211> LENGTH: 10
<212> TYPE: PRT
<213> ORGANISM: Hepatitis D virus

<400> SEQUENCE: 13

Arg Lys Leu Lys Lys Lys Ile Lys Lys Leu
1               5                   10

<210> SEQ ID NO 14
```

```
<211> LENGTH: 10
<212> TYPE: PRT
<213> ORGANISM: Mus sp.

<400> SEQUENCE: 14

Arg Glu Lys Lys Lys Phe Leu Lys Arg Arg
1               5                   10

<210> SEQ ID NO 15
<211> LENGTH: 20
<212> TYPE: PRT
<213> ORGANISM: Homo sapiens

<400> SEQUENCE: 15

Lys Arg Lys Gly Asp Glu Val Asp Gly Val Asp Glu Val Ala Lys Lys
1               5                   10                  15

Lys Ser Lys Lys
            20

<210> SEQ ID NO 16
<211> LENGTH: 17
<212> TYPE: PRT
<213> ORGANISM: Homo sapiens

<400> SEQUENCE: 16

Arg Lys Cys Leu Gln Ala Gly Met Asn Leu Glu Ala Arg Lys Thr Lys
1               5                   10                  15

Lys

<210> SEQ ID NO 17
<211> LENGTH: 288
<212> TYPE: PRT
<213> ORGANISM: Artificial Sequence
<220> FEATURE:
<223> OTHER INFORMATION: Synthetic

<400> SEQUENCE: 17

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
                20                  25                  30

Ser Pro Pro Ala Gly Gly Pro Leu Asp Gly Leu Pro Ala Arg Arg Thr
            35                  40                  45

Met Ser Arg Thr Arg Leu Pro Ser Pro Pro Ala Pro Ser Pro Ala Phe
        50                  55                  60

Ser Ala Asp Ser Phe Ser Asp Leu Leu Arg Gln Phe Asp Pro Ser Leu
65                  70                  75                  80

Phe Asn Thr Ser Leu Phe Asp Ser Leu Pro Pro Phe Gly Ala His His
                85                  90                  95

Thr Glu Ala Ala Thr Gly Glu Trp Asp Glu Val Gln Ser Gly Leu Arg
                100                 105                 110

Ala Ala Asp Ala Pro Pro Pro Thr Met Arg Val Ala Val Thr Ala Ala
            115                 120                 125

Arg Pro Pro Arg Ala Lys Pro Ala Pro Arg Arg Ala Ala Gln Pro
        130                 135                 140

Ser Asp Ala Ser Pro Ala Ala Gln Val Asp Leu Arg Thr Leu Gly Tyr
145                 150                 155                 160

Ser Gln Gln Gln Gln Glu Lys Ile Lys Pro Lys Val Arg Ser Thr Val
                165                 170                 175
```

```
Ala Gln His His Glu Ala Leu Val Gly His Gly Phe Thr His Ala His
            180                 185                 190

Ile Val Ala Leu Ser Gln His Pro Ala Ala Leu Gly Thr Val Ala Val
        195                 200                 205

Lys Tyr Gln Asp Met Ile Ala Ala Leu Pro Glu Ala Thr His Glu Ala
        210                 215                 220

Ile Val Gly Val Gly Lys Gln Trp Ser Gly Ala Arg Ala Leu Glu Ala
225                 230                 235                 240

Leu Leu Thr Val Ala Gly Glu Leu Arg Gly Pro Pro Leu Gln Leu Asp
                245                 250                 255

Thr Gly Gln Leu Leu Lys Ile Ala Lys Arg Gly Gly Val Thr Ala Val
        260                 265                 270

Glu Ala Val His Ala Trp Arg Asn Ala Leu Thr Gly Ala Pro Leu Asn
        275                 280                 285

<210> SEQ ID NO 18
<211> LENGTH: 183
<212> TYPE: PRT
<213> ORGANISM: Artificial Sequence
<220> FEATURE:
<223> OTHER INFORMATION: Synthetic

<400> SEQUENCE: 18

Arg Pro Ala Leu Glu Ser Ile Val Ala Gln Leu Ser Arg Pro Asp Pro
1               5                   10                  15

Ala Leu Ala Ala Leu Thr Asn Asp His Leu Val Ala Leu Ala Cys Leu
            20                  25                  30

Gly Gly Arg Pro Ala Leu Asp Ala Val Lys Lys Gly Leu Pro His Ala
        35                  40                  45

Pro Ala Leu Ile Lys Arg Thr Asn Arg Arg Ile Pro Glu Arg Thr Ser
    50                  55                  60

His Arg Val Ala Asp His Ala Gln Val Val Arg Val Leu Gly Phe Phe
65                  70                  75                  80

Gln Cys His Ser His Pro Ala Gln Ala Phe Asp Asp Ala Met Thr Gln
                85                  90                  95

Phe Gly Met Ser Arg His Gly Leu Leu Gln Leu Phe Arg Arg Val Gly
            100                 105                 110

Val Thr Glu Leu Glu Ala Arg Ser Gly Thr Leu Pro Pro Ala Ser Gln
        115                 120                 125

Arg Trp Asp Arg Ile Leu Gln Ala Ser Gly Met Lys Arg Ala Lys Pro
    130                 135                 140

Ser Pro Thr Ser Thr Gln Thr Pro Asp Gln Ala Ser Leu His Ala Phe
145                 150                 155                 160

Ala Asp Ser Leu Glu Arg Asp Leu Asp Ala Pro Ser Pro Met His Glu
                165                 170                 175

Gly Asp Gln Thr Arg Ala Ser
            180
```

MARKERS OF ACTIVE HIV RESERVOIR

CROSS-REFERENCE TO RELATED APPLICATIONS

This application is the U.S. National Stage Application under 35 U.S.C. § 371 of Patent Cooperation Treaty application No.: PCT/US2018/056167, filed on Oct. 16, 2018, which claims the benefit of U.S. Provisional Application No. 62/573,025, filed Oct. 16, 2017. The entire contents of the above-identified applications are hereby fully incorporated herein by reference.

FEDERAL FUNDING LEGEND

This invention was made with federal funding under Grant No. GM119419 awarded by the National Institutes of Health. The government has certain rights to the invention.

REFERENCE TO AN ELECTRONIC SEQUENCE LISTING

The contents of the electronic sequence listing (BROD-2920US.ST25.txt"; Size is 8 Kilobytes and it was created on Jun. 5, 2023) is herein incorporated by reference in its entirety.

TECHNICAL FIELD

The subject matter disclosed herein is generally directed to a cell atlas of different cell types in healthy and disease states. The subject matter further relates to novel cell specific and disease specific markers. This invention relates generally to compositions and methods identifying and exploiting target genes or target gene products that modulate, control or otherwise influence cell-cell communication, differential expression, immune response in a variety of therapeutic and/or diagnostic indications.

BACKGROUND

Immune systems play an essential role in ensuring our health. From decades of laboratory and clinical work, there has been a basic understanding of immune balance and its importance for a healthy immune system. For example, hyperactivity can lead to allergy, inflammation, tissue damage, autoimmune disease and excessive cellular death. On the other hand, immunodeficiency can lead to outgrowth of cancers and the inability to kill or suppress external invaders. The immune system has evolved multiple modalities and redundancies that balance the system, including but not limited to memory, exhaustion, anergy, and senescence. Despite this basic understanding, a comprehensive landscape of immune regulations remains missing. Given the importance of the immune system, a systematic understanding of immune regulations on cell, tissue, and organism levels is crucial for clinicians and researchers to efficiently diagnose and develop treatments for immune system related disease.

Different cells and tissues in a diseased organism are often not impacted at the same level. Analyzing immune regulations with a comprehensive approach allows for identification of cells and tissues that are impacted and that are representative of the disease, interaction between cells, as well as pathways that can be specifically targeted to restore diseased cell or tissues to a normal state. In practice, certain tissues or specimens, for example blood or body fluids, are more easily obtainable than others from a patient. A systematic understanding of immune responses allows clinicians to use easily obtainable tissues as a proxy to diagnose disease and monitor disease state through easily obtainable tissues, and may further allow for treatment or amelioration of symptoms by restoring the state of suppressed immune cells or eliminating severely infected cells, for example, cells impacted with a chronic infection such as HIV infected cells/MTB infected cells.

HIV is a member of the lentivirus family of animal retroviruses, which include the visna virus of sheep and the bovine, feline, and simian immunodeficiency viruses (SIV). HIV preferentially infects CD4 T cells, reverse transcribes its DNA, and integrates into the host genome. During early infection, the host cell experiences a spike in viral load of HIV. Because of such high viral load in plasma, as infected T cells migrate throughout the entire host organism, all tissues can be exposed to HIV, causing profound and often irreversible changes to the adaptive and innate immune systems and establishing a permanent pool of integrated HIV in T cells, known as the HIV reservoir. Standard of care for HIV infection treatment involves anti-retroviral therapies that block various stages of the HIV life cycle. This treatment increases CD4 T cell counts and can decrease HIV levels to below the limit of detection by clinical assays. However, integrated HIV in the HIV reservoir persist and maintain active replication, in low levels of HIV harboring cells and tissues. These persistent HIV reservoir cells remain a critical barrier to cure, and are responsible for ongoing inflammation and pathology even under treatment.

SUMMARY

In one aspect, the invention provides a method of modulating a cell or tissue comprising a latent HIV or anti-retroviral therapy (ART)-resistant HIV infection. The method may comprise contacting the cell or tissue with a modulating agent in an amount sufficient to modify the HIV latency or ART-resistance of the cell or tissue as compared to the HIV latency or ART-resistance in the absence of the modulating agent, whereby the HIV latency or ART-resistance of the cell directly influences the latent HIV or ART-resistant HIV infection.

In alternative embodiments, the invention comprises a method of modulating a cell or tissue comprising a hepatitis B or hepatitis C virus infection.

In some embodiments, the modulating of a cell or tissue comprises modulating an immune cell. In some embodiments, the modulating of a cell or tissue comprises modulating a lymph node immune cell. In some embodiments, the modulating of a cell or tissue comprises modulating a T cell or T cell subset. In some embodiments, the modulating of a cell or tissue comprises modulating a $CD3^+CD4^+PD1^+CXCR4^+$ T follicular helper cell or a $CD45RA^-CCR7^+CD27^+$ memory T cell. In some embodiments, the modulating of a cell or tissue comprises modulating a gene or product of one or more genes that is enriched for expression in $HIV^+$ cells. In some embodiments, the gene or gene product of two or more genes may be modulated. The one or more genes may be from Table 1 or Table 2.

The modulating of a cell or tissue may comprise modulating a gene or product of one or more genes that is enriched for expression in $HIV^-$ cells. As such, the method may comprise modulating a gene or product of two or more genes. The one or more genes may be selected from the genes of Table 3.

The method may comprise modulating a gene or product of one or more genes that is enriched for expression in HIV+ cells and a gene or product of one or more genes that is enriched for expression in HIV⁻ cells.

The T cell or T cell subset may be a CD4+ T cell, and the modulating of a cell or tissue may comprise modulating a gene selected from the group consisting of genes involved in unfolded protein response, HTLV-1 infection, herpes simplex infection, interferon gamma signaling pathway, antigen processing and presentation via MEW class I, positive regulation of apoptotic processes, T cell receptor signaling, virion assembly, and viral transcription.

In another aspect, provided herein is a method of diagnosing a cell or tissue in a subject having a latent HIV or anti-retroviral therapy (ART)-resistant HIV infection. The method may comprise detecting a gene expression profile in one or more cells or tissues associated with latent HIV or ART-resistant HIV infection.

In yet another aspect, provided herein is a method of diagnosing a latent HIV or ART-resistant HIV infection in a cell or tissue, the method comprising detecting whether one or more genes from Table 1 or Table 2 is overexpressed compared to a cell that is HIV⁻.

In yet another aspect, provided herein is a method of diagnosing a latent HIV or anti-retroviral therapy (ART)-resistant HIV infection in a cell or tissue, the method comprising detecting whether one or more genes from Table 3 is underexpressed compared to a cell that is HIV⁻.

In yet another aspect, the invention provides a method of monitoring treatment of a latent HIV or anti-retroviral therapy (ART)-resistant HIV infection in a cell or tissue, the method comprising detecting whether one or more genes from Table 1 or Table 2 is overexpressed compared to a cell that is HIV⁻.

In another aspect, the invention provides a method of monitoring treatment of a latent HIV or anti-retroviral therapy (ART)-resistant HIV infection in a cell or tissue, the method comprising detecting whether one or more genes from Table 3 is underexpressed compared to a cell that is HIV⁻.

In another aspect, the invention provides a method of treating HIV comprising detecting one or more genes or gene signatures from Tables 1 or 2; determining whether the patient has a latent HIV or ART-resistant HIV infection based on the presence of one or more genes or gene signatures from Tables 1 or 2; and administering an anti-HIV therapeutic if one or more genes or gene signatures from Tables 1 or 2 are present.

In some embodiments, the step of detecting comprises detecting the presence of a marker using an immunological assay. The immunological assay may comprise detection of specific binding between an antibody and the marker. The marker may be a peptide, polypeptide, or protein.

In another aspect, the invention provides a method of monitoring HIV disease progression and/or treatment comprising detecting expression of one or more genes or gene products from Tables 1, 2 and 3 prior to administration of an anti-HIV therapy; administering a first round of an anti-HIV therapy; detecting expression of one or more genes or gene products from Tables 1, 2 and 3 after administration of the anti-HIV therapeutic; and administering an additional or alternative round of anti-HIV therapy if expression of one or more genes from Table 1 or 2 has increased or not decreased, or if expression of one or more genes in Table 3 has decreased relative to prior to administering the first anti-HIV therapy.

In some embodiments, the additional or alternative round of anti-HIV therapy comprises the same drug or combination of drugs as the first round of anti-HIV therapy. In alternative embodiments, the additional or alternative round of anti-HIV therapy comprises a different drug or combination of drugs than the first round of anti-HIV therapy.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 22B Certain subsets have equal representation between healthy and SHIV, such as CD8 T cells or macrophages, while CD4 T cells and B cells, show major deviations due to prior SHIV infection. FIG. 22C Differential expression of genes in healthy and SHIV-infected CD4 T cells. As in humans, animals with suppressed viral replication as detected in blood show signatures in lymphoid resident T cells associated with ongoing viral replication and response to virus.

FIG. 24A Single cell genomics of cells from lymphoid tissue and ileum compared. FIG. 24B In the mesenteric LN, T cells are affected by prior HIV infection, but in the ileum, a significant effect is not observed. FIG. 24C In the small intestine, T cells are more similar, but largest differential expression occurs among the epithelial enterocytes. FIG. 24D Identification of cell subsets altered by SHIV infection.

FIG. 26A shows data for $HIV^-$ PBMCs. FIG. 26B shows data for $HIV^+$ (LN276) with stringent gating. FIG. 26C shows data for $HIV^+$ (LN276) with non-stringent gating.

FIG. 32 shows a schematic of matched full-length sequencing of the HIV genome.

Figure 1:
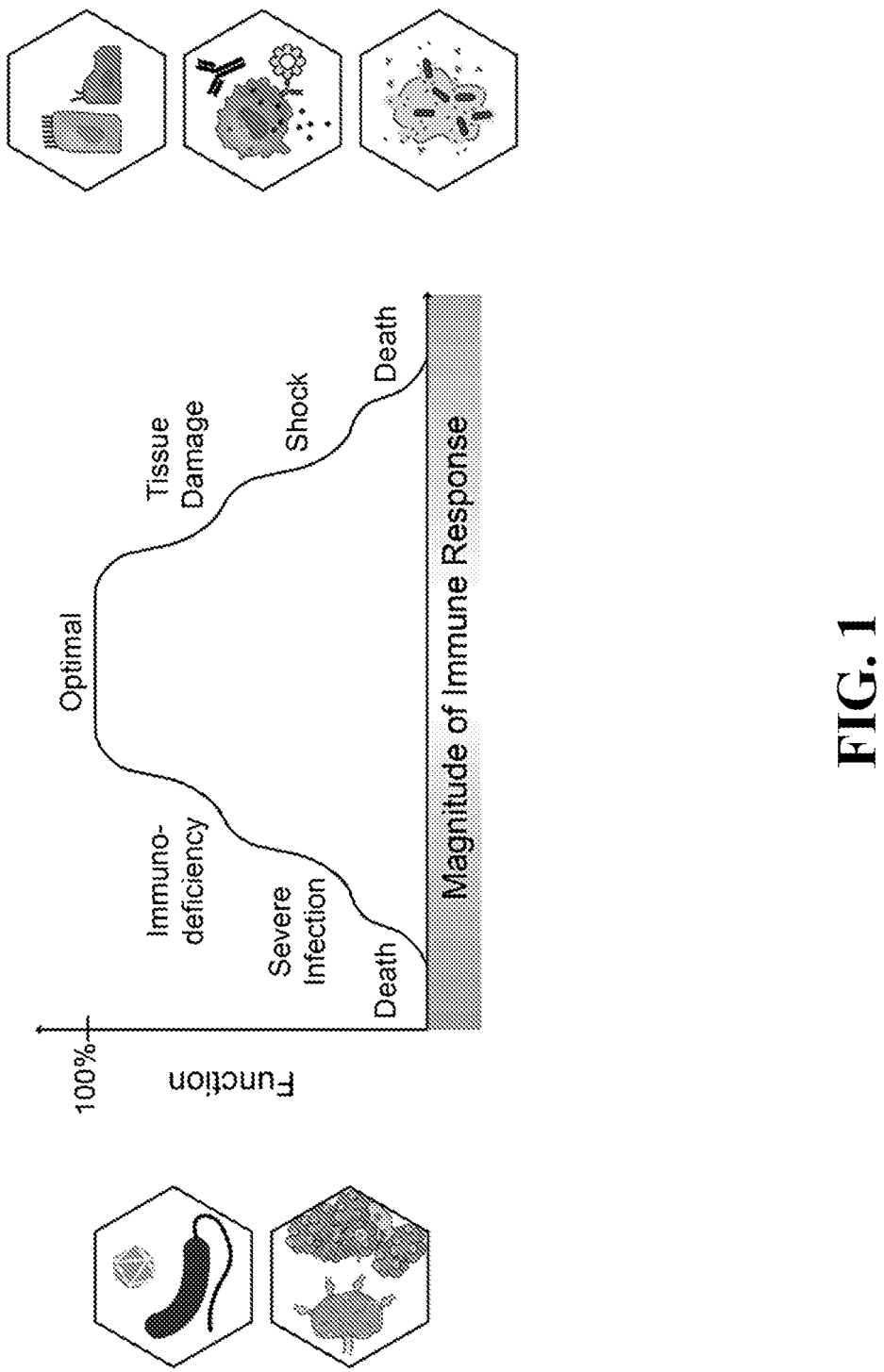
FIG. 1—Balance in the immune system determines health vs. disease. Hyperactivity can lead to tissue damage, allergy, inflammation, and cell death. Immunodeficiency can lead to outgrowth of cancers or external pathogens.
Figure 2:
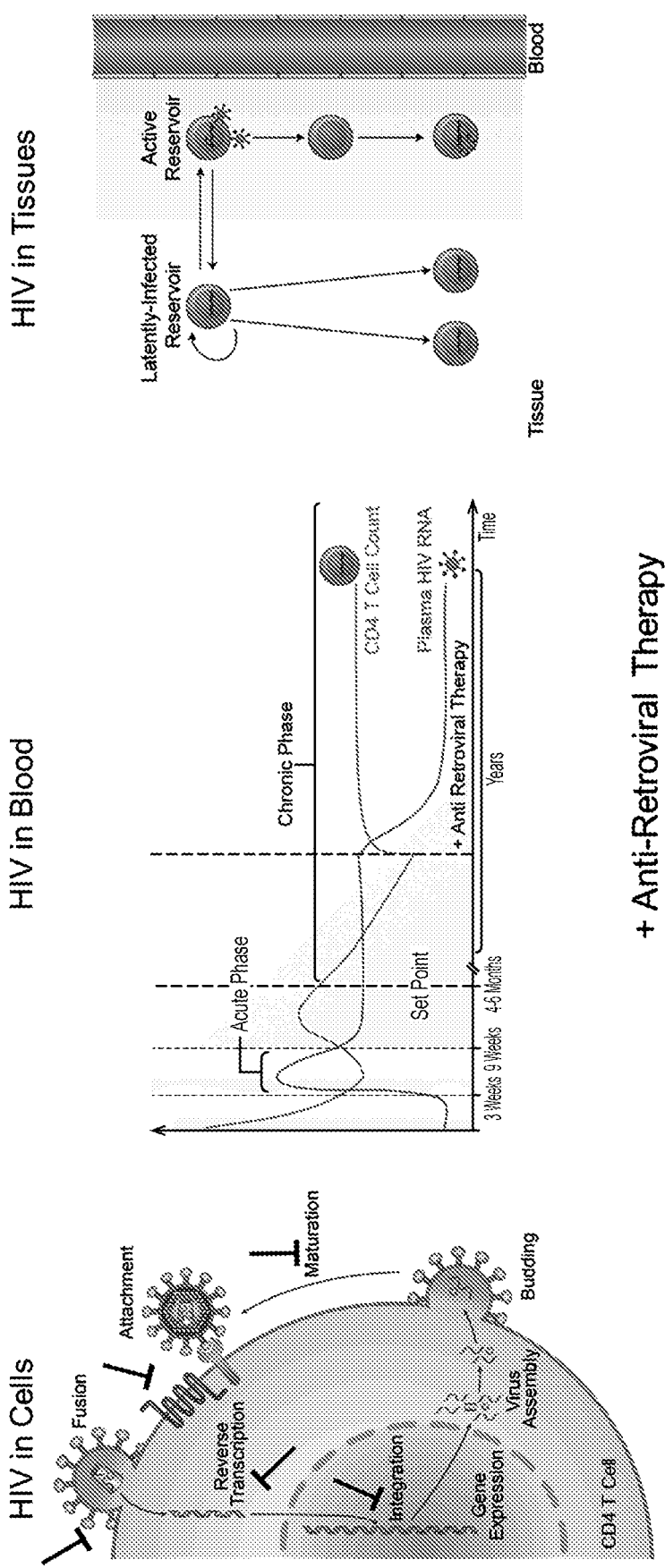
FIG. 2—Host-Pathogen Dynamics of HIV Infection. HIV preferentially infects CD4 T cells, reverse transcribes its DNA, and integrates into the host genome. Infection progresses through a spike in viral load, followed by a progressive decrease in CD4+ T cell count. Because of the high plasma viral load, and because T cells migrate throughout different locations, virtually all tissues can be exposed to the virus, causing profound, and often irreversible changes to the adaptive and innate immune systems, and establishing a permanent pool of integrated HIV termed the "reservoir."
Figure 3:
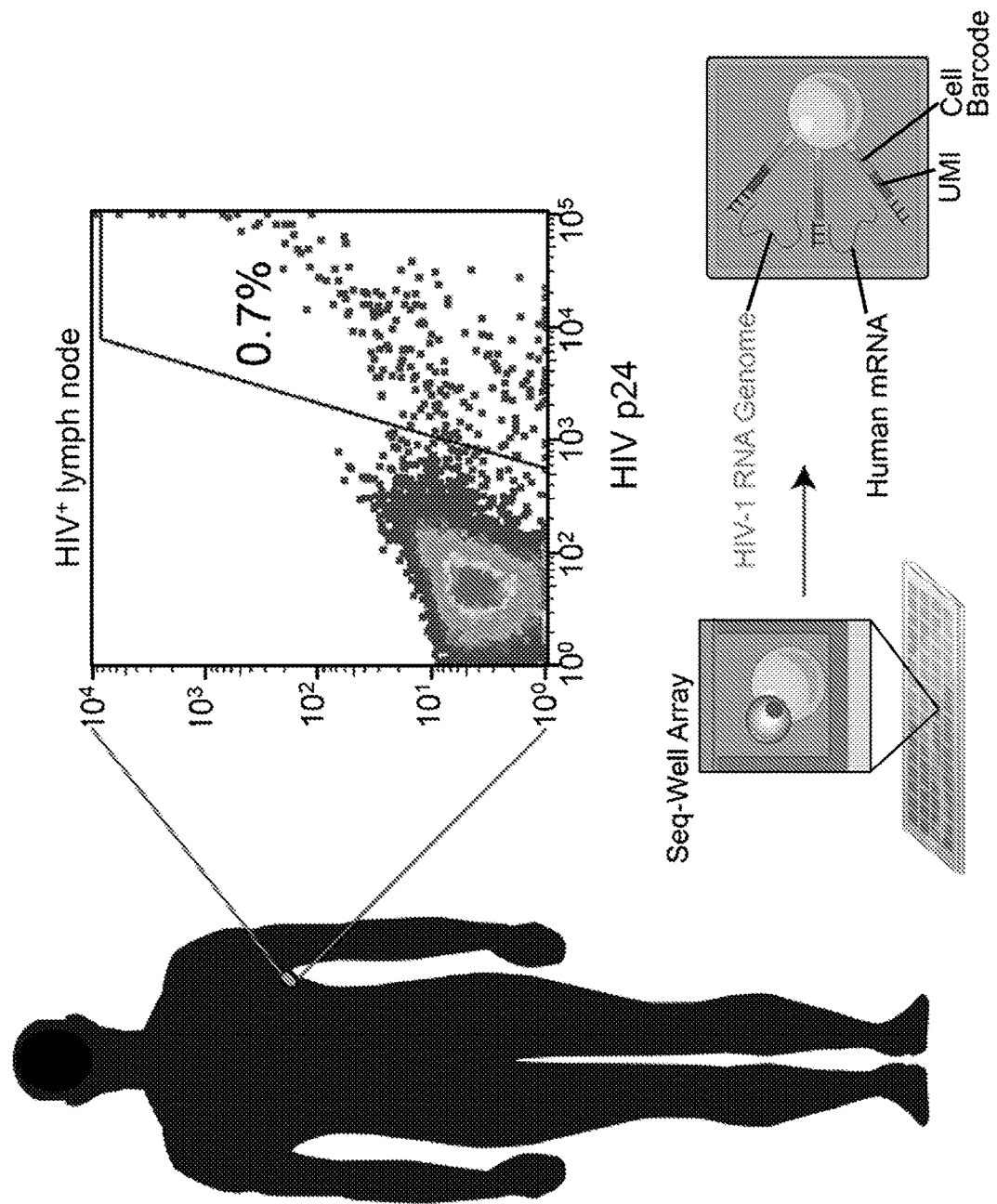
FIG. 3— Lymph node cells stain positive for HIV proteins such as p24 by flow cytometry indicating a significant fraction of cells are actively producing virus.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide a pan-tissue cell from healthy and diseased subjects. The atlas was obtained by single cell sequencing. The present invention discloses novel markers for cell types. Moreover, genes associated with chronic infection and disease, including those associated with HIV infection are identified. The invention provides for diagnostic assays based on gene markers and cell composition, as well as therapeutic targets for controlling differentiation, proliferation, maintenance and/or function of the cell types disclosed herein. In addition, novel cell types and methods of quantitating, detecting and isolating the cell types are disclosed.

In certain example embodiments, using Seq-Well for massively parallel scRNA-seq (Shalek reference Re: Seqwell) of surgical resections from individuals infected by HIV (HIV+) and healthy individuals (HIV−), cells and tissues representative of infection states were located, and biomarkers related to (latent) infection in specific cells were identified.

Methods of Modulating

Methods as disclosed herein are directed to modulating a cell or tissue infected with a viral infection. Such infections include, but are not necessarily limited to, Hepatitis B, Hepatitis C, or HIV. In specific embodiments, the methods comprise contacting a cell or tissue with a modulating agent in an amount sufficient to modify the HIV latency or ART-resistance of the cell or tissue as compared to the HIV latency or ART-resistance in the absence of the modulating agent. The methods of modulating may include modulating one or more host genes, or product of one or more host genes, which may include increasing or decreasing expression of particular host genes or gene products. Modulating may be based on the gene expression detected, and may be determined by the gene whose expression is increased in a cell infected with HIV. The order of steps provided herein is exemplary, certain steps may be carried out simultaneously or in a different order.

Contacting

The contacting may take place in vitro, in vivo, ex vivo. In some instances contacting can be performed by incubating a cell or tissue having a certain phenotype with the candidate modulating agent. In some instances contacting can be performed by delivering the candidate modulating agent to a subject in need thereof. The step of contacting is performed under conditions and for a time sufficient to allow the modulating agent and the cell, tissue, gene, or gene product to interact.

In some embodiments, the cells or population of cells may be obtained from a biological sample. The biological sample may be obtained from a subject suffering from a disease. The biological sample may be a tumor sample. The tumor may be any tumor. This may include, without limitation, liquid tumors such as leukemia (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease, non-Hodgkin's disease), Waldenstrom's macroglobulinemia, heavy chain disease, or multiple myeloma.

As used herein, a "biological sample" may contain whole cells and/or tissue and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Modulating Agent

The modulating agent can be any composition that induces, represses, or otherwise affects a gene or gene product. Modulating agents may be selected in some instances, based on a particular pathway, degree of infection, and/or a gene expression signature that may have been detected.

As used herein, modulating, or to modulate, generally means either reducing or inhibiting the expression or activity of, or alternatively increasing the expression or activity of a target gene. In particular, modulating can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An increase or decrease refers to a statistically significant increase or decrease respectively. For the avoidance of doubt, an increase or decrease will be at least 10% relative to a reference, such as at least 10%, at least 20%, at least 30%, at least 40%, at least 50%, at least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. Modulating can also involve effecting a change (which can either be an increase or a decrease) in affinity, avidity, specificity and/or selectivity of a target or antigen, such as a receptor and ligand. Modulating can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved. Accordingly, a modulating agent in an amount sufficient to modify the *Mycobacterium Tuberculosis* infection in a cell or tissue would provide the agent in an amount to effect a change in the amount of infection compared to the amount of infection in the cell or tissue in the absence of modulating agent, or untreated. The amount of modulating agent will vary according to the pathway, gene, or gene product targeted, the host, the tissue or cell, and the amount or copy number of the TB infection.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

As used herein, an "agent" can refer to a protein-binding agent that permits modulation of activity of proteins or disrupts interactions of proteins and other biomolecules, such as but not limited to disrupting protein-protein interaction, ligand-receptor interaction, or protein-nucleic acid interaction. Agents can also refer to DNA targeting or RNA targeting agents. Agents may include a fragment, derivative and analog of an active agent. The terms "fragment," "derivative" and "analog" when referring to polypeptides as used herein refers to polypeptides which either retain substantially the same biological function or activity as such polypeptides. An analog includes a proprotein which can be activated by cleavage of the proprotein portion to produce an active mature polypeptide. Such agents include, but are not limited to, antibodies ("antibodies" includes antigen-binding portions of antibodies such as epitope- or antigen-binding peptides, paratopes, functional CDRs; recombinant antibodies; chimeric antibodies; humanized antibodies; nanobodies; tribodies; midibodies; or antigen-binding derivatives, analogs, variants, portions, or fragments thereof), protein-binding agents, nucleic acid molecules, small molecules, recombinant protein, peptides, aptamers, avimers and protein-binding derivatives, portions or fragments thereof. An "agent" as used herein, may also refer to an agent that inhibits expression of a gene, such as but not limited to a DNA targeting agent (e.g., CRISPR system, TALE, Zinc finger protein) or RNA targeting agent (e.g., inhibitory nucleic acid molecules such as RNAi, miRNA, ribozyme).

The agents of the present invention may be modified, such that they acquire advantageous properties for therapeutic use (e.g., stability and specificity), but maintain their biological activity.

It is well known that the properties of certain proteins can be modulated by attachment of polyethylene glycol (PEG) polymers, which increases the hydrodynamic volume of the protein and thereby slows its clearance by kidney filtration. (See, e.g., Clark et al., J. Biol. Chem. 271: 21969-21977 (1996)). Therefore, it is envisioned that certain agents can be PEGylated (e.g., on peptide residues) to provide enhanced therapeutic benefits such as, for example, increased efficacy by extending half-life in vivo. In certain embodiments, PEGylation of the agents may be used to extend the serum half-life of the agents and allow for particular agents to be capable of crossing the blood-brain barrier.

In regards to peptide PEGylation methods, reference is made to Lu et al., Int. J. Pept. Protein Res. 43: 127-38 (1994); Lu et al., Pept. Res. 6: 140-6 (1993); Felix et al., Int. J. Pept. Protein Res. 46: 253-64 (1995); Gaertner et al., Bioconjug. Chem. 7: 38-44 (1996); Tsutsumi et al., Thromb. Haemost. 77: 168-73 (1997); Francis et al., hit. J. Hematol. 68: 1-18 (1998); Roberts et al., J. Pharm. Sci. 87: 1440-45 (1998); and Tan et al., Protein Expr. Purif. 12: 45-52 (1998). Polyethylene glycol or PEG is meant to encompass any of the forms of PEG that have been used to derivatize other proteins, including, but not limited to, mono-(C1-10) alkoxy or aryloxy-polyethylene glycol. Suitable PEG moieties include, for example, 40 kDa methoxy poly(ethylene glycol) propionaldehyde (Dow, Midland, Mich.); 60 kDa methoxy poly(ethylene glycol) propionaldehyde (Dow, Midland, Mich.); 40 kDa methoxy poly(ethylene glycol) maleimido-propionamide (Dow, Midland, Mich.); 31 kDa alpha-methyl-w-(3-oxopropoxy), polyoxyethylene (NOF Corporation, Tokyo); mPEG2-NHS-40k (Nektar); mPEG2-MAL-40k (Nektar), SUNBRIGHT GL2-400MA ((PEG)240 kDa) (NOF Corporation, Tokyo), SUNBRIGHT ME-200MA (PEG20 kDa) (NOF Corporation, Tokyo). The PEG groups are generally attached to the peptide (e.g., neuromedin U receptor agonists or antagonists) via acylation or alkylation through a reactive group on the PEG moiety (for example, a maleimide, an aldehyde, amino, thiol, or ester group) to a reactive group on the peptide (for example, an aldehyde, amino, thiol, a maleimide, or ester group).

The PEG molecule(s) may be covalently attached to any Lys, Cys, or K(CO(CH2)2SH) residues at any position in a peptide. In certain embodiments, the neuromedin U receptor agonists described herein can be PEGylated directly to any amino acid at the N-terminus by way of the N-terminal amino group. A "linker arm" may be added to a peptide to facilitate PEGylation. PEGylation at the thiol side-chain of cysteine has been widely reported (see, e.g., Caliceti & Veronese, Adv. Drug Deliv. Rev. 55: 1261-77 (2003)). If there is no cysteine residue in the peptide, a cysteine residue can be introduced through substitution or by adding a cysteine to the N-terminal amino acid.

As used herein the term "altered expression" may particularly denote altered production of the recited gene products by a cell. As used herein, the term "gene product(s)" includes RNA transcribed from a gene (e.g., mRNA), or a polypeptide encoded by a gene or translated from RNA. Also, "altered expression" as intended herein may encompass modulating the activity of one or more endogenous gene products. Accordingly, "altered expression", "altering expression", "modulating expression", or "detecting expression" or similar may be used interchangeably with respectively "altered expression or activity", "altering expression or activity", "modulating expression or activity", or "detecting expression or activity" or similar. As used herein, "modulating" or "to modulate" generally means either reducing or inhibiting the activity of a target or antigen, or alternatively increasing the activity of the target or antigen, as measured using a suitable in vitro, cellular or in vivo assay. In particular, "modulating" or "to modulate" can mean either reducing or inhibiting the (relevant or intended) activity of, or alternatively increasing the (relevant or intended) biological activity of the target or antigen, as measured using a suitable in vitro, cellular or in vivo assay (which will usually depend on the target or antigen involved), by at least 5%, at least 10%, at least 25%, at least 50%, at least 60%, at least 70%, at least 80%, or 90% or more, compared to activity of the target or antigen in the same assay under the same conditions but without the presence of the inhibitor/antagonist agents or activator/agonist agents described herein.

As will be clear to the skilled person, "modulating" can also involve affecting a change (which can either be an increase or a decrease) in affinity, avidity, specificity and/or selectivity of a target or antigen, for one or more of its targets compared to the same conditions but without the presence of a modulating agent. Again, this can be determined in any suitable manner and/or using any suitable assay known per se, depending on the target. In particular, an action as an inhibitor/antagonist or activator/agonist can be such that an intended biological or physiological activity is increased or decreased, respectively, by at least 5%, at least 10%, at least 25%, at least 50%, at least 60%, at least 70%, at least 80%, or 90% or more, compared to the biological or physiological activity in the same assay under the same conditions but without the presence of the inhibitor/antagonist agent or activator/agonist agent. Modulating can also involve activating the target or antigen or the mechanism or pathway in which it is involved.

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

Upon infection, HIV remains latent in infected cells, a state in which it is present, but not actively producing viral particles. Latent HIV reservoirs are established during the earliest stage of HIV infection. Although ART can reduce the level of HIV in the blood to an undetectable level, latent reservoirs of HIV continue to survive so that, when a latently infected cell is reactivated, the cell begins to produce viral particles again. Although ART can suppress HIV levels, the therapy cannot eliminate latent HIV reservoirs, and thus cannot cure the infection. Termination of ART leads to almost immediate reactivation and replication of HIV genes within a couple of weeks upon termination of therapy. Furthermore, certain viral strains are resistant to ART treatment, causing HIV treatment to fail in certain individuals. Such individuals are said to have an ART-resistant HIV infection.

The term "amount sufficient", "effective amount", or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

For example, in methods for treating cancer in a subject, an effective amount of a combination of inhibitors targeting epigenetic genes is any amount that provides an anti-cancer effect, such as reduces or prevents proliferation of a cancer cell or is cytotoxic towards a cancer cell. In certain embodiments, the effective amount of an inhibitor targeting an epigenetic gene is reduced when an inhibitor is administered concomitantly or in combination with one or more additional inhibitors targeting epigenetic genes as compared to the effective amount of the inhibitor when administered in the absence of one or more additional inhibitors targeting epigenetic genes. In certain embodiments, the inhibitor targeting an epigenetic gene does not reduce or prevent proliferation of a cancer cell when administered in the absence of one or more additional inhibitors targeting epigenetic genes.

In specific embodiments, in methods for modulating a cell or tissue having a latent HIV or ART-resistant HIV infection, an amount of a modulating agent sufficient to modify the HIV latency or ART-resistance of the cell or tissue is any amount that increases or decreases the expression of genes or gene products from Tables 1, 2, or 3 in that cell or tissue relative to a cell or tissue not exposed to or contacted with that modulating agent.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

In some embodiments, the viral or latent viral infection in the cell or tissue is a latent HIV or anti-ART-resistant HIV infection as described herein.

In some embodiments, the viral infection is a hepatitis infection. In specific embodiments, the hepatitis infection is hepatitis B or hepatitis C. The pathway by which hepatic viruses cause viral hepatitis is best understood in the case of hepatitis B and C. The viruses do not directly cause apoptosis (cell death), rather, infection of liver cells activates the innate and adaptive arms of the immune system leading to an inflammatory response which causes cellular damage and death (Nakamoto et al. *Curr Molec Med* 3(6):537-544; 2003). Depending on the strength of the immune response, the types of immune cells involved and the ability of the virus to evade the body's defense, infection can either lead to clearance (acute disease) or persistence (chronic disease) of the virus. The chronic presence of the virus within liver cells results in multiple waves of inflammation, injury and wound healing that over time lead to scarring or fibrosis and culminate in hepatocellular carcinoma (Nakamoto et al. *Curr Molec Med* 3(6):537-544 (2003); Wong *Clin Molec Hepatol* 20(3):228-236 (2014)). Individuals with an impaired immune response are at greater risk of developing chronic infection. Natural killer cells are the primary drivers of the initial innate response and create a cytokine environment that results in the recruitment of CD4 T-helper and CD8 cytotoxic T-cells (Rehermann *Cell Molec Gastr Hepatol* 1(6):578-588 (2015); Heim et al. *J Hepatol* 61(1 Suppl): S14-25 (2014)). Type I interferons are the cytokines that drive the antiviral response (Heim et al. *J Hepatol* 61(1 Suppl): S14-25 (2014)). In chronic Hepatitis B and C, natural killer cell function is impaired (Rehermann *Cell Molec Gastr Hepatol* 1(6):578-588 (2015)).

In some embodiments, the HIV latency or ART-resistance of the cell directly influences the latent HIV or ART-resistant HIV infection, in that the state of the cell has an effect or impact on the viral infection.

The term "immune cell" as used throughout this specification generally encompasses any cell derived from a hematopoietic stem cell that plays a role in the immune response. The term is intended to encompass immune cells both of the innate or adaptive immune system. The immune cell as referred to herein may be a leukocyte, at any stage of differentiation (e.g., a stem cell, a progenitor cell, a mature cell) or any activation stage. Immune cells include lymphocytes (such as natural killer cells, T-cells (including, e.g., thymocytes, Th or Tc; Th1, Th2, Th17, Thαβ, CD4$^+$, CD8$^+$, effector Th, memory Th, regulatory Th, CD4$^+$/CD8$^+$ thymocytes, CD4−/CD8− thymocytes, γδ T cells, etc.) or B-cells (including, e.g., pro-B cells, early pro-B cells, late pro-B cells, pre-B cells, large pre-B cells, small pre-B cells, immature or mature B-cells, producing antibodies of any isotype, T1 B-cells, T2 B-cells, naïve B-cells, GC B-cells, plasmablasts, memory B-cells, plasma cells, follicular B-cells, marginal zone B-cells, B-1 cells, B-2 cells, regulatory B cells, etc.), such as for instance, monocytes (including, e.g., classical, non-classical, or intermediate monocytes), (segmented or banded) neutrophils, eosinophils, basophils, mast cells, histiocytes, microglia, including various subtypes, maturation, differentiation, or activation stages, such as for instance hematopoietic stem cells, myeloid progenitors, lymphoid progenitors, myeloblasts, promyelocytes, myelocytes, metamyelocytes, monoblasts, promonocytes, lymphoblasts, prolymphocytes, small lymphocytes, macrophages (including, e.g., Kupffer cells, stellate macrophages, M1 or M2 macrophages), (myeloid or lymphoid) dendritic cells (including, e.g., Langerhans cells, conventional or myeloid dendritic cells, plasmacytoid dendritic cells, mDC-1, mDC-2, Mo-DC, HP-DC, veiled cells), granulocytes, polymorphonuclear cells, antigen-presenting cells (APC), etc.

As used throughout this specification, "immune response" refers to a response by a cell of the immune system, such as a B cell, T cell (CD4$^+$ or CD8$^+$), regulatory T cell, antigen-presenting cell, dendritic cell, monocyte, macrophage, NKT cell, NK cell, basophil, eosinophil, or neutrophil, to a stimulus. In some embodiments, the response is specific for a particular antigen (an "antigen-specific response"), and refers to a response by a CD4 T cell, CD8 T cell, or B cell via their antigen-specific receptor. In some embodiments, an immune response is a T cell response, such as a CD4$^+$ response or a CD8$^+$ response. Such responses by these cells can include, for example, cytotoxicity, proliferation, cytokine or chemokine production, trafficking, or phagocytosis, and can be dependent on the nature of the immune cell undergoing the response.

T cell response refers more specifically to an immune response in which T cells directly or indirectly mediate or otherwise contribute to an immune response in a subject. T cell-mediated response may be associated with cell mediated effects, cytokine mediated effects, and even effects associated with B cells if the B cells are stimulated, for example, by cytokines secreted by T cells. By means of an example but without limitation, effector functions of MHC class I restricted Cytotoxic T lymphocytes (CTLs), may include cytokine and/or cytolytic capabilities, such as lysis of target cells presenting an antigen peptide recognised by the T cell receptor (naturally-occurring TCR or genetically engineered TCR, e.g., chimeric antigen receptor, CAR), secretion of cytokines, preferably IFN gamma, TNF alpha and/or or more immunostimulatory cytokines, such as IL-2, and/or antigen peptide-induced secretion of cytotoxic effector molecules, such as granzymes, perforins or granulysin. By means of example but without limitation, for MEW class II restricted T helper (Th) cells, effector functions may be antigen peptide-induced secretion of cytokines, preferably, IFN gamma, TNF alpha, IL-4, IL5, IL-10, and/or IL-2. By means of example but without limitation, for T regulatory (Treg) cells, effector functions may be antigen peptide-induced secretion of cytokines, preferably, IL-10, IL-35, and/or TGF-beta. B cell response refers more specifically to an immune response in which B cells directly or indirectly mediate or otherwise contribute to an immune response in a subject. Effector functions of B cells may include in particular production and secretion of antigen-specific antibodies by B cells (e.g., polyclonal B cell response to a plurality of the epitopes of an antigen (antigen-specific antibody response)), antigen presentation, and/or cytokine secretion.

During persistent immune activation, such as during uncontrolled tumor growth or chronic infections, subpopulations of immune cells, particularly of CD8+ or CD4+ T cells, become compromised to different extents with respect to their cytokine and/or cytolytic capabilities. Such immune cells, particularly CD8+ or CD4+ T cells, are commonly referred to as "dysfunctional" or as "functionally exhausted" or "exhausted". As used herein, the term "dysfunctional" or "functional exhaustion" refer to a state of a cell where the cell does not perform its usual function or activity in response to normal input signals, and includes refractivity of immune cells to stimulation, such as stimulation via an activating receptor or a cytokine. Such a function or activity includes, but is not limited to, proliferation (e.g., in response to a cytokine, such as IFN-gamma) or cell division, entrance into the cell cycle, cytokine production, cytotoxicity, migration and trafficking, phagocytotic activity, or any combination thereof. Normal input signals can include, but are not limited to, stimulation via a receptor (e.g., T cell receptor, B cell receptor, co-stimulatory receptor). Unresponsive immune cells can have a reduction of at least 10%, 20%, 30%, 40%, 50%, 60%, 70%, 80%, 90%, 95%, or even 100% in cytotoxic activity, cytokine production, proliferation, trafficking, phagocytotic activity, or any combination thereof, relative to a corresponding control immune cell of the same type. In some particular embodiments of the aspects described herein, a cell that is dysfunctional is a CD8+ T cell that expresses the CD8+ cell surface marker. Such CD8+ cells normally proliferate and produce cell killing enzymes, e.g., they can release the cytotoxins perform, granzymes, and granulysin. However, exhausted/dysfunctional T cells do not respond adequately to TCR stimulation, and display poor effector function, sustained expression of inhibitory receptors and a transcriptional state distinct from that of functional effector or memory T cells. Dysfunction/exhaustion of T cells thus prevents optimal control of infection and tumors. Exhausted/dysfunctional immune cells, such as T cells, such as CD8+ T cells, may produce reduced amounts of IFN-gamma, TNF-alpha and/or one or more immunostimulatory cytokines, such as IL-2, compared to functional immune cells. Exhausted/dysfunctional immune cells, such as T cells, such as CD8+ T cells, may further produce (increased amounts of) one or more immunosuppressive transcription factors or cytokines, such as IL-10 and/or Foxp3, compared to functional immune cells, thereby contributing to local immunosuppression. Dysfunctional CD8+ T cells can be both protective and detrimental against disease control.

CD8+ T cell function is associated with their cytokine profiles. It has been reported that effector CD8+ T cells with the ability to simultaneously produce multiple cytokines (polyfunctional CD8+ T cells) are associated with protective immunity in patients with controlled chronic viral infections as well as cancer patients responsive to immune therapy (Spranger et al., 2014, J. Immunother. Cancer, vol. 2, 3). In the presence of persistent antigen CD8+ T cells were found to have lost cytolytic activity completely over time (Moskophidis et al., 1993, Nature, vol. 362, 758-761). It was subsequently found that dysfunctional T cells can differentially produce IL-2, TNFa and IFNg in a hierarchical order (Wherry et al., 2003, J. Virol., vol. 77, 4911-4927). Decoupled dysfunctional and activated CD8+ cell states have also been described (see, e.g., Singer, et al. (2016). A Distinct Gene Module for Dysfunction Uncoupled from Activation in Tumor-Infiltrating T Cells. Cell 166, 1500-1511 e1509; and WO/2017/075478).

The invention also provides compositions and methods for modulating T cell balance. The invention provides T cell modulating agents that modulate T cell balance. For example, in some embodiments, the invention provides T cell modulating agents and methods of using these T cell modulating agents to regulate, influence or otherwise impact the level of and/or balance between T cell types, e.g., between Th17 and other T cell types, for example, regulatory T cells (Tregs). For example, in some embodiments, the invention provides T cell modulating agents and methods of using these T cell modulating agents to regulate, influence or otherwise impact the level of and/or balance between Th17 activity and inflammatory potential. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3.

In some embodiments, the modulating of a cell or tissue comprises modulating a lymph node immune cell. A lymph node is an organ of the lymphatic system and of the adaptive immune system, that is widely present throughout the body. Lymph nodes are linked by the lymphatic vessels as a part of the circulatory system and are major sites of B and T lymphocytes. The term "lymph node immune cell" as described herein, refers to B and T lymphocytes, and other white blood cells as described herein and listed above.

In some embodiments, the modulating of a cell or tissue as described herein comprises modulating a T cell or T cell subset. Specific subsets of T cells may include, but are not necessarily limited to, CD4+ T cells, CD8+ T cells, Tregs, T helper cells, NK cells. In specific embodiments, specific subsets of T cells as described herein, include, but are not necessarily limited to, $CD3^+CD4^+PD1^+CXCR4^+$ T follicular helper cells or $CD45RA^-CCR7^+CD27^+$ memory T cells.

In some embodiments, the modulating of a cell or tissue may comprise modulating a gene or gene product that is enriched for expression in $HIV^+$ cells. Such genes or gene products may be more prominently expressed in $HIV^+$ cells, such as for example, but not necessarily limited to, the genes and gene products listed in Tables 1 and 2.

Identifying Modulating Agents

A further aspect of the invention relates to a method for identifying an agent capable of modulating one or more phenotypic aspects of a pathogen infected cell, comprising: a) applying a candidate agent to the cell or cell population; b) detecting modulation of one or more phenotypic aspects of the cell or cell population by the candidate agent, thereby identifying the agent.

The term "modulate" broadly denotes a qualitative and/or quantitative alteration, change or variation in that which is being modulated. Where modulation can be assessed quantitatively—for example, where modulation comprises or consists of a change in a quantifiable variable such as a quantifiable property of a cell or where a quantifiable variable provides a suitable surrogate for the modulation—modulation specifically encompasses both increase (e.g., activation) or decrease (e.g., inhibition) in the measured variable. The term encompasses any extent of such modulation, e.g., any extent of such increase or decrease, and may more particularly refer to statistically significant increase or decrease in the measured variable. By means of example, modulation may encompass an increase in the value of the measured variable by at least about 10%, e.g., by at least about 20%, preferably by at least about 30%, e.g., by at least about 40%, more preferably by at least about 50%, e.g., by at least about 75%, even more preferably by at least about 100%, e.g., by at least about 150%, 200%, 250%, 300%, 400% or by at least about 500%, compared to a reference situation without said modulation; or modulation may encompass a decrease or reduction in the value of the measured variable by at least about 10%, e.g., by at least about 20%, by at least about 30%, e.g., by at least about 40%, by at least about 50%, e.g., by at least about 60%, by at least about 70%, e.g., by at least about 80%, by at least about 90%, e.g., by at least about 95%, such as by at least about 96%, 97%, 98%, 99% or even by 100%, compared to a reference situation without said modulation. Preferably, modulation may be specific or selective, hence, one or more desired phenotypic aspects of a gut cell or gut cell population may be modulated without substantially altering other (unintended, undesired) phenotypic aspect(s).

The term "agent" broadly encompasses any condition, substance or agent capable of modulating one or more phenotypic aspects of cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of an gut cell or gut cell population as disclosed herein in a method comprising applying the candidate agent to the gut cell or gut cell population (e.g., exposing the gut cell or gut cell population to the candidate agent or contacting the gut cell or gut cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof.

By means of example but without limitation, agents can include low molecular weight compounds, but may also be larger compounds, or any organic or inorganic molecule effective in the given situation, including modified and unmodified nucleic acids such as antisense nucleic acids, RNAi, such as siRNA or shRNA, CRISPR/Cas systems, peptides, peptidomimetics, receptors, ligands, and antibodies, aptamers, polypeptides, nucleic acid analogues or variants thereof. Examples include an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof. Agents can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide—nucleic acid (PNA), pseudo-complementary PNA (pc-PNA), locked nucleic acid (LNA), modified RNA (mod-RNA), single guide RNA etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides, CRISPR guide RNA, for example that target a CRISPR enzyme to a specific DNA target sequence etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein modulator of a gene within the cell. In some embodiments, the agent is any chemical, entity or moiety, including without limitation synthetic and naturally-occurring non-proteinaceous entities. In certain embodiments, the agent is a small molecule having a chemical moiety. Agents can be known to have a desired activity and/or property, or can be selected from a library of diverse compounds.

In certain embodiments, an agent may be a hormone, a cytokine, a lymphokine, a growth factor, a chemokine, a cell surface receptor ligand such as a cell surface receptor agonist or antagonist, or a mitogen.

Non-limiting examples of hormones include growth hormone (GH), adrenocorticotropic hormone (ACTH), dehydroepiandrosterone (DHEA), cortisol, epinephrine, thyroid hormone, estrogen, progesterone, testosterone, or combinations thereof.

Non-limiting examples of cytokines include lymphokines (e.g., interferon-γ, IL-2, IL-3, IL-4, IL-6, granulocyte-macrophage colony-stimulating factor (GM-CSF), interferon-γ, leukocyte migration inhibitory factors (T-LIF, B-LIF), lymphotoxin-alpha, macrophage-activating factor (MAF), macrophage migration-inhibitory factor (MIF), neuroleukin, immunologic suppressor factors, transfer factors, or combinations thereof), monokines (e.g., IL-1, TNF-alpha, interferon-α, interferon-β, colony stimulating factors, e.g., CSF2, CSF3, macrophage CSF or GM-CSF, or combinations thereof), chemokines (e.g., beta-thromboglobulin, C chemokines, CC chemokines, CXC chemokines, CX3C chemokines, macrophage inflammatory protein (MIP), or combinations thereof), interleukins (e.g., IL-1, IL-2, IL-3, IL-4, IL-5, IL-6, IL-7, IL-8, IL-9, IL-10, IL-11, IL-12, IL-13, IL-14, IL-15, IL-17, IL-18, IL-19, IL-20, IL-21, IL-22, IL-23, IL-24, IL-25, IL-26, IL-27, IL-28, IL-29, IL-30, IL-31, IL-32, IL-33, IL-34, IL-35, IL-36, or combinations thereof), and several related signaling molecules, such as tumour necrosis factor (TNF) and interferons (e.g., interferon-α, interferon-β, interferon-γ, interferon-λ, or combinations thereof).

Non-limiting examples of growth factors include those of fibroblast growth factor (FGF) family, bone morphogenic protein (BMP) family, platelet derived growth factor (PDGF) family, transforming growth factor beta (TGFbeta) family, nerve growth factor (NGF) family, epidermal growth factor (EGF) family, insulin related growth factor (IGF)

family, hepatocyte growth factor (HGF) family, hematopoietic growth factors (HeGFs), platelet-derived endothelial cell growth factor (PD-ECGF), angiopoietin, vascular endothelial growth factor (VEGF) family, glucocorticoids, or combinations thereof.

Non-limiting examples of mitogens include phytohaemagglutinin (PHA), concanavalin A (conA), lipopolysaccharide (LPS), pokeweed mitogen (PWM), phorbol ester such as phorbol myristate acetate (PMA) with or without ionomycin, or combinations thereof.

Non-limiting examples of cell surface receptors the ligands of which may act as agents include Toll-like receptors (TLRs) (e.g., TLR1, TLR2, TLR3, TLR4, TLR5, TLR6, TLR7, TLR8, TLR9, TLR10, TLR11, TLR12 or TLR13), CD80, CD86, CD40, CCR7, or C-type lectin receptors.

Particular screening applications of this invention relate to the testing of pharmaceutical compounds in drug research. The reader is referred generally to the standard textbook In vitro Methods in Pharmaceutical Research, Academic Press, 1997, and U.S. Pat. No. 5,030,015. In certain aspects of this invention, the culture of the invention is used to grow and differentiate a cachectic target cell to play the role of test cells for standard drug screening and toxicity assays. Assessment of the activity of candidate pharmaceutical compounds generally involves combining the target cell (e.g., a myocyte, an adipocyte, a cardiomyocyte or a hepatocyte) with the candidate compound, determining any change in the morphology, marker phenotype, or metabolic activity of the cells that is attributable to the candidate compound (compared with untreated cells or cells treated with an inert compound, such as vehicle), and then correlating the effect of the candidate compound with the observed change. The screening may be done because the candidate compound is designed to have a pharmacological effect on the target cell, or because a candidate compound may have unintended side effects on the target cell. Alternatively, libraries can be screened without any predetermined expectations in hopes of identifying compounds with desired effects.

Cytotoxicity can be determined in the first instance by the effect on cell viability and morphology. In certain embodiments, toxicity may be assessed by observation of vital staining techniques, ELISA assays, immunohistochemistry, and the like or by analyzing the cellular content of the culture, e.g., by total cell counts, and differential cell counts or by metabolic markers such as MTT and XTT.

Additional further uses of the culture of the invention include, but are not limited to, its use in research e.g., to elucidate mechanisms leading to the identification of novel targets for therapies, and to generate genotype-specific cells for disease modeling, including the generation of new therapies customized to different genotypes. Such customization can reduce adverse drug effects and help identify therapies appropriate to the patient's genotype.

In certain embodiments, the present invention provides method for high-throughput screening. "High-throughput screening" (HTS) refers to a process that uses a combination of modern robotics, data processing and control software, liquid handling devices, and/or sensitive detectors, to efficiently process a large amount of (e.g., thousands, hundreds of thousands, or millions of) samples in biochemical, genetic or pharmacological experiments, either in parallel or in sequence, within a reasonably short period of time (e.g., days). Preferably, the process is amenable to automation, such as robotic simultaneous handling of 96 samples, 384 samples, 1536 samples or more. A typical HTS robot tests up to 100,000 to a few hundred thousand compounds per day. The samples are often in small volumes, such as no more than 1 mL, 500 µl, 200 µl, 100 µl, 50 µl or less. Through this process, one can rapidly identify active compounds, small molecules, antibodies, proteins or polynucleotides which modulate a particular biomolecular/genetic pathway. The results of these experiments provide starting points for further drug design and for understanding the interaction or role of a particular biochemical process in biology. Thus "high-throughput screening" as used herein does not include handling large quantities of radioactive materials, slow and complicated operator-dependent screening steps, and/or prohibitively expensive reagent costs, etc.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures of the present invention may be used to screen for drugs that induce or reduce the signature in immune cells as described herein. The signature may be used for GE-HTS (Gene Expression-based High-Throughput Screening). In certain embodiments, pharmacological screens may be used to identify drugs that selectively activate gut cells.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature of the present invention in silico.

Genetic Modification

In certain embodiments, one or more endogenous genes may be modified using a nuclease. The term "nuclease" as used herein broadly refers to an agent, for example a protein or a small molecule, capable of cleaving a phosphodiester bond connecting nucleotide residues in a nucleic acid molecule. In some embodiments, a nuclease may be a protein, e.g., an enzyme that can bind a nucleic acid molecule and cleave a phosphodiester bond connecting nucleotide residues within the nucleic acid molecule. A nuclease may be an endonuclease, cleaving a phosphodiester bonds within a polynucleotide chain, or an exonuclease, cleaving a phosphodiester bond at the end of the polynucleotide chain. Preferably, the nuclease is an endonuclease. Preferably, the nuclease is a site-specific nuclease, binding and/or cleaving a specific phosphodiester bond within a specific nucleotide sequence, which may be referred to as "recognition sequence", "nuclease target site", or "target site". In some embodiments, a nuclease may recognize a single stranded target site, in other embodiments a nuclease may recognize a double-stranded target site, for example a double-stranded DNA target site. Some endonucleases cut a double-stranded nucleic acid target site symmetrically, i.e., cutting both strands at the same position so that the ends comprise base-paired nucleotides, also known as blunt ends. Other endonucleases cut a double-stranded nucleic acid target sites asymmetrically, i.e., cutting each strand at a different position so that the ends comprise unpaired nucleotides. Unpaired nucleotides at the end of a double-stranded DNA molecule are also referred to as "overhangs", e.g., "5'-overhang" or "3'-overhang", depending on whether the unpaired nucleotide(s) form(s) the 5' or the 5' end of the respective DNA strand.

The nuclease may introduce one or more single-strand nicks and/or double-strand breaks in the endogenous gene, whereupon the sequence of the endogenous gene may be modified or mutated via non-homologous end joining (NHEJ) or homology-directed repair (HDR).

In certain embodiments, the nuclease may comprise (i) a DNA-binding portion configured to specifically bind to the endogenous gene and (ii) a DNA cleavage portion. Generally, the DNA cleavage portion will cleave the nucleic acid within or in the vicinity of the sequence to which the DNA-binding portion is configured to bind.

In certain embodiments, the DNA-binding portion may comprise a zinc finger protein or DNA-binding domain thereof, a transcription activator-like effector (TALE) protein or DNA-binding domain thereof, or an RNA-guided protein or DNA-binding domain thereof.

In certain embodiments, the DNA-binding portion may comprise (i) Cas9 or Cpf1 or any Cas protein described herein modified to eliminate its nuclease activity, or (ii) DNA-binding domain of Cas9 or Cpf1 or any Cas protein described herein.

In certain embodiments, the DNA cleavage portion comprises FokI or variant thereof or DNA cleavage domain of FokI or variant thereof.

In certain embodiments, the nuclease may be an RNA-guided nuclease, such as Cas9 or Cpf1 or any Cas protein described herein.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. application 62/091,462, 12 Dec. 14, DEAD GUIDES FOR CRISPR TRANSCRIP- TION FACTORS; U.S. application 62/096,324, 23 Dec. 14, DEAD GUIDES FOR CRISPR TRANSCRIPTION FACTORS; U.S. application 62/091,456, 12 Dec. 14, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, RNA-TARGETING SYSTEM; U.S. application 62/096,656, 24 Dec. 14, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTI-FUNCTIONAL-CRISPR COMPLEXES AND/OR OPTIMIZED ENZYME LINKED FUNCTIONAL-CRISPR COMPLEXES; U.S. application 62/087,475, 4 Dec. 14, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14, MULTI-FUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

Zetsche et al., "Cpf1 Is a Single RNA-Guided Endonuclease of a Class 2 CRISPR-Cas System," Cell 163, 1-13 (Oct. 22, 2015)

Shmakov et al., "Discovery and Functional Characterization of Diverse Class 2 CRISPR-Cas Systems," Molecular Cell 60, 1-13 (Available online Oct. 22, 2015)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Cas to a target genomic locus, are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10 30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas system, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e. an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also, the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al. (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 1); the NLS from nucleoplasmin (e.g. the nucleoplasmin bipartite NLS with the sequence KRPAATKKAGQAKKKK) (SEQ ID NO: 2); the c-myc NLS having the amino acid sequence PAAKRVKLD (SEQ ID NO: 3) or RQRRNELKRSP (SEQ ID NO: 4); the hRNPA1 M9 NLS having the sequence NQSSNFGPMKGGNFGGRSSGPYGGGGQYFAK-PRNQGGY (SEQ ID NO: 5); the sequence RMRIZFKNKGKDTAELRRRRVEVSVELRKAKKD-EQILKRRNV (SEQ ID NO: 6) of the IBB domain from importin-alpha; the sequences VSRKRPRP (SEQ ID NO: 7) and PPKKARED (SEQ ID NO: 8) of the myoma T protein; the sequence POPKKKPL (SEQ ID NO: 9) of human p53; the sequence SALIKKKKKMAP (SEQ ID NO: 10) of mouse c-abl IV; the sequences DRLRR (SEQ ID NO: 11) and PKQKKRK (SEQ ID NO: 12) of the influenza virus NS1; the sequence RKLKKKIKKL (SEQ ID NO: 13) of the Hepatitis virus delta antigen; the sequence REKKKFLKRR (SEQ ID NO: 14) of the mouse Mx1 protein; the sequence KRKGDEVDGVDEVAKKKSKK (SEQ ID NO: 15) of the human poly(ADP-ribose) polymerase; and the sequence RKCLQAGMNLEARKTKK (SEQ ID NO: 16) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

Zinc Finger and TALE

One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In advantageous embodiments of the invention, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is X1-11-(X12X13)-X14-33 or 34 or 35, where the subscript indicates the amino acid position and X represents any amino acid. X12X13 indicate the RVDs. In some polypeptide monomers, the variable amino acid at position 13 is missing or absent and in such monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)-X14-33 or 34 or 35)z, where in an advantageous embodiment, z is at least 5 to 40. In a further advantageous embodiment, z is at least 10 to 26.

The TALE monomers have a nucleotide binding affinity that is determined by the identity of the amino acids in its RVD. For example, polypeptide monomers with an RVD of NI preferentially bind to adenine (A), monomers with an RVD of NG preferentially bind to thymine (T), monomers with an RVD of HD preferentially bind to cytosine (C) and monomers with an RVD of NN preferentially bind to both adenine (A) and guanine (G). In yet another embodiment of the invention, monomers with an RVD of IG preferentially bind to T. Thus, the number and order of the polypeptide monomer repeats in the nucleic acid binding domain of a TALE determines its nucleic acid target specificity. In still further embodiments of the invention, monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

The polypeptides used in methods of the invention are isolated, non-naturally occurring, recombinant or engineered nucleic acid-binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In a preferred embodiment of the invention, polypeptide monomers having RVDs RN, NN, NK, SN, NH, KN, HN, NQ, HH, RG, KH, RH and SS preferentially bind to guanine. In a much more advantageous embodiment of the invention, polypeptide monomers having RVDs RN, NK, NQ, HH, KH, RH, SS and SN preferentially bind to guanine and thereby allow the generation of TALE polypeptides with high binding specificity for guanine containing target nucleic acid sequences. In an even more advantageous embodiment of the invention, polypeptide monomers having RVDs HH, KH, NH, NK, NQ, RH, RN and SS preferentially bind to guanine and thereby allow the generation of TALE polypeptides with high binding specificity for guanine containing target nucleic acid sequences. In a further advantageous embodiment, the RVDs that have high binding specificity for guanine are RN, NH RH and KH. Furthermore, polypeptide monomers having an RVD of NV preferentially bind to adenine and guanine. In more preferred embodiments of the invention, monomers having RVDs of H*, HA, KA, N*, NA, NC, NS, RA, and S* bind to adenine, guanine, cytosine and thymine with comparable affinity.

Figure 8:
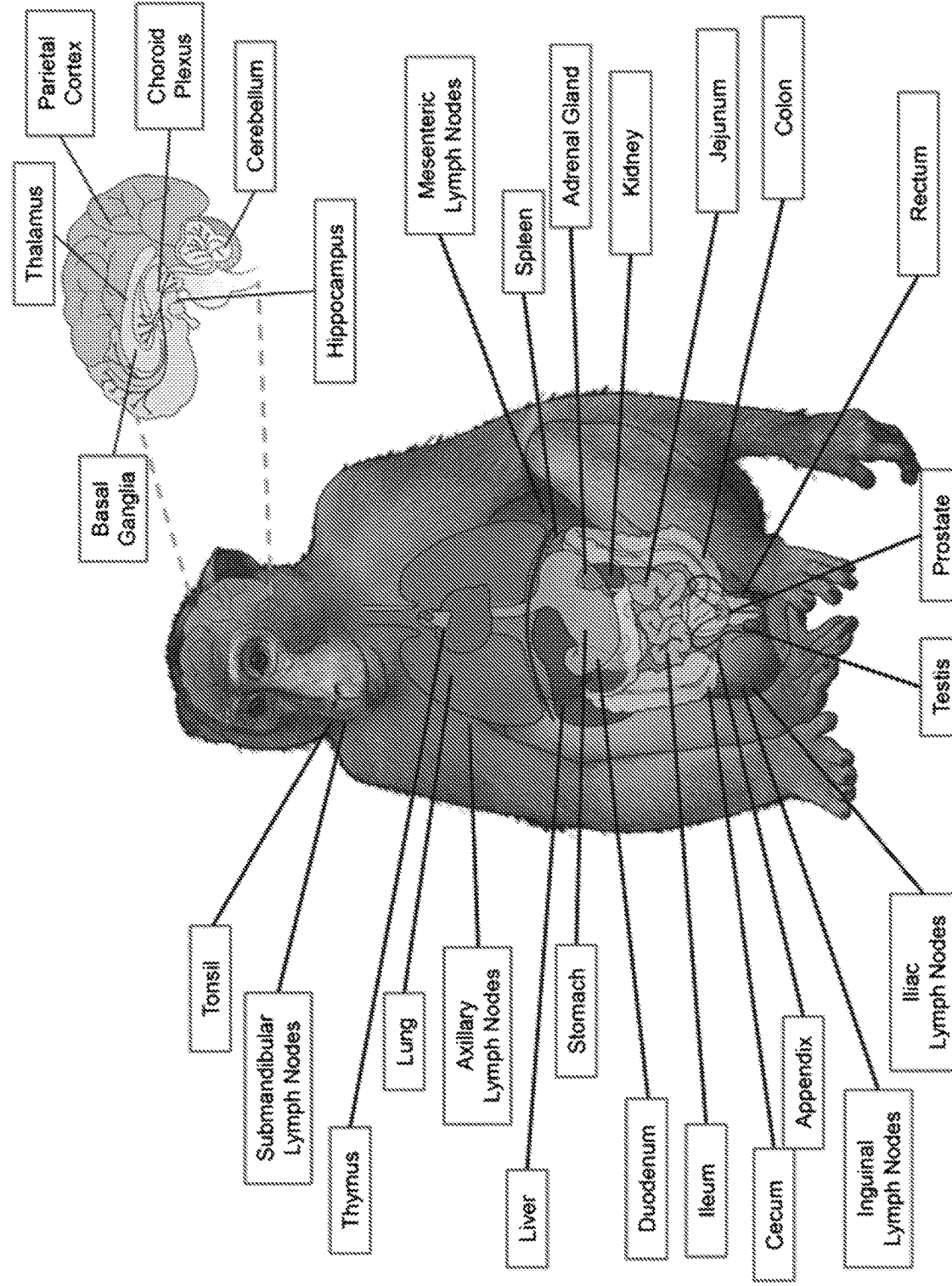
FIG. 8— Non-human primate model showing examples of cells and tissues useful for elaborating gene signatures associated with diseases and disorders.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full length TALE monomer and this half repeat may be referred to as a half-monomer (FIG. 8). Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 17)
M D P I R S R T P S P A R E L L S G P Q P D G V
Q P T A D R G V S P P A G G P L D G L P A R R T
M S R T R L P S P P A P S P A F S A D S F S D L
L R Q F D P S L F N T S L F D S L P P F G A H H
T E A A T G E W D E V Q S G L R A A D A P P P T
M R V A V T A A R P P R A K P A P R R R A A Q P
S D A S P A A Q V D L R T L G Y S Q Q Q Q E K I
K P K V R S T V A Q H H E A L V G H G F T H A H
I V A L S Q H P A A L G T V A V K Y Q D M I A A
L P E A T H E A I V G V G K Q W S G A R A L E A
L L T V A G E L R G P P L Q L D T G Q L L K I A
K R G G V T A V E A V H A W R N A L T G A P L N

An exemplary amino acid sequence of a C-terminal camping region is:

(SEQ ID NO: 18)
R P A L E S I V A Q L S R P D P A L A A L T N D
H L V A L A C L G G R P A L D A V K K G L P H A
P A L I K R T N R R I P E R T S H R V A D H A Q
V V R V L G F F Q C H S H P A Q A F D D A M T Q
F G M S R H G L L Q L F R R V G V T E L E A R S
G T L P P A S Q R W D R I L Q A S G M K R A K P
S P T S T Q T P D Q A S L H A F A D S L E R D L
D A P S P M H E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., Nature Biotechnology 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full length capping region, while fragments that include the C-terminal 20 amino acids retain greater than 50% of the efficacy of the full length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies may be generated by any of a number of computer programs known in the art, which include but are not limited to BLAST or FASTA. Suitable computer program for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In advantageous embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Krüppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination the activities described herein.

Methods of Diagnosing

Also provided within the scope of the invention are methods of diagnosing viral or latent viral infections. Such infections include, but are not necessarily limited to, Hepatitis B, Hepatitis C, latent HIV or ART-resistant HIV infection in a cell or tissue in a subject. Such methods may comprise detecting a gene expression profile in one or more cells or tissues associated with latent HIV or ART-resistant HIV infection.

Gene Expression Profiles

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

In certain embodiments, markers, including any peptides, polypeptides, proteins, or nucleic acids, may originate from non-human primates, i.e., their primary sequence may be the same as a corresponding primary sequence of or present in a naturally occurring non-human primate markers. Hence, the qualifier "non-human primate" in this connection relates to the primary sequence of the respective markers, rather than to their origin or source. For example, such markers may be present in or isolated from samples of non-human primate subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endonucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example ≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example ≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as central nerve system cells, stem cells, and immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

The present invention is also directed to signatures and uses thereof. As used herein a "signature" may encompass any gene or genes, protein or proteins, or epigenetic element(s) whose expression profile or whose occurrence is associated with a specific cell type, subtype, or cell state of a specific cell type or subtype within a population of cells. For ease of discussion, when discussing gene expression, any gene or genes, protein or proteins, or epigenetic element(s) may be substituted. Reference to a gene name throughout the specification encompasses the human gene, non-human primate gene, mouse gene and all other orthologues as known in the art in other organisms. As used herein, the terms "signature", "expression profile", or "expression program" may be used interchangeably. It is to be understood that also when referring to proteins (e.g. differentially expressed proteins), such may fall within the definition of "gene" signature. Levels of expression or activity or prevalence may be compared between different cells in order to characterize or identify for instance signatures specific for cell (sub)populations. Increased or decreased expression or activity of signature genes may be compared between different cells in order to characterize or identify for instance specific cell (sub)populations. The detection of a signature in single cells may be used to identify and quantitate for instance specific cell (sub)populations. A signature may include a gene or genes, protein or proteins, or epigenetic element(s) whose expression or occurrence is specific to a cell (sub)population, such that expression or occurrence is exclusive to the cell (sub) population. A gene signature as used herein, may thus refer to any set of up- and down-regulated genes that are representative of a cell type or subtype. A gene signature as used herein, may also refer to any set of up- and down-regulated genes between different cells or cell (sub)populations derived from a gene-expression profile. For example, a gene signature may comprise a list of genes differentially expressed in a distinction of interest.

The signature as defined herein (being it a gene signature, protein signature or other genetic or epigenetic signature) can be used to indicate the presence of a cell type, a subtype of the cell type, the state of the microenvironment of a population of cells, a particular cell type population or subpopulation, and/or the overall status of the entire cell (sub)population. Furthermore, the signature may be indicative of cells within a population of cells in vivo. The signature may also be used to suggest for instance particular therapies, or to follow up treatment, or to suggest ways to modulate immune systems. The signatures of the present invention may be discovered by analysis of expression profiles of single-cells within a population of cells from isolated samples (e.g. tumor samples), thus allowing the discovery of novel cell subtypes or cell states that were previously invisible or unrecognized. The presence of subtypes or cell states may be determined by subtype specific or cell state specific signatures. The presence of these specific cell (sub)types or cell states may be determined by applying the signature genes to bulk sequencing data in a sample. Not being bound by a theory the signatures of the present invention may be microenvironment specific, such as their expression in a particular spatio-temporal context. Not being bound by a theory, signatures as discussed herein are specific to a particular pathological context. Not being bound by a theory, a combination of cell subtypes having a particular signature may indicate an outcome. Not being bound by a theory, the signatures can be used to deconvolute the network of cells present in a particular pathological condition. Not being bound by a theory, the signatures can be used to indicate cell-cell interaction in a particular pathological or physiological condition. Not being bound by a theory, the signatures may be indicative of regulatory pathways in immune regulations. Not being bound by a theory, the presence of specific cells and cell subtypes are indicative of a particular response to treatment, such as including increased or decreased susceptibility to treatment. The signature may indicate the presence of one particular cell type.

The signature according to certain embodiments of the present invention may comprise or consist of one or more genes, proteins and/or epigenetic elements, such as for instance 1, 2, 3, 4, 5, 6, 7, 8, 9, 10 or more. In certain embodiments, the signature may comprise or consist of two or more genes, proteins and/or epigenetic elements, such as for instance 2, 3, 4, 5, 6, 7, 8, 9, 10 or more. In certain embodiments, the signature may comprise or consist of three or more genes, proteins and/or epigenetic elements, such as for instance 3, 4, 5, 6, 7, 8, 9, 10 or more. In certain embodiments, the signature may comprise or consist of four or more genes, proteins and/or epigenetic elements, such as for instance 4, 5, 6, 7, 8, 9, 10 or more. In certain embodiments, the signature may comprise or consist of five or more genes, proteins and/or epigenetic elements, such as for instance 5, 6, 7, 8, 9, 10 or more. In certain embodiments, the signature may comprise or consist of six or more genes, proteins and/or epigenetic elements, such as for instance 6, 7, 8, 9, 10 or more. In certain embodiments, the signature may comprise or consist of seven or more genes, proteins and/or epigenetic elements, such as for instance 7, 8, 9, 10 or more. In certain embodiments, the signature may comprise or consist of eight or more genes, proteins and/or epigenetic elements, such as for instance 8, 9, 10 or more. In certain embodiments, the signature may comprise or consist of nine or more genes, proteins and/or epigenetic elements, such as for instance 9, 10 or more. In certain embodiments, the signature may comprise or consist of ten or more genes, proteins and/or epigenetic elements, such as for instance 10, 11, 12, 13, 14, 15, or more. It is to be understood that a signature according to the invention may for instance also include genes or proteins as well as epigenetic elements combined.

In certain embodiments, a signature is characterized as being specific for a particular cell or cell (sub)population state if it is upregulated or only present, detected or detectable in that particular cell or cell (sub)population state (e.g., disease or healthy), or alternatively is downregulated or only absent, or undetectable in that particular cell or cell (sub) population state. In this context, a signature consists of one or more differentially expressed genes/proteins or differential epigenetic elements when comparing different cells or cell (sub)populations, including comparing different gut cell or gut cell (sub)populations, as well as comparing gut cell or gut cell (sub)populations with healthy or disease (sub) populations. It is to be understood that "differentially expressed" genes/proteins include genes/proteins which are up- or down-regulated as well as genes/proteins which are turned on or off. When referring to up- or down-regulation, in certain embodiments, such up- or down-regulation is preferably at least two-fold, such as two-fold, three-fold, four-fold, five-fold, or more, such as for instance at least ten-fold, at least 20-fold, at least 30-fold, at least 40-fold, at least 50-fold, or more. Alternatively, or in addition, differential expression may be determined based on common statistical tests, as is known in the art.

As discussed herein, differentially expressed genes/proteins, or differential epigenetic elements may be differentially expressed on a single cell level, or may be differentially expressed on a cell population level. Preferably, the differentially expressed genes/proteins or epigenetic elements as discussed herein, such as constituting the gene signatures as discussed herein, when as to the cell population or subpopulation level, refer to genes that are differentially expressed in all or substantially all cells of the population or subpopulation (such as at least 80%, preferably at least 90%, such as at least 95% of the individual cells). This allows one to define a particular subpopulation of immune cells. As referred to herein, a "subpopulation" of cells preferably refers to a particular subset of cells of a particular cell type which can be distinguished or are uniquely identifiable and set apart from other cells of this cell type. The cell subpopulation may be phenotypically characterized, and is preferably characterized by the signature as discussed herein. A cell (sub)population as referred to herein may constitute of a (sub)population of cells of a particular cell type characterized by a specific cell state.

When referring to induction, or alternatively suppression of a particular signature, preferably it is meant: induction or alternatively suppression (or upregulation or downregulation) of at least one gene/protein and/or epigenetic element of the signature, such as for instance at least two, at least three, at least four, at least five, at least six, or all genes/proteins and/or epigenetic elements of the signature.

In certain embodiments, signature genes and biomarkers related to HIV-infection may be identified by comparing single cell expression profiles obtained from HIV-infected individuals with healthy individuals.

In certain embodiments, signature genes and biomarkers related to HIV-infection may be identified by comparing single cell expression profiles obtained from healthy individuals with cART treated HIV infected individuals. In another embodiment, signature genes and biomarkers related to HIV-infection may be identified by comparing single cell expression profiles obtained from healthy individuals and single cell expression profile from cells obtained from cART treated HIV infected individuals and further reactivated.

Various aspects and embodiments of the invention may involve analyzing gene signatures, protein signature, and/or other genetic or epigenetic signature based on single cell analyses (e.g. single cell RNA sequencing) or alternatively based on cell population analyses, as is defined herein elsewhere.

In certain example embodiments, the signature genes may be used to distinguish cell types, characterize individual cell phenotypes, cell signatures, cell expression profiles or expression programs, and identify cell-cell interaction in the network of cells within a sampled population present in HIV infected individual or cells based on comparing them to data from bulk analysis of HIV infected sample. In certain example embodiments, the presence of specific immune cells and immune cell subtypes may be indicative of HIV infection, latent HIV infection, and/or resistance to treatment. In certain example embodiments, induction or suppression of specific signature genes may be indicative of HIV infection, latent HIV infection, and/or resistance to treatment. In one example embodiment, detection of one or more signature genes may indicate the presence of a particular cell type or cell types. In certain example embodiments, the presence of immune cell types within HIV infected cell population may indicate that the cells will be sensitive to a treatment.

Detection of Cell Sub-Populations

In one embodiment, the method comprises detecting or quantifying HIV infected cells in a biological sample. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In one embodiment, the method comprises detecting or quantifying a sub-population of cells harboring persistent or latent HIV-infection in a biological sample. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

In a preferred embodiment, the method comprises detecting or quantifying pathogen in an easily obtainable sample such as blood or body fluid as a proxy or surrogate indicative of infection states of the tested sub population of cells, a different sub population of cells, a different tissue, or the whole organism.

The terms "sample" or "biological sample" as used throughout this specification include any biological specimen obtained from a subject. Particularly useful samples are those known to comprise, or expected or predicted to comprise gut cells as taught herein. Preferably, a sample may be readily obtainable by minimally invasive methods, such as blood collection or tissue biopsy, allowing the removal/isolation/provision of the sample from the subject (e.g., colonoscopy).

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1×SD or ±2×SD or ±3×SD, or ±1×SE or ±2×SE or ±3×SE). Deviation may also refer to a value falling outside of a reference range defined by values in a given population (for example, outside of a range which comprises ≥40%, ≥50%, ≥60%, ≥70%, ≥75% or ≥80% or ≥85% or ≥90% or ≥95% or even ≥100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR−), Youden index, or similar.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

Methods of Detection and Isolation of Cell Types Using Biomarkers

In certain embodiments, the cell types disclosed herein may be detected, quantified or isolated using a technique selected from the group consisting of flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH) and combinations thereof. The technique may employ one or more agents capable of specifically binding to one or more gene products expressed or not expressed by the gut cells, preferably on the cell surface of the gut cells. The one or more agents may be one or more antibodies. Other methods including absorbance assays and colorimetric assays are known in the art and may be used herein.

Depending on factors that can be evaluated and decided on by a skilled person, such as, inter alia, the type of a marker (e.g., peptide, polypeptide, protein, or nucleic acid), the type of the tested object (e.g., a cell, cell population, tissue, organ, or organism, e.g., the type of biological sample of a subject, e.g., whole blood, plasma, serum, tissue biopsy), the expected abundance of the marker in the tested object, the type, robustness, sensitivity and/or specificity of the detection method used to detect the marker, etc., the marker may be measured directly in the tested object, or the tested object may be subjected to one or more processing steps aimed at achieving an adequate measurement of the marker.

In other example embodiments, detection of a marker may include immunological assay methods, wherein the ability of an assay to separate, detect and/or quantify a marker (such as, preferably, peptide, polypeptide, or protein) is conferred by specific binding between a separable, detectable and/or quantifiable immunological binding agent (antibody) and the marker. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (MA), Western blot, etc.

In certain example embodiments, detection of a marker or signature may include biochemical assay methods, including inter alia assays of enzymatic activity, membrane channel activity, substance-binding activity, gene regulatory activity, or cell signaling activity of a marker, e.g., peptide, polypeptide, protein, or nucleic acid.

In other example embodiments, detection of a marker may include mass spectrometry analysis methods. Generally, any mass spectrometric (MS) techniques that are capable of obtaining precise information on the mass of peptides, and preferably also on fragmentation and/or (partial) amino acid sequence of selected peptides (e.g., in tandem mass spectrometry, MS/MS; or in post source decay, TOF MS), may be useful herein for separation, detection and/or quantification of markers (such as, preferably, peptides, polypeptides, or proteins). Suitable peptide MS and MS/MS techniques and systems are well-known per se (see, e.g., Methods in Molecular Biology, vol. 146: "Mass Spectrometry of Proteins and Peptides", by Chapman, ed., Humana Press 2000, ISBN 089603609x; Biemann 1990. Methods Enzymol 193: 455-79; or Methods in Enzymology, vol. 402: "Biological Mass Spectrometry", by Burlingame, ed., Academic Press 2005, ISBN 9780121828073) and may be used herein. MS arrangements, instruments and systems suitable for biomarker peptide analysis may include, without limitation, matrix-assisted laser desorption/ionisation time-of-flight (MALDI-TOF) MS; MALDI-TOF post-source-decay (PSD); MALDI-TOF/TOF; surface-enhanced laser desorption/ionization time-of-flight mass spectrometry (SELDI-TOF) MS; electrospray ionization mass spectrometry (ESI-MS); ESI-MS/MS; ESI-MS/(MS)n (n is an integer greater than zero); ESI 3D or linear (2D) ion trap MS; ESI triple quadrupole MS; ESI quadrupole orthogonal TOF (Q-TOF); ESI Fourier transform MS systems; desorption/ionization on silicon (DIOS); secondary ion mass spectrometry (SIMS); atmospheric pressure chemical ionization mass spectrometry (APCI-MS); APCI-MS/MS; APCI-(MS)n; atmospheric pressure photoionization mass spectrometry (APPI-MS); APPI-MS/MS; and APPI-(MS)n. Peptide ion fragmentation in tandem MS (MS/MS) arrangements may be achieved using manners established in the art, such as, e.g., collision induced dissociation (CID). Detection and quantification of markers by mass spectrometry may involve multiple reaction monitoring (MRM), such as described among others by Kuhn et al. 2004 (Proteomics 4: 1175-86). MS peptide analysis methods may be advantageously combined with upstream peptide or protein separation or fractionation methods, such as for example with the chromatographic and other methods.

In other example embodiments, detection of a marker may include chromatography methods. In a one example embodiment, chromatography refers to a process in which a mixture of substances (analytes) carried by a moving stream of liquid or gas ("mobile phase") is separated into components as a result of differential distribution of the analytes, as they flow around or over a stationary liquid or solid phase ("stationary phase"), between said mobile phase and said stationary phase. The stationary phase may be usually a finely divided solid, a sheet of filter material, or a thin film of a liquid on the surface of a solid, or the like. Chromatography may be columnar. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction chromatography (HILIC), hydrophobic interaction chromatography (HIC), size exclusion chromatography (SEC) including gel filtration chromatography or gel permeation chromatography, chromatofocusing, affinity chromatography such as immunoaffinity, immobilised metal affinity chromatography, and the like.

In certain embodiments, further techniques for separating, detecting and/or quantifying markers may be used in conjunction with any of the above described detection methods. Such methods include, without limitation, chemical extraction partitioning, isoelectric focusing (IEF) including capillary isoelectric focusing (CIEF), capillary isotachophoresis (CITP), capillary electrochromatography (CEC), and the like, one-dimensional polyacrylamide gel electrophoresis (PAGE), two-dimensional polyacrylamide gel electrophoresis (2D-PAGE), capillary gel electrophoresis (CGE), capillary zone electrophoresis (CZE), micellar electrokinetic chromatography (MEKC), free flow electrophoresis (FFE), etc.

In certain examples, such methods may include separating, detecting and/or quantifying markers at the nucleic acid level, more particularly RNA level, e.g., at the level of hnRNA, pre-mRNA, mRNA, or cDNA. Standard quantitative RNA or cDNA measurement tools known in the art may be used. Non-limiting examples include hybridization-based analysis, microarray expression analysis, digital gene expression profiling (DGE), RNA-in-situ hybridization (RISH), Northern-blot analysis and the like; PCR, RT-PCR, RT-qPCR, end-point PCR, digital PCR or the like; supported oligonucleotide detection, pyrosequencing, polony cyclic sequencing by synthesis, simultaneous bi-directional sequencing, single-molecule sequencing, single molecule real time sequencing, true single molecule sequencing, hybridization-assisted nanopore sequencing, sequencing by synthesis, single-cell RNA sequencing (scRNA-seq), or the like. By means of an example, methods to profile the RNA content of large numbers of individual cells have been recently developed. The cell of origin is determined by a cellular barcode. In certain embodiments, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. In these regards, reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; and Rosenberg et al., 2017, "Scaling single cell transcriptomics through split pool barcoding" bioRxiv preprint first posted online Feb. 2, 2017, doi: dx.doi.org/10.1101/105163, all the contents and disclosure of each of which are herein incorporated by reference in their entirety.

In certain embodiments, the invention involves single nucleus RNA sequencing. In this regard, reference is made to Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety.

The terms "isolating" or "purifying" as used throughout this specification with reference to a particular component of a composition or mixture (e.g., the tested object such as the biological sample) encompass processes or techniques whereby such component is separated from one or more or (substantially) all other components of the composition or mixture (e.g., the tested object such as the biological sample). The terms do not require absolute purity. Instead, isolating or purifying the component will produce a discrete environment in which the abundance of the component relative to one or more or all other components is greater than in the starting composition or mixture (e.g., the tested object such as the biological sample). A discrete environment may denote a single medium, such as for example a single solution, dispersion, gel, precipitate, etc. Isolating or purifying the specified cells from the tested object such as the biological sample may increase the abundance of the specified cells relative to all other cells comprised in the tested object such as the biological sample, or relative to other cells of a select subset of the cells comprised in the tested object such as the biological sample, e.g., relative to other white blood cells, peripheral blood mononuclear cells, immune cells, antigen presenting cells, or dendritic cells comprised in the tested object such as the biological sample. By means of example, isolating or purifying the specified cells from the tested object such as the biological sample may yield a cell population, in which the specified cells constitute at least 40% (by number) of all cells of said cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of said cell population.

The method may allow a skilled person to detect or conclude the presence or absence of the specified cells in a tested object (e.g., in a cell population, tissue, organ, organism, or in a biological sample of a subject). The method may also allow a skilled person to quantify the specified cells in a tested object (e.g., in a cell population, tissue, organ, organism, or in a biological sample of a subject). The quantity of the specified cells in the tested object such as the biological sample may be suitably expressed for example as the number (count) of the specified immune cells per standard unit of volume (e.g., ml, µl or nl) or weight (e.g., g or mg or ng) of the tested object such as the biological sample. The quantity of the specified cells in the tested object such as the biological sample may also be suitably expressed as a percentage or fraction (by number) of all cells comprised in the tested object such as the biological sample, or as a percentage or fraction (by number) of a select subset of the cells comprised in the tested object such as the biological sample, e.g., as a percentage or fraction (by number) of white blood cells, peripheral blood mononuclear cells, immune cells, antigen presenting cells, or dendritic cells comprised in the tested object such as the biological sample. The quantity of the specified cells in the tested object such as the biological sample may also be suitably represented by an absolute or relative quantity of a suitable surrogate analyte, such as a peptide, polypeptide, protein, or nucleic acid expressed or comprised by the specified cells.

Where a marker is detected in or on a cell, the cell may be conventionally denoted as positive ($^+$) or negative ($-$) for the marker. Semi-quantitative denotations of marker expression in cells are also commonplace in the art, such as particularly in flow cytometry quantifications, for example, "dim" vs. "bright", or "low" vs. "medium"/"intermediate" vs. "high", or "$-$" vs. "$^+$" vs. "$^{++}$", commonly controlled in flow cytometry quantifications by setting of the gates. Where a marker is quantified in or on a cell, absolute quantity of the marker may also be expressed for example as the number of molecules of the marker comprised by the cell.

Where a marker is detected and/or quantified on a single cell level in a cell population, the quantity of the marker may also be expressed as a percentage or fraction (by number) of cells comprised in said population that are positive for said marker, or as percentages or fractions (by number) of cells comprised in said population that are "dim" or "bright", or that are "low" or "medium"/"intermediate" or "high", or that are "−" or "+" or "++". By means of an example, a sizeable proportion of the tested cells of the cell population may be positive for the marker, e.g., at least about 20%, at least about 40%, at least about 50%, at least about 60%, at least about 70%, at least about 80%, at least about 90%, at least about 95%, or up to 100%.

Use of Specific Binding Agents

In certain embodiments, the aforementioned methods and techniques may employ agent(s) capable of specifically binding to one or more gene products, e.g., peptides, polypeptides, proteins, or nucleic acids, expressed or not expressed by the immune cells as taught herein. In certain preferred embodiments, such one or more gene products, e.g., peptides, polypeptides, or proteins, may be expressed on the cell surface of the immune cells (i.e., cell surface markers, e.g., transmembrane peptides, polypeptides or proteins, or secreted peptides, polypeptides or proteins which remain associated with the cell surface). Hence, further disclosed are binding agents capable of specifically binding to markers, such as genes or gene products, e.g., peptides, polypeptides, proteins, or nucleic acids as taught herein. Binding agents as intended throughout this specification may include inter alia antibodies, aptamers, spiegelmers (L-aptamers), photoaptamers, protein, peptides, peptidomimetics, nucleic acids such as oligonucleotides (e.g., hybridization probes or amplification or sequencing primers and primer pairs), small molecules, or combinations thereof.

The term "aptamer" refers to single-stranded or double-stranded oligo-DNA, oligo-RNA or oligo-DNA/RNA or any analogue thereof that specifically binds to a target molecule such as a peptide. Advantageously, aptamers display fairly high specificity and affinity (e.g., KA in the order $1 \times 10^9$ M-1) for their targets. Aptamer production is described inter alia in U.S. Pat. No. 5,270,163; Ellington & Szostak 1990 (Nature 346: 818-822); Tuerk & Gold 1990 (Science 249: 505-510); or "The Aptamer Handbook: Functional Oligonucleotides and Their Applications", by Klussmann, ed., Wiley-VCH 2006, ISBN 3527310592, incorporated by reference herein. The term "photoaptamer" refers to an aptamer that contains one or more photoreactive functional groups that can covalently bind to or crosslink with a target molecule. The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides. The term "peptidomimetic" refers to a non-peptide agent that is a topological analogue of a corresponding peptide. Methods of rationally designing peptidomimetics of peptides are known in the art. For example, the rational design of three peptidomimetics based on the sulphated 8-mer peptide CCK26-33, and of two peptidomimetics based on the 11-mer peptide Substance P, and related peptidomimetic design principles, are described in Horwell 1995 (Trends Biotechnol 13: 132-134).

Binding agents may be in various forms, e.g., lyophilised, free in solution, or immobilised on a solid phase. They may be, e.g., provided in a multi-well plate or as an array or microarray, or they may be packaged separately, individually, or in combination.

The term "specifically bind" as used throughout this specification means that an agent (denoted herein also as "specific-binding agent") binds to one or more desired molecules or analytes (e.g., peptides, polypeptides, proteins, or nucleic acids) substantially to the exclusion of other molecules which are random or unrelated, and optionally substantially to the exclusion of other molecules that are structurally related. The term "specifically bind" does not necessarily require that an agent binds exclusively to its intended target(s). For example, an agent may be said to specifically bind to target(s) of interest if its affinity for such intended target(s) under the conditions of binding is at least about 2-fold greater, preferably at least about 5-fold greater, more preferably at least about 10-fold greater, yet more preferably at least about 25-fold greater, still more preferably at least about 50-fold greater, and even more preferably at least about 100-fold, or at least about 1000-fold, or at least about 104-fold, or at least about 105-fold, or at least about 106-fold or more greater, than its affinity for a non-target molecule, such as for a suitable control molecule (e.g., bovine serum albumin, casein).

Preferably, the specific binding agent may bind to its intended target(s) with affinity constant (KA) of such binding KA≥$1 \times 10^6$ M-1, more preferably KA≥$1 \times 10^7$ M-1, yet more preferably KA≥$1 \times 10^8$ M-1, even more preferably KA≥$1 \times 10^9$ M-1, and still more preferably KA≥$1 \times 10^{10}$ M-1 or KA≥$1 \times 10^{11}$ M-1 or KA≥$1 \times 10^{12}$ M-1, wherein KA= [SBA_T]/[SBA][T], SBA denotes the specific-binding agent, T denotes the intended target. Determination of KA can be carried out by methods known in the art, such as for example, using equilibrium dialysis and Scatchard plot analysis.

In certain embodiments, the one or more binding agents may be one or more antibodies. As used herein, the term "antibody" is used in its broadest sense and generally refers to any immunologic binding agent. The term specifically encompasses intact monoclonal antibodies, polyclonal antibodies, multivalent (e.g., 2-, 3- or more-valent) and/or multi-specific antibodies (e.g., bi- or more-specific antibodies) formed from at least two intact antibodies, and antibody fragments insofar they exhibit the desired biological activity (particularly, ability to specifically bind an antigen of interest, i.e., antigen-binding fragments), as well as multivalent and/or multi-specific composites of such fragments. The term "antibody" is not only inclusive of antibodies generated by methods comprising immunization, but also includes any polypeptide, e.g., a recombinantly expressed polypeptide, which is made to encompass at least one complementarity-determining region (CDR) capable of specifically binding to an epitope on an antigen of interest. Hence, the term applies to such molecules regardless whether they are produced in vitro or in vivo. Antibodies also encompasses chimeric, humanized and fully humanized antibodies.

An antibody may be any of IgA, IgD, IgE, IgG and IgM classes, and preferably IgG class antibody. An antibody may be a polyclonal antibody, e.g., an antiserum or immunoglobulins purified there from (e.g., affinity-purified). An antibody may be a monoclonal antibody or a mixture of monoclonal antibodies. Monoclonal antibodies can target a particular antigen or a particular epitope within an antigen with greater selectivity and reproducibility. By means of example and not limitation, monoclonal antibodies may be made by the hybridoma method first described by Kohler et al. 1975 (Nature 256: 495), or may be made by recombinant DNA methods (e.g., as in U.S. Pat. No. 4,816,567). Monoclonal antibodies may also be isolated from phage antibody libraries using techniques as described by Clackson et al. 1991 (Nature 352: 624-628) and Marks et al. 1991 (J Mol Biol 222: 581-597), for example.

Antibody binding agents may be antibody fragments. "Antibody fragments" comprise a portion of an intact antibody, comprising the antigen-binding or variable region thereof. Examples of antibody fragments include Fab, Fab', F(ab')2, Fv and scFv fragments, single domain (sd) Fv, such as VH domains, VL domains and VHH domains; diabodies; linear antibodies; single-chain antibody molecules, in particular heavy-chain antibodies; and multivalent and/or multispecific antibodies formed from antibody fragment(s), e.g., diabodies, tribodies, and multibodies. The above designations Fab, Fab', F(ab')2, Fv, scFv etc. are intended to have their art-established meaning.

The term antibody includes antibodies originating from or comprising one or more portions derived from any animal species, preferably vertebrate species, including, e.g., birds and mammals. Without limitation, the antibodies may be chicken, turkey, goose, duck, guinea fowl, quail or pheasant. Also without limitation, the antibodies may be human, murine (e.g., mouse, rat, etc.), donkey, rabbit, goat, sheep, guinea pig, camel (e.g., *Camelus bactrianus* and *Camelus dromedarius*), llama (e.g., *Lama pacos, Lama glama* or *Lama vicugna*) or horse.

A skilled person will understand that an antibody can include one or more amino acid deletions, additions and/or substitutions (e.g., conservative substitutions), insofar such alterations preserve its binding of the respective antigen. An antibody may also include one or more native or artificial modifications of its constituent amino acid residues (e.g., glycosylation, etc.).

Methods of producing polyclonal and monoclonal antibodies as well as fragments thereof are well known in the art, as are methods to produce recombinant antibodies or fragments thereof (see for example, Harlow and Lane, "Antibodies: A Laboratory Manual", Cold Spring Harbour Laboratory, New York, 1988; Harlow and Lane, "Using Antibodies: A Laboratory Manual", Cold Spring Harbour Laboratory, New York, 1999, ISBN 0879695447; "Monoclonal Antibodies: A Manual of Techniques", by Zola, ed., CRC Press 1987, ISBN 0849364760; "Monoclonal Antibodies: A Practical Approach", by Dean & Shepherd, eds., Oxford University Press 2000, ISBN 0199637229; Methods in Molecular Biology, vol. 248: "Antibody Engineering: Methods and Protocols", Lo, ed., Humana Press 2004, ISBN 1588290921).

Nucleic acid binding agents, such as oligonucleotide binding agents, are typically at least partly antisense to a target nucleic acid of interest. The term "antisense" generally refers to an agent (e.g., an oligonucleotide) configured to specifically anneal with (hybridise to) a given sequence in a target nucleic acid, such as for example in a target DNA, hnRNA, pre-mRNA or mRNA, and typically comprises, consist essentially of or consist of a nucleic acid sequence that is complementary or substantially complementary to said target nucleic acid sequence. Antisense agents suitable for use herein, such as hybridisation probes or amplification or sequencing primers and primer pairs) may typically be capable of annealing with (hybridizing to) the respective target nucleic acid sequences at high stringency conditions, and capable of hybridising specifically to the target under physiological conditions. The terms "complementary" or "complementarity" as used throughout this specification with reference to nucleic acids, refer to the normal binding of single-stranded nucleic acids under permissive salt (ionic strength) and temperature conditions by base pairing, preferably Watson-Crick base pairing. By means of example, complementary Watson-Crick base pairing occurs between the bases A and T, A and U or G and C. For example, the sequence 5'-A-G-U-3' is complementary to sequence 5'-A-C-U-3'.

The reference to oligonucleotides may in particular but without limitation include hybridization probes and/or amplification primers and/or sequencing primers, etc., as commonly used in nucleic acid detection technologies.

Binding agents as discussed herein may suitably comprise a detectable label. The term "label" refers to any atom, molecule, moiety or biomolecule that may be used to provide a detectable and preferably quantifiable read-out or property, and that may be attached to or made part of an entity of interest, such as a binding agent. Labels may be suitably detectable by for example mass spectrometric, spectroscopic, optical, colorimetric, magnetic, photochemical, biochemical, immunochemical or chemical means. Labels include without limitation dyes; radiolabels such as 32P, 33P, 35S, 125I, 131I; electron-dense reagents; enzymes (e.g., horse-radish peroxidase or alkaline phosphatase as commonly used in immunoassays); binding moieties such as biotin-streptavidin; haptens such as digoxigenin; luminogenic, phosphorescent or fluorogenic moieties; mass tags; and fluorescent dyes alone or in combination with moieties that may suppress or shift emission spectra by fluorescence resonance energy transfer (FRET).

In some embodiments, binding agents may be provided with a tag that permits detection with another agent (e.g., with a probe binding partner). Such tags may be, for example, biotin, streptavidin, his-tag, myc tag, maltose, maltose binding protein or any other kind of tag known in the art that has a binding partner. Example of associations which may be utilised in the probe:binding partner arrangement may be any, and includes, for example biotin: streptavidin, his-tag:metal ion (e.g., Ni2+), maltose:maltose binding protein, etc.

The marker-binding agent conjugate may be associated with or attached to a detection agent to facilitate detection. Examples of detection agents include, but are not limited to, luminescent labels; colorimetric labels, such as dyes; fluorescent labels; or chemical labels, such as electroactive agents (e.g., ferrocyanide); enzymes; radioactive labels; or radiofrequency labels. The detection agent may be a particle. Examples of such particles include, but are not limited to, colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; colloidal lead selenide particles; colloidal cadmium selenide particles; colloidal metal phosphate particles; colloidal metal ferrite particles; any of the above-mentioned colloidal particles coated with organic or inorganic layers; protein or peptide molecules; liposomes; or organic polymer latex particles, such as polystyrene latex beads. Preferable particles may be colloidal gold particles.

In certain embodiments, the one or more binding agents are configured for use in a technique selected from the group consisting of flow cytometry, fluorescence activated cell sorting, mass cytometry, fluorescence microscopy, affinity separation, magnetic cell separation, microfluidic separation, and combinations thereof.

In some embodiments, provided herein are methods for diagnosing a latent HIV or ART-resistant HIV infection in a cell or tissue, the method comprising detecting whether one or more genes from Table 1 or Table 2 is overexpressed, or has a higher or increased level of expression compared to a cell that is HIV−.

In some embodiments, provided herein are methods for diagnosing a latent HIV or ART-resistant HIV infection in a cell or tissue, the method comprising detecting whether one or more genes from Table 3 is underexpressed, or has a lower or reduced level of expression compared to a cell that is HIV−.

Methods of Monitoring

Also provided within the scope of the invention are methods of monitoring treatment of a viral or latent viral infection. Such infections include, but are not necessarily limited to, Hepatitis B, Hepatitis C, HIV or ART-resistant HIV infection in a cell or tissue. Such methods may comprise detecting whether one or more genes from Table 1 or Table 2 is overexpressed, or has a higher or increased level of expression compared to a cell that is HIV−.

As described herein, the terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

In some embodiments, methods of monitoring are provided, comprising detecting whether one or more genes from Table 3 is underexpressed, or has a lower or reduced level of expression compared to a cell that is HIV⁻.

As described herein, the term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

Also provided within the scope of the invention are methods of monitoring HIV disease progression and/or treatment. Such methods may comprise detecting expression of one or more genes or gene products from Tables 1, 2 and 3 prior to administration of an anti-HIV therapy; administering a first round of an anti-HIV therapy; detecting expression of one or more genes or gene products from Tables 1, 2 and 3 after administration of the anti-HIV therapeutic; and administering an additional or alternative round or anti-HIV therapy if expression of one or more genes from Table 1 or 2 has increased or not decreased, or if expression of one or more genes in Table 3 has decreased relative to prior to administering the first anti-HIV therapy.

Anti-HIV therapy used within the scope of the invention includes, but is not necessarily limited to any anti-HIV therapy known in the art. Such therapies include entry or fusion inhibitors, nucleoside reverse transcriptase inhibitors (NRTI), non-nucleoside reverse transcriptase inhibitors (NNRTI), protease inhibitors (PI), or integrase inhibitors. Common entry inhibitors include, but are not necessarily limited to, maraviroc and enfuvirtide. Common NRTIs include, but are not necessarily limited to, zidovudine, abacavir, lamivudine, emtricitabine, and tenofovir. Common NNRTIs include, but are not necessarily limited to, nevirapine, efavirenz, etravirine, and rilpivirine. Common PIs include, but are not necessarily limited to, lopinavir, indinavir, nelfinavir, amprenavir, ritonavir, darunavir, atazanavir. Common integrase inhibitors include, but are not necessarily limited to, raltegravir, elvitegravir, and dolutegravir.

These therapies may be used in single doses, multiple doses, single drug, or combinations of drugs, in any combination. Fixed-dose combinations are multiple antiretroviral drugs combined into a single pill.

In some embodiments, the additional or alternative round of anti-HIV therapy may comprise the same drug or combination of drugs as the first round of anti-HIV therapy.

In alternative embodiments, the additional or alternative round of anti-HIV therapy may comprise a different drug or combination of drugs than the first round of anti-HIV therapy.

Methods of Treating

Provided herein are also methods of treating viral infections. Such viral infections may include, but are not necessarily limited to, HIV, by detecting one or more genes or gene signatures from Tables 1 or 2; determining whether the patient has a latent HIV or ART-resistant HIV infection based on the presence of one or more genes or gene signatures from Tables 1 or 2; and administering an anti-HIV therapeutic if one or more genes or gene signatures from Tables 1 or 2 are present.

Detection may be done by means of any of the methods know in the art or described herein. A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

Based on the detection of the presence of one or more genes or gene signatures from Tables 1 or 2, one may then determine or conclude whether the patient has a latent HIV or ART-resistant HIV infection, as described herein.

The patient may then be administered an anti-HIV therapeutic if one or more genes or gene signatures from Tables 1 or 2 are present.

It will be appreciated that administration of therapeutic entities in accordance with the invention will occur with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203 (1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

The agents disclosed herein (e.g., antibodies) may be used in a pharmaceutical composition when combined with a pharmaceutically acceptable carrier. Such compositions comprise a therapeutically-effective amount of the agent and a pharmaceutically acceptable carrier. Such a composition may also further comprise (in addition to an agent and a carrier) diluents, fillers, salts, buffers, stabilizers, solubilizers, and other materials well known in the art. Compositions comprising the agent can be administered in the form of salts provided the salts are pharmaceutically acceptable. Salts may be prepared using standard procedures known to those skilled in the art of synthetic organic chemistry.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methyl sulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycolylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, tri ethi odi de, lactate, pamoate, valerate, and the like which can be used as a dosage form for modifying the solubility or hydrolysis characteristics or can be used in sustained release or prodrug formulations. It will be understood that, as used herein, references to specific agents (e.g., neuromedin U receptor agonists or antagonists), also include the pharmaceutically acceptable salts thereof.

Methods of administering the pharmacological compositions, including agonists, antagonists, antibodies or fragments thereof, to an individual include, but are not limited to, intradermal, intrathecal, intramuscular, intraperitoneal, intravenous, subcutaneous, intranasal, epidural, by inhalation, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor or infected tissue), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition, and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. In general, the daily dose range of a drug lie within the range known in the art for a particular drug or biologic. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

Methods for administering antibodies for therapeutic use is well known to one skilled in the art. In certain embodiments, small particle aerosols of antibodies or fragments thereof may be administered (see e.g., Piazza et al., J. Infect. Dis., Vol. 166, pp. 1422-1424, 1992; and Brown, Aerosol Science and Technology, Vol. 24, pp. 45-56, 1996). In certain embodiments, antibodies are administered in metered-dose propellant driven aerosols. In certain embodiments, antibodies may be administered in liposomes, i.e., immunoliposomes (see, e.g., Maruyama et al., Biochim. Biophys. Acta, Vol. 1234, pp. 74-80, 1995). In certain embodiments, immunoconjugates, immunoliposomes or immunomicrospheres containing an agent of the present invention is administered by inhalation.

In certain embodiments, antibodies may be topically administered to mucosa, such as the oropharynx, nasal cavity, respiratory tract, gastrointestinal tract, eye such as the conjunctival mucosa, vagina, urogenital mucosa, or for dermal application. In certain embodiments, antibodies are administered to the nasal, bronchial or pulmonary mucosa. In order to obtain optimal delivery of the antibodies to the pulmonary cavity in particular, it may be advantageous to add a surfactant such as a phosphoglyceride, e.g. phosphatidylcholine, and/or a hydrophilic or hydrophobic complex of a positively or negatively charged excipient and a charged antibody of the opposite charge.

Other excipients suitable for pharmaceutical compositions intended for delivery of antibodies to the respiratory tract mucosa may be a) carbohydrates, e.g., monosaccharides such as fructose, galactose, glucose. D-mannose, sorbose, and the like; disaccharides, such as lactose, trehalose, cellobiose, and the like; cyclodextrins, such as 2-hydroxypropyl-β-cyclodextrin; and polysaccharides, such as raffinose, maltodextrins, dextrans, and the like; b) amino acids, such as glycine, arginine, aspartic acid, glutamic acid, cysteine, lysine and the like; c) organic salts prepared from organic acids and bases, such as sodium citrate, sodium ascorbate, magnesium gluconate, sodium gluconate, tromethamine hydrochloride, and the like: d) peptides and proteins, such as aspartame, human serum albumin, gelatin, and the like; e) alditols, such mannitol, xylitol, and the like, and f) polycationic polymers, such as chitosan or a chitosan salt or derivative.

For dermal application, the antibodies of the present invention may suitably be formulated with one or more of the following excipients: solvents, buffering agents, preservatives, humectants, chelating agents, antioxidants, stabilizers, emulsifying agents, suspending agents, gel-forming agents, ointment bases, penetration enhancers, and skin protective agents.

Examples of solvents are e.g. water, alcohols, vegetable or marine oils (e.g. edible oils like almond oil, castor oil, cacao butter, coconut oil, corn oil, cottonseed oil, linseed oil, olive oil, palm oil, peanut oil, poppy seed oil, rapeseed oil, sesame oil, soybean oil, sunflower oil, and tea seed oil), mineral oils, fatty oils, liquid paraffin, polyethylene glycols, propylene glycols, glycerol, liquid polyalkylsiloxanes, and mixtures thereof.

Examples of buffering agents are e.g. citric acid, acetic acid, tartaric acid, lactic acid, hydrogenphosphoric acid, diethyl amine etc. Suitable examples of preservatives for use in compositions are parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalkonium chloride, and benzylalcohol, or mixtures of preservatives.

Examples of humectants are glycerin, propylene glycol, sorbitol, lactic acid, urea, and mixtures thereof.

Examples of antioxidants are butylated hydroxy anisole (BHA), ascorbic acid and derivatives thereof, tocopherol and derivatives thereof, cysteine, and mixtures thereof.

Examples of emulsifying agents are naturally occurring gums, e.g. gum acacia or gum tragacanth; naturally occurring phosphatides, e.g. soybean lecithin, sorbitan monooleate derivatives: wool fats; wool alcohols; sorbitan esters; monoglycerides; fatty alcohols; fatty acid esters (e.g. triglycerides of fatty acids); and mixtures thereof.

Examples of suspending agents are e.g. celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Examples of gel bases, viscosity-increasing agents or components which are able to take up exudate from a wound are: liquid paraffin, polyethylene, fatty oils, colloidal silica or aluminum, zinc soaps, glycerol, propylene glycol, tragacanth, carboxyvinyl polymers, magnesium-aluminum silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carrageenans, hyaluronates (e.g. hyaluronate gel optionally containing sodium chloride), and alginates including propylene glycol alginate.

Examples of ointment bases are e.g. beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Examples of hydrophobic or water-emulsifying ointment bases are paraffins, vegetable oils, animal fats, synthetic glycerides, waxes, lanolin, and liquid polyalkylsiloxanes. Examples of hydrophilic ointment bases are solid macrogols (polyethylene glycols). Other examples of ointment bases are triethanolamine soaps, sulphated fatty alcohol and polysorbates.

Examples of other excipients are polymers such as carmellose, sodium carmellose, hydroxypropylmethylcellulose, hydroxyethylcellulose, hydroxypropylcellulose, pectin, xanthan gum, locust bean gum, acacia gum, gelatin, carbomer, emulsifiers like vitamin E, glyceryl stearates, cetearyl glucoside, collagen, carrageenan, hyaluronates and alginates and chitosans.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transduction with viral (typically lentivirus, adeno associated virus (AAV) and adenovirus) vectors.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included. The composition may include one or more cell protective molecules, cell regenerative molecules, growth factors, anti-apoptotic factors or factors that regulate gene expression in the cells. Such substances may render the cells independent of their environment. Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ. In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a modulating infection in a population of infected cells as taught herein. The terms "cell population" or "population" denote a set of cells having characteristics in common. The characteristics may include in particular the one or more marker(s) or gene or gene product signature(s) as taught herein. The cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated cells, cells, or populations thereof as disclosed throughout this specification may be suitably cultured or cultivated in vitro. The term "in vitro" generally denotes outside, or external to, a body, e.g., an animal or human body. The term encompasses "ex vivo". The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v CO2 and >95% humidity. The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

In some embodiments, patients may be administered an anti-HIV therapeutic for ART-resistant strains of HIV. Such regimens may include, but are not necessarily limited to, second-line ART or third-line ART (Global Action Plan on HIV Drug Resistance 2017-2021 (WHO) 2017). Second-line ART may include, but is not necessarily limited to, a boosted PI plus two NRTIs. Third-line ART may include, but is not necessarily limited to, integrase inhibitors and second-generation NNRTIs and PIs.

In some embodiments, the step of detecting one or more genes or gene signatures from Table 1 or Table 2 may comprise detecting the presence of a marker using an immunological assay as described herein. In some embodiments, the immunological assay may comprise detection of specific binding between an antibody and the marker. The marker may be a peptide, polypeptide, or protein as described herein.

Pharmaceuticals

Another aspect of the invention provides a composition, pharmaceutical composition or vaccine comprising the immune cells or populations thereof, as taught herein.

One aspect of the invention provides for a composition, pharmaceutical composition or vaccine directed to HIV-infected cells, including cells harbouring persistent HIV infections One aspect of the invention provides for a composition, pharmaceutical composition or vaccine directed to Hepatitis B- or Hepatitis C-infected cells.

A "pharmaceutical composition" refers to a composition that usually contains an excipient, such as a pharmaceutically acceptable carrier that is conventional in the art and that is suitable for administration to cells or to a subject.

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilisers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavourings, aromatisers, thickeners, agents for achieving a depot effect, coatings, antifungal agents, preservatives, stabilisers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infuse. The skilled person will understand that compositions which are to be administered orally or topically will usually not comprise cells, although it may be envisioned for oral compositions to also comprise cells, for example when gastro-intestinal tract indications are treated. Each of the cells or active components (e.g., modulants, immunomodulants, antigens) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

If desired, cell preparation can be administered on a support, scaffold, matrix or material to provide improved tissue regeneration. For example, the material can be a granular ceramic, or a biopolymer such as gelatine, collagen, or fibrinogen. Porous matrices can be synthesized according to standard techniques (e.g., Mikos et al., Biomaterials 14: 323, 1993; Mikos et al., Polymer 35:1068, 1994; Cook et al., J. Biomed. Mater. Res. 35:513, 1997). Such support, scaffold, matrix or material may be biodegradable or non-biodegradable. Hence, the cells may be transferred to and/or cultured on suitable substrate, such as porous or non-porous substrate, to provide for implants.

For example, cells that have proliferated, or that are being differentiated in culture dishes, can be transferred onto three-dimensional solid supports in order to cause them to multiply and/or continue the differentiation process by incubating the solid support in a liquid nutrient medium of the invention, if necessary. Cells can be transferred onto a three-dimensional solid support, e.g. by impregnating the support with a liquid suspension containing the cells. The impregnated supports obtained in this way can be implanted in a human subject. Such impregnated supports can also be re-cultured by immersing them in a liquid culture medium, prior to being finally implanted. The three-dimensional solid support needs to be biocompatible so as to enable it to be implanted in a human. It may be biodegradable or non-biodegradable.

The cells or cell populations can be administered in a manner that permits them to survive, grow, propagate and/or differentiate towards desired cell types (e.g. differentiation) or cell states. The cells or cell populations may be grafted to or may migrate to and engraft within the intended organ.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified intestinal epithelial cells, intestinal epithelial stem cells, or intestinal immune cells (preferably intestinal epithelial cells) and/or other active components. The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

A further aspect of the invention provides a population of the epithelial cells, epithelial stem cells, or epithelial immune cells as taught herein. The terms "cell population" or "population" denote a set of cells having characteristics in common. The characteristics may include in particular the one or more marker(s) or gene or gene product signature(s) as taught herein. The epithelial cells, epithelial stem cells, or epithelial immune cells (preferably mucosal immune cells) cells as taught herein may be comprised in a cell population. By means of example, the specified cells may constitute at least 40% (by number) of all cells of the cell population, for example, at least 45%, preferably at least 50%, at least 55%, more preferably at least 60%, at least 65%, still more preferably at least 70%, at least 75%, even more preferably at least 80%, at least 85%, and yet more preferably at least 90%, at least 95%, at least 96%, at least 97%, at least 98%, at least 99%, or even 100% of all cells of the cell population.

The isolated intestinal epithelial cells, intestinal epithelial stem cells, or intestinal immune cells (preferably intestinal epithelial cells) of populations thereof as disclosed throughout this specification may be suitably cultured or cultivated in vitro. The term "in vitro" generally denotes outside, or external to, a body, e.g., an animal or human body. The term encompasses "ex vivo".

The terms "culturing" or "cell culture" are common in the art and broadly refer to maintenance of cells and potentially expansion (proliferation, propagation) of cells in vitro. Typically, animal cells, such as mammalian cells, such as human cells, are cultured by exposing them to (i.e., contacting them with) a suitable cell culture medium in a vessel or container adequate for the purpose (e.g., a 96-, 24-, or 6-well plate, a T-25, T-75, T-150 or T-225 flask, or a cell factory), at art-known conditions conducive to in vitro cell culture, such as temperature of 37° C., 5% v/v $CO_2$ and >95% humidity.

The term "medium" as used herein broadly encompasses any cell culture medium conducive to maintenance of cells, preferably conducive to proliferation of cells. Typically, the medium will be a liquid culture medium, which facilitates easy manipulation (e.g., decantation, pipetting, centrifugation, filtration, and such) thereof.

In certain example embodiments, the agent modulates HIV-infected cells by modulating one or more of the genes listed in Table 1. The genes identified in Table 1 and subsequent tables were determined using scRNA-seq analysis of a combination of healthy control, infected with HIV.

In certain example embodiments, the agent modulates HIV-infected cells by modulating one or more of the genes listed in Table 2. In another example embodiment, the agent modulates HIV-infected cells by modulating one or more of the genes listed in Table 2 (expression induced/increased in HIV+ cells) and/or Table 3 (expression suppressed/decreased in HIV+ cells). The cluster numbers in Table 2 and Table 3 refer to the clusters and cell types as labeled.

The invention having now been described by way of written description, those of skill in the art will recognize that the invention can be practiced in a variety of embodiments and that the foregoing description and examples below are for purposes of illustration and not limitation of the claims that follow.

Although the present invention and its advantages have been described in detail, it should be understood that various changes, substitutions and alterations can be made herein without departing from the spirit and scope of the invention as defined in the appended claims.

EXAMPLES

Example 1

HIV preferentially infects CD4+ T cells, reverse transcribes its DNA, and integrates into the host genome. Infection progresses through a spike in viral load, followed by a progressive decrease in CD4+ T cell count. Because of the high plasma viral load, and because T cells migrate throughout different locations, virtually all tissues can be exposed to the virus, causing profound, and often irreversible changes to the adaptive and innate immune systems, and establishing a permanent pool of integrated HIV termed the "reservoir."

Patients treated with anti-retrovirals may have undetectable virus in peripheral blood, but demonstrate HIV viral production and replication in about 1% of cells in harvested lymph nodes. Lymph nodes from suppressed donors were thawed, "reactivated/reanimated" for 18 hours with PHA/IL2 and sorted into Seq-Well arrays and evaluated for gene expression.

Figure 4:
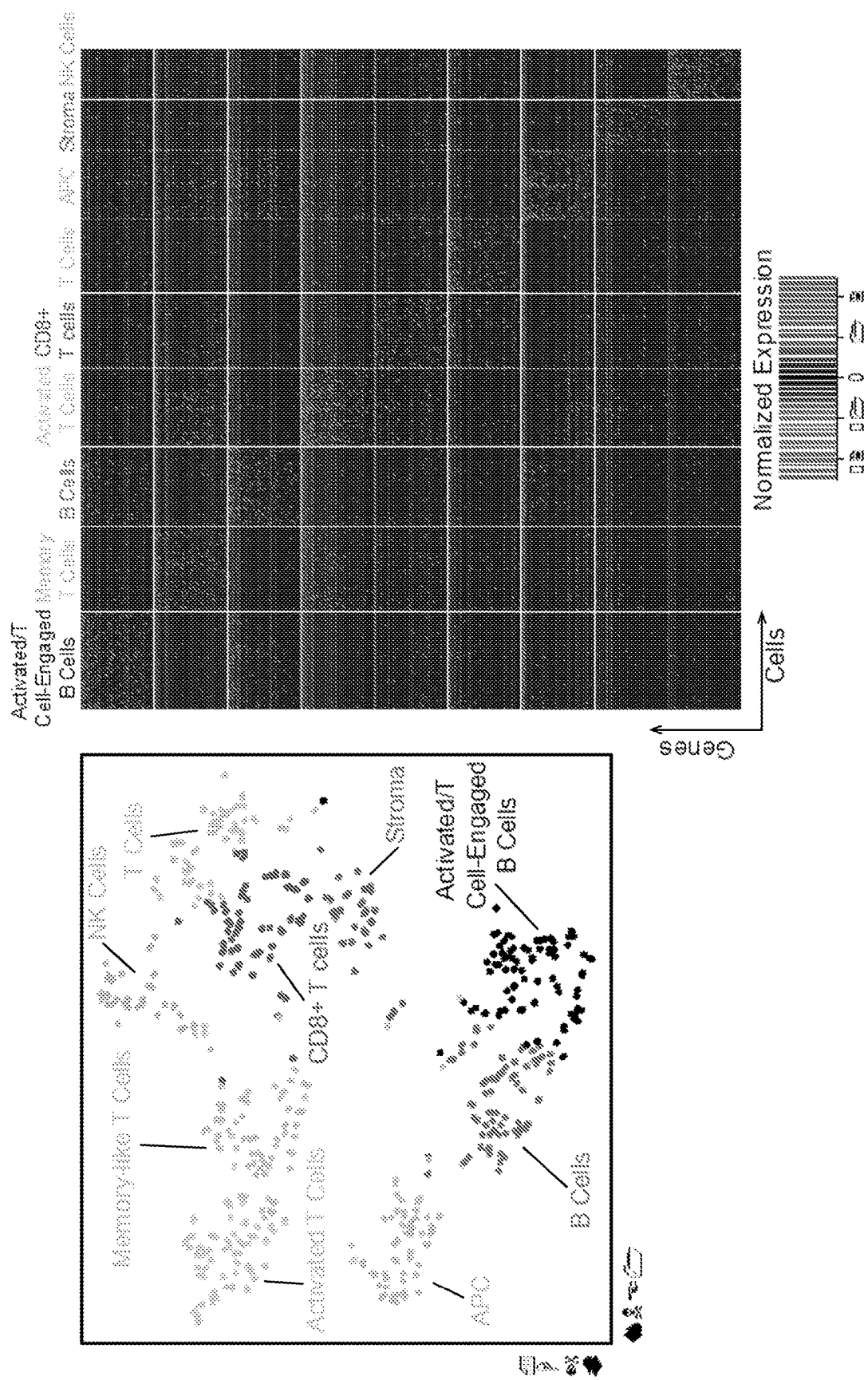
FIG. 4— Lymph node from an HIV-infected, antiretroviral-treated patient.
Figure 5:
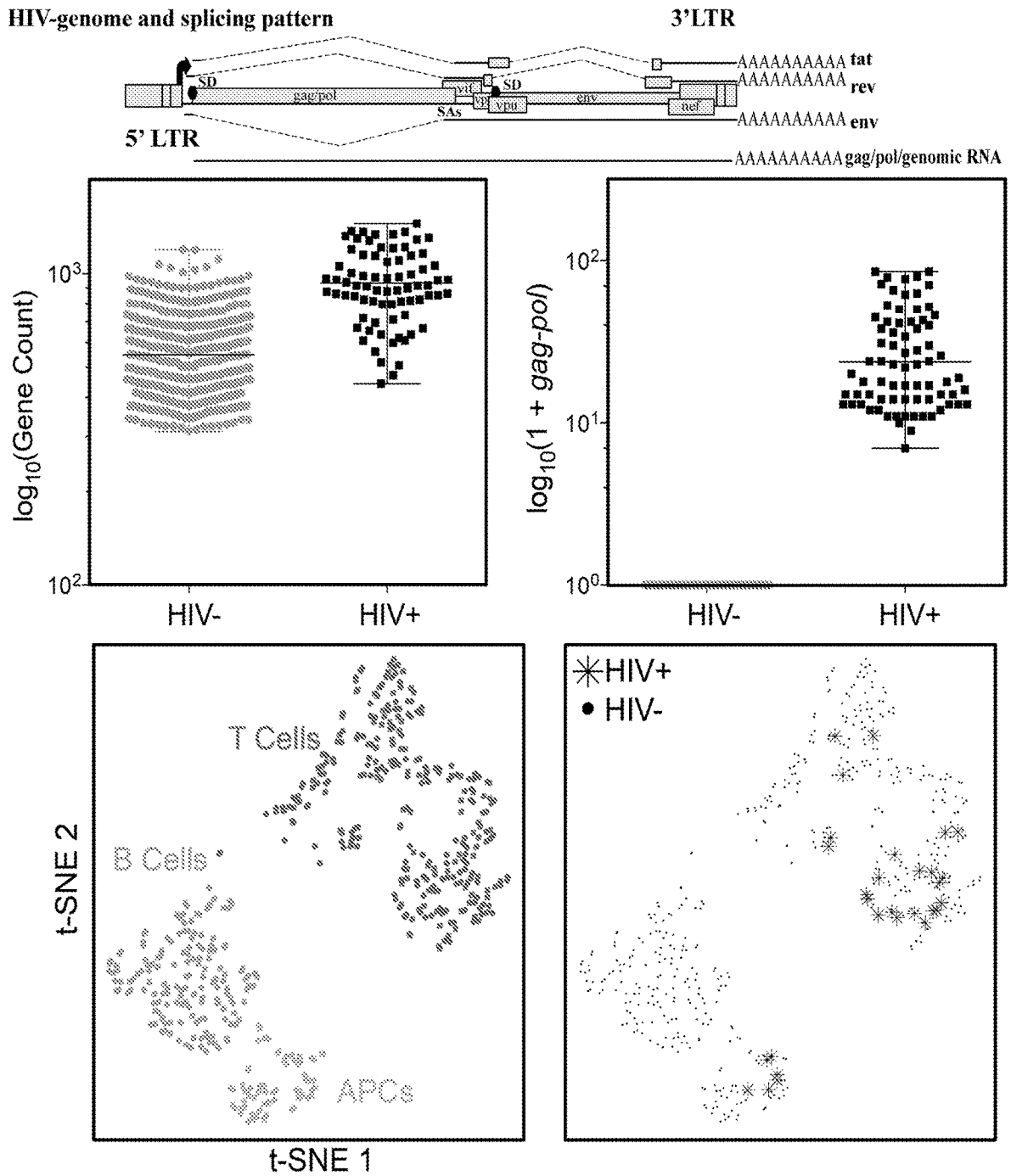
FIG. 5— HIV infection status of single cells. Detection of host mRNA and HIV-1 RNA from the same cell.
Figure 6:
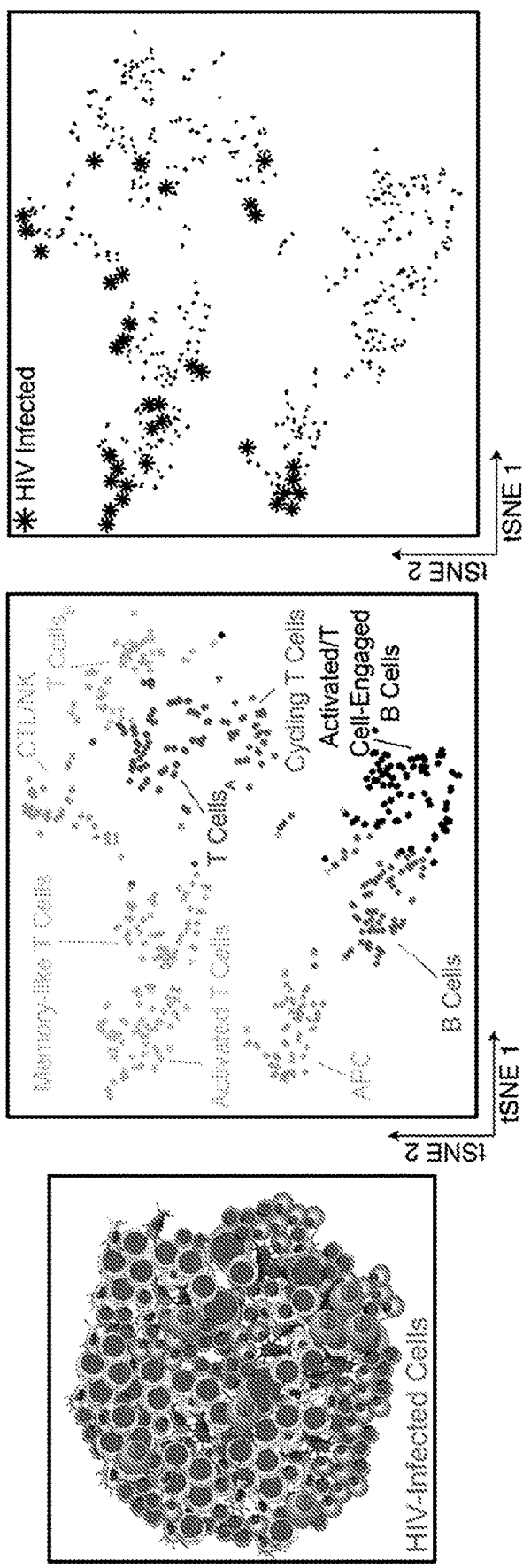
FIG. 6— HIV infection status of single cells. Detection of host mRNA and HIV-1 RNA from the same cell.

FIG. 4 provides an expression profile from lymph node from an HIV-infected, antiretroviral-treated patient. FIG. 5 shows HIV infection of subsets of T Cells and APCs. FIG. 6 shows infection status of single cells and HIV infection of subsets of T Cells and APCs.

Figure 7:
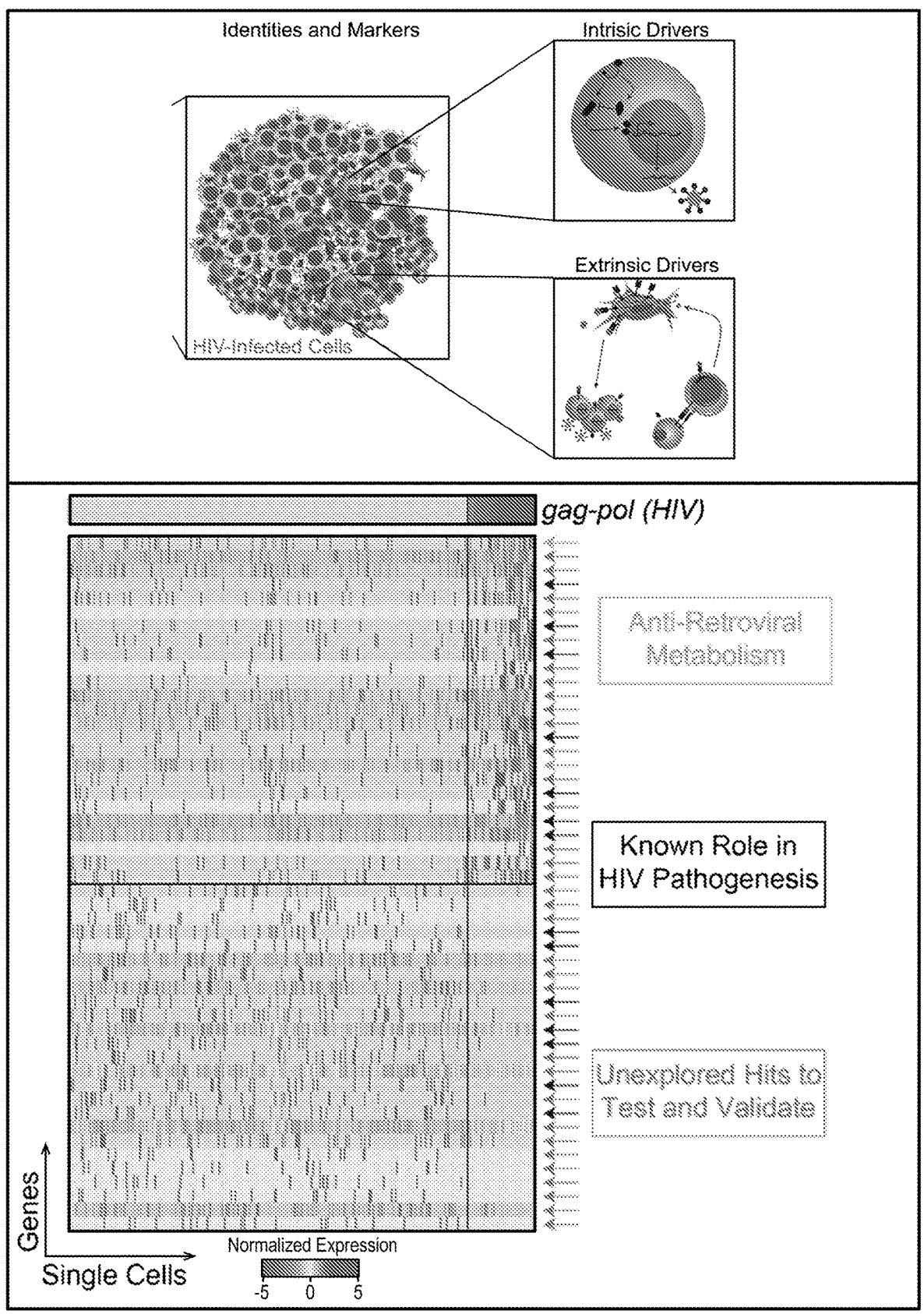
FIG. 7— Cellular identities of Active HIV Reservoir. Top: Single cell RNA detection distinguishes cells, including markers and pathways, that contribute to ongoing HIV replication. Bottom: Differential expression between HIV+ and HIV⁻ cells shown by gag-pol abundance identifies genes that drive HIV replication such as transcription factors that bind to HIV promoter regions. Genes associated with metabolism of anti-retroviral drugs are also detected and novel differentially expressed genes identified.

FIG. 7 demonstrates host cell gene expression in HIV infected cells of genes involved in anti-retroviral metabolism, HIV pathogenesis, as well as genes of unexplored function.

The following tables provide genes differentially expressed in HIV infected cell.

Approximately 16,000 genes were evaluated for differential expression between HIV+ and HIV− cells. Table 1 identifies genes whose expression most positively correlated with HIV infection. Table 2 provides a larger list of genes positively correlated with HIV infection, though to a lesser extent (lower cutoff). Table 3 provides host genes most positively correlated with cells free of HIV.

TABLE 1

HIV+ high cutoff

| Category | Count | Genes |
|---|---|---|
| Proteomics identification | 57 | TGOLN2, UTP18, CAPZA2, STOML2, TCEAL8, CNOT7, SKAP1, THADA, KLHL7, NDUFS6, GTF2E2, WDR73, NUDCD1, RAE1, MAPKAP1, EIF1AY, PTBP3, BCL10, NCOA7, TOPBP1, MESDC2, CCDC137, ARL16, CCNC, RBBP7, MFN2, PYCR1, DOK2, DCUN1D1, NCOA4, ADSL, LRCH3, SNRPG, SNX9, MEAF6, CRLF3, NOB1, PXK, ARF5, VARS, SRRT, CCDC124, NFAT5, STK38L, USP33, TFDP1, PRPF40A, GPS1, GCDH, TMEM120B, RBMX, PTPN11, PWP1, PSMG4, MRPL28, CUL4A, SNRNP25 |
| Acetylation | 28 | MEAF6, SNX9, CRLF3, CAPZA2, STOML2, VARS, SRRT, NDUFS6, GTF2E2, ATAD3B, MAPKAP1, NFAT5, PTBP3, DDA1, STK38L, PRPF40A, TFDP1, STX6, GCDH, BCL10, NCOA7, RBBP7, RBMX, PTPN11, PYCR1, DCUN1D1, ADSL, HIGD2A |
| Phosphoprotein | 43 | TGOLN2, SNX9, MEAF6, UTP18, CAPZA2, NOC3L, NOB1, STOML2, VARS, SKAP1, THADA, SRRT, GTF2E2, NUDCD1, RAE1, CCDC124, MAPKAP1, NFAT5, PTBP3, DDA1, STK38L, USP33, TFDP1, PRPF40A, STX6, GPS1, BCL10, EFCAB14, NCOA7, CCNC, CCDC137, TOPBP1, RBBP7, RBMX, PWP1, NOC2L, PTPN11, MFN2, PYCR1, DOK2, CUL4A, ADSL, LRCH3 |
| nucleoplasm | 22 | TGOLN2, GPS1, MEAF6, UTP18, NOB1, TOPBP1, CCNC, CNOT7, RBBP7, RBMX, NOC2L, KLHL7, SRRT, GTF2E2, CUL4A, MAPKAP1, NFAT5, USP33, SNRNP25, TFDP1, SNRPG, PRPF40A |
| Nucleus | 30 | MEAF6, UTP18, NOC3L, NOB1, TCEAL8, CNOT7, SKAP1, KLHL7, SRRT, GTF2E2, NUDCD1, RAE1, MAPKAP1, NFAT5, TFDP1, PRPF40A, GPS1, TMEM120B, NCOA7, CCNC, TOPBP1, RBBP7, RBMX, PTPN11, NOC2L, PWP1, DCUN1D1, EIF5AL1, SNRNP25, SNRPG |
| GO:0044822~poly(A) RNA binding | 12 | SRRT, GTF2E2, MRPL28, CCDC124, UTP18, NOC3L, PTBP3, CCDC137, RBMX, PRPF40A, NOC2L, SNRPG |
| GO:0042101~T cell receptor complex | 3 | BCL10, STOML2, SKAP1 |
| Activator | 8 | SRRT, MEAF6, NCOA4, NFAT5, NCOA7, CCNC, RBMX, TFDP1 |
| GO:0000398~mRNA splicing, via spliceosome | 5 | SRRT, RBMX, SNRNP25, PRPF40A, SNRPG |
| SM00320:WD40 | 5 | WDR73, UTP18, RAE1, RBBP7, PWP1 |
| GO:1901796~regulation of signal transduction by p53 class mediator | 4 | MEAF6, TOPBP1, RBBP7, NOC2L |
| mRNA splicing | 5 | PTBP3, RBMX, SNRNP25, PRPF40A, SNRPG |
| GO:0005515~protein binding | 31 | SNX9, MEAF6, CRLF3, STOML2, ARF5, VARS, CNOT7, SKAP1, SRRT, GTF2E2, STK38L, USP33, TFDP1, PRPF40A, STX6, BCL10, ARL16, CCNC, TOPBP1, RBBP7, RBMX, NOC2L, PTPN11, MFN2, PYCR1, DCUN1D1, MRPL28, CUL4A, HSPA13, SNRNP25, SNRPG |
| repeat:WD 3 | 5 | WDR73, UTP18, RAE1, RBBP7, PWP1 |
| GO:0003723~RNA binding | 7 | RAE1, PTBP3, CNOT7, RBBP7, RBMX, PRPF40A, SNRPG |
| WD repeat | 5 | WDR73, UTP18, RAE1, RBBP7, PWP1 |
| repeat:WD 2 | 5 | WDR73, UTP18, RAE1, RBBP7, PWP1 |
| repeat:WD 1 | 5 | WDR73, UTP18, RAE1, RBBP7, PWP1 |
| IPR001680:WD40 repeat | 5 | WDR73, UTP18, RAE1, RBBP7, PWP1 |
| IPR019775:WD40 repeat, conserved site | 4 | UTP18, RAE1, RBBP7, PWP1 |
| mRNA processing | 5 | PTBP3, RBMX, SNRNP25, PRPF40A, SNRPG |
| IPR017986:WD40-repeat-containing domain | 5 | WDR73, UTP18, RAE1, RBBP7, PWP1 |
| Ubl conjugation | 12 | MFN2, SNX9, MEAF6, CUL4A, EIF1AY, NFAT5, ADSL, TOPBP1, RBBP7, RBMX, USP33, PRPF40A |
| GO:0005730~nucleolus | 8 | KLHL7, MEAF6, UTP18, RAE1, NOC3L, CCDC137, PWP1, NOC2L |

TABLE 1-continued

| Category | Count | Genes |
|---|---|---|
| HIV+ high cutoff | | |
| GO:0043130~ubiquitin binding | 3 | BCL10, RAE1, USP33 |
| IPR015943:WD40/YVTN repeat-like-containing domain | 5 | WDR73, UTP18, RAE1, RBBP7, PWP1 |
| GO:0015629~actin cytoskeleton | 4 | CAPZA2, STOML2, TOPBP1, STK38L |
| Repressor | 6 | CCNC, PTBP3, CNOT7, RBBP7, RBMX, NOC2L |
| IPR020472:G-protein beta WD-40 repeat | 3 | RAE1, RBBP7, PWP1 |
| IPR011991:Winged helix-turn-helix DNA-binding domain | 4 | GPS1, GTF2E2, CUL4A, TFDP1 |
| GO:0005634~nucleus | 26 | UTP18, NOC3L, TCEAL8, PXK, CNOT7, SKAP1, KLHL7, GTF2E2, NUDCD1, RAE1, MAPKAP1, NFAT5, PTBP3, TFDP1, BCL10, NCOA7, TOPBP1, CCNC, RBBP7, RBMX, PWP1, NOC2L, PTPN11, DCUN1D1, NCOA4, SNRNP25 |
| repeat:WD 4 | 4 | UTP18, RAE1, RBBP7, PWP1 |
| mutagenesis site | 13 | TGOLN2, GCDH, BCL10, NCOA7, PXK, SKAP1, PTPN11, MFN2, CUL4A, NCOA4, EIF5AL1, USP33, STK38L |
| Mitochondrion inner membrane | 4 | NDUFS6, ATAD3B, STOML2, HIGD2A |
| Coiled coil | 16 | STX6, MEAF6, CRLF3, TMEM120B, NOC3L, STOML2, NCOA7, CCDC137, TCEAL8, ARF5, VARS, THADA, MFN2, SRRT, ATAD3B, CCDC124 |
| GO:0071004~U2-type prespliceosome | 2 | PRPF40A, SNRPG |
| GO:0045944~positive regulation of transcription from RNA polymerase II promoter | 8 | CRLF3, NFAT5, NCOA7, CCNC, CNOT7, SKAP1, RBMX, TFDP1 |
| GO:0005737~cytoplasm | 25 | GPS1, BCL10, SNX9, MEAF6, CRLF3, TOPBP1, PXK, ARF5, SKAP1, PTPN11, NOC2L, KLHL7, SRRT, GTF2E2, NUDCD1, MRPL28, CCDC124, RAE1, MAPKAP1, NFAT5, LRCH3, USP33, STK38L, SNRNP25, PRPF40A |
| GO:0005685~U1 snRNP | 2 | PRPF40A, SNRPG |
| GO:0070469~respiratory chain | 2 | NDUFS6, HIGD2A |
| Spliceosome | 3 | RBMX, SNRNP25, SNRPG |
| GO:0005743~mitochondrial inner membrane | 5 | NDUFS6, ATAD3B, MRPL28, STOML2, HIGD2A |
| Mitochondrion | 8 | MFN2, GCDH, PYCR1, NDUFS6, ATAD3B, MRPL28, STOML2, HIGD2A |
| Isopeptide bond | 8 | MEAF6, CUL4A, EIF1AY, NFAT5, ADSL, RBBP7, RBMX, PRPF40A |
| hsa03040:Spliceosome | 3 | RBMX, PRPF40A, SNRPG |
| GO:0031625~ubiquitin protein ligase binding | 4 | MFN2, BCL10, SNX9, CUL4A |
| GO:0005794~Golgi apparatus | 7 | TGOLN2, STX6, MAPKAP1, TOPBP1, ARF5, USP33, PWP1 |
| GO:0005802~trans-Golgi network | 3 | TGOLN2, STX6, SNX9 |
| Transcription | 13 | SRRT, MEAF6, GTF2E2, NCOA4, NFAT5, NCOA7, CCNC, TCEAL8, CNOT7, RBBP7, RBMX, NOC2L, TFDP1 |
| GO:0000715~nucleotide-excision repair, DNA damage recognition | 2 | GPS1, CUL4A |
| GO:0046580~negative regulation of Ras protein signal transduction | 2 | MFN2, MAPKAP1 |
| GO:0005689~U12-type spliceosomal complex | 2 | SNRNP25, SNRPG |
| Protein biosynthesis | 3 | EIF5AL1, EIF1AY, VARS |
| Chromosomal rearrangement | 4 | BCL10, MEAF6, NCOA4, THADA |
| GO:0050852~T cell receptor signaling pathway | 3 | BCL10, STOML2, SKAP1 |

TABLE 2

| Category | Count | Genes |
|---|---|---|
| HIV + low cutoff | | |
| Enrichment Score: 5.645742662204743 | | |
| Mitochondrion | 43 | HSD17B10, MRPS35, OXA1L, NDUFB6, MRPS33, COA3, FKBP4, TIMM10, STOML2, PTRH2, MTIF3, HADHA, NDUFS6, MRPL13, ATAD3B, DDX3X, TIMM9, REXO2, MRPL54, ABHD10, YRDC, APEX1, GCDH, MRPS26, MRPL4, NDUFA2, MMADHC, HCLS1, AK2, TOMM40, TMEM126B, SOD2, MFN2, PYCR1, MRPL22, MRPL28, PPM1K, CLPP, ATP5C1, MRPL48, SLC25A39, BCO2, HIGD2A |
| GO: 0005743~mitochondrial inner membrane | 24 | MRPS35, MRPS26, MRPL4, NDUFA2, OXA1L, MRPS33, NDUFB6, TIMM10, STOML2, AK2, TMEM126B, HADHA, SOD2, NDUFS6, MRPL22, MRPL13, ATAD3B, MRPL28, TIMM9, MRPL54, ATP5C1, MRPL48, SLC25A39, HIGD2A |
| transit peptide: Mitochondrion | 20 | GCDH, MRPS35, MRPS26, OXA1L, MMADHC, PTRH2, MTIF3, HADHA, SOD2, NDUFS6, MRPL22, MRPL28, PPM1K, CLPP, REXO2, MRPL54, ATP5C1, ABHD10, YRDC, MRPL48 |
| Transit peptide | 21 | GCDH, MRPS35, MRPS26, OXA1L, MMADHC, STOML2, PTRH2, MTIF3, HADHA, SOD2, NDUFS6, MRPL22, MRPL28, PPM1K, REXO2, CLPP, MRPL54, ATP5C1, ABHD10, YRDC, MRPL48 |
| Enrichment Score: 4.175905846577495 | | |
| mRNA splicing | 20 | HNRNPA1L2, SRSF1, DDX39A, PRPF4B, YTHDC1, PRPF39, RBMX, GCFC2, PRPF6, CIR1, CD2BP2, CDC40, DHX15, RBMXL1, PTBP3, SREK1IP1, SNRNP25, THOC1, SNRPG, PRPF40A |
| mRNA processing | 21 | HNRNPA1L2, SRSF1, DDX39A, PRPF4B, YTHDC1, PRPF39, RBMX, GCFC2, SLBP, PRPF6, CIR1, CD2BP2, CDC40, DHX15, RBMXL1, PTBP3, SREK1IP1, SNRNP25, THOC1, SNRPG, PRPF40A |
| GO: 0000398~mRNA splicing, via spliceosome | 15 | SRSF1, DDX39A, PRPF4B, POLR2K, CWC27, RBMX, PRPF6, SRRT, CD2BP2, HTATSF1, CDC40, DHX15, SNRNP25, SNRPG, PRPF40A |
| GO: 0008380~RNA splicing | 12 | HNRNPA1L2, CIR1, PRPF4B, CDC40, DHX15, RBMXL1, PTBP3, SREK1IP1, SNRNP25, THOC1, PRPF6, SNRPG |
| hsa03040: Spliceosome | 10 | HNRNPA1L2, SRSF1, CDC40, DHX15, RBMXL1, RBMX, THOC1, PRPF6, PRPF40A, SNRPG |
| Spliceosome | 8 | HNRNPA1L2, SRSF1, PRPF4B, CDC40, RBMX, SNRNP25, PRPF6, SNRPG |
| GO: 0071013~catalytic step 2 spliceosome | 7 | SRSF1, PRPF4B, CWC27, CDC40, RBMX, PRPF6, SNRPG |
| GO: 0005681~spliceosomal complex | 5 | HNRNPA1L2, DDX39A, CDC40, PRPF6, SNRPG |
| Enrichment Score: 3.1886930162792817 | | |
| Protein biosynthesis | 16 | AARS, DENR, VARS, ETF1, MTIF3, EIF2S1, EIF5AL1, EIF3F, EIF1AY, HARS, TCEB3, TCEA1, EIF1, SUPT5H, MCTS1, EIF4E2 |
| Initiation factor | 8 | EIF2S1, EIF1AY, EIF3F, EIF1, DENR, MCTS1, MTIF3, EIF4E2 |
| GO: 0003743~translation initiation factor activity | 8 | EIF2S1, EIF1AY, EIF3F, EIF1, DENR, MCTS1, MTIF3, EIF4E2 |
| GO: 0032790~ribosome disassembly | 3 | DENR, MCTS1, MTIF3 |
| hsa03013: RNA transport | 10 | NXT1, NUP62, RAE1, EIF2S1, EIF1AY, PABPC4, EIF3F, EIF1, EIF4E2, THOC1 |
| GO: 0006413~translational initiation | 7 | EIF2S1, EIF1AY, EIF3F, RPL35, EIF1, RPL39, EIF4E2 |
| GO: 0001731~formation of translation preinitiation complex | 3 | EIF3F, DENR, MCTS1 |
| GO: 0008135~translation factor activity, RNA binding | 3 | EIF1, MTIF3, EIF4E2 |
| Enrichment Score: 3.1727290299421798 | | |
| Ribonucleoprotein | 18 | HNRNPA1L2, MRPS35, MRPS26, MRPL4, MRPS33, RPL35, RPL39, SRP19, RBMX, RPS19BP1, SLBP, MRPL22, MRPL13, MRPL28, MRPL54, RBMXL1, MRPL48, SNRPG |
| GO: 0070125~mitochondrial translational elongation | 9 | MRPS35, MRPS26, MRPL22, MRPL4, MRPL13, MRPS33, MRPL28, MRPL54, MRPL48 |
| GO: 0070126~mitochondrial translational termination | 9 | MRPS35, MRPS26, MRPL22, MRPL4, MRPL13, MRPS33, MRPL28, MRPL54, MRPL48 |

TABLE 2-continued

HIV + low cutoff

| Category | Count | Genes |
|---|---|---|
| Ribosomal protein | 12 | MRPS35, MRPS26, MRPL22, MRPL4, MRPL13, MRPS33, MRPL28, MRPL54, RPL35, MRPL48, RPL39, RPS19BP1 |
| GO: 0006412~translation | 10 | MRPL22, MRPL4, MRPL13, MRPS33, MRPL28, PABPC4, HARS, RPL35, SLC25A39, RPL39 |
| GO: 0003735~structural constituent of ribosome | 9 | MRPS35, MRPL22, MRPL4, MRPL13, MRPS33, MRPL28, RPL35, SLC25A39, RPL39 |
| hsa03010: Ribosome | 6 | MRPL22, MRPL4, MRPL13, MRPL28, RPL35, RPL39 |
| | | Enrichment Score: 2.5160173816834086 |
| GO: 0006406~mRNA export from nucleus | 9 | NXT1, SRSF1, DDX39A, NUP62, RAE1, CDC40, SMG1, SLBP, THOC1 |
| GO: 0006405~RNA export from nucleus | 6 | NXT1, SRSF1, DDX39A, NUP62, CDC40, THOC1 |
| GO: 0006369~ termination of RNA polymerase II transcription | 6 | SRSF1, DDX39A, CDC40, SLBP, THOC1, SNRPG |
| GO: 0031124~mRNA 3'-end processing | 4 | SRSF1, DDX39A, CDC40, THOC1 |
| | | Enrichment Score: 2.126966020626473 |
| GO: 0006368~ transcription elongation from RNA polymerase II promoter | 7 | TAF11, ADRM1, GTF2E2, POLR2K, TCEB3, TCEA1, SUPT5H |
| Elongation factor | 4 | EIF5AL1, TCEB3, TCEA1, SUPT5H |
| GO: 0003746~ translation elongation factor activity | 4 | EIF5AL1, TCEB3, TCEA1, SUPT5H |
| | | Enrichment Score: 1.874526987901123 |
| DNA repair | 12 | UBE2N, PSMD14, CUL4A, BABAM1, SMG1, PRKDC, TOPBP1, USP10, APEX1, SMC3, TRIP12, BOD1L1 |
| DNA damage | 13 | PRKDC, SMG1, TOPBP1, SMC3, BOD1L1, UBE2N, PSMD14, CUL4A, BABAM1, USP10, APEX1, MCTS1, TRIP12 |
| GO: 0006281~DNA repair | 7 | SMG1, TOPBP1, APEX1, ASF1A, SMC3, TRIP12, BOD1L1 |
| | | Enrichment Score: 1.8713442584451319 |
| Neuropathy | 7 | MFN2, AARS, LMNA, HARS, WNK1, DNMT1, DNM2 |
| Charcot-Marie-Tooth disease | 5 | MFN2, AARS, LMNA, HARS, DNM2 |
| Neurodegeneration | 7 | MFN2, ELOVL5, AARS, LMNA, HARS, WNK1, DNM2 |
| | | Enrichment Score: 1.8468573086564095 |
| Cell division | 13 | SNX9, ATAD3B, GNAI2, CCDC124, IST1, CDC40, CKS2, CENPV, BABAM1, SMC2, SMC3, MCM5, PRPF40A |
| Cell cycle | 18 | SNX9, USP8, GNAI2, SMC2, MCM4, SMC3, MCM5, ATAD3B, CSNK2A1, CCDC124, IST1, CDC40, BABAM1, CENPV, CKS2, MCTS1, TFDP1, PRPF40A |
| GO: 0051301~cell division | 12 | ATAD3B, GNAI2, CCDC124, IST1, CDC40, CKS2, CENPV, BABAM1, SMC2, MCM5, SMC3, PRPF40A |
| | | Enrichment Score: 1.679241294734509 |
| Isomerase | 7 | TOP1, FKBP4, CWC27, PPID, FKBP3, TOPBP1, TSTA3 |
| Rotamase | 4 | FKBP4, CWC27, PPID, FKBP3 |
| GO: 0061077~chaperone-mediated protein folding | 4 | CSNK2A1, FKBP4, PPID, FKBP3 |
| GO: 0000413~protein peptidyl-prolyl isomerization | 4 | FKBP4, CWC27, PPID, FKBP3 |
| GO: 0003755~ peptidyl-prolyl cis-trans isomerase activity | 4 | FKBP4, CWC27, PPID, FKBP3 |
| | | Enrichment Score: 1.6747845841936386 |
| Repressor | 20 | RCOR1, CCNC, NFKB2, MAF1, CNOT7, RBBP7, RBMX, GCFC2, NOC2L, SUZ12, KDM1A, CIR1, SP3, MLX, DNMT1, PTBP3, SUPT5H, APEX1, C1D, KAT6A |
| Activator | 19 | MEAF6, FOXO1, NCOA7, PHF11, CCNC, NFKB2, RBMX, PURA, SRRT, NCOA4, SP3, HTATSF1, MLX, NFAT5, DNMT1, SUPT5H, APEX1, KAT6A, TFDP1 |

TABLE 2-continued

HIV + low cutoff

| Category | Count | Genes |
|---|---|---|
| Transcription | 46 | MEAF6, POLR2K, FOXO1, TCEAL8, NFKB2, MAF1, CNOT7, VPS72, PRIM1, SRRT, KDM1A, GTF2E2, CSNK2A1, CIR1, DDX3X, HTATSF1, GTF3C6, NFAT5, TCEA1, SUPT5H, ASF1A, APEX1, TFDP1, CHD3, RCOR1, NCOA7, POLR1C, CCNC, PHF11, RBBP7, UBE2L3, RBMX, GCFC2, PURA, NOC2L, TAF11, SUZ12, NCOA4, MLX, SP3, TCEB3, DNMT1, MCTS1, THOC1, KAT6A, C1D |
| Transcription regulation | 41 | MEAF6, FOXO1, TCEAL8, NFKB2, CNOT7, MAF1, VPS72, SRRT, KDM1A, GTF2E2, CSNK2A1, CIR1, DDX3X, HTATSF1, NFAT5, TCEA1, SUPT5H, ASF1A, APEX1, TFDP1, CHD3, RCOR1, NCOA7, CCNC, PHF11, RBBP7, UBE2L3, GCFC2, PURA, NOC2L, TAF11, SUZ12, NCOA4, MLX, SP3, TCEB3, DNMT1, MCTS1, THOC1, KAT6A, C1D |
| GO: 0006351~ transcription, DNA-templated | 38 | MEAF6, POLR2K, FOXO1, TCEAL8, CNOT7, MAF1, VPS72, KDM1A, CIR1, CSNK2A1, DDX3X, HTATSF1, GTF3C6, TCEA1, ASF1A, APEX1, TFDP1, CHD3, RCOR1, NCOA7, POLR1C, PHF11, RBBP7, UBE2L3, GCFC2, PURA, PWP1, NOC2L, SUZ12, NUP62, NCOA4, MLX, SP3, DNMT1, TCEB3, MCTS1, KAT6A, C1D |
| | | Enrichment Score: 1.6402823990813864 |
| Nucleotide-binding | 40 | PRPF4B, GNAI2, DTYMK, CTPS1, RAB1B, UBA6, PRKDC, ASNS, ARF5, VARS, HPRT1, ATAD3B, CSNK2A1, DDX3X, DHX15, STK38L, CHD3, DDX39A, ITK, AARS, ATP11B, WNK1, AK2, SMG1, ACLY, ARL16, UBE2L3, MCM4, SMC2, MCM5, SMC3, MFN2, UBE2N, HYOU1, PSMC4, RFK, ARF3, HARS, HSPA13, DNM2 |
| ATP-binding | 32 | PRPF4B, DTYMK, CTPS1, UBA6, PRKDC, ASNS, VARS, ATAD3B, CSNK2A1, DDX3X, DHX15, STK38L, CHD3, DDX39A, ITK, AARS, ATP11B, WNK1, SMG1, AK2, ACLY, UBE2L3, SMC2, MCM4, MCM5, SMC3, UBE2N, HYOU1, PSMC4, RFK, HARS, HSPA13 |
| GO: 0005524~ATP binding | 35 | PRPF4B, FKBP4, DTYMK, CTPS1, UBA6, PRKDC, ASNS, PXK, VARS, ATAD3B, CSNK2A1, DDX3X, DHX15, STK38L, CHD3, DDX39A, ITK, SMCHD1, AARS, ATP11B, WNK1, SMG1, AK2, ACLY, UBE2L3, SMC2, MCM4, MCM5, SMC3, UBE2N, HYOU1, PSMC4, RFK, HARS, HSPA13 |
| nucleotide phosphate-binding region: ATP | 19 | DDX39A, ITK, PRPF4B, DTYMK, WNK1, UBA6, AK2, ACLY, SMC2, MCM4, SMC3, MCM5, ATAD3B, CSNK2A1, DDX3X, PSMC4, DHX15, STK38L, CHD3 |
| | | Enrichment Score: 1.5505018585302555 |
| GO: 0006890~ retrograde vesicle-mediated transport, Golgi to ER | 7 | COPB2, KDELR2, ARF3, TMED10, RAB1B, LMAN2, ARF5 |
| GO: 0030133~ transport vesicle | 6 | TGOLN2, COPB2, KDELR2, ERP29, TMED10, RAB1B |
| GO: 0033116~ endoplasmic reticulum-Golgi intermediate compartment membrane | 4 | TMED10, RAB1B, LMAN2, ERGIC3 |
| GO: 0006888~ER to Golgi vesicle-mediated transport | 5 | HYOU1, COPB2, TMED10, RAB1B, LMAN2 |
| | | Enrichment Score: 1.3417297598441402 |
| GO: 0006270~DNA replication initiation | 5 | PRIM1, TOPBP1, MCM4, MCM5, PURA |
| hsa03030: DNA replication | 4 | PRIM1, POLE4, MCM4, MCM5 |
| GO: 0000082~G1/S transition of mitotic cell cycle | 5 | PRIM1, CUL4A, CRLF3, MCM4, MCM5 |
| DNA replication | 4 | PRIM1, RBBP7, MCM4, MCM5 |
| GO: 0006260~DNA replication | 5 | TOP1, TOPBP1, RBBP7, MCM4, MCM5 |
| | | Enrichment Score: 1.312801362788877 |
| hsa00240: Pyrimidine metabolism | 7 | PRIM1, POLE4, POLR2K, DTYMK, CTPS1, POLR1C, ENTPD4 |
| hsa00230: Purine metabolism | 8 | PRIM1, POLE4, POLR2K, ADSL, AK2, POLR1C, ENTPD4, HPRT1 |
| DNA-directed RNA polymerase | 3 | PRIM1, POLR2K, POLR1C |
| | | Enrichment Score: 1.3089793413612678 |
| SM00320: WD40 | 10 | COPB2, WDR36, WDR73, UTP18, RAE1, CDC40, AAMP, WDR4, RBBP7, PWP1 |
| repeat: WD 3 | 10 | COPB2, WDR36, WDR73, UTP18, RAE1, CDC40, AAMP, WDR4, RBBP7, PWP1 |

TABLE 2-continued

| | HIV + low cutoff | |
|---|---|---|
| Category | Count | Genes |
| WD repeat | 10 | COPB2, WDR36, WDR73, UTP18, RAE1, CDC40, AAMP, WDR4, RBBP7, PWP1 |
| repeat: WD 1 | 10 | COPB2, WDR36, WDR73, UTP18, RAE1, CDC40, AAMP, WDR4, RBBP7, PWP1 |
| repeat: WD 2 | 10 | COPB2, WDR36, WDR73, UTP18, RAE1, CDC40, AAMP, WDR4, RBBP7, PWP1 |
| IPR001680: WD40 repeat | 10 | COPB2, WDR36, WDR73, UTP18, RAE1, CDC40, AAMP, WDR4, RBBP7, PWP1 |
| repeat: WD 4 | 9 | COPB2, WDR36, UTP18, RAE1, CDC40, AAMP, WDR4, RBBP7, PWP1 |
| IPR019775: WD40 repeat, conserved site | 7 | WDR36, UTP18, RAE1, CDC40, AAMP, RBBP7, PWP1 |
| IPR017986: WD40-repeat-containing domain | 10 | COPB2, WDR36, WDR73, UTP18, RAE1, CDC40, AAMP, WDR4, RBBP7, PWP1 |
| IPR015943: WD40/YVTN repeat-like-containing domain | 10 | COPB2, WDR36, WDR73, UTP18, RAE1, CDC40, AAMP, WDR4, RBBP7, PWP1 |
| repeat: WD 5 | 7 | COPB2, WDR36, UTP18, CDC40, AAMP, RBBP7, PWP1 |
| repeat: WD 6 | 6 | COPB2, WDR36, UTP18, CDC40, AAMP, RBBP7 |
| IPR020472: G-protein beta WD-40 repeat | 4 | COPB2, RAE1, RBBP7, PWP1 |
| repeat: WD 7 | 5 | COPB2, WDR36, CDC40, AAMP, RBBP7 |
| repeat: WD 8 | 3 | COPB2, WDR36, AAMP |
| | | Enrichment Score: 1.2247677909485253 |
| SM00360: RRM | 8 | HNRNPA1L2, SRSF1, HTATSF1, PABPC4, RBMXL1, RBM6, PTBP3, RBMX |
| SM00361: RRM_1 | 3 | PABPC4, RBMXL1, RBMX |
| IPR012677: Nucleotide-binding, alpha-beta plait | 9 | HNRNPA1L2, SRSF1, SRRT, HTATSF1, PABPC4, RBMXL1, RBM6, PTBP3, RBMX |
| GO: 0000166~nucleotide binding | 11 | HNRNPA1L2, SRSF1, SRRT, HTATSF1, PABPC4, RBMXL1, RBM6, PTBP3, PXK, HPRT1, RBMX |
| IPR003954: RNA recognition motif domain, eukaryote | 3 | PABPC4, RBMXL1, RBMX |
| IPR000504: RNA recognition motif domain | 8 | HNRNPA1L2, SRSF1, HTATSF1, PABPC4, RBMXL1, RBM6, PTBP3, RBMX |
| GO: 0030529~intracellular ribonucleoprotein complex | 6 | HNRNPA1L2, NUP62, PABPC4, RBMXL1, RBMX, SLBP |
| domain: RRM 1 | 5 | HNRNPA1L2, SRSF1, HTATSF1, PABPC4, PTBP3 |
| domain: RRM 2 | 5 | HNRNPA1L2, SRSF1, HTATSF1, PABPC4, PTBP3 |
| | | Enrichment Score: 1.1799339425906339 |
| GO: 0050852~T cell receptor signaling pathway | 9 | UBE2N, ITK, BCL10, PSMB4, PSMD14, PSMB7, PSMC4, STOML2, SKAP1 |
| GO: 0038061~NIK/NF-kappaB signaling | 6 | PSMB4, PSMD14, PSMB7, PSMC4, NFKB2, PPP4C |
| Proteasome | 5 | PSMB4, ADRM1, PSMD14, PSMB7, PSMC4 |
| GO: 0000502~proteasome complex | 5 | PSMB4, ADRM1, PSMD14, PSMB7, PSMC4 |
| GO: 0038095~Fc-epsilon receptor signaling pathway | 8 | UBE2N, ITK, BCL10, PSMB4, PSMD14, PSMB7, PSMC4, PPP3R1 |
| GO: 0002223~stimulatory C-type lectin receptor signaling pathway | 6 | UBE2N, BCL10, PSMB4, PSMD14, PSMB7, PSMC4 |
| GO: 0006521~regulation of cellular amino acid metabolic process | 4 | PSMB4, PSMD14, PSMB7, PSMC4 |
| hsa03050: Proteasome | 4 | PSMB4, PSMD14, PSMB7, PSMC4 |
| GO: 0000209~protein polyubiquitination | 7 | PSMB4, PSMD14, PSMB7, PSMC4, UBE2V2, UBE2L3, TRIP12 |

TABLE 2-continued

| Category | Count | Genes |
|---|---|---|
| HIV + low cutoff | | |
| GO: 0002479~antigen processing and presentation of exogenous peptide antigen via MHC class I, TAP-dependent | 4 | PSMB4, PSMD14, PSMB7, PSMC4 |
| GO: 0043488~regulation of mRNA stability | 5 | PSMB4, PSMD14, PSMB7, PSMC4, APEX1 |
| GO: 0051436~negative regulation of ubiquitin-protein ligase activity involved in mitotic cell cycle | 4 | PSMB4, PSMD14, PSMB7, PSMC4 |
| GO: 0051437~positive regulation of ubiquitin-protein ligase activity involved in regulation of mitotic cell cycle transition | 4 | PSMB4, PSMD14, PSMB7, PSMC4 |
| GO: 0031145~anaphase-promoting complex-dependent catabolic process | 4 | PSMB4, PSMD14, PSMB7, PSMC4 |
| GO: 0060071~Wnt signaling pathway, planar cell polarity pathway | 4 | PSMB4, PSMD14, PSMB7, PSMC4 |
| GO: 0090090~negative regulation of canonical Wnt signaling pathway | 5 | PSMB4, PSMD14, PSMB7, PSMC4, FOXO1 |
| GO: 0033209~tumor necrosis factor-mediated signaling pathway | 4 | PSMB4, PSMD14, PSMB7, PSMC4 |
| GO: 0090263~positive regulation of canonical Wnt signaling pathway | 4 | PSMB4, PSMD14, PSMB7, PSMC4 |
| GO: 0043161~proteasome-mediated ubiquitin-dependent protein catabolic process | 5 | PSMB4, PSMD14, PSMB7, CUL4A, PSMC4 |
| GO: 0000165~MAPK cascade | 5 | PSMB4, PSMD14, PSMB7, PSMC4, CCL5 |
| Enrichment Score: 0.9835956335357907 | | |
| GO: 0005643~nuclear pore | 5 | NXT1, NUP62, RAE1, EIF5AL1, KPNA3 |
| GO: 0075733~intracellular transport of virus | 3 | NUP62, RAE1, KPNA3 |
| GO: 0006606~protein import into nucleus | 3 | NUP62, RAE1, KPNA3 |
| Enrichment Score: 0.9465955034396142 | | |
| GO: 0032981~mitochondrial respiratory chain complex I assembly | 5 | NDUFS6, NDUFA2, OXA1L, NDUFB6, TMEM126B |
| hsa05010: Alzheimer's disease | 8 | HSD17B10, NDUFS6, NDUFA2, CASP3, NDUFB6, PPP3R1, ATP5C1, ITPR3 |
| Respiratory chain | 4 | NDUFS6, NDUFA2, NDUFB6, HIGD2A |
| hsa05012: Parkinson's disease | 7 | NDUFS6, NDUFA2, CASP3, NDUFB6, GNAI2, ATP5C1, UBE2L3 |
| hsa05016: Huntington's disease | 8 | NDUFS6, NDUFA2, CASP3, NDUFB6, POLR2K, RCOR1, ATP5C1, SOD2 |
| GO: 0005747~mitochondrial respiratory chain complex I | 3 | NDUFS6, NDUFA2, NDUFB6 |

TABLE 2-continued

| Category | Count | Genes |
|---|---|---|
| HIV + low cutoff | | |
| hsa04932: Non-alcoholic fatty liver disease (NAFLD) | 6 | NDUFS6, NDUFA2, CASP3, NDUFB6, EIF2S1, MLX |
| GO: 0008137~NADH dehydrogenase (ubiquinone) activity | 3 | NDUFS6, NDUFA2, NDUFB6 |
| GO: 0006120~mitochondrial electron transport, NADH to ubiquinone | 3 | NDUFS6, NDUFA2, NDUFB6 |
| Electron transport | 4 | NDUFS6, NDUFA2, NDUFB6, HIGD2A |
| hsa00190: Oxidative phosphorylation | 4 | NDUFS6, NDUFA2, NDUFB6, ATP5C1 |
| | | Enrichment Score: 0.9077271811850836 |
| h_tnfr1Pathway: TNFR1 Signaling Pathway | 3 | CASP3, LMNA, PRKDC |
| h_fasPathway: FAS signaling pathway (CD95) | 3 | CASP3, LMNA, PRKDC |
| h_hivnefPathway: HIV-I Nef: negative effector of Fas and TNF | 3 | CASP3, LMNA, PRKDC |
| | | Enrichment Score: 0.8974242711787185 |
| Helicase | 6 | DDX39A, DDX3X, DHX15, MCM4, MCM5, CHD3 |
| GO: 0004003~ATP-dependent DNA helicase activity | 3 | DDX3X, MCM4, CHD3 |
| GO: 0004386~helicase activity | 3 | DDX3X, MCM4, CHD3 |
| | | Enrichment Score: 0.8844871978021877 |
| GO: 0005794~Golgi apparatus | 23 | TGOLN2, STX6, KDELR2, USP8, ATP11B, NDFIP2, RAB1B, TOPBP1, ARF5, LMAN2, ERGIC3, PWP1, TAF11, EI24, SP3, ARF3, MAPKAP1, STX16, TMED10, USP33, FGD3, DNM2, KAT6A |
| Golgi apparatus | 15 | TGOLN2, STX6, SNX9, ATP11B, NDFIP2, ARF5, LMAN2, UXS1, ERGIC3, COPB2, ARF3, STX16, TMED10, ENTPD4, USP33 |
| GO: 0000139~Golgi membrane | 10 | STX6, COPB2, KDELR2, ARF3, STX16, NDFIP2, TMED10, RAB1B, LMAN2, DNM2 |
| | | Enrichment Score: 0.8697007217508498 |
| IPR016135: Ubiquitin-conjugating enzyme/RWD-like | 4 | UBE2N, UFC1, UBE2V2, UBE2L3 |
| GO: 0061631~ubiquitin conjugating enzyme activity | 3 | UBE2N, UBE2V2, UBE2L3 |
| IPR000608: Ubiquitin-conjugating enzyme, E2 | 3 | UBE2N, UBE2V2, UBE2L3 |
| GO: 0016567~protein ubiquitination | 7 | KLHL7, UBE2N, NUB1, UBA6, UBE2V2, UBE2L3, TRAF4 |
| | | Enrichment Score: 0.8007359177589985 |
| SM00312: PX domain: PX | 3 | SNX9, PXK, SNX10 |
| | 3 | SNX9, PXK, SNX10 |
| GO: 0035091~phosphatidylinositol binding | 4 | SNX9, PXK, ITPR3, SNX10 |
| IPR001683: Phox homologous domain | 3 | SNX9, PXK, SNX10 |
| | | Enrichment Score: 0.7905595110088506 |
| Thiol protease | 6 | CASP3, USP8, EIF3F, USP10, USP33, ALG13 |
| GO: 0004197~cysteine-type endopeptidase activity | 4 | CASP3, USP8, USP10, USP33 |
| GO: 0004843~thiol-dependent ubiquitin-specific protease activity | 4 | USP8, EIF3F, USP10, USP33 |

TABLE 2-continued

HIV + low cutoff

| Category | Count | Genes |
|---|---|---|
| GO: 0016579~protein deubiquitination | 4 | USP8, EIF3F, USP10, USP33 |
| IPR018200: Peptidase C19, ubiquitin carboxyl-terminal hydrolase 2, conserved site | 3 | USP8, USP10, USP33 |
| IPR001394: Peptidase C19, ubiquitin carboxyl-terminal hydrolase 2 | 3 | USP8, USP10, USP33 |
| | | Enrichment Score: 0.7329253582520423 |
| active site: Glycyl thioester intermediate | 5 | UBE2N, UFC1, UBA6, UBE2L3, TRIP12 |
| GO: 0042787~protein ubiquitination involved in ubiquitin-dependent protein catabolic process | 5 | KLHL7, CUL4A, UBA6, UBE2L3, TRIP12 |
| GO: 0006464~cellular protein modification process | 4 | UBE2N, UBA6, PRKDC, UBE2L3 |
| hsa04120: Ubiquitin mediated proteolysis | 5 | UBE2N, CUL4A, UBA6, UBE2L3, TRIP12 |
| GO: 0004842~ubiquitin-protein transferase activity | 6 | KLHL7, UBE2N, UBE2L3, TTC3, TRIP12, TRAF4 |
| | | Enrichment Score: 0.7159098666001777 |
| Helicase | 6 | DDX39A, DDX3X, DHX15, MCM4, MCM5, CHD3 |
| SM00490: HELICc | 4 | DDX39A, DDX3X, DHX15, CHD3 |
| SM00487: DEXDc | 4 | DDX39A, DDX3X, DHX15, CHD3 |
| domain: Helicase C-terminal | 4 | DDX39A, DDX3X, DHX15, CHD3 |
| domain: Helicase ATP-binding | 4 | DDX39A, DDX3X, DHX15, CHD3 |
| IPR001650: Helicase, C-terminal | 4 | DDX39A, DDX3X, DHX15, CHD3 |
| IPR014001: Helicase, superfamily 1/2, ATP-binding domain | 4 | DDX39A, DDX3X, DHX15, CHD3 |
| GO: 0004004~ATP-dependent RNA helicase activity | 3 | DDX39A, DDX3X, DHX15 |
| IPR011545: DNA/RNA helicase, DEAD/DEAH box type, N-terminal | 3 | DDX39A, DDX3X, DHX15 |
| | | Enrichment Score: 0.69498312277083 |
| Aminoacyl-tRNA synthetase | 3 | AARS, HARS, VARS |
| GO: 0006418~tRNA aminoacylation for protein translation | 3 | AARS, HARS, VARS |
| Ligase | 8 | AARS, HARS, UBA6, CTPS1, ASNS, VARS, TTC3, TRIP12 |
| hsa00970: Aminoacyl-tRNA biosynthesis | 3 | AARS, HARS, VARS |
| | | Enrichment Score: 0.5293095748164424 |
| lipid moiety-binding region: N-myristoyl glycine | 5 | HPCAL1, GNAI2, ARF3, PPP3R1, ARF5 |
| Myristate | 5 | HPCAL1, GNAI2, ARF3, PPP3R1, ARF5 |
| GO: 0003924~GTPase activity | 6 | MFN2, DDX3X, GNAI2, ARF3, ARF5, DNM2 |
| Lipoprotein | 10 | RGS10, HPCAL1, S1PR1, GNAI2, ARF3, PPP3R1, LMNA, RAB1B, STOML2, ARF5 |

TABLE 2-continued

HIV + low cutoff

| Category | Count | Genes |
|---|---|---|
| Enrichment Score: 0.5161555683114979 | | |
| IPR024156: Small GTPase superfamily, ARF type | 3 | ARF3, ARL16, ARF5 |
| IPR006689: Small GTPase superfamily, ARF/SAR type | 3 | ARF3, ARL16, ARF5 |
| nucleotide phosphate-binding region: GTP | 7 | MFN2, GNAI2, ARF3, RAB1B, ARL16, ARF5, DNM2 |
| GO: 0003924~GTPase activity | 6 | MFN2, DDX3X, GNAI2, ARF3, ARF5, DNM2 |
| GTP-binding | 7 | MFN2, GNAI2, ARF3, RAB1B, ARL16, ARF5, DNM2 |
| GO: 0005525~GTP binding | 8 | MFN2, GNAI2, FKBP4, ARF3, RAB1B, ARL16, ARF5, DNM2 |
| IPR005225: Small GTP-binding protein domain | 3 | ARF3, RAB1B, ARF5 |
| GO: 0007264~small GTPase mediated signal transduction | 4 | ARF3, RAB1B, ARL16, ARF5 |
| Enrichment Score: 0.49661457171690665 | | |
| IPR011990: Tetratricopeptide-like helical | 7 | GPS1, NUB1, FKBP4, PPID, PRPF39, TTC3, PRPF6 |
| SM00028: TPR | 4 | FKBP4, PPID, TTC3, PRPF6 |
| IPR013026: Tetratricopeptide repeat-containing domain | 4 | FKBP4, PPID, TTC3, PRPF6 |
| IPR019734: Tetratricopeptide repeat | 4 | FKBP4, PPID, TTC3, PRPF6 |
| repeat: TPR 3 | 4 | FKBP4, PPID, PRKDC, TTC3 |
| TPR repeat | 4 | FKBP4, PPID, PRKDC, TTC3 |
| repeat: TPR 2 | 4 | FKBP4, PPID, PRKDC, TTC3 |
| repeat: TPR 1 | 4 | FKBP4, PPID, PRKDC, TTC3 |
| Enrichment Score: 0.46491176000453827 | | |
| IPR002909: Cell surface receptor IPT/TIG | 3 | NFAT5, NFKB2, EXOC2 |
| IPR014756: Immuno globulin E-set | 3 | NFAT5, NFKB2, EXOC2 |
| IPR013783: Immuno globulin-like fold | 4 | CRLF3, NFAT5, NFKB2, EXOC2 |
| Enrichment Score: 0.4285527179810236 | | |
| GO: 0016491~ oxidoreductase activity | 6 | HSD17B10, KDM1A, AKR1A1, TSTA3, KIAA1191, APEX1 |
| GO: 0055114~ oxidation-reduction process | 12 | GLRX3, HSD17B10, KDM1A, PYCR1, OXA1L, AKR1A1, TSTA3, KIAA1191, APEX1, BCO2, HIGD2A, SOD2 |
| Oxidoreductase | 10 | GCDH, HSD17B10, KDM1A, PYCR1, AKR1A1, TSTA3, KIAA1191, HADHA, BCO2, SOD2 |
| NADP | 4 | PYCR1, AKR1A1, TSTA3, KIAA1191 |
| Enrichment Score: 0.36591445625467517 | | |
| SM00249: PHD | 3 | PHF11, CHD3, KAT6A |
| IPR011011: Zinc finger, FYVE/PHD-type | 4 | PHF11, FGD3, CHD3, KAT6A |
| IPR001965: Zinc finger, PHD-type | 3 | PHF11, CHD3, KAT6A |
| IPR013083: Zinc finger, RING/FYVE/PHD-type | 7 | PHF11, USP33, TTC3, TRAF4, FGD3, CHD3, KAT6A |
| Enrichment Score: 0.25507693482602034 | | |
| domain: SH3 | 4 | ITK, SNX9, HCLS1, SKAP1 |
| SM00326: SH3 | 4 | ITK, SNX9, HCLS1, SKAP1 |
| SH3 domain | 4 | ITK, SNX9, HCLS1, SKAP1 |
| IPR001452: Src homology-3 domain | 4 | ITK, SNX9, HCLS1, SKAP1 |

TABLE 2-continued

| Category | Count | Genes |
|---|---|---|
| HIV + low cutoff | | |
| Enrichment Score: 0.2406171678396523 | | |
| SM00233: PH domain: PH | 5 | ITK, DOK2, SKAP1, FGD3, DNM2 |
| | 5 | ITK, ADRM1, DOK2, SKAP1, DNM2 |
| IPR001849: Pleckstrin homology domain | 5 | ITK, DOK2, SKAP1, FGD3, DNM2 |
| IPR011993: Pleckstrin homology-like domain | 6 | ITK, DOK2, EPB41, SKAP1, FGD3, DNM2 |
| Enrichment Score: 0.1905601056044362 | | |
| hsa04924: Renin secretion | 3 | GNAI2, PPP3R1, ITPR3 |
| hsa04724: Glutamatergic synapse | 3 | GNAI2, PPP3R1, ITPR3 |
| hsa04921: Oxytocin signaling pathway | 3 | GNAI2, PPP3R1, ITPR3 |
| hsa04022: cGMP-PKG signaling pathway | 3 | GNAI2, PPP3R1, ITPR3 |
| Enrichment Score: 0.1700736372529799 | | |
| Kinase | 13 | ITK, PRPF4B, DTYMK, WNK1, SMG1, PRKDC, AK2, PXK, DOK2, CSNK2A1, RFK, MAPKAP1, STK38L |
| GO: 0004672~protein kinase activity | 8 | PRPF4B, CSNK2A1, WNK1, SMG1, PRKDC, PXK, CCL5, STK38L |
| GO: 0004674~protein serine/threonine kinase activity | 8 | PRPF4B, CSNK2A1, WNK1, SMG1, PRKDC, CCNC, CPNE3, STK38L |
| GO: 0018105~peptidyl-serine phosphorylation | 3 | SMG1, PRKDC, STK38L |
| Serine/threonine-protein kinase | 6 | PRPF4B, CSNK2A1, WNK1, SMG1, PRKDC, STK38L |
| IPR011009: Protein kinase-like domain | 8 | ITK, PRPF4B, CSNK2A1, WNK1, SMG1, PRKDC, PXK, STK38L |
| GO: 0006468~protein phosphorylation | 7 | PRPF4B, CSNK2A1, WNK1, CCNC, CPNE3, PXK, STK38L |
| active site: Proton acceptor | 9 | GCDH, HSD17B10, ITK, PRPF4B, CSNK2A1, WNK1, ADSL, APEX1, STK38L |
| binding site: ATP | 7 | ITK, PRPF4B, CSNK2A1, RFK, WNK1, VARS, STK38L |
| domain: Protein kinase | 6 | ITK, PRPF4B, CSNK2A1, WNK1, PXK, STK38L |
| SM00220: S_TKc | 4 | PRPF4B, CSNK2A1, WNK1, STK38L |
| IPR008271: Serine/threonine-protein kinase, active site | 4 | PRPF4B, CSNK2A1, WNK1, STK38L |
| IPR000719: Protein kinase, catalytic domain | 6 | ITK, PRPF4B, CSNK2A1, WNK1, PXK, STK38L |
| IPR017441: Protein kinase, ATP binding site | 3 | ITK, CSNK2A1, STK38L |
| Enrichment Score: 0.11135414381747946 | | |
| topological domain: Lumenal | 10 | KDELR2, SEC11A, ALG5, TMED10, SPCS1, LMAN2, ENTPD4, UXS1, SSR2, ERGIC3 |
| topological domain: Cytoplasmic | 21 | TGOLN2, STX6, KDELR2, SEC11A, GPR171, ATP11B, ALG5, CD99, LMAN2, ITPR3, UXS1, ERGIC3, MFN2, S1PR1, STX16, TMEM170A, TMED10, SPCS1, ENTPD4, SSR2, HIGD2A |
| signal peptide | 15 | TGOLN2, HYOU1, CST7, ERP29, CNPY3, CCDC47, TMED10, CD99, LRCH3, MESDC2, HSPA13, LMAN2, CCL5, SSR2, SOD2 |
| Glycoprotein | 23 | TGOLN2, EPB41, CWC27, GPR171, WNK1, CNPY3, ALG5, CCDC47, CD99, MESDC2, LMAN2, CCL5, UXS1, RBMX, ERGIC3, HYOU1, S1PR1, NUP62, CST7, TMEM170A, TMED10, ENTPD4, SSR2 |
| Signal | 18 | TGOLN2, ERP29, WNK1, CNPY3, CCDC47, CD99, MESDC2, LMAN2, CCL5, HYOU1, RAE1, CST7, TMED10, ABHD10, LRCH3, HSPA13, BCO2, SSR2 |
| glycosylation site: N-linked (GlcNAc . . . ) | 17 | TGOLN2, CWC27, GPR171, CNPY3, ALG5, CCDC47, MESDC2, LMAN2, UXS1, ERGIC3, HYOU1, S1PR1, CST7, TMEM170A, TMED10, ENTPD4, SSR2 |
| Enrichment Score: 0.0903744092851981 | | |
| repeat: 5 | 3 | TGOLN2, NUP62, DNMT1 |
| repeat: 4 | 3 | TGOLN2, NUP62, DNMT1 |

TABLE 2-continued

HIV + low cutoff

| Category | Count | Genes |
|---|---|---|
| repeat: 3 | 3 | TGOLN2, NUP62, DNMT1 |
| repeat: 1 | 3 | TGOLN2, NUP62, DNMT1 |
| repeat: 2 | 3 | TGOLN2, NUP62, DNMT1 |
| | | Enrichment Score: 0.069370372136031 |
| GO: 0098609~cell-cell adhesion | 4 | SNX9, USP8, DDX3X, IST1 |
| GO: 0098641~cadherin binding involved in cell-cell adhesion | 4 | SNX9, USP8, DDX3X, IST1 |
| GO: 0005913~cell-cell adherens junction | 4 | SNX9, USP8, DDX3X, IST1 |
| | | Enrichment Score: 0.05747010288539574 |
| domain: EF-hand 2 | 3 | HPCAL1, EFCAB14, PPP3R1 |
| domain: EF-hand 1 | 3 | HPCAL1, EFCAB14, PPP3R1 |
| IPR002048: EF-hand domain | 3 | HPCAL1, EFCAB14, PPP3R1 |
| IPR011992: EF-hand-like domain | 3 | HPCAL1, EFCAB14, PPP3R1 |
| Calcium | 7 | HPCAL1, EFCAB14, PPP3R1, TKT, LMAN2, ENTPD4, ITPR3 |
| GO: 0005509~calcium ion binding | 5 | HPCAL1, EFCAB14, PPP3R1, CCDC47, ITPR3 |
| | | Enrichment Score: 0.04306870373594361 |
| IPR013083: Zinc finger, RING/FYVE/PHD-type | 7 | PHF11, USP33, TTC3, TRAF4, FGD3, CHD3, KAT6A |
| GO: 0008270~zinc ion binding | 13 | POLR2K, TIMM9, AARS, TIMM10, DNMT1, PHF11, TCEA1, SREK1IP1, USP33, TTC3, TRAF4, CHD3, KAT6A |
| Zinc | 24 | VPS29, ITK, POLR2K, AARS, TIMM10, NOB1, PHF11, TTC3, SUZ12, PRIM1, LAP3, PSMD14, RFK, SP3, TIMM9, DNMT1, TCEA1, SREK1IP1, USP33, FGD3, TRAF4, GPATCH8, CHD3, KAT6A |
| Zinc-finger | 15 | ITK, POLR2K, PHF11, TTC3, SUZ12, SP3, DNMT1, TCEA1, SREK1IP1, USP33, TRAF4, GPATCH8, FGD3, CHD3, KAT6A |
| | | Enrichment Score: 9.170272943712669E−6 |
| Membrane | 78 | TGOLN2, OXA1L, COA3, UTP18, CAPZA2, DNAJB14, ALG5, STOML2, RAB1B, LINC00116, SKAP1, UXS1, THADA, NDUFS6, COPB2, ATAD3B, S1PR1, ELOVL5, DNAJC9, MAPKAP1, TIMM9, YRDC, STX6, KDELR2, BCL10, GPR171, CCDC47, TMEM126B, ERGIC3, MFN2, EIF5AL1, TMEM170A, ATP5C1, AAMP, LRCH3, SLC25A39, VPS26B, SNX10, HIGD2A, VPS29, SNX9, USP8, NDUFB6, GNAI2, CRLF3, PPP3R1, TIMM10, UBA6, ARF5, LMAN2, PXK, PTRH2, DDX3X, STX16, NFAT5, TMED10, ENTPD4, STK38L, TRAF4, NDUFA2, HPCAL1, SMCHD1, FIBP, HCLS1, SEC11A, TMEM120B, FDPS, ATP11B, CD99, TOMM40, NDFIP2, ITPR3, EI24, SPCS1, CPNE3, TEX10, SSR2, DNM2 |
| GO: 0016021~integral component of membrane | 46 | TGOLN2, OXA1L, NDUFB6, COA3, CRLF3, UTP18, CAPZA2, DNAJB14, UBA6, ALG5, LINC00116, PTRH2, UXS1, THADA, S1PR1, ELOVL5, STX16, NFAT5, TMED10, ENTPD4, STX6, KDELR2, SMCHD1, SEC11A, GPR171, TMEM120B, ATP11B, FDPS, NDFIP2, CCDC47, TOMM40, CD99, TMEM126B, ITPR3, ERGIC3, MFN2, EI24, TMEM170A, TCEB3, LRCH3, SPCS1, SLC25A39, VPS26B, TEX10, SSR2, HIGD2A |
| Transmembmne | 46 | TGOLN2, OXA1L, NDUFB6, COA3, CRLF3, UTP18, CAPZA2, DNAJB14, UBA6, ALG5, LINC00116, LMAN2, PTRH2, UXS1, THADA, S1PR1, ELOVL5, STX16, NFAT5, TMED10, ENTPD4, STX6, KDELR2, SMCHD1, SEC11A, GPR171, TMEM120B, ATP11B, FDPS, NDFIP2, CCDC47, TOMM40, CD99, TMEM126B, ITPR3, ERGIC3, MFN2, EI24, TMEM170A, LRCH3, SPCS1, SLC25A39, VPS26B, TEX10, SSR2, HIGD2A |
| Transmembmne helix | 45 | TGOLN2, OXA1L, NDUFB6, COA3, UTP18, CRLF3, CAPZA2, DNAJB14, UBA6, ALG5, LINC00116, LMAN2, PTRH2, UXS1, THADA, S1PR1, ELOVL5, STX16, NFAT5, TMED10, ENTPD4, STX6, KDELR2, SMCHD1, SEC11A, GPR171, TMEM120B, ATP11B, FDPS, NDFIP2, CCDC47, CD99, TMEM126B, ITPR3, ERGIC3, MFN2, EI24, TMEM170A, LRCH3, SPCS1, SLC25A39, VPS26B, TEX10, SSR2, HIGD2A |
| topological domain: Cytoplasmic | 21 | TGOLN2, STX6, KDELR2, SEC11A, GPR171, ATP11B, ALG5, CD99, LMAN2, ITPR3, UXS1, ERGIC3, MFN2, S1PR1, STX16, TMEM170A, TMED10, SPCS1, ENTPD4, SSR2, HIGD2A |
| transmembmne region | 35 | TGOLN2, OXA1L, NDUFB6, COA3, DNAJB14, ALG5, LINC00116, LMAN2, UXS1, S1PR1, ELOVL5, STX16, TMED10, ENTPD4, SREK1IP1, STX6, KDELR2, SEC11A, GPR171, TMEM120B, ATP11B, NDFIP2, CCDC47, CD99, TMEM126B, ITPR3, ERGIC3, MFN2, EI24, TMEM170A, SPCS1, SLC25A39, SSR2, TEX10, HIGD2A |

TABLE 2-continued

HIV + low cutoff

| Category | Count | Genes |
|---|---|---|
| Acetylation | 143 | MRPS33, PRPF4B, CAPZA2, DTYMK, RAB1B, STOML2, FOXO1, PRIM1, TOP1, GTF2E2, S1PR1, ELOVL5, VPS13D, TIMM9, EIF1, PTBP3, PPP4C, SUPT5H, DDX39A, BCL10, AARS, ERGIC3, ADRM1, PYCR1, DCUN1D1, EIF2S1, CLPP, ATP5C1, HARS, ADSL, HIGD2A, SNX9, MEAF6, HSD17B10, UBA6, CTPS1, UBE2V2, BANF1, HADHA, PSMB4, POLE4, DDX3X, HTATSF1, MTPN, EIF3F, STK38L, TFDP1, PRPF40A, GCDH, ARL14EP, SMCHD1, FIBP, CCDC25, MMADHC, FDPS, AK2, SMG1, TKT, DENR, TPD52L2, UBE2L3, RBMX, PTPN11, HYOU1, EI24, NUP62, PSMC4, PPID, METTL10, WDR4, BABAM1, RBMXL1, DNMT1, EIF4E2, GPATCH8, KAT6A, SRSF1, HNRNPA1L2, COA3, TCOF1, BOD1L1, COPB2, NDUFS6, CASP3, ATAD3B, MAPKAP1, USP10, DDA1, STX6, NCOA7, POLR1C, RBBP7, MCM4, MCM5, PURA, UBE2N, TAF11, LAP3, KPNA3, THOC1, VPS29, GLRX3, NXT1, NDUFB6, CRLF3, FKBP4, FKBP3, RNH1, RPL35, PRKDC, ASNS, VARS, HPRT1, SRRT, MRPL13, FAM107B, AKR1A1, CD2BP2, REXO2, DHX15, NFAT5, GTF3C6, TCEA1, APEX1, EXOC2, TRIP12, NDUFA2, CWC27, HCLS1, LMNA, ACLY, ETF1, COTL1, SMC2, SMC3, SOD2, PPP1R2, SP3, CKS2, TCEB3, PSAT1, SSNA1, DNM2 |
| Proteomics identification | 235 | TGOLN2, OXA1L, DNAJB14, RAB1B, STOML2, UXS1, PRIM1, C1ORF109, WDR73, VPS13D, RAE1, EIF1AY, PTBP3, SREK1IP1, SUPT5H, RCOR1, AARS, WNK1, CCDC137, ERGIC3, EIF2S1, HARS, ADSL, LRCH3, MRPL48, CPSF3L, HSD17B10, GNAI2, PABPC4, UBA6, PXK, ARF5, BANF1, HADHA, HTATSF1, STX16, CDC40, TMED10, PRPF40A, GCDH, HPCAL1, TMEM120B, ATP11B, NDFIP2, YTHDC1, TKT, TPD52L2, GCFC2, PTPN11, HYOU1, EI24, NUP62, MLX, METTL10, UTP14A, SNRNP25, ALG13, BCO2, KAT6A, SRSF1, UTP18, TCOF1, NFKB2, RPS19BP1, BOD1L1, COPB2, WDR36, USP10, KDELR2, MRPL4, CNPY3, PRPF39, POLR1C, CCNC, MESDC2, RBBP7, DOK2, THOC1, USP8, POLR2K, NOB1, RPL35, SRRT, MRPL13, CIR1, REXO2, TCEA1, TSTA3, USP33, EXOC2, TRIP12, NUB1, CWC27, HCLS1, LMNA, ACLY, PHF11, ETF1, SOD2, PSMD14, MRPL22, PPP1R2, MRPL28, IST1, TCEB3, SSNA1, SSR2, TEX10, DNM2, MRPS35, MRPS33, PRPF4B, CAPZA2, DTYMK, RBM6, TCEAL8, SRP19, CNOT7, MAF1, KLHL7, KDM1A, GTF2E2, CSNK2A1, NUDCD1, ELOVL5, TIMM9, EIF1, PPP4C, IFRD2, DDX39A, BCL10, ERP29, HMCES, ARL16, TOPBP1, TMEM126B, SUZ12, ADRM1, PYCR1, DCUN1D1, SMARCE1, RFK, CLPP, SLC25A39, VPS26B, SNRPG, SNX9, MEAF6, UBE2V2, LMAN2, PTRH2, CCL5, FAM207A, TTC3, PSMB7, DDX3X, MTPN, EIF3F, ENTPD4, STK38L, TRAF4, TFDP1, ITK, ARL14EP, SMCHD1, FIBP, CCDC25, EPB41, MMADHC, SEC11A, FDPS, AK2, TOMM40, SMG1, THUMPD2, DENR, RBMX, PPID, BABAM1, DNMT1, CPNE3, SPCS1, EIF4E2, GPATCH8, COA3, SKAP1, THADA, NDUFS6, CASP3, MAPKAP1, ABHD10, FTSJ3, METTL5, CCDC47, NCOA7, MCM4, MCM5, LAP3, MFN2, UBE2N, NCOA4, PPM1K, AAMP, KPNA3, KIAA1191, SNX10, C1D, VPS29, NDUFB6, CRLF3, FKBP4, FKBP3, PPP3R1, RNH1, PRKDC, ASNS, VARS, AKR1A1, FAM107B, UFM1, CCDC124, NFAT5, APEX1, CHD3, GPS1, CD99, COTL1, SMC2, RSBN1, SLBP, PWP1, PSMG4, CUL4A, SP3, CENPV |
| Phosphoprotein | 193 | TGOLN2, OXA1L, STOML2, RAB1B, UXS1, S1PR1, RAE1, VPS13D, PTBP3, SUPT5H, SREK1IP1, EFCAB14, RCOR1, AARS, WNK1, KRT10, CCDC137, ERGIC3, EIF2S1, HARS, ATP5C1, ADSL, LRCH3, MCTS1, NOC3L, PABPC4, UBA6, BANF1, HADHA, VPS72, HTATSF1, CDC40, STX16, PRPF40A, ATP11B, NDFIP2, YTHDC1, TKT, TPD52L2, GCFC2, PTPN11, HYOU1, EI24, NUP62, MLX, METTL10, RBMXL1, UTP14A, KAT6A, SRSF1, UTP18, TCOF1, NFKB2, RPS19BP1, BOD1L1, COPB2, WDR36, USP10, STX6, PRPF39, CCNC, POLR1C, RBBP7, NOC2L, DOK2, THOC1, USP8, RPL35, NOB1, HPRT1, NUFIP2, SRRT, CIR1, CD2BP2, REXO2, DHX15, TCEA1, USP33, TRIP12, EXOC2, HCLS1, CWC27, LMNA, ACLY, ITPR3, ETF1, PSMD14, PPP1R2, IST1, TCEB3, PSAT1, TEX10, DNM2, PRPF4B, CAPZA2, FOXO1, RBM6, MAF1, TOP1, KDM1A, GTF2E2, CSNK2A1, ELOVL5, NUDCD1, DNAJC9, EIF1, DDX39A, BCL10, ERP29, HMCES, TMEM126B, TOPBP1, SUZ12, PYCR1, ADRM1, SMARCE1, VPS26B, MEAF6, SNX9, CTPS1, TTC3, FAM207A, PSMB4, POLE4, DDX3X, MTPN, EIF3F, ASF1A, STK38L, TRAF4, FGD3, TFDP1, ARL14EP, ITK, SMCHD1, CCDC25, EPB41, SMG1, AK2, DENR, RBMX, PSMC4, PPID, BABAM1, WDR4, DNMT1, CPNE3, GPATCH8, EIF4E2, HNRNPA1L2, SKAP1, THADA, CASP3, MAPKAP1, YRDC, DDA1, FTSJ3, NCOA7, MCM4, MCM5, PRPF6, PURA, LAP3, MFN2, PPM1K, AAMP, KIAA1191, KPNA3, C1D, GLRX3, FKBP4, FKBP3, PPP3R1, RNH1, PRKDC, ASNS, VARS, RGS10, AKR1A1, CCDC124, GTF3C6, NFAT5, APEX1, CHD3, GPS1, CD99, RSBN1, SMC3, PWP1, SLBP, CUL4A, SP3, CENPV |
| GO: 0044822~poly (A) RNA binding | 63 | SRSF1, MRPS35, PRPF4B, UTP18, TCOF1, RBM6, SRP19, RPS19BP1, TOP1, GTF2E2, WDR36, USP10, PTBP3, EIF1, SUPT5H, FTSJ3, DDX39A, MRPL4, CCDC47, CCDC137, PURA, NOC2L, PRPF6, UBE2N, EIF2S1, ATP5C1, SNRPG, GLRX3, HSD17B10, FKBP4, NOC3L, FKBP3, PABPC4, RPL35, PRKDC, NUFIP2, SRRT, MRPL13, DDX3X, CCDC124, HTATSF1, CDC40, MRPL54, DHX15, APEX1, CHD3, PRPF40A, MRPS26, FDPS, SMG1, YTHDC1, TPD52L2, ETF1, UBE2L3, RBMX, SLBP, MRPL22, MRPL28, CPNE3, UTP14A, ALG13, EIF4E2, GPATCH8 |

TABLE 2-continued

HIV + low cutoff

| Category | Count | Genes |
|---|---|---|
| GO: 0005654~ nucleoplasm | 100 | TGOLN2, PRPF4B, FOXO1, MAF1, CNOT7, KLHL7, PRIM1, TOP1, KDM1A, GTF2E2, CSNK2A1, SUPT5H, PPP4C, DDX39A, RCOR1, TOPBP1, SUZ12, ADRM1, SMARCE1, SNRPG, CPSF3L, MEAF6, GNAI2, UBE2V2, BANF1, VPS72, PSMB4, PSMB7, HTATSF1, CDC40, ASF1A, TFDP1, PRPF40A, MRPS26, FDPS, TOMM40, TKT, RBMX, GCFC2, PSMC4, PPID, BABAM1, WDR4, DNMT1, UTP14A, SNRNP25, KAT6A, SRSF1, UTP18, NFKB2, RPS19BP1, BOD1L1, CASP3, WDR36, MAPKAP1, USP10, CCNC, POLR1C, RBBP7, MCM4, MCM5, PRPF6, NOC2L, UBE2N, TAF11, LAP3, KPNA3, C1D, THOC1, NXT1, NDUFB6, USP8, POLR2K, FKBP4, RNH1, NOB1, PPP3R1, PRKDC, SRRT, CD2BP2, GTF3C6, NFAT5, TCEA1, APEX1, USP33, TRIP12, CHD3, GPS1, LMNA, ACLY, ITPR3, SMC2, SMC3, SLBP, PSMD14, CUL4A, SP3, CENPV, TCEB3, TEX10 |
| Nucleus | 128 | PRPF4B, RBM6, FOXO1, TCEAL8, CNOT7, MAF1, KLHL7, KDM1A, TOP1, GTF2E2, CSNK2A1, NUDCD1, RAE1, DNAJC9, PPP4C, SUPT5H, DDX39A, RCOR1, TOPBP1, SUZ12, ADRM1, DCUN1D1, SMARCE1, TMEM170A, SNRPG, CPSF3L, MEAF6, NOC3L, BANF1, TTC3, VPS72, PSMB4, POLE4, PSMB7, DDX3X, MTPN, HTATSF1, CDC40, ASF1A, TRAF4, TFDP1, PRPF40A, FIBP, EPB41, TMEM120B, YTHDC1, SMG1, UBE2L3, RBMX, GCFC2, PTPN11, EI24, NUP62, PSMC4, PPID, MLX, WDR4, BABAM1, RBMXL1, DNMT1, CPNE3, UTP14A, SNRNP25, KAT6A, HNRNPA1L2, SRSF1, UTP18, TCOF1, NFKB2, SKAP1, RPS19BP1, WDR36, MAPKAP1, USP10, FTSJ3, NCOA7, PRPF39, CCNC, POLR1C, RBBP7, MCM4, MCM5, PURA, PRPF6, NOC2L, UBE2N, TAF11, EIF5AL1, KPNA3, THOC1, C1D, NXT1, USP8, POLR2K, FKBP4, FKBP3, NOB1, PRKDC, NUFIP2, RGS10, SRRT, CIR1, CD2BP2, UFM1, REXO2, DHX15, NFAT5, GTF3C6, TCEA1, APEX1, TRIP12, CHD3, GPS1, NUB1, LMNA, PHF11, COTL1, SMC2, SMC3, RSBN1, SLBP, PWP1, IST1, SP3, CENPV, TCEB3, SSNA1, TEX10 |
| Ubl conjugation | 59 | SRSF1, PRPF4B, TCOF1, RBM6, FOXO1, NFKB2, MAF1, BOD1L1, TOP1, EIF1AY, USP10, SUPT5H, DDX39A, AARS, WNK1, HMCES, TOPBP1, RBBP7, MCM4, UBE2N, SUZ12, MIN2, ADRM1, SMARCE1, ADSL, C1D, THOC1, SNX9, MEAF6, USP8, FKBP4, PRKDC, PTRH2, HPRT1, NUFIP2, DDX3X, UFM1, NFAT5, TCEA1, USP33, APEX1, TRAF4, CHD3, PRPF40A, ITK, SMCHD1, LMNA, NDIFP2, YTHDC1, ACLY, UBE2L3, RBMX, RSBN1, CUL4A, SP3, DNMT1, RBMXL1, UTP14A, EIF4E2 |
| GO: 0005737~ cytoplasm | 127 | MRPS35, FOXO1, SRP19, MAF1, KLHL7, GTF2E2, NUDCD1, RAE1, DNAJC9, EIF1, PDRG1, PPP4C, DDX39A, BCL10, AARS, WNK1, KRT10, TOPBP1, ADRM1, RFK, CST7, EIF2S1, HARS, LRCH3, MCTS1, CPSF3L, SNX9, MEAF6, HSD17B10, GNAI2, PABPC4, UBA6, UBE2V2, ARF5, PXK, CCL5, BANF1, TTC3, PSMB4, PSMB7, DDX3X, STX16, STK38L, TRAF4, FGD3, PRPF40A, ARL14EP, EPB41, MMADHC, FDPS, NDFIP2, TOMM40, SMG1, TPD52L2, UBE2L3, PTPN11, EI24, NUP62, PSMC4, PPID, MLX, METTL10, WDR4, BABAM1, DNMT1, CPNE3, EIF4E2, SNRNP25, SRSF1, HNRNPA1L2, TCOF1, UFC1, NFKB2, SKAP1, RPS19BP1, CASP3, MAPKAP1, USP10, YRDC, PURA, NOC2L, UBE2N, LAP3, AAMP, KPNA3, KIAA1191, THOC1, C1D, VPS29, NXT1, USP8, CRLF3, FKBP4, RNH1, RPL35, HPRT1, NUFIP2, SRRT, CIR1, CCDC124, UFM1, DHX15, NFAT5, TSTA3, USP33, APEX1, TRIP12, CHD3, GPS1, NUB1, HCLS1, LMNA, CD99, ACLY, COTL1, ITPR3, ETF1, SMC2, SMC3, SLBP, MRPL28, SP3, CENPV, PSAT1, TEX10, DNM2 |
| Protein biosynthesis | 16 | AARS, DENR, VARS, ETF1, MTIF3, EIF2S1, EIF5AL1, EIF3F, EIF1AY, HARS, TCEB3, TCEA1, EIF1, SUPT5H, MCTS1, EIF4E2 |
| mRNA splicing | 20 | HNRNPA1L2, SRSF1, DDX39A, PRPF4B, YTHDC1, PRPF39, RBMX, GCFC2, PRPF6, CIR1, CD2BP2, CDC40, DHX15, RBMXL1, PTBP3, SREK1IP1, SNRNP25, THOC1, SNRPG, PRPF40A |
| Mitochondrion | 43 | HSD17B10, MRPS35, OXA1L, NDUFB6, MRPS33, COA3, FKBP4, TIMM10, STOML2, PTRH2, MTIF3, HADHA, NDUFS6, MRPL13, ATAD3B, DDX3X, TIMM9, REXO2, MRPL54, ABHD10, YRDC, APEX1, GCDH, MRPS26, MRPL4, NDUFA2, MMADHC, HCLS1, AK2, TOMM40, TMEM126B, SOD2, MFN2, PYCR1, MRPL22, MRPL28, PPM1K, CLPP, ATP5C1, MRPL48, SLC25A39, BCO2, HIGD2A |
| Isopeptide bond | 43 | SRSF1, MEAF6, PRPF4B, FKBP4, TCOF1, RBM6, NFKB2, PTRH2, MAF1, HPRT1, NUFIP2, BOD1L1, TOP1, DDX3X, UFM1, EIF1AY, NFAT5, TCEA1, SUPT5H, PRPF40A, CHD3, DDX39A, SMCHD1, HMCES, LMNA, YTHDC1, ACLY, RBBP7, RBMX, RSBN1, UBE2N, SUZ12, ADRM1, CUL4A, SMARCE1, SP3, RBMXL1, ADSL, DNMT1, UTP14A, EIF4E2, THOC1, C1D |
| GO: 0005515~protein binding | 145 | OXA1L, PRPF4B, RAB1B, STOML2, FOXO1, CNOT7, KDM1A, C1ORF109, TOP1, GTF2E2, CSNK2A1, ELOVL5, PPP4C, SUPT5H, SREK1IP1, DDX39A, BCL10, RCOR1, ARL16, TOPBP1, SUZ12, ADRM1, PYCR1, DCUN1D1, SMARCE1, EIF2S1, CLPP, TMEM170A, MRPL48, SNRPG, CPSF3L, SNX9, MEAF6, HSD17B10, GNAI2, UBA6, UBE2V2, ARF5, PTRH2, CCL5, BANF1, TTC3, VPS72, POLE4, PSMB7, DDX3X, STX16, EIF3F, TMED10, STK38L, ASF1A, TRAF4, TFDP1, PRPF40A, ITK, HPCAL1, EPB41, TSR2, MMADHC, ATP11B, YTHDC1, NDFIP2, SMG1, UBE2L3, RBMX, PTPN11, PSMC4, NUP62, PPID, WDR4, BABAM1, DNMT1, SPCS1, CPNE3, HSPA13, EIF4E2, SNRNP25, KAT6A, SRSF1, COA3, UFC1, NFKB2, SKAP1, RPS19BP1, CASP3, USP10, STX6, CCNC, POLR1C, RBBP7, MCM4, MCM5, PURA, |

TABLE 2-continued

HIV + low cutoff

| Category | Count | Genes |
|---|---|---|
| | | PRPF6, NOC2L, MFN2, UBE2N, TAF11, PPM1K, KPNA3, SNX10, THOC1, C1D, VPS29, GLRX3, NXT1, USP8, CRLF3, FKBP4, RNH1, PPP3R1, PRKDC, HPRT1, VARS, NUFIP2, SRRT, MRPL13, CIR1, CD2BP2, DHX15, GTF3C6, USP33, APEX1, EXOC2, TRIP12, CHD3, NUB1, HCLS1, LMNA, ACLY, ITPR3, ETF1, SMC2, SMC3, SLBP, PSMD14, PPP1R2, CUL4A, MRPL28, IST1, SP3, CKS2, TCEB3, SSNA1, DNM2 |
| mRNA processing | 21 | HNRNPA1L2, SRSF1, DDX39A, PRPF4B, YTHDC1, PRPF39, RBMX, GCFC2, SLBP, PRPF6, CIR1, CD2BP2, CDC40, DHX15, RBMXL1, PTBP3, SREK1IP1, SNRNP25, THOC1, SNRPG, PRPF40A |
| GO: 0005739~mitochondrion | 47 | HSD17B10, MRPS35, OXA1L, NDUFB6, MRPS33, COA3, FKBP4, DTYMK, PPP3R1, TIMM10, FOXO1, RAB1B, PTRH2, SRP19, VARS, UXS1, MTIF3, HADHA, TIMM9, REXO2, ABHD10, YRDC, APEX1, TFDP1, GCDH, MRPS26, MRPL4, FIBP, MMADHC, HCLS1, AARS, NDFIP2, TOMM40, PTPN11, SOD2, MIN2, LAP3, PYCR1, MRPL22, MRPL28, RFK, PPM1K, CLPP, HARS, ATP5C1, ADSL, BCO2 |
| GO: 0005743~mitochondrial inner membrane | 24 | MRPS35, MRPS26, MRPL4, NDUFA2, OXA1L, MRPS33, NDUFB6, TIMM10, STOML2, AK2, TMEM126B, HADHA, SOD2, NDUFS6, MRPL22, MRPL13, ATAD3B, MRPL28, MRPL54, ATP5C1, MRPL48, SLC25A39, HIGD2A |
| Cytoplasm | 106 | RAB1B, STOML2, FOXO1, CNOT7, MAF1, SRP19, WDR73, NUDCD1, RAE1, DNAJC9, PDRG1, PPP4C, DDX39A, BCL10, AARS, WNK1, TOPBP1, ADRM1, RFK, CST7, HARS, VPS26B, MCTS1, SNRPG, CPSF3L, SNX9, GNAI2, PABPC4, ARF5, PXK, BANF1, PSMB4, PSMB7, DDX3X, MTPN, EIF3F, STX16, STK38L, TRAF4, FGD3, ARL14EP, ITK, EPB41, MMADHC, FDPS, SMG1, UBE2L3, PTPN11, EI24, NUP62, PSMC4, PPID, ARF3, MLX, METTL10, BABAM1, CPNE3, HNRNPA1L2, SRSF1, NFKB2, SKAP1, COPB2, CASP3, USP10, UBE2N, LAP3, EIF5AL1, AAMP, KPNA3, KIAA1191, SNX10, THOC1, C1D, VPS29, GLRX3, NXT1, USP8, CRLF3, FKBP4, RNH1, PPP3R1, HPRT1, NUFIP2, RGS10, SRRT, CIR1, CCDC124, CD2BP2, UFM1, REXO2, NFAT5, APEX1, USP33, CHD3, GPS1, HCLS1, ACLY, COTL1, ETF1, SMC2, SLBP, IST1, CENPV, SSNA1, TEX10, DNM2 |
| GO: 0005634~nucleus | 122 | DTYMK, RBM6, FOXO1, TCEAL8, SRP19, CNOT7, MAF1, KLHL7, KDM1A, TOP1, GTF2E2, CSNK2A1, NUDCD1, RAE1, DNAJC9, PTBP3, EIF1, PPP4C, SUPT5H, IFRD2, DDX39A, BCL10, RCOR1, KRT10, TOPBP1, SUZ12, ADRM1, DCUN1D1, SMARCE1, EIF2S1, PABPC4, NOC3L, UBE2V2, PXK, BANF1, TTC3, VPS72, PSMB4, POLE4, PSMB7, DDX3X, MTPN, HTATSF1, ASF1A, TRAF4, TFDP1, EPB41, FIBP, TSR2, YTHDC1, SMG1, TKT, UBE2L3, RBMX, GCFC2, PTPN11, PSMC4, PPID, MLX, WDR4, BABAM1, RBMXL1, DNMT1, CPNE3, SNRNP25, KAT6A, SRSF1, UTP18, TCOF1, NFKB2, SKAP1, CASP3, MAPKAP1, USP10, FTSJ3, NCOA7, CCNC, RBBP7, MCM4, MCM5, PURA, PRPF6, NOC2L, UBE2N, LAP3, NCOA4, KPNA3, SNX10, THOC1, C1D, GLRX3, POLR2K, FKBP4, NUFIP2, RGS10, CIR1, CD2BP2, UFM1, REXO2, DHX15, NFAT5, TCEA1, APEX1, TRIP12, CHD3, NUB1, HCLS1, LMNA, PHF11, COTL1, ETF1, SMC2, SMC3, RSBN1, SLBP, PWP1, PSMD14, SP3, CENPV, TCEB3, SSNA1, DNM2 |
| Chaperone | 15 | FKBP4, TIMM10, DNAJB14, CNPY3, MESDC2, TMEM126B, RBBP7, COTL1, HYOU1, PSMG4, DNAJC9, PPID, TIMM9, PDRG1, ASF1A |
| Ribonucleoprotein | 18 | HNRNPA1L2, MRPS35, MRPS26, MRPL4, MRPS33, RPL35, RPL39, SRP19, RBMX, RPS19BP1, SLBP, MRPL22, MRPL13, MRPL28, MRPL54, RBMXL1, MRPL48, SNRPG |
| GO: 0005730~nucleolus | 34 | MEAF6, UTP18, NOC3L, TCOF1, RPL35, PRKDC, SRP19, MAF1, RPS19BP1, TTC3, KLHL7, TOP1, WDR36, RAE1, REXO2, DHX15, TCEA1, APEX1, FTSJ3, CHD3, NUB1, CCDC137, ITPR3, SMC2, GCFC2, PWP1, NOC2L, SUZ12, UBE2N, PPID, UTP14A, TEX10, KAT6A, C1D |
| GO: 0003723~RNA binding | 27 | HNRNPA1L2, SRSF1, PABPC4, RBM6, CNOT7, RPL39, NUFIP2, DDX3X, RAE1, HTATSF1, PTBP3, PRPF40A, MRPL4, YTHDC1, THUMPD2, ETF1, RBBP7, RBMX, PRPF6, PURA, SUZ12, SMARCE1, DNMT1, RBMXL1, THOC1, C1D, SNRPG |
| GO: 0005829~cytosol | 83 | TGOLN2, CAPZA2, DTYMK, FOXO1, NFKB2, SRP19, MAF1, CNOT7, SKAP1, COPB2, CASP3, WDR73, CSNK2A1, S1PR1, MAPKAP1, ABHD10, STX6, BCL10, AARS, WNK1, POLR1C, MFN2, UBE2N, DOK2, RFK, EIF2S1, HARS, ADSL, VPS26B, KPNA3, SNRPG, VPS29, NXT1, USP8, GNAI2, POLR2K, FKBP4, PPP3R1, NOB1, RPL35, UBA6, CTPS1, PRKDC, ASNS, HPRT1, VARS, RPL39, PTRH2, BANF1, PSMB4, RGS10, PSMB7, AKR1A1, MTPN, EIF3F, STX16, TSTA3, EXOC2, TRIP12, FGD3, ITK, MMADHC, LMNA, FDPS, AK2, SMG1, TKT, ACLY, ITPR3, ETF1, SMC2, SMC3, PTPN11, SLBP, PSMD14, PSMC4, IST1, WDR4, CPNE3, PSAT1, SSNA1, EIF4E2, DNM2 |
| GO: 0000398~mRNA splicing, via spliceosome | 15 | SRSF1, DDX39A, PRPF4B, POLR2K, CWC27, RBMX, PRPF6, SRRT, CD2BP2, HTATSF1, CDC40, DHX15, SNRNP25, SNRPG, PRPF40A |
| Initiation factor | 8 | EIF2S1, EIF1AY, EIF3F, EIF1, DENR, MCTS1, MTIF3, EIF4E2 |
| GO: 0003743~translation initiation factor activity | 8 | EIF2S1, EIF1AY, EIF3F, EIF1, DENR, MCTS1, MTIF3, EIF4E2 |

TABLE 2-continued

HIV + low cutoff

| Category | Count | Genes |
|---|---|---|
| GO: 0070125~mitochondrial translational elongation | 9 | MRPS35, MRPS26, MRPL22, MRPL4, MRPL13, MRPS33, MRPL28, MRPL54, MRPL48 |
| mutagenesis site | 55 | SRSF1, TGOLN2, FOXO1, UFC1, RAB1B, NFKB2, SKAP1, KDM1A, TOP1, S1PR1, USP10, SUPT5H, PPP4C, BCL10, NCOA7, UBE2N, MFN2, PPM1K, NCOA4, EIF5AL1, MCTS1, THOC1, CPSF3L, VPS29, NXT1, PRKDC, UBA6, ASNS, PXK, BANF1, DDX3X, AKR1A1, UFM1, HTATSF1, REXO2, ASF1A, STK38L, USP33, APEX1, GCDH, EPB41, NUB1, LMNA, SMG1, COTL1, SLBP, PTPN11, SOD2, CUL4A, SP3, IST1, CENPV, DNMT1, EIF4E2, KAT6A |
| GO: 0070126~mitochondrial translational termination | 9 | MRPS35, MRPS26, MRPL22, MRPL4, MRPL13, MRPS33, MRPL28, MRPL54, MRPL48 |
| Ribosomal protein | 12 | MRPS35, MRPS26, MRPL22, MRPL4, MRPL13, MRPS33, MRPL28, MRPL54, RPL35, MRPL48, RPL39, RPS19BP1 |
| transit peptide: Mitochondrion | 20 | GCDH, MRPS35, MRPS26, OXA1L, MMADHC, PTRH2, MTIF3, HADHA, SOD2, NDUFS6, MRPL22, MRPL28, PPM1K, CLPP, REXO2, MRPL54, ATP5C1, ABHD10, YRDC, MRPL48 |
| RNA-binding | 24 | HNRNPA1L2, DDX39A, SRSF1, PABPC4, AARS, YTHDC1, RBM6, THUMPD2, CNOT7, SRP19, RBMX, NUFIP2, SLBP, DDX3X, EIF5AL1, HTATSF1, EIF2S1, RBMXL1, PTBP3, APEX1, EIF4E2, THOC1, C1D, SNRPG |
| Transit peptide | 21 | GCDH, MRPS35, MRPS26, OXA1L, MMADHC, STOML2, PTRH2, MTIF3, HADHA, SOD2, NDUFS6, MRPL22, MRPL28, PPM1K, REXO2, CLPP, MRPL54, ATP5C1, ABHD10, YRDC, MRPL48 |
| GO: 0008380~RNA splicing | 12 | HNRNPA1L2, CIR1, PRPF4B, CDC40, DHX15, RBMXL1, PTBP3, SREK1IP1, SNRNP25, THOC1, PRPF6, SNRPG |
| Protein transport | 22 | VPS29, NXT1, STX6, SNX9, KDELR2, TIMM10, RAB1B, TOMM40, ARF5, LMAN2, COPB2, NUP62, PPID, EIF5AL1, ARF3, STX16, TIMM9, TMED10, VPS26B, KPNA3, SNX10, EXOC2 |
| GO: 0006406~mRNA export from nucleus | 9 | NXT1, SRSF1, DDX39A, NUP62, RAE1, CDC40, SMG1, SLBP, THOC1 |
| GO: 0016607~nuclear speck | 12 | NXT1, SRSF1, CIR1, DDX3X, CD2BP2, NOC3L, LMNA, YTHDC1, APEX1, THOC1, PRPF6, PRPF40A |
| Coiled coil | 65 | MRPS35, COA3, TCOF1, RBM6, STOML2, TCEAL8, NFKB2, THADA, COPB2, KDM1A, TOP1, ATAD3B, DNAJC9, SREK1IP1, SUPT5H, FTSJ3, STX6, RCOR1, WNK1, CNPY3, CCDC47, NCOA7, KRT10, CCDC137, PURA, MFN2, SMARCE1, EIF2S1, HARS, MEAF6, USP8, CRLF3, FKBP4, NOC3L, ARF5, VARS, TTC3, SRRT, FAM107B, CCDC124, STX16, EXOC2, TRAF4, CHD3, SMCHD1, CCDC25, NUB1, CWC27, HCLS1, TMEM120B, LMNA, SMG1, YTHDC1, TPD52L2, ITPR3, SMC2, GCFC2, SMC3, NUP62, PSMC4, IST1, MLX, UTP14A, SSNA1, GPATCH8 |
| GO: 0003682~chromatin binding | 17 | NOC3L, FOXO1, NFKB2, RBMX, SMC3, MCM5, NOC2L, KDM1A, TOP1, SMARCE1, NUP62, SP3, CKS2, DNMT1, SUPT5H, ASF1A, TEX10 |
| Repressor | 20 | RCOR1, CCNC, NFKB2, MAF1, CNOT7, RBBP7, RBMX, GCFC2, NOC2L, SUZ12, KDM1A, CIR1, SP3, MLX, DNMT1, PTBP3, SUPT5H, APEX1, C1D, KAT6A |
| hsa03040: Spliceosome | 10 | HNRNPA1L2, SRSF1, CDC40, DHX15, RBMXL1, RBMX, THOC1, PRPF6, PRPF40A, SNRPG |
| GO: 0032784~regulation of DNA-templated transcription, elongation | 4 | HTATSF1, TCEA1, SUPT5H, THOC1 |
| hsa03008: Ribosome biogenesis in eukaryotes | 8 | NXT1, WDR36, CSNK2A1, UTP18, REXO2, TCOF1, NOB1, UTP14A |
| Mitochondrion inner membrane | 12 | NDUFS6, NDUFA2, OXA1L, NDUFB6, ATAD3B, COA3, TIMM9, TIMM10, ATP5C1, STOML2, SLC25A39, HIGD2A |
| GO: 0006270~DNA replication initiation | 5 | PRIM1, TOPBP1, MCM4, MCM5, PURA |
| Neuropathy | 7 | MFN2, AARS, LMNA, HARS, WNK1, DNMT1, DNM2 |
| GO: 0006890~retrograde vesicle-mediated transport, Golgi to ER | 7 | COPB2, KDELR2, ARF3, TMED10, RAB1B, LMAN2, ARF5 |
| GO: 0006405~RNA export from nucleus | 6 | NXT1, SRSF1, DDX39A, NUP62, CDC40, THOC1 |
| Spliceosome | 8 | HNRNPA1L2, SRSF1, PRPF4B, CDC40, RBMX, SNRNP25, PRPF6, SNRPG |
| SM00968: SM00968 | 3 | SMCHD1, SMC2, SMC3 |
| GO: 0006368~transcription elongation from RNA polymerase II promoter | 7 | TAF11, ADRM1, GTF2E2, POLR2K, TCEB3, TCEA1, SUPT5H |

TABLE 2-continued

HIV + low cutoff

| Category | Count | Genes |
|---|---|---|
| Chromatin regulator | 12 | SUZ12, KDM1A, MEAF6, SMARCE1, RCOR1, BABAM1, DNMT1, RBBP7, ASF1A, VPS72, CHD3, KAT6A |
| GO: 0071013~catalytic step 2 spliceosome | 7 | SRSF1, PRPF4B, CWC27, CDC40, RBMX, PRPF6, SNRPG |
| GO: 0006511~ubiquitin-dependent protein catabolic process | 10 | UBE2N, PSMD14, USP8, CUL4A, NUB1, UBA6, USP10, UBE2L3, USP33, TTC3 |
| DNA repair | 12 | UBE2N, PSMD14, CUL4A, BABAM1, SMG1, PRKDC, TOPBP1, USP10, APEX1, SMC3, TRIP12, BOD1L1 |
| GO: 0050852~T cell receptor signaling pathway | 9 | UBE2N, ITK, BCL10, PSMB4, PSMD14, PSMB7, PSMC4, STOML2, SKAP1 |
| IPR010935: SMCs flexible hinge | 3 | SMCHD1, SMC2, SMC3 |
| GO: 0006369~termination of RNA polymerase II transcription | 6 | SRSF1, DDX39A, CDC40, SLBP, THOC1, SNRPG |
| GO: 0000784~nuclear chromosome, telomeric region | 8 | KDM1A, SMCHD1, PRKDC, APEX1, MCM4, MCM5, THOC1, PURA |
| DNA damage | 13 | PRKDC, SMG1, TOPBP1, SMC3, BOD1L1, UBE2N, PSMD14, CUL4A, BABAM1, USP10, APEX1, MCTS1, TRIP12 |
| GO: 1901796~regulation of signal transduction by p53 class mediator | 8 | TAF11, MEAF6, CSNK2A1, TOPBP1, RBBP7, CHD3, KAT6A, NOC2L |
| GO: 0038061~NIK/ NF-kappaB signaling | 6 | PSMB4, PSMD14, PSMB7, PSMC4, NFKB2, PPP4C |
| Nucleotide-binding | 40 | PRPF4B, GNAI2, DTYMK, CTPS1, RAB1B, UBA6, PRKDC, ASNS, ARF5, VARS, HPRT1, ATAD3B, CSNK2A1, DDX3X, DHX15, STK38L, CHD3, DDX39A, ITK, AARS, ATP11B, WNK1, AK2, SMG1, ACLY, ARL16, UBE2L3, MCM4, SMC2, MCM5, SMC3, MFN2, UBE2N, HYOU1, PSMC4, RFK, ARF3, HARS, HSPA13, DNM2 |
| GO: 0043234~protein complex | 15 | BCL10, OXA1L, EPB41, FKBP4, PXK, VPS72, PTPN11, UBE2N, KDM1A, SMARCE1, NUP62, DNMT1, USP10, ASF1A, DNM2 |
| Translation, ribosomal structure and biogenesis | 6 | CPSF3L, METTL5, EIF2S1, HARS, MCTS1, MTIF3 |
| GO: 0005694~ chromosome | 7 | TOP1, PRPF4B, SMCHD1, CCDC137, TOPBP1, SMC3, BOD1L 1 |
| Charcot-Marie-Tooth disease | 5 | MFN2, AARS, LMNA, HARS, DNM2 |
| GO: 0005758~ mitochondrial intermembrane space | 6 | DTYMK, REXO2, TIMM9, TIMM10, AK2, STOML2 |
| GO: 0070536~ protein K63-linked deubiquitination | 4 | PSMD14, USP8, BABAM1, USP33 |
| Activator | 19 | MEAF6, FOXO1, NCOA7, PHF11, CCNC, NFKB2, RBMX, PURA, SRRT, NCOA4, SP3, HTATSF1, MLX, NFAT5, DNMT1, SUPT5H, APEX1, KAT6A, TFDP1 |
| Proteasome | 5 | PSMB4, ADRM1, PSMD14, PSMB7, PSMC4 |
| GO: 0032790~ ribosome disassembly | 3 | DENR, MCTS1, MTIF3 |
| hsa03013: RNA transport | 10 | NXT1, NUP62, RAE1, EIF2S1, EIF1AY, PABPC4, EIF3F, EIF1, EIF4E2, THOC1 |
| GO: 0043130~ ubiquitin binding | 6 | UBE2N, BCL10, NUP62, RAE1, CKS2, USP33 |
| GO: 0043022~ ribosome binding | 5 | EIF5AL1, EIF2S1, SPCS1, ETF1, MTIF3 |
| Isomerase | 7 | TOP1, FKBP4, CWC27, PPID, FKBP3, TOPBP1, TSTA3 |
| Ubl conjugation pathway | 19 | USP8, UFC1, UBA6, UBE2V2, UBE2L3, TTC3, UBE2N, KLHL7, DCUN1D1, PSMD14, CUL4A, UFM1, EIF3F, BABAM1, DDA1, USP10, USP33, ALG13, TRIP12 |
| Elongation factor | 4 | EIF5AL1, TCEB3, TCEA1, SUPT5H |
| ATP-binding | 32 | PRPF4B, DTYMK, CTPS1, UBA6, PRKDC, ASNS, VARS, ATAD3B, CSNK2A1, DDX3X, DHX15, STK38L, CHD3, DDX39A, ITK, AARS, ATP11B, WNK1, SMG1, AK2, ACLY, UBE2L3, SMC2, MCM4, MCM5, SMC3, UBE2N, HYOU1, PSMC4, RFK, HARS, HSPA13 |
| Cell division | 13 | SNX9, ATAD3B, GNAI2, CCDC124, IST1, CDC40, CKS2, CENPV, BABAM1, SMC2, SMC3, MCM5, PRPF40A |

TABLE 2-continued

HIV + low cutoff

| Category | Count | Genes |
|---|---|---|
| SM00320: WD40 | 10 | COPB2, WDR36, WDR73, UTP18, RAE1, CDC40, AAMP, WDR4, RBBP7, PWP1 |
| hsa01130: Biosynthesis of antibiotics | 11 | GCDH, HSD17B10, PYCR1, AKR1A1, FDPS, ADSL, AK2, ACLY, TKT, PSAT1, HADHA |
| GO: 0006457~protein folding | 9 | CSNK2A1, GNAI2, FKBP4, CWC27, PPID, ERP29, AARS, MESDC2, PDRG1 |
| hsa03060: Protein export | 4 | OXA1L, SEC11A, SPCS1, SRP19 |
| ER-Golgi transport | 6 | COPB2, KDELR2, ARF3, TMED10, ARF5, ERGIC3 |
| Cell cycle | 18 | SNX9, USP8, GNAI2, SMC2, MCM4, SMC3, MCM5, ATAD3B, CSNK2A1, CCDC124, IST1, CDC40, BABAM1, CENPV, CKS2, MCTS1, TFDP1, PRPF40A |
| GO: 0045739~positive regulation of DNA repair | 4 | UBE2N, BABAM1, UBE2V2, APEX1 |
| GO: 0050699~WW domain binding | 4 | NDFIP2, TCEAL8, TRAF4, DNM2 |
| GO: 0000502~ proteasome complex | 5 | PSMB4, ADRM1, PSMD14, PSMB7, PSMC4 |
| GO: 0005794~Golgi apparatus | 23 | TGOLN2, STX6, KDELR2, USP8, ATP11B, NDFIP2, RAB1B, TOPBP1, ARF5, LMAN2, ERGIC3, PWP1, TAF11, EI24, SP3, ARF3, MAPKAP1, STX16, TMED10, USP33, FGD3, DNM2, KAT6A |
| GO: 0038095~Fc-epsilon receptor signaling pathway | 8 | UBE2N, ITK, BCL10, PSMB4, PSMD14, PSMB7, PSMC4, PPP3R1 |
| GO: 0005840~ribosome | 8 | MRPL4, MRPL13, MRPS33, EIF2S1, MRPL54, RPL35, APEX1, RPS19BP1 |
| Rotamase | 4 | FKBP4, CWC27, PPID, FKBP3 |
| GO: 0030133~ transport vesicle | 6 | TGOLN2, COPB2, KDELR2, ERP29, TMED10, RAB1B |
| hsa00240: Pyrimidine metabolism | 7 | PRIM1, POLE4, POLR2K, DTYMK, CTPS1, POLR1C, ENTPD4 |
| repeat: WD 3 | 10 | COPB2, WDR36, WDR73, UTP18, RAE1, CDC40, AAMP, WDR4, RBBP7, PWP1 |
| GO: 0010494~ cytoplasmic stress granule | 4 | DDX3X, EIF2S1, PABPC4, NUFIP2 |
| GO: 0003746~ translation elongation factor activity | 4 | EIF5AL1, TCEB3, TCEA1, SUPT5H |
| GO: 0006303~ double-strand break repair via nonhomologous end joining | 5 | UBE2N, PSMD14, BABAM1, PRKDC, UBE2V2 |
| GO: 0006626~protein targeting to mitochondrion | 4 | MFN2, TIMM9, TIMM10, TOMM40 |
| GO: 0032981~ mitochondrial respiratory chain complex I assembly | 5 | NDUFS6, NDUFA2, OXA1L, NDUFB6, TMEM126B |
| WD repeat | 10 | COPB2, WDR36, WDR73, UTP18, RAE1, CDC40, AAMP, WDR4, RBBP7, PWP1 |
| active site: Glycyl thioester intermediate | 5 | UBE2N, UFC1, UBA6, UBE2L3, TRIP12 |
| GO: 0061077~chaperone-mediated protein folding | 4 | CSNK2A1, FKBP4, PPID, FKBP3 |
| GO: 0003713~ transcription coactivator activity | 10 | TAF11, BCL10, SMARCE1, NCOA4, NFKB2, UBE2L3, APEX1, PRPF6, KAT6A, TFDP1 |
| repeat: WD 1 | 10 | COPB2, WDR36, WDR73, UTP18, RAE1, CDC40, AAMP, WDR4, RBBP7, PWP1 |
| repeat: WD 2 | 10 | COPB2, WDR36, WDR73, UTP18, RAE1, CDC40, AAMP, WDR4, RBBP7, PWP1 |
| Chromosomal rearrangement | 11 | SUZ12, HSD17B10, BCL10, TOP1, MEAF6, NCOA4, FOXO1, TCEA1, NFKB2, THADA, KAT6A |
| GO: 0006974~cellular response to DNA damage stimulus | 9 | DDX39A, CASP3, CUL4A, FOXO1, TOPBP1, USP10, MCTS1, TRIP12, BOD1L1 |
| IPR001680: WD40 repeat | 10 | COPB2, WDR36, WDR73, UTP18, RAE1, CDC40, AAMP, WDR4, RBBP7, PWP1 |
| SM00360: RRM | 8 | HNRNPA1L2, SRSF1, HTATSF1, PABPC4, RBMXL1, RBM6, PTBP3, RBMX |
| GO: 0005643~nuclear pore | 5 | NXT1, NUP62, RAE1, EIF5AL1, KPNA3 |
| GO: 0006412~translation | 10 | MRPL22, MRPL4, MRPL13, MRPS33, MRPL28, PABPC4, HARS, RPL35, SLC25A39, RPL39 |

TABLE 2-continued

| Category | Count | Genes |
|---|---|---|
| GO: 0006450~regulation of translational fidelity | 3 | AARS, YRDC, VARS |
| GO: 00044074~histone deacetylase activity | 4 | KDM1A, RCOR1, RBBP7, CHD3 |
| GO: 0006413~translational initiation | 7 | EIF2S1, EIF1AY, EIF3F, RPL35, EIF1, RPL39, EIF4E2 |
| GO: 0051301~cell division | 12 | ATAD3B, GNAI2, CCDC124, IST1, CDC40, CKS2, CENPV, BABAM1, SMC2, MCM5, SMC3, PRPF40A |
| GO: 0042795~snRNA transcription from RNA polymerase II promoter | 5 | TAF11, CPSF3L, SRRT, GTF2E2, POLR2K |
| GO: 0005682~U5 snRNP | 3 | CD2BP2, PRPF6, SNRPG |
| GO: 0071004~U2-type prespliceosome | 3 | PRPF39, PRPF40A, SNRPG |
| GO: 0002223~stimulatory C-type lectin receptor signaling pathway | 6 | UBE2N, BCL10, PSMB4, PSMD14, PSMB7, PSMC4 |
| GO: 0031072~heat shock protein binding | 4 | FKBP4, DNAJC9, PPID, LMAN2 |
| GO: 0005759~mitochondrial matrix | 11 | GCDH, HSD17B10, PYCR1, PPM1K, DTYMK, REXO2, CLPP, ATP5C1, ABHD10, BCO2, SOD2 |
| GO: 0008565~protein transporter activity | 5 | VPS29, TIMM9, TIMM10, KPNA3, VPS26B |
| GO: 0031372~UBC13-MMS2 complex | 2 | UBE2N, UBE2V2 |
| GO: 0042101~T cell receptor complex | 3 | BCL10, STOML2, SKAP1 |
| GO: 0016581~NuRD complex | 3 | CSNK2A1, RBBP7, CHD3 |
| GO: 0006376~mRNA splice site selection | 3 | SRSF1, YTHDC1, RBMXL1 |
| GO: 0051262~protein tetramerization | 4 | OXA1L, ADSL, CCL5, UXS1 |
| GO: 0005524~ATP binding | 35 | PRPF4B, FKBP4, DTYMK, CTPS1, UBA6, PRKDC, ASNS, PXK, VARS, ATAD3B, CSNK2A1, DDX3X, DHX15, STK38L, CHD3, DDX39A, ITK, SMCHD1, AARS, ATP11B, WNK1, SMG1, AK2, ACLY, UBE2L3, SMC2, MCM4, MCM5, SMC3, UBE2N, HYOU1, PSMC4, RFK, HARS, HSPA13 |
| GO: 0003735~structural constituent of ribosome | 9 | MRPS35, MRPL22, MRPL4, MRPL13, MRPS33, MRPL28, RPL35, SLC25A39, RPL39 |
| Transcription | 46 | MEAF6, POLR2K, FOXO1, TCEAL8, NFKB2, MAF1, CNOT7, VPS72, PRIM1, SRRT, KDM1A, GTF2E2, CSNK2A1, CIR1, DDX3X, HTATSF1, GTF3C6, NFAT5, TCEA1, SUPT5H, ASF1A, APEX1, TFDP1, CHD3, RCOR1, NCOA7, POLR1C, CCNC, PHF11, RBBP7, UBE2L3, RBMX, GCFC2, PURA, NOC2L, TAF11, SUZ12, NCOA4, MLX, SP3, TCEB3, DNMT1, MCTS1, THOC1, KAT6A, C1D |
| GO: 0000413~protein peptidyl-prolyl isomerization | 4 | FKBP4, CWC27, PPID, FKBP3 |
| repeat: WD 4 | 9 | COPB2, WDR36, UTP18, RAE1, CDC40, AAMP, WDR4, RBBP7, PWP1 |
| GO: 0005685~U1 snRNP | 3 | PRPF39, PRPF40A, SNRPG |
| hsa03030: DNA replication | 4 | PRIM1, POLE4, MCM4, MCM5 |
| rRNA processing | 5 | WDR36, TSR2, UTP18, FTSJ3, C1D |
| GO: 0007077~mitotic nuclear envelope disassembly | 4 | NUP62, RAE1, LMNA, BANF1 |
| IPR012340: Nucleic acid-binding, OB-fold | 5 | EIF5AL1, EIF2S1, EIF1AY, MCM4, MCM5 |
| GO: 0048037~cofactor binding | 3 | ACLY, TKT, ASNS |
| compositionally biased region: Poly-Lys | 8 | HTATSF1, TCOF1, MRPL48, TTC3, RSBN1, THADA, CHD3, KAT6A |
| GO: 0006886~intracellular protein transport | 9 | STX6, VPS29, SNX9, COPB2, KDELR2, STX16, ERP29, TMED10, VPS26B |

TABLE 2-continued

HIV + low cutoff

| Category | Count | Genes |
| --- | --- | --- |
| GO: 0005545~1-phosphatidylinositol binding | 3 | SNX9, EPB41, SNX10 |
| IPR019775: WD40 repeat, conserved site | 7 | WDR36, UTP18, RAE1, CDC40, AAMP, RBBP7, PWP1 |
| GO: 0003755~peptidyl-prolyl cis-trans isomerase activity | 4 | FKBP4, CWC27, PPID, FKBP3 |
| GO: 0031625~ubiquitin protein ligase binding | 10 | MFN2, UBE2N, BCL10, SNX9, CUL4A, FOXO1, UBE2V2, UBE2L3, EIF4E2, TRAF4 |
| GO: 0008134~transcription factor binding | 10 | KDM1A, BCL10, DDX3X, RCOR1, PPID, MLX, PRKDC, KAT6A, TFDP1, PURA |
| GO: 0071008~U2-type post-mRNA release spliceosomal complex | 2 | DHX15, GCFC2 |
| GO: 1900087~positive regulation of G1/S transition of mitotic cell cycle | 3 | DDX3X, CUL4A, APEX1 |
| SM00361: RRM_1 | 3 | PABPC4, RBMXL1, RBMX |
| IPR017986: WD40-repeat-containing domain | 10 | COPB2, WDR36, WDR73, UTP18, RAE1, CDC40, AAMP, WDR4, RBBP7, PWP1 |
| GO: 0031124~mRNA 3'-end processing | 4 | SRSF1, DDX39A, CDC40, THOC1 |
| Protease | 14 | LAP3, PSMB4, PSMD14, CASP3, PSMB7, USP8, SEC11A, EIF3F, CLPP, HMCES, SPCS1, USP10, USP33, ALG13 |
| GO: 0051443~positive regulation of ubiquitin-protein transferase activity | 3 | UBE2N, DCUN1D1, UBE2L3 |
| GO: 0006521~regulation of cellular amino acid metabolic process | 4 | PSMB4, PSMD14, PSMB7, PSMC4 |
| GO: 0032481~positive regulation of type I interferon production | 4 | POLR2K, PRKDC, POLR1C, NFKB2 |
| hsa05010: Alzheimer's disease | 8 | HSD17B10, NDUFS6, NDUFA2, CASP3, NDUFB6, PPP3R1, ATP5C1, ITPR3 |
| Amino-acid biosynthesis | 3 | PYCR1, ASNS, PSAT1 |
| GO: 0017053~transcriptional repressor complex | 4 | SMARCE1, RCOR1, SP3, CID |
| Hydrolase | 33 | CPSF3L, USP8, PTRH2, CNOT7, PSMB4, CASP3, PSMB7, DDX3X, REXO2, EIF3F, DHX15, ABHD10, USP10, ENTPD4, PPP4C, USP33, APEX1, CHD3, DDX39A, SEC11A, HMCES, ATP11B, MCM4, MCM5, PTPN11, LAP3, MFN2, PSMD14, PPM1K, CLPP, SPCS1, ALG13, DNM2 |
| IPR012677: Nucleotide-binding, alpha-beta plait | 9 | HNRNPA1L2, SRSF1, SRRT, HTATSF1, PABPC4, RBMXL1, RBM6, PTBP3, RBMX |
| GO: 0001731~formation of translation preinitiation complex | 3 | EIF3F, DENR, MCTS1 |
| Helicase | 6 | DDX39A, DDX3X, DHX15, MCM4, MCM5, CHD3 |
| GO: 0005802~trans-Golgi network | 6 | TGOLN2, STX6, LAP3, SNX9, STX16, DNM2 |
| IPR016135: Ubiquitin-conjugating enzyme/RWD-like | 4 | UBE2N, UFC1, UBE2V2, UBE2L3 |
| GO: 0006357~regulation of transcription from RNA polymerase II promoter | 13 | TCEAL8, NFKB2, PURA, SOD2, KDM1A, CIR1, SMARCE1, HTATSF1, TCEB3, TCEA1, SUPT5H, CHD3, TFDP1 |

TABLE 2-continued

HIV + low cutoff

| Category | Count | Genes |
|---|---|---|
| GO: 0032403~protein complex binding | 8 | CASP3, IST1, HCLS1, TMED10, APEX1, SKAP1, HADHA, DNM2 |
| GO: 0005763~mitochondrial small ribosomal subunit | 3 | MRPS35, MRPS26, MRPS33 |
| hsa03050: Proteasome | 4 | PSMB4, PSMD14, PSMB7, PSMC4 |
| GO: 0005681~spliceosomal complex | 5 | HNRNPA1L2, DDX39A, CDC40, PRPF6, SNRPG |
| GO: 0000166~nucleotide binding | 11 | HNRNPA1L2, SRSF1, SRRT, HTATSF1, PABPC4, RBMXL1, RBM6, PTBP3, PXK, HPRT1, RBMX |
| Proto-oncogene | 8 | SUZ12, TOP1, DCUN1D1, CSNK2A1, NCOA4, FOXO1, NFKB2, KAT6A |
| IPR016040: NAD(P)-binding domain | 7 | HSD17B10, PYCR1, UBA6, ACLY, TSTA3, UXS1, HADHA |
| IPR024969: Rpn11/EIF3F C-terminal domain | 2 | PSMD14, EIF3F |
| IPR001950: Translation initiation factor SUI1 | 2 | EIF1, DENR |
| GO: 1990391~DNA repair complex | 2 | KDM1A, RCOR1 |
| GO: 0030906~retromer, cargo-selective complex | 2 | VPS29, VPS26B |
| IPR003954: RNA recognition motif domain, eukaryote | 3 | PABPC4, RBMXL1, RBMX |
| GO: 0005689~U12-type spliceosomal complex | 3 | DHX15, SNRNP25, SNRPG |
| GO: 0009055~electron carrier activity | 5 | GLRX3, GCDH, NDUFS6, AKR1A1, TSTA3 |
| GO: 0070062~extracellular exosome | 54 | SRSF1, CAPZA2, RAB1B, UFC1, UXS1, VPS13D, KDELR2, ERP29, AARS, KRT10, LAP3, UBE2N, EIF2S1, ATP5C1, VPS29, GLRX3, SNX9, GNAI2, FKBP4, RNH1, UBE2V2, LMAN2, ARF5, HPRT1, BANF1, PSMB4, PSMB7, AKR1A1, DDX3X, UFM1, MTPN, TMED10, TSTA3, HPCAL1, FIBP, CCDC25, SEC11A, AK2, TOMM40, ACLY, TKT, UBE2L3, COTL1, SMC2, RBMX, SOD2, HYOU1, PSMD14, IST1, ARF3, CPNE3, HSPA13, PSAT1, DNM2 |
| Respiratory chain | 4 | NDUFS6, NDUFA2, NDUFB6, HIGD2A |
| GO: 0015031~protein transport | 12 | VPS29, KDELR2, IST1, ARF3, EIF5AL1, PPID, TIMM9, RAB1B, LMAN2, ARF5, SNX10, EXOC2 |
| IPR000504: RNA recognition motif domain | 8 | HNRNPA1L2, SRSF1, HTATSF1, PABPC4, RBMXL1, RBM6, PTBP3, RBMX |
| hsa00230: Purine metabolism | 8 | PRIM1, POLE4, POLR2K, ADSL, AK2, POLR1C, ENTPD4, HPRT1 |
| Mental retardation | 9 | HSD17B10, WDR73, DDX3X, SMARCE1, ASNS, RBMX, SMC3, KAT6A, PURA |
| GO: 0015949~nucleobase-containing small molecule interconversion | 3 | DTYMK, CTPS1, AK2 |
| GO: 0046580~negative regulation of Ras protein signal transduction | 3 | MFN2, NUP62, MAPKAP1 |
| GO: 0030529~intracellular ribonucleoprotein complex | 6 | HNRNPA1L2, NUP62, PABPC4, RBMXL1, RBMX, SLBP |
| hsa05012: Parkinson's disease | 7 | NDUFS6, NDUFA2, CASP3, NDUFB6, GNAI2, ATP5C1, UBE2L3 |
| Thiol protease | 6 | CASP3, USP8, EIF3F, USP10, USP33, ALG13 |
| Ribosome biogenesis | 4 | WDR36, DDX3X, UTP14A, FTSJ3 |
| GO: 0006364~rRNA processing | 8 | WDR36, UTP18, NOB1, RPL35, RPL39, UTP14A, TEX10, C1D |
| GO: 0045070~positive regulation of viral genome replication | 3 | DDX3X, PPID, CCL5 |
| GO: 0000245~spliceosomal complex assembly | 3 | GCFC2, PRPF6, SNRPG |

TABLE 2-continued

HIV + low cutoff

| Category | Count | Genes |
|---|---|---|
| mRNA transport | 5 | HNRNPA1L2, SRSF1, NUP62, EIF5AL1, THOC1 |
| GO: 0005761~mitochondrial ribosome | 3 | MRPL13, MRPL28, MRPL48 |
| GO: 0014823~response to activity | 4 | DNMT1, PRKDC, CCL5, SOD2 |
| IPR015943: WD40/YVTN repeat-like-containing domain | 10 | COPB2, WDR36, WDR73, UTP18, RAE1, CDC40, AAMP, WDR4, RBBP7, PWP1 |
| GO: 0051879~Hsp90 protein binding | 3 | CSNK2A1, NUP62, PPID |
| GO: 0046966~thyroid hormone receptor binding | 3 | TAF11, NUP62, TRIP12 |
| GO: 0030687~preribosome, large subunit precursor | 3 | AAMP, FTSJ3, TEX10 |
| IPR024704: Structural maintenance of chromosomes protein | 2 | SMC2, SMC3 |
| IPR001509: NAD-dependent epimerase/dehydratase | 2 | TSTA3, UXS1 |
| GO: 0042719~mitochondrial intermembrane space protein transporter complex | 2 | TIMM9, TIMM10 |
| GO: 0031313~extrinsic component of endosome membrane | 2 | USP8, SNX10 |
| GO: 0047485~protein N-terminus binding | 5 | TAF11, CSNK2A1, SMARCE1, BANF1, EXOC2 |
| GO: 0006397~mRNA processing | 7 | HNRNPA1L2, SRSF1, CIR1, DHX15, RBMXL1, PTBP3, SREK1IP1 |
| GO: 0033116~endoplasmic reticulum-Golgi intermediate compartment membrane | 4 | TMED10, RAB1B, LMAN2, ERGIC3 |
| GO: 0048471~perinuclear region of cytoplasm | 16 | STX6, BCL10, FKBP4, LMNA, NDFIP2, ARF5, TPD52L2, MAF1, ITPR3, ARF3, MTPN, STX16, APEX1, USP33, TRAF4, DNM2 |
| GO: 0051881~regulation of mitochondrial membrane potential | 3 | PYCR1, BCO2, SOD2 |
| SM01343: SM01343 | 2 | SMG1, PRKDC |
| GO: 0004197~cysteine-type endopeptidase activity | 4 | CASP3, USP8, USP10, USP33 |
| GO: 0002192~IRES-dependent translational initiation | 2 | DENR, MCTS1 |
| GO: 0071569~protein ufmylation | 2 | UFM1, UFC1 |
| GO: 1990592~protein K69-linked ufmylation | 2 | UFM1, UFC1 |
| GO: 0051169~nuclear transport | 2 | NUP62, BANF1 |
| GO: 0042531~positive regulation of tyrosine phosphorylation of STAT protein | 2 | HCLS1, CCL5 |
| GO: 0045039~protein import into mitochondrial inner membrane | 2 | TIMM9, TIMM10 |
| GO: 0008283~cell proliferation | 11 | SRRT, KDM1A, USP8, GNAI2, DTYMK, CKS2, PRKDC, UBE2V2, RBBP7, UBE2L3, TFDP1 |

TABLE 2-continued

HIV + low cutoff

| Category | Count | Genes |
|---|---|---|
| GO: 0000209~protein polyubiquitination | 7 | PSMB4, PSMD14, PSMB7, PSMC4, UBE2V2, UBE2L3, TRIP12 |
| GO: 0061631~ ubiquitin conjugating enzyme activity | 3 | UBE2N, UBE2V2, UBE2L3 |
| GO: 0008135~ translation factor activity, RNA binding | 3 | EIF1, MTIF3, EIF4E2 |
| h_tnfr1Pathway: TNFR1 Signaling Pathway | 3 | CASP3, LMNA, PRKDC |
| Endoplasmic reticulum | 22 | KDELR2, SEC11A, ERP29, ATP11B, DNAJB14, CNPY3, ALG5, MESDC2, LMAN2, ITPR3, ERGIC3, HYOU1, EI24, ELOVL5, EIF5AL1, TMEM170A, TMED10, SPCS1, HSPA13, APEX1, ALG13, SSR2 |
| IPR002909: Cell surface receptor IPT/TIG | 3 | NFAT5, NFKB2, EXOC2 |
| GO: 0016020~ membrane | 43 | GNAI2, CAPZA2, RPL35, DNAJB14, PRKDC, CTPS1, STOML2, ALG5, LMAN2, CNOT7, PTRH2, NUFIP2, PRIM1, ELOVL5, STX16, EIF3F, YRDC, STK38L, EXOC2, PRPF40A, DDX39A, HPCAL1, FIBP, HCLS1, ERP29, AARS, ATP11B, WNK1, CCDC47, KRT10, ACLY, ITPR3, MCM4, RBMX, MCM5, PRPF6, ERGIC3, ADRM1, HYOU1, EI24, PSMC4, EIF2S1, ATP5C1 |
| GO: 0002479~antigen processing and presentation of exogenous peptide antigen via MHC class I, TAP-dependent | 4 | PSMB4, PSMD14, PSMB7, PSMC4 |
| domain: FATC | 2 | SMG1, PRKDC |
| domain: FAT | 2 | SMG1, PRKDC |
| short sequence motif: Twin CX3C motif | 2 | TIMM9, TIMM10 |
| IPR027417: P-loop containing nucleoside triphosphate hydrolase | 20 | DDX39A, GNAI2, DTYMK, AK2, RAB1B, CTPS1, ARL16, ARF5, SMC2, MCM4, SMC3, MCM5, MFN2, ATAD3B, DDX3X, PSMC4, ARF3, DHX15, CHD3, DNM2 |
| GO: 0000082~G1/S transition of mitotic cell cycle | 5 | PRIM1, CUL4A, CRLF3, MCM4, MCM5 |
| IPR024156: Small GTPase superfamily, ARF type | 3 | ARF3, ARL16, ARF5 |
| GO: 0005762~ mitochondrial large ribosomal subunit | 3 | MRPL22, MRPL13, MRPL28 |
| Apoptosis | 13 | BCL10, FOXO1, PTRH2, NOC2L, MFN2, EI24, CASP3, CSNK2A1, DDX3X, PPID, TRAF4, C1D, THOC1 |
| GO: 0043488~ regulation of mRNA stability | 5 | PSMB4, PSMD14, PSMB7, PSMC4, APEX1 |
| IPR004217: Tim10/ DDP family zinc finger | 2 | TIMM9, TIMM10 |
| IPR003152: PIK-related kinase, FATC | 2 | SMG1, PRKDC |
| IPR014009: PIK-related kinase | 2 | SMG1, PRKDC |
| IPR018525: Mini-chromosome maintenance, conserved site | 2 | MCM4, MCM5 |
| hsa05016: Huntington's disease | 8 | NDUFS6, NDUFA2, CASP3, NDUFB6, POLR2K, RCOR1, ATP5C1, SOD2 |
| lipid moiety-binding region: N-myristoyl glycine | 5 | HPCAL1, GNAI2, ARF3, PPP3R1, ARF5 |
| GO: 0004003~ATP-dependent DNA helicase activity | 3 | DDX3X, MCM4, CHD3 |
| h_fasPathway: FAS signaling pathway (CD95) | 3 | CASP3, LMNA, PRKDC |

TABLE 2-continued

HIV + low cutoff

| Category | Count | Genes |
|---|---|---|
| GO: 0051573~negative regulation of histone H3-K9 methylation | 2 | KDM1A, DNMT1 |
| GO: 0000395~mRNA 5'-splice site recognition | 2 | SRSF1, PRPF39 |
| GO: 0019076~viral release from host cell | 2 | IST1, PPID |
| GO: 0046939~nucleotide phosphorylation | 2 | DTYMK, AK2 |
| GO: 0061133~endopeptidase activator activity | 2 | ADRM1, PSMD14 |
| GO: 0007032~endosome organization | 3 | STX6, USP8, SNX10 |
| GO: 0070911~global genome nucleotide-excision repair | 3 | UBE2N, CUL4A, UBE2V2 |
| IPR006689: Small GTPase superfamily, ARF/SAR type | 3 | ARF3, ARL16, ARF5 |
| Magnesium | 13 | GNAI2, FDPS, ATP11B, TKT, ACLY, HPRT1, CNOT7, LAP3, PPM1K, RFK, ENTPD4, APEX1, STK38L |
| repeat: HAT 7 | 2 | PRPF39, PRPF6 |
| region of interest: Flexible hinge | 2 | SMC2, SMC3 |
| PIRSF005719: structural maintenance of chromosomes protein | 2 | SMC2, SMC3 |
| GO: 0042147~retrograde transport, endosome to Golgi | 4 | STX6, VPS29, STX16, VPS26B |

TABLE 3

HIV- low cutoff

| Category | Count | Genes |
|---|---|---|
| Enrichment Score: 8.518413481739762 | | |
| Zinc-finger | 282 | UTRN, RP9, RNF216, RORA, ZNF638, ZNRF1, BRPF1, CUL9, ZFP90, ZNF106, ZNF394, ZNF101, ZNF43, ESCO1, POLK, RNF220, ZC3HC1, PAN3, ZNF44, ROCK1, ZNF644, RXRB, ROCK2, ZHX1, VPS41, UBR2, OPTN, BRAP, ZNF37A, UHRF2, UBR7, PIAS4, PARP12, MTF2, MLLT10, TRMT13, ACAP1, ACAP2, PRDM2, AMFR, PIAS1, ZNHIT3, ZNF131, ZNF511, ASAP1, MYO9B, RFFL, DIDO1, NR1H2, TCF20, ARIH2, RCHY1, PLAGL2, ASXL2, IKZF5, DNMT3A, ESRRA, ZNF529, IKZF2, ZC3H18, KLF13, ZNF121, KLF10, CREBBP, RYBP, ZBTB40, CBLB, RNF4, IRF2BPL, JAZF1, HGS, KAT6B, RERE, TAF1B, ZNF292, ZNF534, ZMAT5, ZNF675, HELZ, ZEB1, ZBTB38, SMAP1, MBTD1, ASH2L, ZNF148, NSMCE1, NSMCE2, USP16, ZNF493, ZFP36, ZCCHC10, BRF1, ZC3H7A, BRF2, POGZ, ZC3H7B, APTX, GTF2H3, HERC2, MBD1, GTF2B, PJA2, ASH1L, ZNF277, USP22, ZNF746, ZNF740, REV3L, ZNF276, ZNF275, ZNF274, USP3, ZBTB10, ZBTB11, WRNIP1, USP5, PML, TRIM14, EEA1, CBLL1, ZNF780B, ZNF780A, POLR2B, MYCBP2, ZFP36L2, DGKE, MORC3, GATAD2A, ZSCAN25, THAP1, THAP2, MLLT6, BAZ2B, ZNF268, BAZ2A, RASA2, RBM22, BRD1, ZNF28, TRIM27, TRIM26, PPP1R10, PHF10, DGKH, TRIM25, SF3A2, ATMIN, TRIM22, ZNF664, ZNF672, PLEKHF2, PHF14, YAF2, ARAF, WHSC1L1, MEX3C, DGKZ, ZBTB2, ZNF764, ZNF766, BARD1, MKRN1, ZNF583, ZC3HAV1, GATA3, RBCK1, RNF149, RBM10, RNF146, PHRF1, MTA2, NEIL2, ZNF814, ZNF7, TRERF1, TRIM38, EP300, TRIM33, KDM2A, MIB2, NBR1, RNF139, RNF138, SLU7, PYGO2, AKAP8, ZNF587, ZNF586, ZFAND6, TRAF2, ARFGAP2, ZFAND5, ZNF430, AGFG2, ZFAND1, ZNF330, CXXC1, RNF166, TRIM69, RNF168, RNF10, RNF167, RUNX1, TRAF5, TRAF3, ZMYM2, TRIP4, VAV3, ZMYM4, ZMYM5, NR4A1, KAT5, FOXP3, VAV1, MSL2, PHF3, PDZD8, PHF1, HIVEP2, HIVEP1, CTCF, ZKSCAN1, CBFA2T2, ZZEF1, TRIM4, PCGF5, PEX2, RSPRY1, ZNF721, RANBP2, ZCCHC6, KDM5B, |

TABLE 3-continued

HIV- low cutoff

| Category | Count | Genes |
|---|---|---|
| | | KDM5C, ZCCHC7, NFX1, INO80B, EGR1, ZCCHC3, ZFX, PRKCI, PRKCH, IRF2BP2, PRKCD, PRKCB, XPA, BPTF, ZFAND2A, ZFAND2B, CPSF4, JMJD1C, MDM4, PRKD3, DPF2, ING4, ING3, ING2, KMT2A, XIAP, KMT2C, ZNF800, EGLN1, RNF125, RPA1, RNF126, MAP3K1, XAF1, ZC3H12D, DUS3L, L3MBTL2, CBL, RAF1, TAB3, ZBED2, RNF115, RPAP2, SP1, ZBED5, KDM4C, ARAP2, RNF113A, RNF111 |
| Zinc | 339 | UTRN, RP9, RNF216, RORA, ZNF638, ZNRF1, BRPF1, CUL9, ZFP90, ERAP1, ZNF106, ZNF394, ZNF101, ZNF43, ESCO1, POLK, RNF220, PAN3, ZC3HC1, ZNF44, ROCK1, ZNF644, RXRB, ROCK2, ZHX1, VPS41, UBR2, OPTN, BRAP, ZNF37A, UHRF2, UBR7, PIAS4, PARP12, MTF2, MLLT10, TRMT13, ACAP1, ACAP2, PRDM2, PIAS1, AMFR, ZNHIT3, MOB4, ZNF131, ZNF511, ASAP1, UBA5, MYO9B, DUSP12, RFFL, DIDO1, NR1H2, TCF20, ARIH2, RCHY1, PLAGL2, IKZF5, ASXL2, DNMT3A, ESRRA, ZNF529, IKZF2, ZC3H18, KLF13, ZNF121, KLF10, CREBBP, RYBP, ZBTB40, SMAD3, CSRP1, CBLB, RNF4, LASP1, IRF2BPL, JAZF1, HGS, KAT6B, RERE, TAF1B, SPG7, LIMA1, ZNF292, ZNF534, FAM96A, ZMAT5, ZNF675, HELZ, ZEB1, ZBTB38, LNPEP, SMAP1, MBTD1, ASH2L, ZNF148, NSMCE1, NSMCE2, USP16, ZNF493, ZFP36, ZCCHC10, BRF1, POGZ, BRF2, ZC3H7A, ZC3H7B, POLR1A, GTF2H3, APTX, HERC2, GTF2B, MBD1, RAD50, PJA2, ASH1L, ZNF277, USP22, ZNF746, ZNF740, REV3L, ZNF276, ZNF275, LIMS1, ZNF274, USP3, ZBTB10, YPEL5, ZBTB11, WRNIP1, USP5, YPEL3, USP4, MKNK2, PML, TRIM14, EEA1, CBLL1, QTRT1, ZNF780B, ZNF780A, POLR2B, MYCBP2, ZFP36L2, LPXN, DGKE, MORC3, PITRM1, GATAD2A, PPP3CB, ZSCAN25, THAP1, THAP2, MLLT6, BAZ2B, ZNF268, BAZ2A, RASA2, RBM22, BRD1, ZNF28, TRIM27, TRIM26, PHF10, MSRB1, PPP1R10, DGKH, TRIM25, SF3A2, ATMIN, TRIM22, MT1X, ZNF664, DNPEP, ZNF672, PLEKHF2, PHF14, YAF2, ARAF, WHSC1L1, MEX3C, DGKZ, NLN, ZBTB2, ZNF764, ZNF766, BARD1, MKRN1, ZNF583, ZC3HAV1, IDE, APOBEC3G, APOBEC3C, APOBEC3D, GATA3, RBCK1, RNF149, RBM10, RNF146, PHRF1, PDXK, MTA2, NEIL2, ZNF814, ZNF7, TRERF1, TIMM8A, TRIM38, EP300, TRIM33, KDM2A, MIB2, NBR1, RNF139, RNF138, SLU7, PYGO2, AKAP8, ZNF587, FBXO11, ZNF586, ZFAND6, TRAF2, ARFGAP2, ZFAND5, ZNF430, ELAC2, AGFG2, ZFAND1, ZNF330, CXXC1, RNF166, TRIM69, STAMBPL1, SLC30A5, RNF168, RNF10, RNF167, RUNX1, TRAF5, TRAF3, SETDB1, ZMYM2, TRIP4, VAV3, EHMT1, RABIF, ZMYM4, ZMYM5, NR4A1, KAT5, FOXP3, VAV1, MSL2, PDZD8, PHF3, PHF1, MTR, HIVEP2, HIVEP1, UTY, CTCF, ZKSCAN1, CBFA2T2, ZZEF1, TRIM4, PCGF5, PEX2, RSPRY1, MOB3A, ZYX, ZNF721, RANBP2, ZCCHC6, KDM5B, KDM5C, ZCCHC7, NFX1, INO80B, EGR1, ZCCHC3, ZFX, PRKCI, PRKCH, IRF2BP2, PRKCD, PRKCB, HAGH, XPA, BPTF, ZFAND2A, ZFAND2B, MDM4, CPSF4, JMJD1C, CPSF3, PRKD3, ABLIM1, DPF2, ING4, ING3, MOB1B, ING2, KMT2A, XIAP, KMT2C, MGMT, ZNF800, EGLN1, NGLY1, RNF125, RPA1, RNF126, MAP3K1, SLC39A6, CCS, XAF1, SLC39A3, ZC3H12D, DUS3L, STAMBP, DCTD, L3MBTL2, CBL, SAMHD1, RAF1, SIRT6, SIRT7, TAB3, SIRT2, ZBED2, RNF115, RPAP2, SP1, ZBED5, KDM4C, ARAP2, RNF113A, RNF111 |
| GO:0008270~zinc ion binding | 202 | UTRN, ZNF638, RORA, ZNRF1, BRPF1, CUL9, ERAP1, ZC3HC1, RNF220, RXRB, UBR2, VPS41, BRAP, UHRF2, PIAS4, UBR7, MTF2, MLLT10, PRDM2, AMFR, PIAS1, DUSP12, OAS1, MYO9B, OAS2, RFFL, DIDO1, NR1H2, TCF20, ARIH2, RCHY1, ESRRA, CREBBP, RYBP, SMAD3, CSRP1, CBLB, RNF4, LASP1, KAT6B, RERE, LIMA1, SPG7, ZMAT5, ZNF675, ZEB1, PTER, LNPEP, MBTD1, NSMCE1, NSMCE2, USP16, ZCCHC10, BRF1, ZDHHC3, BRF2, ZDHHC8, POLR1A, HERC2, MBD1, GTF2B, TTF2, PJA2, CHMP1A, ZDHHC16, ASH1L, ZDHHC12, USP22, ZNF276, LIMS1, USP3, USP5, TRIM14, PML, EEA1, CBLL1, MYCBP2, LPXN, MORC3, PITRM1, GATAD2A, THAP1, BAZ2B, MLLT6, BAZ2A, BRD1, TRIM27, TRIM26, MSRB1, PHF10, TRIM25, SF3A2, TRIM22, MT1X, DNPEP, PHF14, YAF2, WHSC1L1, MEX3C, BARD1, MKRN1, CNDP2, IDE, APOBEC3G, APOBEC3C, APOBEC3D, GATA3, RBCK1, RNF149, RBM10, RNF146, PHRF1, PDXK, MTA2, NEIL2, TRIM38, EP300, KDM2A, TRIM33, MIB2, NBR1, RNF139, PYGO2, SLU7, RNF138, AKAP8, FBXO11, TRAF1, ZFAND6, TRAF2, ZFAND5, ZFAND1, ZNF330, CXXC1, RNF166, TRIM69, SLC30A5, RNF10, RNF168, RNF167, TRAF5, TRAF3, SETDB1, ZMYM2, EHMT1, TRIP4, ZMYM4, RABIF, ZMYM5, NR4A1, MSL2, PHF3, PHF1, MTR, CRYZL1, UQCRC1, CTCF, ZZEF1, TRIM4, PCGF5, RSPRY1, PEX2, RANBP2, ZYX, KDM5B, ZCCHC6, ZCCHC7, KDM5C, NFX1, EGR1, ZCCHC3, PRKCB, BPTF, ZFAND2A, ZFAND2B, COMMD3, CPSF4, MDM4, DPF2, ABLIM1, ING4, ING3, ING2, XIAP, KMT2A, KMT2C, RNF125, RNF126, MAP3K1, CCS, XAF1, DCTD, L3MBTL2, CBL, SAMHD1, SIRT6, SIRT2, TAB3, RNF115, KDM4C, RNF113A, RNF111 |
| Metal-binding | 467 | RP9, ZNF638, RORA, OGDH, CIAPIN1, BRPF1, PGP, CUL9, ZNF106, ZNF394, MAP2K7, ZNF101, ZNF43, ZNF44, ROCK1, ZNF644, RXRB, ROCK2, ZHX1, VPS41, BRAP, MARK2, ZNF37A, NME3, ZNHIT3, MOB4, ZNF131, ZNF511, UBA5, DUSP12, DIDO1, ARIH2, RCHY1, ASXL2, DNMT3A, MGAT4A, ESRRA, ZNF529, ZC3H18, KLF13, ZNF121, KLF10, ATP11A, HSPB11, LASP1, HGS, RERE, TAF1B, LIMA1, ZNF292, ZNF534, |

TABLE 3-continued

| | HIV- low cutoff | | |
|---|---|---|---|
| Category | | Count | Genes |
| | | | ZNF675, LATS1, LNPEP, SMAP1, ZNF148, USP16, ZNF493, BRF1, ZC3H7A, BRF2, ZC3H7B, GTF2H3, PAPD5, PJA2, ZNF277, CHSY1, ZNF746, USP22, ZNF740, ZNF276, ZNF275, ZNF274, REPS1, WRNIP1, MKNK2, PML, TRIM14, EEA1, ERI3, CBLL1, QTRT1, ZNF780B, HSCB, ZNF780A, MYCBP2, SNRK, DGKE, PITRM1, PPP2CB, PPP3CB, ILVBL, ZSCAN25, ZNF268, C1GALT1, RASA2, BRD1, MAT2A, ZNF28, TRIM27, TRIM26, PPP1R10, PHF10, DGKH, TRIM25, SF3A2, PCK2, TRIM22, MT1X, ZNF664, RPS6KA3, ZNF672, PLEKHF2, PHF14, SDHC, ARAF, MCFD2, WHSC1L1, DGKZ, ZBTB2, ZNF764, ZNF766, BARD1, GNA13, ZNF583, CNOT8, NT5C3A, ATOX1, CNDP2, IDE, IDH3G, PDE4B, CTDSP1, ENOPH1, RNF149, SAR1B, RNF146, PHRF1, NUDT1, PDXK, NUDT4, ACTN4, MTA2, NUDT5, NEIL2, STIM1, PDE4D, ZNF7, TATDN3, EP300, KDM2A, MIB2, RNF139, RNF138, ZNF587, FBXO11, ZNF586, ARFGAP2, TRAF2, ZNF430, ELAC2, ME2, ZNF330, CXXC1, RNF166, RNF168, LIAS, RNF167, TRAF5, SDF4, TRAF3, B4GALT3, VAV3, TRIP4, EHMT1, SYT11, IREB2, NR4A1, HDDC3, VAV1, FURIN, PDZD8, PDE7A, NDUFV2, HIVEP2, HIVEP1, ABL2, DICER1, CTCF, ZKSCAN1, TRIM4, PEX2, CDK5RAP1, KDM5B, ZCCHC6, NDUFS1, KDM5C, ZCCHC7, NFX1, INO80B, ZCCHC3, ZFX, IRF2BP2, CDK2, ARL3, HAGH, ZFAND2A, ZFAND2B, CPSF4, JMJD1C, CPSF3, ABLIM1, DPF2, GALNT2, KMT2A, ETHE1, KMT2C, PPM1A, EGLN1, NGLY1, RNF125, RNF126, CCS, XAF1, EHD1, EHD4, ALKBH7, CBL, ANXA1, SAMHD1, RAF1, TAB3, ADI1, ZBED2, RNF115, ZBED5, KDM4C, JAK2, ALKBH5, RNF113A, RNF111, RCN2, S100A4, ADCY7, UTRN, RNASEH1, RNF216, ZNRF1, ATP2B4, ZFP90, ERAP1, YDJC, ESCO1, POLK, RNF220, ZC3HC1, PAN3, CAPNS1, TRABD2A, PIM1, POLB, UBR2, OPTN, MGAT1, UHRF2, UBR7, PIAS4, PARP12, ATP2C1, MTF2, TRMT13, ACAP1, MLLT10, PGM1, ACAP2, FBXL5, PRDM2, AMFR, PIAS1, ASAP1, OAS1, MYO9B, RFFL, OAS2, PPAT, NR1H2, TCF20, KRAS, IDH2, PLAGL2, IKZF5, IKZF2, CREBBP, S100A11, RYBP, ZBTB40, SMAD3, OXSR1, CSRP1, CBLB, ATP13A1, RNF4, IRF2BPL, DCP2, JAZF1, KAT6B, SPG7, FAM96A, ZMAT5, HELZ, ZEB1, ZBTB38, EFHD2, PTER, MBTD1, ASH2L, NSMCE1, NSMCE2, TOP2B, NT5C, ZFP36, ZCCHC10, POGZ, POLR1A, APTX, CYB5A, HERC2, MBD1, GTF2B, RAD50, ASH1L, MAP3K13, REV3L, LIMS1, USP3, ZBTB10, YPEL5, ZBTB11, USP5, USP4, YPEL3, CETN2, POLR2B, ZFP36L2, LPXN, GNPTAB, MORC3, TYW1, GATAD2A, AGO2, THAP1, PRKAA1, THAP2, NENF, MLLT6, BAZ2B, BAZ2A, RBM22, MSRB1, ATMIN, DNPEP, JMJD6, YAF2, MEX3C, NLN, MKRN1, ZC3HAV1, APOBEC3G, APOBEC3C, APOBEC3D, GATA3, RBCK1, RBM10, ZNF814, CHP1, PPP1CB, TRERF1, TIMM8A, TRIM38, TRIM33, NBR1, SLU7, PYGO2, AKAP8, PRPS2, PRPS1, ZFAND6, ZFAND5, AGFG2, ITGAE, AGMAT, ZFAND1, ITGB1, PEF1, TRIM69, CNOT6L, STAMBPL1, RNF10, RUNX1, SETDB1, ZMYM2, RABIF, ZMYM4, ZMYM5, KAT5, FOXP3, MSL2, PHF3, PHF1, MTR, RHOT1, RHOT2, UTY, FOXK2, UQCRFS1, ZZEF1, CBFA2T2, GSS, PCGF5, TPP1, RSPRY1, MOB3A, DBR1, ATP8B2, ZYX, ZNF721, RANBP2, EGR1, PFKL, PRKCI, PRKCH, PRKCD, PRKCB, NUCB1, XPA, BPTF, NUCB2, COMMD1, MDM4, PRKD3, ING4, GLRX5, MOB1B, ING3, ING2, XIAP, MGMT, ZNF800, RSAD2, GLRX2, RPA1, MTHFS, MAP3K3, MAP3K1, ZC3H12D, SCO2, DUS3L, STAMBP, DCTD, L3MBTL2, SIRT6, SIRT7, SIRT2, RPAP2, SP1, TDP2, ARAP2 |
| Enrichment Score: 6.51824669041824 | | | |
| IPR019787:Zinc finger, PHD-finger | | 31 | DPF2, ING4, ING3, ING2, KMT2A, KMT2C, DIDO1, CXXC1, BRPF1, BAZ2B, MLLT6, KDM5B, BAZ2A, KDM5C, NFX1, BRD1, PHRF1, PHF10, PHF3, UHRF2, KDM2A, PHF14, BPTF, TRIM33, PHF1, MTF2, MLLT10, WHSC1L1, ASH1L, PYGO2, KAT6B |
| SM00249:PHD | | 32 | DPF2, ING4, ING3, ING2, KMT2A, KMT2C, DIDO1, CXXC1, TCF20, BRPF1, BAZ2B, MLLT6, KDM5B, BAZ2A, KDM5C, BRD1, PHRF1, PHF10, PHF3, UHRF2, KDM2A, BPTF, TRIM33, PHF14, PHF1, MTF2, MLLT10, WHSC1L1, ASH1L, KDM4C, PYGO2, KAT6B |
| IPR001965:Zinc finger, PHD-type | | 32 | DPF2, ING4, ING3, ING2, KMT2A, KMT2C, DIDO1, CXXC1, TCF20, BRPF1, BAZ2B, MLLT6, KDM5B, BAZ2A, KDM5C, BRD1, PHRF1, PHF10, PHF3, UHRF2, KDM2A, BPTF, TRIM33, PHF14, PHF1, MTF2, MLLT10, WHSC1L1, ASH1L, KDM4C, PYGO2, KAT6B |
| IPR011011:Zinc finger, FYVE/PHD-type | | 38 | DPF2, ING4, ING3, ING2, KMT2A, KMT2C, EEA1, RFFL, DIDO1, CXXC1, BRPF1, BAZ2B, MLLT6, KDM5B, BAZ2A, KDM5C, BRD1, PHRF1, CREBBP, PHF10, PHF3, PLEKHF2, UHRF2, KDM2A, UBR7, BPTF, TRIM33, PHF14, PHF1, MTF2, MLLT10, WHSC1L1, ASH1L, KDM4C, HGS, PYGO2, SYTL3, KAT6B |
| IPR019786:Zinc finger, PHD-type, conserved site | | 23 | ING4, BRD1, PHRF1, ING3, ING2, DIDO1, CXXC1, BRPF1, PHF3, PHF14, KDM2A, BPTF, PHF1, TRIM33, MTF2, MLLT10, WHSC1L1, ASH1L, PYGO2, MLLT6, KDM5B, KDM5C, NFX1 |
| zinc finger region:PHD-type 2 | | 14 | DPF2, PHF14, BPTF, KMT2A, PHF1, MTF2, MLLT10, KMT2C, WHSC1L1, KDM4C, KAT6B, MLLT6, KDM5B, KDM5C |
| zinc finger region:PHD-type 1 | | 14 | DPF2, PHF14, BPTF, KMT2A, PHF1, MTF2, MLLT10, KMT2C, WHSC1L1, KDM4C, KAT6B, MLLT6, KDM5B, KDM5C |

TABLE 3-continued

HIV- low cutoff

| Category | Count | Genes |
|---|---|---|
| zinc finger region:PHD-type Enrichment Score: 6.341978088960009 | 16 | BRD1, ING4, PHRF1, ING3, ING2, DIDO1, CXXC1, BRPF1, PHF3, UHRF2, KDM2A, TRIM33, ASH1L, PYGO2, BAZ2B, BAZ2A |
| Ubl conjugation pathway | 142 | MKRN1, RNF216, SAE1, ZNRF1, CUL3, CUL2, CUL9, KLHL9, FBXO25, RBCK1, RNF149, RNF146, ZC3HC1, RNF220, SOCS3, ANAPC4, SOCS1, UBE2J1, UBR2, UBE2J2, BRAP, TRIM38, UHRF2, KDM2A, UBR7, PIAS4, TRIM33, MIB2, FBXL5, RNF139, RNF138, PIAS1, AMFR, FBXO11, TRAF2, ZFAND5, UBA5, ANAPC10, KEAP1, RFFL, COMMD9, UBAC1, COMMD10, UBE2D4, FBXW7, ARIH2, KRAS, FBXW5, TRIM69, FBXO6, STAMBPL1, FBXW2, HECTD4, RNF168, RCHY1, RNF167, TRAF3, HECTD1, SPOP, PELI1, KIAA1586, CDC23, MALT1, CDC27, ATE1, MSL2, CBLB, RNF4, UBA3, SMURF2, FBXO34, UBE2E1, UBE2G1, BAP1, TRIM4, NSMCE2, RANBP2, USP16, FBXL15, USP15, DCAF16, DCAF15, NFX1, VCPIP1, TBL1XR1, UBE2A, HERC6, HERC5, HERC2, PJA2, WDR48, UFL1, ATG4B, MED8, DDB2, COMMD3, UBE2W, COMMD1, UCHL3, CAND1, USP22, USP24, OTUD5, UBE2Z, USP3, XIAP, USP5, USP4, CBLL1, FEM1B, STUB1, FEM1A, UBE2R2, MYCBP2, PRPF19, RNF125, RNF126, USP36, USP34, FBXW11, STAMBP, WDTC1, USP40, UBE4A, VHL, LRRC41, CBL, TRIM27, BIRC6, TRIM25, TRIM22, NAE1, WSB1, RNF115, USP47, MEX3C, TRPC4AP, CUL4B, TBL1X, USP42, RNF111, BARD1 |
| IPR013083:Zinc finger, RING/FYVE/PHD-type | 96 | MKRN1, ZNRF1, TRIM4, PCGF5, BRPF1, PEX2, RSPRY1, NSMCE2, RBCK1, RNF149, USP16, KDM5B, KDM5C, RNF146, PHRF1, RNF220, VPS41, BRAP, PJA2, TRIM38, UHRF2, KDM2A, PIAS4, TRIM33, BPTF, UBR7, MTF2, MIB2, MLLT10, ASH1L, COMMD3, RNF139, PYGO2, RNF138, MDM4, USP22, AMFR, ZNHIT3, DPF2, TRAF2, ING4, ING3, ING2, KMT2A, USP3, USP5, KMT2C, PML, EEA1, RFFL, CBLL1, STUB1, DIDO1, CXXC1, MYCBP2, RNF125, PRPF19, RNF126, ARIH2, RNF166, TRIM69, MAP3K1, RNF10, RNF168, RNF167, RCHY1, MLLT6, BAZ2B, TRAF5, BAZ2A, TRAF3, BRD1, UBE4A, CBL, CREBBP, TRIM27, TRIM26, PHF10, TRIM25, TRIM22, CBLB, PHF3, RNF115, PLEKHF2, PHF1, PHF14, RNF4, WHSC1L1, MEX3C, HGS, KDM4C, SYTL3, KAT6B, RNF113A, BARD1, RNF111 |
| Ligase | 76 | MKRN1, SAE1, RNF216, ZNRF1, GSS, TRIM4, NSMCE1, RBCK1, NSMCE2, RNF149, RANBP2, RNF146, NFX1, RNF220, HERC6, HERC5, UBR2, HERC2, GMPS, BRAP, UFL1, PJA2, TRIM38, GLUL, UHRF2, PIAS4, TRIM33, UBR7, MIB2, FARSB, RNF139, RNF138, AMFR, YARS2, PIAS1, PCCB, TRAF2, XIAP, FARS2, WARS2, RFFL, CBLL1, STUB1, MYCBP2, RNF125, PRPF19, MTHFS, RNF126, ARIH2, TRIM69, HECTD4, RNF168, RNF167, RCHY1, ACSL4, ACSL3, ACSL5, TRAF3, HECTD1, PELI1, KIAA1586, UBE4A, CBL, TRIM27, BIRC6, TRIM25, TRIM22, MSL2, CBLB, RNF115, RNF4, UBA3, MEX3C, SMURF2, BARD1, RNF111 |
| GO:0016874~ligase activity | 63 | MKRN1, RNF216, ZNRF1, TRIM4, NSMCE1, RBCK1, NSMCE2, RNF149, RANBP2, RNF146, NFX1, RNF220, HERC6, HERC5, UBR2, HERC2, BRAP, PJA2, UFL1, TRIM38, UHRF2, PIAS4, TRIM33, UBR7, MIB2, RNF139, RNF138, AMFR, PIAS1, PCCB, TRAF2, XIAP, RFFL, CBLL1, STUB1, MYCBP2, PRPF19, RNF125, RNF126, ARIH2, TRIM69, HECTD4, RNF168, RNF167, RCHY1, ACSL3, TRAF3, HECTD1, PELI1, KIAA1586, UBE4A, CBL, TRIM27, BIRC6, TRIM22, MSL2, CBLB, RNF115, RNF4, MEX3C, SMURF2, BARD1, RNF111 |
| GO:0004842~ubiquitin-protein transferase activity | 71 | MKRN1, BACH2, UBE2G1, RNF216, ZNRF1, CUL3, NSMCE1, KLHL9, FBXO25, RBCK1, KLHL24, FBXL15, RNF146, UBE2A, RNF220, HERC6, ANAPC4, HERC5, UBR2, HERC2, BRAP, PJA2, UHRF2, TRIM33, MIB2, DDB2, RNF139, FBXL5, UBE2W, AMFR, FBXO11, TRAF2, XIAP, KEAP1, CBLL1, FEM1B, STUB1, FEM1A, UBE2R2, PRPF19, UBE2D4, ARIH2, FBXW7, KBTBD2, TRIM69, FBXO6, FBXW2, HECTD4, RNF10, RNF168, RNF167, RCHY1, TRAF5, FBXW11, TRAF3, HECTD1, VHL, CBL, TRIM27, CDC23, BIRC6, MALT1, TRIM25, TSPAN17, WSB1, CBLB, RNF115, RNF4, SMURF2, UBE2E1, BARD1 |
| GO:0016567~protein ubiquitination | 73 | BACH2, SAE1, CUL3, TRIM4, NSMCE1, CUL9, KLHL9, FBXO25, KLHL24, RNF149, FBXL15, DCAF16, VCPIP1, DCAF15, ZC3HC1, RNF220, SOCS3, SOCS1, UBE2J1, MED11, HERC2, TMEM189, BRAP, PJA2, UHRF2, TRIM33, UBR7, MED17, MED8, FBXL5, RNF139, RNF138, CAND1, NFE2L2, MDM4, MED1, FBXO11, XIAP, KEAP1, CBLL1, UBAC1, FEM1B, STUB1, FEM1A, MYCBP2, UBE2D4, ARIH2, FBXW7, KBTBD2, FBXW5, FBXW2, RNF168, RCHY1, TRAF5, FBXW11, TRAF3, WDTC1, VHL, LRRC41, SPSB3, CBL, BIRC6, MALT1, TSPAN17, TRIM22, WSB1, MED31, MSL2, RNF4, TRPC4AP, UBE2E1, BARD1, RNF111 |
| IPR001841:Zinc finger, RING-type | 58 | MKRN1, ZNRF1, TRIM4, PCGF5, RSPRY1, PEX2, CUL9, NSMCE1, RBCK1, RNF149, RNF146, NFX1, PHRF1, RNF220, VPS41, BRAP, PJA2, TRIM38, UHRF2, TRIM33, MIB2, COMMD3, RNF139, RNF138, AMFR, MDM4, TRAF2, XIAP, KMT2C, PML, RFFL, CBLL1, MYCBP2, RNF125, RNF126, ARIH2, RNF166, TRIM69, MAP3K1, RNF168, RNF10, RCHY1, RNF167, TRAF5, TRAF3, CBL, TRIM27, TRIM26, TRIM25, TRIM22, MSL2, CBLB, RNF115, RNF4, MEX3C, RNF113A, RNF111, BARD1 |

TABLE 3-continued

HIV- low cutoff

| Category | Count | Genes |
|---|---|---|
| SM00184:RING | 48 | MKRN1, TRAF2, XIAP, KMT2C, PML, RFFL, ZNRF1, MYCBP2, TRIM4, RNF125, PCGF5, RNF126, ARIH2, RNF166, RSPRY1, PEX2, TRIM69, RBCK1, RNF168, RNF10, RCHY1, RNF149, RNF167, TRAF5, RNF146, NFX1, PHRF1, CBL, TRIM27, TRIM26, TRIM25, TRIM22, BRAP, PJA2, TRIM38, CBLB, UHRF2, RNF115, TRIM33, RNF4, MIB2, COMMD3, MEX3C, RNF139, RNF138, AMFR, RNF113A, RNF111 |
| zinc finger region:RING-type | 44 | MKRN1, TRAF2, CHMP3, XIAP, KMT2C, PML, RFFL, CBLL1, TRIM4, RNF125, PCGF5, RNF126, RNF166, RSPRY1, PEX2, TRIM69, MAP3K1, RBCK1, RNF168, RNF10, RCHY1, TRAF5, RNF146, TRAF3, RNF220, CBL, TRIM27, TRIM26, TRIM25, TRIM22, BRAP, TRIM38, MSL2, CBLB, UHRF2, RNF115, TRIM33, RNF4, MEX3C, RNF138, MDM4, AMFR, RNF113A, BARD1 |
| IPR017907:Zinc finger, RING-type, conserved site | 30 | MKRN1, TRAF2, PML, CBLL1, RNF125, TRIM4, PCGF5, ARIH2, RNF166, PEX2, TRIM69, CUL9, RBCK1, RNF10, TRAF5, RNF146, TRAF3, PHRF1, CBL, TRIM27, TRIM25, TRIM22, TRIM38, CBLB, UHRF2, TRIM33, RNF4, COMMD3, BARD1, RNF113A |

Enrichment Score: 5.35889838477318

| Category | Count | Genes |
|---|---|---|
| GO:0051607~defense response to virus | 43 | ABCF3, CD8A, IFITM1, ZC3HAV1, IFITM2, UNC93B1, PML, BNIP3, RSAD2, OAS1, APOBEC3G, OAS2, APOBEC3C, APOBEC3D, SERINC3, NLRC5, BCL2, C19ORF66, IFNG, PYCARD, MX1, MX2, POLR3F, POLR3H, RELA, FAM111A, EXOSC5, HERC5, SAMHD1, FADD, TRIM25, POLR3C, TRIM22, POLR3E, IFNAR1, IFIT3, IFNAR2, PLSCR1, UNC13D, IFIT5, BNIP3L, IRF3, GBP3 |
| Antiviral defense | 31 | ABCF3, IFITM1, ZC3HAV1, IFITM2, UNC93B1, PML, RSAD2, OAS1, APOBEC3G, OAS2, APOBEC3C, APOBEC3D, SERINC3, C19ORF66, IFNG, MX1, MX2, POLR3F, POLR3H, FAM111A, HERC5, SAMHD1, TRIM25, POLR3C, TRIM22, POLR3E, IFIT3, PLSCR1, IFIT5, IRF3, GBP3 |
| Innate immunity | 50 | ZC3HAV1, APOBEC3G, APOBEC3C, APOBEC3D, TRIM4, NLRC5, ANKRD17, GATA3, MX1, MX2, IRAK1, LY96, HERC5, FADD, ECSIT, CD84, TRIM38, CHID1, RIPK2, AKAP8, IFITM1, IFITM2, CSF1, PML, UNC93B1, RSAD2, OAS1, OAS2, SEC14L1, SERINC3, IRAK4, PSTPIP1, PYCARD, MR1, TBKBP1, POLR3F, POLR3H, ANXA1, MSRB1, SAMHD1, TRIM25, SLAMF7, POLR3C, POLR3E, SIRT2, IFIT3, CD55, IFIT5, JAK2, IRF3 |

Enrichment Score: 5.143098283847529

| Category | Count | Genes |
|---|---|---|
| Cell cycle | 120 | ITGB3BP, CHMP3, MAU2, KNTC1, INO80, CASP8AP2, KLHL9, RALB, VPS4A, TLK1, CDCA4, STAG1, ESCO1, ZC3HC1, ANAPC4, RINT1, PIM1, HMG20B, PPP1CB, MAPK1, UHRF2, EP300, RCC2, MAPK6, PRCC, BIN3, CDCA7L, PDCD6IP, ARL8B, MPLKIP, CACUL1, STK10, AHCTF1, ARF6, CEP164, ANAPC10, CCNG1, CCNG2, NIPBL, PPP2R2D, SSSCA1, CINP, WDR6, CDC23, PMF1, CDC27, ATM, CDKN1B, DMTF1, UBA3, CCNT2, E2F3, E2F4, TSG101, CCNT1, LATS1, NDE1, NSMCE2, CDK10, USP16, CDK13, ARL2, RBBP4, POGZ, CCNH, DYNLT3, PKN2, DYNLT1, PAPD5, BANP, CDK7, PRKCD, RAD50, CDK2, MCM6, ARL3, GAK, SASS6, CHMP1A, NSL1, CDK11B, MAPRE2, WASL, USP22, MAPRE1, PDCD2L, SPAST, HAUS3, ING4, HAUS6, RABGAP1, ASUN, USP3, HAUS2, HAUS1, CETN2, NUMA1, MAP10, TSPYL2, MDC1, RB1CC1, NPAT, PAFAH1B1, THAP1, FBXW11, TERF2, TERF1, CSNK1A1, BOD1, PDS5B, SMC5, BIRC6, RGS14, SIRT2, NAE1, SMC4, RPS6KA3, MAPK13, CUL4B, C9ORF69 |
| Cell division | 73 | ITGB3BP, CCNT2, CHMP3, MAU2, TSG101, CCNT1, KNTC1, INO80, LATS1, NDE1, KLHL9, RALB, VPS4A, NSMCE2, CDK10, USP16, CDCA4, CDK13, STAG1, ZC3HC1, POGZ, ANAPC4, PKN2, DYNLT3, DYNLT1, PAPD5, CDK7, PPP1CB, CDK2, ARL3, CHMP1A, RCC2, NSL1, BIN3, CDK11B, MAPRE2, CDCA7L, ARL8B, WASL, MAPRE1, PDCD6IP, SPAST, HAUS3, HAUS6, ASUN, MPLKIP, HAUS2, HAUS1, CETN2, AHCTF1, ARF6, ANAPC10, CEP164, CCNG1, CCNG2, NUMA1, MAP10, PAFAH1B1, PPP2R2D, TERF1, CSNK1A1, SSSCA1, BOD1, PDS5B, CINP, SMC5, CDC23, BIRC6, PMF1, CDC27, SIRT2, RGS14, SMC4 |
| GO:0051301~cell division | 66 | ITGB3BP, CCNT2, MAU2, TSG101, CCNT1, KNTC1, INO80, LATS1, NDE1, NSMCE2, VPS4A, CDK10, TUBA1A, USP16, CDCA4, TUBA1C, CDK13, STAG1, ZC3HC1, POGZ, ANAPC4, PKN2, DYNLT3, PAPD5, DYNLT1, CDK7, PPP1CB, CDK2, CHMP1A, RCC2, NSL1, CDK11B, MAPRE2, CDCA7L, ARL8B, WASL, MAPRE1, HAUS3, HAUS6, ASUN, MPLKIP, HAUS2, HAUS1, CETN2, ARF6, ANAPC10, CEP164, CCNG1, CCNG2, NUMA1, MAP10, PPP2R2D, TERF1, CSNK1A1, SSSCA1, BOD1, PDS5B, CINP, SMC5, CDC23, BIRC6, PMF1, CDC27, SIRT2, RGS14, SMC4 |
| GO:0007067~mitotic nuclear division | 49 | ITGB3BP, HAUS3, HAUS6, ASUN, MPLKIP, HAUS2, HAUS1, KNTC1, CETN2, ANAPC10, CEP164, CLTC, CCNG1, CCNG2, LATS1, OFD1, NUMA1, FBXW5, KLHL9, NSMCE2, PAFAH1B1, USP16, PPP2R2D, STAG1, TERF1, VCPIP1, CSNK1A1, SSSCA1, BOD1, ZC3HC1, TADA2A, ANAPC4, SMC5, DYNLT3, CDC23, BIRC6, PAPD5, DYNLT1, PMF1, SIRT2, RGS14, CDK2, RCC2, NSL1, CDK11B, MAPRE2, MAPRE1, WASL, AKAP8 |

TABLE 3-continued

HIV- low cutoff

| Category | Count | Genes |
|---|---|---|
| Mitosis | 46 | ITGB3BP, HAUS3, HAUS6, ASUN, MPLKIP, MAU2, HAUS2, HAUS1, KNTC1, INO80, CETN2, CEP164, ANAPC10, CCNG1, CCNG2, LATS1, NUMA1, NDE1, KLHL9, NSMCE2, PAFAH1B1, USP16, PPP2R2D, STAG1, TERF1, CSNK1A1, SSSCA1, BOD1, ZC3HC1, PDS5B, ANAPC4, SMC5, DYNLT3, CDC23, BIRC6, PAPD5, DYNLT1, PMF1, SIRT2, CDK2, SMC4, RCC2, NSL1, MAPRE2, MAPRE1, WASL |
| Enrichment Score: 5.023865225499397 | | |
| DNA damage | 68 | RAD51C, INO80, NSMCE1, AEN, NSMCE2, TLK1, BRD4, INO80D, INO80C, INO80B, POLK, UBE2A, NEIL2, FMR1, APTX, GTF2H3, CDK9, MBD4, POLB, HERC2, CDK7, CDK2, RAD50, RAD1, XPA, NABP1, XPC, HIPK2, DDB2, RNF138, UBE2W, PSME4, REV3L, USP3, WRNIP1, HUS1, MGMT, CETN2, MUM1, CEP164, MAPKAPK2, STUB1, XAB2, PRPF19, RPA1, CHD1L, MDC1, FBXO6, RNF168, ACTL6A, ERCC3, MSH6, MSH2, TAOK1, TP53BP1, CINP, SMC5, SMC6, ATMIN, UIMC1, ATM, MPG, PHF1, TDP2, USP47, CUL4B, OGG1, BARD1 |
| DNA repair | 56 | RAD51C, INO80, NSMCE1, NSMCE2, INO80D, INO80C, INO80B, POLK, UBE2A, NEIL2, APTX, GTF2H3, CDK9, MBD4, POLB, HERC2, CDK7, CDK2, RAD50, RAD1, XPA, NABP1, XPC, DDB2, UBE2W, RNF138, PSME4, REV3L, MGMT, CETN2, MUM1, CEP164, STUB1, XAB2, RPA1, PRPF19, CHD1L, MDC1, FBXO6, RNF168, ACTL6A, ERCC3, MSH6, TAOK1, MSH2, TP53BP1, CINP, SMC5, SMC6, UIMC1, MPG, TDP2, USP47, CUL4B, OGG1, BARD1 |
| GO:0006281~DNA repair | 49 | RAD51C, USP3, MGMT, HUS1, INO80, MUM1, HSPA1A, CEP164, TRRAP, STUB1, RPA1, CHD1L, NSMCE1, FBXO6, ACTL6A, ERCC3, INO80D, INO80C, INO80B, POLK, MSH6, UBE2A, NUDT1, PDS5B, TAOK1, MSH2, NEIL2, CINP, APTX, GTF2H3, CDK9, MBD4, POLB, ATM, RAD50, CDK2, RAD1, XPA, RECQL, NABP1, XPC, CSNK1D, BTG2, CSNK1E, DDB2, UBE2W, PSME4, PARP4, OGG1 |
| Enrichment Score: 4.995051000869093 | | |
| Nucleotide-binding | 267 | RAD51C, DYNC1LI2, ADCY7, ATP2B4, PSKH1, CLK2, CUL9, CLK4, ILK, DHX34, VPS4A, TLK1, DDX10, MAP2K7, PAN3, TNIK, ROCK1, ROCK2, PIM1, UBE2J1, UBE2J2, MARK2, MAPK1, GLUL, NME3, RAB18, MAPK6, DHX29, CAMK4, ATP2C1, RFC2, MAPK8, ARL8B, CLCN3, PFKFB3, FARS2, UBA5, WARS2, HSPA1A, OAS1, MYO9B, ARF6, OAS2, MTIF2, NAGK, UHMK1, MOV10, KRAS, VRK3, RAC1, ZAP70, NAT10, KIF3B, MOCS2, TAOK1, MAP2K4, ATP11A, OXSR1, ATM, ATP13A1, UBA3, ARF4, RIT1, SPG7, ABCF3, RAB5B, RAB5C, FASTK, UBE2G1, GTPBP10, GNL3L, HELZ, PMVK, LATS1, ATAD3A, LONP1, ARL5A, DYNC1H1, TOP2B, NT5C, SRPK2, RAP2C, PIK3C2A, PI4KB, DGUOK, GMPS, SRPK1, RAD50, TTF2, CBWD2, TRAP1, RIPK1, RRM1, RAB5A, FARSB, CDK11B, MAP3K14, ARL4C, MAP3K13, ARL4A, WRNIP1, MKNK2, KTI12, SNRK, DGKE, STK40, DDX19A, TYW1, RAB11B, DHX16, PRKAA1, CERK, ACSL4, ACSL3, SPATA5, ACSL5, CSNK1A1, DNM3, MAT2A, PDK3, DGKH, PCK2, NRAS, RPS6KA3, RAB30, CSNK1D, CSNK1E, MAPK13, RAB35, GSK3B, ARAF, DGKZ, GNA13, NT5C3A, IDE, PASK, HBS1L, INO80, DSTYK, PI4K2B, NLRC5, PRKAR2A, IDH3G, DDX23, AAK1, ORC4, RALB, PRKACB, SAR1B, MX1, MX2, MATK, PDXK, CSNK1G2, EFTUD2, RIPK2, CSNK1G3, YARS2, SMARCA2, PCCB, GBP3, PRPS2, PRPS1, GPN3, MVD, STK10, MAPKAPK5, MAP4K1, MAPKAPK2, RRAGC, IRAK4, UBE2D4, GFM2, FICD, GFM1, DDX42, NIN, RYK, MYO1G, ABCB7, RAB33A, RAB33B, PSMC5, PSMC2, ULK3, DYRK1A, GTF2F2, DDX50, RHOT1, RHOT2, ABL2, DDX51, UBE2E1, ATL3, PRKAG2, DICER1, HINT2, PPIP5K2, SKIV2L2, SLFN5, PIP5K1A, GSS, SLK, CDK12, MKKS, ATP8B2, CDK10, TUBA1A, RHOF, CHUK, TUBA1C, CDK13, AKT2, ARL2, IRAK1, UBE2A, PFKL, PRKCI, PKN2, PRKCH, CDK9, CDK7, PRKCD, CDK2, ARL3, PRKCB, GAK, MCM6, TOR2A, PANK4, RECQL, PANK2, HIPK1, HIPK2, UBE2W, PRKD3, SPAST, NKIRAS2, BTAF1, PGS1, UBE2Z, DCK, UBE2R2, N4BP2, MTHFS, CHD9, CHD7, CHD1L, MAP3K3, MAP3K1, UCK1, HSPA4, ERCC3, EHD1, CHD6, EHD4, MSH6, GIMAP5, MSH2, SMC5, SMC6, RAF1, DRG1, DRG2, SMC4, GIMAP1, JAK2 |
| SM00220:S_TKc | 74 | PASK, DSTYK, LATS1, PSKH1, SLK, CLK2, AAK1, CLK4, CDK12, TLK1, CDK10, PRKACB, MAP2K7, CHUK, CDK13, AKT2, SRPK2, IRAK1, TNIK, ROCK1, CSNK1G2, ROCK2, PRKCI, PKN2, PIM1, PRKCH, CDK9, CDK7, PRKCD, SRPK1, CDK2, MARK2, GAK, PRKCB, MAPK1, MAPK6, CAMK4, HIPK1, RIPK1, HIPK2, RIPK2, CDK11B, MAPK8, CSNK1G3, MAP3K14, MAP3K13, PRKD3, STK10, MAPKAPK5, MKNK2, MAP4K1, MAPKAPK2, UHMK1, TRIB2, IRAK4, MAP3K3, VRK3, SNRK, STK40, MAP3K1, PRKAA1, CSNK1A1, TAOK1, MAP2K4, RAF1, OXSR1, RPS6KA3, CSNK1D, CSNK1E, MAPK13, GSK3B, ARAF, ULK3, DYRK1A |
| ATP-binding | 210 | RAD51C, DYNC1LI2, ADCY7, ATP2B4, PSKH1, CLK2, CUL9, CLK4, ILK, DHX34, VPS4A, TLK1, DDX10, MAP2K7, PAN3, TNIK, ROCK1, ROCK2, UBE2J1, PIM1, UBE2J2, MARK2, MAPK1, GLUL, NME3, MAPK6, DHX29, |

TABLE 3-continued

HIV- low cutoff

| Category | Count | Genes |
|---|---|---|
| | | CAMK4, RFC2, ATP2C1, MAPK8, CLCN3, PFKFB3, FARS2, UBA5, WARS2, HSPA1A, OAS1, MYO9B, OAS2, NAGK, UHMK1, MOV10, KRAS, ZAP70, NAT10, KIF3B, TAOK1, MAP2K4, ATP11A, OXSR1, ATM, ATP13A1, UBA3, ABCF3, SPG7, FASTK, UBE2G1, HELZ, PMVK, LATS1, LONP1, ATAD3A, DYNC1H1, TOP2B, SRPK2, PIK3C2A, DGUOK, PI4KB, GMPS, SRPK1, RAD50, TTF2, CBWD2, TRAP1, RIPK1, RRM1, FARSB, CDK11B, MAP3K14, MAP3K13, WRNIP1, MKNK2, SNRK, DGKE, STK40, KTI12, DDX19A, DHX16, PRKAA1, CERK, ACSL4, ACSL3, SPATA5, ACSL5, CSNK1A1, MAT2A, PDK3, DGKH, RPS6KA3, CSNK1D, CSNK1E, MAPK13, GSK3B, ARAF, DGKZ, PASK, IDE, DSTYK, INO80, PI4K2B, NLRC5, IDH3G, DDX23, AAK1, ORC4, PRKACB, MATK, PDXK, CSNK1G2, RIPK2, CSNK1G3, YARS2, PCCB, SMARCA2, PRPS2, PRPS1, MVD, STK10, MAPKAPK5, MAP4K1, MAPKAPK2, IRAK4, UBE2D4, FICD, DDX42, RYK, MYO1G, ABCB7, PSMC5, PSMC2, ULK3, DYRK1A, GTF2F2, DDX50, ABL2, DDX51, UBE2E1, DICER1, PRKAG2, PPIP5K2, SKIV2L2, SLFN5, PIP5K1A, GSS, SLK, CDK12, MKKS, ATP8B2, CDK10, CHUK, CDK13, AKT2, IRAK1, UBE2A, PFKL, PRKCI, PKN2, PRKCH, CDK9, CDK7, PRKCD, CDK2, PRKCB, GAK, MCM6, TOR2A, PANK4, RECQL, PANK2, HIPK1, HIPK2, UBE2W, PRKD3, SPAST, BTAF1, PGS1, UBE2Z, DCK, UBE2R2, N4BP2, CHD9, MTHFS, CHD1L, CHD7, MAP3K3, MAP3K1, UCK1, HSPA4, CHD6, ERCC3, EHD1, EHD4, MSH6, MSH2, SMC5, SMC6, RAF1, SMC4, JAK2 |
| IPR008271:Serine/threonine-protein kinase, active site | 66 | PASK, DSTYK, LATS1, PSKH1, SLK, CLK2, AAK1, CLK4, CDK12, TLK1, CDK10, PRKACB, MAP2K7, CHUK, CDK13, AKT2, SRPK2, IRAK1, TNIK, ROCK1, CSNK1G2, ROCK2, PRKCI, PKN2, PIM1, PRKCH, CDK9, CDK7, PRKCD, SRPK1, CDK2, MARK2, GAK, PRKCB, MAPK1, MAPK6, CAMK4, HIPK1, RIPK1, HIPK2, RIPK2, CDK11B, MAPK8, CSNK1G3, MAP3K14, MAP3K13, PRKD3, MAPKAPK5, STK10, MKNK2, MAPKAPK2, SNRK, STK40, MAP3K1, PRKAA1, CSNK1A1, TAOK1, MAP2K4, RAF1, RPS6KA3, CSNK1D, CSNK1E, GSK3B, ARAF, ULK3, DYRK1A |
| Serine/threonine-protein kinase | 75 | FASTK, PASK, DSTYK, LATS1, PSKH1, SLK, CLK2, AAK1, CLK4, ILK, CDK12, TLK1, CDK10, PRKACB, MAP2K7, CHUK, CDK13, AKT2, SRPK2, IRAK1, TNIK, ROCK1, CSNK1G2, ROCK2, PRKCI, PKN2, PIM1, PRKCH, CDK9, CDK7, PRKCD, SRPK1, CDK2, MARK2, GAK, PRKCB, MAPK1, MAPK6, CAMK4, HIPK1, RIPK1, HIPK2, RIPK2, CDK11B, MAPK8, CSNK1G3, MAP3K14, MAP3K13, PRKD3, MAPKAPK5, STK10, MKNK2, MAP4K1, MAPKAPK2, UHMK1, IRAK4, MAP3K3, SNRK, STK40, MAP3K1, PRKAA1, CSNK1A1, TAOK1, MAP2K4, RAF1, OXSR1, ATM, RPS6KA3, CSNK1D, CSNK1E, MAPK13, GSK3B, ARAF, ULK3, DYRK1A |
| nucleotide phosphate-binding region:ATP | 156 | RAD51C, DYNC1LI2, PASK, INO80, DSTYK, NLRC5, PSKH1, IDH3G, DDX23, CLK2, CUL9, AAK1, CLK4, ILK, DHX34, ORC4, VPS4A, TLK1, PRKACB, DDX10, MAP2K7, MATK, TNIK, PDXK, ROCK1, CSNK1G2, ROCK2, PIM1, MARK2, MAPK1, MAPK6, DHX29, CAMK4, RFC2, RIPK2, MAPK8, CSNK1G3, SMARCA2, PRPS2, PRPS1, CLCN3, PFKFB3, MAPKAPK5, STK10, MAP4K1, MYO9B, MAPKAPK2, NAGK, UHMK1, IRAK4, MOV10, VRK3, ZAP70, NAT10, DDX42, KIF3B, RYK, TAOK1, MAP2K4, OXSR1, ABCB7, PSMC5, PSMC2, UBA3, GTF2F2, DYRK1A, ULK3, DDX50, ABL2, DDX51, SPG7, DICER1, HELZ, SKIV2L2, SLFN5, PMVK, LATS1, GSS, ATAD3A, LONP1, SLK, CDK12, MKKS, CDK10, TOP2B, DYNC1H1, CHUK, CDK13, AKT2, SRPK2, IRAK1, PFKL, PRKCI, PKN2, PRKCH, CDK9, DGUOK, CDK7, GMPS, PRKCD, SRPK1, CDK2, RAD50, TTF2, PRKCB, MCM6, CBWD2, TOR2A, RECQL, HIPK1, RIPK1, HIPK2, CDK11B, MAP3K14, MAP3K13, PRKD3, SPAST, BTAF1, PGS1, WRNIP1, MKNK2, DCK, N4BP2, CHD9, MTHFS, CHD1L, CHD7, KTI12, STK40, MAP3K3, SNRK, DDX19A, MAP3K1, DHX16, PRKAA1, UCK1, CHD6, EHD1, ERCC3, EHD4, CSNK1A1, MSH6, MAT2A, MSH2, PDK3, SMC5, SMC6, RAF1, SMC4, RPS6KA3, CSNK1D, CSNK1E, MAPK13, GSK3B, ARAF, JAK2 |
| Kinase | 120 | PASK, NELL2, DSTYK, PI4K2B, PRKAR2A, PSKH1, CLK2, AAK1, CLK4, ILK, TLK1, PRKACB, MAP2K7, MATK, TNIK, PDXK, ROCK1, CSNK1G2, ROCK2, PRKAB1, PIM1, PKIA, MARK2, WDR83, MAPK1, NME3, CAMK4, MAPK6, RIPK2, MAPK8, CSNK1G3, PRPS2, PRPS1, PHKA2, PFKFB3, STK10, MAPKAPK5, MAP4K1, AKAP10, MAPKAPK2, NAGK, UHMK1, IRAK4, VRK3, PRKRA, ZAP70, TAOK1, RYK, CINP, MAP2K4, FN3KRP, OXSR1, ATM, CDKN1B, DYRK1A, ULK3, HGS, ABL2, FASTK, PRKAG2, PPIP5K2, PIP5K1A, PMVK, LATS1, SLK, CDK12, CDK10, CHUK, CDK13, AKT2, SRPK2, IRAK1, PFKL, PIK3C2A, PKN2, PRKCI, CDK9, PRKCH, DGUOK, PI4KB, CDK7, PRKCD, SRPK1, CDK2, GAK, PRKCB, PANK4, PANK2, HIPK1, RIPK1, HIPK2, CDK11B, MAP3K14, MAP3K13, PRKD3, MOB1B, DCK, MKNK2, MAP3K3, STK40, DGKE, SNRK, MAP3K1, UCK1, PRKAA1, CERK, PIK3R1, CSNK1A1, PDK3, RAF1, DGKH, PCK2, RPS6KA3, CSNK1D, CSNK1E, MAPK13, GSK3B, ARAF, DGKZ, JAK2 |
| binding site:ATP | 94 | SPG7, PASK, DSTYK, PMVK, LATS1, GSS, PSKH1, SLK, CLK2, AAK1, CLK4, ILK, CDK12, TLK1, CDK10, PRKACB, MAP2K7, CHUK, CDK13, AKT2, MATK, SRPK2, IRAK1, TNIK, ROCK1, CSNK1G2, ROCK2, PIM1, PKN2, PRKCI, CDK9, PRKCH, CDK7, PRKCD, SRPK1, CDK2, MARK2, PRKCB, TRAP1, MAPK1, NME3, HIPK1, CAMK4, MAPK6, RIPK1, HIPK2, |

TABLE 3-continued

HIV- low cutoff

| Category | Count | Genes |
|---|---|---|
| | | RIPK2, CDK11B, MAPK8, CSNK1G3, YARS2, MAP3K14, MAP3K13, PRKD3, PRPS2, PRPS1, STK10, MAPKAPK5, MKNK2, MAP4K1, UBA5, MAPKAPK2, NAGK, UHMK1, IRAK4, MTHFS, MAP3K3, VRK3, SNRK, STK40, MAP3K1, ZAP70, PRKAA1, UCK1, EHD1, EHD4, CSNK1A1, MAT2A, RYK, TAOK1, PDK3, MAP2K4, RAF1, OXSR1, RPS6KA3, CSNK1D, CSNK1E, MAPK13, GSK3B, ARAF, ULK3, DYRK1A, JAK2, ABL2 |
| GO:0004674~protein serine/threonine kinase activity | 72 | CCNT2, FASTK, PASK, CCNT1, DSTYK, LATS1, PSKH1, SLK, CLK2, AAK1, CLK4, ILK, TLK1, CDK10, PRKACB, CDK13, AKT2, SRPK2, IRAK1, TNIK, ROCK1, CSNK1G2, ROCK2, PRKCI, PKN2, PIM1, PRKCH, CDK9, CDK7, PRKCD, SRPK1, CDK2, MARK2, GAK, PRKCB, MAPK1, MAPK6, HIPK1, RIPK1, HIPK2, RIPK2, CDK11B, MAPK8, CSNK1G3, MAP3K14, MAP3K13, MAPKAPK5, STK10, MKNK2, MAP4K1, MAPKAPK2, UHMK1, IRAK4, VRK3, SNRK, STK40, MAP3K1, PRKAA1, CSNK1A1, TAOK1, PDK3, RAF1, OXSR1, ATM, RPS6KA3, CSNK1D, CSNK1E, MAPK13, GSK3B, ARAF, ULK3, DYRK1A |
| GO:0006468~protein phosphorylation | 83 | CCNT2, FASTK, PRKAG2, PASK, CCNT1, LATS1, ST3GAL1, PSKH1, CLK2, AAK1, ILK, TLK1, CDK10, PRKACB, CHUK, MATK, SRPK2, IRAK1, CTBP1, PAN3, TNIK, ROCK1, CSNK1G2, ROCK2, CCNH, PIM1, PRKCI, PKN2, PRKAB1, PRKCH, CDK9, DGUOK, CDK7, PRKCD, SRPK1, MARK2, GAK, HCST, PRKCB, MAPK1, MAPK6, CAMK4, HIPK1, HIPK2, CDK11B, MAPK8, MAP3K13, PRKD3, PHKA2, STK10, HUS1, MKNK2, MAP4K1, MAPKAPK2, NPRL2, TRIB2, SNRK, STK40, MORC3, MAP3K1, PRKRA, PPP3CB, ZAP70, PRKAA1, ERCC3, PIK3R1, CSNK1A1, FYB, TAOK1, RYK, CREB1, RAF1, BIRC6, OXSR1, ATM, GMFB, RPS6KA3, CSNK1D, CSNK1E, RSRC1, GSK3B, DYRK1A, JAK2 |
| active site:Proton acceptor | 105 | CNDP2, PASK, IDE, DSTYK, PSKH1, CLK2, AAK1, CLK4, TLK1, PRKACB, MAP2K7, MATK, TNIK, ROCK1, CSNK1G2, ROCK2, PIM1, MARK2, MAPK1, CAMK4, MAPK6, RIPK2, KDSR, MAPK8, CSNK1G3, MDH1, HSD17B11, ME2, STK10, MAPKAPK5, MAP4K1, MAPKAPK2, ACAT2, UHMK1, IRAK4, GALM, VRK3, IVD, ZAP70, TAOK1, RYK, MAP2K4, OXSR1, ULK3, DYRK1A, ABL2, DCXR, HTATIP2, DHRSX, LATS1, SLK, CDK12, CDK10, CHUK, CDK13, AKT2, IRAK1, SRPK2, PFKL, PKN2, PRKCI, CDK9, PRKCH, CDK7, PRKCD, CDK2, SRPK1, GAK, DHRS7, PRKCB, G6PD, HIPK1, RIPK1, TGDS, HIPK2, RRM1, TXNRD1, CDK11B, MAP3K14, MAP3K13, PRKD3, ALDH9A1, MKNK2, ERI3, MAP3K3, STK40, SNRK, MAP3K1, PITRM1, PRKAA1, HSD17B8, CSNK1A1, RAF1, SIRT6, SIRT7, SIRT2, SDHA, RPS6KA3, CSNK1D, CSNK1E, TDP2, MAPK13, GSK3B, ARAF, JAK2 |
| GO:0004672~protein kinase activity | 67 | FASTK, PASK, CLK2, AAK1, ILK, CDK12, CDK10, MAP2K7, CHUK, CDK13, AKT2, SRPK2, IRAK1, TNIK, PAN3, ROCK1, CSNK1G2, PRKCI, PKN2, PRKAB1, GTF2H3, PRKCH, CDK9, CDK7, PRKCD, SRPK1, CDK2, MARK2, GAK, PRKCB, CAMK4, HIPK1, RIPK1, HIPK2, CDK11B, CSNK1G3, MAP3K14, CCL3, MAPKAPK5, MKNK2, MAP4K1, MAPKAPK2, NPRL2, TRIB2, IRAK4, VRK3, SNRK, MAP3K3, MAP3K1, PRKAA1, ERCC3, CSNK1A1, TAOK1, RYK, PDK3, MAP2K4, RAF1, RPS6KA3, CSNK1D, CSNK1E, MAPK13, GSK3B, ARAF, ULK3, DYRK1A, JAK2, ABL2 |
| domain:Protein kinase | 79 | PASK, DSTYK, LATS1, PSKH1, SLK, CLK2, AAK1, CLK4, ILK, CDK12, TLK1, CDK10, PRKACB, MAP2K7, CHUK, CDK13, AKT2, MATK, SRPK2, IRAK1, PAN3, TNIK, ROCK1, CSNK1G2, ROCK2, PIM1, PRKCI, PKN2, PRKCH, CDK9, CDK7, PRKCD, SRPK1, CDK2, MARK2, GAK, PRKCB, MAPK1, MAPK6, CAMK4, HIPK1, RIPK1, HIPK2, RIPK2, CDK11B, MAPK8, CSNK1G3, MAP3K14, MAP3K13, PRKD3, STK10, MAPKAPK5, MKNK2, MAP4K1, MAPKAPK2, UHMK1, TRIB2, IRAK4, MAP3K3, VRK3, SNRK, STK40, MAP3K1, ZAP70, PRKAA1, CSNK1A1, TAOK1, RYK, MAP2K4, RAF1, OXSR1, CSNK1D, CSNK1E, MAPK13, GSK3B, ARAF, ULK3, DYRK1A, ABL2 |
| IPR000719:Protein kinase, catalytic domain | 81 | PASK, DSTYK, LATS1, PSKH1, SLK, CLK2, AAK1, CLK4, ILK, CDK12, TLK1, CDK10, PRKACB, MAP2K7, CHUK, CDK13, AKT2, MATK, SRPK2, IRAK1, PAN3, TNIK, ROCK1, CSNK1G2, ROCK2, PIM1, PRKCI, PKN2, PRKCH, CDK9, CDK7, PRKCD, SRPK1, CDK2, MARK2, GAK, PRKCB, MAPK1, CAMK4, MAPK6, HIPK1, RIPK1, HIPK2, RIPK2, CDK11B, MAPK8, CSNK1G3, MAP3K14, MAP3K13, PRKD3, STK10, MAPKAPK5, MKNK2, MAP4K1, MAPKAPK2, UHMK1, TRIB2, IRAK4, MAP3K3, VRK3, SNRK, STK40, MAP3K1, ZAP70, PRKAA1, CSNK1A1, TAOK1, RYK, MAP2K4, RAF1, OXSR1, RPS6KA3, CSNK1D, CSNK1E, MAPK13, GSK3B, ARAF, ULK3, DYRK1A, JAK2, ABL2 |
| IPR011009:Protein kinase-like domain | 86 | PASK, DSTYK, LATS1, PSKH1, SLK, CLK2, AAK1, CLK4, ILK, CDK12, TLK1, CDK10, PRKACB, MAP2K7, CHUK, CDK13, AKT2, MATK, SRPK2, IRAK1, PAN3, TNIK, ROCK1, CSNK1G2, ROCK2, PIK3C2A, PIM1, PRKCI, PKN2, CDK9, PRKCH, PI4KB, CDK7, PRKCD, SRPK1, CDK2, GAK, MARK2, PRKCB, MAPK1, CAMK4, MAPK6, HIPK1, RIPK1, HIPK2, RIPK2, CDK11B, MAPK8, CSNK1G3, MAP3K14, MAP3K13, PRKD3, STK10, MAPKAPK5, MKNK2, MAP4K1, MAPKAPK2, TRRAP, UHMK1, TRIB2, IRAK4, MAP3K3, VRK3, SNRK, STK40, MAP3K1, ZAP70, PRKAA1, CSNK1A1, TAOK1, RYK, MAP2K4, RAF1, FN3KRP, OXSR1, ATM, RPS6KA3, CSNK1D, CSNK1E, MAPK13, GSK3B, ARAF, ULK3, DYRK1A, JAK2, ABL2 |

TABLE 3-continued

HIV- low cutoff

| Category | Count | Genes |
| --- | --- | --- |
| GO:0005524~ATP binding | 216 | RAD51C, DYNC1LI2, ADCY7, ATP2B4, PSKH1, CLK2, CUL9, CLK4, ILK, DHX34, VPS4A, TLK1, DDX10, MAP2K7, PAN3, TNIK, ROCK1, ROCK2, UBE2J1, PIM1, UBE2J2, MARK2, MAPK1, GLUL, NME3, MAPK6, DHX29, CAMK4, ATP2C1, RFC2, MAPK8, CLCN3, PFKFB3, FARS2, UBA5, WARS2, HSPA1A, OAS1, MYO9B, OAS2, NAGK, UHMK1, MOV10, KRAS, VRK3, ZAP70, NAT10, KIF3B, TAOK1, MAP2K4, ATP11A, OXSR1, ATM, ATP13A1, UBA3, ABCF3, SPG7, FASTK, UBE2G1, HELZ, PMVK, LATS1, LONP1, ATAD3A, DYNC1H1, TOP2B, SRPK2, PIK3C2A, DGUOK, PI4KB, GMPS, SRPK1, RAD50, TTF2, CBWD2, TRAP1, RIPK1, RRM1, FARSB, CDK11B, MAP3K14, MAP3K13, WRNIP1, MKNK2, SNRK, DGKE, STK40, KTI12, DDX19A, DHX16, PRKAA1, CERK, ACSL4, ACSL3, SPATA5, ACSL5, CSNK1A1, PDS5B, MAT2A, PDK3, DGKH, RPS6KA3, CSNK1D, CSNK1E, MAPK13, GSK3B, ARAF, DGKZ, PASK, IDE, DSTYK, INO80, PI4K2B, NLRC5, IDH3G, DDX23, AAK1, ORC4, PRKACB, MATK, PDXK, CSNK1G2, PNPLA8, RIPK2, CSNK1G3, YARS2, SLFN12L, SMARCA2, PCCB, PRPS2, PRPS1, MVD, STK10, MAPKAPK5, MAP4K1, MAPKAPK2, IRAK4, UBE2D4, FICD, RUNX1, DDX42, RYK, MYO1G, ABCB7, PSMC5, PSMC2, ULK3, DYRK1A, GTF2F2, DDX50, ABL2, DDX51, UBE2E1, DICER1, PRKAG2, PPIP5K2, SKIV2L2, SLFN5, PIP5K1A, GSS, SLK, CDK12, MKKS, ATP8B2, CDK10, CHUK, CDK13, AKT2, IRAK1, UBE2A, PFKL, PRKCI, PKN2, PRKCH, CDK9, CDK7, PRKCD, CDK2, PRKCB, GAK, MCM6, TOR2A, PANK4, RECQL, PANK2, HIPK1, HIPK2, UBE2W, PRKD3, SPAST, BTAF1, PGS1, UBE2Z, DCK, TRIB2, UBE2R2, N4BP2, CHD9, MTHFS, CHD1L, CHD7, MAP3K3, MAP3K1, UCK1, HSPA4, CHD6, ERCC3, EHD1, EHD4, MSH6, MSH2, SMC5, SMC6, RAF1, SMC4, JAK2 |
| IPR017441:Protein kinase, ATP binding site | 62 | PASK, DSTYK, PSKH1, SLK, CLK2, CLK4, CDK12, TLK1, CDK10, PRKACB, CHUK, CDK13, MATK, AKT2, IRAK1, SRPK2, TNIK, ROCK1, CSNK1G2, ROCK2, PRKCI, PKN2, PIM1, PRKCH, CDK9, CDK7, PRKCD, CDK2, SRPK1, MARK2, PRKCB, MAPK1, MAPK6, CAMK4, HIPK1, HIPK2, CSNK1G3, MAP3K14, PRKD3, STK10, MKNK2, MAP4K1, MAPKAPK2, SNRK, MAP3K1, ZAP70, PRKAA1, CSNK1A1, TAOK1, MAP2K4, RAF1, OXSR1, RPS6KA3, CSNK1D, CSNK1E, MAPK13, GSK3B, ARAF, ULK3, DYRK1A, JAK2, ABL2 |
| Enrichment Score: 4.4354405219010475 | | |
| Mitochondrion | 173 | RAD51C, TSPO, MRPL42, CMC2, MALSU1, GFER, MPV17, TMEM11, OGDH, CIAPIN1, FAM210A, HIBADH, MFF, IDH3G, VPS13C, CASP8AP2, CPOX, SLC25A28, MRPL34, MRPL35, TIMMDC1, CRLS1, NUDT1, BCL2L11, TIMM8A, NFU1, SLC25A32, GLUL, SLC25A38, YARS2, TFB1M, PCCB, MTFMT, MPST, MRPL44, ME2, ELAC2, MRPS14, MCL1, GLUD2, TXN2, FARS2, MRPS11, SFXN4, WARS2, AKAP10, OAS1, CHCHD4, OAS2, RBFA, PIN4, AGMAT, MTIF2, SDHAF1, FAM65B, SLC11A2, FIS1, GFM2, C12ORF10, IVD, GFM1, BLOC1S1, IDH2, MRPL55, LIAS, TRAF3, FH, MRPS23, MRPS25, C21ORF33, MPC1, MPC2, GLOD4, MRRF, ABCB7, PPIF, TEFM, NDUFV3, METTL12, SYNE2, BBC3, NDUFV2, RHOT1, RHOT2, SLC25A16, C19ORF12, PHYKPL, METTL17, NDUFAF4, SPG7, COX11, UQCRC1, FASTK, HINT2, BNIP3, UQCRFS1, ARL2BP, ACOT9, LONP1, DNAJC15, ATAD3A, PARL, DNAJC11, ATP5H, NDUFS1, ARL2, SQRDL, AIFM1, DGUOK, PI4KB, ECSIT, RHBDD1, NDUFA10, MRPS2, TIMM22, IMMP1L, HAGH, TRAP1, PANK2, MRPS9, BNIP1, TCHP, ATPAF1, C7ORF73, GLRX5, PGS1, BCAT2, NDUFB7, ETHE1, RSAD2, QTRT1, HSCB, TACO1, GLRX2, NUDT9, BCL2, PITRM1, MRPL16, PYCARD, XAF1, ACSL4, LACTB, PDHX, ACSL3, SPATA5, SCO2, ACSL5, ETFA, C14ORF119, HSD17B8, ECI1, DLST, ALKBH7, ECI2, GIMAP5, IMMT, NDUFA9, PDK3, RAF1, BAD, PCK2, IFIT3, SDHA, MPG, APOPT1, SDHC, TSFM, MTFP1, BNIP3L, NLN, OGG1, SCP2, SLC25A53 |
| Transit peptide | 87 | COX11, MRPL42, UQCRC1, HINT2, OGDH, UQCRFS1, HIBADH, ACOT9, LONP1, IDH3G, PARL, CPOX, MRPL34, NDUFS1, MRPL35, SQRDL, NUDT1, AIFM1, DGUOK, NDUFA10, ECSIT, HAGH, TRAP1, NFU1, PANK2, MRPS9, YARS2, TFB1M, ATPAF1, PCCB, MTFMT, MRPL44, PGS1, GLRX5, BCAT2, ELAC2, ME2, TXN2, GLUD2, FARS2, ETHE1, MRPS11, WARS2, AKAP10, RBFA, MTIF2, AGMAT, HSCB, GLRX2, GFM2, C12ORF10, NUDT9, IVD, GFM1, MRPL16, PITRM1, IDH2, MRPL55, LIAS, LACTB, PDHX, SCO2, ETFA, FH, ECI1, ECI2, DLST, ALKBH7, NDUFA9, IMMT, PDK3, C21ORF33, PCK2, MRRF, ABCB7, NDUFV3, TEFM, PPIF, SDHA, METTL12, MPG, APOPT1, SDHC, TSFM, NDUFV2, NLN, METTL17 |
| transit peptide:Mitochondrion | 80 | COX11, MRPL42, UQCRC1, HINT2, OGDH, UQCRFS1, HIBADH, ACOT9, LONP1, IDH3G, PARL, CPOX, MRPL34, NDUFS1, MRPL35, SQRDL, AIFM1, DGUOK, NDUFA10, ECSIT, HAGH, TRAP1, NFU1, PANK2, MRPS9, YARS2, TFB1M, ATPAF1, PCCB, MTFMT, MRPL44, PGS1, BCAT2, ME2, TXN2, GLUD2, FARS2, ETHE1, MRPS11, WARS2, AKAP10, RBFA, MTIF2, AGMAT, HSCB, GLRX2, GFM2, C12ORF10, NUDT9, IVD, GFM1, MRPL16, PITRM1, IDH2, MRPL55, LIAS, LACTB, PDHX, SCO2, ETFA, FH, ECI1, DLST, ECI2, NDUFA9, PDK3, C21ORF33, PCK2, MRRF, ABCB7, NDUFV3, PPIF, SDHA, METTL12, TXNDC12, SDHC, TSFM, NDUFV2, NLN, METTL17 |

TABLE 3-continued

| | HIV- low cutoff | |
|---|---|---|
| Category | Count | Genes |
| GO:0005759~mitochondrial matrix | 57 | FASTK, MALSU1, OGDH, HIBADH, ARL2BP, ACOT9, GPX1, LONP1, IDH3G, NDUFS1, ARL2, NUDT1, DGUOK, NDUFA10, HAGH, TRAP1, YARS2, TFB1M, PCCB, GLRX5, ME2, ELAC2, BCAT2, MCL1, TXN2, ETHE1, FARS2, WARS2, PIN4, SDHAF1, GLRX2, MTHFS, GFM2, NUDT9, IVD, GFM1, PITRM1, BLOC1S1, IDH2, LIAS, PDHX, SCO2, ETFA, HSD17B8, FH, ECI1, ALKBH7, DLST, NDUFA9, CREB1, PDK3, MRRF, PCK2, TEFM, PPIF, TSFM, PHYKPL |
| Enrichment Score: 4.367762624189855 | | |
| domain:MBD | 8 | SETDB1, MECP2, MBD6, MBD5, MBD4, BAZ2B, MBD1, BAZ2A |
| SM0039:MBD | 8 | SETDB1, MECP2, MBD6, MBD5, MBD4, BAZ2B, MBD1, BAZ2A |
| IPR016177:DNA-binding, integrase-type | 8 | SETDB1, MECP2, MBD6, MBD5, MBD4, BAZ2B, MBD1, BAZ2A |
| IPR001739:Methyl-CpG DNA binding | 8 | SETDB1, MECP2, MBD6, MBD5, MBD4, BAZ2B, MBD1, BAZ2A |
| Enrichment Score: 4.255632723903859 | | |
| SM00320:WD40 | 55 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, NUP214, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |
| IPR017986:WD40-repeat-containing domain | 62 | COPA, TAF1C, SEC31B, SEC31A, KNTC1, STRN, TSSC1, WDR74, SHKBP1, WDR77, ZNF106, MLST8, NSMAF, ITFG2, TBL1XR1, ELP2, RBBP4, GNB1L, STRN3, ANAPC4, TLE3, VPS41, PRPF4, ARPC1A, WDR48, WDR83, EML3, SMU1, MED16, DDB2, NOL10, THOC6, NOL11, DYNC1I2, WDR45, LRBA, WDR60, SF3B3, WDR45B, PRPF19, PHIP, FBXW7, WDR54, FBXW5, WDR12, FBXW2, PAFAH1B1, FBXW11, VPS39, PPP2R2D, GEMIN5, WDTC1, WDR5, WDR6, WIPI2, PWP2, WSB1, POC1B, WDR26, WRAP73, TBL1X, CSTF1 |
| repeat:WD 3 | 54 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, HERC2, PRPF4, ARPC1A, WDR48, WDR83, EML3, SMU1, MED16, NOL10, DDB2, THOC6, DYNC1I2, WDR45, WDR60, LRBA, PRPF19, PHIP, FBXW7, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |
| IPR001680:WD40 repeat | 55 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, NUP214, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |
| repeat:WD 1 | 55 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, HERC2, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |
| repeat:WD 2 | 55 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, HERC2, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |
| repeat:WD 4 | 51 | COPA, SEC31B, SEC31A, STRN, TSSC1, SHKBP1, WDR74, WDR77, ZNF106, MLST8, NSMAF, TBL1XR1, ELP2, RBBP4, GNB1L, STRN3, TLE3, HERC2, PRPF4, ARPC1A, WDR48, WDR83, EML3, SMU1, MED16, NOL10, DDB2, THOC6, DYNC1I2, WDR60, LRBA, PRPF19, PHIP, FBXW7, WDR54, FBXW2, WDR12, PAFAH1B1, FBXW11, PPP2R2D, GEMIN5, WDTC1, WDR5, WDR6, PWP2, WSB1, POC1B, WDR26, WRAP73, TBL1X, CSTF1 |
| WD repeat | 54 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, TLE3, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, WDR54, FBXW5, FBXW2, WDR12, PAFAH1B1, FBXW11, PPP2R2D, GEMIN5, WDTC1, WDR5, WDR6, WIPI2, PWP2, WSB1, POC1B, WDR26, WRAP73, TBL1X, CSTF1 |

TABLE 3-continued

HIV- low cutoff

| Category | Count | Genes |
|---|---|---|
| repeat:WD 6 | 42 | COPA, SEC31B, SEC31A, LRBA, STRN, WDR74, PRPF19, PHIP, FBXW7, WDR12, ZNF106, PAFAH1B1, MLST8, NSMAF, FBXW11, PPP2R2D, GEMIN5, TBL1XR1, ELP2, WDTC1, RBBP4, GNB1L, STRN3, WDR5, WDR6, TLE3, HERC2, PRPF4, PWP2, WDR48, ARPC1A, WSB1, WDR83, EML3, SMU1, POC1B, WDR26, WRAP73, THOC6, TBL1X, CSTF1, DYNC1I2 |
| repeat:WD 5 | 48 | COPA, SEC31B, SEC31A, LRBA, STRN, TSSC1, WDR74, PRPF19, SHKBP1, PHIP, FBXW7, WDR77, WDR12, PAFAH1B1, ZNF106, MLST8, NSMAF, FBXW11, PPP2R2D, GEMIN5, TBL1XR1, ELP2, WDTC1, RBBP4, GNB1L, STRN3, WDR5, WDR6, TLE3, HERC2, PRPF4, PWP2, WDR48, ARPC1A, WSB1, WDR83, EML3, SMU1, POC1B, WDR26, WRAP73, MED16, NOL10, THOC6, DDB2, TBL1X, CSTF1, DYNC1I2 |
| IPR020472:G-protein beta WD-40 repeat | 24 | COPA, TBL1XR1, RBBP4, STRN3, WDR5, STRN, PRPF4, PWP2, WDR48, WDR83, PRPF19, WSB1, SMU1, FBXW7, POC1B, WDR26, FBXW2, WDR12, PAFAH1B1, MLST8, TBL1X, CSTF1, FBXW11, GEMIN5 |
| IPR015943:WD40/YVTN repeat-like-containing domain | 58 | COPA, SEC31B, SEC31A, STRN, TSSC1, WDR74, SHKBP1, WDR77, ZNF106, MLST8, NSMAF, TBL1XR1, ELP2, RBBP4, GNB1L, STRN3, ANAPC4, TLE3, VPS41, PRPF4, ARPC1A, WDR48, WDR83, EML3, SMU1, MED16, NOL10, DDB2, THOC6, DYNC1I2, WDR45, WDR60, LRBA, WDR45B, PRPF19, PHIP, FBXW7, NUP214, WDR54, FBXW5, WDR12, FBXW2, PAFAH1B1, FBXW11, PPP2R2D, GEMIN5, WDTC1, WDR5, WDR6, BIRC6, WIPI2, PWP2, WSB1, POC1B, WDR26, WRAP73, TBL1X, CSTF1 |
| IPR019775:WD40 repeat, conserved site | 31 | COPA, SEC31B, STRN, TSSC1, PRPF19, PHIP, FBXW7, WDR77, FBXW2, WDR12, PAFAH1B1, MLST8, FBXW11, GEMIN5, TBL1XR1, RBBP4, GNB1L, WDR5, STRN3, TLE3, PRPF4, PWP2, WDR48, WDR83, WSB1, SMU1, POC1B, THOC6, DDB2, TBL1X, CSTF1 |
| repeat:WD 7 | 26 | SEC31B, SEC31A, PHIP, PRPF19, FBXW7, WDR12, PAFAH1B1, MLST8, FBXW11, PPP2R2D, GEMIN5, TBL1XR1, WDTC1, ELP2, WDR5, WDR6, TLE3, PRPF4, PWP2, WDR48, WDR83, EML3, POC1B, THOC6, TBL1X, DYNC1I2 |
| Enrichment Score: 3.829453652617158 | | |
| Transcription | 336 | ITGB3BP, MEF2A, BBX, MED23, RORA, ZNF638, MXI1, TBPL2, BRPF1, SIN3A, ZFP90, ZNF394, TBPL1, ZNF101, ZNF43, ZNF44, TADA2A, ZNF644, RXRB, PCBD1, ZHX1, MECP2, MED11, HMG20B, MED13, PPARGC1A, ZNF37A, MED19, MAPK1, PIAS4, ASCC2, HES4, MED16, MLLT10, JUN, MED17, PRDM2, CDCA7L, PIAS1, SUDS3, CRTC3, CRTC2, ZNF131, TAF9B, ZNF511, XAB2, NR1H2, MOV10, TCF20, LEO1, TCF3, PLAGL2, IKZF5, ASXL2, TCF7, ESRRA, ZNF529, IKZF2, NRBF2, KLF13, TP53BP1, ZNF121, KLF10, CREBBP, RYBP, ZBTB40, SMAD3, PMF1, RNF4, DMTF1, PPRC1, JAZF1, HOPX, KAT6B, RERE, NCOR2, NKAP, CCNT2, CREBRF, TAF1B, TAF1C, ZNF292, ELF2, BACH2, ZNF534, EZH1, CCNT1, COPRS, ZNF675, ZEB1, RFXANK, DAXX, ZBTB38, DNAJC17, MBTD1, ASH2L, ZNF148, BRD4, USP16, TWISTNB, MYB, DEDD2, ZNF493, SERTAD2, BRD8, ATF7IP, NFKBIZ, CTBP1, BRF1, RBBP4, POLR1E, BRF2, CCNH, POLR1A, TLE3, GTF2H3, SPEN, MBD1, GTF2B, TTF2, MXD4, TAF10, TAF13, CHMP1A, GTF2I, MED8, ASH1L, ZNF277, NOL11, CNOT11, USP22, ZNF746, ZNF740, MED1, ZNF276, ZNF275, ETV7, ZNF274, ZBTB10, ZBTB11, PML, ZNF780B, ZNF780A, POLR2B, MYCBP2, STAT6, LPXN, RB1CC1, NPAT, GATAD2A, ZSCAN25, BCL3, AGO2, THAP1, ACTL6A, PRKAA1, HBP1, BAZ2B, ZNF268, BAZ2A, POLR3F, POLR3H, ZNF28, PPHLN1, TRIM27, PHF10, POLR3C, ATMIN, TRIM22, POLR3E, IWS1, ZNF664, ZNF672, BRMS1, JMJD6, YAF2, MAPK13, WHSC1L1, ZBTB2, ZNF764, ZNF766, RALY, ZNF583, CNOT8, IL16, TBP, CBX7, TCEAL4, GABPB1, DPY30, CASP8AP2, CGGBP1, MDFIC, TARDBP, GATA3, RELA, ZNF7, ARID1B, TRERF1, EP300, TRIM33, KDM2A, NFE2L2, AKAP8, NFE2L3, ZNF587, TFB1M, SMARCA2, ZNF586, CAMTA2, ZNF430, LITAF, SETD1A, KEAP1, C14ORF166, ELK3, TRRAP, COMMD9, SRF, COMMD10, CXXC1, PELP1, CNOT6L, RNF10, RUNX1, SETDB1, ZMYM2, TRIP4, CREBZF, TAF6, RFX5, WDR5, ZMYM5, NR4A1, SNW1, KAT5, MED13L, FOXP3, ATF7IP2, UIMC1, SAFB2, SREBF2, CTR9, TEFM, ATF6, ATF5, NRF1, PHF1, GTF2F1, GTF2F2, CPNE1, HIVEP2, HIVEP1, E2F3, E2F4, ARID4A, GPBP1, YLPM1, FOXK2, CTCF, ZKSCAN1, CBFA2T2, PCGF5, GTF2A1, ZNF721, INO80D, KDM5B, INO80C, KDM5C, NFX1, INO80B, ELMSAN1, EGR1, TBL1XR1, ELP2, SSBP3, LRIF1, ELP6, ELP5, ARID5A, ZFX, PKN2, CDK9, IRF2BP2, BANP, CDK7, FOXJ3, LPIN1, NRIP1, PRKCB, NCOA1, NCOA2, BTG2, BPTF, HIPK1, FAM120B, HIPK2, KHSRP, COMMD3, COMMD1, WASL, JMJD1C, DPF2, ING3, SBNO2, ING2, KMT2A, FRYL, KMT2C, ZNF800, NFYC, NFYB, PAXBP1, CHD9, CHD7, TSPYL2, ECD, NFATC2, ERCC3, CHD6, GTF3C1, GTF3C3, L3MBTL2, L3MBTL3, CREB1, SIRT7, MRGBP, SIRT2, MED31, RPAP2, SP1, DR1, KDM4C, IRF3, TBL1X, VPS25 |
| Transcription regulation | 324 | ITGB3BP, MEF2A, BBX, MED23, RORA, ZNF638, MXI1, TBPL2, BRPF1, SIN3A, ZFP90, ZNF394, TBPL1, ZNF101, ZNF43, ZNF44, TADA2A, ZNF644, RXRB, PCBD1, ZHX1, MECP2, MED11, HMG20B, MED13, PPARGC1A, ZNF37A, MED19, MAPK1, PIAS4, ASCC2, HES4, MED16, MLLT10, JUN, |

TABLE 3-continued

HIV- low cutoff

| Category | Count | Genes |
|---|---|---|
| | | MED17, PRDM2, CDCA7L, PIAS1, SUDS3, CRTC3, CRTC2, ZNF131, TAF9B, ZNF511, NR1H2, MOV10, TCF20, LEO1, TCF3, PLAGL2, IKZF5, ASXL2, TCF7, ESRRA, ZNF529, IKZF2, NRBF2, KLF13, TP53BP1, ZNF121, KLF10, CREBBP, RYBP, ZBTB40, SMAD3, PMF1, RNF4, DMTF1, PPRC1, JAZF1, HOPX, KAT6B, RERE, NCOR2, NKAP, CCNT2, CREBRF, TAF1B, TAF1C, ZNF292, ELF2, ZNF534, BACH2, EZH1, CCNT1, COPRS, ZNF675, ZEB1, RFXANK, DAXX, ZBTB38, DNAJC17, MBTD1, ASH2L, ZNF148, BRD4, USP16, MYB, DEDD2, ZNF493, SERTAD2, BRD8, ATF7IP, NFKBIZ, CTBP1, BRF1, RBBP4, BRF2, CCNH, TLE3, GTF2H3, SPEN, MBD1, GTF2B, TTF2, MXD4, TAF10, TAF13, CHMP1A, GTF2I, MED8, ASH1L, ZNF277, NOL11, CNOT11, USP22, ZNF746, ZNF740, MED1, ZNF276, ZNF275, ETV7, ZNF274, ZBTB10, ZBTB11, PML, ZNF780B, ZNF780A, MYCBP2, STAT6, LPXN, RB1CC1, NPAT, GATAD2A, ZSCAN25, BCL3, AGO2, THAP1, ACTL6A, PRKAA1, HBP1, BAZ2B, ZNF268, BAZ2A, ZNF28, PPHLN1, TRIM27, PHF10, ATMIN, TRIM22, IWS1, ZNF664, ZNF672, BRMS1, JMJD6, YAF2, MAPK13, WHSC1L1, ZBTB2, ZNF764, ZNF766, RALY, ZNF583, CNOT8, IL16, TBP, CBX7, TCEAL4, GABPB1, DPY30, CASP8AP2, CGGBP1, MDFIC, TARDBP, GATA3, RELA, ZNF7, ARID1B, TRERF1, EP300, TRIM33, KDM2A, NFE2L2, AKAP8, NFE2L3, ZNF587, TFB1M, SMARCA2, ZNF586, CAMTA2, ZNF430, LITAF, SETD1A, KEAP1, C14ORF166, ELK3, TRRAP, COMMD9, SRF, COMMD10, CXXC1, CNOT6L, RNF10, RUNX1, SETDB1, ZMYM2, TRIP4, CREBZF, TAF6, RFX5, WDR5, ZMYM5, NR4A1, SNW1, KAT5, MED13L, FOXP3, ATF7IP2, UIMC1, SAFB2, SREBF2, CTR9, ATF6, TEFM, ATF5, NRF1, PHF1, GTF2F1, GTF2F2, CPNE1, HIVEP2, HIVEP1, E2F3, E2F4, ARID4A, GPBP1, YLPM1, FOXK2, CTCF, ZKSCAN1, CBFA2T2, PCGF5, GTF2A1, ZNF721, INO80D, KDM5B, INO80C, KDM5C, NFX1, INO80B, ELMSAN1, EGR1, TBL1XR1, ELP2, SSBP3, LRIF1, ELP6, ELP5, ZFX, ARID5A, PKN2, CDK9, IRF2BP2, BANP, CDK7, FOXJ3, LPIN1, NRIP1, PRKCB, NCOA1, NCOA2, BTG2, BPTF, HIPK1, FAM120B, HIPK2, KHSRP, COMMD3, COMMD1, WASL, JMJD1C, DPF2, ING3, SBNO2, ING2, KMT2A, FRYL, KMT2C, ZNF800, NFYC, NFYB, PAXBP1, CHD9, CHD7, TSPYL2, ECD, NFATC2, ERCC3, CHD6, L3MBTL2, L3MBTL3, CREB1, SIRT7, MRGBP, SIRT2, MED31, RPAP2, SP1, DR1, KDM4C, IRF3, TBL1X, VPS25 |
| GO:0006351~transcription, DNA-templated | 271 | ITGB3BP, MEF2A, BBX, RORA, ZNF638, MXI1, BRPF1, SIN3A, ZFP90, ZNF394, ZNF101, ZNF43, ZNF44, ZNF644, RXRB, PCBD1, ZHX1, MECP2, MED11, HMG20B, ZNF37A, MED19, MAPK1, PIAS4, ASCC2, HES4, MLLT10, PRDM2, CDCA7L, PIAS1, SUDS3, CRTC3, CRTC2, NFKBIB, ZNF131, ZNF511, DIDO1, XAB2, NR1H2, MOV10, TCF20, TCF3, ASXL2, IKZF5, ESRRA, TCF7, ZNF529, IKZF2, TP53BP1, ZNF121, KLF10, RYBP, ZBTB40, SMAD3, RNF4, DMTF1, HOPX, JAZF1, PPRC1, KAT6B, RERE, NCOR2, NKAP, CCNT2, CREBRF, TAF1B, ELF2, ZNF534, EZH1, CCNT1, COPRS, ZNF675, ZEB1, RFXANK, DAXX, ZBTB38, DNAJC17, MBTD1, ASH2L, BRD4, USP16, DEDD2, ZNF493, BRD8, SERTAD2, ATF7IP, NFKBIZ, CTBP1, RBBP4, POLR1E, LIN52, CCNH, POLR1A, TLE3, SPEN, MXD4, CHMP1A, ZNF277, NOL11, CNOT11, USP22, ZNF746, ZNF740, ZNF276, ZNF275, ZNF274, ZBTB10, ZBTB11, PML, ZNF780B, ZNF780A, POLR2B, MYCBP2, STAT6, LPXN, RB1CC1, NPAT, GATAD2A, ZSCAN25, BCL3, AGO2, THAP1, ACTL6A, PRKAA1, HBP1, BAZ2B, ZNF268, BAZ2A, POLR3H, ZNF28, PPHLN1, TRIM27, PPP1R10, PHF10, POLR3C, ATMIN, TRIM22, POLR3E, IWS1, ZNF664, ZNF672, BRMS1, JMJD6, YAF2, MAPK13, WHSC1L1, ZBTB2, ZNF764, ZNF766, RALY, ZNF583, CNOT8, IL16, INO80, CBX7, TCEAL4, GABPB1, DPY30, CASP8AP2, MDFIC, CGGBP1, ZNF7, ARID1B, TRERF1, TRIM33, KDM2A, NFE2L2, AKAP8, NFE2L3, ZNF587, TFB1M, SMARCA2, ZNF586, ZNF430, LITAF, SETD1A, KEAP1, C14ORF166, TRRAP, COMMD9, COMMD10, RRAGC, CXXC1, PELP1, CNOT6L, RNF10, SETDB1, ZMYM2, TRIP4, CREBZF, RFX5, WDR5, ZMYM5, NR4A1, KAT5, MED13L, FOXP3, ATF7IP2, UIMC1, SAFB2, SREBF2, CTR9, ATF6, PHF3, PHF1, CPNE1, E2F3, E2F4, GPBP1, YLPM1, ZKSCAN1, CBFA2T2, PCGF5, ZNF721, INO80D, KDM5B, KDM5C, INO80C, ELMSAN1, INO80B, TBL1XR1, SSBP3, LRIF1, ELP6, LDB1, ELP5, ZFX, ARID5A, PKN2, BANP, IRF2BP2, FOXJ3, LPIN1, NRIP1, PRKCB, NCOA1, NCOA2, BPTF, HIPK1, BTG2, FAM120B, HIPK2, COMMD3, KHSRP, COMMD1, WASL, JMJD1C, DPF2, ING3, SBNO2, ING2, FRYL, KMT2C, ZNF800, NFYB, PAXBP1, CHD9, CHD7, TSPYL2, CHD6, GTF3C1, GTF3C3, L3MBTL2, L3MBTL3, DRG1, MRGBP, SIRT2, DR1, KDM4C, TBL1X, VPS25 |
| GO:0006355~regulation of transcription, DNA-templated | 196 | ITGB3BP, MEF2A, BBX, MED23, ZNF638, RORA, MXI1, SIN3A, ZFP90, ZNF394, TBPL1, ZNF101, ZNF43, ZNF44, ZNF644, RXRB, HMG20B, PPARGC1A, ZNF37A, ASCC2, HES4, CDCA7L, PRDM2, ZNHIT3, ZNF131, ZNF511, AHCTF1, TCF20, MOV10, TCF3, ASXL2, IKZF5, ZNF529, ESRRA, NRBF2, ZNF121, CREBBP, ZBTB40, SMAD3, PMF1, DMTF1, KAT6B, TAF1B, CREBRF, TAF1C, ZNF534, COPRS, ZNF675, DAXX, MBTD1, ASH2L, MYB, ZNF493, BRD8, RBBP4, BRF1, BRF2, TLE3, GTF2H3, GTF2B, TTF2, TAF10, POGK, ZNF277, CNOT11, CDK11B, ZNF746, ZNF740, ZNF276, ZNF275, ZNF274, ZBTB10, ZBTB11, PML, ZNF780B, ZNF780A, MLF2, MYCBP2, ZFP36L2, LPXN, RB1CC1, ZSCAN25, PRKAA1, HBP1, THAP1, ZNF268, BAZ2B, USP34, MLLT6, BAZ2A, ZNF28, PPHLN1, PHF10, AFF1, |

TABLE 3-continued

HIV- low cutoff

| Category | Count | Genes |
|---|---|---|
| | | TRIM22, IWS1, ZNF664, ZNF672, MAPK13, JMJD6, WHSC1L1, ZBTB2, ZNF764, OGG1, ZNF766, GOLGB1, RALY, CNOT8, ZNF583, IL16, AKAP17A, CASP8AP2, ZNF814, ZNF7, RALGAPA1, EP300, KDM2A, AKAP8, TFB1M, ZNF587, SMARCA2, ZNF586, ZNF430, SETD1A, KEAP1, TRRAP, COMMD9, CXXC1, COMMD10, CNOT6L, TRIP4, RFX5, FOXP3, KAT5, VAV1, ATF7IP2, CTR9, SAFB2, TEFM, ATF5, PHF1, CDKN2AIP, CPNE1, HIVEP2, GPBP1, FOXK2, YLPM1, ZKSCAN1, GTF2A1, RBAK-RBAKDN, ZNF721, ZNF720, INO80D, INO80C, INO80B, SSBP2, LRIF1, LDB1, ZFX, ELP5, PKN2, IRF2BP2, NCOA1, NCOA2, HIPK1, BPTF, FAM120B, COMMD3, KHSRP, JMJD1C, WASL, DPF2, SBNO1, SBNO2, ING3, ING2, FRYL, KMT2C, ZNF800, NFYC, NFYB, GLRX2, CHD9, TSC22D3, TSPYL2, CHD7, NFATC2, L3MBTL2, L3MBTL3, VHL, CREB1, CBL, RGS19, SP1, POFUT1, VPS25 |
| DNA-binding | 227 | RAD51C, HMGN3, MEF2A, BBX, H1FX, ZNF638, RORA, MXI1, HMGN4, TBPL2, BRPF1, ZFP90, ZNF394, TBPL1, ZNF101, ZNF43, POLK, ZNF44, ZNF644, TADA2A, RXRB, ZHX1, MECP2, HMG20B, POLB, TOX4, ZNF37A, MAPK1, UHRF2, PIAS4, MTF2, HES4, MLLT10, JUN, PRDM2, PIAS1, ZNF131, AHCTF1, ZNF511, PIN4, NR1H2, TCF20, TCF3, PLAGL2, IKZF5, DNMT3A, ZNF529, ESRRA, TCF7, IKZF2, KLF13, ZNF121, KLF10, TP53BP1, RYBP, ZBTB40, SMAD3, ATM, RNF4, DMTF1, H3F3A, NCOR2, TAF1B, TAF1C, ZNF292, ELF2, ZNF534, BACH2, ZNF675, ZEB1, RFXANK, ZBTB38, LONP1, ASH2L, ZNF148, TOP2B, MYB, DEDD2, ZNF493, ZFP36, POGZ, AIFM1, APTX, MBD4, PAPD5, SPEN, MBD1, TTF2, MXD4, POGK, GTF2I, ZNF277, ZNF746, MED1, REV3L, ZNF276, ZNF275, ETV7, ZNF274, ZBTB10, ZBTB11, PML, ZNF780B, ZNF780A, STAT6, ZFP36L2, ZSCAN25, THAP1, HBP1, THAP2, BAZ2B, ZNF268, BAZ2A, ZNF28, TRIM27, PPP1R10, ZNF664, PLSCR1, ZNF672, ZBTB2, ZNF764, ZNF766, ZNF583, INO80, TBP, CGGBP1, TARDBP, GATA3, ORC4, RELA, MTA2, NEIL2, ZNF7, ARID1B, TRERF1, NABP1, TRIM33, KDM2A, RNF138, AKAP8, NFE2L2, TFB1M, ZNF587, NFE2L3, SMARCA2, ZNF586, ZNF430, CERS6, CERS4, ELK3, SRF, CXXC1, POLE3, CERS2, RNF10, RUNX1, RFX5, NR4A1, TSN, FOXP3, SAFB2, SREBF2, ATF6, ATF5, NRF1, GTF2F1, GTF2F2, HIVEP2, HIVEP1, GLYR1, IER2, HIST4H4, E2F3, E2F4, GPBP1, FOXK2, ZKSCAN1, CTCF, FOS, ZNF721, NFX1, ELMSAN1, EGR1, SSBP3, SSBP2, ZFX, ARID5A, BANP, FOXJ3, MCM6, NUCB1, XPA, RECQL, XPC, HIPK1, HIPK2, NUCB2, DDB2, KHSRP, BTAF1, KMT2A, KMT2C, MGMT, ZNF800, NFYC, NFYB, PAXBP1, APLP2, RPA1, CHD9, CHD7, HMGXB4, HMGXB3, NFATC2, ERCC3, CHD6, GTF3C1, TERF2, GTF3C3, TERF1, MSH6, MSH2, CREB1, TOX, SP1, DR1, IRF3 |
| Enrichment Score: 3.4484346569016893 | | |
| Immunity | 81 | CD8A, ZC3HAV1, CD8B, PTPN22, APOBEC3G, PDCD1, APOBEC3C, APOBEC3D, TRIM4, ANKRD17, NLRC5, GATA3, IL4R, ERAP1, JAGN1, MX1, MX2, DBNL, IRAK1, SIT1, LY96, HERC5, FADD, ECSIT, PRKCB, CD84, TRIM38, BTN3A1, CHID1, TNFSF13B, CAMK4, RIPK2, LRMP, HLA-DPA1, AKAP8, GBP3, BTN3A2, ORAI1, IFITM1, IFITM2, CSF1, UNC93B1, PML, RSAD2, OAS1, OAS2, SEC14L1, RNF125, IRAK4, SERINC3, PYCARD, ZAP70, PSTPIP1, HLA-DPB1, INPP5D, MR1, TBKBP1, TRAF3, POLR3F, POLR3H, MYO1G, CTLA4, ANXA1, SAMHD1, MSRB1, TRIM25, PIBF1, SLAMF7, POLR3C, LGALS9, POLR3E, SIRT2, IFIT3, BTLA, CD55, IFIT5, CD79B, JAK2, IRF3, TAPBPL, IL2 |
| Innate immunity | 50 | ZC3HAV1, APOBEC3G, APOBEC3C, APOBEC3D, TRIM4, NLRC5, ANKRD17, GATA3, MX1, MX2, IRAK1, LY96, HERC5, FADD, ECSIT, CD84, TRIM38, CHID1, RIPK2, AKAP8, IFITM1, IFITM2, CSF1, PML, UNC93B1, RSAD2, OAS1, OAS2, SEC14L1, SERINC3, IRAK4, PSTPIP1, PYCARD, MR1, TBKBP1, POLR3F, POLR3H, ANXA1, MSRB1, SAMHD1, TRIM25, SLAMF7, POLR3C, POLR3E, SIRT2, IFIT3, CD55, IFIT5, JAK2, IRF3 |
| GO:0045087~innate immune response | 56 | ZC3HAV1, APOBEC3G, IGHM, APOBEC3C, APOBEC3D, TRIM4, NLRC5, ANKRD17, GATA3, MX1, KLRD1, MX2, CHUK, MATK, IRAK1, SRPK2, LY96, HERC5, FADD, ECSIT, SRPK1, CD84, CHID1, IPO7, RIPK2, AKAP8, CSF1, PML, TRIM14, UNC93B1, TRDC, SEC14L1, SERINC3, IRAK4, PSTPIP1, ZAP70, PYCARD, MR1, TBKBP1, TRAF3, POLR3F, POLR3H, TRIM27, ANXA1, TRIM26, MSRB1, MALT1, TRIM25, POLR3C, POLR3E, SIRT2, CD55, APOL1, IFIT5, JAK2, ABL2 |
| Enrichment Score: 3.4148927968910225 | | |
| hsa04668:TNF signaling pathway | 31 | TRAF1, CSF2, TRAF2, CSF1, LIF, TNFRSF1A, BAG4, FOS, CASP7, CASP8, BCL3, MAP2K7, TRAF5, CHUK, PIK3R1, AKT2, TRAF3, ICAM1, IL18R1, SOCS3, CREB1, RELA, MAP2K4, FADD, TAB3, MAPK1, MAPK13, JUN, RIPK1, MAPK8, MAP3K14 |
| hsa04620:Toll-like receptor signaling pathway | 24 | IRAK1, CCL3, LY96, RELA, MAP2K4, FADD, CCL4, IFNAR1, IRAK4, MAPK1, FOS, IFNAR2, MAPK13, JUN, RIPK1, CASP8, RAC1, IRF3, MAPK8, MAP2K7, CHUK, PIK3R1, AKT2, TRAF3 |

TABLE 3-continued

HIV- low cutoff

| Category | Count | Genes |
| --- | --- | --- |
| hsa04380:Osteoclast differentiation | 25 | TRAF2, CSF1, FOS, TNFRSF1A, IFNG, RAC1, PPP3CB, NFATC2, MAP2K7, IFNGR2, PIK3R1, CHUK, AKT2, SOCS3, RELA, CREB1, SOCS1, IFNAR1, MAPK1, IFNAR2, CAMK4, MAPK13, JUN, MAPK8, MAP3K14 |
| Enrichment Score: 3.2064615359892623 | | |
| Bromodomain | 14 | BRD1, KMT2A, CREBBP, PHIP, BRPF1, EP300, TRIM33, BPTF, ASH1L, BRD4, BAZ2B, BAZ2A, SMARCA2, BRD8 |
| SM00297:BROMO | 14 | BRD1, KMT2A, CREBBP, PHIP, BRPF1, EP300, TRIM33, BPTF, ASH1L, BRD4, BAZ2B, BAZ2A, SMARCA2, BRD8 |
| IPR001487:Bromodomain | 14 | BRD1, KMT2A, CREBBP, PHIP, BRPF1, EP300, TRIM33, BPTF, ASH1L, BRD4, BAZ2B, BAZ2A, SMARCA2, BRD8 |
| IPR018359:Bromodomain, conserved site | 10 | PHIP, BRD1, BRPF1, EP300, BPTF, CREBBP, BRD4, BAZ2B, SMARCA2, BAZ2A |
| domain:Bromo | 10 | BRD1, BRPF1, EP300, TRIM33, BPTF, CREBBP, ASH1L, BAZ2B, SMARCA2, BAZ2A |
| Enrichment Score: 3.1111268555872935 | | |
| mRNA processing | 63 | RALY, SCAF1, CRNKL1, ZMAT5, U2AF2, SKIV2L2, SART3, SART1, AKAP17A, DDX23, TARDBP, CDK12, QKI, DBR1, LSM3, RBM10, LSM1, TSEN2, CDK13, SRPK2, SYMPK, PAN3, EFTUD2, FMR1, PAPD5, CSTF2T, PRPF4, SRPK1, TTF2, WDR83, PCF11, KHSRP, THOC6, SLU7, CPSF4, CPSF3, FIP1L1, XAB2, SF3B4, SF3B3, PRPF19, CNOT6L, ECD, ISY1, DHX16, GEMIN6, RBM28, GEMIN5, RBM22, TSEN54, SREK1, ALYREF, SNW1, CASC3, SF3A2, IWS1, SUGP1, CLASRP, JMJD6, RSRC1, LSM10, RNPC3, CSTF1 |
| mRNA splicing | 50 | RALY, SCAF1, ZMAT5, CRNKL1, U2AF2, SKIV2L2, SART3, SART1, AKAP17A, DDX23, TARDBP, CDK12, QKI, LSM3, LSM1, RBM10, CDK13, SRPK2, EFTUD2, FMR1, PRPF4, TTF2, SRPK1, WDR83, KHSRP, THOC6, SLU7, XAB2, SF3B4, SF3B3, PRPF19, ECD, ISY1, DHX16, GEMIN6, RBM28, GEMIN5, RBM22, SREK1, ALYREF, SNW1, CASC3, SF3A2, IWS1, SUGP1, CLASRP, JMJD6, RSRC1, LSM10, RNPC3 |
| GO:0008380~RNA splicing | 36 | SCAF1, ZMAT5, RP9, ZNF638, IVNS1ABP, SF3B4, SF3B3, RRAGC, AKAP17A, DDX23, TARDBP, ECD, CDK12, QKI, DHX16, RBM10, LSM1, RBM28, SRPK2, EFTUD2, SREK1, FMR1, SF3A2, PPARGC1A, PRPF4, IWS1, TTF2, SRPK1, PPIG, CLASRP, JMJD6, RSRC1, KHSRP, THOC6, LSM10, RNPC3 |
| GO:0000398~mRNA splicing, via spliceosome | 44 | RALY, FIP1L1, ZMAT5, CRNKL1, U2AF2, SKIV2L2, SART3, SF3B4, XAB2, SART1, SF3B3, POLR2B, PRPF19, METTL3, DDX23, ISY1, DHX16, DBR1, LSM3, GEMIN6, GEMIN5, RBM22, EFTUD2, ALYREF, ELAVL1, SNW1, CASC3, SPEN, SF3A2, PRPF4, WDR83, PCF11, HNRNPH2, UPF3B, SUGP1, GTF2F1, RSRC1, GTF2F2, RBMX2, SLU7, RNPC3, CPSF3, RBM15, CSTF1 |
| Spliceosome | 27 | RALY, ZMAT5, CRNKL1, U2AF2, SKIV2L2, SF3B4, XAB2, SART1, SF3B3, PRPF19, AKAP17A, DDX23, ISY1, LSM3, RBM28, RBM22, SREK1, EFTUD2, ALYREF, SNW1, SF3A2, PRPF4, TTF2, WDR83, SUGP1, SLU7, RNPC3 |
| GO:0006397~mRNA processing | 37 | SCAF1, U2AF2, HNRNPLL, SF3B4, SF3B3, AKAP17A, METTL3, CNOT6L, TARDBP, ECD, CDK12, QKI, LSM3, TSEN2, RBM10, LSM1, RBM28, PHRF1, TSEN54, RBM23, PAN3, EFTUD2, SREK1, FMR1, PAPD5, CASC3, SF3A2, PPARGC1A, IWS1, TTF2, SRPK1, CLASRP, JMJD6, KHSRP, LSM10, CPSF4, ALKBH5 |
| GO:0071013~catalytic step 2 spliceosome | 18 | RBM22, RALY, CRNKL1, EFTUD2, ALYREF, SKIV2L2, SNW1, SF3A2, XAB2, SART1, SF3B3, WDR83, PRPF19, DDX23, ISY1, RBMX2, SLU7, LSM3 |
| hsa03040:Spliceosome | 22 | RBM22, CHERP, CRNKL1, CCDC12, U2AF2, EFTUD2, ALYREF, SNW1, HSPA1A, SF3A2, PRPF4, XAB2, SF3B4, SART1, SF3B3, PRPF19, DDX23, ISY1, SLU7, DHX16, LSM3, DDX42 |
| Enrichment Score: 3.0807772438702044 | | |
| hsa03022:Basal transcription factors | 16 | TAF6, CCNH, TAF9B, GTF2H3, TBP, CDK7, GTF2B, TBPL2, TAF10, TAF13, GTF2A1, GTF2I, GTF2F1, GTF2F2, ERCC3, TBPL1 |
| GO:0006367~transcription initiation from RNA polymerase II promoter | 33 | E2F3, TAF9B, MED23, TBP, RORA, POLR2B, NR1H2, GTF2A1, ERCC3, ESRRA, NRBF2, TAF6, CCNH, RXRB, CREBBP, GTF2H3, CDK9, NR4A1, SNW1, MED13, CDK7, GTF2B, PPARGC1A, MED31, TAF10, TAF13, GTF2I, MED16, GTF2F1, MED8, MED17, GTF2F2, MED1 |
| GO:0006368~transcription elongation from RNA polymerase II promoter | 19 | CCNT2, ELP2, TAF6, CCNH, CCNT1, TAF9B, GTF2H3, CDK9, TBP, CDK7, GTF2B, POLR2B, TAF10, TAF13, GTF2A1, GTF2F1, GTF2F2, LEO1, ERCC3 |

TABLE 3-continued

HIV- low cutoff

| Category | Count | Genes |
|---|---|---|
| Enrichment Score: 3.020215334274786 | | |
| hsa04662:B cell receptor signaling pathway | 22 | VAV3, NFKBIB, RELA, RAF1, MALT1, VAV1, NRAS, MAPK1, FOS, KRAS, JUN, GSK3B, SOS1, CD81, RAC1, PPP3CB, CD79B, INPP5D, NFATC2, CHUK, PIK3R1, AKT2 |
| h_fcer1Pathway:Fc Epsilon Receptor I Signaling in Mast Cells | 14 | MAP2K4, RAF1, VAV1, PRKCB, MAPK1, FOS, MAP3K1, SOS1, JUN, PPP3CB, MAPK8, NFATC2, MAP2K7, PIK3R1 |
| GO:0038095~Fc-epsilon receptor signaling pathway | 30 | PSMB10, FOS, KRAS, MAP3K1, SOS1, RAC1, PPP3CB, PSMD3, PSMD5, NFATC2, MAP2K7, FBXW11, CHUK, PIK3R1, VAV3, RELA, MAP2K4, MALT1, VAV1, TAB3, NRAS, MAPK1, PSMC5, PSMD13, PSMD12, JUN, PSMC2, MAPK8, PSME4, GRAP2 |
| Enrichment Score: 2.697299540563712 | | |
| hsa04722:Neurotrophin signaling pathway | 30 | ZNF274, NFKBIB, MAPKAPK2, IRAK4, KRAS, MAP3K3, BCL2, SOS1, MAP3K1, RAC1, MAP2K7, RAPGEF1, PIK3R1, MATK, AKT2, IRAK1, RELA, RAF1, BAD, PRKCD, NRAS, MAPK1, RPS6KA3, CRKL, CAMK4, MAPK13, JUN, GSK3B, RIPK2, MAPK8 |
| hsa04012:ErbB signaling pathway | 21 | MAP2K4, CBL, RAF1, BAD, PRKCB, NRAS, MAPK1, NCK2, CBLB, CRKL, KRAS, CDKN1B, JUN, GSK3B, SOS1, ARAF, MAPK8, MAP2K7, ABL2, PIK3R1, AKT2 |
| hsa04912:GnRH signaling pathway | 17 | ADCY7, MAP2K4, RAF1, PRKCD, PRKCB, ITPR2, NRAS, MAPK1, KRAS, MAP3K3, MAPK13, JUN, MAP3K1, SOS1, MAPK8, PRKACB, MAP2K7 |
| Enrichment Score: 2.6555136612397368 | | |
| domain:LisH | 10 | OFD1, TBL1XR1, SMU1, MKLN1, SSBP3, SSBP2, WDR26, NPAT, PAFAH1B1, TBL1X |
| SM00667:LisH | 9 | OFD1, TBL1XR1, SMU1, MKLN1, SSBP3, SSBP2, NPAT, PAFAH1B1, TBL1X |
| IPR006594:LisH dimerisation motif | 10 | OFD1, TBL1XR1, SMU1, MKLN1, SSBP3, SSBP2, WDR26, NPAT, PAFAH1B1, TBL1X |
| Enrichment Score: 2.5486858895909723 | | |
| Nuclear pore complex | 17 | NUP98, NUP160, AHCTF1, NUP93, NUP85, NUP188, PARP11, NUP155, NDC1, NUP214, DDX19A, NUP210, RANBP2, XPO7, MX2, EIF5A2, MVP |
| GO:0016925~protein sumoylation | 30 | NUP98, NUP160, PML, NUP93, CETN2, SAE1, NUP188, RANGAP1, NDC1, RPA1, NUP214, MDC1, NUP210, NSMCE1, NSMCE2, RNF168, RANBP2, TOP2B, STAG1, L3MBTL2, KIAA1586, TP53BP1, SMC5, SMC6, NUP85, HERC2, NUP155, XPC, PIAS4, PIAS1 |
| GO:1900034~regulation of cellular response to heat | 22 | NUP98, NUP160, CREBBP, NUP93, NUP85, NUP188, HSPA1A, MAPKAPK2, NUP155, ATM, NDC1, RPA1, BAG5, BAG4, MAPK1, NUP214, EP300, GSK3B, NUP210, MLST8, RANBP2, DNAJB6 |
| mRNA transport | 26 | NUP98, NUP160, NUP93, AHCTF1, NUP188, NDC1, NUP214, DDX19A, NUP210, QKI, RANBP2, MX2, FMR1, ALYREF, NUP85, PARP11, CASC3, NUP155, IWS1, UPF3B, POLDIP3, THOC6, KHSRP, XPO7, EIF5A2, MVP |
| Translocation | 21 | NUP98, NUP160, AHCTF1, NUP93, NUP85, NUP188, PARP11, CHCHD4, NUP155, TIMM22, TIMM8A, NDC1, NUP214, DNAJC15, DDX19A, NUP210, RANBP2, XPO7, MX2, EIF5A2, MVP |
| GO:0005643~nuclear pore | 19 | NUP98, NUP160, AHCTF1, NUP93, PARP11, RANGAP1, NUP155, NDC1, IPO7, DDX19A, NUP210, KPNA6, NUTF2, RANBP2, XPO7, MX2, EIF5A2, KPNA1, MVP |
| GO:0006406~mRNA export from nucleus | 24 | NUP98, FIP1L1, NUP160, SMG5, U2AF2, ALYREF, NUP93, NUP85, NUP188, CASC3, NUP155, NDC1, NUP214, UPF3B, EIF4E, DDX19A, POLDIP3, NUP210, RBMX2, THOC6, SLU7, RANBP2, CPSF3, ALKBH5 |
| GO:0007077~mitotic nuclear envelope disassembly | 13 | NDC1, NUP214, NUP98, NUP160, NUP210, NUP93, CNEP1R1, NUP85, NUP188, RANBP2, NUP155, LPIN1, PRKCB |
| hsa03013:RNA transport | 32 | RPP38, NUP98, ELAC2, NUP160, NUP93, RANGAP1, NUP188, NDC1, NUP214, EIF4EBP2, NUP210, RANBP2, GEMIN6, EIF2B4, EIF2B5, GEMIN5, ALYREF, FMR1, NUP85, EIF1B, CASC3, FXR2, NUP155, TACC3, EIF2B1, EIF4G3, EIF4E, UPF3B, THOC6, POP4, POP5, POP7 |
| GO:0006409~tRNA export from nucleus | 10 | NDC1, NUP214, NUP98, NUP160, NUP210, NUP93, NUP85, NUP188, RANBP2, NUP155 |
| GO:0010827~regulation of glucose transport | 10 | NDC1, NUP214, NUP98, NUP160, NUP210, NUP93, NUP85, NUP188, RANBP2, NUP155 |
| GO:0075733~intracellular transport of virus | 13 | NDC1, NUP214, NUP98, NUP160, TSG101, NUP210, NUP93, VPS37B, NUP85, NUP188, RANBP2, NUP155, KPNA1 |

TABLE 3-continued

| Category | Count | Genes |
|---|---|---|
| HIV- low cutoff | | |
| GO:0017056~structural constituent of nuclear pore | 7 | NDC1, NUP214, NUP98, NUP93, NUP85, NUP188, NUP155 |
| GO:0031047~gene silencing by RNA | 21 | NUP98, HIST4H4, NUP160, FMR1, DICER1, NUP93, NUP85, NUP188, TSN, NUP155, POLR2B, NDC1, NUP214, CNOT6L, NUP210, PRKRA, CNOT11, H3F3A, AGO2, RANBP2, TNRC6A |
| GO:0006606~protein import into nucleus | 11 | NUP214, IPO7, PTTG1IP, NUP93, KPNA6, PPP1R10, NUP85, NUTF2, NUP188, NUP155, KPNA1 |
| GO:0019083~viral transcription | 11 | NDC1, RPL17, NUP214, NUP98, NUP160, NUP210, NUP93, NUP85, NUP188, RANBP2, NUP155 |
| Enrichment Score: 2.3663661637495768 | | |
| IPR009060:UBA-like | 18 | USP5, CBL, UBAC1, LATS1, N4BP2, CBLB, C6ORF106, ASCC2, TDP2, NBR1, TSFM, UBAP2L, FAF2, UBASH3A, SPATS2L, UBAP2, USP24, UBAP1 |
| IPR015940:Ubiquitin-associated/translation elongation factor EF1B, N-terminal, eukaryote | 13 | USP5, CBL, UBAC1, LATS1, MARK2, CBLB, SNRK, NBR1, UBAP2L, UBASH3A, UBAP2, USP24, UBAP1 |
| domain:UBA | 11 | CBLB, SNRK, NBR1, CBL, UBAP2L, UBASH3A, FAF2, UBAP2, USP24, LATS1, MARK2 |
| SM00165:UBA | 7 | CBLB, USP5, CBL, UBAP2L, UBAC1, UBAP2, MARK2 |
| Enrichment Score: 2.185234142205886 | | |
| GO:1904115~axon cytoplasm | 13 | KIF3B, SPG7, NDEL1, BLOC1S5, AP3M2, AP3M1, BLOC1S1, AP3S1, SNAPIN, RANGAP1, PAFAH1B1, DTNBP1, SPAST |
| GO:0008089~anterograde axonal transport | 10 | SPG7, KIF3B, BLOC1S5, AP3M2, AP3M1, BLOC1S1, AP3S1, SNAPIN, DTNBP1, SPAST |
| GO:0048490~anterograde synaptic vesicle transport | 7 | BLOC1S5, AP3M2, AP3M1, BLOC1S1, AP3S1, SNAPIN, DTNBP1 |
| GO:0031083~BLOC-1 complex | 6 | BLOC1S5, KXD1, BLOC1S1, KIAA1033, SNAPIN, DTNBP1 |
| GO:0032438~melanosome organization | 5 | BLOC1S5, AP1G1, BLOC1S1, SNAPIN, DTNBP1 |
| Enrichment Score: 2.109254171296502 | | |
| IPR004939:Anaphase-promoting complex, subunit 10/DOC domain | 6 | HSPB11, CUL9, ANAPC10, HERC2, ZZEF1, MYCBP2 |
| SM01337:SM01337 | 5 | CUL9, ANAPC10, HERC2, ZZEF1, MYCBP2 |
| domain:DOC | 5 | CUL9, ANAPC10, HERC2, ZZEF1, MYCBP2 |
| IPR008979:Galactose-binding domain-like | 13 | ANAPC10, HERC2, FURIN, ZZEF1, MYCBP2, NGLY1, MKLN1, HSPB11, CUL9, FBXO6, PCSK7, HECTD1, SUCO |
| Enrichment Score: 2.052960731204601 | | |
| GO:0005913~cell-cell adherens junction | 54 | RTN4, ABCF3, LIMA1, ZC3HAV1, VAPB, H1FX, RANGAP1, EFHD2, SLK, LRRC59, ZYX, DBNL, BSG, PKN2, TXNDC9, CLIC1, FLNA, MARK2, CRKL, DHX29, USO1, SDCBP, MAPRE1, UBAP2, CD226, ADD1, SNX2, ASAP1, KEAP1, HSPA1A, ITGB1, SH3GLB2, RAB11B, FASN, CNN2, CCS, EHD1, EHD4, PLEC, APC, CBL, ARFIP2, S100A11, ANXA1, TRIM25, GLOD4, TMEM2, ANXA2, TIGIT, CSNK1D, LASP1, AHSA1, YKT6, CD200 |
| GO:0098641~cadherin binding involved in cell-cell adhesion | 48 | RTN4, ABCF3, LIMA1, ZC3HAV1, VAPB, SNX2, ASAP1, H1FX, HSPA1A, RANGAP1, ITGB1, EFHD2, SLK, SH3GLB2, LRRC59, FASN, RAB11B, CNN2, CCS, EHD1, PLEC, EHD4, DBNL, BSG, CBL, ANXA1, S100A11, ARFIP2, PKN2, TRIM25, TXNDC9, CLIC1, GLOD4, FLNA, ANXA2, MARK2, TMEM2, CRKL, CSNK1D, DHX29, LASP1, USO1, SDCBP, MAPRE1, UBAP2, YKT6, AHSA1, ADD1 |
| GO:0098609~cell-cell adhesion | 45 | RTN4, LIMA1, ABCF3, ZC3HAV1, VAPB, SNX2, ASAP1, H1FX, HSPA1A, RANGAP1, EFHD2, SLK, SH3GLB2, LRRC59, FASN, RAB11B, CNN2, CCS, EHD1, PLEC, EHD4, DBNL, BSG, CREBBP, CBL, S100A11, ARFIP2, PKN2, TRIM25, TXNDC9, GLOD4, ANXA2, MARK2, TMEM2, CRKL, CSNK1D, DHX29, LASP1, USO1, SDCBP, MAPRE1, UBAP2, YKT6, AHSA1, ADD1 |

TABLE 3-continued

| HIV- low cutoff | | |
|---|---|---|
| Category | Count | Genes |
| Enrichment Score: 1.9864300666381447 | | |
| IPR005225:Small GTP-binding protein domain | 34 | RAB5B, RAB5C, ARF6, MTIF2, GFM2, ARL5A, KRAS, GFM1, RAC1, RALB, RAB11B, SAR1B, RHOF, ARL2, RAP2C, EFTUD2, DRG1, DRG2, RAB33A, RAB33B, ARL3, NRAS, RAB30, RAB18, RAB35, ARF4, RHOT1, RAB5A, RHOT2, RIT1, ARL8B, ARL4C, NKIRAS2, ARL4A |
| GO:0007264~small GTPase mediated signal transduction | 47 | RAB5B, RAB5C, RGL4, IQGAP2, ARF6, RRAGC, DOCK2, ARL5A, KRAS, SOS1, RAC1, RAPGEF6, RAB11B, DOCK10, RAPGEF1, RHOF, ARL2, RAP2C, VAV3, RABIF, RALBP1, ARFIP2, RGS19, CHP1, DOCK8, VAV1, RAB33A, RALGDS, RAB33B, ARL3, ARHGAP30, NRAS, SH2D3C, RAB30, SH2D3A, RAB18, RAB35, KRIT1, ARF4, RAB5A, RHOT1, RHOT2, RIT1, ARL8B, ARL4C, NKIRAS2, ARL4A |
| GO:0003924~GTPase activity | 41 | GNA13, RAB5B, RAB5C, HBS1L, GTPBP10, ATL3, GNL3L, ARF6, MTIF2, RRAGC, GFM2, KRAS, GFM1, RAC1, RAB11B, RALB, TUBA1A, MX1, SAR1B, RHOF, MX2, TUBA1C, ARL2, DNM3, NUDT1, EFTUD2, RAB33A, RAB33B, ARL3, RAB30, RAB18, RAB35, ARF4, RAB5A, RHOT1, RHOT2, RIT1, ARL8B, ARL4C, GBP3, NKIRAS2 |
| nucleotide phosphate-binding region:GTP | 48 | GNA13, GPN3, RAB5B, RAB5C, HBS1L, GTPBP10, ATL3, GNL3L, ARF6, MTIF2, RRAGC, GFM2, ARL5A, KRAS, GFM1, RAC1, RAB11B, RALB, TUBA1A, MX1, SAR1B, RHOF, MX2, TUBA1C, ARL2, DNM3, RAP2C, GIMAP5, NIN, EFTUD2, DRG1, DRG2, PCK2, RAB33A, RAB33B, ARL3, NRAS, RAB30, RAB18, RAB35, ARF4, RAB5A, RIT1, ARL8B, ARL4C, GBP3, NKIRAS2, ARL4A |
| GTP-binding | 51 | GNA13, RAB5B, RAB5C, GTPBP10, ATL3, HBS1L, GNL3L, ARL5A, RALB, SAR1B, MX1, TUBA1A, RHOF, MX2, TUBA1C, ARL2, RAP2C, EFTUD2, ARL3, RAB18, RAB5A, ARL8B, GBP3, ARL4C, NKIRAS2, ARL4A, GPN3, ARF6, MTIF2, RRAGC, GFM2, KRAS, GFM1, RAC1, RAB11B, DNM3, GIMAP5, NIN, DRG1, DRG2, PCK2, RAB33A, RAB33B, GIMAP1, NRAS, RAB30, RAB35, ARF4, RHOT1, RHOT2, RIT1 |
| IPR027417:P-loop containing nucleoside triphosphate hydrolase | 119 | GNA13, RAD51C, DYNC1LI2, HBS1L, IQGAP2, INO80, NLRC5, DDX23, DHX34, RALB, AAGAB, ORC4, VPS4A, DDX10, MX1, SAR1B, MX2, EFTUD2, IFI44, DHX29, RAB18, RFC2, ARL8B, GBP3, SMARCA2, GPN3, PFKFB3, MYO9B, ARF6, MTIF2, RRAGC, GFM2, MOV10, KRAS, GFM1, RAC1, DDX42, SMG9, KIF3B, MYO1G, ABCB7, RAB33A, RAB33B, PSMC5, PSMC2, ARF4, RHOT1, DDX50, RHOT2, RIT1, DDX51, ABCF3, SPG7, RAB5B, RAB5C, ATL3, GTPBP10, DICER1, YLPM1, GNL3L, HELZ, SKIV2L2, SLFN5, PMVK, ARL5A, ATAD3A, LONP1, DYNC1H1, RHOF, ARL2, RAP2C, MPP6, DGUOK, NDUFA10, TTF2, RAD50, MCM6, ARL3, TOR2A, CBWD2, RECQL, RAB5A, ARL4C, NKIRAS2, SPAST, ARL4A, BTAF1, SBNO1, SBNO2, WRNIP1, DCK, N4BP2, CHD9, CHD1L, CHD7, KTI12, DDX19A, RAB11B, DHX16, UCK1, CHD6, EHD1, ERCC3, SPATA5, EHD4, DNM3, MSH6, GIMAP5, MSH2, SMC5, SMC6, DRG1, DRG2, GIMAP1, SMC4, NRAS, RAB30, RAB35, SAMD9 |
| GO:0005525~GTP binding | 58 | GNA13, RAB5B, RAB5C, HBS1L, GTPBP10, ATL3, GNL3L, ARL5A, RALB, TUBA1A, SAR1B, MX1, RHOF, MX2, TUBA1C, ARL2, RAP2C, EFTUD2, ARL3, RAB18, RAB5A, ARL8B, IRGQ, GBP3, ARL4C, NKIRAS2, ARL4A, GPN3, GLUD2, ARF6, MTIF2, RRAGC, GFM2, KRAS, GFM1, RAC1, RAB11B, ERCC3, EHD1, EHD4, DNM3, GIMAP5, NIN, ARFIP2, DRG1, DRG2, PCK2, RAB33A, GIMAP1, RAB33B, NRAS, RAB30, RAB35, ARF4, RHOT1, RHOT2, RIT1, C9ORF69 |
| IPR001806:Small GTPase superfamily | 19 | RAP2C, RAB5B, RAB5C, RAB33A, RAB33B, NRAS, RAB30, KRAS, RAB18, RAB35, RAC1, RALB, RAB11B, RHOT1, RAB5A, RHOT2, RIT1, RHOF, NKIRAS2 |
| Enrichment Score: 1.9444899254576018 | | |
| GO:0097296~activation of cysteine-type endopeptidase activity involved in apoptotic signaling pathway | 7 | TNFRSF10A, TRAF2, RIPK1, CASP8, SMAD3, FADD, JAK2 |
| GO:0097191~extrinsic apoptotic signaling pathway | 11 | TNFRSF10A, HIPK1, RIPK1, CASP8, IFNG, PML, SMAD3, FADD, JAK2, BAD, CD27 |
| GO:0006919~activation of cysteine-type endopeptidase activity involved in apoptotic process | 17 | TRAF2, AIFM1, PML, SMAD3, FADD, BAD, BCL2L11, TNFRSF10A, SLC11A2, CDKN1B, CASP8AP2, BBC3, RIPK1, CASP8, PYCARD, JAK2, DAP |

TABLE 3-continued

HIV- low cutoff

| Category | Count | Genes |
|---|---|---|
| Enrichment Score: 1.9286031923588833 | | |
| SM00291:ZnF_ZZ | 7 | EP300, NBR1, MIB2, UTRN, CREBBP, HERC2, ZZEF1 |
| IPR000433:Zinc finger, ZZ-type | 7 | EP300, NBR1, MIB2, UTRN, CREBBP, HERC2, ZZEF1 |
| zinc finger region:ZZ-type | 6 | EP300, NBR1, MIB2, UTRN, CREBBP, HERC2 |
| Enrichment Score: 1.9043308100071867 | | |
| IPR000571:Zinc finger, CCCH-type | 17 | ZFP36, RBM22, MKRN1, PAN3, ZC3H7A, ZMAT5, ZC3HAV1, ZC3H18, ZC3H7B, PPP1R10, HELZ, ZFP36L2, PARP12, CPSF4, ZC3H12D, RNF113A, DUS3L |
| SM00356:ZnF_C3H1 | 14 | ZFP36, MKRN1, RBM22, PAN3, ZMAT5, ZC3H18, ZC3H7A, ZC3H7B, PPP1R10, HELZ, ZFP36L2, PARP12, CPSF4, RNF113A |
| zinc finger region:C3H1-type 2 | 9 | ZFP36, MKRN1, ZFP36L2, ZC3H7A, ZC3HAV1, PARP12, ZC3H7B, CPSF4, DUS3L |
| zinc finger region:C3H1-type 1 | 9 | ZFP36, MKRN1, ZFP36L2, ZC3H7A, ZC3HAV1, PARP12, ZC3H7B, CPSF4, DUS3L |
| zinc finger region:C3H1-type | 7 | RBM22, ZC3H18, ZMAT5, PPP1R10, HELZ, ZC3H12D, RNF113A |
| zinc finger region:C3H1-type 4 | 5 | MKRN1, ZC3HAV1, PARP12, ZC3H7B, CPSF4 |
| zinc finger region:C3H1-type 3 | 6 | MKRN1, ZC3H7A, ZC3HAV1, PARP12, ZC3H7B, CPSF4 |
| Enrichment Score: 1.889023537159269 | | |
| active site:Glycyl thioester intermediate | 18 | UBE2A, UBE2Z, UBE2G1, HERC6, UBE2J1, HERC5, BIRC6, UBA5, HERC2, UBE2J2, UBE2R2, UBE2D4, UBA3, UBE2W, SMURF2, HECTD4, HECTD1, UBE2E1 |
| IPR016135:Ubiquitin-conjugating enzyme/RWD-like | 14 | UBE2A, UBE2Z, TSG101, UBE2G1, IMPACT, UBE2J1, BIRC6, UBE2J2, UBE2R2, UBE2D4, KRAS, UBE2W, RWDD3, UBE2E1 |
| GO:0061631~ubiquitin conjugating enzyme activity | 9 | UBE2D4, UBE2A, UBE2Z, UBE2G1, UBE2J1, BIRC6, UBE2J2, UBE2E1, UBE2R2 |
| IPR000608:Ubiquitin-conjugating enzyme, E2 | 11 | UBE2D4, UBE2A, UBE2Z, KRAS, UBE2G1, UBE2J1, UBE2W, BIRC6, UBE2J2, UBE2E1, UBE2R2 |
| IPR023313:Ubiquitin-conjugating enzyme, active site | 6 | UBE2D4, UBE2A, KRAS, UBE2G1, UBE2E1, UBE2R2 |
| Enrichment Score: 1.888346683338545 | | |
| IPR000313:PWWP | 8 | BRD1, DNMT3A, MSH6, BRPF1, PWWP2A, WHSC1L1, MBD5, GLYR1 |
| domain:PWWP | 7 | BRD1, DNMT3A, MSH6, BRPF1, PWWP2A, MBD5, GLYR1 |
| SM00293:PWWP | 7 | BRD1, DNMT3A, MSH6, BRPF1, PWWP2A, WHSC1L1, GLYR1 |
| Enrichment Score: 1.8759534254878043 | | |
| short sequence motif:LXXLL motif 1 | 9 | ASXL2, CHD9, NCOA1, NCOA2, PELP1, MED13, MED13L, NRIP1, MED1 |
| short sequence motif:LXXLL motif 2 | 9 | ASXL2, CHD9, NCOA1, NCOA2, PELP1, MED13, MED13L, NRIP1, MED1 |
| short sequence motif:LXXLL motif 4 | 5 | CHD9, NCOA1, NCOA2, PELP1, NRIP1 |
| short sequence motif:LXXLL motif 3 | 5 | CHD9, NCOA1, NCOA2, PELP1, NRIP1 |
| short sequence motif:LXXLL motif 5 | 4 | CHD9, NCOA1, PELP1, NRIP1 |
| short sequence motif:LXXLL motif 7 | 3 | NCOA1, PELP1, NRIP1 |
| GO:0035257~nuclear hormone receptor binding | 7 | NCOA1, NCOA2, EP300, ACTN4, SNW1, NRIP1, MED1 |

TABLE 3-continued

| Category | Count | Genes |
|---|---|---|
| HIV- low cutoff | | |
| short sequence motif:LXXLL motif 6 Enrichment Score: 1.8475951130819195 | 3 | NCOA1, PELP1, NRIP1 |
| GO:0036258~multivesicular body assembly | 14 | CHMP3, TSG101, VTA1, CHMP6, CHMP4A, STAM2, CHMP7, VPS37B, CHMP1A, VPS4A, HGS, STAM, PDCD6IP, VPS25 |
| GO:0016197~endosomal transport | 19 | CHMP3, TSG101, STAM2, CHMP6, VTA1, CHMP4A, CHMP7, KIAA0196, VPS37B, WAS, DPY30, RAB35, BLOC1S1, KIAA1033, VPS4A, HGS, STAM, AP5M1, VPS25 |
| GO:0006997~nucleus organization | 10 | NUMA1, CHMP1A, CHMP3, CHMP4A, CHMP6, CHMP7, VPS4A, H3F3A, PDCD6IP, BIN1 |
| GO:0039702~viral budding via host ESCRT complex | 9 | CHMP1A, CHMP3, TSG101, CHMP4A, CHMP6, CHMP7, VPS4A, VPS37B, PDCD6IP |
| GO:0000815~ESCRT III complex | 6 | CHMP1A, CHMP3, CHMP4A, CHMP6, CHMP7, VPS4A |
| GO:0019058~viral life cycle | 10 | CHMP3, TSG101, CHMP4A, CHMP6, VTA1, CHMP7, VPS4A, VPS37B, PDCD6IP, FURIN |
| GO:0000920~cell separation after cytokinesis | 7 | CHMP1A, CHMP3, CHMP4A, CHMP6, CHMP7, VPS4A, PDCD6IP |
| GO:0007080~mitotic metaphase plate congression | 10 | CUL3, CHMP1A, CHMP3, CHMP4A, CHMP6, CHMP7, VPS4A, CDC23, PIBF1, PDCD6IP |
| GO:1903774~positive regulation of viral budding via host ESCRT complex | 3 | TSG101, VPS4A, VPS37B |
| IPR005024:Snf7 | 5 | CHMP1A, CHMP3, CHMP4A, CHMP6, CHMP7 |
| GO:0007034~vacuolar transport | 5 | CHMP1A, CHMP4A, CHMP6, CHMP7, ATP6V0D1 |
| GO:1904903~ESCRT III complex disassembly | 4 | CHMP1A, VTA1, CHMP7, VPS4A |
| GO:1902188~positive regulation of viral release from host cell | 4 | CHMP3, TSG101, VPS4A, VPS37B |
| GO:0010824~regulation of centrosome duplication | 4 | CHMP1A, CHMP3, FBXW5, PDCD6IP |
| GO:1901673~regulation of mitotic spindle assembly Enrichment Score: 1.827917602900078 | 3 | CHMP1A, CHMP3, PDCD6IP |
| GO:0003684~damaged DNA binding | 19 | MSH6, POLK, MSH2, CREBBP, NEIL2, MGMT, APTX, GTF2H3, POLB, RAD1, RPA1, XPA, MPG, XPC, EP300, DDB2, CUL4B, OGG1, ERCC3 |
| GO:0006294~nucleotide-excision repair, preincision complex assembly | 11 | RPA1, XPA, XPC, CHD1L, CCNH, DDB2, GTF2H3, CETN2, CDK7, CUL4B, ERCC3 |
| GO:0000717~nucleotide-excision repair, DNA duplex unwinding | 8 | XPA, XPC, CHD1L, DDB2, GTF2H3, CETN2, CUL4B, ERCC3 |
| GO:0006283~transcription-coupled nucleotide-excision repair | 17 | POLK, CCNH, COPS7A, GTF2H3, COPS7B, CDK7, COPS8, XAB2, POLR2B, PRPF19, RPA1, XPA, EP300, RFC2, ISY1, CUL4B, ERCC3 |
| GO:0000715~nucleotide-excision repair, DNA damage recognition | 8 | XPA, XPC, DDB2, COPS7A, CETN2, COPS7B, COPS8, CUL4B |
| hsa03420:Nucleotide excision repair | 12 | RPA1, XPA, XPC, CCNH, POLE3, RFC2, DDB2, GTF2H3, CETN2, CDK7, CUL4B, ERCC3 |
| GO:0070911~global genome nucleotide-excision repair | 9 | XPA, XPC, CHD1L, DDB2, GTF2H3, CETN2, CUL4B, ERCC3, RNF111 |
| GO:0033683~nucleotide-excision repair, DNA incision | 10 | RPA1, XPA, POLK, CHD1L, RFC2, DDB2, GTF2H3, CUL4B, OGG1, ERCC3 |

TABLE 3-continued

| HIV- low cutoff | | |
|---|---|---|
| Category | Count | Genes |
| GO:0006293~nucleotide-excision repair, preincision complex stabilization | 7 | RPA1, XPA, CHD1L, DDB2, GTF2H3, CUL4B, ERCC3 |
| GO:0070914~UV-damage excision repair | 5 | XPA, XPC, DDB2, INO80, CUL4B |
| GO:0006295~nucleotide-excision repair, DNA incision, 3'-to lesion | 7 | RPA1, XPA, CHD1L, DDB2, GTF2H3, CUL4B, ERCC3 |
| GO:0006289~nucleotide-excision repair | 10 | RPA1, XPA, XPC, NEIL2, HUS1, DDB2, GTF2H3, CETN2, OGG1, ERCC3 |
| GO:0006296~nucleotide-excision repair, DNA incision, 5'-to lesion | 9 | RPA1, XPA, POLK, CHD1L, RFC2, DDB2, GTF2H3, CUL4B, ERCC3 |
| Xeroderma pigmentosum Enrichment Score: 1.8167726915130153 | 4 | XPA, XPC, DDB2, ERCC3 |
| SM00154:ZnF_AN1 | 5 | ZFAND6, ZFAND5, ZFAND2A, ZFAND2B, ZFAND1 |
| IPR000058:Zinc finger, AN1-type | 5 | ZFAND6, ZFAND5, ZFAND2A, ZFAND2B, ZFAND1 |
| zinc finger region:AN1-type 2 | 3 | ZFAND2A, ZFAND2B, ZFAND1 |
| zinc finger region:AN1-type 1 Enrichment Score: 1.8153950109695944 | 3 | ZFAND2A, ZFAND2B, ZFAND1 |
| Centromere | 27 | ITGB3BP, ZNF276, PPP2R5A, KNTC1, AHCTF1, CTCF, RANGAP1, DAXX, ZNF330, NDE1, PPP2CB, STAG1, CSNK1A1, BOD1, CENPM, KANSL1, TP53BP1, FMR1, DYNLT3, NUP85, DCTN5, PMF1, DCTN6, NDEL1, RCC2, NSL1, NGDN |
| Kinetochore | 18 | CSNK1A1, ZNF276, ITGB3BP, BOD1, CENPM, KANSL1, TP53BP1, KNTC1, DYNLT3, AHCTF1, NUP85, DCTN5, RANGAP1, PMF1, DCTN6, NDE1, NDEL1, NSL1 |
| GO:0000777~condensed chromosome kinetochore Enrichment Score: 1.7131033299195293 | 16 | CSNK1A1, ITGB3BP, ZNF276, BOD1, CENPM, KANSL1, TP53BP1, KNTC1, DYNLT3, AHCTF1, NUP85, DCTN5, RANGAP1, DCTN6, NDE1, NDEL1 |
| hsa05210:Colorectal cancer | 19 | MSH6, TCF7, MSH2, RAF1, SMAD3, BAD, RALGDS, MAPK1, FOS, KRAS, JUN, BCL2, GSK3B, ARAF, RAC1, MAPK8, PIK3R1, AKT2, APC |
| hsa05211:Renal cell carcinoma | 18 | VHL, CREBBP, RAF1, EGLN1, CUL2, NRAS, MAPK1, EP300, CRKL, KRAS, JUN, SOS1, RAC1, ARAF, RAPGEF1, PIK3R1, AKT2, FH |
| hsa04012:ErbB signaling pathway | 21 | MAP2K4, CBL, RAF1, BAD, PRKCB, NRAS, MAPK1, NCK2, CBLB, CRKL, KRAS, CDKN1B, JUN, GSK3B, SOS1, ARAF, MAPK8, MAP2K7, ABL2, PIK3R1, AKT2 |
| hsa05215:Prostate cancer | 21 | E2F3, TCF7, CREB1, RELA, CREBBP, RAF1, BAD, PTEN, CDK2, NRAS, MAPK1, EP300, KRAS, CDKN1B, BCL2, GSK3B, SOS1, ARAF, CHUK, PIK3R1, AKT2 |
| hsa05160:Hepatitis C | 28 | TRAF2, OAS1, OAS2, TNFRSF1A, KRAS, SOS1, PPP2CB, PPP2R2D, PIK3R1, CHUK, AKT2, TRAF3, SOCS3, RELA, RAF1, BAD, IFNAR1, NRAS, MAPK1, IFNAR2, MAPK13, GSK3B, RIPK1, ARAF, CD81, IRF3, MAPK8, PIAS1 |
| hsa05220:Chronic myeloid leukemia | 18 | CTBP1, E2F3, RELA, CBL, RAF1, BAD, NRAS, MAPK1, CBLB, CRKL, KRAS, CDKN1B, SOS1, ARAF, RUNX1, CHUK, PIK3R1, AKT2 |
| hsa05221:Acute myeloid leukemia | 15 | TCF7, RELA, PML, PIM1, RAF1, BAD, NRAS, MAPK1, KRAS, SOS1, ARAF, RUNX1, PIK3R1, CHUK, AKT2 |
| hsa04664:Fc epsilon RI signaling pathway | 17 | CSF2, VAV3, MAP2K4, RAF1, VAV1, PRKCB, NRAS, MAPK1, KRAS, MAPK13, SOS1, RAC1, MAPK8, INPP5D, MAP2K7, PIK3R1, AKT2 |
| hsa05213:Endometrial cancer | 14 | TCF7, RAF1, BAD, PTEN, NRAS, MAPK1, KRAS, SOS1, GSK3B, ARAF, ILK, PIK3R1, AKT2, APC |
| hsa05212:Pancreatic cancer | 16 | E2F3, RALBP1, RELA, RAF1, SMAD3, BAD, RALGDS, MAPK1, KRAS, ARAF, RAC1, RALB, MAPK8, PIK3R1, CHUK, AKT2 |
| hsa04370:VEGF signaling pathway | 15 | RAF1, BAD, MAPKAPK2, PRKCB, SH2D2A, NRAS, MAPK1, KRAS, MAPK13, RAC1, PPP3CB, HSPB1, NFATC2, PIK3R1, AKT2 |
| hsa04917:Prolactin signaling pathway | 16 | SOCS3, RELA, SOCS1, LHCGR, RAF1, NRAS, MAPK1, FOS, KRAS, MAPK13, SOS1, GSK3B, MAPK8, JAK2, PIK3R1, AKT2 |
| hsa05223:Non-small cell lung cancer | 12 | MAPK1, NRAS, E2F3, KRAS, RXRB, SOS1, ARAF, RAF1, BAD, PIK3R1, PRKCB, AKT2 |

TABLE 3-continued

HIV- low cutoff

| Category | Count | Genes |
| --- | --- | --- |
| hsa05214:Glioma | 11 | MAPK1, NRAS, E2F3, KRAS, SOS1, ARAF, RAF1, PTEN, PIK3R1, PRKCB, AKT2 |
| hsa05230:Central carbon metabolism in cancer | 10 | MAPK1, NRAS, KRAS, G6PD, PFKL, RAF1, SIRT6, PTEN, PIK3R1, AKT2 |
| hsa04730:Long-term depression | 9 | GNA13, MAPK1, NRAS, KRAS, PPP2CB, ARAF, RAF1, PRKCB, ITPR2 |
| hsa05218:Melanoma | 10 | MAPK1, NRAS, E2F3, KRAS, ARAF, RAF1, BAD, PTEN, PIK3R1, AKT2 |
| hsa05219:Bladder cancer | 6 | MAPK1, NRAS, E2F3, KRAS, ARAF, RAF1 |
| hsa04550:Signaling pathways regulating pluripotency of stem cells | 16 | SETDB1, IL6ST, RAF1, SMAD3, LIF, PCGF5, NRAS, MAPK1, KRAS, MAPK13, GSK3B, JAK2, TCF3, PIK3R1, AKT2, APC |
| hsa04726:Serotonergic synapse | 8 | MAPK1, NRAS, KRAS, ARAF, RAF1, PRKACB, PRKCB, ITPR2 |
| Enrichment Score: 1.6875120920381086 | | |
| GO:0015035~protein disulfide oxidoreductase activity | 9 | GLRX5, ENOX2, TXN2, GFER, CCS, TXNRD1, CHCHD4, GLRX2, GLRX |
| Redox-active center | 12 | TXNDC12, GLRX5, TXNDC11, TXN2, TMX3, TXNRD1, CHCHD4, PDIA4, MIEN1, GLRX2, GLRX, MPST |
| domain:Glutaredoxin | 4 | GLRX5, TXNRD1, GLRX2, GLRX |
| IPR002109:Glutaredoxin | 4 | GLRX5, TXNRD1, GLRX2, GLRX |
| Enrichment Score: 1.6621257484122156 | | |
| GO:0006406~mRNA export from nucleus | 24 | NUP98, FIP1L1, NUP160, SMG5, U2AF2, ALYREF, NUP93, NUP85, NUP188, CASC3, NUP155, NDC1, NUP214, UPF3B, EIF4E, DDX19A, POLDIP3, NUP210, RBMX2, THOC6, SLU7, RANBP2, CPSF3, ALKBH5 |
| GO:0006405~RNA export from nucleus | 12 | NUP214, NUP98, EIF4E, UPF3B, POLDIP3, U2AF2, ALYREF, THOC6, SLU7, NUP188, CASC3, NUP155 |
| GO:0031124~mRNA 3'-end processing | 11 | PCF11, FIP1L1, UPF3B, POLDIP3, U2AF2, ALYREF, THOC6, SLU7, CASC3, CPSF3, CSTF1 |
| GO:0006369~termination of RNA polymerase II transcription | 13 | PCF11, FIP1L1, UPF3B, POLDIP3, U2AF2, ALYREF, THOC6, SLU7, LSM10, CASC3, CPSF3, CSTF1, TTF2 |
| Enrichment Score: 1.6151522301062358 | | |
| IPR012677:Nucleotide-binding, alpha-beta plait | 48 | RALY, RBM33, ENOX2, U2AF2, SETD1A, KIAA0430, TMEM63A, ZNF638, HNRNPLL, SART3, SF3B4, UHMK1, DNAJC17, R3HCC1L, AKAP17A, TIA1, TARDBP, PPIL4, MSI2, RBM10, RBM28, TNRC6A, RBM22, R3HCC1, RBM42, RBM23, SREK1, ALYREF, ELAVL1, MTHFSD, SPEN, CSTF2T, RCAN3, PPARGC1A, LARP4B, BRAP, SAFB2, TRNAU1AP, HNRNPH2, UPF3B, POLDIP3, RBM18, PPRC1, RBMX2, DDX50, RBM19, RNPC3, RBM15 |
| SM00360:RRM | 37 | RALY, RBM33, ENOX2, U2AF2, KIAA0430, SETD1A, ZNF638, HNRNPLL, SART3, SF3B4, UHMK1, TARDBP, TIA1, PPIL4, MSI2, RBM10, RBM28, RBM22, RBM42, RBM23, SREK1, ALYREF, ELAVL1, MTHFSD, SPEN, CSTF2T, PPARGC1A, SAFB2, TRNAU1AP, HNRNPH2, POLDIP3, RBM18, PPRC1, RBMX2, RBM19, RNPC3, RBM15 |
| IPR000504:RNA recognition motif domain | 38 | RALY, RBM33, ENOX2, U2AF2, KIAA0430, SETD1A, ZNF638, HNRNPLL, SART3, SF3B4, UHMK1, DNAJC17, TARDBP, TIA1, PPIL4, MSI2, RBM10, RBM28, RBM22, RBM42, RBM23, SREK1, ALYREF, ELAVL1, MTHFSD, SPEN, CSTF2T, PPARGC1A, SAFB2, TRNAU1AP, HNRNPH2, POLDIP3, RBM18, PPRC1, RBMX2, RBM19, RNPC3, RBM15 |
| GO:0000166~nucleotide binding | 54 | RALY, ENOX2, NT5C3A, U2AF2, KIAA0430, HINT2, HNRNPLL, ZNF638, SART3, DNAJC17, AKAP17A, TIA1, TARDBP, ORC4, RBM10, R3HCC1, RBM42, SPEN, CSTF2T, PPARGC1A, BRAP, TRNAU1AP, RBMX2, REV3L, RBM33, SETD1A, TMEM63A, SF3B4, TRIB2, EXOSC10, R3HCC1L, CHD1L, PPIL4, MSI2, RBM28, TNRC6A, RBM22, RBM23, MOCS2, SREK1, ALYREF, ELAVL1, MTHFSD, RCAN3, LARP4B, SAFB2, HNRNPH2, UPF3B, POLDIP3, PPRC1, RBM18, RBM19, RNPC3, RBM15 |
| domain:RRM | 23 | RBM22, RALY, RBM33, RBM42, ENOX2, SREK1, ALYREF, KIAA0430, SETD1A, MTHFSD, CSTF2T, PPARGC1A, LARP4B, UHMK1, SAFB2, DNAJC17, AKAP17A, POLDIP3, PPIL4, RBM18, PPRC1, RBMX2, TNRC6A |
| domain:RRM 2 | 19 | RBM23, U2AF2, ELAVL1, ZNF638, HNRNPLL, SPEN, SART3, SF3B4, TRNAU1AP, HNRNPH2, TARDBP, TIA1, CPNE1, RBM19, MSI2, RNPC3, RBM10, RBM28, RBM15 |

TABLE 3-continued

HIV- low cutoff

| Category | Count | Genes |
|---|---|---|
| domain:RRM 1 | 19 | RBM23, U2AF2, ELAVL1, ZNF638, HNRNPLL, SPEN, SART3, SF3B4, TRNAU1AP, HNRNPH2, TARDBP, TIA1, CPNE1, RBM19, MSI2, RNPC3, RBM10, RBM28, RBM15 |
| domain:RRM 3 | 10 | HNRNPH2, TIA1, U2AF2, CPNE1, ELAVL1, RBM19, SPEN, HNRNPLL, RBM28, RBM15 |
| Enrichment Score: 1.6134569375887315 | | |
| GO:0006362~transcription elongation from RNA polymerase I promoter | 10 | TAF1B, TAF1C, POLR1E, CCNH, POLR1A, GTF2H3, TBP, CDK7, TWISTNB, ERCC3 |
| GO:0006363~termination of RNA polymerase I transcription | 10 | TAF1B, TAF1C, POLR1E, CCNH, POLR1A, GTF2H3, TBP, CDK7, TWISTNB, ERCC3 |
| GO:0006361~transcription initiation from RNA polymerase I promoter | 10 | TAF1B, TAF1C, POLR1E, CCNH, POLR1A, GTF2H3, TBP, CDK7, TWISTNB, ERCC3 |
| GO:0005675~holo TFIIH complex | 5 | CCNH, GTF2F2, GTF2H3, CDK7, ERCC3 |
| GO:0045815~positive regulation of gene expression, epigenetic | 9 | TAF1B, TAF1C, HIST4H4, EP300, POLR1E, POLR1A, H3F3A, TBP, TWISTNB |
| Enrichment Score: 1.611575588162036 | | |
| GO:0000178~exosome (RNase complex) | 10 | DIS3, ZFP36, EXOSC10, EXOSC6, EXOSC7, EXOSC5, KHSRP, EXOSC3, SKIV2L2, MPHOSPH6 |
| hsa03018:RNA degradation | 21 | CNOT8, PAN3, PFKL, EXOSC6, EXOSC7, TTC37, EXOSC5, EXOSC3, SKIV2L2, PAPD5, EXOSC10, DIS3, BTG2, CNOT6L, DCP2, DCP1A, LSM3, MPHOSPH6, LSM1, TOB2, ZCCHC7 |
| rRNA processing | 20 | EXOSC6, EXOSC7, EXOSC5, EXOSC3, LAS1L, SKIV2L2, PAPD5, RBFA, RPF1, EXOSC10, DIS3, CHD7, NOL11, WDR12, NAT10, TFB1M, MPHOSPH6, UTP20, NSUN5, DDX51 |
| GO:0000176~nuclear exosome (RNase complex) | 7 | DIS3, EXOSC10, EXOSC6, EXOSC7, EXOSC5, EXOSC3, MPHOSPH6 |
| GO:0043928~exonucleolytic nuclear-transcribed mRNA catabolic process involved in deadenylation-dependent decay | 10 | DIS3, CNOT8, EXOSC6, DCP2, EXOSC7, DCP1A, EXOSC5, EXOSC3, LSM3, LSM1 |
| Exosome | 6 | DIS3, EXOSC10, EXOSC6, EXOSC7, EXOSC5, EXOSC3 |
| GO:0000175~3'-5'-exoribonuclease activity | 7 | DIS3, EXOSC10, CNOT8, EXOSC7, EXOSC5, EXOSC3, ISG20L2 |
| GO:0000177~cytoplasmic exosome (RNase complex) | 5 | DIS3, EXOSC6, EXOSC7, EXOSC5, EXOSC3 |
| GO:0034475~U4 snRNA 3'-end processing | 4 | EXOSC6, EXOSC7, EXOSC5, EXOSC3 |
| GO:0045006~DNA deamination | 3 | EXOSC6, EXOSC5, EXOSC3 |
| GO:0071034~CUT catabolic process | 3 | DIS3, EXOSC10, EXOSC3 |
| GO:0004532~exoribonuclease activity | 5 | EXOSC10, EXOSC6, EXOSC7, EXOSC5, EXOSC3 |
| GO:0034427~nuclear-transcribed mRNA catabolic process, exonucleolytic, 3'-5' | 4 | EXOSC6, EXOSC7, EXOSC5, EXOSC3 |
| GO:0071028~nuclear mRNA surveillance | 4 | EXOSC10, EXOSC6, EXOSC7, EXOSC5 |
| GO:0035327~transcriptionally active chromatin | 6 | EXOSC10, PELP1, EXOSC5, TTC37, EXOSC3, CTR9 |

TABLE 3-continued

| Category | Count | Genes |
|---|---|---|
| HIV- low cutoff | | |
| GO:0071051~polyadenylation-dependent snoRNA 3'-end processing | 3 | EXOSC6, EXOSC5, EXOSC3 |
| GO:0016075~rRNA catabolic process | 4 | DIS3, EXOSC6, EXOSC5, DEDD2 |
| IPR027408:PNPase/RNase PH domain | 3 | EXOSC6, EXOSC7, EXOSC5 |
| GO:0071035~nuclear polyadenylation-dependent rRNA catabolic process | 3 | EXOSC10, EXOSC7, EXOSC3 |
| IPR001247:Exoribonuclease, phosphorolytic domain 1 | 3 | EXOSC6, EXOSC7, EXOSC5 |
| IPR015847:Exoribonuclease, phosphorolytic domain 2 | 3 | EXOSC6, EXOSC7, EXOSC5 |
| Enrichment Score: 1.610351623898193 | | |
| h_tnfr1Pathway:TNFR1 Signaling Pathway | 12 | TRAF2, TNFRSF1A, BAG4, LMNB2, MADD, JUN, RIPK1, MAP3K1, CASP8, MAP2K4, MAPK8, FADD |
| h_fasPathway:FAS signaling pathway (CD95) | 11 | LMNB2, CASP7, JUN, MAP3K1, CASP8, MAP2K4, RIPK2, MAPK8, FADD, FAF1, DAXX |
| 77.IkBa__Kinase__JNK__MEKK1 | 4 | JUN, MAP3K1, MAP2K4, MAPK8 |
| Enrichment Score: 1.591424971929435 | | |
| IPR002219:Protein kinase C-like, phorbol ester/diacylglycerol binding | 17 | VAV3, ROCK1, ROCK2, PRKCI, PRKCH, RAF1, DGKH, MYO9B, PRKCD, VAV1, PRKCB, PDZD8, DGKE, NSMCE1, ARAF, DGKZ, PRKD3 |
| SM00109:C1 | 16 | VAV3, ROCK1, ROCK2, PRKCI, PRKCH, RAF1, DGKH, MYO9B, VAV1, PRKCD, PRKCB, PDZD8, DGKE, ARAF, DGKZ, PRKD3 |
| GO:0004697~protein kinase C activity | 6 | PRKCI, PKN2, PRKCH, PRKCD, PRKD3, PRKCB |
| zinc finger region:Phorbol-ester/DAG-type 2 | 7 | DGKE, DGKZ, PRKCH, DGKH, PRKCD, PRKD3, PRKCB |
| zinc finger region:Phorbol-ester/DAG-type 1 | 7 | DGKE, DGKZ, PRKCH, DGKH, PRKCD, PRKD3, PRKCB |
| IPR020454:Diacylglycerol/phorbol-ester binding | 7 | ARAF, PRKCI, PRKCH, RAF1, PRKCD, PRKD3, PRKCB |
| zinc finger region:Phorbol-ester/DAG-type | 9 | PDZD8, VAV3, ROCK1, ROCK2, ARAF, PRKCI, RAF1, MYO9B, VAV1 |
| GO:0030168~platelet activation | 17 | GNA13, VAV3, PRKCH, RAF1, DGKH, PRKCD, VAV1, SRF, FLNA, PRKCB, ITPR2, PLSCR1, MAPK1, DGKE, RAC1, DGKZ, PIK3R1 |
| Enrichment Score: 1.5519301743432432 | | |
| h_PPARgPathway:Role of PPAR-gamma Coactivators in Obesity and Thermogenesis | 6 | NCOA1, NCOA2, EP300, CREBBP, PPARGC1A, MED1 |
| IPR009110:Nuclear receptor coactivator, interlocking | 4 | NCOA1, NCOA2, EP300, CREBBP |
| GO:0035257~nuclear hormone receptor binding | 7 | NCOA1, NCOA2, EP300, ACTN4, SNW1, NRIP1, MED1 |
| h_vdrPathway:Control of Gene Expression by Vitamin D Receptor | 7 | NCOA1, NCOA2, EP300, CREBBP, ACTL6A, TOP2B, MED1 |

TABLE 3-continued

| HIV- low cutoff | | |
|---|---|---|
| Category | Count | Genes |
| Enrichment Score: 1.5475594146838438 | | |
| GO:0042800~histone methyltransferase activity (H3-K4 specific) | 8 | DPY30, ASH2L, KMT2A, KMT2C, WDR5, SETD1A, ASH1L, CXXC1 |
| hsa00310:Lysine degradation | 14 | SETDB1, DLST, EHMT1, KMT2A, KMT2C, SETD1A, OGDH, ACAT2, COLGALT1, ALDH3A2, WHSC1L1, ASH1L, PHYKPL, ALDH9A1 |
| GO:0051568~histone H3-K4 methylation | 8 | DPY30, ASH2L, KMT2A, KMT2C, WDR5, SETD1A, ASH1L, CXXC1 |
| Methyltransferase | 33 | KMT2A, EZH1, KMT2C, MGMT, TRMT2B, SETD1A, VCPKMT, ASH2L, METTL3, ASMTL, NSUN3, NSUN5, SETDB1, DNMT3A, EHMT1, METTL6, METTL2A, METTL2B, METTL12, METTL13, KDM2A, JMJD6, TRMT13, WHSC1L1, MTR, ASH1L, SETD6, PCMTD1, PRDM2, TFB1M, SETD4, METTL17, COMTD1 |
| GO:0018024~histone-lysine N-methyltransferase activity | 11 | SETDB1, DPY30, EHMT1, ASH2L, KMT2A, EZH1, KMT2C, WDR5, WHSC1L1, SETD1A, PRDM2 |
| domain:Post-SET | 6 | SETDB1, KMT2A, KMT2C, WHSC1L1, SETD1A, ASH1L |
| IPR003616:Post-SET domain | 6 | SETDB1, KMT2A, KMT2C, WHSC1L1, SETD1A, ASH1L |
| GO:0048188~Set1C/COMPASS complex | 5 | DPY30, ASH2L, WDR5, SETD1A, CXXC1 |
| S-adenosyl-L-methionine | 28 | KMT2A, KMT2C, EZH1, TRMT2B, SETD1A, RSAD2, VCPKMT, METTL3, TYW1, ASMTL, LIAS, NSUN3, CDK5RAP1, NSUN5, SETDB1, DNMT3A, EHMT1, METTL2A, METTL2B, TRMT13, WHSC1L1, MTR, ASH1L, SETD6, PRDM2, TFB1M, SETD4, COMTD1 |
| domain:SET | 11 | SETDB1, EHMT1, KMT2A, EZH1, KMT2C, WHSC1L1, SETD1A, ASH1L, SETD6, PRDM2, SETD4 |
| GO:0035097~histone methyltransferase complex | 7 | DPY30, ASH2L, KMT2A, KMT2C, WDR5, SETD1A, CXXC1 |
| SM00317:SET | 9 | SETDB1, EHMT1, KMT2A, EZH1, KMT2C, WHSC1L1, SETD1A, ASH1L, PRDM2 |
| IPR001214:SET domain | 11 | SETDB1, EHMT1, KMT2A, EZH1, KMT2C, WHSC1L1, SETD1A, ASH1L, SETD6, PRDM2, SETD4 |
| GO:0018026~peptidyl-lysine monomethylation | 4 | EHMT1, KMT2A, SETD6, SETD4 |
| GO:0044666~MLL3/4 complex | 4 | DPY30, ASH2L, KMT2C, WDR5 |
| zinc finger region:PHD-type 3 | 4 | KMT2A, KMT2C, WHSC1L1, KDM5B |
| SM00508:PostSET | 4 | KMT2A, KMT2C, WHSC1L1, SETD1A |
| GO:0034968~histone lysine methylation | 4 | SETDB1, WHSC1L1, SETD6, PRDM2 |
| Enrichment Score: 1.4904218811914152 | | |
| h_ceramidePathway: Ceramide Signaling Pathway | 15 | TRAF2, AIFM1, RELA, MAP2K4, RAF1, FADD, BAD, MAPK1, TNFRSF1A, MAP3K1, BCL2, RIPK1, CASP8, MAPK8, NSMAF |
| GO:0071550~death-inducing signaling complex assembly | 6 | TRAF2, TNFRSF1A, RIPK1, CASP8, RAF1, FADD |
| GO:0097296~activation of cysteine-type endopeptidase activity involved in apoptotic signaling pathway | 7 | TNFRSF10A, TRAF2, RIPK1, CASP8, SMAD3, FADD, JAK2 |
| h_tnfr1Pathway:TNFR1 Signaling Pathway | 12 | TRAF2, TNFRSF1A, BAG4, LMNB2, MADD, JUN, RIPK1, MAP3K1, CASP8, MAP2K4, MAPK8, FADD |
| GO:0005123~death receptor binding | 7 | CASP8AP2, MADD, RIPK1, CASP8, FADD, TMBIM1, FEM1B |
| GO:0010803~regulation of tumor necrosis factor-mediated signaling pathway | 10 | TRAF1, TRAF2, TNFRSF1A, HIPK1, MADD, RIPK1, CASP8, PYCARD, RBCK1, CHUK |

TABLE 3-continued

HIV- low cutoff

| Category | Count | Genes |
|---|---|---|
| GO:1902041~regulation of extrinsic apoptotic signaling pathway via death domain receptors | 7 | TNFRSF10A, TRAF2, MADD, RIPK1, CASP8, FADD, FEM1B |
| GO:1902042~negative regulation of extrinsic apoptotic signaling pathway via death domain receptors | 10 | TNFRSF10A, ICAM1, TRAF2, GPX1, RIPK1, CASP8, RAF1, FADD, TMBIM1, RFFL |
| h_soddPathway:SODD/TNFR1 Signaling Pathway | 6 | TRAF2, TNFRSF1A, BAG4, RIPK1, CASP8, FADD |
| 99.NF-kB_activation | 9 | IRAK1, TRAF2, TNFRSF1A, RELA, BCL2, CREBBP, FADD, MAP3K14, TRAF5 |
| h_deathPathway:Induction of apoptosis through DR3 and DR4/5 Death Receptors | 11 | TNFRSF10A, TRAF2, XIAP, CASP7, RELA, RIPK1, BCL2, CASP8, FADD, MAP3K14, CHUK |
| h_relaPathway:Acetylation and Deacetylation of RelA in The Nucleus | 7 | TNFRSF1A, EP300, RELA, RIPK1, CREBBP, FADD, CHUK |
| GO:0036462~TRAIL-activated apoptotic signaling pathway | 3 | TNFRSF10A, CASP8, FADD |
| GO:0045651~positive regulation of macrophage differentiation | 5 | LIF, CSF1, RIPK1, CASP8, FADD |
| h_nfkbPathway:NF-kB Signaling Pathway | 8 | IRAK1, TNFRSF1A, RELA, RIPK1, MAP3K1, FADD, MAP3K14, CHUK |
| GO:2001238~positive regulation of extrinsic apoptotic signaling pathway | 7 | TRAF2, RIPK1, PML, PYCARD, RBCK1, FADD, DEDD2 |
| 46.P13K_PTEN | 6 | TNFRSF1A, CASP7, BCL2, CASP8, FADD, BAD |
| GO:0035666~TRIF-dependent toll-like receptor signaling pathway | 7 | LY96, RIPK1, CASP8, FADD, IRF3, CHUK, TRAF3 |
| 40.Deg_of_Chrom_DNA_TNF-ind_apoptosis | 5 | TRAF2, TNFRSF1A, RIPK1, CASP8, FADD |
| 44.Sig_Trans_TNFR1-DR3-DR4_DR5 | 4 | TRAF2, RIPK1, CASP8, FADD |
| GO:0010939~regulation of necrotic cell death | 4 | PPIF, TRAF2, RIPK1, CASP8 |
| domain:Death | 7 | TNFRSF10A, IRAK4, TNFRSF1A, MADD, RIPK1, FADD, MALT1 |
| GO:0031264~death-inducing signaling complex | 3 | RIPK1, CASP8, FADD |
| GO:0097342~ripoptosome | 3 | RIPK1, CASP8, FADD |
| 72.IAP_interaction_with_cell_death_pathways | 5 | TNFRSF1A, XIAP, CASP7, CASP8, FADD |
| IPR011029:Death-like domain | 12 | TNFRSF10A, IRAK4, IRAK1, TNFRSF1A, CARD16, RIPK1, CASP8, PYCARD, RIPK2, FADD, MALT1, DEDD2 |
| 150.caspase_and_NFKB_activation | 5 | TNFRSF1A, RELA, RIPK1, CASP8, FADD |
| IPR000488:Death domain | 5 | TNFRSF10A, IRAK1, TNFRSF1A, RIPK1, FADD |
| SM00005:DEATH Enrichment Score: 1.45222941807591 | 4 | TNFRSF10A, TNFRSF1A, RIPK1, FADD |
| domain:VHS | 5 | STAM2, HGS, STAM, GGA1, GGA3 |
| SM00288:VHS | 5 | STAM2, HGS, STAM, GGA1, GGA3 |
| IPR002014:VHS | 5 | STAM2, HGS, STAM, GGA1, GGA3 |
| GO:0033565~ESCRT-0 complex | 3 | STAM2, HGS, STAM |
| repeat:UIM | 4 | RNF166, STAM2, HGS, STAM |
| IPR008942:ENTH/VHS | 7 | PCF11, CHERP, STAM2, HGS, STAM, GGA1, GGA3 |

TABLE 3-continued

HIV- low cutoff

| Category | Count | Genes |
|---|---|---|
| IPR003903:Ubiquitin interacting motif | 6 | STAM2, ZFAND2B, HGS, DNAJB2, STAM, UIMC1 |
| GO:0042059~negative regulation of epidermal growth factor receptor signaling pathway | 8 | RNF126, RNF115, TSG101, AP2A1, STAM2, CBL, HGS, STAM |
| Enrichment Score: 1.419973773347531 | | |
| hsa04130:SNARE interactions in vesicular transport | 12 | SNAP29, BNIP1, STX17, BET1, VAMP5, USE1, SEC22B, BET1L, SNAP23, VAMP2, STX10, YKT6 |
| GO:0061025~membrane fusion | 13 | SNAP29, DNM3, RABIF, UBXN2A, UBXN2B, STX17, USO1, CHP1, BET1L, NAPA, SNAP23, VAMP2, STX10 |
| GO:0031201~SNARE complex | 14 | SNAP29, BET1, STXBP2, NAPA, SNX4, BNIP1, STX17, VAMP5, SEC22B, BET1L, VAMP2, SNAP23, STX10, YKT6 |
| GO:0005484~SNAP receptor activity | 10 | SNAP29, BNIP1, STX17, VAMP5, SEC22B, BET1L, SNAP23, VAMP2, STX10, YKT6 |
| IPR000727:Target SNARE coiled-coil domain | 6 | SNAP29, STX17, BET1, BET1L, SNAP23, STX10 |
| domain:t-SNARE coiled-coil homology | 5 | SNAP29, STX17, BET1, BET1L, STX10 |
| SM00397:t_SNARE | 5 | SNAP29, STX17, BET1, SNAP23, STX10 |
| GO:0019905~syntaxin binding | 9 | SNAP29, SYT11, BET1, SEC22B, NAPA, SYTL3, SNAP23, VAMP2, STX10 |
| Enrichment Score: 1.4061663679110412 | | |
| h_41BBPathway:The 4-1BB-dependent immune response | 9 | TRAF2, TNFRSF9, RELA, JUN, MAP3K1, IFNG, MAPK8, CHUK, IL2 |
| h_tall1Pathway:TACI and BCMA stimulation of B cell immune responses. | 8 | TRAF2, TNFSF13B, RELA, MAPK8, MAP3K14, TRAF5, CHUK, TRAF3 |
| h_stressPathway:TNF/ Stress Related Signaling | 10 | TRAF2, TNFRSF1A, RELA, JUN, RIPK1, MAP3K1, MAP2K4, MAPK8, MAP3K14, CHUK |
| h_tnfr2Pathway:TNFR2 Signaling Pathway | 8 | TRAF1, TRAF2, RELA, RIPK1, MAP3K1, MAP3K14, CHUK, TRAF3 |
| h_nfkbPathway:NF-kB Signaling Pathway | 8 | IRAK1, TNFRSF1A, RELA, RIPK1, MAP3K1, FADD, MAP3K14, CHUK |
| h_tollPathway:Toll-Like Receptor Pathway | 11 | IRAK1, FOS, LY96, RELA, JUN, MAP3K1, MAP2K4, MAPK8, MAP3K14, ECSIT, CHUK |
| h_cd40Pathway:CD40L Signaling Pathway | 5 | RELA, MAP3K1, MAP3K14, CHUK, TRAF3 |
| h_il1rPathway:Signal transduction through IL1R | 8 | IRAK1, RELA, JUN, MAP3K1, MAPK8, MAP3K14, ECSIT, CHUK |
| h_rnaPathway:Double Stranded RNA Induced Gene Expression | 3 | RELA, MAP3K14, CHUK |
| Enrichment Score: 1.3724915407975329 | | |
| GO:0000781~chromosome, telomeric region | 12 | DPY30, TP53BP1, NSMCE1, SMC5, NSMCE2, SMC6, TINF2, SIRT2, TERF2, ATM, CDK2, TERF1 |
| GO:0090398~cellular senescence | 8 | ULK3, PML, SMC5, NSMCE2, SMC6, PRKCD, SRF, TERF2 |
| GO:0030915~Smc5-Smc6 complex | 4 | NSMCE1, SMC5, NSMCE2, SMC6 |
| Telomere | 8 | NSMCE1, SMC5, NSMCE2, SMC6, TINF2, TERF2, RAD50, TERF1 |
| GO:0000722~telomere maintenance via recombination | 7 | RPA1, RAD51C, RFC2, SMC5, NSMCE2, SMC6, RAD50 |

TABLE 3-continued

HIV- low cutoff

| Category | Count | Genes |
|---|---|---|
| Enrichment Score: 1.3688179640343465 | | |
| Biological rhythms | 25 | ENOX2, KMT2A, ROCK2, CREB1, KLF10, CREBBP, PML, RORA, PPARGC1A, PPP1CB, NRIP1, EP300, NCOA2, SIN3A, SP1, CSNK1D, METTL3, CSNK1E, GSK3B, GFPT1, MAPK8, PRKAA1, KDM5B, FBXW11, KDM5C |
| GO:0042752~regulation of circadian rhythm | 10 | CSNK1D, CSNK1E, ROCK2, CREB1, KLF10, PML, PRKAA1, MAPK8, PPARGC1A, PPP1CB |
| GO:0032922~circadian regulation of gene expression | 10 | NCOA2, CSNK1D, KMT2A, CSNK1E, GFPT1, PML, RORA, PPARGC1A, PPP1CB, NRIP1 |
| Enrichment Score: 1.341911280785786 | | |
| repeat:RCC1 1 | 7 | IBTK, SERGEF, RCC2, HERC6, HERC5, HERC2, MYCBP2 |
| repeat:RCC1 2 | 7 | IBTK, SERGEF, RCC2, HERC6, HERC5, HERC2, MYCBP2 |
| repeat:RCC1 3 | 7 | IBTK, SERGEF, RCC2, HERC6, HERC5, HERC2, MYCBP2 |
| IPR000408:Regulator of chromosome condensation, RCC1 | 7 | IBTK, SERGEF, RCC2, HERC6, HERC5, HERC2, MYCBP2 |
| IPR009091:Regulator of chromosome condensation 1/beta-lactamase-inhibitor protein II | 7 | IBTK, SERGEF, RCC2, HERC6, HERC5, HERC2, MYCBP2 |
| repeat:RCC1 5 | 6 | SERGEF, RCC2, HERC6, HERC5, HERC2, MYCBP2 |
| repeat:RCC1 4 | 6 | SERGEF, RCC2, HERC6, HERC5, HERC2, MYCBP2 |
| Cell division and chromosome partitioning/ Cytoskeleton | 7 | IBTK, SERGEF, RCC2, HERC6, HERC5, HERC2, MYCBP2 |
| repeat:RCC1 7 | 3 | SERGEF, RCC2, HERC2 |
| repeat:RCC1 6 | 3 | SERGEF, RCC2, HERC2 |
| Enrichment Score: 1.3338979660581836 | | |
| SM00490:HELICc | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| domain:Helicase C-terminal | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| SM00487:DEXDc | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| Helicase | 25 | BTAF1, DICER1, INO80, HELZ, SKIV2L2, CHD9, MOV10, CHD1L, CHD7, DDX23, DDX19A, DHX34, DHX16, DDX10, ERCC3, CHD6, DDX42, TTF2, MCM6, RECQL, DHX29, GTF2F2, DDX50, SMARCA2, DDX51 |
| IPR001650:Helicase, C-terminal | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| IPR014001:Helicase, superfamily 1/2, ATP-binding domain | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| domain:Helicase ATP-binding | 21 | BTAF1, DICER1, INO80, SKIV2L2, TTF2, CHD9, RECQL, CHD7, CHD1L, DHX29, DDX23, DDX19A, DHX34, DDX50, DHX16, DDX10, CHD6, ERCC3, SMARCA2, DDX51, DDX42 |
| GO:0004386~helicase activity | 17 | BTAF1, DICER1, ANXA1, HELZ, CHD9, MOV10, CHD7, DDX23, DDX19A, GTF2F2, DHX34, DDX50, DDX10, ERCC3, SMARCA2, DDX51, DDX42 |
| IPR000330:SNF2-related | 8 | CHD9, BTAF1, CHD7, CHD1L, INO80, CHD6, SMARCA2, TTF2 |
| GO:0008026~ATP-dependent helicase activity | 7 | RECQL, CHD1L, DDX23, DHX29, DHX16, CHD6, TTF2 |
| IPR011545:DNA/RNA helicase, DEAD/DEAH box type, N-terminal | 12 | RECQL, DDX23, DHX29, DDX19A, DICER1, DHX34, DDX50, DHX16, SKIV2L2, DDX10, DDX51, DDX42 |
| IPR002464:DNA/RNA helicase, ATP-dependent, DEAH-box type, conserved site | 5 | CHD1L, DHX29, DHX16, CHD6, TTF2 |

TABLE 3-continued

HIV- low cutoff

| Category | Count | Genes |
|---|---|---|
| short sequence motif:DEAH box | 7 | CHD9, CHD7, CHD1L, DHX29, DHX16, CHD6, TTF2 |
| GO:0004004~ATP-dependent RNA helicase activity Enrichment Score: 1.3229064054856214 | 9 | DDX23, DHX29, DDX19A, DHX34, DDX50, DHX16, DDX10, DDX51, DDX42 |
| domain:PCI | 7 | PSMD13, PSMD12, PCID2, COPS7A, PSMD3, COPS7B, COPS8 |
| IPR000717:Proteasome component (PCI) domain | 6 | PSMD13, PSMD12, PCID2, COPS7A, PSMD3, COPS7B |
| GO:0022624~proteasome accessory complex | 6 | PSMD13, PSMC5, PSMD12, PSMC2, PSMD3, PSMD5 |
| SM00088:PINT | 5 | PSMD13, PSMD12, COPS7A, PSMD3, COPS7B |
| GO:0008541~proteasome regulatory particle, lid subcomplex Enrichment Score: 1.318551447098944 | 3 | PSMD13, PSMD12, PSMD3 |
| Iron-sulfur | 13 | GLRX5, TYW1, NDUFV2, IREB2, RSAD2, LIAS, UQCRFS1, CDK5RAP1, CIAPIN1, NDUFS1, PPAT, GLRX2, REV3L |
| 2Fe—2S | 6 | GLRX5, NDUFV2, UQCRFS1, CIAPIN1, NDUFS1, GLRX2 |
| GO:0051537~2 iron, 2 sulfur cluster binding Enrichment Score: 1.309987729796792 | 6 | GLRX5, NDUFV2, UQCRFS1, CIAPIN1, NDUFS1, GLRX2 |
| IPR016159:Cullin repeat-like-containing domain | 6 | CUL3, CUL2, EXOC7, CACUL1, VPS51, CUL4B |
| IPR001373:Cullin, N-terminal | 5 | CUL3, CUL2, CACUL1, CUL9, CUL4B |
| IPR016157:Cullin, conserved site | 4 | CUL3, CUL2, CUL9, CUL4B |
| SM00884:SM00884 | 4 | CUL3, CUL2, CUL9, CUL4B |
| IPR019559:Cullin protein, neddylation domain | 4 | CUL3, CUL2, CUL9, CUL4B |
| IPR016158:Cullin homology | 4 | CUL3, CUL2, CUL9, CUL4B |
| GO:0031461~cullin-RING ubiquitin ligase complex | 4 | CUL3, CUL2, CUL9, CAND1 |
| cross-link:Glycyl lysine isopeptide (Lys-Gly) (interchain with G-Cter in NEDD8) | 3 | CUL3, CUL2, CUL4B |
| SM00182:CULLIN Enrichment Score: 1.3095823857533413 | 3 | CUL3, CUL2, CUL4B |
| zinc finger region:RanBP2-type | 6 | YAF2, RYBP, RBCK1, MDM4, RBM10, TAB3 |
| IPR001876:Zinc finger, RanBP2-type | 7 | YAF2, RYBP, RBCK1, MDM4, RANBP2, RBM10, TAB3 |
| SM00547:ZnF_RBZ Enrichment Score: 1.3076994990472324 | 6 | YAF2, RYBP, RBCK1, RANBP2, RBM10, TAB3 |
| active site:Glycyl thioester intermediate | 18 | UBE2A, UBE2Z, UBE2G1, HERC6, UBE2J1, HERC5, BIRC6, UBA5, HERC2, UBE2J2, UBE2R2, UBE2D4, UBA3, UBE2W, SMURF2, HECTD4, HECTD1, UBE2E1 |
| repeat:RCC1 5 | 6 | SERGEF, RCC2, HERC6, HERC5, HERC2, MYCBP2 |
| repeat:RCC1 4 | 6 | SERGEF, RCC2, HERC6, HERC5, HERC2, MYCBP2 |
| domain:HECT | 6 | HERC6, HERC5, HECTD4, SMURF2, HERC2, HECTD1 |
| SM00119:HECTc | 6 | HERC6, HERC5, HECTD4, SMURF2, HERC2, HECTD1 |
| IPR000569:HECT | 6 | HERC6, HERC5, HECTD4, SMURF2, HERC2, HECTD1 |

TABLE 3-continued

HIV- low cutoff

| Category | Count | Genes |
|---|---|---|
| Enrichment Score: 1.303394556655991 | | |
| h_metPathway:Signaling of Hepatocyte Growth Factor Receptor | 13 | MAP4K1, RAF1, ITGB1, PTEN, FOS, MAPK1, CRKL, SOS1, JUN, MAPK8, RAPGEF1, RASA1, PIK3R1 |
| h_integrinPathway:Integrin Signaling Pathway | 11 | MAPK1, CAPNS1, CRKL, ROCK1, JUN, SOS1, RAF1, MAPK8, ZYX, RAPGEF1, ITGB1 |
| hsa04510:Focal adhesion | 27 | XIAP, ITGB1, PTEN, SOS1, BCL2, ILK, RAC1, ZYX, RAPGEF1, PIK3R1, AKT2, PARVG, VAV3, ACTN4, ROCK1, ROCK2, RAF1, BAD, VAV1, PPP1CB, FLNA, PRKCB, MAPK1, CRKL, JUN, GSK3B, MAPK8 |
| Enrichment Score: 1.3018570193497914 | | |
| GO:0000175~3'-5'-exoribonuclease activity | 7 | DIS3, EXOSC10, CNOT8, EXOSC7, EXOSC5, EXOSC3, ISG20L2 |
| GO:0090503~RNA phosphodiester bond hydrolysis, exonucleolytic | 8 | DIS3, EXOSC10, CNOT8, PAN3, CNOT6L, DCP2, EXOSC5, ISG20L2 |
| Exonuclease | 9 | DIS3, EXOSC10, RAD1, CNOT8, CNOT6L, AEN, REXO1, ERI3, ISG20L2 |
| Enrichment Score: 1.3001157372818273 | | |
| domain:J | 12 | DNAJC17, DNAJC15, DNAJC16, DNAJB9, DNAJC11, SACS, DNAJC5, DNAJB2, HSCB, DNAJB6, DNAJC30, GAK |
| IPR001623:DnaJ domain | 12 | DNAJC17, DNAJC15, DNAJC16, DNAJB9, DNAJC11, SACS, DNAJC5, DNAJB2, HSCB, DNAJB6, DNAJC30, GAK |
| SM00271:DnaJ | 10 | DNAJC17, DNAJC15, DNAJC16, DNAJB9, DNAJC11, DNAJC5, DNAJB2, DNAJB6, DNAJC30, GAK |
| IPR018253:DnaJ domain, conserved site | 6 | DNAJC16, DNAJB9, DNAJC11, DNAJC5, DNAJB2, DNAJB6 |
| Enrichment Score: 1.296835482359286 | | |
| hsa04130:SNARE interactions in vesicular transport | 12 | SNAP29, BNIP1, STX17, BET1, VAMP5, USE1, SEC22B, BET1L, SNAP23, VAMP2, STX10, YKT6 |
| GO:0005484~SNAP receptor activity | 10 | SNAP29, BNIP1, STX17, VAMP5, SEC22B, BET1L, SNAP23, VAMP2, STX10, YKT6 |
| domain:v-SNARE coiled-coil homology | 4 | VAMP5, SEC22B, VAMP2, YKT6 |
| IPR001388:Synaptobrevin | 4 | VAMP5, SEC22B, VAMP2, YKT6 |
| GO:0000149~SNARE binding | 7 | GABARAPL2, STX17, VAMP5, SEC22B, SNAPIN, VAMP2, YKT6 |
| Enrichment Score: 1.2920732660982135 | | |
| GO:0016578~histone deubiquitination | 6 | TAF10, USP3, USP22, TRRAP, USP16, USP34 |
| zinc finger region:UBP-type | 5 | USP3, USP5, USP22, USP16, BRAP |
| IPR001607:Zinc finger, UBP-type | 5 | USP3, USP5, USP22, USP16, BRAP |
| SM00290:ZnF_UBP | 4 | USP3, USP5, USP16, BRAP |
| Enrichment Score: 1.271806287569803 | | |
| GO:0042809~vitamin D receptor binding | 6 | MED16, MED17, SNW1, MED13, TOB2, MED1 |
| GO:0046966~thyroid hormone receptor binding | 8 | HMGN3, MED16, MED17, JMJD1C, MED13, GTF2B, MED1, ZNHIT3 |
| GO:0016592~mediator complex | 9 | MED31, MED19, MED16, MED8, MED17, MED11, MED13, MED13L, MED1 |
| GO:0030518~intracellular steroid hormone receptor signaling pathway | 4 | MED16, MED17, MED13, MED1 |

TABLE 3-continued

HIV- low cutoff

| Category | Count | Genes |
| --- | --- | --- |
| Enrichment Score: 1.271330707752596 | | |
| zinc finger region:TFIIB-type | 3 | BRF1, BRF2, GTF2B |
| IPR000812:Transcription factor TFIIB | 3 | BRF1, BRF2, GTF2B |
| IPR013137:Zinc finger, TFIIB-type | 3 | BRF1, BRF2, GTF2B |
| IPR013763:Cyclin-like | 9 | CCNT2, BRF1, BRF2, CCNH, CCNT1, CCNG1, CCNG2, GTF2B, CASD1 |
| Enrichment Score: 1.269935983244461 | | |
| h_tcrPathway:T Cell Receptor Signaling Pathway | 18 | PTPN7, RELA, CD247, MAP2K4, RAF1, VAV1, PRKCB, FOS, JUN, MAP3K1, SOS1, RAC1, ZAP70, PPP3CB, MAPK8, NFATC2, RASA1, PIK3R1 |
| h_gleevecPathway:Inhibition of Cellular Proliferation by Gleevec | 11 | FOS, CRKL, JUN, SOS1, MAP3K1, MAP2K4, RAF1, MAPK8, JAK2, BAD, PIK3R1 |
| h_fcer1Pathway:Fc Epsilon Receptor I Signaling in Mast Cells | 14 | MAP2K4, RAF1, VAV1, PRKCB, MAPK1, FOS, MAP3K1, SOS1, JUN, PPP3CB, MAPK8, NFATC2, MAP2K7, PIK3R1 |
| h_egfPathway:EGF Signaling Pathway | 11 | FOS, JUN, SOS1, MAP3K1, MAP2K4, RAF1, MAPK8, SRF, PIK3R1, RASA1, PRKCB |
| h_metPathway:Signaling of Hepatocyte Growth Factor Receptor | 13 | MAP4K1, RAF1, ITGB1, PTEN, FOS, MAPK1, CRKL, SOS1, JUN, MAPK8, RAPGEF1, RASA1, PIK3R1 |
| h_pdgfPathway:PDGF Signaling Pathway | 11 | FOS, JUN, SOS1, MAP3K1, MAP2K4, RAF1, MAPK8, SRF, PIK3R1, RASA1, PRKCB |
| h_arenrf2Pathway:Oxidative Stress Induced Gene Expression Via Nrf2 | 9 | MAPK1, FOS, JUN, CREB1, AKR7A2, MAPK8, KEAP1, NFE2L2, PRKCB |
| h_bcrPathway:BCR Signaling Pathway | 12 | FOS, JUN, SOS1, MAP3K1, RAC1, PPP3CB, RAF1, MAPK8, CD79B, NFATC2, VAV1, PRKCB |
| h_pyk2Pathway:Links between Pyk2 and Map Kinases | 10 | MAPK1, CRKL, JUN, SOS1, MAP3K1, RAC1, MAP2K4, RAF1, MAPK8, PRKCB |
| h_insulinPathway:Insulin Signaling Pathway | 8 | FOS, JUN, SOS1, RAF1, MAPK8, SRF, PIK3R1, RASA1 |
| h_igf1Pathway:IGF-1 Signaling Pathway | 8 | FOS, JUN, SOS1, RAF1, MAPK8, SRF, PIK3R1, RASA1 |
| hsa04912:GnRH signaling pathway | 17 | ADCY7, MAP2K4, RAF1, PRKCD, PRKCB, ITPR2, NRAS, MAPK1, KRAS, MAP3K3, MAPK13, JUN, MAP3K1, SOS1, MAPK8, PRKACB, MAP2K7 |
| h_at1rPathway:Angiotensin II mediated activation of JNK Pathway via Pyk2 dependent signaling | 10 | MAPK1, MEF2A, JUN, SOS1, MAP3K1, RAC1, MAP2K4, RAF1, MAPK8, PRKCB |
| h_malPathway:Role of MAL in Rho-Mediated Activation of SRF | 7 | MAPK1, ROCK1, MAP3K1, RAC1, RAF1, MAPK8, SRF |
| h_tpoPathway:TPO Signaling Pathway | 8 | FOS, JUN, SOS1, RAF1, JAK2, PIK3R1, RASA1, PRKCB |
| 102.Cholesterol_Stress_Response | 4 | MAP3K1, RAC1, RAF1, MAPK8 |
| 67.Ikaros_and_signaling_inhibitors | 9 | MAPK1, FOS, CD8A, JUN, SOS1, RAF1, NFATC2, VAV1, IL2 |
| h_il6Pathway:IL 6 signaling pathway | 7 | FOS, IL6ST, JUN, SOS1, RAF1, JAK2, SRF |
| h_cdmacPathway:Cadmium induces DNA synthesis and proliferation in macrophages | 6 | MAPK1, FOS, RELA, JUN, RAF1, PRKCB |
| h_ccr5Pathway:Pertussis toxin-insensitive CCR5 Signaling in Macrophage | 6 | FOS, CXCR4, JUN, MAPK8, CCL4, PRKCB |

TABLE 3-continued

| HIV- low cutoff | | |
|---|---|---|
| Category | Count | Genes |
| h_il2Pathway:IL 2 signaling pathway | 7 | FOS, IL2RB, JUN, SOS1, RAF1, MAPK8, IL2 |
| h_crebPathway:Transcription factor CREB and its extracellular signals | 8 | MAPK1, PRKAR2A, CREB1, SOS1, RAC1, PRKACB, PIK3R1, PRKCB |
| h_ghPathway:Growth Hormone Signaling Pathway | 8 | MAPK1, SOS1, SOCS1, RAF1, JAK2, SRF, PIK3R1, PRKCB |
| 68.Mitogen_signaling_in_growth_control | 4 | MAPK1, SOS1, MAP3K1, RAF1 |
| GO:0051090~regulation of sequence-specific DNA binding transcription factor activity | 6 | MAPK1, FOS, TAF6, CREBZF, JUN, MAPK8 |
| h_epoPathway:EPO Signaling Pathway | 6 | FOS, JUN, SOS1, RAF1, MAPK8, JAK2 |
| 77.IkBa_Kinase_JNK_MEKK1 | 4 | JUN, MAP3K1, MAP2K4, MAPK8 |
| h_ngfPathway:Nerve growth factor pathway (NGF) | 6 | FOS, JUN, SOS1, RAF1, MAPK8, PIK3R1 |
| 3.T_cell_receptor | 7 | FOS, JUN, CTLA4, ZAP70, MAPK8, VAV1, IL2 |
| GO:0035994~response to muscle stretch | 4 | FOS, RELA, JUN, RAF1 |
| 100.MAPK_signaling_cascades | 7 | MAPK1, MAP3K3, MAP3K1, MAP2K4, RAF1, MAPK8, MAP2K7 |
| h_il3Pathway:IL 3 signaling pathway | 4 | FOS, SOS1, RAF1, JAK2 |
| GO:0061029~eyelid development in camera-type eye | 3 | JUN, SOS1, SRF |
| h_trkaPathway:Trka Receptor Signaling Pathway | 3 | SOS1, PIK3R1, PRKCB |
| Enrichment Score: 1.263372828431808 | | |
| h_tall1Pathway:TACI and BCMA stimulation of B cell immune responses. | 8 | TRAF2, TNFSF13B, RELA, MAPK8, MAP3K14, TRAF5, CHUK, TRAF3 |
| h_tnfr2Pathway:TNFR2 Signaling Pathway | 8 | TRAF1, TRAF2, RELA, RIPK1, MAP3K1, MAP3K14, CHUK, TRAF3 |
| GO:0031996~thioesterase binding | 6 | TRAF1, TRAF2, RAC1, ARF6, TRAF5, TRAF3 |
| IPR012227:TNF receptor-associated factor TRAF | 4 | TRAF1, TRAF2, TRAF5, TRAF3 |
| PIRSF015614:TNF receptor-associated factor (TRAF) | 4 | TRAF1, TRAF2, TRAF5, TRAF3 |
| domain:MATH | 5 | TRAF1, TRAF2, TRAF5, SPOP, TRAF3 |
| SM00061:MATH | 5 | TRAF1, TRAF2, TRAF5, SPOP, TRAF3 |
| IPR002083:MATH | 5 | TRAF1, TRAF2, TRAF5, SPOP, TRAF3 |
| zinc finger region:TRAF-type 1 | 3 | TRAF2, TRAF5, TRAF3 |
| zinc finger region:TRAF-type 2 | 3 | TRAF2, TRAF5, TRAF3 |
| GO:0005164~tumor necrosis factor receptor binding | 7 | TRAF1, TRAF2, TRAP1, TNFSF13B, CASP8, FADD, TRAF3 |
| GO:0035631~CD40 receptor complex | 4 | TRAF2, TRAF5, CHUK, TRAF3 |
| IPR008974:TRAF-like | 6 | TRAF1, TRAF2, XAF1, TRAF5, SPOP, TRAF3 |
| IPR001293:Zinc finger, TRAF-type | 4 | TRAF2, XAF1, TRAF5, TRAF3 |
| 51.CD40_and_EBV | 4 | TRAF1, TRAF2, MAPK8, TRAF3 |
| IPR018957:Zinc finger, C3HC4 RING-type | 5 | MKRN1, TRAF2, PEX2, TRAF5, TRAF3 |
| Enrichment Score: 1.261550763230275 | | |
| DNA-binding region:A.T hook 2 | 5 | PDS5B, KMT2A, ASH1L, MECP2, BAZ2A |

TABLE 3-continued

HIV- low cutoff

| Category | Count | Genes |
|---|---|---|
| DNA-binding region:A.T hook 1 | 5 | PDS5B, KMT2A, ASH1L, MECP2, BAZ2A |
| DNA-binding region:A.T hook 3 | 4 | PDS5B, KMT2A, ASH1L, BAZ2A |
| Enrichment Score: 1.2578929146832885 | | |
| Redox-active center | 12 | TXNDC12, GLRX5, TXNDC11, TXN2, TMX3, TXNRD1, CHCHD4, PDIA4, MIEN1, GLRX2, GLRX, MPST |
| GO:0045454~cell redox homeostasis | 17 | TMX2, GLRX5, TXN2, AIFM1, TMX3, TXNDC9, PDIA4, GLRX2, GPX1, TXNDC12, TXNDC11, DNAJC16, KRIT1, TXNRD1, NFE2L2, SCO2, GLRX |
| IPR012336:Thioredoxin-like fold | 24 | TMX2, GLRX5, TXN2, MRPS25, TMX3, TXNDC9, PDIA4, CLIC1, AAED1, MIEN1, GLRX2, GPX1, SH3BGRL, TXNDC12, TXNDC11, DNAJC16, EEF1E1, NDUFV2, FAF2, TXNRD1, FAF1, GPX7, SCO2, GLRX |
| IPR013766:Thioredoxin domain | 9 | TMX2, TXNDC12, TXNDC11, DNAJC16, TXN2, TMX3, TXNDC9, PDIA4, SCO2 |
| domain:Thioredoxin | 6 | TMX2, DNAJC16, TXN2, TMX3, TXNDC9, SCO2 |
| GO:0005623~cell | 13 | TMX2, TXNDC11, DNAJC16, AIFM1, TXN2, NELL2, TMX3, MCPH1, SLC41A1, TXNRD1, PDIA4, XCL1, GLRX2 |
| Enrichment Score: 1.2512406598500696 | | |
| GO:0035267~NuA4 histone acetyltransferase complex | 6 | ING3, ACTL6A, TRRAP, KAT5, MRGBP, BRD8 |
| GO:0040008~regulation of growth | 12 | ING3, ING2, ENOX2, SOCS3, NELL2, SOCS1, CD81, IFNG, ACTL6A, KAT5, MRGBP, BRD8 |
| Growth regulation | 11 | ING3, ING2, ENOX2, TSG101, SOCS3, SOCS1, IFNG, ACTL6A, KAT5, MRGBP, BRD8 |
| Enrichment Score: 1.2449747006931964 | | |
| GO:0008536~Ran GTPase binding | 9 | XPO6, IPO7, RANGAP1, NUTF2, RANGRF, RANBP2, TNPO2, XPO7, TNPO1 |
| domain:Importin N-terminal | 5 | XPO6, IPO7, TNPO2, XPO7, TNPO1 |
| SM00913:SM00913 | 5 | XPO6, IPO7, TNPO2, XPO7, TNPO1 |
| IPR001494:Importin-beta, N-terminal | 5 | XPO6, IPO7, TNPO2, XPO7, TNPO1 |
| Enrichment Score: 1.219152476389818 | | |
| SM00455:RBD | 4 | TIAM1, ARAF, RAF1, RGS14 |
| IPR003116:Raf-like Ras-binding | 4 | TIAM1, ARAF, RAF1, RGS14 |
| GO:0005057~receptor signaling protein activity | 9 | BAG4, IFITM1, TIAM1, IL4R, ARAF, RAF1, NSMAF, DAXX, RGS14 |
| domain:RBD | 3 | TIAM1, ARAF, RAF1 |
| Enrichment Score: 1.2191033373017977 | | |
| GO:0000974~Prp19 complex | 6 | RBM22, PRPF19, CRNKL1, U2AF2, ISY1, XAB2 |
| GO:0071014~post-mRNA release spliceosomal complex | 3 | CRNKL1, ISY1, XAB2 |
| GO:0071012~catalytic step 1 spliceosome | 3 | CRNKL1, ISY1, XAB2 |
| Enrichment Score: 1.2188361598202275 | | |
| IPR000814:TATA-box binding protein | 3 | TBPL2, TBP, TBPL1 |
| GO:0006352~DNA-templated transcription, initiation | 9 | TBPL2, TAF10, TAF13, HIST4H4, BRF2, TAF6, TBP, GTF2B, TBPL1 |
| IPR012295:Beta2-adaptin/TBP, C-terminal domain | 3 | TBPL2, TBP, TBPL1 |

TABLE 3-continued

| Category | Count | Genes |
|---|---|---|
| HIV- low cutoff | | |
| Enrichment Score: 1.2120424551901947 | | |
| GO:0004697~protein kinase C activity | 6 | PRKCI, PKN2, PRKCH, PRKCD, PRKD3, PRKCB |
| GO:0034351~negative regulation of glial cell apoptotic process | 4 | TRAF2, PRKCI, PRKCH, PRKCD |
| IPR020454:Diacylglycerol/ phorbol-ester binding | 7 | ARAF, PRKCI, PRKCH, RAF1, PRKCD, PRKD3, PRKCB |
| domain:AGC-kinase C-terminal | 11 | RPS6KA3, ROCK1, ROCK2, PRKCI, PKN2, PRKCH, PRKACB, PRKCD, LATS1, PRKCB, AKT2 |
| SM00133:S_TK_X | 10 | RPS6KA3, ROCK1, ROCK2, PRKCI, PKN2, PRKCH, PRKACB, PRKCD, PRKCB, AKT2 |
| IPR000961:AGC-kinase, C-terminal | 11 | RPS6KA3, ROCK1, ROCK2, PRKCI, PKN2, PRKCH, PRKACB, PRKCD, LATS1, PRKCB, AKT2 |
| IPR017892:Protein kinase, C-terminal | 7 | RPS6KA3, PRKCI, PKN2, PRKCH, PRKCD, PRKCB, AKT2 |
| Enrichment Score: 1.1705954418260636 | | |
| IPR027267:Arfaptin homology (AH) domain/BAR domain | 9 | ICA1, SH3GLB2, ACAP1, ACAP2, ARFIP2, ASAP1, ARHGAP17, BIN3, BIN1 |
| domain:BAR | 6 | SH3GLB2, ACAP1, ACAP2, ARHGAP17, BIN3, BIN1 |
| SM00721:BAR | 4 | SH3GLB2, ARHGAP17, BIN3, BIN1 |
| IPR004148:BAR domain | 4 | SH3GLB2, ARHGAP17, BIN3, BIN1 |
| Enrichment Score: 1.167006763733174 | | |
| IPR006689:Small GTPase superfamily, ARF/SAR type | 9 | ARL2, ARL5A, ARF4, ARF6, ARL8B, SAR1B, ARL4C, ARL3, ARL4A |
| IPR024156:Small GTPase superfamily, ARF type | 8 | ARL2, ARL5A, ARF4, ARF6, ARL8B, ARL4C, ARL3, ARL4A |
| binding site:GTP; via amide nitrogen | 3 | ARL2, ARL5A, ARL3 |
| Enrichment Score: 1.1575764161081228 | | |
| GO:0009165~nucleotide biosynthetic process | 6 | DCTD, DCK, DGUOK, PRPS2, PRPS1, PRPSAP2 |
| Nucleotide biosynthesis | 4 | DCTD, PRPS2, PRPS1, PRPSAP2 |
| IPR005946:Ribose-phosphate diphosphokinase | 3 | PRPS2, PRPS1, PRPSAP2 |
| GO:0004749~ribose phosphate diphosphokinase activity | 3 | PRPS2, PRPS1, PRPSAP2 |
| IPR000836:Phosphoribosyltransferase domain | 4 | PRPS2, PPAT, PRPS1, PRPSAP2 |
| Enrichment Score: 1.1356123741363102 | | |
| domain:ARID | 5 | ARID4A, ARID5A, ARID1B, KDM5B, KDM5C |
| SM00501:BRIGHT | 5 | ARID4A, ARID5A, ARID1B, KDM5B, KDM5C |
| IPR001606:ARID/BRIGHT DNA-binding domain | 5 | ARID4A, ARID5A, ARID1B, KDM5B, KDM5C |
| Enrichment Score: 1.1355492828606781 | | |
| hsa00020:Citrate cycle (TCA cycle) | 9 | SDHA, DLST, IDH3G, SDHC, IDH2, PCK2, OGDH, MDH1, FH |
| Tricarboxylic acid cycle | 7 | SDHA, DLST, IDH3G, SDHC, IDH2, MDH1, FH |
| GO:0006099~tricarboxylic acid cycle | 8 | SDHA, DLST, IDH3G, SDHC, IDH2, OGDH, MDH1, FH |

TABLE 3-continued

HIV- low cutoff

| Category | Count | Genes |
|---|---|---|
| GO:0006734~NADH metabolic process | 4 | DLST, IDH3G, OGDH, MDH1 |
| hsa01200:Carbon metabolism | 18 | DLST, ME2, PFKL, GLUD2, OGDH, ACAT2, SDHA, PGP, G6PD, IDH3G, SDHC, PHGDH, IDH2, PCCB, PRPS2, MDH1, FH, PRPS1 |
| GO:0006103~2-oxoglutarate metabolic process | 4 | DLST, IDH3G, IDH2, OGDH |
| Enrichment Score: 1.1310275733652524 | | |
| hsa05212:Pancreatic cancer | 16 | E2F3, RALBP1, RELA, RAF1, SMAD3, BAD, RALGDS, MAPK1, KRAS, ARAF, RAC1, RALB, MAPK8, PIK3R1, CHUK, AKT2 |
| h_rasPathway:Ras Signaling Pathway | 8 | RALBP1, RELA, RAC1, RAF1, BAD, PIK3R1, CHUK, RALGDS |
| h_raccycdPathway:Influence of Ras and Rho proteins on G1 to S Transition | 8 | MAPK1, CDKN1B, RELA, RAC1, RAF1, PIK3R1, CHUK, CDK2 |
| h_aktPathway:AKT Signaling Pathway | 4 | RELA, BAD, PIK3R1, CHUK |
| Enrichment Score: 1.1043180593977402 | | |
| zinc finger region:C4-type | 16 | ARFGAP2, TRIP4, AGFG2, GTF2H3, ASAP1, POLR2B, RPA1, BRPF1, SMAP1, ASH2L, ACAP1, MLLT10, ACAP2, MLLT6, ARAP2, REV3L |
| domain:Arf-GAP | 7 | ARFGAP2, SMAP1, AGFG2, ACAP1, ACAP2, ASAP1, ARAP2 |
| SM00105:ArfGap | 7 | ARFGAP2, SMAP1, AGFG2, ACAP1, ACAP2, ASAP1, ARAP2 |
| IPR001164:Arf GTPase activating protein | 7 | ARFGAP2, SMAP1, AGFG2, ACAP1, ACAP2, ASAP1, ARAP2 |
| Enrichment Score: 1.0984383664834843 | | |
| GO:0060334~regulation of interferon-gamma-mediated signaling pathway | 6 | SOCS3, SOCS1, IFNG, JAK2, PIAS1, IFNGR2 |
| h_tidPathway:Chaperones modulate interferon Signaling Pathway | 6 | TNFRSF1A, RELA, IFNG, HSPA1A, JAK2, IFNGR2 |
| h_ifngPathway:IFN gamma signaling pathway | 3 | IFNG, JAK2, IFNGR2 |
| Enrichment Score: 1.0873412249855727 | | |
| GO:0001844~protein insertion into mitochondrial membrane involved in apoptotic signaling pathway | 4 | MOAP1, BBC3, BAD, BCL2L11 |
| GO:2001244~positive regulation of intrinsic apoptotic signaling pathway | 8 | FIS1, BBC3, BCL2, PRKRA, BAD, BCL2L11, PLAGL2, BCAP31 |
| short sequence motif:BH3 | 5 | MCL1, BBC3, BCL2, BAD, BCL2L11 |
| GO:1900740~positive regulation of protein insertion into mitochondrial membrane involved in apoptotic signaling pathway | 7 | BBC3, BCL2, CASP8, MAPK8, GZMB, BAD, BCL2L11 |
| Enrichment Score: 1.0840410197958643 | | |
| TPR repeat | 29 | MAU2, UTY, FKBP5, FEM1B, FEM1A, STUB1, FIS1, FICD, KLC1, VPS13A, RANBP2, GTF3C3, TTC31, TTC14, WDTC1, ZC3H7A, ZC3H7B, TTC37, CDC23, NAA25, CLUH, CDC27, SGTB, TTC17, CTR9, IFIT3, RPAP3, IFIT5, EMC2 |

TABLE 3-continued

HIV- low cutoff

| Category | Count | Genes |
|---|---|---|
| IPR011990:Tetratricopeptide-like helical | 37 | CRNKL1, MAU2, FKBP5, UTY, NAPA, HELZ, TRRAP, CLTC, SART3, STUB1, FEM1A, XAB2, FIS1, FICD, KLC1, PSMD3, RANBP2, GTF3C3, TTC31, TTC14, WDTC1, ZC3H7A, ZC3H7B, SMG5, TTC37, NAA25, CDC23, CLUH, VPS41, TTC17, CDC27, SGTB, CTR9, IFIT3, RPAP3, IFIT5, EMC2 |
| IPR013026:Tetratricopeptide repeat-containing domain | 24 | TTC31, TTC14, WDTC1, CRNKL1, ZC3H7B, UTY, FKBP5, TTC37, NAA25, CDC23, CDC27, TTC17, XAB2, SGTB, STUB1, CTR9, IFIT3, RPAP3, FICD, KLC1, IFIT5, EMC2, RANBP2, GTF3C3 |
| SM00028:TPR | 22 | TTC31, TTC14, WDTC1, MAU2, ZC3H7B, UTY, FKBP5, TTC37, CDC23, CDC27, TTC17, STUB1, XAB2, SGTB, CTR9, IFIT3, RPAP3, KLC1, IFIT5, EMC2, RANBP2, GTF3C3 |
| repeat:TPR 1 | 26 | MAU2, FKBP5, UTY, STUB1, FEM1A, FICD, KLC1, VPS13A, GTF3C3, TTC31, WDTC1, TTC14, ZC3H7A, ZC3H7B, TTC37, CDC23, NAA25, CLUH, SGTB, TTC17, CDC27, CTR9, RPAP3, IFIT3, IFIT5, EMC2 |
| repeat:TPR 2 | 26 | MAU2, FKBP5, UTY, STUB1, FEM1A, FICD, KLC1, VPS13A, GTF3C3, TTC31, WDTC1, TTC14, ZC3H7A, ZC3H7B, TTC37, CDC23, NAA25, CLUH, SGTB, TTC17, CDC27, CTR9, RPAP3, IFIT3, IFIT5, EMC2 |
| IPR019734:Tetratricopeptide repeat | 23 | TTC31, TTC14, WDTC1, MAU2, ZC3H7B, UTY, FKBP5, TTC37, CDC23, CDC27, TTC17, STUB1, XAB2, SGTB, CTR9, IFIT3, RPAP3, FICD, KLC1, IFIT5, EMC2, RANBP2 |
| repeat:TPR 4 | 17 | TTC14, MAU2, UTY, TTC37, CDC23, NAA25, CLUH, CDC27, SGTB, TTC17, CTR9, IFIT3, RPAP3, KLC1, IFIT5, VPS13A, GTF3C3 |
| repeat:TPR 3 | 23 | TTC31, TTC14, ZC3H7A, MAU2, ZC3H7B, UTY, FKBP5, TTC37, NAA25, CDC23, CLUH, CDC27, TTC17, SGTB, STUB1, CTR9, IFIT3, RPAP3, KLC1, IFIT5, VPS13A, EMC2, GTF3C3 |
| repeat:TPR 6 | 12 | RPAP3, IFIT3, UTY, KLC1, IFIT5, TTC37, CDC23, VPS13A, CDC27, TTC17, GTF3C3, CTR9 |
| repeat:TPR 8 | 9 | IFIT3, UTY, IFIT5, TTC37, CDC23, VPS13A, CDC27, GTF3C3, CTR9 |
| repeat:TPR 7 | 10 | RPAP3, IFIT3, UTY, IFIT5, TTC37, CDC23, VPS13A, CDC27, GTF3C3, CTR9 |
| repeat:TPR 5 | 12 | RPAP3, IFIT3, UTY, KLC1, IFIT5, TTC37, CDC23, VPS13A, CDC27, TTC17, GTF3C3, CTR9 |
| repeat:TPR 9 | 6 | TTC37, CDC23, VPS13A, CDC27, GTF3C3, CTR9 |
| repeat:TPR 10 | 4 | TTC37, VPS13A, GTF3C3, CTR9 |
| repeat:TPR 11 Enrichment Score: 1.0812045401748829 | 3 | TTC37, GTF3C3, CTR9 |
| GO:0051287~NAD binding | 11 | CTBP1, ME2, IDH3G, PHGDH, IDH2, AHCYL1, GRHPR, GLYR1, HIBADH, ALDH9A1, MDH1 |
| nucleotide phosphate-binding region:NAD | 15 | CTBP1, ME2, SIRT6, SIRT7, HIBADH, ALDH3A2, SIRT2, DHRS7, IDH3G, PHGDH, OXNAD1, GLYR1, ALDH9A1, MDH1, HSD17B8 |
| binding site:NAD Enrichment Score: 1.0596664654758672 | 6 | CTBP1, ME2, PHGDH, GLYR1, HIBADH, MDH1 |
| GO:0032481~positive regulation of type I interferon production | 13 | IRAK1, POLR3F, POLR3H, ZC3HAV1, RELA, CREBBP, PTPN22, POLR3GL, POLR3C, POLR3E, STAT6, EP300, IRF3 |
| hsa00240:Pyrimidine metabolism | 21 | DCTD, POLR3F, POLR3H, NT5C3A, POLR1E, POLR1A, UPP1, DCK, POLR3GL, POLR3C, PNP, POLR2B, POLR3E, NME3, POLE3, RRM1, ENTPD6, TXNRD1, UCK1, TWISTNB, NT5C |
| hsa03020:RNA polymerase | 9 | POLR3F, POLR3H, POLR1E, POLR1A, POLR3GL, TWISTNB, POLR3C, POLR2B, POLR3E |
| GO:0006383~transcription from RNA polymerase III promoter | 9 | POLR3F, POLR3H, BRF1, TBP, IVNS1ABP, POLR3C, GTF3C1, POLR3E, GTF3C3 |
| DNA-directed RNA polymerase | 8 | POLR3F, POLR3H, POLR1E, POLR1A, TWISTNB, POLR3C, POLR2B, POLR3E |
| hsa04623:Cytosolic DNA-sensing pathway | 12 | POLR3F, POLR3H, RELA, NFKBIB, RIPK1, PYCARD, POLR3GL, IRF3, POLR3C, CCL4, CHUK, POLR3E |
| GO:0006359~regulation of transcription from RNA polymerase III promoter | 4 | POLR3F, BRF2, POLR3GL, POLR3C |
| GO:0003899~DNA-directed RNA polymerase activity | 8 | POLR3F, POLR3H, POLR1E, POLR1A, TWISTNB, POLR3C, POLR2B, POLR3E |
| GO:0001056~RNA polymerase III activity | 5 | POLR3F, POLR3H, POLR3GL, POLR3C, POLR3E |

TABLE 3-continued

| Category | Count | Genes |
|---|---|---|
| HIV- low cutoff | | |
| GO:0005666~DNA-directed RNA polymerase III complex | 5 | POLR3F, POLR3H, POLR3GL, POLR3C, POLR3E |
| GO:0001054~RNA polymerase I activity | 3 | POLR1E, POLR1A, TWISTNB |
| GO:0005736~DNA-directed RNA polymerase I complex | 3 | POLR1E, POLR1A, TWISTNB |
| Enrichment Score: 1.0231268518510328 | | |
| GO:0051536~iron-sulfur cluster binding | 7 | NFU1, TYW1, RSAD2, CDK5RAP1, CIAPIN1, NDUFS1, PPAT |
| Iron-sulfur | 13 | GLRX5, TYW1, NDUFV2, IREB2, RSAD2, LIAS, UQCRFS1, CDK5RAP1, CIAPIN1, NDUFS1, PPAT, GLRX2, REV3L |
| IPR007197:Radical SAM | 4 | TYW1, RSAD2, LIAS, CDK5RAP1 |
| 4Fe—4S | 8 | TYW1, IREB2, RSAD2, LIAS, CDK5RAP1, NDUFS1, PPAT, REV3L |
| GO:0051539~4 iron, 4 sulfur cluster binding | 9 | NFU1, TYW1, IREB2, RSAD2, LIAS, CDK5RAP1, NDUFS1, PPAT, REV3L |
| metal ion-binding site:Iron-sulfur (4Fe—4S—S-AdoMet) | 3 | TYW1, RSAD2, CDK5RAP1 |
| SM00729:Elp3 | 3 | RSAD2, LIAS, CDK5RAP1 |
| IPR006638:Elongator protein 3/MiaB/NifB | 3 | RSAD2, LIAS, CDK5RAP1 |
| metal ion-binding site:Iron-sulfur (4Fe—4S) | 3 | IREB2, CDK5RAP1, PPAT |
| Enrichment Score: 1.0174059112189755 | | |
| SM00800:uDENN | 5 | DENND5A, SBF1, MADD, DENND4B, DENND2D |
| SM00799:DENN | 5 | DENND5A, SBF1, MADD, DENND4B, DENND2D |
| SM00801:dDENN | 5 | DENND5A, SBF1, MADD, DENND4B, DENND2D |
| IPR005113:uDENN domain | 5 | DENND5A, SBF1, MADD, DENND4B, DENND2D |
| IPR001194:DENN domain | 5 | DENND5A, SBF1, MADD, DENND4B, DENND2D |
| IPR005112:dDENN domain | 5 | DENND5A, SBF1, MADD, DENND4B, DENND2D |
| domain:uDENN | 5 | DENND5A, SBF1, MADD, DENND4B, DENND2D |
| domain:DENN | 5 | DENND5A, SBF1, MADD, DENND4B, DENND2D |
| domain:dDENN | 5 | DENND5A, SBF1, MADD, DENND4B, DENND2D |
| GO:0017112~Rab guanyl-nucleotide exchange factor activity | 7 | RAB3GAP2, DENND5A, SBF1, MADD, TRAPPC4, DENND4B, DENND2D |
| Enrichment Score: 1.013340358660417 | | |
| SM00809:Alpha_adaptinC2 | 4 | AP1G1, AP2A1, GGA1, GGA3 |
| IPR008152:Clathrin adaptor, alpha/beta/gamma-adaptin, appendage, Ig-like subdomain | 4 | AP1G1, AP2A1, GGA1, GGA3 |
| domain:GAE | 3 | AP1G1, GGA1, GGA3 |
| GO:0030131~clathrin adaptor complex | 5 | AP3M2, AP1G1, AP3M1, GGA1, GGA3 |
| IPR008153:Clathrin adaptor, gamma-adaptin, appendage | 3 | AP1G1, GGA1, GGA3 |
| IPR013041:Coatomer/clathrin adaptor appendage, Ig-like subdomain | 4 | AP1G1, AP2A1, GGA1, GGA3 |

TABLE 3-continued

| | HIV- low cutoff | |
|---|---|---|
| Category | Count | Genes |
| Enrichment Score: 0.997471155798655 | | |
| domain:CUE | 4 | N4BP2, ASCC2, AMFR, TAB3 |
| IPR003892:Ubiquitin system component Cue | 4 | N4BP2, ASCC2, AMFR, TAB3 |
| SM00546:CUE | 3 | ASCC2, AMFR, TAB3 |
| Enrichment Score: 0.9788942570619484 | | |
| GO:0035267~NuA4 histone acetyltransferase complex | 6 | ING3, ACTL6A, TRRAP, KAT5, MRGBP, BRD8 |
| GO:0000812~Swr1 complex | 4 | ING3, TRRAP, KAT5, BRD8 |
| GO:0043967~histone H4 acetylation | 7 | ING3, NCOA1, EP300, ACTL6A, USP22, TRRAP, BRD8 |
| GO:0043968~histone H2A acetylation | 4 | ING3, ACTL6A, TRRAP, BRD8 |
| Enrichment Score: 0.9757250476428545 | | |
| IPR005225:Small GTP-binding protein domain | 34 | RAB5B, RAB5C, ARF6, MTIF2, GFM2, ARL5A, KRAS, GFM1, RAC1, RALB, RAB11B, SAR1B, RHOF, ARL2, RAP2C, EFTUD2, DRG1, DRG2, RAB33A, RAB33B, ARL3, NRAS, RAB30, RAB18, RAB35, ARF4, RHOT1, RAB5A, RHOT2, RIT1, ARL8B, ARL4C, NKIRAS2, ARL4A |
| GO:0019003~GDP binding | 13 | RAP2C, RAB5B, RAB5C, RRAGC, ARL3, KRAS, RAB18, RAB35, RALB, RAB11B, RAB5A, ARL8B, PRPS1 |
| IPR001806:Small GTPase superfamily | 19 | RAP2C, RAB5B, RAB5C, RAB33A, RAB33B, NRAS, RAB30, KRAS, RAB18, RAB35, RAC1, RALB, RAB11B, RHOT1, RAB5A, RHOT2, RIT1, RHOF, NKIRAS2 |
| short sequence motif:Effector region | 14 | RAP2C, RAB5B, RAB5C, NRAS, RAB30, KRAS, RAB18, RAB35, RAC1, RAB11B, RAB5A, RALB, RHOF, NKIRAS2 |
| Prenylation | 21 | PHKA2, RAP2C, RAB5B, RAB5C, LMNB2, BROX, MIEN1, RAB33A, RAB33B, NRAS, RAB30, KRAS, RAB18, PEX19, RAB35, RAC1, RALB, RAB11B, RAB5A, YKT6, RHOF |
| lipid moiety-binding region:S-geranylgeranyl cysteine | 13 | RAP2C, RAB30, RAB18, RAB5B, RAB5C, RAB35, RAC1, RALB, RAB5A, RAB11B, RHOF, RAB33A, RAB33B |
| propeptide:Removed in mature form | 13 | PSMB10, NRAS, CD55, RAP2C, KRAS, RAB30, RAB18, TPP1, CD59, RAC1, RALB, RAB11B, RHOF |
| Enrichment Score: 0.9749120956358032 | | |
| GO:0005777~peroxisome | 20 | MVD, IDE, KIAA0430, MPV17, AKAP11, SZT2, PEX3, PMVK, ALDH3A2, ACBD5, FAR1, MFF, FIS1, PNPLA8, GBF1, PEX19, PEX16, IDH2, GNPAT, SCP2 |
| GO:0016557~peroxisome membrane biogenesis | 3 | PEX19, PEX16, PEX3 |
| Peroxisome biogenesis | 4 | PEX19, PEX2, PEX16, PEX3 |
| Peroxisome | 16 | ECI2, KIAA0430, SZT2, PEX3, PMVK, ACBD5, FAR1, MFF, FIS1, PEX19, PEX2, PEX16, GNPAT, ACSL4, ACSL3, SCP2 |
| GO:0005778~peroxisomal membrane | 11 | FAR1, PNPLA8, PEX19, PEX2, PEX16, GNPAT, PEX3, ACSL4, ACSL3, ALDH3A2, ACBD5 |
| Zellweger syndrome | 4 | PEX19, PEX2, PEX16, PEX3 |
| GO:0045046~protein import into peroxisome membrane | 3 | PEX19, PEX16, PEX3 |
| GO:0007031~peroxisome organization | 5 | PEX19, PEX2, PEX16, PEX3, SCP2 |
| hsa04146:Peroxisome | 14 | ECI2, MPV17, PEX3, PMVK, FAR1, PEX19, PEX2, PEX16, IDH2, GNPAT, ACSL4, ACSL3, SCP2, ACSL5 |
| GO:0005779~integral component of peroxisomal membrane | 4 | FIS1, PEX2, PEX16, PEX3 |
| Peroxisome biogenesis disorder | 4 | PEX19, PEX2, PEX16, PEX3 |

TABLE 3-continued

HIV- low cutoff

| Category | Count | Genes |
|---|---|---|
| Enrichment Score: 0.9705769247177995 | | |
| SM00571:DDT | 3 | BPTF, BAZ2B, BAZ2A |
| IPR018501:DDT domain superfamily | 3 | BPTF, BAZ2B, BAZ2A |
| domain:DDT | 3 | BPTF, BAZ2B, BAZ2A |
| Enrichment Score: 0.9586769438708357 | | |
| GO:0043015~gamma-tubulin binding | 7 | OFD1, TUBGCP5, CEP57, PDE4B, B9D2, MZT1, TUBGCP2 |
| GO:0000923~equatorial microtubule organizing center | 3 | TUBGCP5, MZT1, TUBGCP2 |
| GO:0051415~interphase microtubule nucleation by interphase microtubule organizing center | 3 | TUBGCP5, MZT1, TUBGCP2 |
| Enrichment Score: 0.9480710390828481 | | |
| compositionally biased region:Ala/Asp-rich (DA-box) | 4 | SMC5, SMC6, RAD50, SMC4 |
| region of interest:Flexible hinge | 3 | SMC5, SMC6, SMC4 |
| IPR003395:RecF/RecN/SMC | 3 | SMC5, SMC6, SMC4 |
| Enrichment Score: 0.9463520308175999 | | |
| SM00592:BRK | 4 | CHD9, CHD7, CHD6, SMARCA2 |
| IPR006576:BRK domain | 4 | CHD9, CHD7, CHD6, SMARCA2 |
| IPR000330:SNF2-related | 8 | CHD9, BTAF1, CHD7, CHD1L, INO80, CHD6, SMARCA2, TTF2 |
| IPR016197:Chromo domain-like | 7 | CHD9, CHD7, ARID4A, CBX1, KAT5, CHD6, CBX7 |
| SM00298:CHROMO | 7 | CHD9, CHD7, ARID4A, CBX1, KAT5, CHD6, CBX7 |
| IPR000953:Chromo domain/shadow | 7 | CHD9, CHD7, ARID4A, CBX1, KAT5, CHD6, CBX7 |
| domain:Chromo 1 | 4 | CHD9, CHD7, CBX1, CHD6 |
| domain:Chromo 2 | 3 | CHD9, CHD7, CHD6 |
| short sequence motif:DEAH box | 7 | CHD9, CHD7, CHD1L, DHX29, DHX16, CHD6, TTF2 |
| IPR023780:Chromo domain | 5 | CHD9, CHD7, CBX1, CHD6, CBX7 |
| Enrichment Score: 0.9456837667749796 | | |
| domain:PCI | 7 | PSMD13, PSMD12, PCID2, COPS7A, PSMD3, COPS7B, COPS8 |
| Signalosome | 4 | COPS7A, COPS7B, COPS8, TESPA1 |
| GO:0010388~cullin deneddylation | 3 | COPS7A, COPS7B, COPS8 |
| GO:0008180~COP9 signalosome | 5 | WDR6, COPS7A, COPS7B, COPS8, TESPA1 |
| Enrichment Score: 0.9432970300617087 | | |
| GO:0003950~NAD + ADP-ribosyltransferase activity | 7 | ZC3HAV1, PARP12, PARP8, PARP11, SIRT6, PARP4, SIRT2 |
| domain:PARP catalytic | 5 | ZC3HAV1, PARP12, PARP8, PARP11, PARP4 |
| IPR012317:Poly(ADP-ribose) polymerase, catalytic domain | 5 | ZC3HAV1, PARP12, PARP8, PARP11, PARP4 |
| IPR004170:WWE domain | 4 | ZC3HAV1, PARP12, PARP11, RNF146 |

TABLE 3-continued

HIV- low cutoff

| Category | Count | Genes |
|---|---|---|
| Enrichment Score: 0.916012864240317 | | |
| active site:Schiff-base intermediate with DNA | 3 | NEIL2, POLB, OGG1 |
| GO:0006284~base-excision repair | 8 | RPA1, XPA, MPG, NEIL2, USP47, SIRT6, POLB, OGG1 |
| hsa03410:Base excision repair | 7 | MPG, POLE3, NEIL2, MBD4, POLB, PARP4, OGG1 |
| Enrichment Score: 0.9063741277695219 | | |
| Protein biosynthesis | 25 | FARS2, HBS1L, WARS2, MTIF2, TCEAL4, GFM2, EIF4EBP2, GFM1, EIF2B4, EIF2B5, EIF4ENIF1, BRF1, EIF1B, MRRF, EIF2B1, EIF4G3, TRNAU1AP, EIF4E, DHX29, TSFM, EEF1E1, FARSB, YARS2, EIF5A2, MTFMT |
| Initiation factor | 11 | EIF4ENIF1, EIF4G3, EIF4EBP2, EIF4E, BRF1, DHX29, EIF1B, MTIF2, EIF2B1, EIF2B4, EIF2B5 |
| GO:0003743~translation initiation factor activity | 12 | EIF4ENIF1, EIF4G3, EIF4EBP2, EIF4E, BRF1, DHX29, AGO2, EIF1B, MTIF2, EIF2B1, EIF2B4, EIF2B5 |
| GO:0006413~translational initiation | 10 | RPL17, EIF4G3, EIF4E, DHX29, AGO2, EIF1B, EIF2B1, MTFMT, EIF2B4, EIF2B5 |
| Enrichment Score: 0.9057102063061746 | | |
| IPR014721:Ribosomal protein S5 domain 2-type fold, subgroup | 7 | GFM2, LONP1, MRPS9, MVD, GFM1, EFTUD2, TOP2B |
| GO:0032790~ribosome disassembly | 4 | GFM2, HBS1L, MTIF2, MRRF |
| SM00889:SM00889 | 3 | GFM2, GFM1, EFTUD2 |
| IPR005517:Translation elongation factor EFG/EF2, domain IV | 3 | GFM2, GFM1, EFTUD2 |
| SM00838:SM00838 | 3 | GFM2, GFM1, EFTUD2 |
| IPR000640:Translation elongation factor EFG, V domain | 3 | GFM2, GFM1, EFTUD2 |
| IPR009022:Elongation factor G, III-V domain | 3 | GFM2, GFM1, EFTUD2 |
| IPR000795:Elongation factor, GTP-binding domain | 5 | GFM2, GFM1, EFTUD2, HBS1L, MTIF2 |
| GO:0003746~translation elongation factor activity | 7 | GFM2, TSFM, EEF1E1, GFM1, HBS1L, EIF5A2, TCEAL4 |
| Elongation factor | 6 | GFM2, TSFM, GFM1, HBS1L, EIF5A2, TCEAL4 |
| IPR004161:Translation elongation factor EFTu/EF1A, domain 2 | 4 | GFM2, GFM1, EFTUD2, HBS1L |
| IPR009000:Translation elongation/initiation factor/Ribosomal, beta-barrel | 5 | GFM2, GFM1, EFTUD2, HBS1L, MTIF2 |
| Enrichment Score: 0.9035692912975634 | | |
| GO:0070652~HAUS complex | 4 | HAUS3, HAUS6, HAUS2, HAUS1 |
| GO:0051297~centrosome organization | 7 | ARL2, HAUS3, HAUS6, CEP120, BNIP2, HAUS2, HAUS1 |
| GO:0051225~spindle assembly | 6 | HAUS3, HAUS6, CSNK1D, HAUS2, HAUS1, INO80 |
| Enrichment Score: 0.9019097275135531 | | |
| GO:0090630~activation of GTPase activity | 19 | TBC1D10C, RABGAP1, RALGAPB, RABGAP1L, PIP5K1A, TBC1D22B, TBC1D15, RALGAPA1, NDEL1, TSC1, RCC2, SGSM2, TIAM1, SIPA1L1, TBC1D13, TBC1D4, TBC1D1, AKT2, TBC1D9B |
| GO:0031338~regulation of vesicle fusion | 10 | TBC1D15, RABGAP1, TBC1D10C, SGSM2, TBC1D13, TBC1D4, RABGAP1L, TBC1D1, TBC1D22B, TBC1D9B |

TABLE 3-continued

HIV- low cutoff

| Category | Count | Genes |
|---|---|---|
| domain:Rab-GAP TBC | 10 | TBC1D15, RABGAP1, TBC1D10C, SGSM2, TBC1D13, TBC1D4, RABGAP1L, TBC1D1, TBC1D22B, TBC1D9B |
| GO:0017137~Rab GTPase binding | 22 | RAB3GAP2, DENND5A, TBC1D10C, RABGAP1, AP1G1, RABGAP1L, OPTN, TBC1D22B, ANXA2, TBC1D15, UNC13D, PDE6D, SGSM2, AP3M1, TBC1D13, RAC1, ACAP2, TBC1D4, SYTL3, EHD1, TBC1D1, TBC1D9B |
| GO:0012505~endomembrane system | 19 | RABGAP1, TBC1D10C, TBC1D22B, BCL2L11, RTN3, TBC1D15, DOCK2, CHMP1A, SGSM2, PGRMC1, PGRMC2, TBC1D13, TBC1D4, RNF167, NSMAF, TBC1D1, NENF, CDC42EP3, TBC1D9B |
| SM00164:TBC | 10 | TBC1D15, RABGAP1, TBC1D10C, SGSM2, TBC1D13, TBC1D4, RABGAP1L, TBC1D1, TBC1D22B, TBC1D9B |
| IPR000195:Rab-GTPase-TBC domain | 10 | TBC1D15, RABGAP1, TBC1D10C, SGSM2, TBC1D13, TBC1D4, RABGAP1L, TBC1D1, TBC1D22B, TBC1D9B |
| GO:1902017~regulation of cilium assembly | 7 | TBC1D15, RABGAP1, TBC1D10C, TBC1D13, TBC1D1, TBC1D22B, TBC1D9B |
| domain:PID | 4 | ANKS1A, RABGAP1, RABGAP1L, TBC1D1 |
| SM00462:PTB | 5 | ANKS1A, RABGAP1, TBC1D4, RABGAP1L, TBC1D1 |
| IPR006020:Phosphotyrosine interaction domain | 5 | ANKS1A, RABGAP1, TBC1D4, RABGAP1L, TBC1D1 |
| Enrichment Score: 0.8869149577293349 | | |
| SM00717:SANT | 11 | TADA2A, DMTF1, MTA2, EZH1, MYB, TRERF1, NCOR2, RERE, TERF2, ELMSAN1, TERF1 |
| IPR001005:SANT/Myb domain | 11 | TADA2A, DMTF1, MTA2, EZH1, MYB, TRERF1, NCOR2, RERE, TERF2, ELMSAN1, TERF1 |
| IPR017930:Myb domain | 4 | DMTF1, MYB, TERF2, TERF1 |
| GO:0000118~histone deacetylase complex | 8 | TBL1XR1, MTA2, TBL1X, TRERF1, NCOR2, RERE, NRIP1, ELMSAN1 |
| domain:SANT | 5 | TADA2A, MTA2, TRERF1, RERE, ELMSAN1 |
| IPR017884:SANT domain | 6 | TADA2A, MTA2, TRERF1, NCOR2, RERE, ELMSAN1 |
| domain:ELM2 | 4 | MTA2, TRERF1, RERE, ELMSAN1 |
| SM01189:SM01189 | 4 | MTA2, TRERF1, RERE, ELMSAN1 |
| IPR000949:ELM2 domain | 4 | MTA2, TRERF1, RERE, ELMSAN1 |
| domain:HTH myb-type | 3 | DMTF1, TERF2, TERF1 |
| DNA-binding region:H-T-H motif | 4 | DMTF1, MYB, TERF2, TERF1 |
| IPR009057:Homeodomain-like | 20 | RABGAP1, POGZ, TADA2A, MTA2, ZHX1, CERS6, CERS4, ZEB1, TRERF1, CASP8AP2, POGK, CERS2, DMTF1, HOPX, MYB, NCOR2, TERF2, RERE, ELMSAN1, TERF1 |
| Enrichment Score: 0.8828129877584019 | | |
| GO:0070979~protein K11-linked ubiquitination | 8 | UBE2D4, UBE2A, RNF4, ANAPC4, UBE2W, CDC23, ANAPC10, CDC27 |
| GO:0051439~regulation of ubiquitin-protein ligase activity involved in mitotic cell cycle | 6 | ANAPC4, CDC23, ANAPC10, CDC27, CDK2, UBE2E1 |
| GO:0005680~anaphase-promoting complex | 5 | CACUL1, ANAPC4, CDC23, ANAPC10, CDC27 |
| GO:0030071~regulation of mitotic metaphase/anaphase transition | 3 | ANAPC4, CDC23, ANAPC10 |
| Enrichment Score: 0.8760120979730552 | | |
| domain:Cytochrome b5 heme-binding | 5 | PGRMC1, PGRMC2, CYB5A, HERC2, NENF |
| SM01117:SM01117 | 5 | PGRMC1, PGRMC2, CYB5A, HERC2, NENF |
| IPR001199:Cytochrome b5-like heme/steroid binding domain | 5 | PGRMC1, PGRMC2, CYB5A, HERC2, NENF |

TABLE 3-continued

HIV- low cutoff

| Category | Count | Genes |
|---|---|---|
| GO:0020037~heme binding<br>Enrichment Score: 0.8696720280102501 | 5 | PGRMC1, SDHC, PGRMC2, CYB5A, JAK2 |
| domain:EH | 3 | SYNRG, EHD1, EHD4 |
| SM00027:EH | 4 | SYNRG, REPS1, EHD1, EHD4 |
| IPR000261:EPS15 homology (EH) | 4 | SYNRG, REPS1, EHD1, EHD4 |
| domain:EF-hand<br>Enrichment Score: 0.859210233084765 | 7 | GNPTAB, REPS1, STIM1, EHD1, ZZEF1, EHD4, TBC1D9B |
| GO:0045862~positive regulation of proteolysis | 6 | EP300, CASP8, FADD, BAD, FBXW11, CLN6 |
| 46.P13K_PTEN | 6 | TNFRSF1A, CASP7, BCL2, CASP8, FADD, BAD |
| GO:0097202~activation of cysteine-type endopeptidase activity | 4 | CASP8, PYCARD, FADD, BAD |
| 86.Apoptosis_Nematode&_Vert<br>Enrichment Score: 0.8578437407621964 | 4 | BCL2, CASP8, FADD, BAD |
| IPR020850:GTPase effector domain, GED | 4 | DNM3, CREBZF, MX1, MX2 |
| IPR022812:Dynamin | 5 | DNM3, MX1, EHD1, MX2, EHD4 |
| SM00302:GED | 3 | DNM3, MX1, MX2 |
| IPR019762:Dynamin, GTPase region, conserved site | 3 | DNM3, MX1, MX2 |
| IPR000375:Dynamin central domain | 3 | DNM3, MX1, MX2 |
| domain:GED | 3 | DNM3, MX1, MX2 |
| SM00053:DYNc | 3 | DNM3, MX1, MX2 |
| IPR003130:Dynamin GTPase effector | 3 | DNM3, MX1, MX2 |
| IPR001401:Dynamin, GTPase domain<br>Enrichment Score: 0.85187387805759 | 3 | DNM3, MX1, MX2 |
| GO:0000422~mitophagy | 11 | ATG2B, GABARAPL2, FIS1, ATG4B, RB1CC1, BNIP3, WIPI2, PPARGC1A, WDR45B, WDR45, MARK2 |
| GO:0034045~pre-autophagosomal structure membrane | 5 | ATG2B, RB1CC1, WIPI2, WDR45B, WDR45 |
| GO:0044804~nucleophagy | 5 | ATG2B, ATG4B, WIPI2, WDR45B, WDR45 |
| GO:0034497~protein localization to pre-autophagosomal structure | 4 | STX17, WIPI2, WDR45B, WDR45 |
| GO:0080025~phosphatidylinositol-3,5-bisphosphate binding | 5 | GBF1, COMMD1, WIPI2, WDR45B, WDR45 |
| GO:0000045~autophagosome assembly | 7 | ATG2B, GABARAPL2, ATG4B, RB1CC1, WIPI2, WDR45B, WDR45 |
| GO:0006497~protein lipidation | 3 | WIPI2, WDR45B, WDR45 |
| GO:0032266~phosphatidylinositol-3-phosphate binding<br>Enrichment Score: 0.842501378699483 | 5 | SNX19, WIPI2, SNX13, WDR45B, WDR45 |
| GO:0061158~3'-UTR-mediated mRNA destabilization | 5 | ZFP36, ZFP36L2, KHSRP, QKI, ZC3H12D |
| GO:0017091~AU-rich element binding | 5 | ZFP36, ZFP36L2, EXOSC7, TIA1, ELAVL1 |
| GO:0035925~mRNA 3'-UTR AU-rich region binding | 4 | ZFP36, ZFP36L2, KHSRP, ELAVL1 |

TABLE 3-continued

HIV- low cutoff

| Category | Count | Genes |
|---|---|---|
| GO:0006402~mRNA catabolic process | 5 | DIS3, ZFP36, ZFP36L2, DCP2, KHSRP |
| GO:0003730~mRNA 3'-UTR binding | 7 | ZFP36, ZFP36L2, TARDBP, FMR1, KHSRP, PUM1, ELAVL1 |
| Enrichment Score: 0.8299126897208382 | | |
| IPR000980:SH2 domain | 21 | VAV3, SOCS3, SOCS1, CBL, VAV1, STAT6, NCK2, SH2D3C, SH2D2A, CBLB, SH2D3A, CRKL, RINL, ZAP70, JAK2, INPP5D, GRAP2, ABL2, RASA1, PIK3R1, MATK |
| SM00252:SH2 | 18 | VAV3, SOCS3, SOCS1, VAV1, STAT6, NCK2, SH2D3C, SH2D2A, SH2D3A, CRKL, ZAP70, JAK2, INPP5D, GRAP2, ABL2, RASA1, PIK3R1, MATK |
| SH2 domain | 18 | VAV3, SOCS3, SOCS1, VAV1, STAT6, NCK2, SH2D3C, SH2D2A, SH2D3A, CRKL, ZAP70, JAK2, INPP5D, GRAP2, ABL2, RASA1, PIK3R1, MATK |
| GO:0005070~SH3/SH2 adaptor activity | 10 | SH2D2A, NCK2, SH2D3C, SH3BGRL, VAV3, CRKL, SH2D3A, LASP1, STAM, GRAP2 |
| domain:SH2 | 14 | VAV3, SOCS3, SOCS1, VAV1, STAT6, SH2D3C, SH2D2A, NCK2, SH2D3A, CRKL, INPP5D, GRAP2, ABL2, MATK |
| domain:SH3 1 | 5 | NCK2, VAV3, CRKL, GRAP2, VAV1 |
| domain:SH3 2 | 5 | NCK2, VAV3, CRKL, GRAP2, VAV1 |
| Enrichment Score: 0.8204630664582663 | | |
| GO:0050072~m7G(5')pppN diphosphatase activity | 5 | NUDT1, NUDT4, DCP2, NUDT5, NUDT16L1 |
| domain:Nudix hydrolase | 6 | NUDT1, NUDT4, DCP2, NUDT9, NUDT22, NUDT5 |
| IPR020084:NUDIX hydrolase, conserved site | 4 | NUDT1, NUDT4, DCP2, NUDT5 |
| IPR000086:NUDIX hydrolase domain | 6 | NUDT1, NUDT4, DCP2, NUDT9, NUDT22, NUDT5 |
| GO:0034656~nucleobase-containing small molecule catabolic process | 3 | NUDT1, NUDT9, NUDT5 |
| IPR015797:NUDIX hydrolase domain-like | 6 | NUDT1, NUDT4, DCP2, NUDT9, NUDT5, NUDT16L1 |
| short sequence motif:Nudix box | 5 | NUDT1, NUDT4, DCP2, NUDT9, NUDT5 |
| GO:0030515~snoRNA binding | 5 | NUDT1, NUDT4, NUDT5, NUDT16L1, PWP2 |
| Enrichment Score: 0.8167271376205175 | | |
| zinc finger region:MYM-type 2 | 3 | ZMYM2, ZMYM4, ZMYM5 |
| zinc finger region:MYM-type 3 | 3 | ZMYM2, ZMYM4, ZMYM5 |
| zinc finger region:MYM-type 1 | 3 | ZMYM2, ZMYM4, ZMYM5 |
| zinc finger region:MYM-type 4 | 3 | ZMYM2, ZMYM4, ZMYM5 |
| IPR010507:Zinc finger, MYM-type | 3 | ZMYM2, ZMYM4, ZMYM5 |
| SM00746:TRASH | 3 | ZMYM2, ZMYM4, ZMYM5 |
| IPR011017:TRASH domain | 3 | ZMYM2, ZMYM4, ZMYM5 |
| Enrichment Score: 0.8116396013515808 | | |
| repeat:HAT 6 | 4 | CRNKL1, SFI1, SART3, XAB2 |
| repeat:HAT 5 | 4 | CRNKL1, SFI1, SART3, XAB2 |
| repeat:HAT 8 | 3 | CRNKL1, SART3, XAB2 |
| repeat:HAT 4 | 4 | CRNKL1, SFI1, SART3, XAB2 |
| repeat:HAT 2 | 4 | CRNKL1, SFI1, SART3, XAB2 |
| repeat:HAT 1 | 4 | CRNKL1, SFI1, SART3, XAB2 |
| repeat:HAT 3 | 4 | CRNKL1, SFI1, SART3, XAB2 |
| repeat:HAT 7 | 3 | CRNKL1, SART3, XAB2 |
| SM00386:HAT | 3 | CRNKL1, SART3, XAB2 |
| IPR003107:RNA-processing protein, HAT helix | 3 | CRNKL1, SART3, XAB2 |

TABLE 3-continued

HIV- low cutoff

| Category | Count | Genes |
|---|---|---|
| Enrichment Score: 0.8053738526498081 | | |
| GO:0005655~nucleolar ribonuclease P complex | 4 | RPP38, POP4, POP5, POP7 |
| GO:0004526~ribonuclease P activity | 4 | RPP38, POP4, POP5, POP7 |
| GO:0001682~tRNA 5'-leader removal | 4 | RPP38, POP4, POP5, POP7 |
| hsa03008:Ribosome biogenesis in eukaryotes | 10 | RPP38, REXO1, GNL3L, NAT10, POP4, POP5, SPATA5, RBM28, POP7, PWP2 |
| Enrichment Score: 0.8035933138094512 | | |
| GO:0004722~protein serine/threonine phosphatase activity | 12 | MTMR14, RPAP2, PPP2CB, PPP3CB, DUSP23, PPM1A, MTMR6, PPP1R15B, UBLCP1, PTEN, PPP1CB, PPP2R2D |
| Protein phosphatase | 20 | PTPN7, PTPRE, PTPRA, STYX, DUSP23, PPM1A, DUSP22, PTPN22, DUSP12, PPP1CB, PTEN, DUSP4, DUSP28, PGP, RPAP2, PPP2CB, DUSP16, PPP3CB, CTDSP1, UBLCP1 |
| GO:0006470~protein dephosphorylation | 16 | PTPN7, PTPRE, STYX, PPM1A, DUSP22, PTPN22, PPP1CB, PTEN, SBF1, BCL2, PPP2CB, PPP3CB, CTDSP1, UBLCP1, MTMR6, FBXW11 |
| Enrichment Score: 0.8010857129206969 | | |
| GO:0034450~ubiquitin-ubiquitin ligase activity | 5 | PRPF19, PELI1, UBE4A, AMFR, STUB1 |
| domain:U-box | 3 | PRPF19, UBE4A, STUB1 |
| SM00504:Ubox | 3 | PRPF19, UBE4A, STUB1 |
| IPR003613:U box domain | 3 | PRPF19, UBE4A, STUB1 |
| Enrichment Score: 0.7901368844841442 | | |
| GO:0005868~cytoplasmic dynein complex | 8 | DYNC1LI2, DYNLT3, SNX4, DYNLT1, DYNC1H1, DYNLRB1, BCL2L11, DYNC1I2 |
| Dynein | 6 | DYNC1LI2, DYNLT3, DYNLT1, DYNC1H1, DYNLRB1, DYNC1I2 |
| GO:0007018~microtubule-based movement | 9 | KIF3B, DYNC1LI2, SNX29, AP2A1, KLC1, DYNC1H1, DYNLRB1, DYNC1I2, ACTR10 |
| GO:0003777~microtubule motor activity | 7 | KIF3B, DYNC1LI2, SNX29, KLC1, DYNC1H1, DYNLRB1, DYNC1I2 |
| Motor protein | 11 | DNM3, KIF3B, DYNC1LI2, KLC1, MYO1G, DYNLT3, MYO9B, DYNLT1, DYNC1H1, DYNLRB1, DYNC1I2 |
| Enrichment Score: 0.7810728163809908 | | |
| domain:Leucine-zipper | 23 | E2F3, BACH2, E2F4, CREBZF, CREB1, TSN, MED13L, FOXP3, SREBF2, ATF6, ATF5, FOS, TSC22D3, TCF20, JUN, MLLT10, NFE2L2, MLLT6, MYB, NFE2L3, TCF3, CHUK, API5 |
| IPR004827:Basic-leucine zipper domain | 10 | CREBRF, ATF6, ATF5, FOS, BACH2, CREBZF, JUN, CREB1, NFE2L2, NFE2L3 |
| IPR008917:Eukaryotic transcription factor, Skn-1-like, DNA-binding | 4 | BACH2, JUN, NFE2L2, NFE2L3 |
| SM00338:BRLZ | 8 | ATF6, ATF5, FOS, BACH2, JUN, CREB1, NFE2L2, NFE2L3 |
| IPR004826:Basic leucine zipper domain, Maf-type | 3 | BACH2, NFE2L2, NFE2L3 |
| DNA-binding region:Basic motif | 16 | BACH2, CREBZF, CREB1, MXI1, MXD4, SREBF2, ATF6, ATF5, FOS, NCOA1, NCOA2, HES4, JUN, NFE2L2, NFE2L3, TCF3 |
| Enrichment Score: 0.7790223053007594 | | |
| IPR018503:Tetraspanin, conserved site | 6 | CD37, TSPAN5, CD81, CD63, CD151, TSPAN17 |
| PIRSF002419:tetraspanin | 7 | CD37, TSPAN31, TSPAN5, CD81, CD63, CD151, TSPAN17 |
| IPR000301:Tetraspanin | 7 | CD37, TSPAN31, TSPAN5, CD81, CD63, CD151, TSPAN17 |
| IPR018499:Tetraspanin/Peripherin | 7 | CD37, TSPAN31, TSPAN5, CD81, CD63, CD151, TSPAN17 |

TABLE 3-continued

| | HIV- low cutoff | |
|---|---|---|
| Category | Count | Genes |
| IPR008952:Tetraspanin, EC2 domain | 6 | CD37, TSPAN5, CD81, CD63, CD151, TSPAN17 |
| 73.Integrins__and__other__cell-surface__receptors Enrichment Score: 0.7789647933825644 | 4 | CD37, CD81, CD63, CD151 |
| Steroid biosynthesis | 9 | HSD17B11, EBP, MSMO1, MVD, HINT2, HMGCS1, PRKAA1, PMVK, HSD17B8 |
| Sterol biosynthesis | 6 | EBP, MSMO1, MVD, HMGCS1, PRKAA1, PMVK |
| Cholesterol biosynthesis | 5 | EBP, MVD, HMGCS1, PRKAA1, PMVK |
| Cholesterol metabolism | 10 | SOAT1, EBP, APOL1, NPC2, INSIG2, MVD, HMGCS1, PRKAA1, PMVK, SREBF2 |
| GO:0006695~cholesterol biosynthetic process | 8 | EBP, MSMO1, G6PD, INSIG2, MVD, HMGCS1, PRKAA1, PMVK |
| Sterol metabolism | 11 | SOAT1, EBP, APOL1, MSMO1, NPC2, INSIG2, MVD, HMGCS1, PRKAA1, PMVK, SREBF2 |
| hsa00900:Terpenoid backbone biosynthesis | 5 | NUS1, MVD, HMGCS1, PMVK, ACAT2 |
| Steroid metabolism | 11 | SOAT1, EBP, APOL1, MSMO1, NPC2, INSIG2, MVD, HMGCS1, PRKAA1, PMVK, SREBF2 |
| GO:0008203~cholesterol metabolic process Enrichment Score: 0.7599731845015745 | 9 | STARD3, SOAT1, APOL2, EBP, APOL1, NPC2, INSIG2, CLN6, SREBF2 |
| zinc finger region:UBR-type | 3 | UBR7, UBR2, FBXO11 |
| SM00396:ZnF_UBR1 | 3 | UBR7, UBR2, FBXO11 |
| IPR003126:Zinc finger, N-recognin Enrichment Score: 0.7582256458667048 | 3 | UBR7, UBR2, FBXO11 |
| GO:0008654~phospholipid biosynthetic process | 11 | CDIPT, CRLS1, PGS1, DGKE, LPGAT1, SERINC1, HEXB, MBOAT1, PCYT1A, PIP5K1A, PTDSS1 |
| Phospholipid metabolism | 9 | CDIPT, CRLS1, PGS1, LPGAT1, SERINC1, MBOAT1, ABHD3, PCYT1A, PTDSS1 |
| GO:0016780~phosphotransferase activity, for other substituted phosphate groups | 3 | CDIPT, CRLS1, PGS1 |
| Phospholipid biosynthesis | 8 | CDIPT, CRLS1, PGS1, LPGAT1, SERINC1, MBOAT1, PCYT1A, PTDSS1 |
| GO:0047144~2-acylglycerol-3-phosphate O-acyltransferase activity | 3 | CRLS1, LPGAT1, MBOAT1 |
| hsa00564:Glycerophospholipid metabolism | 13 | PLD3, CDIPT, CRLS1, PGS1, DGKE, LPGAT1, MBOAT1, DGKZ, GNPAT, DGKH, PCYT1A, PTDSS1, LPIN1 |
| GO:0003841~1-acylglycerol-3-phosphate O-acyltransferase activity Enrichment Score: 0.7529768935912621 | 3 | CRLS1, LPGAT1, MBOAT1 |
| GO:0000123~histone acetyltransferase complex | 7 | ING4, ELP2, EP300, KANSL1, WDR5, CREBBP, TRRAP |
| GO:0043984~histone H4—K16 acetylation | 6 | MSL2, ING4, KANSL1, KMT2A, MSL1, WDR5 |
| GO:0043981~histone H4—K5 acetylation | 3 | ING4, KANSL1, WDR5 |
| GO:0043982~histone H4—K8 acetylation | 3 | ING4, KANSL1, WDR5 |

TABLE 3-continued

HIV- low cutoff

| Category | Count | Genes |
|---|---|---|
| Enrichment Score: 0.7505920508733883 | | |
| GO:0000724~double-strand break repair via homologous recombination | 14 | RAD51C, HUS1, SMC5, INO80, SMC6, RAD50, ATM, WDR48, RPA1, RECQL, NABP1, NSMCE1, RNF138, NSMCE2 |
| GO:0000722~telomere maintenance via recombination | 7 | RPA1, RAD51C, RFC2, SMC5, NSMCE2, SMC6, RAD50 |
| DNA recombination | 11 | RPA1, RAD51C, NSMCE1, SMC5, INO80, NSMCE2, SMC6, ACTL6A, INO80D, INO80C, INO80B |
| Enrichment Score: 0.7363395749707299 | | |
| GO:0030422~production of siRNA involved in RNA interference | 3 | PRKRA, DICER1, MRPL44 |
| GO:0031054~pre-miRNA processing | 4 | PRKRA, DICER1, AGO2, MRPL44 |
| IPR014720:Double-stranded RNA-binding-like domain | 6 | CDKN2AIP, PRKRA, DICER1, STAU2, STAU1, MRPL44 |
| Enrichment Score: 0.7343641660048325 | | |
| repeat:HEAT 5 | 8 | BTAF1, EIF4G3, NIPBL, KIAA0368, CAND1, PSME4, TNPO2, TNPO1 |
| repeat:HEAT 3 | 10 | HEATR6, BTAF1, EIF4G3, NIPBL, KIAA0368, TBCD, CAND1, PSME4, TNPO2, TNPO1 |
| repeat:HEAT 4 | 9 | HEATR6, BTAF1, EIF4G3, NIPBL, KIAA0368, CAND1, PSME4, TNPO2, TNPO1 |
| repeat:HEAT 2 | 11 | HEATR6, BTAF1, EIF4G3, NIPBL, KIAA0368, TBCD, CAND1, PSME4, TNPO2, UTP20, TNPO1 |
| repeat:HEAT 1 | 11 | HEATR6, BTAF1, EIF4G3, NIPBL, KIAA0368, TBCD, CAND1, PSME4, TNPO2, UTP20, TNPO1 |
| repeat:HEAT 8 | 5 | BTAF1, KIAA0368, CAND1, TNPO2, TNPO1 |
| repeat:HEAT 6 | 6 | BTAF1, KIAA0368, CAND1, PSME4, TNPO2, TNPO1 |
| repeat:HEAT 7 | 5 | BTAF1, KIAA0368, CAND1, TNPO2, TNPO1 |
| repeat:HEAT 13 | 3 | KIAA0368, CAND1, TNPO2 |
| repeat:HEAT 12 | 3 | KIAA0368, CAND1, TNPO2 |
| repeat:HEAT 11 | 3 | KIAA0368, CAND1, TNPO2 |
| repeat:HEAT 10 | 3 | KIAA0368, CAND1, TNPO2 |
| repeat:HEAT 9 | 3 | KIAA0368, CAND1, TNPO2 |
| Enrichment Score: 0.7306880194943396 | | |
| GO:0070555~response to interleukin-1 | 8 | IRAK1, RELA, IGBP1, CREBBP, ANXA1, PRKCI, RIPK2, LGALS9 |
| GO:0034134~toll-like receptor 2 signaling pathway | 3 | IRAK1, RIPK2, LGALS9 |
| GO:0034142~toll-like receptor 4 signaling pathway | 4 | IRAK1, LY96, RIPK2, LGALS9 |
| Enrichment Score: 0.7265386581976017 | | |
| domain:JmjC | 8 | KDM2A, UTY, JMJD6, JMJD8, KDM4C, JMJD1C, KDM5B, KDM5C |
| IPR003347:JmjC domain | 8 | KDM2A, UTY, JMJD6, JMJD8, KDM4C, JMJD1C, KDM5B, KDM5C |
| SM00558:JmjC | 7 | KDM2A, UTY, JMJD6, KDM4C, JMJD1C, KDM5B, KDM5C |
| GO:0032452~histone demethylase activity | 6 | KDM2A, UTY, JMJD6, KDM4C, KDM5B, KDM5C |
| domain:JmjN | 3 | KDM4C, KDM5B, KDM5C |
| Dioxygenase | 12 | ADI1, ALKBH7, KDM2A, UTY, JMJD6, ETHE1, KDM4C, EGLN1, JMJD1C, KDM5B, ALKBH5, KDM5C |
| SM00545:JmjN | 3 | KDM4C, KDM5B, KDM5C |
| IPR003349:Transcription factor jumonji, JmjN | 3 | KDM4C, KDM5B, KDM5C |
| GO:0051213~dioxygenase activity | 4 | ALKBH7, UTY, KDM4C, JMJD1C |
| metal ion-binding site:Iron; catalytic | 4 | KDM2A, JMJD6, KDM4C, JMJD1C |

TABLE 3-continued

HIV- low cutoff

| Category | Count | Genes |
|---|---|---|
| Enrichment Score: 0.7246856105034599 | | |
| zinc finger region:SP-RING-type | 3 | PIAS4, NSMCE2, PIAS1 |
| IPR004181:Zinc finger, MIZ-type | 3 | PIAS4, NSMCE2, PIAS1 |
| GO:0019789~SUMO transferase activity | 4 | PIAS4, NSMCE2, PIAS1, RANBP2 |
| Enrichment Score: 0.7213724303242848 | | |
| GO:0002223~stimulatory C-type lectin receptor signaling pathway | 21 | PSMB10, RELA, CREBBP, ICAM3, RAF1, MALT1, PRKCD, TAB3, NRAS, PSMD13, PSMC5, EP300, KRAS, PSMD12, PSMC2, PSMD3, PRKACB, PSMD5, PSME4, FBXW11, CHUK |
| GO:0022624~proteasome accessory complex | 6 | PSMD13, PSMC5, PSMD12, PSMC2, PSMD3, PSMD5 |
| GO:0033209~tumor necrosis factor-mediated signaling pathway | 20 | PSMB10, TRAF2, TNFRSF10A, TNFRSF1A, BAG4, TNFRSF9, PSMD13, PSMC5, PSMD12, TNFSF13B, PSMC2, RIPK1, PYCARD, PSMD3, JAK2, PSMD5, PSME4, MAP3K14, CD27, TRAF3 |
| GO:0051436~negative regulation of ubiquitin-protein ligase activity involved in mitotic cell cycle | 13 | PSMB10, ANAPC4, CDC23, ANAPC10, CDC27, CDK2, PSMD13, PSMC5, PSMD12, PSMC2, PSMD3, PSMD5, UBE2E1 |
| GO:0031145~anaphase-promoting complex-dependent catabolic process | 14 | PSMB10, ANAPC4, CDC23, ANAPC10, CDC27, CUL3, PSMD13, PSMC5, PSMD12, PSMC2, PSMD3, PSMD5, PSME4, UBE2E1 |
| GO:0038061~NIK/NF-kappaB signaling | 12 | PSMB10, PSMD13, PSMC5, PSMD12, PSMC2, UBA3, PSMD3, PSME4, PSMD5, MAP3K14, FBXW11, CHUK |
| GO:0000502~proteasome complex | 11 | PSMB10, PSMD13, PSMC5, PSMD12, KIAA0368, ZFAND2A, PSMC2, HSPB1, PSMD3, PSME4, PSMD5 |
| GO:0051437~positive regulation of ubiquitin-protein ligase activity involved in regulation of mitotic cell cycle transition | 13 | PSMB10, ANAPC4, CDC23, ANAPC10, CDC27, PSMD13, PSMC5, PSMD12, PSMC2, PSMD3, PSMD5, PSME4, UBE2E1 |
| GO:0008541~proteasome regulatory particle, lid subcomplex | 3 | PSMD13, PSMD12, PSMD3 |
| GO:0031595~nuclear proteasome complex | 3 | PSMC5, PSMD12, PSMC2 |
| GO:0006521~regulation of cellular amino acid metabolic process | 9 | PSMB10, PSMD13, PSMC5, PSMD12, PSMC2, PSMD3, AZIN1, PSME4, PSMD5 |
| hsa03050:Proteasome | 8 | PSMB10, PSMD13, PSMC5, PSMD12, PSMC2, IFNG, PSMD3, PSME4 |
| Proteasome | 8 | PSMB10, PSMD13, PSMC5, PSMD12, KIAA0368, PSMC2, PSMD3, PSME4 |
| GO:0060071~Wnt signaling pathway, planar cell polarity pathway | 13 | PSMB10, PSMD13, PSMC5, PSMD12, TIAM1, AP2A1, PSMC2, RAC1, PSMD3, SMURF2, PSME4, PSMD5, CLTC |
| GO:0008540~proteasome regulatory particle, base subcomplex | 3 | PSMC5, PSMC2, PSMD5 |
| GO:0090263~positive regulation of canonical Wnt signaling pathway | 16 | PSMB10, RNF220, XIAP, PSMD13, PSMC5, PSMD12, CSNK1D, CSNK1E, PSMC2, ILK, PSMD3, SMURF2, PSMD5, PSME4, USP34, RNF146 |

TABLE 3-continued

| HIV- low cutoff | | |
|---|---|---|
| Category | Count | Genes |
| GO:0002479~antigen processing and presentation of exogenous peptide antigen via MHC class I, TAP-dependent | 8 | PSMB10, PSMD13, PSMC5, PSMD12, PSMC2, PSMD3, PSME4, PSMD5 |
| GO:0090090~negative regulation of canonical Wnt signaling pathway Enrichment Score: 0.7193769298441833 | 17 | CSNK1A1, PSMB10, EGR1, RGS19, LATS1, CUL3, PSMD13, PSMC5, PSMD12, GSK3B, PSMC2, KIAA0922, PSMD3, PSMD5, PSME4, RAPGEF1, APC |
| domain:UBX | 4 | UBXN2A, UBXN2B, FAF2, FAF1 |
| IPR001012:UBX | 4 | UBXN2A, UBXN2B, FAF2, FAF1 |
| SM00166:UBX Enrichment Score: 0.7013692853684937 | 3 | UBXN2A, UBXN2B, FAF1 |
| GO:0004843~thiol-dependent ubiquitin-specific protease activity | 15 | STAMBP, OTUD5, USP3, USP5, USP4, BAP1, USP47, USP36, UCHL3, USP22, USP34, USP16, USP15, USP42, VCPIP1 |
| Thiol protease | 23 | CAPN7, OTUD5, USP40, USPL1, USP3, USP5, USP4, BAP1, CTSL, ATG4B, CASP7, CASP8, USP47, USP36, CTSC, UCHL3, USP22, USP34, USP16, USP24, USP15, USP42, VCPIP1 |
| IPR018200:Peptidase C19, ubiquitin carboxyl-terminal hydrolase 2, conserved site | 12 | USP40, USP3, USP5, USP4, USP47, USP36, USP22, USP16, USP34, USP24, USP42, USP15 |
| GO:0016579~protein deubiquitination | 15 | STAMBP, OTUD5, USP40, USP3, USP5, USP4, BAP1, WDR48, UCHL3, USP36, USP22, USP34, USP24, USP15, USP42 |
| IPR001394:Peptidase C19, ubiquitin carboxyl-terminal hydrolase 2 | 12 | USP40, USP3, USP5, USP4, USP47, USP36, USP22, USP16, USP34, USP24, USP42, USP15 |
| GO:0036459~thiol-dependent ubiquitinyl hydrolase activity Enrichment Score: 0.694228209931004 | 9 | USP40, USP3, USP4, USP36, USP22, USP34, USP24, USP42, USP15 |
| Glucose metabolism | 5 | G6PD, PDK3, PGM1, DCXR, AKT2 |
| Carbohydrate metabolism | 14 | PHKA2, GNPDA2, PDK3, PPP1CB, GALM, PGP, G6PD, GSK3B, PGM1, POFUT1, DCXR, YDJC, AKT2, PYGB |
| GO:0006006~glucose metabolic process Enrichment Score: 0.6913577368544611 | 11 | GALM, WDTC1, G6PD, GNPDA2, PDK3, PGM1, HECTD4, PRKAA1, OAS1, DCXR, AKT2 |
| zinc finger region:Phorbol-ester/DAG-type 2 | 7 | DGKE, DGKZ, PRKCH, DGKH, PRKCD, PRKD3, PRKCB |
| zinc finger region:Phorbol-ester/DAG-type 1 | 7 | DGKE, DGKZ, PRKCH, DGKH, PRKCD, PRKD3, PRKCB |
| SM00046:DAGKc | 4 | DGKE, DGKZ, DGKH, CERK |
| domain:DAGKc | 4 | DGKE, DGKZ, DGKH, CERK |
| IPR001206:Diacylglycerol kinase, catalytic domain | 4 | DGKE, DGKZ, DGKH, CERK |
| IPR016064:ATP-NAD kinase-like domain | 4 | DGKE, DGKZ, DGKH, CERK |
| SM00045:DAGKa | 3 | DGKE, DGKZ, DGKH |
| IPR000756:Diacylglycerol kinase, accessory domain | 3 | DGKE, DGKZ, DGKH |
| hsa00561:Glycerolipid metabolism | 9 | DGKE, GLA, AKR1B1, MBOAT1, DGKZ, DGKH, LPIN1, ALDH3A2, ALDH9A1 |
| GO:0004143~diacylglycerol kinase activity | 3 | DGKE, DGKZ, DGKH |

TABLE 3-continued

HIV- low cutoff

| Category | Count | Genes |
|---|---|---|
| GO:0046834~lipid phosphorylation | 3 | DGKE, DGKZ, CERK |
| GO:0007205~protein kinase C-activating G-protein coupled receptor signaling pathway Enrichment Score: 0.6727450347449508 | 5 | DGKE, DGKZ, DGKH, PRKD3, IL2 |
| domain:Exonuclease | 4 | AEN, REXO1, ERI3, ISG20L2 |
| Exonuclease | 9 | DIS3, EXOSC10, RAD1, CNOT8, CNOT6L, AEN, REXO1, ERI3, ISG20L2 |
| SM00479:EXOIII | 4 | AEN, REXO1, ERI3, ISG20L2 |
| IPR013520:Exonuclease, RNase T/DNA polymerase III | 4 | AEN, REXO1, ERI3, ISG20L2 |
| IPR012337:Ribonuclease H-like domain | 12 | EXOSC10, TEFM, CNOT8, KIAA1586, ZBED5, AEN, REXO1, AGO2, RNASEH1, ERI3, ISG20L2, REV3L |
| GO:0004527~exonuclease activity Enrichment Score: 0.6697712403636995 | 3 | AEN, REXO1, ERI3 |
| domain:BRCT 2 | 4 | MDC1, TP53BP1, MCPH1, BARD1 |
| domain:BRCT 1 | 4 | MDC1, TP53BP1, MCPH1, BARD1 |
| SM00292:BRCT | 4 | TP53BP1, MCPH1, PARP4, BARD1 |
| IPR001357:BRCT domain Enrichment Score: 0.667787729765459 | 5 | MDC1, TP53BP1, MCPH1, PARP4, BARD1 |
| GO:0031146~SCF-dependent proteasomal ubiquitin-dependent protein catabolic process | 6 | FBXW7, FBXW5, FBXO6, FBXL5, FBXL15, FBXW11 |
| GO:0019005~SCF ubiquitin ligase complex | 9 | FBXW7, FBXW5, FBXO6, USP47, FBXL5, FBXO25, FBXL15, FBXW11, SPOP |
| SM00256:FBOX | 7 | FBXW7, FBXW5, FBXO6, FBXL5, FBXW2, FBXW11, FBXO11 |
| domain:F-box | 11 | FBXW7, KDM2A, FBXW5, FBXO6, FBXL5, FBXO25, FBXW2, FBXO34, FBXL15, FBXW11, FBXO11 |
| IPR001810:F-box domain, cyclin-like Enrichment Score: 0.6636972705479839 | 11 | FBXW7, KDM2A, FBXW5, FBXO6, FBXL5, FBXO25, FBXW2, FBXO34, FBXL15, FBXW11, FBXO11 |
| GO:1904354~negative regulation of telomere capping | 3 | TERF2, ATM, RAD50 |
| Telomere | 8 | NSMCE1, SMC5, NSMCE2, SMC6, TINF2, TERF2, RAD50, TERF1 |
| GO:0003691~double-stranded telomeric DNA binding | 3 | TERF2, RAD50, TERF1 |
| GO:0007004~telomere maintenance via telomerase | 4 | TERF2, ATM, RAD50, TERF1 |
| GO:0000723~telomere maintenance Enrichment Score: 0.6493097279002905 | 6 | RPA1, HSPA1A, TERF2, ATM, RAD50, TERF1 |
| domain:Deacetylase sirtuin-type | 3 | SIRT6, SIRT7, SIRT2 |
| IPR003000:Sirtuin family | 3 | SIRT6, SIRT7, SIRT2 |
| IPR026590:Sirtuin family, catalytic core domain | 3 | SIRT6, SIRT7, SIRT2 |
| GO:0070403~NAD + binding | 3 | SIRT6, SIRT7, SIRT2 |

TABLE 3-continued

HIV- low cutoff

| Category | Count | Genes |
|---|---|---|
| Enrichment Score: 0.633804002670718 | | |
| domain:PI3K/PI4K | 5 | PIK3C2A, PI4K2B, TRRAP, PI4KB, ATM |
| IPR000403:Phosphatidylinositol 3-/4- kinase, catalytic domain | 5 | PIK3C2A, PI4K2B, TRRAP, PI4KB, ATM |
| SM00146:PI3Kc | 4 | PIK3C2A, TRRAP, PI4KB, ATM |
| IPR018936:Phosphatidylinositol 3/4- kinase, conserved site | 3 | PIK3C2A, PI4KB, ATM |
| Enrichment Score: 0.6336349362349432 | | |
| SM00147:RasGEF | 7 | SH2D3C, SH2D3A, SOS1, RAPGEF6, RGL4, RAPGEF1, RALGDS |
| IPR023578:Ras guanine nucleotide exchange factor, domain | 7 | SH2D3C, SH2D3A, SOS1, RAPGEF6, RGL4, RAPGEF1, RALGDS |
| IPR001895:Guanine-nucleotide dissociation stimulator CDC25 | 7 | SH2D3C, SH2D3A, SOS1, RAPGEF6, RGL4, RAPGEF1, RALGDS |
| domain:Ras-GEF | 6 | SH2D3C, SOS1, RAPGEF6, RGL4, RAPGEF1, RALGDS |
| SM00229:RasGEFN | 4 | SOS1, RAPGEF6, RAPGEF1, RALGDS |
| domain:N-terminal Ras-GEF | 4 | SOS1, RAPGEF6, RAPGEF1, RALGDS |
| IPR000651:Ras-like guanine nucleotide exchange factor, N-terminal | 4 | SOS1, RAPGEF6, RAPGEF1, RALGDS |
| IPR019804:Ras guanine-nucleotide exchange factor, conserved site | 3 | SOS1, RAPGEF1, RALGDS |
| Enrichment Score: 0.6315415331478075 | | |
| GO:0005086~ARF guanyl-nucleotide exchange factor activity | 6 | NCK2, GBF1, ARF4, PSD4, CYTH2, ARFGEF2 |
| h_arapPathway:ADP-Ribosylation Factor | 6 | COPA, GBF1, ASAP1, CYTH2, ARFGEF2, ARAP2 |
| IPR023394:SEC7-like, alpha orthogonal bundle | 4 | GBF1, PSD4, CYTH2, ARFGEF2 |
| SM00222:Sec7 | 4 | GBF1, PSD4, CYTH2, ARFGEF2 |
| IPR000904:SEC7-like | 4 | GBF1, PSD4, CYTH2, ARFGEF2 |
| domain:SEC7 | 4 | GBF1, PSD4, CYTH2, ARFGEF2 |
| GO:0032012~regulation of ARF protein signal transduction | 4 | GBF1, PSD4, CYTH2, ARFGEF2 |
| Enrichment Score: 0.6256109532042883 | | |
| repeat:MBT 3 | 3 | MBTD1, L3MBTL2, L3MBTL3 |
| repeat:MBT 2 | 3 | MBTD1, L3MBTL2, L3MBTL3 |
| repeat:MBT 1 | 3 | MBTD1, L3MBTL2, L3MBTL3 |
| SM00561:MBT | 3 | MBTD1, L3MBTL2, L3MBTL3 |
| IPR004092:Mbt repeat | 3 | MBTD1, L3MBTL2, L3MBTL3 |
| Enrichment Score: 0.6246957617788174 | | |
| DNA-binding region:HMG box | 8 | TOX, TCF7, HMGXB4, BBX, HMGXB3, HMG20B, HBP1, TOX4 |
| SM00398:HMG | 9 | TOX, TCF7, HMGXB4, KMT2C, BBX, HMGXB3, HMG20B, HBP1, TOX4 |
| IPR009071:High mobility group (HMG) box domain | 9 | TOX, TCF7, HMGXB4, KMT2C, BBX, HMGXB3, HMG20B, HBP1, TOX4 |

TABLE 3-continued

HIV- low cutoff

| Category | Count | Genes |
|---|---|---|
| Enrichment Score: 0.6234949961410196 | | |
| GO:0031588~nucleotide-activated protein kinase complex | 5 | PRKAR2A, PRKAG2, PRKAB1, PRKAA1, SESN2 |
| hsa04710:Circadian rhythm | 8 | CSNK1D, CSNK1E, CREB1, PRKAG2, PRKAB1, PRKAA1, RORA, FBXW11 |
| GO:0004679~AMP-activated protein kinase activity | 3 | PRKAG2, PRKAB1, PRKAA1 |
| GO:0006633~fatty acid biosynthetic process | 9 | ELOVL1, MSMO1, PRKAG2, PRKAB1, FASN, PRKAA1, ACSL3, PCCB, HSD17B8 |
| h_chrebpPathway:ChREBP regulation by carbohydrates and cAMP | 5 | PRKAR2A, PRKAG2, PRKAB1, PRKAA1, PRKACB |
| h_leptinPathway:Reversal of Insulin Resistance by Leptin | 3 | PRKAG2, PRKAB1, PRKAA1 |
| Fatty acid biosynthesis | 6 | ELOVL1, PRKAG2, PRKAB1, FASN, PRKAA1, HSD17B8 |
| hsa05410:Hypertrophic cardiomyopathy (HCM) | 4 | PRKAG2, PRKAB1, PRKAA1, ITGB1 |
| Enrichment Score: 0.6150311927361685 | | |
| Isomerase | 19 | ECI1, FUOM, ECI2, EBP, FKBP5, TMX3, PDIA4, PIN4, PMM2, PUS7, NKTR, PPIF, GALM, PPIG, PGM1, PPIL4, TOP2B, FKBP11, TRUB2 |
| Cyclosporin | 3 | PPIF, PPIG, NKTR |
| GO:0016018~cyclosporin A binding | 3 | PPIF, PPIG, NKTR |
| Rotamase | 7 | PPIF, PPIG, FKBP5, PPIL4, PIN4, FKBP11, NKTR |
| GO:0000413~protein peptidyl-prolyl isomerization | 8 | PPIF, PPIG, FKBP5, PPIL4, RANBP2, PIN4, FKBP11, NKTR |
| domain:PPIase cyclophilin-type | 5 | PPIF, PPIG, PPIL4, RANBP2, NKTR |
| IPR002130:Cyclophilin-like peptidyl-prolyl cis-trans isomerase domain | 5 | PPIF, PPIG, PPIL4, RANBP2, NKTR |
| GO:0003755~peptidyl-prolyl cis-trans isomerase activity | 8 | PPIF, PPIG, FKBP5, PPIL4, RANBP2, PIN4, FKBP11, NKTR |
| IPR020892:Cyclophilin-type peptidyl-prolyl cis-trans isomerase, conserved site | 4 | PPIF, PPIG, RANBP2, NKTR |
| IPR024936:Cyclophilin-type peptidyl-prolyl cis-trans isomerase | 4 | PPIF, PPIG, PPIL4, NKTR |
| Enrichment Score: 0.6145856221059713 | | |
| SM00666:PB1 | 4 | MAP3K3, NBR1, PRKCI, TFG |
| IPR000270:Phox/Bem1p | 4 | MAP3K3, NBR1, PRKCI, TFG |
| domain:OPR | 3 | MAP3K3, NBR1, PRKCI |
| Enrichment Score: 0.6107555591477245 | | |
| GO:0000159~protein phosphatase type 2A complex | 6 | PPP2R5A, STRN3, PPP2CB, STRN, PPP2R5E, PPP2R2D |
| GO:0008601~protein phosphatase type 2A regulator activity | 4 | PPP2R5A, IGBP1, PPP2R5E, PPP2R2D |
| GO:0034047~regulation of protein phosphatase type 2A activity | 4 | PPP2R5A, IGBP1, PPP2R5E, PPP2R2D |

TABLE 3-continued

| HIV- low cutoff | | |
|---|---|---|
| Category | Count | Genes |
| Enrichment Score: 0.6081273857570164 | | |
| domain:DRBM 3 | 3 | PRKRA, STAU2, STAU1 |
| IPR014720:Double-stranded RNA-binding-like domain | 6 | CDKN2AIP, PRKRA, DICER1, STAU2, STAU1, MRPL44 |
| SM00358:DSRM | 4 | PRKRA, DICER1, STAU2, STAU1 |
| domain:DRBM 2 | 3 | PRKRA, STAU2, STAU1 |
| domain:DRBM 1 | 3 | PRKRA, STAU2, STAU1 |
| Enrichment Score: 0.6034239543605878 | | |
| GO:0070412~R-SMAD binding | 6 | FOS, TRIM33, JUN, PPM1A, SMAD3, LDLRAD4 |
| GO:1902895~positive regulation of pri-miRNA transcription from RNA polymerase II promoter | 5 | FOS, RELA, JUN, SMAD3, SRF |
| GO:0060395~SMAD protein signal transduction | 6 | LNPEP, FOS, JUN, HIPK2, NUP93, SMAD3 |
| Enrichment Score: 0.5981131911799106 | | |
| GO:0008625~extrinsic apoptotic signaling pathway via death domain receptors | 12 | TNFRSF10A, TNFRSF9, TNFRSF1A, MOAP1, CASP8AP2, BCL2, FADD, BAD, DAXX, PIK3R1, DEDD2, CD27 |
| SM00208:TNFR | 4 | TNFRSF10A, TNFRSF9, TNFRSF1A, CD27 |
| repeat:TNFR-Cys 3 | 4 | TNFRSF10A, TNFRSF9, TNFRSF1A, CD27 |
| IPR001368:TNFR/NGFR cysteine-rich region | 4 | TNFRSF10A, TNFRSF9, TNFRSF1A, CD27 |
| GO:0005031~tumor necrosis factor-activated receptor activity | 4 | TNFRSF10A, TNFRSF9, TNFRSF1A, CD27 |
| repeat:TNFR-Cys 2 | 4 | TNFRSF10A, TNFRSF9, TNFRSF1A, CD27 |
| repeat:TNFR-Cys 1 | 4 | TNFRSF10A, TNFRSF9, TNFRSF1A, CD27 |
| Enrichment Score: 0.5972512359197256 | | |
| GO:0006661~phosphatidylinositol biosynthetic process | 12 | CDIPT, SH3YL1, MTMR14, PIK3C2A, INPP5D, PI4K2B, PIP5K1A, PI4KB, MTMR6, PTEN, PIK3R1, SACM1L |
| hsa04070:Phosphatidylinositol signaling system | 17 | CDIPT, PIK3C2A, PPIP5K2, DGKH, PI4K2B, PIP5K1A, PI4KB, PTEN, TMEM55B, PRKCB, ITPR2, MTMR14, DGKE, DGKZ, INPP5D, MTMR6, PIK3R1 |
| hsa00562:Inositol phosphate metabolism | 9 | CDIPT, MTMR14, PIK3C2A, INPP5D, PI4K2B, PIP5K1A, PI4KB, MTMR6, PTEN |
| GO:0046854~phosphatidylinositol phosphorylation | 6 | PIK3C2A, PI4K2B, PIP5K1A, PI4KB, VAV1, PIK3R1 |
| Enrichment Score: 0.5959966330149766 | | |
| IPR011249:Metalloenzyme, LuxS/M16 peptidase-like | 3 | UQCRC1, IDE, PITRM1 |
| IPR011237:Peptidase M16 domain | 3 | UQCRC1, IDE, PITRM1 |
| IPR011765:Peptidase M16, N-terminal | 3 | UQCRC1, IDE, PITRM1 |
| IPR007863:Peptidase M16, C-terminal domain | 3 | UQCRC1, IDE, PITRM1 |
| GO:0004222~metalloendopeptidase activity | 6 | SPG7, UQCRC1, TRABD2A, IDE, PITRM1, NLN |
| Enrichment Score: 0.5695312810104746 | | |
| IPR003903:Ubiquitin interacting motif | 6 | STAM2, ZFAND2B, HGS, DNAJB2, STAM, UIMC1 |

TABLE 3-continued

HIV- low cutoff

| Category | Count | Genes |
| --- | --- | --- |
| SM00726:UIM | 4 | STAM2, ZFAND2B, DNAJB2, UIMC1 |
| repeat:UIM 2 | 3 | ZFAND2B, DNAJB2, UIMC1 |
| repeat:UIM 1 | 3 | ZFAND2B, DNAJB2, UIMC1 |
| Enrichment Score: 0.5600728887088808 | | |
| | | |
| Telomere | 8 | NSMCE1, SMC5, NSMCE2, SMC6, TINF2, TERF2, RAD50, TERF1 |
| GO:0070187~telosome | 3 | TINF2, TERF2, TERF1 |
| GO:0000783~nuclear telomere cap complex | 3 | TINF2, TERF2, TERF1 |
| GO:0016233~telomere capping | 4 | HIST4H4, TINF2, TERF2, TERF1 |
| GO:0042162~telomeric DNA binding | 4 | SMG5, TINF2, TERF2, TERF1 |
| Enrichment Score: 0.5582412750967661 | | |
| | | |
| 2.Cytokine_Receptors | 5 | MAPK1, SOS1, RAF1, VAV1, PIK3R1 |
| h_il2rbPathway:IL-2 Receptor Beta Chain in T cell Activation | 12 | MAPK1, FOS, IL2RB, CRKL, SOCS3, BCL2, SOS1, SOCS1, CBL, RAF1, BAD, PIK3R1 |
| h_ptenPathway:PTEN dependent cell cycle arrest and apoptosis | 7 | MAPK1, CDKN1B, SOS1, ILK, PTEN, ITGB1, PIK3R1 |
| h_cdmacPathway:Cadmium induces DNA synthesis and proliferation in macrophages | 6 | MAPK1, FOS, RELA, JUN, RAF1, PRKCB |
| h_ghPathway:Growth Hormone Signaling Pathway | 8 | MAPK1, SOS1, SOCS1, RAF1, JAK2, SRF, PIK3R1, PRKCB |
| 68.Mitogen_signaling_in_growth_control | 4 | MAPK1, SOS1, MAP3K1, RAF1 |
| h_igf1rPathway:Multiple antiapoptotic pathways from IGF-1R signaling lead to BAD phosphorylation | 7 | MAPK1, PRKAR2A, SOS1, RAF1, PRKACB, BAD, PIK3R1 |
| 82.TCR_and_Cap_or_SMAC | 5 | MAPK1, ZAP70, MAPK8, VAV1, WAS |
| h_ngfPathway:Nerve growth factor pathway (NGF) | 6 | FOS, JUN, SOS1, RAF1, MAPK8, PIK3R1 |
| h_her2Pathway:Role of ERBB2 in Signal Transduction and Oncology | 6 | MAPK1, EP300, IL6ST, SOS1, RAF1, PIK3R1 |
| 54.T-cell_anergy | 6 | MAPK1, SOS1, ZAP70, RAF1, MAPK8, IL2 |
| h_spryPathway:Sprouty regulation of tyrosine kinase signals | 5 | MAPK1, SOS1, CBL, RAF1, RASA1 |
| h_cxcr4Pathway:CXCR4 Signaling Pathway | 6 | MAPK1, CXCR4, RELA, RAF1, PIK3R1, PRKCB |
| 107.mRNA_translation-protein_synthesis | 5 | MAPK1, EIF4E, RAF1, EIF2B1, PIK3R1 |
| 63.LAT_couples_T-cell_receptor | 5 | MAPK1, SOS1, ZAP70, VAV1, PIK3R1 |
| h_ecmPathway:Erk and PI-3 Kinase Are Necessary for Collagen Binding in Corneal Epithelia | 5 | MAPK1, ROCK1, RAF1, ITGB1, PIK3R1 |
| 106.Glycogen_synthase-synthesis | 3 | MAPK1, RAF1, PIK3R1 |
| h_tffPathway:Trefoil Factors Initiate Mucosal Healing | 5 | MAPK1, SOS1, BAD, ITGB1, PIK3R1 |
| h_sppaPathway:Aspirin Blocks Signaling Pathway Involved in Platelet Activation | 4 | MAPK1, RAF1, ITGB1, PRKCB |

TABLE 3-continued

HIV- low cutoff

| Category | Count | Genes |
|---|---|---|
| 105.Signaling_glucose_uptake | 3 | MAPK1, RAF1, PIK3R1 |
| h_erkPathway:Erk1/Erk2 Mapk Signaling pathway | 5 | MAPK1, SOS1, MKNK2, RAF1, ITGB1 |
| h_ccr3Pathway:CCR3 signaling in Eosinophils | 4 | MAPK1, ROCK2, RAF1, PRKCB |
| h_biopeptidesPathway:Bioactive Peptide Induced Signaling Pathway | 6 | MAPK1, SOS1, RAF1, MAPK8, JAK2, PRKCB |
| 104.Insulin_signaling | 4 | MAPK1, SOS1, RAF1, PIK3R1 |
| GO:0014066~regulation of phosphatidylinositol 3-kinase signaling Enrichment Score: 0.5573531878002459 | 5 | MAPK1, C3ORF58, PIP5K1A, VAV1, PIK3R1 |
| zinc finger region:RING-type 2 | 4 | ARIH2, CUL9, MIB2, RNF216 |
| IPR002867:Zinc finger, C6HC-type | 4 | ARIH2, CUL9, RBCK1, RNF216 |
| zinc finger region:IBR-type | 3 | ARIH2, CUL9, RNF216 |
| SM00647:IBR Enrichment Score: 0.5552661855962138 | 3 | ARIH2, CUL9, RNF216 |
| h_crebPathway:Transcription factor CREB and its extracellular signals | 8 | MAPK1, PRKAR2A, CREB1, SOS1, RAC1, PRKACB, PIK3R1, PRKCB |
| h_igf1rPathway:Multiple antiapoptotic pathways from IGF-1R signaling lead to BAD phosphorylation | 7 | MAPK1, PRKAR2A, SOS1, RAF1, PRKACB, BAD, PIK3R1 |
| h_badPathway:Regulation of BAD phosphorylation | 6 | MAPK1, PRKAR2A, BCL2, PRKACB, BAD, PIK3R1 |
| h_mPRPathway:How Progesterone Initiates the Oocyte Maturation Enrichment Score: 0.5494432470362846 | 4 | ARPC1A, MAPK1, PRKAR2A, PRKACB |
| SM00568:GRAM | 4 | SBF1, NSMAF, GRAMD1A, TBC1D9B |
| domain:GRAM | 4 | TSC22D3, SBF1, NSMAF, GRAMD1A |
| IPR004182:GRAM Enrichment Score: 0.547117417296358 | 4 | SBF1, NSMAF, GRAMD1A, TBC1D9B |
| GO:1904885~beta-catenin destruction complex assembly | 3 | CSNK1A1, GSK3B, APC |
| GO:0030877~beta-catenin destruction complex | 4 | CSNK1A1, GSK3B, RGS19, APC |
| h_wntPathway:WNT Signaling Pathway | 6 | CSNK1A1, CTBP1, CSNK1D, GSK3B, CREBBP, APC |
| GO:1904886~beta-catenin destruction complex disassembly Enrichment Score: 0.5364694676464031 | 3 | CSNK1A1, GSK3B, APC |
| IPR013763:Cyclin-like | 9 | CCNT2, BRF1, BRF2, CCNH, CCNT1, CCNG1, CCNG2, GTF2B, CASD1 |
| GO:0000079~regulation of cyclin-dependent protein serine/threonine kinase activity | 8 | CCNT2, CDKN1B, CCNT1, HERC5, CNPPD1, CDK7, CCNG1, PTEN |

TABLE 3-continued

| HIV- low cutoff | | |
|---|---|---|
| Category | Count | Genes |
| SM00385:CYCLIN | 7 | CCNT2, BRF1, CCNH, CCNT1, CCNG1, CCNG2, GTF2B |
| GO:1901409~positive regulation of phosphorylation of RNA polymerase II C-terminal domain | 3 | CCNT2, CCNH, CCNT1 |
| Cyclin | 6 | CCNT2, CDKN1B, CCNH, CCNT1, CCNG1, CCNG2 |
| GO:0016538~cyclin-dependent protein serine/threonine kinase regulator activity | 3 | CCNT2, CCNH, CCNT1 |
| IPR006671:Cyclin, N-terminal | 5 | CCNT2, CCNH, CCNT1, CCNG1, CCNG2 |
| GO:0045737~positive regulation of cyclin-dependent protein serine/threonine kinase activity | 4 | CCNT2, CDKN1B, CCNH, CCNT1 |
| Enrichment Score: 0.5349369033767776 | | |
| IPR016192:APOBEC/CMP deaminase, zinc-binding | 4 | DCTD, APOBEC3G, APOBEC3C, APOBEC3D |
| GO:0010529~negative regulation of transposition | 3 | APOBEC3G, APOBEC3C, APOBEC3D |
| IPR016193:Cytidine deaminase-like | 4 | DCTD, APOBEC3G, APOBEC3C, APOBEC3D |
| IPR002125:CMP/dCMP deaminase, zinc-binding | 4 | DCTD, APOBEC3G, APOBEC3C, APOBEC3D |
| GO:0016814~hydrolase activity, acting on carbon-nitrogen (but not peptide) bonds, in cyclic amidines | 3 | APOBEC3G, APOBEC3C, APOBEC3D |
| IPR013158:APOBEC-like, N-terminal | 3 | APOBEC3G, APOBEC3C, APOBEC3D |
| Enrichment Score: 0.5346599394830712 | | |
| SM00233:PH | 34 | OSBP, ASAP1, CYTH2, ARHGAP15, APBB1IP, TIAM1, SOS1, SNTB1, RTKN2, IPCEF1, DOCK10, RASA1, RASA2, AKT2, DNM3, ARHGEF3, OSBPL3, VAV3, ARHGEF1, ROCK1, ROCK2, PSD4, DGKH, VAV1, PLEKHA3, PLEKHF2, SBF1, DEF6, ACAP1, ACAP2, OSBPL11, ARAP2, PRKD3, PLEKHA1 |
| IPR011993:Pleckstrin homology-like domain | 53 | OSBP, ARHGAP15, TIAM1, NECAP2, SNTB1, NECAP1, MSN, RANBP2, NSMAF, DOCK10, AKT2, ARHGEF3, ANKS1A, ARHGEF1, ROCK1, ROCK2, PSD4, WAS, MTMR12, SBF1, DEF6, ACAP1, FRMD4B, ACAP2, OSBPL11, WASL, PRKD3, RABGAP1, LRBA, ASAP1, RABGAP1L, CYTH2, APBB1IP, SOS1, RTKN2, TBC1D4, IPCEF1, TBC1D1, MTMR6, RASA1, RASA2, DNM3, OSBPL3, VAV3, EVL, DGKH, VAV1, PLEKHA3, PLEKHF2, DCP1A, JAK2, ARAP2, PLEKHA1 |
| domain:PH | 30 | OSBP, ASAP1, CYTH2, ARHGAP15, APBB1IP, SOS1, RTKN2, IPCEF1, DOCK10, RASA1, RASA2, AKT2, DNM3, ARHGEF3, OSBPL3, VAV3, ARHGEF1, ROCK1, ROCK2, PSD4, DGKH, VAV1, PLEKHA3, PLEKHF2, SBF1, DEF6, ACAP1, ACAP2, OSBPL11, PRKD3 |
| IPR001849:Pleckstrin homology domain | 34 | OSBP, ASAP1, CYTH2, ARHGAP15, APBB1IP, TIAM1, SOS1, SNTB1, RTKN2, IPCEF1, DOCK10, RASA1, RASA2, AKT2, DNM3, ARHGEF3, OSBPL3, VAV3, ARHGEF1, ROCK1, ROCK2, PSD4, DGKH, VAV1, PLEKHA3, PLEKHF2, SBF1, DEF6, ACAP1, ACAP2, OSBPL11, ARAP2, PRKD3, PLEKHA1 |
| Enrichment Score: 0.5310103373589384 | | |
| domain:Ubiquitin-like | 9 | DDI2, HERPUD1, UHRF2, UBL4A, RBCK1, TMUB1, UBAC1, UBLCP1, HERPUD2 |
| IPR000626:Ubiquitin | 9 | DDI2, HERPUD1, UHRF2, UBL4A, SACS, RBCK1, TMUB1, UBLCP1, HERPUD2 |
| SM00213:UBQ | 5 | HERPUD1, UHRF2, UBL4A, UBLCP1, HERPUD2 |

TABLE 3-continued

| Category | Count | Genes |
|---|---|---|
| HIV- low cutoff | | |
| Enrichment Score: 0.5255766583646028 | | |
| GO:0004386~helicase activity | 17 | BTAF1, DICER1, ANXA1, HELZ, CHD9, MOV10, CHD7, DDX23, DDX19A, GTF2F2, DHX34, DDX50, DDX10, ERCC3, SMARCA2, DDX51, DDX42 |
| IPR011545:DNA/RNA helicase, DEAD/DEAH box type, N-terminal | 12 | RECQL, DDX23, DHX29, DDX19A, DICER1, DHX34, DDX50, DHX16, SKIV2L2, DDX10, DDX51, DDX42 |
| IPR000629:RNA helicase, ATP-dependent, DEAD-box, conserved site | 5 | DDX23, CETN2, DDX10, DDX51, DDX42 |
| GO:0010501~RNA secondary structure unwinding | 7 | DDX23, DDX19A, DDX50, AGO2, DDX10, DDX51, DDX42 |
| short sequence motif:Q motif | 6 | DDX23, DDX19A, DDX50, DDX10, DDX51, DDX42 |
| GO:0004004~ATP-dependent RNA helicase activity | 9 | DDX23, DHX29, DDX19A, DHX34, DDX50, DHX16, DDX10, DDX51, DDX42 |
| short sequence motif:DEAD box | 5 | DDX23, DDX19A, DDX10, DDX51, DDX42 |
| IPR014014:RNA helicase, DEAD-box type, Q motif | 5 | DDX23, DDX19A, DDX50, DDX10, DDX42 |
| Enrichment Score: 0.5235257150362578 | | |
| IPR003959:ATPase, AAA-type, core | 11 | SPG7, LONP1, ATAD3A, PSMC5, RFC2, PSMC2, WRNIP1, ORC4, VPS4A, SPATA5, SPAST |
| IPR003960:ATPase, AAA-type, conserved site | 5 | PSMC5, PSMC2, VPS4A, SPATA5, SPAST |
| SM00382:AAA | 15 | ABCF3, SPG7, WRNIP1, ABCB7, TOR2A, ATAD3A, LONP1, PSMC5, RFC2, PSMC2, ORC4, VPS4A, DYNC1H1, SPATA5, SPAST |
| IPR003593:AAA+ ATPase domain | 15 | ABCF3, SPG7, WRNIP1, ABCB7, TOR2A, ATAD3A, LONP1, PSMC5, RFC2, PSMC2, ORC4, VPS4A, DYNC1H1, SPATA5, SPAST |
| Enrichment Score: 0.5084367621409388 | | |
| GO:0002230~positive regulation of defense response to virus by host | 20 | TMEM203, TNIK, CRNKL1, PML, PTPN22, MBD5, NUP93, APOBEC3G, PEX3, FXR2, ANXA5, MRPS2, FAM13B, SIN3A, CD93, DNAAF2, RBM18, PYCARD, ALKBH5, MDH1 |
| GO:0098792~xenophagy | 16 | TMEM203, TNIK, CRNKL1, MBD5, NUP93, OPTN, PEX3, ANXA5, FXR2, FAM13B, MRPS2, CD93, DNAAF2, RBM18, ALKBH5, MDH1 |
| GO:0098779~mitophagy in response to mitochondrial depolarization | 15 | TMEM203, CNRKL1, MBD5, NUP93, LARP1B, PEX3, ANXA5, FAM13B, MRPS2, CD93, DNAAF2, BLOC1S1, MEX3C, KRCC1, MDH1 |
| Enrichment Score: 0.505808532604712 | | |
| domain:BAH | 3 | MTA2, ASH1L, RERE |
| SM00439:BAH | 3 | MTA2, ASH1L, RERE |
| IPR001025:Bromo adjacent homology (BAH) domain | 3 | MTA2, ASH1L, RERE |
| Enrichment Score: 0.4971762083345744 | | |
| GO:0019706~protein-cysteine S-palmitoyltransferase activity | 6 | GOLGA7, ZDHHC16, ZDHHC3, ZDHHC8, ZDHHC12, YKT6 |
| zinc finger region:DHHC-type | 5 | ZDHHC16, ZDHHC3, KMT2X, ZDHHC8, ZDHHC12 |
| GO:0016409~palmitoyltransferase activity | 4 | ZDHHC16, ZDHHC3, ZDHHC8, ZDHHC12 |
| IPR001594:Zinc finger, DHHC-type, palmitoyltransferase | 5 | ZDHHC16, ZDHHC3, KMT2C, ZDHHC8, ZDHHC12 |
| GO:0018345~protein palmitoylation | 4 | ZDHHC16, ZDHHC3, ZDHHC8, ZDHHC12 |

TABLE 3-continued

| Category | Count | Genes |
|---|---|---|
| HIV- low cutoff | | |
| Enrichment Score: 0.48722466637005296 | | |
| short sequence motif:TXY | 4 | MAPK1, MAPK6, MAPK13, MAPK8 |
| GO:0004707~MAP kinase activity | 4 | MAPK1, MAPK6, MAPK13, MAPK8 |
| IPR003527:Mitogen-activated protein (MAP) kinase, conserved site | 3 | MAPK1, MAPK13, MAPK8 |
| has04723:Retrograde endocannabinoid signaling | 7 | MAPK1, ADCY7, MAPK13, MAPK8, PRKACB, PRKCB, ITPR2 |
| Enrichment Score: 0.4869638417073476 | | |
| h_cdmacPathway:Cadmium induces DNA synthesis and proliferation in macrophages | 6 | MAPK1, FOS, RELA, JUN, RAF1, PRKCB |
| GO:1902895~positive regulation of pri-miRNA transcription from RNA polymerase II promoter | 5 | FOS, RELA, JUN, SMAD3, SRF |
| GO:0035994~response to muscle stretch | 4 | FOS, RELA, JUN, RAF1 |
| h_cardiacEGFPathway:Role of EGF Receptor Transactivation by GPCRs in Cardiac Hypertrophy | 4 | FOS, RELA, JUN, PRKCB |
| GO:0051591~response to cAMP | 5 | FOS, BSG, RELA, JUN, CDK2 |
| Enrichment Score: 0.48175618712662555 | | |
| GO:0016791~phosphatase activity | 9 | DUSP4, DUSP28, DUSP16, DUSP23, CTDSP1, PTPN22, DUSP12, PPP1CB, SACM1L |
| Protein phosphatase | 20 | PTPN7, PTPRE, PTPRA, STYX, DUSP23, PPM1A, DUSP22, PTPN22, DUSP12, PPP1CB, PTEN, DUSP4, DUSP28, PGP, RPAP2, PPP2CB, DUSP16, PPP3CB, CTDSP1, UBLCP1 |
| SM00195:DSPc | 7 | DUSP4, DUSP28, DUSP16, STYX, DUSP23, DUSP22, DUSP12 |
| IPR000340:Dual specificity phosphatase, catalytic domain | 8 | DUSP4, DUSP28, DUSP16, STYX, DUSP23, DUSP22, DUSP12, PTEN |
| IPR020422:Dual specificity phosphatase, subgroup, catalytic domain | 7 | DUSP4, DUSP28, DUSP16, STYX, DUSP23, DUSP22, DUSP12 |
| GO:0008138~protein tyrosine/serine/threonine phosphatase activity | 7 | DUSP28, SBF1, STYX, DUSP23, DUSP22, DUSP12, PTEN |
| IPR024950:Dual specificity phosphatase | 6 | DUSP4, DUSP28, DUSP16, STYX, DUSP22, DUSP12 |
| active site:Phosphocysteine intermediate | 12 | PTPN7, DUSP4, DUSP28, PTPRE, PTPRA, DUSP16, DUSP23, DUSP22, PTPN22, DUSP12, MTMR6, PTEN |
| domain:Tyrosine-protein phosphatase | 9 | PTPN7, DUSP4, DUSP28, DUSP16, STYX, DUSP23, DUSP22, PTPN22, DUSP12 |
| GO:0035335~peptidyl-tyrosine dephosphorylation | 14 | PTPN7, PTPRE, PTPRA, DUSP23, PTPN22, DUSP22, DUSP12, PTEN, DUSP4, MTMR14, PGP, DUSP28, DUSP16, MTMR6 |
| GO:0004725~protein tyrosine phosphatase activity | 14 | PTPN7, PTPRE, PTPRA, DUSP23, PTPN22, DUSP22, DUSP12, PTEN, DUSP4, MTMR14, PGP, DUSP28, DUSP16, MTMR6 |

TABLE 3-continued

HIV- low cutoff

| Category | Count | Genes |
|---|---|---|
| IPR000387:Protein-tyrosine/Dual specificity phosphatase | 11 | PTPN7, DUSP4, DUSP28, PTPRE, PTPRA, DUSP16, STYX, DUSP23, DUSP22, PTPN22, DUSP12 |
| IPR016130:Protein-tyrosine phosphatase, active site | 10 | PTPN7, DUSP4, MTMR14, PTPRE, PTPRA, DUSP16, DUSP23, PTPN22, MTMR6, PTEN |
| SM00404:PTPc_motif | 8 | PTPN7, DUSP4, PTPRE, PTPRA, DUSP23, PTPN22, MTMR6, PTEN |
| IPR003595:Protein-tyrosine phosphatase, catalytic | 8 | PTPN7, DUSP4, PTPRE, PTPRA, DUSP23, PTPN22, MTMR6, PTEN |
| GO:0000188~inactivation of MAPK activity | 4 | DUSP4, DUSP16, DUSP22, GPS2 |
| SM00194:PTPc | 4 | PTPN7, PTPRE, PTPRA, PTPN22 |
| IPR000242:Protein-tyrosine phosphatase, receptor/non-receptor type | 4 | PTPN7, PTPRE, PTPRA, PTPN22 |
| Enrichment Score: 0.480513926399985 | | |
| IPR001715:Calponin homology domain | 14 | PARVG, VAV3, ACTN4, CEP95, UTRN, IQGAP2, VAV1, FLNA, SYNE2, CAMSAP1, MAPRE2, CNN2, MAPRE1, PLEC |
| domain:CH 2 | 6 | PARVG, SYNE2, ACTN4, UTRN, FLNA, PLEC |
| domain:CH 1 | 6 | PARVG, SYNE2, ACTN4, UTRN, FLNA, PLEC |
| domain:Actin-binding | 5 | SYNE2, ACTN4, UTRN, FLNA, PLEC |
| IPR001589:Actinin-type, actin-binding, conserved site | 5 | SYNE2, ACTN4, UTRN, FLNA, PLEC |
| SM00033:CH | 10 | PARVG, VAV3, SYNE2, ACTN4, UTRN, IQGAP2, CNN2, VAV1, FLNA, PLEC |
| repeat:Spectrin 4 | 4 | SYNE2, ACTN4, UTRN, PLEC |
| repeat:Spectrin 3 | 4 | SYNE2, ACTN4, UTRN, PLEC |
| domain:CH | 6 | VAV3, IQGAP2, MAPRE2, CNN2, MAPRE1, VAV1 |
| repeat:Spectrin 2 | 4 | SYNE2, ACTN4, UTRN, PLEC |
| repeat:Spectrin 1 | 4 | SYNE2, ACTN4, UTRN, PLEC |
| SM00150:SPEC | 4 | SYNE2, ACTN4, UTRN, PLEC |
| IPR018159:Spectrin/alpha-actinin | 4 | SYNE2, ACTN4, UTRN, PLEC |
| IPR002017:Spectrin repeat | 3 | SYNE2, ACTN4, UTRN |
| Enrichment Score: 0.46920356835197363 | | |
| hsa04720:Long-term potentiation | 14 | CREBBP, RAF1, PPP1CB, PRKCB, ITPR2, NRAS, MAPK1, RPS6KA3, EP300, KRAS, CAMK4, ARAF, PPP3CB, PRKACB |
| hsa05223:Non-small cell lung cancer | 12 | MAPK1, NRAS, E2F3, KRAS, RXRB, SOS1, ARAF, RAF1, BAD, PIK3R1, PRKCB, AKT2 |
| hsa05214:Glioma | 11 | MAPK1, NRAS, E2F3, KRAS, SOS1, ARAF, RAF1, PTEN, PIK3R1, PRKCB, AKT2 |
| 65.Integrin_affinity_modulation | 3 | MAPK1, NRAS, KRAS |
| hsa04730:Long-term depression | 9 | GNA13, MAPK1, NRAS, KRAS, PPP2CB, ARAF, RAF1, PRKCB, ITPR2 |
| hsa05218:Melanoma | 10 | MAPK1, NRAS, E2F3, KRAS, ARAF, RAF1, BAD, PTEN, PIK3R1, AKT2 |
| hsa04540:Gap junction | 12 | MAPK1, NRAS, KRAS, CSNK1D, ADCY7, SOS1, RAF1, PRKACB, TUBA1A, TUBA1C, PRKCB, ITPR2 |
| hsa04921:Oxytocin signaling pathway | 20 | ROCK1, ADCY7, ROCK2, PRKAG2, PRKAB1, RAF1, PPP1CB, PRKCB, ITPR2, FOS, NRAS, MAPK1, KRAS, CAMK4, JUN, PPP3CB, PRKAA1, PRKACB, NFATC2, PIK3R1 |
| hsa05219:Bladder cancer | 6 | MAPK1, NRAS, E2F3, KRAS, ARAF, RAF1 |
| hsa04725:Cholinergic synapse | 14 | ADCY7, CREB1, PRKCB, ITPR2, NRAS, MAPK1, FOS, KRAS, CAMK4, BCL2, JAK2, PRKACB, PIK3R1, AKT2 |
| hsa04916:Melanogenesis | 12 | MAPK1, NRAS, TCF7, KRAS, EP300, ADCY7, CREB1, GSK3B, CREBBP, RAF1, PRKACB, PRKCB |
| hsa04726:Serotonergic synapse | 8 | MAPK1, NRAS, KRAS, ARAF, RAF1, PRKACB, PRKCB, ITPR2 |
| hsa05034:Alcoholism | 12 | MAPK1, NRAS, HIST4H4, KRAS, CAMK4, CREB1, SOS1, ARAF, RAF1, H3F3A, PKIA, PPP1CB |

TABLE 3-continued

| Category | Count | Genes |
|---|---|---|
| HIV- low cutoff | | |
| Enrichment Score: 0.4584026793393616 | | |
| domain:DHR-2 | 3 | DOCK2, DOCK8, DOCK10 |
| domain:DHR-1 | 3 | DOCK2, DOCK8, DOCK10 |
| IPR027357:DHR-2 domain | 3 | DOCK2, DOCK8, DOCK10 |
| IPR027007:DHR-1 domain | 3 | DOCK2, DOCK8, DOCK10 |
| IPR026791:Dedicator of cytokinesis | 3 | DOCK2, DOCK8, DOCK10 |
| IPR010703:Dedicator of cytokinesis C-terminal | 3 | DOCK2, DOCK8, DOCK10 |
| Enrichment Score: 0.45728497291694326 | | |
| Nucleotidyltransferase | 13 | POLK, FICD, CMAS, POLE3, POLR1A, OAS1, POLB, PCYT1A, PAPD5, OAS2, ZCCHC6, POLR2B, REV3L |
| DNA-directed DNA polymerase | 5 | POLK, POLE3, POLB, PAPD5, REV3L |
| GO:0003887~DNA-directed DNA polymerase activity | 5 | POLK, POLE3, POLB, PAPD5, REV3L |
| GO:0071897~DNA biosynthetic process | 3 | POLE3, POLB, PAPD5 |
| Enrichment Score: 0.44605748185239036 | | |
| Signal transduction inhibitor | 9 | RGS1, SOCS3, GSK3B, SOCS1, RGS19, SNX13, LDLRAD4, RGS14, SEC14L1 |
| GO:0001965~G-protein alpha-subunit binding | 5 | NUCB1, RGS1, IGF2R, RGS19, RGS14 |
| IPR016137:Regulator of G protein signalling superfamily | 6 | ARHGEF1, RGS1, RGS19, AKAP10, SNX13, RGS14 |
| SM00315:RGS | 5 | RGS1, RGS19, AKAP10, SNX13, RGS14 |
| domain:RGS | 4 | RGS1, RGS19, SNX13, RGS14 |
| IPR024066:Regulator of G-protein signaling, domain 1 | 3 | RGS1, RGS19, RGS14 |
| Enrichment Score: 0.4417241398856797 | | |
| GO:0000729~DNA double-strand break processing | 4 | KAT5, ATM, RAD50, BARD1 |
| GO:0000732~strand displacement | 5 | RAD51C, KAT5, ATM, RAD50, BARD1 |
| GO:0000731~DNA synthesis involved in DNA repair | 6 | RAD51C, WRNIP1, KAT5, ATM, RAD50, BARD1 |
| GO:0007131~reciprocal meiotic recombination | 5 | RAD51C, MSH6, MSH2, ATM, RAD50 |
| Enrichment Score: 0.4412701245717094 | | |
| zinc finger region:CCHC-type 3 | 3 | ZCCHC3, ZCCHC6, ZCCHC7 |
| zinc finger region:CCHC-type 2 | 3 | ZCCHC3, ZCCHC6, ZCCHC7 |
| zinc finger region:CCHC-type 1 | 3 | ZCCHC3, ZCCHC6, ZCCHC7 |
| SM00343:ZnF_C2HC | 4 | ZCCHC3, CPSF4, ZCCHC6, ZCCHC7 |
| IPR001878:Zinc finger, CCHC-type | 5 | ZCCHC3, ZCCHC10, CPSF4, ZCCHC6, ZCCHC7 |
| Enrichment Score: 0.42704739477485376 | | |
| h_crebPathway:Transcription factor CREB and its extracellular signals | 8 | MAPK1, PRKAR2A, CREB1, SOS1, RAC1, PRKACB, PIK3R1, PRKCB |

TABLE 3-continued

HIV- low cutoff

| Category | Count | Genes |
|---|---|---|
| h_agpcrPathway:Attenuation of GPCR Signaling | 3 | PRKAR2A, PRKACB, PRKCB |
| h_nos1Pathway:Nitric Oxide Signaling Pathway | 4 | PRKAR2A, PPP3CB, PRKACB, PRKCB |
| Enrichment Score: 0.42570578914927665 | | |
| h_gpcrPathway:Signaling Pathway from G-Protein Families | 10 | FOS, PRKAR2A, RPS6KA3, JUN, CREB1, PPP3CB, RAF1, PRKACB, NFATC2, PRKCB |
| h_dreamPathway:Repression of Pain Sensation by the Transcriptional Regulator DREAM | 5 | FOS, PRKAR2A, JUN, CREB1, PRKACB |
| hsa05031:Amphetamine addiction | 8 | FOS, CAMK4, JUN, CREB1, PPP3CB, PRKACB, PPP1CB, PRKCB |
| hsa05030:Cocaine addiction | 4 | RELA, JUN, CREB1, PRKACB |
| hsa04713:Circadian entrainment | 6 | MAPK1, FOS, ADCY7, CREB1, PRKACB, PRKCB |
| Enrichment Score: 0.4211948096599511 | | |
| GO:0000132~establishment of mitotic spindle orientation | 6 | NUMA1, NDE1, NDEL1, MCPH1, PAFAH1B1, DYNLT1 |
| GO:2000574~regulation of microtubule motor activity | 3 | NDE1, NDEL1, PAFAH1B1 |
| GO:0047496~vesicle transport along microtubule | 3 | NDE1, NDEL1, PAFAH1B1 |
| GO:0001764~neuron migration | 9 | NDE1, NDEL1, CXCR4, CCR4, GATA3, PAFAH1B1, TOP2B, SRF, MARK2 |
| GO:0005871~kinesin complex | 4 | NDE1, NDEL1, KLC1, PAFAH1B1 |
| Enrichment Score: 0.4188790271143383 | | |
| domain:Ras-associating | 6 | RASSF3, RAPGEF6, MYO9B, APBB1IP, ARAP2, RALGDS |
| SM00314:RA | 5 | RASSF3, RAPGEF6, MYO9B, APBB1IP, RALGDS |
| IPR000159:Ras-association | 6 | RASSF3, RAPGEF6, MYO9B, APBB1IP, ARAP2, RALGDS |
| Enrichment Score: 0.41763318415020556 | | |
| GO:0030148~sphingolipid biosynthetic process | 10 | ELOVL1, SPTLC2, CSNK1G2, VAPB, CERS2, CERS6, SPTSSA, KDSR, CERS4, ALDH3A2 |
| IPR016439:Longevity assurance, LAG1/LAC1 | 3 | CERS2, CERS6, CERS4 |
| PIRSF005225:longevity assurance protein LAG1/LAC1 | 3 | CERS2, CERS6, CERS4 |
| GO:0046513~ceramide biosynthetic process | 6 | SAMD8, SPTLC2, CERS2, CERS6, SPTSSA, CERS4 |
| GO:0050291~sphingosine N-acyltransferase activity | 3 | CERS2, CERS6, CERS4 |
| hsa00600:Sphingolipid metabolism | 8 | SPTLC2, GLA, CERS2, CERS6, KDSR, CERS4, CERK, ASAH1 |
| domain:TLC | 3 | CERS2, CERS6, CERS4 |
| SM00724:TLC | 3 | CERS2, CERS6, CERS4 |
| IPR006634:TRAM/LAG1/CLN8 homology domain | 3 | CERS2, CERS6, CERS4 |
| Homeobox | 8 | HIPK1, CERS2, ZHX1, HIPK2, HOPX, CERS6, CERS4, ZEB1 |
| DNA-binding region:Homeobox | 3 | CERS2, CERS6, CERS4 |

TABLE 3-continued

HIV- low cutoff

| Category | Count | Genes |
| --- | --- | --- |
| IPR001356:Homeodomain | 6 | CERS2, ZHX1, HOPX, CERS6, CERS4, ZEB1 |
| SM00389:HOX | 3 | ZHX1, HOPX, ZEB1 |
| Enrichment Score: 0.41325609345633085 | | |
| IPR023214:HAD-like domain | 15 | NT5C3A, CMAS, ATP11A, CECR5, LPIN1, PMM2, PGP, ATP13A1, ATP2B4, ATP2C1, ATP8B2, CTDSP1, ENOPH1, UBLCP1, NT5C |
| active site:4-aspartylphosphate intermediate | 6 | ATP13A1, ATP2B4, ATP2C1, ATP11A, ATP8B2, CTDSP1 |
| IPR018303:P-type ATPase, phosphorylation site | 5 | ATP13A1, ATP2B4, ATP2C1, ATP11A, ATP8B2 |
| IPR023299:P-type ATPase, cytoplasmic domain N | 5 | ATP13A1, ATP2B4, ATP2C1, ATP11A, ATP8B2 |
| IPR008250:P-type ATPase, A domain | 5 | ATP13A1, ATP2B4, ATP2C1, ATP11A, ATP8B2 |
| IPR001757:Cation-transporting P-type ATPase | 5 | ATP13A1, ATP2B4, ATP2C1, ATP11A, ATP8B2 |
| Enrichment Score: 0.40955924999908333 | | |
| IPR016181:Acyl-CoA N-acyltransferase | 8 | NAT6, SAT2, MGEA5, NAT10, KAT6B, KAT5, NAT9, ATE1 |
| GO:0008080~N-acetyltransferase activity | 5 | ESCO1, NAT6, SAT2, NAT10, NAT9 |
| domain:N-acetyltransferase | 4 | NAT6, SAT2, NAT10, NAT9 |
| IPR000182:GNAT domain | 4 | NAT6, SAT2, NAT10, NAT9 |
| Enrichment Score: 0.4082289580528521 | | |
| IPR001180:Citron-like | 4 | TNIK, MAP4K1, VPS39, WDR45 |
| SM00036:CNH | 3 | TNIK, MAP4K1, VPS39 |
| domain:CNH | 3 | TNIK, MAP4K1, VPS39 |
| Enrichment Score: 0.3922449877254785 | | |
| repeat:ANK 25 | 3 | ANKRD52, ANKRD17, ANKRD44 |
| repeat:ANK 24 | 3 | ANKRD52, ANKRD17, ANKRD44 |
| repeat:ANK 22 | 3 | ANKRD52, ANKRD17, ANKRD44 |
| repeat:ANK 23 | 3 | ANKRD52, ANKRD17, ANKRD44 |
| repeat:ANK 20 | 3 | ANKRD52, ANKRD17, ANKRD44 |
| repeat:ANK 21 | 3 | ANKRD52, ANKRD17, ANKRD44 |
| repeat:ANK 7 | 9 | ANKRD52, ANKRD17, ANKRD44, NFKBIZ, EHMT1, MIB2, BCL3, FEM1B, FEM1A |
| repeat:ANK 17 | 3 | ANKRD52, ANKRD17, ANKRD44 |
| repeat:ANK 18 | 3 | ANKRD52, ANKRD17, ANKRD44 |
| repeat:ANK 19 | 3 | ANKRD52, ANKRD17, ANKRD44 |
| repeat:ANK 8 | 7 | ANKRD52, ANKRD17, ANKRD44, EHMT1, MIB2, FEM1B, FEM1A |
| repeat:ANK 16 | 3 | ANKRD52, ANKRD17, ANKRD44 |
| repeat:ANK 13 | 3 | ANKRD52, ANKRD17, ANKRD44 |
| repeat:ANK 14 | 3 | ANKRD52, ANKRD17, ANKRD44 |
| repeat:ANK 15 | 3 | ANKRD52, ANKRD17, ANKRD44 |
| repeat:ANK 12 | 3 | ANKRD52, ANKRD17, ANKRD44 |
| repeat:ANK 9 | 5 | ANKRD52, ANKRD17, ANKRD44, MIB2, FEM1A |
| repeat:ANK 11 | 3 | ANKRD52, ANKRD17, ANKRD44 |
| repeat:ANK 10 | 3 | ANKRD52, ANKRD17, ANKRD44 |
| Enrichment Score: 0.38403808705196346 | | |
| domain:CRIB | 4 | CDC42SE1, WASL, CDC42EP3, WAS |
| IPR000095:PAK-box/P21-Rho-binding | 4 | CDC42SE1, WASL, CDC42EP3, WAS |
| SM00285:PBD | 3 | WASL, CDC42EP3, WAS |

TABLE 3-continued

HIV- low cutoff

| Category | Count | Genes |
|---|---|---|
| Enrichment Score: 0.37683206426825694 | | |
| Host cell receptor for virus entry | 9 | ICAM1, LAMP1, CD55, CXCR4, SLC20A2, IDE, HSPA1A, SLC52A2, ITGB1 |
| GO:0001618~virus receptor activity | 10 | ICAM1, LAMP1, CD55, CXCR4, SLC20A2, IDE, HSPA1A, SLC52A2, ITGB1, DPP4 |
| GO:0046718~viral entry into host cell | 11 | ICAM1, LAMP1, CD55, SLC20A2, IDE, CD81, DYNLT1, HSPA1A, SLC52A2, ITGB1, DPP4 |
| Enrichment Score: 0.37484614935515076 | | |
| SM00461:WH1 | 3 | EVL, WASL, WAS |
| IPR000697:EVH1 | 3 | EVL, WASL, WAS |
| domain:WH1 | 3 | EVL, WASL, WAS |
| GO:0008154~actin polymerization or depolymerization | 3 | EVL, WASL, WAS |
| GO:0007015~actin filament organization | 9 | NCK2, BCL2, PRKCI, BIN3, EVL, WASL, RHOF, WAS, WHAMM |
| Enrichment Score: 0.3728731212996016 | | |
| h_eif4Pathway:Regulation of eIF4e and p70 S6 Kinase | 6 | MAPK1, EIF4G3, EIF4E, PTEN, PIK3R1, PRKCB |
| h_igf1mtorPathway: Skeletal muscle hypertrophy is regulated via AKT/mTOR pathway | 5 | EIF4E, GSK3B, PTEN, PIK3R1, EIF2B5 |
| h_mtorPathway:mTOR Signaling Pathway | 5 | EIF4G3, EIF4E, TSC1, PTEN, PIK3R1 |
| Enrichment Score: 0.3673728728107017 | | |
| GO:1902187~negative regulation of viral release from host cell | 5 | CHMP3, PML, TRIM27, TRIM26, TRIM25 |
| GO:0070206~protein trimerization | 3 | TRIM4, TRIM27, TRIM22 |
| SM00449:SPRY | 13 | TRIM4, TRIM38, BTN3A1, ASH2L, RSPRY1, TRIM69, SPSB3, TRIM27, TRIM14, TRIM26, TRIM25, TRIM22, SPRYD4 |
| domain:B30.2/SPRY | 13 | TRIM4, TRIM38, BTN3A1, ASH2L, RSPRY1, TRIM69, SPSB3, TRIM27, TRIM14, TRIM26, TRIM25, TRIM22, SPRYD4 |
| IPR003877:SPla/RYanodine receptor SPRY | 13 | TRIM4, TRIM38, BTN3A1, ASH2L, RSPRY1, TRIM69, SPSB3, TRIM27, TRIM14, TRIM26, TRIM25, TRIM22, SPRYD4 |
| IPR003879:Butyrophilin-like | 10 | TRIM4, TRIM38, BTN3A1, TRIM69, TRIM14, TRIM27, TRIM26, TRIM25, TRIM22, SPRYD4 |
| SM00589:PRY | 7 | TRIM38, BTN3A1, TRIM69, TRIM14, TRIM27, TRIM26, TRIM25 |
| IPR001870:B30.2/SPRY domain | 13 | TRIM4, TRIM38, BTN3A1, ASH2L, RSPRY1, TRIM69, SPSB3, TRIM27, TRIM14, TRIM26, TRIM25, TRIM22, SPRYD4 |
| IPR006574:SPRY-associated | 7 | TRIM38, BTN3A1, TRIM69, TRIM14, TRIM27, TRIM26, TRIM25 |
| zinc finger region:B box-type | 8 | TRIM4, TRIM38, TRIM14, TRIM27, RBCK1, TRIM26, TRIM22, MYCBP2 |
| SM00336:BBOX | 8 | TRIM4, TRIM38, TRIM33, TRIM14, PML, TRIM27, TRIM26, TRIM22 |
| IPR000315:Zinc finger, B-box | 9 | TRIM4, TRIM38, TRIM33, TRIM69, TRIM14, PML, TRIM27, TRIM26, TRIM22 |
| IPR013320:Concanavalin A-like lectin/glucanase, subgroup | 18 | TSPEAR, SPSB3, NELL2, CLSTN1, TRIM27, LRBA, TRIM14, TRIM26, TRIM25, TRIM22, SPRYD4, LGALS9, TRIM4, TRIM38, BTN3A1, ASH2L, TRIM69, RSPRY1 |
| Enrichment Score: 0.3661268358100964 | | |
| hsa04611:Platelet activation | 18 | GNA13, ORAI1, ARHGEF1, ROCK1, ADCY7, ROCK2, PRKCI, STIM1, APBB1IP, PPP1CB, ITGB1, ITPR2, MAPK1, MAPK13, SNAP23, PRKACB, PIK3R1, AKT2 |

TABLE 3-continued

HIV- low cutoff

| Category | Count | Genes |
|---|---|---|
| hsa05205:Proteoglycans in cancer | 26 | ITGB1, KRAS, TIAM1, SOS1, RAC1, NUDT16L1, PRKACB, MSN, PIK3R1, AKT2, ARHGEF1, ROCK1, ROCK2, CBL, RAF1, CD63, PPP1CB, FLNA, PRKCB, ITPR2, CTSL, NRAS, MAPK1, CBLB, MAPK13, ARAF |
| hsa04270:Vascular smooth muscle contraction | 14 | GNA13, ARHGEF1, ROCK1, ADCY7, ROCK2, PRKCH, RAF1, PPP1CB, PRKCD, PRKCB, ITPR2, MAPK1, ARAF, PRKACB |
| Enrichment Score: 0.3655181734902265 | | |
| IPR004088K: Homology domain, type 1 | 7 | ANKRD17, FMR1, KHSRP, MEX3C, EXOSC3, QKI, FXR2 |
| SM00322:KH | 6 | ANKRD17, FMR1, KHSRP, MEX3C, QKI, FXR2 |
| IPR004087:K Homology domain | 6 | ANKRD17, FMR1, KHSRP, MEX3C, QKI, FXR2 |
| domain:KH 2 | 4 | FMR1, KHSRP, MEX3C, FXR2 |
| domain:KH 1 | 4 | FMR1, KHSRP, MEX3C, FXR2 |
| Enrichment Score: 0.3643845176662146 | | |
| Electron transport | 17 | ENOX2, UQCRC1, NDUFB7, NDUFA9, TXN2, CYB5A, NDUFA10, UQCRFS1, GLRX2, NDUFV3, SDHA, SDHC, NDUFV2, TXNRD1, NDUFS1, ETFA, GLRX |
| hsa05016:Huntington's disease | 27 | UQCRC1, NDUFB7, TBP, CLTC, UQCRFS1, POLR2B, TBPL2, SIN3A, CASP8, ATP5H, NDUFS1, TBPL1, NDUFA9, CREB1, CREBBP, NDUFA10, PPARGC1A, SDHA, PPIF, NDUFV3, NRF1, EP300, SP1, BBC3, AP2A1, SDHC, NDUFV2 |
| hsa05010:Alzheimer's disease | 24 | UQCRC1, APH1A, NDUFB7, NDUFA9, IDE, FADD, BAD, NDUFA10, UQCRFS1, NAE1, ITPR2, NDUFV3, ATF6, CASP7, GSK3B, SDHC, CASP8, NDUFV2, PPP3CB, ATP5H, NDUFS1, TNFRSF1A, MAPK1, |
| GO:0032981~mitochondrial respiratory chain complex I assembly | 10 | NDUFAF4, NDUFV3, TIMMDC1, NDUFB7, AIFM1, NDUFA9, NDUFV2, ECSIT, NDUFA10, NDUFS1 |
| Respiratory chain | 8 | NDUFV3, UQCRC1, NDUFB7, NDUFA9, NDUFV2, UQCRFS1, NDUFA10, NDUFS1 |
| hsa00190:Oxidative phosphorylation | 16 | COX11, UQCRC1, NDUFB7, NDUFA9, ATP6V1H, NDUFA10, UQCRFS1, ATP6V1F, NDUFV3, SDHA, SDHC, ATP6V1E1, NDUFV2, ATP6V0D1, ATP5H, NDUFS1 |
| GO:0005747~mitochondrial respiratory chain complex I | 6 | NDUFV3, NDUFB7, NDUFA9, NDUFV2, NDUFA10, NDUFS1 |
| GO:0008137~NADH dehydrogenase (ubiquinone) activity | 6 | NDUFV3, NDUFB7, NDUFA9, NDUFV2, NDUFA10, NDUFS1 |
| hsa05012:Parkinson's disease | 16 | UQCRC1, NDUFB7, NDUFA9, UBE2G1, UBE2J1, UBE2J2, NDUFA10, UQCRFS1, NDUFV3, PPIF, SDHA, SDHC, NDUFV2, PRKACB, ATP5H, NDUFS1 |
| GO:0006120~mitochondrial electron transport, NADH to ubiquinone | 6 | NDUFV3, NDUFB7, NDUFA9, NDUFV2, NDUFA10, NDUFS1 |
| Ubiquinone | 3 | NDUFV2, NDUFA10, NDUFS1 |
| Enrichment Score: 0.35390729447514874 | | |
| IPR000209:Peptidase S8/S53 domain | 4 | TPP1, TPP2, PCSK7, FURIN |
| IPR023828:Peptidase S8, subtilisin, Ser-active site | 3 | TPP2, PCSK7, FURIN |
| IPR022398:Peptidase S8, subtilisin, His-active site | 3 | TPP2, PCSK7, FURIN |
| IPR015500:Peptidase S8, subtilisin-related | 3 | TPP2, PCSK7, FURIN |
| IPR009020:Proteinase inhibitor, propeptide | 3 | TPP1, PCSK7, FURIN |
| Serine protease | 9 | LONP1, PARL, TPP1, TPP2, GZMB, PCSK7, RHBDD1, FURIN, DPP4 |
| active site:Charge relay system | 11 | APEH, CES2, ABHD17B, TPP1, TPP2, ABHD3, ABHD2, GZMB, PCSK7, FURIN, DPP4 |
| GO:0004252~serine-type endopeptidase activity | 14 | GZMB, RHBDD1, FURIN, RHBDD2, IMMP1L, CTSL, APEH, LONP1, PARL, TPP1, TPP2, CTSC, PCSK7, DPP4 |

TABLE 3-continued

HIV- low cutoff

| Category | Count | Genes |
|---|---|---|
| Enrichment Score: 0.3488604922902843 | | |
| SM00849:SM00849 | 3 | HAGH, ETHE1, CPSF3 |
| IPR001279:Beta-lactamase-like | 4 | HAGH, ELAC2, ETHE1, CPSF3 |
| metal ion-binding site:Zinc 1 | 8 | HAGH, EHMT1, ETHE1, ARAF, PML, RAF1, USP16, CPSF3 |
| Enrichment Score: 0.3388633674945358 | | |
| GO:0005851~eukaryotic translation initiation factor 2B complex | 3 | EIF2B1, EIF2B4, EIF2B5 |
| GO:0043434~response to peptide hormone | 9 | CD55, BSG, CDKN1B, BTG2, SOCS1, ANXA1, EIF2B1, EIF2B4, EIF2B5 |
| h_vegfPathway:VEGF, Hypoxia, and Angiogenesis | 7 | VHL, ELAVL1, EIF2B1, PIK3R1, EIF2B4, PRKCB, EIF2B5 |
| GO:0014003~oligodendrocyte development | 3 | EIF2B1, EIF2B4, EIF2B5 |
| Leukodystrophy | 3 | EIF2B1, EIF2B4, EIF2B5 |
| GO:0009408~response to heat | 6 | SOCS3, HSPA1A, MAP2K7, EIF2B1, EIF2B4, EIF2B5 |
| Enrichment Score: 0.3332483915134039 | | |
| IPR020103:Pseudouridine synthase, catalytic domain | 3 | RPUSD3, TRUB2, PUS7 |
| GO:0009982~pseudouridine synthase activity | 3 | RPUSD3, TRUB2, PUS7 |
| GO:0001522~pseudouridine synthesis | 3 | RPUSD3, TRUB2, PUS7 |
| Enrichment Score: 0.3283640348823858 | | |
| SM00312:PX | 7 | SNX19, SNX29, PIK3C2A, SNX2, SNX4, SNX13, SNX11 |
| GO:0035091~phosphatidylinositol binding | 12 | SNX19, SH3YL1, SNX29, ING2, PIK3C2A, PASK, SNX2, SNX4, PITPNC1, SNX13, SNX11, ITPR2 |
| domain:PX | 7 | SNX19, SNX29, PIK3C2A, SNX2, SNX4, SNX13, SNX11 |
| IPR001683:Phox homologous domain | 7 | SNX19, SNX29, PIK3C2A, SNX2, SNX4, SNX13, SNX11 |
| GO:0016050~vesicle organization | 4 | SNX2, SNX4, WASL, SNX11 |
| Enrichment Score: 0.3248740734594386 | | |
| 72.IAP_interaction_with_cell_death_pathways | 5 | TNFRSF1A, XIAP, CASP7, CASP8, FADD |
| h_mitochondriaPathway:Role of Mitochondria in Apoptotic Signaling | 5 | XIAP, AIFM1, CASP7, BCL2, CASP8 |
| h_caspasePathway:Caspase Cascade in Apoptosis | 5 | XIAP, LMNB2, CASP7, CASP8, GZMB |
| Enrichment Score: 0.3159225008635777 | | |
| GO:0004859~phospholipase inhibitor activity | 3 | ANXA1, ANXA5, ANXA2 |
| Annexin | 3 | ANXA1, ANXA5, ANXA2 |
| SM00335:ANX | 3 | ANXA1, ANXA5, ANXA2 |
| IPR018502:Annexin repeat | 3 | ANXA1, ANXA5, ANXA2 |
| IPR018252:Annexin repeat, conserved site | 3 | ANXA1, ANXA5, ANXA2 |
| IPR001464:Annexin | 3 | ANXA1, ANXA5, ANXA2 |
| Calcium/phospholipid-binding | 3 | ANXA1, ANXA5, ANXA2 |
| repeat:Annexin 1 | 3 | ANXA1, ANXA5, ANXA2 |
| repeat:Annexin 3 | 3 | ANXA1, ANXA5, ANXA2 |

TABLE 3-continued

| HIV- low cutoff | | |
|---|---|---|
| Category | Count | Genes |
| repeat:Annexin 2 | 3 | ANXA1, ANXA5, ANXA2 |
| repeat:Annexin 4 | 3 | ANXA1, ANXA5, ANXA2 |
| GO:0005544~calcium-dependent phospholipid binding | 7 | C2CD5, SYT11, ANXA1, CPNE1, SYTL3, ANXA5, ANXA2 |
| Enrichment Score: 0.31228187414723185 | | |
| h_cxcr4Pathway:CXCR4 Signaling Pathway | 6 | MAPK1, CXCR4, RELA, RAF1, PIK3R1, PRKCB |
| h_eif4Pathway:Regulation of eIF4e and p70 S6 Kinase | 6 | MAPK1, EIF4G3, EIF4E, PTEN, PIK3R1, PRKCB |
| h_edg1Pathway:Phospholipids as signalling intermediaries | 5 | MAPK1, RAC1, PIK3R1, ASAH1, PRKCB |
| hsa04960:Aldosterone-regulated sodium reabsorption | 4 | MAPK1, KRAS, PIK3R1, PRKCB |
| Enrichment Score: 0.3071399535752837 | | |
| SM00323:RasGAP | 3 | IQGAP2, RASA1, RASA2 |
| IPR023152:Ras GTPase-activating protein, conserved site | 3 | IQGAP2, RASA1, RASA2 |
| domain:Ras-GAP | 3 | IQGAP2, RASA1, RASA2 |
| IPR001936:Ras GTPase-activating protein | 3 | IQGAP2, RASA1, RASA2 |
| Enrichment Score: 0.2948433234633509 | | |
| IPR000225:Armadillo | 7 | USO1, KPNA6, ARMCX3, ARMC6, KPNA1, ARMC1, APC |
| repeat:ARM 3 | 6 | USO1, KPNA6, ARMCX3, ARMC6, KPNA1, APC |
| repeat:ARM 2 | 6 | USO1, KPNA6, ARMCX3, ARMC6, KPNA1, APC |
| repeat:ARM 4 | 5 | USO1, KPNA6, ARMC6, KPNA1, APC |
| repeat:ARM 7 | 4 | USO1, KPNA6, KPNA1, APC |
| repeat:ARM 6 | 4 | USO1, KPNA6, KPNA1, APC |
| repeat:ARM 9 | 3 | USO1, KPNA6, KPNA1 |
| repeat:ARM 5 | 4 | USO1, KPNA6, KPNA1, APC |
| SM00185:ARM | 5 | USO1, KPNA6, ARMC6, KPNA1, APC |
| repeat:ARM 1 | 4 | USO1, ARMCX3, ARMC6, APC |
| repeat:ARM 8 | 3 | USO1, KPNA6, KPNA1 |
| Enrichment Score: 0.29256414347139453 | | |
| IPR010920:Like-Sm (LSM) domain | 5 | LSM14A, LSM14B, LSM3, LSM10, LSM1 |
| SM00651:Sm | 3 | LSM3, LSM10, LSM1 |
| IPR001163:Ribonucleoprotein LSM domain | 3 | LSM3, LSM10, LSM1 |
| Enrichment Score: 0.28416826259197325 | | |
| SM00450:RHOD | 4 | DUSP4, DUSP16, TSTD1, MPST |
| IPR001763:Rhodanese-like domain | 4 | DUSP4, DUSP16, TSTD1, MPST |
| domain:Rhodanese | 3 | DUSP4, DUSP16, TSTD1 |
| Enrichment Score: 0.2825610876287823 | | |
| hsa00061:Fatty acid biosynthesis | 4 | FASN, ACSL4, ACSL3, ACSL5 |
| GO:0102391~decanoate--CoA ligase activity | 3 | ACSL4, ACSL3, ACSL5 |
| hsa00071:Fatty acid degradation | 8 | ECI1, ECI2, ACSL4, ACAT2, ACSL3, ALDH3A2, ALDH9A1, ACSL5 |
| GO:0004467~long-chain fatty acid-CoA ligase activity | 3 | ACSL4, ACSL3, ACSL5 |

TABLE 3-continued

| Category | Count | Genes |
|---|---|---|
| HIV- low cutoff | | |
| GO:0035338~long-chain fatty-acyl-CoA biosynthetic process | 6 | ELOVL1, ACOT9, FASN, ACSL4, ACSL3, ACSL5 |
| GO:0001676~long-chain fatty acid metabolic process | 3 | ACSL4, ACSL3, ACSL5 |
| hsa03320:PPAR signaling pathway | 7 | RXRB, ILK, ACSL4, PCK2, ACSL3, SCP2, ACSL5 |
| IPR020845:AMP-binding, conserved site | 3 | ACSL4, ACSL3, ACSL5 |
| hsa01212:Fatty acid metabolism | 5 | FASN, ACSL4, ACAT2, ACSL3, ACSL5 |
| Fatty acid metabolism | 11 | ECI1, ELOVL1, PRKAG2, PRKAB1, FASN, PRKAA1, ACSL4, LPIN1, ACSL3, ACSL5, HSD17B8 |
| IPR000873:AMP-dependent synthetase/ligase Enrichment Score: 0.2825385029515912 | 3 | ACSL4, ACSL3, ACSL5 |
| GO:0051056~regulation of small GTPase mediated signal transduction | 19 | ARHGEF3, VAV3, RALBP1, RALGAPB, ARHGAP17, MYO9B, ARHGAP15, VAV1, FAM13B, ARHGAP30, RALGAPA1, TIAM1, SOS1, SIPA1L1, RAC1, RHOT1, RHOT2, ARAP2, RHOF |
| SM00324:RhoGAP | 8 | ARHGAP30, RALBP1, MYO9B, ARHGAP17, ARHGAP15, ARAP2, PIK3R1, FAM13B |
| IPR008936:Rho GTPase activation protein | 11 | ARHGAP30, RALBP1, IQGAP2, MYO9B, ARHGAP17, ARHGAP15, ARAP2, PIK3R1, RASA1, FAM13B, RASA2 |
| domain:Rho-GAP | 8 | ARHGAP30, RALBP1, MYO9B, ARHGAP17, ARHGAP15, ARAP2, PIK3R1, FAM13B |
| IPR000198:Rho GTPase-activating protein domain Enrichment Score: 0.27812245787260176 | 8 | ARHGAP30, RALBP1, MYO9B, ARHGAP17, ARHGAP15, ARAP2, PIK3R1, FAM13B |
| repeat:ANK 7 | 9 | ANKRD52, ANKRD17, ANKRD44, NFKBIZ, EHMT1, MIB2, BCL3, FEM1B, FEM1A |
| repeat:ANK 3 | 25 | CAMTA2, OSTF1, NFKBID, NFKBIB, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, ANKRD44, ACAP1, KRIT1, MIB2, ACAP2, BARD1 |
| repeat:ANK 1 | 29 | CAMTA2, OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, GPANK1, ANKRD40, ANKRD44, ACAP1, MIB2, KRIT1, ACAP2, DGKZ, BARD1 |
| repeat:ANK 2 | 29 | CAMTA2, OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, GPANK1, ANKRD40, ANKRD44, ACAP1, MIB2, KRIT1, ACAP2, DGKZ, BARD1 |
| repeat:ANK 6 | 12 | ANKRD52, ANKRD17, ANKRD44, NFKBIZ, ANKS1A, EHMT1, NFKBID, MIB2, NFKBIB, BCL3, FEM1B, FEM1A |
| ANK repeat | 29 | CAMTA2, OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, GPANK1, ANKRD40, ANKRD44, ACAP1, MIB2, KRIT1, ACAP2, DGKZ, BARD1 |
| SM00248:ANK | 27 | OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, ANKRD40, ANKRD44, ACAP1, MIB2, KRIT1, ACAP2, DGKZ, BARD1 |
| IPR020683:Ankyrin repeat-containing domain | 29 | CAMTA2, OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, GPANK1, ANKRD40, ANKRD44, ACAP1, MIB2, KRIT1, ACAP2, DGKZ, BARD1 |
| repeat:ANK 4 | 18 | NFKBIZ, ANKS1A, EHMT1, NFKBID, NFKBIB, FEM1B, FEM1A, RFXANK, ANKRD36, ANKRD52, ANKRD17, GABPB1, ANKRD44, MIB2, KRIT1, ILK, BCL3, HECTD1 |
| repeat:ANK 5 | 15 | NFKBIZ, ANKS1A, EHMT1, NFKBID, NFKBIB, FEM1B, RFXANK, FEM1A, ANKRD52, ANKRD17, ANKRD44, GABPB1, MIB2, ILK, BCL3 |
| IPR002110:Ankyrin repeat | 27 | OSTF1, NFKBID, NFKBIB, ASAP1, FEM1B, FEM1A, RFXANK, ANKRD36, ANKRD52, ANKRD17, GABPB1, ILK, ANKRD37, BCL3, HECTD1, IBTK, NFKBIZ, ANKS1A, EHMT1, ANKRD40, ANKRD44, ACAP1, MIB2, KRIT1, ACAP2, DGKZ, BARD1 |

TABLE 3-continued

HIV- low cutoff

| Category | Count | Genes |
|---|---|---|
| Enrichment Score: 0.2668097961653456 | | |
| GO:0042276~error-prone translesion synthesis | 4 | RPA1, POLK, RFC2, REV3L |
| DNA replication | 12 | RPA1, POLK, RBBP4, RFC2, WRNIP1, FAM111A, RRM1, CINP, ORC4, POLB, MCM6, REV3L |
| GO:0006297~nucleotide-excision repair, DNA gap filling | 4 | RPA1, POLK, RFC2, POLB |
| GO:0019985~translesion synthesis | 5 | RPA1, POLK, RFC2, TRIM25, REV3L |
| hsa03460:Fanconi anemia pathway | 5 | WDR48, RPA1, RAD51C, POLK, REV3L |
| Enrichment Score: 0.25720288166374317 | | |
| GO:0004114~3',5'-cyclic-nucleotide phosphodiesterase activity | 5 | PDE6D, PDE7A, PDE4B, PDE4D, RUNX1 |
| IPR002073:3'5'-cyclic nucleotide phosphodiesterase, catalytic domain | 4 | PDE7A, PDE4B, PDE4D, RUNX1 |
| cAMP | 5 | PRKAR2A, PDE7A, PDE4B, PDE4D, PRKACB |
| GO:0004115~3',5'-cyclic-AMP phosphodiesterase activity | 3 | PDE7A, PDE4B, PDE4D |
| GO:0006198~cAMP catabolic process | 3 | PDE7A, PDE4B, PDE4D |
| metal ion-binding site:Divalent metal cation 1 | 4 | PTER, PDE7A, PDE4B, PDE4D |
| metal ion-binding site:Divalent metal cation 2 | 4 | PTER, PDE7A, PDE4B, PDE4D |
| IPR023088:3'5'-cyclic nucleotide phosphodiesterase | 3 | PDE7A, PDE4B, PDE4D |
| IPR023174:3'5'-cyclic nucleotide phosphodiesterase, conserved site | 3 | PDE7A, PDE4B, PDE4D |
| hsa05032:Morphine addiction | 6 | ADCY7, PDE7A, PDE4B, PDE4D, PRKACB, PRKCB |
| Enrichment Score: 0.24930966068454638 | | |
| SM00326:SH3 | 24 | FYB, DBNL, OSTF1, VAV3, STAM2, MPP6, ASAP1, VAV1, NCK2, DOCK2, SH3YL1, CRKL, SH3GLB2, LASP1, PSTPIP1, STAM, UBASH3A, GRAP2, BIN1, ABL2, RASA1, SASH3, PIK3R1, MATK |
| SH3 domain | 24 | FYB, DBNL, OSTF1, VAV3, STAM2, MPP6, ASAP1, VAV1, NCK2, DOCK2, SH3YL1, CRKL, SH3GLB2, LASP1, PSTPIP1, STAM, UBASH3A, GRAP2, BIN1, ABL2, RASA1, SASH3, PIK3R1, MATK |
| domain:SH3 | 19 | FYB, DBNL, OSTF1, STAM2, MPP6, ASAP1, DOCK2, SH3YL1, SH3GLB2, LASP1, PSTPIP1, UBASH3A, STAM, BIN1, ABL2, RASA1, SASH3, PIK3R1, MATK |
| IPR001452:Src homology-3 domain | 24 | FYB, DBNL, OSTF1, VAV3, STAM2, MPP6, ASAP1, VAV1, NCK2, DOCK2, SH3YL1, CRKL, SH3GLB2, LASP1, PSTPIP1, STAM, UBASH3A, GRAP2, BIN1, ABL2, RASA1, SASH3, PIK3R1, MATK |
| Enrichment Score: 0.24872976470051114 | | |
| GO:0004004~ATP-dependent RNA helicase activity | 9 | DDX23, DHX29, DDX19A, DHX34, DDX50, DHX16, DDX10, DDX51, DDX42 |
| IPR011709:Domain of unknown function DUF1605 | 3 | DHX29, DHX34, DHX16 |
| SM00847:SM00847 | 3 | DHX29, DHX34, DHX16 |
| IPR007502:Helicase-associated domain | 3 | DHX29, DHX34, DHX16 |

TABLE 3-continued

| Category | Count | Genes |
|---|---|---|
| HIV- low cutoff | | |
| Enrichment Score: 0.23256970544677066 | | |
| binding site:NADP | 5 | G6PD, AKR7A2, IDH2, GRHPR, DCXR |
| nucleotide phosphate-binding region:NADP | 9 | HSD17B11, HTATIP2, G6PD, AKR1B1, AKR7A2, IDH2, KDSR, GRHPR, DCXR |
| NADP | 15 | HSD17B11, HTATIP2, GLUD2, PYROXD1, GRHPR, FAR1, G6PD, AKR1B1, AKR7A2, FASN, IDH2, KDSR, TXNRD1, DCXR, CRYZL1 |
| Enrichment Score: 0.23055832452848027 | | |
| GO:0070125~mitochondrial translational elongation | 14 | MRPL42, MRPS14, MRPS23, MRPS25, MRPS11, GFM2, MRPS9, TSFM, GFM1, MRPL16, MRPL55, MRPL34, MRPL44, MRPL35 |
| GO:0070126~mitochondrial translational termination | 13 | MRPL42, MRPS23, MRPS14, MRPS25, MRPS11, MRRF, GFM2, MRPS9, MRPL16, MRPL55, MRPL34, MRPL44, MRPL35 |
| GO:0005763~mitochondrial small ribosomal subunit | 5 | MRPL42, MRPS9, MRPS14, MRPS11, MRPS2 |
| Ribonucleoprotein | 31 | RALY, RPL17, MRPL42, MRPS14, MRPS11, LARP1B, HNRNPLL, LSM14A, LSM14B, MRPL16, MRPL55, AGO2, LSM3, LSM1, MRPL34, MRPL35, MRPS23, RXRB, MRPS25, EFTUD2, FMR1, MRPS2, RPS6KA3, HNRNPH2, MRPS9, LSM10, PARP4, CPSF3, METTL17, MVP, MRPL44 |
| GO:0006412~translation | 25 | RPL17, MRPL42, MRPS14, MRPS11, HBS1L, EIF4EBP2, MRPL16, AGO2, MRPL55, SLC25A28, MRPL34, MRPL35, MRPS23, EFTUD2, GTF2H3, MRRF, MRPS2, SLC25A32, MRPS9, SLC25A38, FARSB, YARS2, SLC25A16, SLC25A53, METTL17 |
| Ribosomal protein | 16 | RPL17, MRPL42, MRPS14, MRPS23, RXRB, MRPS25, MRPS11, MRPS2, RPS6KA3, MRPS9, MRPL16, MRPL55, MRPL34, METTL17, MRPL44, MRPL35 |
| GO:0005840~ribosome | 15 | MRPL42, MRPS14, MRPS23, RXRB, MRPS25, MRPS11, MRPS2, RPS6KA3, MRPS9, MRPL16, MRPL55, MRPL34, METTL17, MRPL44, MRPL35 |
| GO:0003735~structural constituent of ribosome | 17 | RPL17, MRPL42, MRPS14, MRPS23, MRPS25, MRPS11, MRPS2, SLC25A32, MRPS9, MRPL16, SLC25A38, SLC25A28, MRPL55, SLC25A16, MRPL34, SLC25A53, MRPL35 |
| hsa03010:Ribosome | 8 | RPL17, MRPS9, MRPS14, MRPL16, MRPS11, MRPL34, MRPS2, MRPL35 |
| Enrichment Score: 0.23040649502848873 | | |
| repeat:WD 8 | 9 | WDR48, PHIP, TBL1XR1, EML3, ELP2, WDR6, TBL1X, PWP2, GEMIN5 |
| repeat:WD 13 | 3 | ELP2, PWP2, GEMIN5 |
| repeat:WD 11 | 4 | ELP2, WDR6, PWP2, GEMIN5 |
| repeat:WD 10 | 4 | ELP2, WDR6, PWP2, GEMIN5 |
| repeat:WD 12 | 3 | ELP2, PWP2, GEMIN5 |
| repeat:WD 9 | 5 | EML3, ELP2, WDR6, PWP2, GEMIN5 |
| Enrichment Score: 0.2297546707824956 | | |
| GO:0033572~transferrin transport | 7 | SLC11A2, ATP6V1E1, RAB11B, ATP6V1H, CLTC, ATP6V0D1, ATP6V1F |
| GO:0016241~regulation of macroautophagy | 7 | CAPNS1, EXOC7, ATP6V1E1, ATP6V1H, MAPK8, ATP6V0D1, VPS26A |
| hsa04721:Synaptic vesicle cycle | 9 | DNM3, AP2A1, ATP6V1E1, ATP6V1H, NAPA, VAMP2, CLTC, ATP6V0D1, ATP6V1F |
| GO:0046961~proton-transporting ATPase activity, rotational mechanism | 4 | ATP6V1E1, ATP6V1H, ATP6V0D1, ATP6V1F |
| hsa05110:*Vibrio cholerae* infection | 7 | ATP6V1E1, ATP6V1H, PRKACB, PDIA4, ATP6V0D1, ATP6V1F, PRKCB |
| GO:0090383~phagosome acidification | 4 | ATP6V1E1, ATP6V1H, ATP6V0D1, ATP6V1F |
| GO:0015991~ATP hydrolysis coupled proton transport | 4 | ATP6V1E1, ATP6V1H, ATP6V0D1, ATP6V1F |
| GO:0015078~hydrogen ion transmembrane transporter activity | 4 | SLC11A2, ATP6V0D1, ATP5H, ATP6V1F |
| Hydrogen ion transport | 5 | ATP6V1E1, ATP6V1H, ATP6V0D1, ATP5H, ATP6V1F |

TABLE 3-continued

| HIV- low cutoff | | |
|---|---|---|
| Category | Count | Genes |
| hsa04966:Collecting duct acid secretion | 3 | ATP6V1E1, ATP6V0D1, ATP6V1F |
| GO:0015992~proton transport | 4 | ATP6V1E1, HVCN1, ATP6V0D1, ATP6V1F |
| Enrichment Score: 0.22901571749480087 | | |
| SM00156:PP2Ac | 3 | PPP2CB, PPP3CB, PPP1CB |
| IPR006186:Serine/threonine-specific protein phosphatase/bis(5-nucleosyl)-tetraphosphatase | 3 | PPP2CB, PPP3CB, PPP1CB |
| IPR004843:Metallophosphoesterase domain | 4 | PPP2CB, PPP3CB, DBR1, PPP1CB |
| GO:0004721~phosphoprotein phosphatase activity | 6 | PGP, PPP2CB, DUSP16, PPP3CB, PTEN, PPP1CB |
| metal ion-binding site:Iron | 4 | PPP2CB, PPP3CB, EGLN1, PPP1CB |
| Enrichment Score: 0.219815162312881 | | |
| domain:G-patch | 4 | CHERP, SUGP1, GPANK1, RBM10 |
| SM00443:G_patch | 4 | CHERP, SUGP1, GPANK1, RBM10 |
| IPR000467:G-patch domain | 4 | CHERP, SUGP1, GPANK1, RBM10 |
| Enrichment Score: 0.21462490830549383 | | |
| SM00516:SEC14 | 4 | TTPAL, GDAP2, BNIP2, SEC14L1 |
| domain:CRAL-TRIO | 4 | TTPAL, GDAP2, BNIP2, SEC14L1 |
| IPR001251:CRAL-TRIO domain | 4 | TTPAL, GDAP2, BNIP2, SEC14L1 |
| Enrichment Score: 0.21380660245611388 | | |
| GO:0005385~zinc ion transmembrane transporter activity | 4 | SLC11A2, SLC30A5, SLC39A6, SLC39A3 |
| GO:0071577~zinc II ion transmembrane transport | 3 | SLC30A5, SLC39A6, SLC39A3 |
| Zinc transport | 3 | SLC30A5, SLC39A6, SLC39A3 |
| Enrichment Score: 0.2125851179351233 | | |
| domain:BTB | 18 | BACH2, ZBTB10, ZBTB11, ZNF131, ZBTB40, KCTD20, KEAP1, KCTD2, IVNS1ABP, KCTD6, ZBTB38, SHKBP1, KBTBD2, KLHL9, KCTD18, ZBTB2, KLHL24, SPOP |
| SM00225:BTB | 19 | IBTK, BACH2, ZBTB10, ZBTB11, ZNF131, BTBD7, ZBTB40, KCTD20, KEAP1, KCTD2, IVNS1ABP, KCTD6, ZBTB38, SHKBP1, KBTBD2, KLHL9, ZBTB2, KLHL24, SPOP |
| GO:0031463~Cul3-RING ubiquitin ligase complex | 8 | CUL3, KBTBD2, BACH2, KLHL9, KEAP1, KLHL24, KCTD2, SPOP |
| IPR000210:BTB/POZ-like | 19 | IBTK, BACH2, ZBTB10, ZBTB11, ZNF131, BTBD7, ZBTB40, KCTD20, KEAP1, KCTD2, IVNS1ABP, KCTD6, ZBTB38, SHKBP1, KBTBD2, KLHL9, ZBTB2, KLHL24, SPOP |
| IPR011333:BTB/POZ fold | 20 | IBTK, BACH2, ZBTB10, ZBTB11, ZNF131, BTBD7, ZBTB40, KCTD20, KEAP1, KCTD2, IVNS1ABP, ZBTB38, KCTD6, SHKBP1, KBTBD2, KLHL9, KCTD18, ZBTB2, KLHL24, SPOP |
| Enrichment Score: 0.20376403779805952 | | |
| Aminopeptidase | 5 | LNPEP, TPP2, ERAP1, DPP4, DNPEP |
| GO:0004177~amino peptidase activity | 4 | LNPEP, TPP2, ERAP1, DNPEP |
| GO:0070006~metalloaminopeptidase activity | 3 | LNPEP, ERAP1, DNPEP |
| GO:0008237~metallopeptidase activity | 7 | STAMBP, LNPEP, CHMP1A, CNDP2, STAMBPL1, ERAP1, DNPEP |

TABLE 3-continued

HIV- low cutoff

| Category | Count | Genes |
|---|---|---|
| Enrichment Score: 0.195467663648754 | | |
| h_cdc42racPathway: Role of PI3K subunit p85 in regulation of Actin Organization and Cell Migration | 4 | ARPC1A, RAC1, WASL, PIK3R1 |
| h_salmonellaPathway:How does salmonella hijack a cell | 3 | ARPC1A, RAC1, WASL |
| h_actinYPathway:Y branching of actin filaments | 3 | ARPC1A, RAC1, WASL |
| Enrichment Score: 0.19234790118499914 | | |
| GO:0030676~Rac guanyl-nucleotide exchange factor activity | 4 | DOCK2, VAV3, TIAM1, VAV1 |
| IPR001331:Guanine-nucleotide dissociation stimulator, CDC24, conserved site | 4 | ARHGEF3, VAV3, TIAM1, VAV1 |
| GO:0035023~regulation of Rho protein signal transduction | 8 | ARHGEF3, VAV3, ARHGEF1, TIAM1, SOS1, RAF1, MYO9B, VAV1 |
| domain:DH | 6 | ARHGEF3, VAV3, ARHGEF1, TIAM1, SOS1, VAV1 |
| SM00325:RhoGEF | 6 | ARHGEF3, VAV3, ARHGEF1, TIAM1, SOS1, VAV1 |
| IPR000219:Dbl homology (DH) domain | 6 | ARHGEF3, VAV3, ARHGEF1, TIAM1, SOS1, VAV1 |
| GO:0005089~Rho guanyl-nucleotide exchange factor activity | 6 | ARHGEF3, VAV3, ARHGEF1, TIAM1, SOS1, VAV1 |
| Enrichment Score: 0.1850282990952521 | | |
| region of interest:Ligand-binding | 5 | NR1H2, RXRB, NR4A1, RORA, MR1 |
| IPR013088:Zinc finger, NHR/GATA-type | 8 | NR1H2, ESRRA, RXRB, GATA3, GATAD2A, NR4A1, RORA, RERE |
| GO:0030522~intracellular receptor signaling pathway | 6 | ESRRA, NCOA1, NCOA2, NR4A1, RORA, BRD8 |
| GO:0004879~RNA polymerase II transcription factor activity, ligand-activated sequence-specific DNA binding | 5 | NR1H2, ESRRA, RXRB, NR4A1, RORA |
| GO:0003707~steroid hormone receptor activity | 7 | NR1H2, ESRRA, RXRB, PGRMC2, NR4A1, ABHD2, RORA |
| GO:0043401~steroid hormone mediated signaling pathway | 7 | NR1H2, ESRRA, RXRB, PGRMC2, NR4A1, ABHD2, RORA |
| DNA-binding region:Nuclear receptor | 5 | NR1H2, ESRRA, RXRB, NR4A1, RORA |
| zinc finger region:NR C4-type | 5 | NR1H2, ESRRA, RXRB, NR4A1, RORA |
| SM00399:ZnF_C4 | 5 | NR1H2, ESRRA, RXRB, NR4A1, RORA |
| IPR001628:Zinc finger, nuclear hormone receptor-type | 5 | NR1H2, ESRRA, RXRB, NR4A1, RORA |

TABLE 3-continued

HIV- low cutoff

| Category | Count | Genes |
|---|---|---|
| SM00430:HOLI | 5 | NR1H2, ESRRA, RXRB, NR4A1, RORA |
| IPR001723:Steroid hormone receptor | 5 | NR1H2, ESRRA, RXRB, NR4A1, RORA |
| IPR000536:Nuclear hormone receptor, ligand-binding, core | 5 | NR1H2, ESRRA, RXRB, NR4A1, RORA |
| Enrichment Score: 0.18471285738684817 | | |
| IPR008984:SMAD/FHA domain | 7 | MDC1, SLMAP, FOXK2, APTX, TIFA, SMAD3, IRF3 |
| IPR000253:Forkhead-associated (FHA) domain | 5 | MDC1, SLMAP, FOXK2, APTX, TIFA |
| SM00240:FHA domain:FHA | 3 | MDC1, SLMAP, FOXK2 |
| | 4 | MDC1, SLMAP, FOXK2, TIFA |
| Enrichment Score: 0.18296343468740298 | | |
| GO:2000503~positive regulation of natural killer cell chemotaxis | 3 | CCL3, XCL1, CCL4 |
| GO:0030593~neutrophil chemotaxis | 11 | CCL3, VAV3, GBF1, PDE4B, CKLF, IFNG, PDE4D, XCL1, VAV1, CCL4, XCL2 |
| Chemotaxis | 11 | CCL3, IL16, CKLF, CMTM7, PLGRKT, CXCR3, XCL1, CMTM3, CCL4, XCL2, LGALS9 |
| GO:0002548~monocyte chemotaxis | 5 | CCL3, ANXA1, XCL1, CCL4, XCL2 |
| GO:0050729~positive regulation of inflammatory response | 8 | TNFRSF1A, CCL3, MAPK13, JAK2, XCL1, CCL4, XCL2, IL2 |
| GO:0071346~cellular response to interferon-gamma | 6 | CCL3, HLA-DPA1, XCL1, CCL4, XCL2, LGALS9 |
| GO:0008009~chemokine activity | 5 | CCL3, CKLF, XCL1, CCL4, XCL2 |
| GO:0070098~chemokine-mediated signaling pathway | 7 | CCL3, CXCR4, CCR4, CXCR3, XCL1, CCL4, XCL2 |
| GO:0071347~cellular response to interleukin-1 | 8 | ICAM1, CCL3, RELA, PYCARD, RORA, XCL1, CCL4, XCL2 |
| SM00199:SCY | 4 | CCL3, XCL1, CCL4, XCL2 |
| IPR001811:Chemokine interleukin-8-like domain | 4 | CCL3, XCL1, CCL4, XCL2 |
| GO:0070374~positive regulation of ERK1 and ERK2 cascade | 13 | ICAM1, FBXW7, CCL3, JUN, PYCARD, RIPK2, DSTYK, PTPN22, XCL1, PTEN, CCL4, XCL2, LGALS9 |
| Enrichment Score: 0.17552852657218157 | | |
| Pharmaceutical | 9 | LIF, CSF2, GLA, SOCS3, IFNG, MS4A1, ANXA1, CTLA4, IL2 |
| h_stemPathway:Regulation of hematopoiesis by cytokines | 4 | CSF2, CD8A, CSF1, IL2 |
| 88.Alternatively_Activated_APC | 3 | CSF2, CSF1, IFNG |
| h_inflamPathway:Cytokines and Inflammatory Response | 4 | CSF2, CSF1, IFNG, IL2 |
| IPR009079:Four-helical cytokine-like, core | 5 | LIF, CSF2, CSF1, IFNG, IL2 |
| IPR012351:Four-helical cytokine, core | 4 | LIF, CSF2, IFNG, IL2 |
| Growth factor | 7 | LIF, GMFB, CSF2, CD320, CSF1, GFER, IL2 |
| GO:0005125~cytokine activity | 11 | LIF, CSF2, IL16, TNFSF13B, FAM3C, CSF1, IFNG, CMTM7, CMTM3, CCL4, IL2 |
| GO:0008083~growth factor activity | 8 | LIF, GMFB, CSF2, CD320, CSF1, GFER, NENF, IL2 |

TABLE 3-continued

| HIV- low cutoff | | |
|---|---|---|
| Category | Count | Genes |
| Enrichment Score: 0.1745910687704443 | | |
| domain:LIM zinc-binding 4 | 3 | ABLIM1, LPXN, LIMS1 |
| domain:LIM zinc-binding 3 | 4 | ABLIM1, LPXN, LIMS1, ZYX |
| LIM domain | 7 | ABLIM1, LIMA1, LPXN, LIMS1, LASP1, CSRP1, ZYX |
| domain:LIM zinc-binding 1 | 5 | ABLIM1, LPXN, LIMS1, CSRP1, ZYX |
| domain:LIM zinc-binding 2 | 5 | ABLIM1, LPXN, LIMS1, CSRP1, ZYX |
| SM00132:LIM | 7 | ABLIM1, LIMA1, LPXN, LIMS1, LASP1, CSRP1, ZYX |
| IPR001781:Zinc finger, LIM-type | 7 | ABLIM1, LIMA1, LPXN, LIMS1, LASP1, CSRP1, ZYX |
| Enrichment Score: 0.16053907483471863 | | |
| GO:0051603~proteolysis involved in cellular protein catabolic process | 7 | PSMB10, CTSL, LONP1, CASP8, IDE, CTSA, CTSC |
| GO:0008234~cysteine-type peptidase activity | 5 | CTSL, ATG4B, CASP7, CASP8, CTSC |
| Zymogen | 11 | PSMB10, CTSL, TPP1, CASP7, CASP8, HEXB, CTSA, CTSC, GZMB, PCSK7, FURIN |
| Enrichment Score: 0.15875242349997273 | | |
| domain:EF-hand 5 | 5 | PEF1, CAPNS1, NIN, SDF4, RCN2 |
| calcium-binding region:2 | 13 | NUCB1, EFHD2, PEF1, CAPNS1, ACTN4, MCFD2, NUCB2, RHOT1, RHOT2, CETN2, CHP1, SDF4, RCN2 |
| domain:EF-hand 4 | 7 | PEF1, CAPNS1, NIN, CETN2, CHP1, SDF4, RCN2 |
| IPR011992:EF-hand-like domain | 30 | S100A4, MCL1, REPS1, SPOCK2, UTRN, CETN2, ZZEF1, EFHD2, STAT6, PEF1, EHD1, SDF4, EHD4, TBC1D9B, SYNRG, CAPNS1, ACTN4, NIN, CBL, S100A11, S100A10, CHP1, NUCB1, CBLB, DEF6, NUCB2, MCFD2, RHOT1, RHOT2, RCN2 |
| calcium-binding region:1 | 13 | NUCB1, EFHD2, PEF1, CAPNS1, ACTN4, MCFD2, NUCB2, RHOT1, RHOT2, CETN2, CHP1, SDF4, RCN2 |
| IPR018247:EF-Hand 1, calcium-binding site | 17 | S100A4, CAPNS1, ACTN4, REPS1, S100A11, CETN2, NUCB1, PEF1, GNPTAB, NUCB2, MCFD2, RHOT1, RHOT2, EHD1, SDF4, RCN2, EHD4 |
| IPR002048:EF-hand domain | 22 | S100A4, CAPNS1, ACTN4, NIN, REPS1, S100A11, CHP1, CETN2, ZZEF1, EFHD2, NUCB1, PEF1, GNPTAB, NUCB2, MCFD2, RHOT1, RHOT2, EHD1, SDF4, RCN2, TBC1D9B, EHD4 |
| domain:EF-hand 2 | 16 | S100A4, CAPNS1, NIN, ACTN4, S100A11, CHP1, CETN2, EFHD2, NUCB1, PEF1, MCFD2, NUCB2, RHOT1, RHOT2, SDF4, RCN2 |
| SM00054:EFh | 12 | S100A4, EFHD2, PEF1, ACTN4, NUCB2, RHOT1, S100A11, CETN2, CHP1, ZZEF1, SDF4, RCN2 |
| domain:EF-hand 1 | 15 | S100A4, NIN, ACTN4, S100A11, CHP1, CETN2, EFHD2, NUCB1, PEF1, MCFD2, NUCB2, RHOT1, RHOT2, SDF4, RCN2 |
| domain:EF-hand 3 | 7 | PEF1, CAPNS1, NIN, CETN2, CHP1, SDF4, RCN2 |
| GO:0005509~calcium ion binding | 46 | S100A4, PGS1, ME2, SPOCK2, REPS1, MGMT, CLSTN1, NELL2, CETN2, ZZEF1, EFHD2, PEF1, CD93, GNPTAB, PPP3CB, RUNX1, EHD1, SDF4, EHD4, TBC1D9B, CAPNS1, NIN, ACTN4, C2CD5, SYT11, CBL, ANXA1, S100A11, S100A10, CHP1, STIM1, ANXA5, ANXA2, ITPR2, NUCB1, PLSCR1, CBLB, BNIP2, ATP2C1, MCFD2, NUCB2, RHOT1, CPNE1, RHOT2, SYTL3, RCN2 |
| Calcium | 49 | S100A4, ORAI1, SPOCK2, REPS1, ITGAE, CLSTN1, NELL2, UTRN, TMEM63A, CETN2, OGDH, ITGB1, EFHD2, PEF1, ATP2B4, GNPTAB, TPP1, SNTB1, ENTPD6, CERK, EHD1, SDF4, EHD4, CAPNS1, ACTN4, C2CD5, SYT11, CBL, ANXA1, S100A11, CHP1, STIM1, ANXA5, FURIN, ANXA2, PRKCB, ITPR2, NUCB1, PLSCR1, CBLB, HSPB11, CAMK4, ATP2C1, MCFD2, NUCB2, RHOT1, RHOT2, TMCO1, RCN2 |
| Enrichment Score: 0.1459899659776129 | | |
| GO:1904355~positive regulation of telomere capping | 3 | MAPK1, MAPKAPK5, MAP2K7 |
| GO:0032212~positive regulation of telomere maintenance via telomerase | 4 | MAPK1, MAPKAPK5, MAP2K7, ATM |

TABLE 3-continued

HIV- low cutoff

| Category | Count | Genes |
|---|---|---|
| GO:0051973~positive regulation of telomerase activity Enrichment Score: 0.14095903672022314 | 3 | MAPK1, MAPKAPK5, MAP2K7 |
| hsa05332:Graft-versus-host disease | 5 | IFNG, GZMB, HLA-DPA1, HLA-DPB1, IL2 |
| hsa05330:Allograft rejection | 5 | IFNG, GZMB, HLA-DPA1, HLA-DPB1, IL2 |
| hsa04672:Intestinal immune network for IgA production | 6 | TNFSF13B, CXCR4, HLA-DPA1, HLA-DPB1, MAP3K14, IL2 |
| hsa04940:Type I diabetes mellitus | 5 | IFNG, GZMB, HLA-DPA1, HLA-DPB1, IL2 |
| hsa05320:Autoimmune thyroid disease | 5 | CTLA4, GZMB, HLA-DPA1, HLA-DPB1, IL2 |
| hsa05322:Systemic lupus erythematosus Enrichment Score: 0.1385599701644631 | 6 | HIST4H4, ACTN4, IFNG, H3F3A, HLA-DPA1, HLA-DPB1 |
| hsa00330:Arginine and proline metabolism | 6 | CNDP2, SAT2, AGMAT, SMS, ALDH3A2, ALDH9A1 |
| hsa00410:beta-Alanine metabolism | 4 | CNDP2, SMS, ALDH3A2, ALDH9A1 |
| hsa00340:Histidine metabolism Enrichment Score: 0.13496059793813844 | 3 | CNDP2, ALDH3A2, ALDH9A1 |
| 15.T-cell_polarization-chemokine_receptors | 5 | CXCR4, CCR4, IFNG, CXCR3, TSN |
| IPR000355:Chemokine receptor family | 3 | CXCR4, CCR4, CXCR3 |
| 14.chemokine_receptor-ligand | 3 | CXCR4, CCR4, CXCR3 |
| GO:0070098~chemokine-mediated signaling pathway | 7 | CCL3, CXCR4, CCR4, CXCR3, XCL1, CCL4, XCL2 |
| IPR000276:G protein-coupled receptor, rhodopsin-like | 9 | P2RY8, P2RY10, RABGAP1, HRH2, CXCR4, LPAR6, CCR4, LHCGR, CXCR3 |
| IPR017452:GPCR, rhodopsin-like, 7TM Enrichment Score: 0.12648159925240066 | 9 | P2RY8, P2RY10, RABGAP1, HRH2, CXCR4, LPAR6, CCR4, LHCGR, CXCR3 |
| domain:SAM | 9 | SAMD8, L3MBTL3, SAMD9, STIM1, SAMHD1, DGKH, ARAP2, SAMD9L, SASH3 |
| SM00454:SAM | 9 | SAMD8, ANKS1A, L3MBTL3, SAMD9, STIM1, SAMHD1, DGKH, ARAP2, SASH3 |
| IPR001660:Sterile alpha motif domain | 10 | SAMD8, ANKS1A, L3MBTL3, SAMD9, STIM1, SAMHD1, DGKH, ARAP2, SAMD9L, SASH3 |
| IPR013761:Sterile alpha motif/pointed domain Enrichment Score: 0.12568460664505718 | 11 | SAMD8, ETV7, ANKS1A, L3MBTL3, SAMD9, STIM1, SAMHD1, DGKH, ARAP2, SAMD9L, SASH3 |
| SM00513:SAP | 3 | PIAS4, PIAS1, SAFB2 |
| domain:SAP | 3 | PIAS4, PIAS1, SAFB2 |
| IPR003034:SAP domain Enrichment Score: 0.12346097305495686 | 3 | PIAS4, PIAS1, SAFB2 |
| domain:C2 | 9 | C2CD5, PIK3C2A, PKN2, PRKCH, WWC2, SMURF2, PRKCD, RASA1, PRKCB |
| IPR000008:C2 calcium-dependent membrane targeting | 17 | CEP120, C2CD5, PIK3C2A, SYT11, PKN2, WWC2, PRKCH, PTEN, PRKCD, PRKCB, GAK, UNC13D, CPNE1, SMURF2, SYTL3, RASA1, RASA2 |

TABLE 3-continued

HIV- low cutoff

| Category | Count | Genes |
|---|---|---|
| SM00239:C2 | 12 | UNC13D, C2CD5, PIK3C2A, SYT11, PKN2, CPNE1, PRKCH, SMURF2, SYTL3, RASA1, RASA2, PRKCB |
| Enrichment Score: 0.1227848794008889 | | |
| repeat:2-1 | 4 | HNRNPH2, PRRC2A, CSTF2T, COIL |
| repeat:2-2 | 4 | HNRNPH2, PRRC2A, CSTF2T, COIL |
| repeat:1-1 | 4 | HNRNPH2, PRRC2A, CSTF2T, COIL |
| repeat:1-2 | 3 | HNRNPH2, PRRC2A, COIL |
| Enrichment Score: 0.1141619803729114 | | |
| SM00253:SOCS | 3 | WSB1, SOCS3, SOCS1 |
| domain:SOCS box | 4 | WSB1, SOCS3, SPSB3, SOCS1 |
| SM00969:SM00969 | 4 | WSB1, SOCS3, SPSB3, SOCS1 |
| IPR001496:SOCS protein, C-terminal | 4 | WSB1, SOCS3, SPSB3, SOCS1 |
| Enrichment Score: 0.1035300297726019 | | |
| GO:0050660~flavin adenine dinucleotide binding | 8 | SDHA, IVD, AIFM1, GFER, TXNRD1, DUS1L, ETFA, DUS3L |
| Flavoprotein | 12 | SDHA, SQRDL, IVD, AIFM1, NDUFA9, PYROXD1, GFER, TXNRD1, NDUFA10, DUS1L, ETFA, DUS3L |
| nucleotide phosphate-binding region:FAD | 6 | SDHA, TXNDC12, IVD, AIFM1, TXNRD1, ETFA |
| FAD | 10 | SDHA, SQRDL, IVD, AIFM1, NDUFA9, PYROXD1, GFER, TXNRD1, NDUFA10, ETFA |
| IPR023753:Pyridine nucleotide-disulphide oxidoreductase, FAD/NAD(P)-binding domain | 5 | SDHA, SQRDL, AIFM1, PYROXD1, TXNRD1 |
| Enrichment Score: 0.09911308677931861 | | |
| IPR001202:WW domain | 6 | UTRN, FNBP4, WWC2, IQGAP2, SMURF2, CEP164 |
| SM00456:WW domain:WW 2 | 5 | UTRN, FNBP4, WWC2, SMURF2, CEP164 |
| domain:WW 1 | 3 | FNBP4, WWC2, SMURF2 |
| | 3 | FNBP4, WWC2, SMURF2 |
| Enrichment Score: 0.09869704499668493 | | |
| IPR014352:FERM/acyl-CoA-binding protein, 3-helical bundle | 6 | ECI2, FRMD8, KRIT1, FRMD4B, MSN, ACBD5 |
| domain:FERM | 5 | FRMD8, KRIT1, FRMD4B, JAK2, MSN |
| SM00295:B41 | 5 | FRMD8, KRIT1, FRMD4B, JAK2, MSN |
| IPR000299:FERM domain | 5 | FRMD8, KRIT1, FRMD4B, JAK2, MSN |
| IPR019749:Band 4.1 domain | 5 | FRMD8, KRIT1, FRMD4B, JAK2, MSN |
| IPR019748:FERM central domain | 5 | FRMD8, KRIT1, FRMD4B, JAK2, MSN |
| Enrichment Score: 0.09404515348769645 | | |
| GO:0004623~phospholipase A2 activity | 5 | RARRES3, PNPLA8, ABHD3, PAFAH1B1, PAFAH1B2 |
| GO:0016042~lipid catabolic process | 7 | PLD3, RARRES3, TBL1XR1, DDHD1, PAFAH1B1, PAFAH1B2, IAH1 |
| Lipid degradation | 8 | PLD3, RARRES3, PNPLA8, DDHD1, ABHD2, PAFAH1B1, PAFAH1B2, IAH1 |
| hsa00565:Ether lipid metabolism | 3 | PLD3, PAFAH1B1, PAFAH1B2 |
| Enrichment Score: 0.09224012967461757 | | |
| GO:0006418~tRNA aminoacylation for protein translation | 5 | EEF1E1, FARS2, FARSB, WARS2, YARS2 |

TABLE 3-continued

HIV- low cutoff

| Category | Count | Genes |
|---|---|---|
| Aminoacyl-tRNA synthetase | 4 | FARS2, FARSB, WARS2, YARS2 |
| hsa00970:Aminoacyl-tRNA biosynthesis | 5 | FARS2, FARSB, WARS2, YARS2, MTFMT |
| Enrichment Score: 0.09104106578512094 | | |
| domain:BACK | 4 | KLHL9, KEAP1, KLHL24, IVNS1ABP |
| IPR015916:Galactose oxidase, beta-propeller | 4 | KLHL9, KEAP1, KLHL24, IVNS1ABP |
| GO:0031463~Cul3-RING ubiquitin ligase complex | 8 | CUL3, KBTBD2, BACH2, KLHL9, KEAP1, KLHL24, KCTD2, SPOP |
| IPR017096:Kelch-like protein, gigaxonin | 5 | KBTBD2, KLHL9, KEAP1, KLHL24, IVNS1ABP |
| PIRSF037037:kelch-like protein, gigaxonin type | 5 | KBTBD2, KLHL9, KEAP1, KLHL24, IVNS1ABP |
| SM00875:SM00875 | 6 | KBTBD2, KLHL9, BTBD7, KEAP1, KLHL24, IVNS1ABP |
| IPR011705:BTB/Kelch-associated | 6 | KBTBD2, KLHL9, BTBD7, KEAP1, KLHL24, IVNS1ABP |
| repeat:Kelch 6 | 5 | MKLN1, KLHL9, KEAP1, KLHL24, IVNS1ABP |
| repeat:Kelch 5 | 6 | MKLN1, KBTBD2, KLHL9, KEAP1, KLHL24, IVNS1ABP |
| IPR006652:Kelch repeat type 1 | 6 | MKLN1, KBTBD2, KLHL9, KEAP1, KLHL24, IVNS1ABP |
| repeat:Kelch 4 | 6 | MKLN1, KBTBD2, KLHL9, KEAP1, KLHL24, IVNS1ABP |
| SM00612:Kelch | 5 | KBTBD2, KLHL9, KEAP1, KLHL24, IVNS1ABP |
| Kelch repeat | 6 | MKLN1, KBTBD2, KLHL9, KEAP1, KLHL24, IVNS1ABP |
| repeat:Kelch 2 | 6 | MKLN1, KBTBD2, KLHL9, KEAP1, KLHL24, IVNS1ABP |
| repeat:Kelch 3 | 6 | MKLN1, KBTBD2, KLHL9, KEAP1, KLHL24, IVNS1ABP |
| repeat:Kelch 1 | 6 | MKLN1, KBTBD2, KLHL9, KEAP1, KLHL24, IVNS1ABP |
| IPR015915:Kelch-type beta propeller | 3 | MKLN1, KBTBD2, KEAP1 |
| Enrichment Score: 0.09096561156622553 | | |
| GO:0008037~cell recognition | 4 | TIGIT, CD5, CD200, CD226 |
| GO:0050839~cell adhesion molecule binding | 5 | TIGIT, MSN, CD200, ITGB1, CD226 |
| GO:0007157~heterophilic cell-cell adhesion via plasma membrane cell adhesion molecules | 4 | TIGIT, ICAM1, CD200, CD226 |
| GO:0007156~homophilic cell adhesion via plasma membrane adhesion molecules | 7 | CD84, TIGIT, ME2, CLSTN1, CD200, ITGB1, CD226 |
| Enrichment Score: 0.08637800045583548 | | |
| GO:0005544~calcium-dependent phospholipid binding | 7 | C2CD5, SYT11, ANXA1, CPNE1, SYTL3, ANXA5, ANXA2 |
| SM00239:C2 | 12 | UNC13D, C2CD5, PIK3C2A, SYT11, PKN2, CPNE1, PRKCH, SMURF2, SYTL3, RASA1, RASA2, PRKCB |
| domain:C2 2 | 5 | UNC13D, SYT11, CPNE1, SYTL3, RASA2 |
| domain:C2 1 | 5 | UNC13D, SYT11, CPNE1, SYTL3, RASA2 |
| Enrichment Score: 0.08611979646447755 | | |
| IPR001751:S100/Calbindin-D9k, conserved site | 3 | S100A4, S100A11, S100A10 |
| SM01394:SM01394 | 3 | S100A4, S100A11, S100A10 |
| IPR013787:S100/CaBP-9k-type, calcium binding, subdomain | 3 | S100A4, S100A11, S100A10 |

TABLE 3-continued

HIV- low cutoff

| Category | Count | Genes |
|---|---|---|
| Enrichment Score: 0.08562305074820027 | | |
| GO:0034199~activation of protein kinase A activity | 3 | PRKAR2A, ADCY7, PRKACB |
| GO:0003091~renal water homeostasis | 3 | PRKAR2A, ADCY7, PRKACB |
| GO:0071377~cellular response to glucagon stimulus | 3 | PRKAR2A, ADCY7, PRKACB |
| Enrichment Score: 0.0850459219054058 | | |
| DNA-binding region:ETS | 3 | ETV7, ELF2, ELK3 |
| SM00413:ETS | 3 | ETV7, ELF2, ELK3 |
| IPR000418:Ets domain | 3 | ETV7, ELF2, ELK3 |
| Enrichment Score: 0.08339481617003926 | | |
| GO:0004715~non-membrane spanning protein tyrosine kinase activity | 7 | DYRK1A, ZAP70, RIPK2, JAK2, ABL2, PRKCD, MATK |
| IPR001245:Serine-threonine/tyrosine-protein kinase catalytic domain | 15 | IRAK1, RYK, DSTYK, RAF1, GAK, IRAK4, RIPK1, ARAF, ILK, ZAP70, RIPK2, JAK2, ABL2, MAP3K13, MATK |
| Tyrosine-protein kinase | 11 | CLK2, RYK, DYRK1A, CLK4, MAP2K4, ZAP70, DSTYK, JAK2, MAP2K7, ABL2, MATK |
| GO:0031234~extrinsic component of cytoplasmic side of plasma membrane | 7 | KRAS, RGS1, TIAM1, ZAP70, JAK2, ABL2, MATK |
| GO:0038083~peptidyl-tyrosine autophosphorylation | 4 | ZAP70, JAK2, ABL2, MATK |
| GO:0004713~protein tyrosine kinase activity | 13 | CSF2, ZMYM2, CLK2, RYK, DYRK1A, CLK4, MAP2K4, ZAP70, DSTYK, JAK2, MAP2K7, ABL2, MATK |
| GO:0018108~peptidyl-tyrosine phosphorylation | 15 | CSF2, ZMYM2, RYK, MAP2K4, TRIM27, DSTYK, PRKCD, CLK2, CLK4, DYRK1A, ZAP70, RIPK2, JAK2, MAP2K7, ABL2 |
| GO:0007169~trans membrane receptor protein tyrosine kinase signaling pathway | 7 | CD8A, CD8B, CSF1, ZAP70, RAPGEF1, ABL2, MATK |
| SM00219:TyrKc | 5 | RYK, ZAP70, JAK2, ABL2, MATK |
| IPR020635:Tyrosine-protein kinase, catalytic domain | 5 | RYK, ZAP70, JAK2, ABL2, MATK |
| IPR008266:Tyrosine-protein kinase, active site | 5 | RYK, ZAP70, JAK2, ABL2, MATK |
| Enrichment Score: 0.07308177427976495 | | |
| GO:0004553~hydrolase activity, hydrolyzing O-glycosyl compounds | 4 | CHID1, GLA, HEXB, HEXDC |
| IPR017853:Glycoside hydrolase, superfamily | 5 | CHID1, GLA, HEXB, MGEA5, HEXDC |
| Glycosidase | 7 | GLA, NEIL2, HEXB, MGEA5, MOGS, OGG1, HEXDC |
| IPR013781:Glycoside hydrolase, catalytic domain | 3 | CHID1, HEXB, HEXDC |
| Enrichment Score: 0.07228030757809481 | | |
| repeat:Solcar 3 | 5 | SLC25A32, SLC25A38, SLC25A28, SLC25A16, SLC25A53 |
| repeat:Solcar 1 | 5 | SLC25A32, SLC25A38, SLC25A28, SLC25A16, SLC25A53 |

TABLE 3-continued

HIV- low cutoff

| Category | Count | Genes |
|---|---|---|
| repeat:Solcar 2 | 5 | SLC25A32, SLC25A38, SLC25A28, SLC25A16, SLC25A53 |
| IPR023395:Mitochondrial carrier domain | 5 | SLC25A32, SLC25A38, SLC25A28, SLC25A16, SLC25A53 |
| IPR018108:Mitochondrial substrate/solute carrier | 5 | SLC25A32, SLC25A38, SLC25A28, SLC25A16, SLC25A53 |
| Enrichment Score: 0.07048632895684756 | | |
| Viral nucleoprotein | 3 | EFTUD2, LARP1B, HNRNPLL |
| GO:0019013~viral nucleocapsid | 3 | EFTUD2, LARP1B, HNRNPLL |
| Virion | 4 | ERVK13-1, EFTUD2, LARP1B, HNRNPLL |
| Enrichment Score: 0.07022853299749594 | | |
| zinc finger region:FYVE-type | 4 | PLEKHF2, HGS, EEA1, RFFL |
| SM00064:FYVE | 3 | PLEKHF2, HGS, EEA1 |
| IPR000306:Zinc finger, FYVE-type | 3 | PLEKHF2, HGS, EEA1 |
| IPR017455:Zinc finger, FYVE-related | 3 | PLEKHF2, HGS, EEA1 |
| Enrichment Score: 0.06811532390904307 | | |
| zinc finger region:C2H2-type 2; degenerate | 11 | ZNF43, ZNF529, ZNF44, ZNF28, ZNF121, ZNF675, ZNF766, ATMIN, ZNF586, ZBTB38, ZNF37A |
| zinc finger region:C2H2-type 4; degenerate | 5 | ZNF43, ZNF28, ZNF131, ZNF675, ZNF493 |
| zinc finger region:C2H2-type 22 | 4 | ZNF43, ZNF721, ZNF268, ZNF493 |
| zinc finger region:C2H2-type 21 | 4 | ZNF43, ZNF268, ZNF780B, ZNF493 |
| GO:0003676~nucleic acid binding | 112 | RALY, ZNF583, CNOT8, RNASEH1, ZNF638, SART3, DDX23, ZFP90, TIA1, TARDBP, DHX34, RBM10, ZNF101, ZNF43, R3HCC1, ZNF44, ZNF644, ZNF814, ZNF7, DHX29, ZNF587, ZNF586, ZNF430, SETD1A, ZNF131, RAC1, PPIL4, DDX42, ZNF529, IKZF2, KIAA1586, KLF13, SREK1, ZNF121, ZBTB40, MTHFSD, ENDOD1, SAFB2, JAZF1, PPRC1, HIVEP1, RNPC3, POP7, DDX51, ZNF292, ZNF534, ENOX2, KIAA0430, ZNF675, ZKSCAN1, HNRNPLL, ZEB1, ZBTB38, ZNF148, AEN, RBAK-RBAKDN, ZNF721, ZNF720, TSEN2, ZCCHC6, ZNF493, ZCCHC7, ZCCHC10, RBM42, ZFX, SPEN, TTF2, RECQL, POGK, RBMX2, ZNF746, CPSF4, ZNF740, ZNF276, ZNF275, ZNF274, RBM33, ZBTB10, ZBTB11, CBLL1, ERB, ZNF780B, ZNF780A, SF3B4, SF3B3, CHD1L, DDX19A, REXO1, AGO2, DHX16, ZSCAN25, MSI2, THAP1, ZNF268, RBM28, EHD4, TTC14, RBM23, ZNF28, ALYREF, TRIM27, RAF1, GPANK1, SAMHD1, SF3A2, ZNF664, ZNF672, POLDIP3, RBM19, ZNF764, ZNF766, RBM15 |
| zinc finger region:C2H2-type 20 | 4 | ZNF43, ZNF268, ZNF780B, ZNF493 |
| zinc finger region:C2H2-type 1; degenerate | 12 | ZNF529, ZNF44, ZNF28, ZNF121, ZNF800, ZNF675, ZNF746, ZNF721, ZNF766, ZNF493, ZNF586, ZNF37A |
| zinc finger region:C2H2-type 17 | 8 | ZNF43, ZNF44, ZNF28, ZNF721, ZNF268, ZNF780B, ZNF780A, ZNF493 |
| zinc finger region:C2H2-type 18 | 6 | ZNF43, ZNF28, ZNF721, ZNF268, ZNF780B, ZNF493 |
| zinc finger region:C2H2-type 19 | 5 | ZNF43, ZNF721, ZNF268, ZNF780B, ZNF493 |
| zinc finger region:C2H2-type 15 | 11 | ZNF43, ZNF44, ZNF534, ZNF28, ZNF675, ZNF7, ZNF721, ZNF268, ZNF780B, ZNF780A, ZNF493 |
| zinc finger region:C2H2-type 16 | 8 | ZNF43, ZNF44, ZNF28, ZNF721, ZNF268, ZNF780B, ZNF780A, ZNF493 |

TABLE 3-continued

| | HIV- low cutoff | |
|---|---|---|
| Category | Count | Genes |
| zinc finger region:C2H2-type 14 | 12 | ZNF43, ZNF44, ZNF672, ZNF534, ZNF28, ZNF675, ZNF7, ZNF721, ZNF268, ZNF780B, ZNF780A, ZNF493 |
| zinc finger region:C2H2-type 1 | 49 | ZNF276, ZNF275, ZNF430, ZNF274, ZNF292, ZNF534, ZNF583, ZBTB10, ZBTB11, ZNF131, ZNF511, CTCF, ZKSCAN1, ZEB1, ZNF780B, ZNF780A, ZBTB38, ZNF148, ZFP90, ZSCAN25, ZNF394, ZNF268, ZNF101, PLAGL2, IKZF5, ZNF43, EGR1, IKZF2, ZNF644, KLF13, KLF10, ZHX1, ZFX, ZBTB40, ZNF7, ATMIN, TRERF1, ZNF664, ZNF672, SP1, ZNF277, JAZF1, HIVEP2, PRDM2, ZBTB2, HIVEP1, ZNF764, ZNF587, ZNF740 |
| zinc finger region:C2H2-type 10 | 28 | ZNF275, ZNF430, ZNF583, ZNF534, ZBTB11, ZNF675, CTCF, ZNF780B, ZNF780A, ZBTB38, ZFP90, ZNF721, ZNF268, ZNF493, ZNF101, ZNF43, ZNF529, ZNF44, ZNF28, ZNF121, ZFX, ZBTB40, ZNF7, ZNF37A, ZNF672, ZNF587, ZNF766, ZNF586 |
| zinc finger region:C2H2-type 9 | 31 | ZNF275, ZNF292, ZNF430, ZNF583, ZNF534, ZBTB11, ZNF675, CTCF, ZNF780B, ZNF780A, ZBTB38, ZFP90, ZNF721, ZNF268, ZNF493, ZNF101, ZNF43, ZNF529, ZNF44, ZNF28, POGZ, ZNF121, ZFX, ZBTB40, ZNF7, ZNF37A, ZNF664, ZNF672, ZNF587, ZNF766, ZNF586 |
| zinc finger region:C2H2-type 11 | 23 | ZNF43, ZNF275, ZNF529, ZNF430, ZNF44, ZNF583, ZNF534, ZNF28, ZNF121, ZBTB11, ZFX, ZNF675, ZNF7, ZNF780B, ZNF780A, ZNF37A, ZNF672, ZFP90, ZNF721, ZNF268, ZNF587, ZNF493, ZNF586 |
| zinc finger region:C2H2-type 12 | 19 | ZNF43, ZNF44, ZNF583, ZNF534, ZNF28, ZBTB11, ZFX, ZBTB40, ZNF675, ZNF7, ZNF780B, ZNF780A, ZNF37A, ZNF672, ZFP90, ZNF721, ZNF268, ZNF587, ZNF493 |
| zinc finger region:C2H2-type 2 | 52 | ZNF292, ZNF583, ZNF534, ZKSCAN1, CTCF, ZEB1, ZNF148, ZFP90, ZNF394, ZNF721, ZNF493, ZNF101, EGR1, ZNF44, ZNF644, POGZ, ZHX1, ZFX, ZNF7, TRERF1, ZNF277, PRDM2, ZNF746, ZNF587, ZNF740, ZNF276, ZNF275, ZNF274, ZNF430, ZBTB10, ZBTB11, ZNF131, ZNF800, ZNF511, ZNF780B, ZNF780A, ZSCAN25, ZNF268, PLAGL2, IKZF5, IKZF2, KLF13, KLF10, ZBTB40, ZNF664, ZNF672, SP1, JAZF1, HIVEP2, HIVEP1, ZBTB2, ZNF764 |
| zinc finger region:C2H2-type 6 | 41 | ZNF275, ZNF430, ZNF292, ZNF583, ZNF534, ZBTB11, ZNF131, ZNF800, ZNF675, ZKSCAN1, CTCF, ZEB1, ZNF780B, ZNF780A, ZBTB38, ZFP90, ZSCAN25, ZNF721, ZNF394, ZNF268, ZNF101, PLAGL2, ZNF43, ZNF529, ZNF44, IKZF2, ZNF644, ZNF28, POGZ, ZNF121, ZFX, ZBTB40, ZNF7, ZNF664, ZNF37A, ZNF672, PRDM2, ZNF764, ZNF587, ZNF766, ZNF586 |
| IPR007087:Zinc finger, C2H2 | 72 | ZNF292, ZNF534, ZNF583, ZNF675, CTCF, ZKSCAN1, ZEB1, ZNF638, ZBTB38, BRPF1, ZNF148, ZFP90, ZNF106, ZNF721, ZNF394, RBM10, ZNF493, ZNF101, ZNF43, EGR1, ZNF44, ZNF644, POGZ, ZFX, ZHX1, ZNF814, APTX, ZNF7, TRERF1, ZNF37A, ZNF277, PRDM2, ZNF746, ZNF587, ZNF740, ZNF586, ZNF276, DPF2, ZNF275, ZNF430, ZNF274, ZBTB10, ZBTB11, ZNF131, ZNF800, ZNF511, DUSP12, EEA1, ZNF780B, ZNF780A, ZSCAN25, ZNF268, PLAGL2, IKZF5, ZNF529, IKZF2, ZNF28, KLF13, ZNF121, KLF10, ZBTB40, FOXP3, ATMIN, ZNF664, ZNF672, SP1, JAZF1, HIVEP2, HIVEP1, ZBTB2, ZNF764, ZNF766 |
| SM00355:ZnF_C2H2 | 66 | ZNF292, ZNF534, ZNF583, ZNF675, CTCF, ZKSCAN1, ZEB1, ZNF638, ZBTB38, ZNF148, ZFP90, ZNF106, ZNF721, ZNF394, ZNF493, ZNF101, ZNF43, EGR1, ZNF44, ZNF644, POGZ, ZFX, ZHX1, ZNF814, ZNF7, TRERF1, ZNF37A, ZNF277, PRDM2, ZNF746, ZNF587, ZNF740, ZNF586, ZNF276, DPF2, ZNF275, ZNF430, ZNF274, ZBTB10, ZBTB11, ZNF131, ZNF800, ZNF511, ZNF780B, ZNF780A, ZSCAN25, ZNF268, PLAGL2, IKZF5, ZNF529, IKZF2, ZNF28, KLF13, ZNF121, KLF10, ZBTB40, ATMIN, ZNF664, ZNF672, SP1, JAZF1, HIVEP2, HIVEP1, ZBTB2, ZNF764, ZNF766 |
| zinc finger region:C2H2-type 13 | 14 | ZNF43, ZNF44, ZNF534, ZNF28, ZFX, ZNF675, ZNF7, ZNF780B, ZNF780A, ZNF672, ZFP90, ZNF268, ZNF587, ZNF493 |
| zinc finger region:C2H2-type 5 | 44 | ZNF276, ZNF275, ZNF430, ZNF274, ZNF292, ZNF583, ZNF534, ZBTB11, ZNF131, ZNF800, ZNF675, ZKSCAN1, CTCF, ZEB1, ZNF780B, ZNF780A, ZBTB38, ZFP90, ZSCAN25, ZNF394, ZNF268, ZNF493, ZNF101, PLAGL2, IKZF5, ZNF43, ZNF529, ZNF44, IKZF2, ZNF644, ZNF28, POGZ, ZNF121, ZFX, ZBTB40, ZNF7, ZNF664, ZNF37A, PRDM2, HIVEP1, ZNF764, ZNF587, ZNF766, ZNF586 |
| domain:KRAB | 25 | ZNF275, ZNF430, ZNF534, ZNF583, ZNF675, ZKSCAN1, ZNF780B, ZNF780A, ZFP90, ZNF394, ZNF268, ZNF720, ZNF101, ZNF43, ZNF529, ZNF44, ZNF28, ZNF7, ZNF37A, POGK, ZNF764, ZNF746, ZNF587, ZNF766, ZNF586 |
| IPR015880:Zinc finger, C2H2-like | 66 | ZNF292, ZNF534, ZNF583, ZNF675, CTCF, ZKSCAN1, ZEB1, ZNF638, ZBTB38, ZNF148, ZFP90, ZNF106, ZNF721, ZNF394, ZNF493, ZNF101, ZNF43, EGR1, ZNF44, ZNF644, POGZ, ZFX, ZHX1, ZNF814, ZNF7, TRERF1, ZNF37A, ZNF277, PRDM2, ZNF746, ZNF587, ZNF740, ZNF586, ZNF276, DPF2, ZNF275, ZNF430, ZNF274, ZBTB10, ZBTB11, ZNF131, ZNF800, ZNF511, ZNF780B, ZNF780A, ZSCAN25, ZNF268, PLAGL2, IKZF5, ZNF529, IKZF2, ZNF28, KLF13, ZNF121, KLF10, ZBTB40, ATMIN, ZNF664, ZNF672, SP1, JAZF1, HIVEP2, HIVEP1, ZBTB2, ZNF764, ZNF766 |

TABLE 3-continued

| | HIV- low cutoff | |
|---|---|---|
| Category | Count | Genes |
| SM00349:KRAB | 29 | ZNF274, ZNF430, ZNF583, ZNF534, ZNF675, ZKSCAN1, ZNF780B, ZNF780A, ZFP90, RBAK-RBAKDN, ZNF394, ZNF721, ZNF268, ZNF720, ZNF493, ZNF101, ZNF43, ZNF529, ZNF44, ZNF28, ZNF814, ZNF7, ZNF37A, POGK, ZNF764, ZNF746, ZNF587, ZNF766, ZNF586 |
| IPR013087:Zinc finger C2H2-type/integrase DNA-binding domain | 60 | ZNF292, ZNF583, ZNF534, ZNF675, ZKSCAN1, CTCF, ZEB1, ZBTB38, ZNF148, ZFP90, ZNF721, ZNF394, ZNF493, ZNF101, ZNF43, EGR1, ZNF44, ZNF644, ZFX, ZNF814, ZNF7, ZNF37A, PRDM2, ZNF746, ZNF587, ZNF740, ZNF586, ZNF276, ZNF275, ZNF430, ZNF274, ZBTB10, ZBTB11, ZNF131, ZNF800, ZNF511, CBLL1, ZNF780B, ZNF780A, ZSCAN25, ZNF268, PLAGL2, IKZF5, ZNF529, IKZF2, ZNF28, KLF13, ZNF121, KLF10, ZBTB40, FOXP3, ZNF664, ZNF672, SP1, JAZF1, HIVEP2, HIVEP1, ZBTB2, ZNF764, ZNF766 |
| zinc finger region:C2H2-type 3 | 50 | ZNF292, ZNF583, ZNF534, ZKSCAN1, CTCF, ZEB1, ZBTB38, ZNF148, ZFP90, ZNF394, ZNF493, EGR1, ZNF44, ZNF644, POGZ, ZFX, ZNF7, TRERF1, ZNF37A, PRDM2, ZNF746, ZNF587, ZNF276, ZNF275, ZNF274, ZNF430, ZBTB11, ZNF131, ZNF800, ZNF511, ZNF780B, ZNF780A, ZSCAN25, ZNF268, PLAGL2, IKZF5, ZNF529, IKZF2, ZNF28, KLF13, ZNF121, KLF10, ZBTB40, ZNF664, ZNF672, SP1, HIVEP2, HIVEP1, ZNF764, ZNF766 |
| IPR001909:Krueppel-associated box | 30 | ZNF274, ZNF430, ZNF583, ZNF534, ZNF675, ZKSCAN1, ZNF780B, ZNF780A, ZFP90, ZSCAN25, RBAK-RBAKDN, ZNF394, ZNF721, ZNF268, ZNF720, ZNF493, ZNF101, ZNF43, ZNF529, ZNF44, ZNF28, ZNF814, ZNF7, ZNF37A, POGK, ZNF746, ZNF764, ZNF587, ZNF766, ZNF586 |
| zinc finger region:C2H2-type 7 | 34 | ZNF275, ZNF430, ZNF292, ZNF583, ZNF534, ZBTB11, ZNF800, ZNF675, CTCF, ZNF780B, ZNF780A, ZBTB38, ZFP90, ZNF721, ZNF394, ZNF268, ZNF101, ZNF43, ZNF529, ZNF44, ZNF644, ZNF28, POGZ, ZNF121, ZFX, ZBTB40, ZNF7, ZNF37A, ZNF664, ZNF672, ZNF764, ZNF587, ZNF766, ZNF586 |
| zinc finger region:C2H2-type 8 | 30 | ZNF275, ZNF292, ZNF430, ZNF583, ZNF534, ZBTB11, ZNF675, CTCF, ZNF780B, ZNF780A, ZBTB38, ZFP90, ZNF721, ZNF268, ZNF101, ZNF43, ZNF529, ZNF44, ZNF28, POGZ, ZNF121, ZFX, ZBTB40, ZNF7, ZNF37A, ZNF664, ZNF672, ZNF587, ZNF766, ZNF586 |
| zinc finger region:C2H2-type 4 | 43 | ZNF276, ZNF275, ZNF430, ZNF274, ZNF292, ZNF583, ZNF534, ZBTB11, ZNF800, ZKSCAN1, CTCF, ZNF780B, ZNF780A, ZBTB38, ZNF148, ZFP90, ZSCAN25, ZNF721, ZNF394, ZNF268, ZNF101, PLAGL2, IKZF5, ZNF529, ZNF44, IKZF2, ZNF644, POGZ, ZNF121, ZFX, ZBTB40, ZNF7, ZNF37A, ZNF664, ZNF672, HIVEP2, PRDM2, HIVEP1, ZNF746, ZNF764, ZNF587, ZNF766, ZNF586 |
| Enrichment Score: 0.06745858636176846 | | |
| short sequence motif:Box 1 motif | 3 | IL2RB, IL6ST, IL4R |
| short sequence motif:WSXWS motif | 3 | IL2RB, IL6ST, IL4R |
| IPR003961:Fibronectin, type III | 9 | ATF7IP, IFNAR2, IL2RB, IL6ST, IL4R, LRRN3, IFNGR2, ATF7IP2, IFNAR1 |
| Enrichment Score: 0.06738194626763314 | | |
| domain:Ig-like C1-type | 4 | HLA-DPA1, MR1, HLA-DPB1, TAPBPL |
| region of interest:Connecting peptide | 4 | HLA-DPA1, MR1, HLA-DPB1, CRYBB2 |
| GO:0042605~peptide antigen binding | 3 | HLA-DPA1, MR1, HLA-DPB1 |
| IPR003597:Immunoglobulin C1-set | 6 | HLA-DPA1, MR1, HLA-DPB1, TRDC, TAPBPL, IGHM |
| IPR003006:Immunoglobulin/major histocompatibility complex, conserved site | 5 | HLA-DPA1, MR1, HLA-DPB1, TAPBPL, IGHM |
| SM00407:IGc1 | 5 | HLA-DPA1, MR1, HLA-DPB1, TAPBPL, IGHM |
| IPR011162:MHC classes I/II-like antigen recognition protein | 3 | HLA-DPA1, MR1, HLA-DPB1 |
| Enrichment Score: 0.0547491368027546 | | |
| IPR023415:Low-density lipoprotein (LDL) receptor class A, conserved site | 4 | DGCR2, CD320, LRP10, LDLRAD4 |

TABLE 3-continued

HIV- low cutoff

| Category | Count | Genes |
|---|---|---|
| SM00192:LDLa | 4 | DGCR2, CD320, LRP10, LDLRAD4 |
| IPR002172:Low-density lipoprotein (LDL) receptor class A repeat<br>Enrichment Score: 0.05398774065645578 | 4 | DGCR2, CD320, LRP10, LDLRAD4 |
| metal ion-binding site:Calcium 3 | 3 | SYT11, PMF1, PRKCB |
| metal ion-binding site:Calcium 2 | 5 | ATP2C1, SYT11, PMF1, FURIN, PRKCB |
| metal ion-binding site:Calcium 1<br>Enrichment Score: 0.05304803073201943 | 4 | SYT11, PMF1, FURIN, PRKCB |
| Thiol protease inhibitor | 4 | XIAP, CARD16, CSTB, BIRC6 |
| GO:0004869~cysteine-type endopeptidase inhibitor activity | 3 | CARD16, CSTB, BIRC6 |
| GO:0010951~negative regulation of endopeptidase activity | 8 | SERPINB9, CARD16, SPOCK2, CSTB, SERPINB1, BIRC6, FURIN, APLP2 |
| Protease inhibitor | 7 | SERPINB9, XIAP, CARD16, CSTB, SERPINB1, BIRC6, APLP2 |
| Serine protease inhibitor | 3 | SERPINB9, SERPINB1, APLP2 |
| GO:0004867~serine-type endopeptidase inhibitor activity<br>Enrichment Score: 0.04732472305636867 | 4 | SERPINB9, SERPINB1, FURIN, APLP2 |
| GO:0046983~protein dimerization activity | 16 | E2F3, E2F4, AIFM1, PEX3, MXI1, ATM, MXD4, SREBF2, PEF1, NCOA1, NCOA2, HES4, NUP210, GATA3, PPP3CB, FBXW11 |
| DNA-binding region:Basic motif | 16 | BACH2, CREBZF, CREB1, MXI1, MXD4, SREBF2, ATF6, ATF5, FOS, NCOA1, NCOA2, HES4, JUN, NFE2L2, NFE2L3, TCF3 |
| SM00353:HLH | 7 | NCOA1, NCOA2, HES4, MXI1, TCF3, MXD4, SREBF2 |
| domain:Helix-loop-helix motif | 7 | NCOA1, NCOA2, HES4, MXI1, TCF3, MXD4, SREBF2 |
| IPR011598:Myc-type, basic helix-loop-helix (bHLH) domain<br>Enrichment Score: 0.04017008442387107 | 7 | NCOA1, NCOA2, HES4, MXI1, TCF3, MXD4, SREBF2 |
| hsa04918:Thyroid hormone synthesis | 9 | GPX1, ADCY7, CREB1, PRKACB, PDIA4, GPX7, TTF2, PRKCB, ITPR2 |
| hsa04925:Aldosterone synthesis and secretion | 9 | ORAI1, CAMK4, ADCY7, CREB1, NR4A1, PRKACB, PRKD3, PRKCB, ITPR2 |
| hsa04750:Inflammatory mediator regulation of TRP channels | 10 | ADCY7, MAPK13, PRKCH, MAPK8, PRKACB, PRKCD, PPP1CB, PIK3R1, PRKCB, ITPR2 |
| hsa04971:Gastric acid secretion | 5 | ADCY7, HRH2, PRKACB, PRKCB, ITPR2 |
| hsa04970:Salivary secretion | 6 | ATP2B4, ADCY7, PRKACB, VAMP2, PRKCB, ITPR2 |
| hsa04723:Retrograde endocannabinoid signaling | 7 | MAPK1, ADCY7, MAPK13, MAPK8, PRKACB, PRKCB, ITPR2 |
| hsa04724:Glutamatergic synapse | 8 | MAPK1, GRM4, GLUL, ADCY7, PPP3CB, PRKACB, PRKCB, ITPR2 |
| hsa05032:Morphine addiction | 6 | ADCY7, PDE7A, PDE4B, PDE4D, PRKACB, PRKCB |
| hsa04713:Circadian entrainment | 6 | MAPK1, FOS, ADCY7, CREB1, PRKACB, PRKCB |
| hsa04020:Calcium signaling pathway | 13 | PHKA2, PPIF, ORAI1, ATP2B4, CAMK4, ADCY7, HRH2, LHCGR, PPP3CB, STIM1, PRKACB, PRKCB, ITPR2 |
| hsa04911:Insulin secretion | 5 | ADCY7, CREB1, PRKACB, VAMP2, PRKCB |

TABLE 3-continued

| HIV- low cutoff | | |
|---|---|---|
| Category | Count | Genes |
| hsa04727:GABAergic synapse | 5 | GABARAPL2, GLUL, ADCY7, PRKACB, PRKCB |
| hsa04972:Pancreatic secretion | 5 | ATP2B4, ADCY7, RAC1, PRKCB, ITPR2 |
| Enrichment Score: 0.03512913972098621 | | |
| domain:IQ 1 | 3 | CAMTA2, IQGAP2, MYO9B |
| domain:IQ 2 | 3 | CAMTA2, IQGAP2, MYO9B |
| IPR000048:IQ motif, EF-hand binding site | 3 | CAMTA2, IQGAP2, MYO9B |
| Enrichment Score: 0.03283703716156655 | | |
| GO:0035025~positive regulation of Rho protein signal transduction | 4 | P2RY8, P2RY10, LPAR6, RAC1 |
| GO:0051482~positive regulation of cytosolic calcium ion concentration involved in phospholipase C-activating G-protein coupled signaling pathway | 3 | P2RY8, P2RY10, LPAR6 |
| hsa04080:Neuroactive ligand-receptor interaction | 7 | P2RY8, GRM4, TSPO, P2RY10, HRH2, LPAR6, LHCGR |
| IPR000276:G protein-coupled receptor, rhodopsin-like | 9 | P2RY8, P2RY10, RABGAP1, HRH2, CXCR4, LPAR6, CCR4, LHCGR, CXCR3 |
| G-protein coupled receptor | 10 | P2RY8, GRM4, P2RY10, RABGAP1, HRH2, CXCR4, LPAR6, CCR4, LHCGR, CXCR3 |
| IPR017452:GPCR, rhodopsin-like, 7TM | 9 | P2RY8, P2RY10, RABGAP1, HRH2, CXCR4, LPAR6, CCR4, LHCGR, CXCR3 |
| GO:0004930~G-protein coupled receptor activity | 9 | P2RY8, GRM4, P2RY10, RABGAP1, TM2D1, CXCR4, LPAR6, IGF2R, TPRA1 |
| Transducer | 11 | GNA13, P2RY8, GRM4, P2RY10, RABGAP1, HRH2, CXCR4, LPAR6, CCR4, LHCGR, CXCR3 |
| Enrichment Score: 0.015490657362452302 | | |
| domain:Ig-like V-type | 13 | TIGIT, BTLA, BSG, CD8A, CD8B, CTLA4, CD79B, TAPBPL, CD200, BTN3A2, LSR, LAG3, PDCD1 |
| Immunoglobulin domain | 29 | CD8A, CD8B, IL6ST, IGHM, LSR, PDCD1, EMB, MR1, LAG3, ICAM1, IL18R1, C10ORF54, BSG, LRRN3, ICAM3, CTLA4, MALT1, SLAMF7, TIGIT, BTLA, CD84, IGSF8, BTN3A1, CD79B, MFAP3, TAPBPL, BTN3A2, CD200, CD226 |
| SM00409:IG | 27 | CD8A, CD8B, IGHM, LSR, PDCD1, EMB, LAG3, ICAM1, IL18R1, C10ORF54, BSG, LRRN3, ICAM3, CTLA4, MALT1, TIGIT, BTLA, CD84, IGSF8, BTN3A1, SP1, CD79B, MFAP3, TAPBPL, CD200, BTN3A2, CD226 |
| IPR003599:Immunoglobulin subtype | 27 | CD8A, CD8B, IGHM, LSR, PDCD1, EMB, LAG3, ICAM1, IL18R1, C10ORF54, BSG, LRRN3, ICAM3, CTLA4, MALT1, TIGIT, BTLA, CD84, IGSF8, BTN3A1, SP1, CD79B, MFAP3, TAPBPL, CD200, BTN3A2, CD226 |
| SM00406:IGv | 8 | BTN3A1, CD8A, CD8B, CTLA4, IGHM, BTN3A2, CD200, PDCD1 |
| IPR013106:Immunoglobulin V-set | 16 | C10ORF54, CD8A, CD8B, CTLA4, SLAMF7, IGHM, PDCD1, TIGIT, BTN3A1, IGSF8, SP1, CD79B, TAPBPL, CD200, CD226, BTN3A2 |
| IPR007110:Immunoglobulin-like domain | 33 | CD8A, IL6ST, CD8B, TRDC, IGHM, LSR, HLA-DPB1, EMB, MR1, LAG3, ICAM1, IL18R1, C10ORF54, BSG, ICAM3, LRRN3, CTLA4, MALT1, SLAMF7, TIGIT, BTLA, CD84, IGSF8, BTN3A1, SP1, CD79B, HLA-DPA1, MFAP3, TAPBPL, BTN3A2, CD200, CD226 |
| IPR013783:Immunoglobulin-like fold | 43 | CD8A, IL6ST, CD8B, TRDC, IGHM, LSR, PDCD1, MYCBP2, IL4R, HLA-DPB1, EMB, MR1, NFATC2, IFNGR2, LAG3, ATF7IP, ICAM1, C10ORF54, IL18R1, IL2RB, BSG, RELA, ICAM3, LRRN3, CTLA4, MALT1, SLAMF7, FLNA, IFNAR1, CD84, TIGIT, BTLA, IFNAR2, BTN3A1, IGSF8, SP1, CD79B, HLA-DPA1, MFAP3, TAPBPL, BTN3A2, CD200, CD226 |
| Enrichment Score: 0.012624733221056823 | | |
| SM00431:SCAN | 4 | ZNF274, ZSCAN25, ZKSCAN1, ZNF394 |
| domain:SCAN box | 4 | ZNF274, ZSCAN25, ZKSCAN1, ZNF394 |

TABLE 3-continued

| | HIV- low cutoff | |
|---|---|---|
| Category | Count | Genes |
| IPR003309:Transcription regulator SCAN | 4 | ZNF274, ZSCAN25, ZKSCAN1, ZNF394 |
| IPR008916:Retrovirus capsid, C-terminal | 4 | ZNF274, ZSCAN25, ZKSCAN1, ZNF394 |
| Enrichment Score: 0.01039742026464367 | | |
| domain:VWFA | 5 | ITGAE, INTS6, CPNE1, PARP4, ITGB1 |
| IPR002035:von Willebrand factor, type A | 5 | ITGAE, INTS6, CPNE1, PARP4, ITGB1 |
| SM00327:VWA | 3 | ITGAE, CPNE1, PARP4 |
| Enrichment Score: 0.010098512996503222 | | |
| SM00339:FH | 3 | FOXK2, FOXJ3, FOXP3 |
| DNA-binding region:Fork-head | 3 | FOXK2, FOXJ3, FOXP3 |
| IPR001766:Transcription factor, fork head | 3 | FOXK2, FOXJ3, FOXP3 |
| Enrichment Score: 0.009453656970068324 | | |
| GO:0014069~postsynaptic density | 15 | DBNL, LZTS3, DNM3, SYT11, FMR1, RGS19, STRN, DTNBP1, RGS14, PJA2, NCOA2, SIPA1L1, SOS1, PDE4B, GOPC |
| Postsynaptic cell membrane | 11 | PJA2, PRR7, LZTS3, SIPA1L1, FMR1, UTRN, CLSTN1, GOPC, TMUB1, DTNBP1, RGS14 |
| Cell junction | 51 | LZTS3, LIMA1, UTRN, CLSTN1, DSTYK, ARHGAP17, ZNRF1, MFF, CXCR4, TIAM1, GOPC, ILK, SNTB1, TMUB1, ZYX, DPP4, PARVG, SYMPK, DBNL, ACTN4, FMR1, PKN2, VEZT, GAK, PJA2, SIPA1L1, KRIT1, TBCD, ASH1L, TCHP, SDCBP, VAMP2, MPST, LIMS1, ARFGEF2, ITGB1, APBB1IP, DTNBP1, PRR7, LPXN, RAB11B, SNAP23, EMB, PLEC, APC, FYB, ICA1, SYT11, SNAPIN, RGS14, SYNE2 |
| GO:0045211~postsynaptic membrane | 13 | LZTS3, FMR1, CLSTN1, UTRN, STRN, PTEN, DTNBP1, RGS14, PRR7, PJA2, SIPA1L1, GOPC, TMUB1 |
| Synapse | 23 | LZTS3, DBNL, ICA1, SYT11, FMR1, UTRN, CLSTN1, SNAPIN, ZNRF1, ARFGEF2, DTNBP1, RGS14, PJA2, PRR7, MFF, SIPA1L1, GOPC, RAB11B, TMUB1, VAMP2, SNAP23, EMB, MPST |
| GO:0030054~cell junction | 32 | LZTS3, OSBP, UTRN, CLSTN1, DSTYK, ZNRF1, ARFGEF2, DTNBP1, PRR7, MFF, CXCR4, GOPC, ILK, RAB11B, TMUB1, EMB, FYB, ICA1, SYT11, FMR1, PKN2, SMC5, SNAPIN, RGS14, NRIP1, PJA2, DCP2, GTF2F1, SIPA1L1, DDB2, VAMP2, MPST |
| Enrichment Score: 0.004733778950614591 | | |
| GO:0005244~voltage-gated ion channel activity | 3 | TMEM109, CLIC1, HVCN1 |
| GO:0034765~regulation of ion transmembrane transport | 3 | TMEM109, CLIC1, HVCN1 |
| Voltage-gated channel | 3 | TMEM109, CLIC1, HVCN1 |
| Enrichment Score: 0.0031554828769724845 | | |
| domain:PDZ | 7 | PDZD8, TIAM1, SIPA1L1, GOPC, RAPGEF6, SNTB1, MPP6 |
| SM00228:PDZ | 9 | PDZD8, IL16, TIAM1, SIPA1L1, GOPC, RAPGEF6, SNTB1, SDCBP, MPP6 |
| IPR001478:PDZ domain | 9 | PDZD8, IL16, TIAM1, SIPA1L1, GOPC, RAPGEF6, SNTB1, SDCBP, MPP6 |
| Enrichment Score: 0.0017938227712904558 | | |
| repeat:LRR 12 | 6 | NLRC5, SYNE2, LRRC8B, LRRN3, LRRC8D, SHOC2 |
| repeat:LRR 11 | 6 | NLRC5, SYNE2, LRRC8B, LRRN3, LRRC8D, SHOC2 |
| repeat:LRR 10 | 7 | NLRC5, SYNE2, PPP1R7, LRRC8B, LRRN3, LRRC8D, SHOC2 |
| repeat:LRR 13 | 4 | NLRC5, SYNE2, LRRC8B, SHOC2 |
| repeat:LRR 9 | 7 | NLRC5, SYNE2, PPP1R7, LRRC8B, LRRN3, LRRC8D, SHOC2 |
| repeat:LRR 7 | 10 | NLRC5, RSU1, SYNE2, PPP1R7, LRRC8B, LRRC41, LRRN3, LRRC8D, LHCGR, SHOC2 |
| repeat:LRR 6 | 12 | NLRC5, RSU1, SYNE2, PPP1R7, LRRC8B, LRRC41, LRRN3, LRRC8D, LHCGR, SHOC2, RANGAP1, XRRA1 |

TABLE 3-continued

HIV- low cutoff

| Category | Count | Genes |
|---|---|---|
| repeat:LRR 8 | 7 | NLRC5, SYNE2, PPP1R7, LRRC8B, LRRN3, LRRC8D, SHOC2 |
| repeat:LRR 5 | 13 | NLRC5, RSU1, SYNE2, PPP1R7, LRRC8B, LRRC41, LRRN3, LRRC8D, LRRC59, LHCGR, SHOC2, RANGAP1, XRRA1 |
| SM00369:LRR_TYP | 9 | RSU1, PPP1R7, LRRC8B, CNOT6L, LRRN3, LRRC8D, LRRC59, SHOC2, XRRA1 |
| IPR003591:Leucine-rich repeat, typical subtype | 9 | RSU1, PPP1R7, LRRC8B, CNOT6L, LRRN3, LRRC8D, LRRC59, SHOC2, XRRA1 |
| repeat:LRR 4 | 14 | NLRC5, RSU1, SYNE2, PPP1R7, LRRC8B, LRRC41, LRRN3, LRRC8D, LRRC59, LHCGR, FBXL5, SHOC2, RANGAP1, XRRA1 |
| repeat:LRR 3 | 16 | RSU1, LRRC8B, LRRC41, LRRC8D, LHCGR, LRRN3, SHOC2, RANGAP1, XRRA1, NLRC5, SYNE2, PPP1R7, KDM2A, CNOT6L, LRRC59, FBXL5 |
| Leucine-rich repeat | 16 | RSU1, LRRC8B, LRRC41, LRRC8D, LHCGR, LRRN3, SHOC2, RANGAP1, XRRA1, NLRC5, PPP1R7, KDM2A, CNOT6L, LRRC59, FBXL5, FBXL15 |
| repeat:LRR 1 | 17 | RSU1, LRRC8B, LRRC41, LRRC8D, LHCGR, LRRN3, SHOC2, RANGAP1, XRRA1, NLRC5, SYNE2, KDM2A, PPP1R7, CNOT6L, LRRC59, FBXL5, HECTD4 |
| repeat:LRR 2 | 17 | RSU1, LRRC8B, LRRC41, LRRC8D, LHCGR, LRRN3, SHOC2, RANGAP1, XRRA1, NLRC5, SYNE2, KDM2A, PPP1R7, CNOT6L, LRRC59, FBXL5, HECTD4 |
| IPR001611:Leucine-rich repeat Enrichment Score: 5.610490263279422E−4 | 13 | RSU1, LRRC8B, LRRN3, LRRC8D, SHOC2, RANGAP1, XRRA1, NLRC5, PPP1R7, CNOT6L, LRRC59, FBXL5, FBXL15 |
| GO:0006814~sodium ion transport | 4 | NDUFA9, COMMD3, SLC38A10, COMMD9 |
| Sodium | 5 | SLC20A2, COMMD3, SLC38A10, POLB, COMMD9 |
| Sodium transport Enrichment Score: 2.1717103654966732E−4 | 4 | SLC20A2, COMMD3, SLC38A10, COMMD9 |
| domain:Ig-like C2-type 4 | 3 | ICAM1, IGSF8, ICAM3 |
| domain:Ig-like C2-type 3 | 5 | ICAM1, IL18R1, IGSF8, ICAM3, LAG3 |
| domain:Ig-like C2-type 1 | 7 | ICAM1, IL18R1, IGSF8, ICAM3, MALT1, CD226, LAG3 |
| domain:Ig-like C2-type 2 Enrichment Score: 1.8372944146090797E−4 | 7 | ICAM1, IL18R1, IGSF8, ICAM3, MALT1, CD226, LAG3 |
| domain:C-type lectin | 3 | DGCR2, CD93, KLRD1 |
| SM00034:CLECT | 3 | DGCR2, CD93, KLRD1 |
| IPR016186:C-type lectin-like | 4 | DGCR2, CLECL1, CD93, KLRD1 |
| IPR001304:C-type lectin | 3 | DGCR2, CD93, KLRD1 |
| IPR016187:C-type lectin fold | 4 | DGCR2, CLECL1, CD93, KLRD1 |
| Lectin Enrichment Score: 1.3260097487500437E−4 | 7 | GALNT2, BSG, DGCR2, CLECL1, CD93, KLRD1, LGALS9 |
| repeat:1 | 16 | BRF1, BRF2, VHL, TBP, GTF2B, IWS1, GLTP, PEF1, CCDC6, IGF2R, KHSRP, HIVEP2, PCYT1A, PIAS1, RANBP2, NFATC2 |
| repeat:2 | 15 | BRF1, BRF2, VHL, TBP, GTF2B, GLTP, IWS1, PEF1, CCDC6, IGF2R, KHSRP, HIVEP2, RANBP2, PIAS1, NFATC2 |
| repeat:8 | 4 | PEF1, VHL, IGF2R, HIVEP2 |
| repeat:9 | 3 | PEF1, IGF2R, HIVEP2 |
| repeat:7 | 4 | PEF1, VHL, IGF2R, HIVEP2 |
| repeat:5 | 5 | PEF1, CCDC6, VHL, IGF2R, HIVEP2 |
| repeat:6 | 4 | PEF1, VHL, IGF2R, HIVEP2 |
| repeat:3 | 7 | PEF1, CCDC6, VHL, IGF2R, KHSRP, HIVEP2, PCYT1A |
| repeat:4 Enrichment Score: 3.460852670649958E−5 | 5 | PEF1, VHL, IGF2R, KHSRP, HIVEP2 |
| Vision | 4 | UNC119, PDE6D, MKKS, CRYBB2 |
| GO:0007601~visual perception | 8 | ABLIM1, ATF6, UNC119, DRAM2, PDE6D, MKKS, CLN6, CRYBB2 |
| Sensory transduction | 5 | UNC119, PDE6D, MKKS, DTNBP1, CRYBB2 |

TABLE 3-continued

HIV- low cutoff

| Category | Count | Genes |
|---|---|---|
| Enrichment Score: 8.483999996378984E−6 | | |
| Membrane | 712 | CCZ1B, CDIPT, USE1, VPS53, STRN, MPV17, RANGAP1, SLC52A2, IGHM, FAM210A, TESPA1, ACBD5, TMEM140, TMEM147, ILK, VPS4A, JAGN1, TMEM14B, GOLGA8A, KLRD1, IBTK, TIMMDC1, BSG, ROCK1, ROCK2, UBE2J1, VPS41, UBE2J2, PIK3IP1, ERGIC1, BCL2L11, MARK2, TMEM131, UNC13D, CD320, TMEM138, SIPA1L1, HLA-DPA1, ARL8B, CD226, ORAI1, KIAA1109, MOB4, C16ORF91, RER1, CCDC91, ARF6, ARFGEF2, SLC29A1, TMEM50B, SYPL1, RAC1, CKLF, ZAP70, HLA-DPB1, CDC42EP3, MGAT4A, LAPTM4A, ATP11A, SPTSSA, MPC1, MPC2, APOL2, TMEM115, SYNE2, APOL1, RGS1, ERVK13-1, ARF4, HGS, SMURF2, SYTL3, TMEM41A, TMEM41B, C19ORF12, CD200, RTN4, LZTS3, ENOX2, SLC20A2, TSG101, BNIP3, AP3S1, FAM169A, RTN3, OFD1, LNPEP, AP1S3, FAM168B, TMEM109, SMAP1, SLMAP, IL4R, SPG21, CLDND1, MYB, LAG3, DPP4, BRD8, PARVG, SYMPK, FMNL3, ZDHHC3, ARHGEF1, RAP2C, PIK3C2A, AIFM1, ZDHHC8, KCTD20, GLCCI1, CLIC1, PI4KB, PJA2, BNIP1, BNIP2, RIPK1, RRM1, TCHP, LRMP, OSBPL11, CHSY1, EIF5A2, ARL4C, GRAMD1A, TMCO1, WDR45, ARL4A, CLN6, SNAP29, MFSD6, RABGAP1, EXOC7, REPS1, CSF1, MFSD5, PML, ABHD3, EEA1, ABHD2, APBB1IP, DGKE, DDX19A, NUP210, MPDU1, RAB11B, ILVBL, ARMCX3, CERK, SNAP23, PCSK7, ACSL4, TRIP11, ACSL3, C1GALT1, ACSL5, SOAT1, NBPF10, VTA1, CTLA4, DGKH, TMEM5, TTC17, TMEM2, NAE1, SDHA, PLSCR1, MPHOSPH9, NRAS, P2RY10, PLEKHF2, CSNK1D, GSK3B, SDHC, BNIP3L, CMTM7, DGKZ, TAPBPL, YKT6, CMTM3, NCLN, GNA13, AP1G1, ATP6AP2, UNC50, HBS1L, TSPAN5, IDE, SLC7A6, ELOVL1, ST3GAL1, MFF, PRKAR2A, SMIM7, PGRMC1, AAK1, SMIM8, PGRMC2, LRRC59, RALB, DNAJC5, RNF149, SAR1B, DDOST, MATK, TMEM205, TMEM203, SPTLC2, FMR1, STIM1, PSD4, ZNF7, PDE4D, TMEM208, HCST, PNPLA8, TMEM106B, RNF139, VAMP5, PCMTD1, VAMP2, MFAP3, SLFN12L, DCUN1D5, PHKA2, ARFGAP2, LITAF, IFITM1, TMEM214, IFITM2, STK10, STAM2, LRBA, CERS6, TMEM219, SLC38A10, CDC42SE1, CERS4, TRDC, P2RY8, DOCK2, FICD, PDE6D, CERS2, PCYT1A, RNF167, FKRP, SDF4, TMEM30A, LYSMD3, TMEM223, HERPUD1, B4GALT3, PHACTR2, PRAF2, TMEM222, MSMO1, SYT11, MYO1G, NIPA2, SNAPIN, PLGRKT, WIPI2, ABCB7, FURIN, HERPUD2, NDUFV3, ATF6, TIGIT, LAMP1, LAMP2, TSC1, NDUFV2, TRAF3IP3, PTTG1IP, NDUFAF4, LRRC8B, ATL3, LRRC8D, CLSTN1, TMEM237, MFSD2A, PEX3, PIP5K1A, MBP, PEX2, SNTB1, VPS16, AP5M1, CCDC107, PTDSS1, RHOF, NDUFS1, EBAG9, TBL1XR1, SIT1, AVL9, C17ORF62, PKN2, STXBP2, TMEM248, BANP, NUP85, LPIN1, M6PR, TMEM245, TIMM22, TMEM243, ARL3, SH2D3C, TNFSF13B, DEF6, TBCD, IGF2R, GINM1, SLC35E1, SLC41A1, MFSD10, EMC1, SNX13, SNX11, SNX19, GALNT2, TAPT1, NUP98, APH1A, TPRA1, PPM1A, NUP93, TMEM259, ALDH3A2, APLP2, RNF125, NDC1, AP3M2, AP3M1, HRH2, TSPAN31, SHISA5, SLC35B4, TMED1, SEC22B, PAFAH1B1, CCS, INPP5D, EHD1, CD5, VPS39, EHD4, GTF3C3, EBP, VHL, ATRAID, CBL, ANXA1, RAF1, DPYSL2, BAD, TSPAN17, TMEM55B, ADI1, CLPTM1, LMBR1L, IFIT5, JAK2, FAF1, GGA1, GGA3, VPS25, RARRES3, SEC31B, TMEM19, MRPL42, CHMP3, SEC31A, B3GALT6, ADCY7, IL6ST, VAPB, CHMP6, NELL2, LHCGR, UTRN, CNPPD1, TMEM11, ZNRF1, PSKH1, ATP2B4, VPS13C, GBF1, INSIG2, RAPGEF6, ERAP1, TMUB1, STAM, C6ORF136, SAYSD1, TBC1D9B, PLD3, DBNL, GPR137, CRLS1, CAPNS1, STRN3, TRABD2A, RINT1, PIM1, NKTR, MGAT1, MGAT2, CD37, BTN3A1, RAB18, ATP2C1, CCR4, LPAR6, ACAP1, ACAP2, CDCA7L, AMFR, TMEM184C, ADD3, BTN3A2, ADD1, SUCO, TMX2, GPATCH2L, GLG1, CLCN3, LMNB2, TMX3, BROX, NPIPB4, ASAP1, SFXN4, AKAP10, RFFL, PPAT, FAM65B, SERINC3, SLC11A2, KRAS, SERINC1, STX17, EMB, STX10, GPR155, ST6GAL1, OSBPL3, TM2D1, S100A10, SLAMF7, CD63, CDC27, BTLA, CD55, ATP13A1, RNF4, CD59, KIAA0922, CNIH4, BET1L, RIT1, SPG7, COX11, RAB5B, RAB5C, VPS37B, HELZ, CD151, HVCN1, ATG2B, FAR1, EFHD2, ATAD3A, DNAJC15, GOLGA7, DNAJC16, PARL, GNPAT, ATP6V0D1, ATP5H, C10ORF54, ICAM1, LPGAT1, JKAMP, ICAM3, VEZT, CYB5A, FAM76B, RHBDD1, METTL2B, MIEN1, RHBDD2, TNFRSF10A, GRM4, TRAP1, CHMP1A, ZDHHC16, NUS1, ZDHHC12, RAB5A, CNEP1R1, ORMDL3, MOSPD1, FKBP11, MAP3K13, LIMS1, BET1, DNAJC30, SFT2D2, LPXN, STT3A, PEX19, GNPTAB, TYW1, BCL2, PEX16, IPCEF1, CD27, IL18R1, IMMT, LRRN3, BIRC6, ITPR2, SAMD8, COG3, COG5, DRAM2, RAB30, SLC16A7, AP2A1, EEF1E1, MTFP1, RAB35, MBOAT1, RBM15, FAM126B, GOLGB1, TSPO, CHMP4A, DSTYK, PI4K2B, STARD3, GLT8D1, TIAM1, CPOX, MS4A1, SLC25A28, PRKACB, LEPROT, MCOLN2, MX1, SPN, TOR1AIP2, SCAMP3, SMIM15, MADD, C2CD5, TOR1AIP1, CHP1, FAM118A, MOGS, TIMM8A, BCAP31, SLC25A32, IGSF8, LRP10, USO1, SLC25A38, SDCBP, KDSR, SMIM20, VPS26A, GBP3, DERL1, MCL1, ITGAE, CEP95, TMEM63A, UNC93B1, SNX2, RABGAP1L, NAPA, SNX4, MUM1, ITGB1, CASD1, PRR7, PEF1, FIS1, SLC30A5, ENTPD6, HECTD4, B3GNT2, RUNX1, YIPF6, RYK, RAB33A, SREBF2, RAB33B, REEP5, PLEKHA3, |

TABLE 3-continued

HIV- low cutoff

| Category | Count | Genes |
|---|---|---|
| | | TXNDC11, RHOT1, CPNE1, RHOT2, CD79B, AHCYL1, SLC25A16, IFI6, DCXR, PLEKHA1, COPA, OSBP, UQCRC1, CD8A, CD8B, UTY, ECHDC1, ARHGAP17, CXCR3, CLTC, UQCRFS1, ARHGAP15, LSR, WHAMM, PDCD1, DGCR2, CD93, PIGF, CXCR4, GOPC, NECAP2, NECAP1, ATP8B2, MKKS, RANBP2, MSN, TM9SF4, IFNGR2, AKT2, TM9SF2, CCDC88B, SYNRG, RALBP1, ELP6, PRKCI, MPP6, PIGS, TMEM189, LDLRAD4, PRKCD, PRKCB, SACM1L, IFNAR1, IMMP1L, CD84, FAM134B, NUCB1, TNFRSF9, FAM134C, IFNAR2, C5ORF15, CLECL1, KRIT1, TMEM69, CD81, NUCB2, UBE2W, COMMD1, C16ORF54, SPAST, PRKD3, C7ORF73, GPR108, FAM173B, FAM173A, NDUFB7, CD247, RSAD2, CYTH2, DTNBP1, TNFRSF1A, PSTPIP1, TMEM87A, SLC39A6, APMAP, MR1, CCZ1, SLC39A3, APC, STAMBP, IL2RB, ICA1, PTPRE, GIMAP5, PTPRA, SUN2, RGS19, TMBIM1, NUP155, SLC10A3, RGS14, SIRT2, CYSTM1, GIMAP1, MPG, TMEM43, SLC6A6, SLC25A53, C9ORF69, COMTD1 |
| Transmembrane | 455 | CDIPT, USE1, MPV17, SLC52A2, IGHM, FAM210A, ACBD5, TMEM140, TMEM147, JAGN1, TMEM14B, KLRD1, TIMMDC1, BSG, UBE2J1, UBE2J2, PIK3IP1, ERGIC1, TMEM131, CD320, TMEM138, HLA-DPA1, CD226, ORAI1, KIAA1109, C16ORF91, RER1, SLC29A1, TMEM50B, SYPL1, CKLF, HLA-DPB1, MGAT4A, LAPTM4A, ATP11A, MPC1, SPTSSA, MPC2, APOL2, TMEM115, SYNE2, APOL1, ERVK13-1, ARF4, SMURF2, TMEM41A, C19ORF12, TMEM41B, CD200, RTN4, SLC20A2, BNIP3, RTN3, FAM168B, LNPEP, OFD1, TMEM109, IL4R, SLMAP, CLDND1, MYB, LAG3, DPP4, BRD8, ZDHHC3, AIFM1, ZDHHC8, KCTD20, CLIC1, GLCCI1, BNIP1, BNIP2, RRM1, LRMP, CHSY1, TMCO1, GRAMD1A, WDR45, CLN6, MFSD6, RABGAP1, CSF1, MFSD5, ABHD3, ABHD2, DGKE, NUP210, MPDU1, ILVBL, ARMCX3, SNAP23, PCSK7, ACSL4, ACSL3, C1GALT1, ACSL5, SOAT1, NBPF10, CTLA4, TMEM5, TMEM2, PLSCR1, P2RY10, SDHC, BNIP3L, CMTM7, TAPBPL, CMTM3, NCLN, ATP6AP2, UNC50, TSPAN5, HBS1L, SLC7A6, ST3GAL1, ELOVL1, MFF, SMIM7, PGRMC1, SMIM8, LRRC59, PGRMC2, DNAJC5, RNF149, DDOST, TMEM205, TMEM203, SPTLC2, STIM1, ZNF7, HCST, TMEM208, TMEM106B, PNPLA8, RNF139, VAMP5, MFAP3, VAMP2, SLFN12L, DCUN1D5, TMEM214, IFITM1, LITAF, IFITM2, LRBA, CERS6, TMEM219, SLC38A10, CERS4, TRDC, P2RY8, FICD, CERS2, RNF167, FKRP, TMEM30A, LYSMD3, TMEM223, HERPUD1, B4GALT3, PRAF2, MSMO1, TMEM222, SYT11, NIPA2, PLGRKT, ABCB7, HERPUD2, FURIN, TIGIT, ATF6, LAMP1, LAMP2, TRAF3IP3, PTTG1IP, LRRC8B, ATL3, LRRC8D, CLSTN1, TMEM237, MFSD2A, PEX3, PEX2, PTDSS1, CCDC107, EBAG9, TBL1XR1, SIT1, AVL9, C17ORF62, PKN2, STXBP2, TMEM248, BANP, TMEM245, M6PR, TMEM243, TIMM22, TNFSF13B, IGF2R, GINM1, SLC35E1, SLC41A1, MFSD10, EMC1, SNX13, TAPT1, GALNT2, APH1A, TPRA1, PPM1A, TMEM259, APLP2, ALDH3A2, NDC1, HRH2, TSPAN31, SLC35B4, SHISA5, TMED1, SEC22B, CCS, CD5, GTF3C3, EBP, ATRAID, TSPAN17, TMEM55B, CLPTM1, LMBR1L, FAF1, RARRES3, MRPL42, TMEM19, ADCY7, B3GALT6, IL6ST, VAPB, NELL2, LHCGR, CNPPD1, TMEM11, ATP2B4, INSIG2, TMUB1, ERAP1, C6ORF136, SAYSD1, TBC1D9B, PLD3, GPR137, CRLS1, TRABD2A, MGAT1, MGAT2, CD37, BTN3A1, ATP2C1, LPAR6, CCR4, CDCA7L, AMFR, TMEM184C, BTN3A2, SUCO, GPATCH2L, GLG1, TMX2, CLCN3, TMX3, NPIPB4, ASAP1, SFXN4, PPAT, SERINC3, SLC11A2, STX17, SERINC1, EMB, STX10, GPR155, ST6GAL1, TM2D1, S100A10, SLAMF7, CD63, CDC27, BTLA, ATP13A1, RNF4, KIAA0922, CNIH4, BET1L, SPG7, COX11, HELZ, CD151, HVCN1, FAR1, DNAJC15, ATAD3A, DNAJC16, PARL, C10ORF54, ICAM1, JKAMP, LPGAT1, ICAM3, CYB5A, VEZT, FAM76B, METTL2B, RHBDD1, RHBDD2, TNFRSF10A, GRM4, ZDHHC16, NUS1, ZDHHC12, CNEP1R1, ORMDL3, MOSPD1, FKBP11, BET1, DNAJC30, SFT2D2, STT3A, GNPTAB, BCL2, TYW1, PEX16, CD27, IL18R1, IMMT, LRRN3, ITPR2, SAMD8, DRAM2, SLC16A7, MTFP1, EEF1E1, MBOAT1, GOLGB1, TSPO, STARD3, GLT8D1, CPOX, MS4A1, SLC25A28, MCOLN2, LEPROT, SPN, TOR1AIP2, SCAMP3, SMIM15, TOR1AIP1, FAM118A, MOGS, BCAP31, SLC25A32, IGSF8, LRP10, SLC25A38, SDCBP, KDSR, SMIM20, DERL1, MCL1, CEP95, ITGAE, TMEM63A, UNC93B1, RABGAP1L, MUM1, ITGB1, CASD1, PRR7, FIS1, SLC30A5, ENTPD6, HECTD4, B3GNT2, RUNX1, YIPF6, RYK, SREBF2, REEP5, TXNDC11, RHOT1, RHOT2, CD79B, SLC25A16, IFI6, CD8A, CD8B, UTY, ECHDC1, CXCR3, UQCRFS1, LSR, PDCD1, DGCR2, CD93, PIGF, CXCR4, MKKS, ATP8B2, TM9SF4, IFNGR2, TM9SF2, ELP6, PIGS, TMEM189, LDLRAD4, IFNAR1, SACM1L, FAM134B, CD84, IFNAR2, FAM134C, C5ORF15, TNFRSF9, CLECL1, TMEM69, CD81, UBE2W, C16ORF54, SPAST, C7ORF73, GPR108, FAM173B, FAM173A, CD247, TNFRSF1A, TMEM87A, SLC39A6, MR1, APMAP, SLC39A3, IL2RB, ICA1, PTPRE, GIMAP5, PTPRA, SUN2, TMBIM1, SLC10A3, CYSTM1, GIMAP1, MPG, TMEM43, SLC6A6, SLC25A53, C9ORF69, COMTD1 |
| Transmembrane helix | 453 | CDIPT, USE1, MPV17, SLC52A2, FAM210A, ACBD5, TMEM140, TMEM147, JAGN1, TMEM14B, KLRD1, TIMMDC1, BSG, UBE2J1, UBE2J2, PIK3IP1, ERGIC1, TMEM131, CD320, TMEM138, HLA-DPA1, CD226, ORAI1, KIAA1109, C16ORF91, RER1, SLC29A1, TMEM50B, SYPL1, CKLF, HLA-DPB1, MGAT4A, LAPTM4A, ATP11A, MPC1, SPTSSA, MPC2, APOL2, |

TABLE 3-continued

HIV- low cutoff

| Category | Count | Genes |
|---|---|---|
| | | TMEM115, SYNE2, APOL1, ERVK13-1, ARF4, SMURF2, TMEM41A, C19ORF12, TMEM41B, CD200, RTN4, SLC20A2, BNIP3, RTN3, FAM168B, LNPEP, OFD1, TMEM109, IL4R, SLMAP, CLDND1, MYB, LAG3, DPP4, BRD8, ZDHHC3, AIFM1, ZDHHC8, KCTD20, CLIC1, GLCCI1, BNIP1, BNIP2, RRM1, LRMP, CHSY1, TMCO1, GRAMD1A, WDR45, CLN6, MFSD6, RABGAP1, CSF1, MFSD5, ABHD3, ABHD2, DGKE, NUP210, MPDU1, ILVBL, ARMCX3, SNAP23, PCSK7, ACSL4, ACSL3, C1GALT1, ACSL5, SOAT1, NBPF10, CTLA4, TMEM5, TMEM2, PLSCR1, P2RY10, SDHC, BNIP3L, CMTM7, TAPBPL, CMTM3, NCLN, ATP6AP2, UNC50, TSPAN5, HBS1L, SLC7A6, ST3GAL1, ELOVL1, MFF, SMIM7, PGRMC1, SMIM8, LRRC59, PGRMC2, DNAJC5, RNF149, DDOST, TMEM205, TMEM203, SPTLC2, STIM1, ZNF7, HCST, TMEM208, TMEM106B, PNPLA8, RNF139, VAMP5, MFAP3, VAMP2, SLFN12L, DCUN1D5, TMEM214, IFITM1, LITAF, IFITM2, LRBA, CERS6, TMEM219, SLC38A10, CERS4, TRDC, P2RY8, FICD, CERS2, RNF167, FKRP, TMEM30A, LYSMD3, TMEM223, HERPUD1, B4GALT3, PRAF2, MSMO1, TMEM222, SYT11, NIPA2, PLGRKT, ABCB7, HERPUD2, FURIN, TIGIT, ATF6, LAMP1, LAMP2, TRAF3IP3, PTTG1IP, LRRC8B, ATL3, LRRC8D, CLSTN1, TMEM237, MFSD2A, PEX3, PEX2, PTDSS1, CCDC107, EBAG9, TBL1XR1, SIT1, AVL9, C17ORF62, PKN2, STXBP2, TMEM248, BANP, TMEM245, M6PR, TMEM243, TIMM22, TNFSF13B, IGF2R, GINM1, SLC35E1, SLC41A1, MFSD10, EMC1, SNX13, TAPT1, GALNT2, APH1A, TPRA1, PPM1A, TMEM259, APLP2, ALDH3A2, NDC1, HRH2, TSPAN31, SLC35B4, SHISA5, TMED1, SEC22B, CCS, CD5, GTF3C3, EBP, ATRAID, TSPAN17, TMEM55B, CLPTM1, LMBR1L, FAF1, RARRES3, MRPL42, TMEM19, ADCY7, B3GALT6, IL6ST, VAPB, NELL2, LHCGR, CNPPD1, TMEM11, ATP2B4, INSIG2, TMUB1, ERAP1, C6ORF136, SAYSD1, TBC1D9B, PLD3, GPR137, CRLS1, TRABD2A, MGAT1, MGAT2, CD37, BTN3A1, ATP2C1, LPAR6, CCR4, CDCA7L, AMFR, TMEM184C, BTN3A2, SUCO, GPATCH2L, GLG1, TMX2, CLCN3, TMX3, NPIPB4, ASAP1, SFXN4, PPAT, SERINC3, SLC11A2, STX17, SERINC1, EMB, STX10, GPR155, ST6GAL1, TM2D1, S100A10, SLAMF7, CD63, CDC27, BTLA, ATP13A1, RNF4, KIAA0922, CNIH4, BET1L, SPG7, COX11, HELZ, CD151, HVCN1, FAR1, DNAJC15, ATAD3A, DNAJC16, PARL, C10ORF54, ICAM1, JKAMP, LPGAT1, ICAM3, CYB5A, VEZT, FAM76B, METTL2B, RHBDD1, RHBDD2, TNFRSF10A, GRM4, ZDHHC16, NUS1, ZDHHC12, CNEP1R1, ORMDL3, MOSPD1, FKBP11, BET1, DNAJC30, SFT2D2, STT3A, GNPTAB, BCL2, TYW1, PEX16, CD27, IL18R1, IMMT, LRRN3, ITPR2, SAMD8, DRAM2, SLC16A7, MTFP1, EEF1E1, MBOAT1, GOLGB1, TSPO, STARD3, GLT8D1, CPOX, MS4A1, SLC25A28, MCOLN2, LEPROT, SPN, TOR1AIP2, SCAMP3, SMIM15, TOR1AIP1, FAM118A, MOGS, BCAP31, SLC25A32, IGSF8, LRP10, SLC25A38, SDCBP, KDSR, SMIM20, DERL1, MCL1, CEP95, ITGAE, TMEM63A, UNC93B1, RABGAP1L, MUM1, ITGB1, CASD1, PRR7, FIS1, SLC30A5, ENTPD6, HECTD4, B3GNT2, YIPF6, RYK, SREBF2, REEP5, TXNDC11, RHOT1, RHOT2, CD79B, SLC25A16, IFI6, CD8A, CD8B, UTY, ECHDC1, CXCR3, UQCRFS1, LSR, PDCD1, DGCR2, CD93, PIGF, CXCR4, MKKS, ATP8B2, TM9SF4, IFNGR2, TM9SF2, ELP6, PIGS, TMEM189, LDLRAD4, IFNAR1, SACM1L, FAM134B, CD84, IFNAR2, FAM134C, C5ORF15, TNFRSF9, CLECL1, TMEM69, CD81, UBE2W, C16ORF54, SPAST, C7ORF73, GPR108, FAM173B, FAM173A, CD247, TNFRSF1A, TMEM87A, SLC39A6, MR1, APMAP, SLC39A3, IL2RB, ICA1, PTPRE, GIMAP5, PTPRA, SUN2, TMBIM1, SLC10A3, CYSTM1, GIMAP1, MPG, TMEM43, SLC6A6, C9ORF69, SLC25A53, COMTD1 |
| GO:0016021~integral component of membrane | 431 | CDIPT, USE1, MPV17, VPS51, IGHM, FAM210A, ACBD5, TMEM140, TMEM147, JAGN1, TMEM41B, KLRD1, TIMMDC1, BSG, UBE2J1, UBE2J2, PIK3IP1, ERGIC1, TMEM131, CD320, TMEM138, HLA-DPA1, CD226, ORAI1, KIAA1109, C16ORF91, RER1, TMEM50B, SYPL1, CKLF, HLA-DPB1, MGAT4A, LAPTM4A, ATP11A, MPC1, SPTSSA, MPC2, APOL2, TMEM115, SYNE2, APOL1, ERVK13-1, ARF4, SMURF2, TMEM41A, C19ORF12, TMEM41B, CD200, RTN4, SLC20A2, BNIP3, RTN3, FAM168B, OFD1, TMEM109, IL4R, SLMAP, CLDND1, MYB, LAG3, DPP4, BRD8, ZDHHC3, AIFM1, ZDHHC8, KCTD20, GLCCI1, BNIP2, RRM1, LRMP, CHSY1, TMCO1, GRAMD1A, WDR45, CLN6, MFSD6, RABGAP1, MFSD5, CSF1, ABHD3, ABHD2, DGKE, NUP210, MPDU1, ILVBL, ARMCX3, PCSK7, SNAP23, CERK, ACSL4, ACSL3, C1GALT1, ACSL5, SOAT1, NBPF10, CTLA4, TMEM5, TMEM2, P2RY10, SDHC, BNIP3L, CMTM7, TAPBPL, CMTM3, YKT6, NCLN, ATP6AP2, UNC50, TSPAN5, HBS1L, SLC7A6, ST3GAL1, ELOVL1, MFF, SMIM7, PGRMC1, SMIM8, LRRC59, PGRMC2, SMIM8, DNAJC5, RNF149, DDOST, TMEM205, TMEM203, SPTLC2, ZNF7, HCST, TMEM208, TMEM106B, PNPLA8, RNF139, MFAP3, VAMP2, SLFN12L, DCUN1D5, TMEM214, IFITM1, LITAF, IFITM2, LRBA, CERS6, TMEM219, SLC38A10, CERS4, TRDC, P2RY8, FICD, CERS2, RNF167, FKRP, TMEM30A, LYSMD3, TMEM223, HERPUD1, B4GALT3, PRAF2, MSMO1, TMEM222, NIPA2, ABCB7, HERPUD2, FURIN, TIGIT, LAMP1, LAMP2, TRAF3IP3, PTTG1IP, LRRC8B, ATL3, LRRC8D, CLSTN1, TMEM237, MFSD2A, PEX2, PTDSS1, CCDC107, EBAG9, TBL1XR1, SIT1, AVL9, C17ORF62, PKN2, STXBP2, TMEM248, BANP, TMEM245, M6PR, |

TABLE 3-continued

| | | HIV- low cutoff |
|---|---|---|
| Category | Count | Genes |
| | | TMEM243, TIMM22, TNFSF13B, IGF2R, GINM1, SLC35E1, MFSD10, SLC41A1, EMC1, SNX13, TAPT1, GALNT2, APH1A, TPRA1, PPM1A, TMEM259, APLP2, ALDH3A2, NDC1, TSPAN31, SLC35B4, SHISA5, TMED1, SEC22B, CCS, CD5, GTF3C3, EBP, ATRAID, TSPAN17, TMED8, TMEM55B, CLPTM1, LMBR1L, FAF1, RARRES3, MRPL42, TMEM19, ADCY7, B3GALT6, IL6ST, VAPB, NELL2, LHCGR, CNPPD1, ATP2B4, INSIG2, TMUB1, ERAP1, C6ORF136, SAYSD1, TBC1D9B, PLD3, GPR137, CRLS1, MGAT1, MGAT2, BTN3A1, CD37, ATP2C1, LPAR6, CCR4, CDCA7L, AMFR, TMEM184C, BTN3A2, SUCO, GPATCH2L, GLG1, TMX2, CLCN3, TMX3, NPIPB4, SFXN4, ASAP1, PPAT, SERINC3, SLC11A2, STX17, SERINC1, EMB, STX10, GPR155, ST6GAL1, TM2D1, S100A10, SLAMF7, CD63, CDC27, BTLA, ATP13A1, RNF4, KIAA0922, CNIH4, BET1L, COX11, SPG7, HELZ, CD151, HVCN1, FAR1, DNAJC15, ATAD3A, DNAJC16, PARL, C10ORF54, ICAM1, JKAMP, LPGAT1, ICAM3, CYB5A, VEZT, FAM76B, METTL2B, RHBDD1, RHBDD2, TNFRSF10A, GRM4, ZDHHC16, NUS1, ZDHHC12, CNEP1R1, ORMDL3, MOSPD1, FKBP11, BET1, SEC14L1, DNAJC30, SFT2D2, STT3A, GNPTAB, PEX19, BCL2, TYW1, IL18R1, IMMT, LRRN3, ITPR2, SAMD8, DRAM2, MTFP1, EEF1E1, MBOAT1, GOLGB1, TSPO, STARD3, GLT8D1, CPOX, SLC25A28, MCOLN2, LEPROT, SPN, TOR1AIP2, SCAMP3, SMIM15, MADD, TOR1AIP1, FAM118A, MOGS, BCAP31, SLC25A32, IGSF8, LRP10, SLC25A38, SDCBP, KDSR, SMIM20, DERL1, MCL1, CEP95, TMEM63A, UNC93B1, RABGAP1L, MUM1, CASD1, PRR7, SLC30A5, ENTPD6, HECTD4, B3GNT2, RUNX1, YIPF6, RYK, REEP5, TXNDC11, RHOT1, SLC25A16, IFI6, CD8A, CD8B, UTY, ECHDC1, CXCR3, LSR, PDCD1, DGCR2, PIGF, CD93, CXCR4, MKKS, ATP8B2, TM9SF4, IFNGR2, TM9SF2, ELP6, TMEM189, LDLRAD4, SACM1L, IFNAR2, FAM134C, C5ORF15, TNFRSF9, CLECL1, SBF1, TMEM69, CD81, UBE2W, C16ORF54, SPAST, C7ORF73, GPR108, FAM173B, FAM173A, CD247, TNFRSF1A, TMEM87A, SLC39A6, MR1, APMAP, SLC39A3, ICA1, PTPRE, GIMAP5, PTPRA, TMBIM1, SLC10A3, CYSTM1, GIMAP1, MPG, TMEM43, SLC6A6, C9ORF69, SLC25A53, COMTD1 |
| transmembrane region | 387 | CDIPT, USE1, MPV17, SLC52A2, FAM210A, ACBD5, TMEM140, TMEM147, JAGN1, TMEM14B, KLRD1, TIMMDC1, BSG, UBE2J1, UBE2J2, PIK3IP1, ERGIC1, TMEM131, CD320, TMEM138, HLA-DPA1, CD226, ORAI1, KIAA1109, C16ORF91, RER1, TMEM50B, SLC29A1, SYPL1, CKLF, HLA-DPB1, MGAT4A, LAPTM4A, SPTSSA, ATP11A, TMEM115, SYNE2, TMEM41A, C19ORF12, TMEM41B, CD200, RTN4, SLC20A2, BNIP3, RTN3, LNPEP, TMEM109, IL4R, SLMAP, CLDND1, DPP4, LAG3, ZDHHC3, ZDHHC8, CLIC1, BNIP1, LRMP, CHSY1, TMCO1, GRAMD1A, CLN6, MFSD6, MFSD5, CSF1, ABHD3, ABHD2, DGKE, NUP210, MPDU1, ARMCX3, ILVBL, PCSK7, ACSL4, ACSL3, C1GALT1, ACSL5, SOAT1, CTLA4, TMEM5, TMEM2, PLSCR1, P2RY10, SDHC, BNIP3L, CMTM7, TAPBPL, CMTM3, NCLN, ATP6AP2, TSPAN5, UNC50, SLC7A6, ST3GAL1, ELOVL1, MFF, SMIM7, PGRMC1, LRRC59, PGRMC2, SMIM8, RNF149, DDOST, TMEM205, TMEM203, SPTLC2, STIM1, HCST, TMEM208, TMEM106B, PNPLA8, VAMP5, RNF139, MFAP3, VAMP2, TMEM214, IFITM1, IFITM2, CERS6, LRBA, SLC38A10, TMEM219, CERS4, P2RY8, FICD, CERS2, RNF167, TMEM30A, LYSMD3, TMEM223, HERPUD1, PRAF2, B4GALT3, MSMO1, TMEM222, SYT11, NIPA2, PLGRKT, ABCB7, HERPUD2, FURIN, TIGIT, ATF6, LAMP1, LAMP2, TRAF3IP3, PTTG1IP, LRRC8B, CLSTN1, LRRC8D, ATL3, TMEM237, MFSD2A, PEX3, PEX2, PTDSS1, CCDC107, EBAG9, SIT1, AVL9, C17ORF62, TMEM248, TMEM245, M6PR, TMEM243, TIMM22, TNFSF13B, GINM1, IGF2R, SLC35E1, MFSD10, SLC41A1, EMC1, TAPT1, GALNT2, APH1A, TPRA1, TMEM259, APLP2, ALDH3A2, NDC1, TSC22D3, HRH2, TSPAN31, TMED1, SLC35B4, SHISA5, SEC22B, CD5, EBP, ATRAID, TSPAN17, TMEM55B, CLPTM1, LMBR1L, ALKBH5, TMEM19, CHMP3, ADCY7, B3GALT6, VAPB, IL6ST, LHCGR, CNPPD1, TMEM11, ATP2B4, INSIG2, TMUB1, ERAP1, SAYSD1, TBC1D9B, PLD3, GPR137, CRLS1, TRABD2A, MGAT1, MGAT2, BTN3A1, CD37, LPAR6, CCR4, ATP2C1, TMEM184C, AMFR, BTN3A2, SUCO, GPATCH2L, GLG1, TMX2, CLCN3, TMX3, SFXN4, SERINC3, SLC11A2, STX17, SERINC1, EMB, STX10, GPR155, ST6GAL1, TM2D1, SLAMF7, CD63, BTLA, ATP13A1, CNIH4, KIAA0922, BET1L, COX11, SPG7, HVCN1, CD151, FAR1, DNAJC15, DNAJC16, PARL, ICAM1, C10ORF54, JKAMP, LPGAT1, ICAM3, CYB5A, VEZT, RHBDD1, RHBDD2, TNFRSF10A, GRM4, ZDHHC16, NUS1, ZDHHC12, CNEP1R1, MOSPD1, ORMDL3, FKBP11, BET1, SFT2D2, STT3A, GNPTAB, BCL2, PEX16, CD27, IL18R1, EPB41L4A-AS1, IMMT, LRRN3, ITPR2, SAMD8, DRAM2, MBOAT1, GOLGB1, TSPO, STARD3, GLT8D1, MS4A1, SLC25A28, MCOLN2, LEPROT, SPN, TOR1AIP2, SCAMP3, SMIM15, MADD, TOR1AIP1, FAM118A, MOGS, BCAP31, SLC25A32, IGSF8, LRP10, SLC25A38, KDSR, SMIM20, GBP3, DERL1, MCL1, ITGAE, UNC93B1, TMEM63A, ITGB1, CASD1, PRR7, FIS1, ENTPD6, SLC30A5, HECTD4, B3GNT2, YIPF6, RYK, REEP5, SREBF2, TXNDC11, RHOT1, RHOT2, CD79B, SLC25A16, IFI6, CD8A, CD8B, CXCR3, LSR, PDCD1, DGCR2, PIGF, CD93, CXCR4, ATP8B2, TM9SF4, IFNGR2, TM9SF2, PIGS, TMEM189, LDLRAD4, IFNAR1, SACM1L, FAM134B, CD84, IFNAR2, |

TABLE 3-continued

HIV- low cutoff

| Category | Count | Genes |
|---|---|---|
| | | FAM134C, C5ORF15, TNFRSF9, CLECL1, TMEM69, CD81, C16ORF54, SPAST, GPR108, FAM173B, FAM173A, CD247, TNFRSF1A, SLC39A6, TMEM87A, MR1, APMAP, SLC39A3, IL2RB, GIMAP5, PTPRE, PTPRA, SUN2, TMBIM1, SLC10A3, GIMAP1, RPAP2, TMEM43, SLC6A6, SLC25A53, COMTD1 |
| topological domain:Cytoplasmic | 213 | B3GALT6, ADCY7, VAPB, IL6ST, LHCGR, USE1, TMEM140, ATP2B4, ERAP1, JAGN1, KLRD1, PLD3, GPR137, BSG, TRABD2A, UBE2J1, UBE2J2, PIK3IP1, ERGIC1, MGAT1, MGAT2, CD37, BTN3A1, CD320, ATP2C1, CCR4, LPAR6, HLA-DPA1, AMFR, CD226, BTN3A2, GLG1, TMX2, ORAI1, CLCN3, C16ORF91, TMX3, SLC11A2, SERINC3, SLC29A1, SYPL1, STX17, SERINC1, HLA-DPB1, EMB, STX10, MGAT4A, ST6GAL1, SPTSSA, ATP11A, SLAMF7, CD63, BTLA, ATP13A1, SYNE2, KIAA0922, BET1L, CD200, RTN4, SLC20A2, CD151, HVCN1, LNPEP, DNAJC16, IL4R, SLMAP, LAG3, DPP4, ICAM1, C10ORF54, ZDHHC3, JKAMP, ZDHHC8, ICAM3, TNFRSF10A, GRM4, ZDHHC16, BNIP1, NUS1, LRMP, CHSY1, CSF1, BET1, SFT2D2, STT3A, NUP210, PEX16, PCSK7, ACSL4, ACSL3, C1GALT1, CD27, ACSL5, IL18R1, EPB41L4A-AS1, LRRN3, CTLA4, TMEM5, ITPR2, SAMD8, PLSCR1, P2RY10, TAPBPL, NCLN, GOLGB1, ATP6AP2, UNC50, TSPAN5, SLC7A6, ST3GAL1, GLT8D1, STARD3, MFF, SMIM7, LRRC59, MS4A1, DDOST, SPN, SCAMP3, STIM1, MOGS, HCST, BCAP31, IGSF8, LRP10, VAMP5, KDSR, VAMP2, MFAP3, DERL1, ITGAE, CERS6, ITGB1, PRR7, P2RY8, FIS1, CERS2, ENTPD6, SLC30A5, B3GNT2, LYSMD3, PRAF2, B4GALT3, TMEM222, RYK, SYT11, NIPA2, SREBF2, ATF6, TIGIT, LAMP1, LAMP2, TRAF3IP3, PTTG1IP, RHOT1, RHOT2, CD79B, CD8A, CD8B, ATL3, CLSTN1, PEX3, CXCR3, LSR, PDCD1, DGCR2, CD93, CXCR4, ATP8B2, IFNGR2, EBAG9, TM9SF2, SIT1, PIGS, M6PR, LDLRAD4, IFNAR1, CD84, TNFRSF9, C5ORF15, IFNAR2, TNFSF13B, CLECL1, GINM1, IGF2R, CD81, EMC1, GALNT2, CD247, ALDH3A2, APLP2, NDC1, TNFRSF1A, HRH2, TSPAN31, TMED1, SHISA5, SEC22B, SLC39A6, MR1, APMAP, SLC39A3, CD5, IL2RB, PTPRE, GIMAP5, ATRAID, PTPRA, TSPAN17, GIMAP1, CLPTM1, LMBR1L, SLC6A6 |
| Enrichment Score: 6.831574760707297E-6 | | |
| IPR003961:Fibronectin, type III | 9 | ATF7IP, IFNAR2, IL2RB, IL6ST, IL4R, LRRN3, IFNGR2, ATF7IP2, IFNAR1 |
| domain:Fibronectin type-III 2 | 3 | IL6ST, IFNGR2, IFNAR1 |
| domain:Fibronectin type-III 1 | 3 | IL6ST, IFNGR2, IFNAR1 |
| Enrichment Score: 1.9767078533785107E-10 | | |
| IPR013032:EGF-like, conserved site | 3 | CD93, ATRAID, NELL2 |
| EGF-like domain | 3 | CD93, ATRAID, NELL2 |
| IPR000742:Epidermal growth factor-like domain | 3 | CD93, ATRAID, NELL2 |
| Enrichment Score:-0.0 | | |
| disulfide bond | 121 | IL6ST, LHCGR, NELL2, GFER, IGHM, ST3GAL1, MS4A1, KLRD1, BSG, PMCH, PIK3IP1, TIMM8A, IGSF8, BTN3A1, NPC2, CD320, LRP10, LPAR6, CCR4, HLA-DPA1, MFAP3, CD226, BTN3A2, CCL3, TXN2, ITGAE, TMX3, CTSA, CCL4, ITGB1, LIF, BLOC1S5, ENTPD6, PCYT1A, HLA-DPB1, EMB, ST6GAL1, B4GALT3, S100A11, MALT1, SLAMF7, PMF1, FURIN, TIGIT, DNASE2, BTLA, TXNDC12, LAMP1, CD55, TXNDC11, LAMP2, CD59, CD79B, XCL1, CD200, XCL2, CD8A, FAM3C, CD8B, HEXB, PDIA4, CXCR3, UQCRFS1, LSR, PDCD1, DGCR2, CD93, CXCR4, IL4R, LAG3, DPP4, ICAM1, C10ORF54, SIT1, AIFM1, LY96, ICAM3, GZMB, CLIC1, LDLRAD4, MIEN1, IFNAR1, CD84, TNFRSF10A, TNFRSF9, IFNAR2, CTSL, TNFSF13B, IGF2R, CD81, RRM1, MGEA5, TXNRD1, CTSC, CSF2, GALNT2, SPOCK2, CSF1, CD247, APLP2, GLRX2, TNFRSF1A, GNPTAB, HRH2, PITRM1, CCS, MR1, CD5, CD27, GLRX, IL18R1, CES2, IL2RB, ATRAID, LRRN3, CTLA4, P2RY10, GLA, IRF3, TAPBPL, IL2 |
| Disulfide bond | 145 | IL6ST, LHCGR, NELL2, PTPN22, GFER, IGHM, SLC7A6, ST3GAL1, MS4A1, ERAP1, KLRD1, BSG, PMCH, PIK3IP1, TIMM8A, HCST, MGAT1, IGSF8, BTN3A1, UHRF2, NPC2, CD320, LRP10, LPAR6, CCR4, HLA-DPA1, MFAP3, CD226, BTN3A2, MPST, CCL3, TXN2, ITGAE, TMX3, CTSA, CHCHD4, TRDC, HEXDC, CCL4, ITGB1, LIF, RAC1, ENTPD6, HLA-DPB1, EMB, FKRP, ST6GAL1, B4GALT3, S100A11, MALT1, SLAMF7, FURIN, BTLA, TIGIT, DNASE2, TXNDC12, LAMP1, LAMP2, CD55, TXNDC11, ERVK13-1, CD59, CD79B, XCL1, CD200, XCL2, BACH2, CD8A, FAM3C, CD8B, HEXB, CXCR3, PDIA4, UQCRFS1, LSR, PDCD1, DGCR2, CD93, TPP1, CXCR4, IL4R, RANBP2, LAG3, DPP4, AKT2, ICAM1, C10ORF54, SIT1, LY96, ICAM3, GZMB, CLIC1, LDLRAD4, MIEN1, IFNAR1, CD84, TNFRSF10A, |

TABLE 3-continued

HIV- low cutoff

| Category | Count | Genes |
|---|---|---|
| signal peptide | 165 | TNFRSF9, GRM4, CTSL, IFNAR2, TNFSF13B, IGF2R, CD81, RRM1, TXNRD1, CTSC, CSF2, GALNT2, NDUFB7, SPOCK2, CSF1, USP5, CD247, APLP2, GLRX2, MYCBP2, TNFRSF1A, GNPTAB, HRH2, PITRM1, CCS, MR1, CD5, C1GALT1, CD27, GLRX, SOAT1, IL18R1, CES2, IL2RB, ATRAID, LRRN3, ANXA1, CTLA4, RAF1, NUP155, P2RY10, GLA, IRF3, TAPBPL, POFUT1, FEZ2, GOLGB1, IL2<br>ATP6AP2, IL6ST, NELL2, LHCGR, SLC52A2, IGHM, SMIM7, IFNG, RNF149, DDOST, IZUMO4, SPN, GPR137, BSG, PMCH, TRABD2A, STIM1, PIK3IP1, CECR5, HCST, IGSF8, ABHD17B, BTN3A1, CHID1, NPC2, LRP10, CD320, HLA-DPA1, KDSR, MFAP3, AMFR, CD226, UGGT1, BTN3A2, SUCO, HSD17B11, GLG1, TMX2, CCL3, C16ORF91, ITGAE, TMX3, CTSA, CCL4, ITGB1, CASD1, LIF, BLOC1S5, C1ORF56, HLA-DPB1, RNF167, EMB, SDF4, FKRP, SDF2, TM2D1, RYK, ENDOD1, SLAMF7, PMF1, FURIN, BTLA, DNASE2, TIGIT, LAMP1, TXNDC12, LAMP2, CD55, APOL1, CD59, KIAA0922, PTTG1IP, CD79B, TMEM41A, XCL1, CD200, XCL2, IFI6, CD8A, CD8B, FAM3C, HEXB, CLSTN1, PDIA4, DHRSX, ASAH1, PDCD1, TMEM109, DGCR2, DNAJC16, CD93, TPP1, RSPRY1, IL4R, GPX7, TM9SF4, CCDC107, IFNGR2, LAG3, ICAM1, TM9SF2, C10ORF54, SIT1, AIFM1, LY96, ICAM3, GZMB, M6PR, DHRS7, IFNAR1, KIAA0100, CD84, TNFRSF10A, NUCB1, TOR2A, TNFRSF9, GRM4, CTSL, IFNAR2, C5ORF15, NUS1, GINM1, IGF2R, NUCB2, OXNAD1, EMC1, CTSC, FKBP11, CSF2, GPR108, TSPEAR, SPOCK2, CSF1, CD247, COLGALT1, APLP2, TNFRSF1A, C12ORF49, NUP210, TMED1, SHISA5, TMEM87A, SLC39A6, PCSK7, MR1, NENF, CD5, CD27, IL18R1, ALKBH7, IL2RB, CES2, PTPRE, ATRAID, PTPRA, LRRN3, CTLA4, C3ORF58, GLA, MCFD2, TAPBPL, POFUT1, NCLN, IL2, RCN2 |

Enrichment Score:−0.0

| Category | Count | Genes |
|---|---|---|
| Glycoprotein | 208 | B3GALT6, ADCY7, IL6ST, LHCGR, NELL2, IGHM, TMEM140, IFNG, ERAP1, KLRD1, IZUMO4, PLD3, GPR137, BSG, TRABD2A, PIK3IP1, ERGIC1, TMEM131, MGAT2, CD37, BTN3A1, NPC2, CAMK4, CD320, CCR4, TMEM138, LPAR6, HLA-DPA1, CD226, BTN3A2, SUCO, GLG1, ORAI1, CLCN3, TMX3, OAS2, SLC11A2, SERINC3, LIF, SLC29A1, SYPL1, SERINC1, RAC1, HLA-DPB1, EMB, MGAT4A, GPR155, ST6GAL1, TM2D1, SLAMF7, CD63, BTLA, CD55, APOL1, ATP13A1, CD59, KIAA0922, TMEM41A, CD200, ENOX2, SLC20A2, AP1AR, CD151, ASAH1, LNPEP, DNAJC16, IL4R, CLDND1, DPP4, LAG3, ICAM1, C10ORF54, LY96, ICAM3, GZMB, TNFRSF10A, GRM4, MTMR14, NUS1, CHSY1, CSF2, CSF1, ABHD2, COLGALT1, NUP214, NUMA1, STT3A, GNPTAB, C12ORF49, NUP210, PCSK7, CD27, IL18R1, CES2, LRRN3, CTLA4, TMEM2, P2RY10, GLA, NCLN, IL2, TSPAN5, ST3GAL1, GLT8D1, RNF149, SPN, TOR1AIP2, TOR1AIP1, STIM1, MOGS, HCST, PNPLA8, TMEM106B, IGSF8, LRP10, MFAP3, UGGT1, TMEM214, ITGAE, CERS6, UNC93B1, TMEM219, CTSA, TRDC, ITGB1, SRF, P2RY8, CERS2, ENTPD6, RNF167, B3GNT2, FKRP, SDF4, TMEM30A, LYSMD3, B4GALT3, YIPF6, RYK, FURIN, ATF6, DNASE2, TIGIT, LAMP1, LAMP2, PTTG1IP, CD79B, LRRC8B, CD8B, HEXB, CLSTN1, MFSD2A, CXCR3, PDCD1, DGCR2, CD93, TPP1, RSPRY1, CXCR4, IFNGR2, AKT2, SIT1, PFKL, PIGS, M6PR, TMEM245, MCM6, IFNAR1, KIAA0100, CD84, NUCB1, TOR2A, TNFRSF9, C5ORF15, IFNAR2, CTSL, TNFSF13B, CLECL1, GINM1, IGF2R, EMC1, CTSC, C16ORF54, GPR108, FAM173A, TSPEAR, SPOCK2, TPRA1, TMEM259, APLP2, TNFRSF1A, HRH2, TSPAN31, TMEM87A, SLC39A6, MR1, APMAP, CD5, IL2RB, PTPRE, ATRAID, PTPRA, SUN2, NUP155, TSPAN17, CLPTM1, SP1, SLC6A6, POFUT1 |
| signal peptide | 165 | ATP6AP2, IL6ST, NELL2, LHCGR, SLC52A2, IGHM, SMIM7, IFNG, RNF149, DDOST, IZUMO4, SPN, GPR137, BSG, PMCH, TRABD2A, STIM1, PIK3IP1, CECR5, HCST, IGSF8, ABHD17B, BTN3A1, CHID1, NPC2, LRP10, CD320, HLA-DPA1, KDSR, MFAP3, AMFR, CD226, UGGT1, BTN3A2, SUCO, HSD17B11, GLG1, TMX2, CCL3, C16ORF91, ITGAE, TMX3, CTSA, CCL4, ITGB1, CASD1, LIF, BLOC1S5, C1ORF56, HLA-DPB1, RNF167, EMB, SDF4, FKRP, SDF2, TM2D1, RYK, ENDOD1, SLAMF7, PMF1, FURIN, BTLA, DNASE2, TIGIT, LAMP1, TXNDC12, LAMP2, CD55, APOL1, CD59, KIAA0922, PTTG1IP, CD79B, TMEM41A, XCL1, CD200, XCL2, IFI6, CD8A, CD8B, FAM3C, HEXB, CLSTN1, PDIA4, DHRSX, ASAH1, PDCD1, TMEM109, DGCR2, DNAJC16, CD93, TPP1, RSPRY1, IL4R, GPX7, TM9SF4, CCDC107, IFNGR2, LAG3, ICAM1, TM9SF2, C10ORF54, SIT1, AIFM1, LY96, ICAM3, GZMB, M6PR, DHRS7, IFNAR1, KIAA0100, CD84, TNFRSF10A, NUCB1, TOR2A, TNFRSF9, GRM4, CTSL, IFNAR2, C5ORF15, NUS1, GINM1, IGF2R, NUCB2, OXNAD1, EMC1, CTSC, FKBP11, CSF2, GPR108, TSPEAR, SPOCK2, CSF1, CD247, COLGALT1, APLP2, TNFRSF1A, C12ORF49, NUP210, TMED1, SHISA5, TMEM87A, SLC39A6, PCSK7, MR1, NENF, CD5, CD27, IL18R1, ALKBH7, IL2RB, CES2, PTPRE, ATRAID, PTPRA, LRRN3, CTLA4, C3ORF58, GLA, MCFD2, TAPBPL, POFUT1, NCLN, IL2, RCN2 |

TABLE 3-continued

HIV- low cutoff

| Category | Count | Genes |
|---|---|---|
| glycosylation site:N-linked (GlcNAc . . .) | 189 | ADCY7, B3GALT6, IL6ST, NELL2, TSPAN5, LHCGR, IGHM, TMEM140, ST3GAL1, GLT8D1, IFNG, ERAP1, RNF149, KLRD1, IZUMO4, SPN, TOR1AIP2, PLD3, GPR137, BSG, TRABD2A, TOR1AIP1, STIM1, MOGS, ERGIC1, TMEM131, MGAT2, PNPLA8, TMEM106B, BTN3A1, CD37, IGSF8, NPC2, LRP10, CD320, CCR4, LPAR6, TMEM138, HLA-DPA1, MFAP3, AMFR, BTN3A2, CD226, UGGT1, SUCO, GLG1, ORAI1, CLCN3, TMEM214, ITGAE, TMX3, TMEM63A, CERS6, UNC93B1, TMEM219, CTSA, ITGB1, SLC29A1, SERINC3, SLC11A2, P2RY8, LIF, SYPL1, CERS2, SERINC1, ENTPD6, HLA-DPB1, EMB, RNF167, B3GNT2, FKRP, SDF4, TMEM30A, LYSMD3, MGAT4A, GPR155, ST6GAL1, B4GALT3, YIPF6, TM2D1, RYK, SLAMF7, CD63, FURIN, BTLA, ATF6, DNASE2, TIGIT, LAMP1, LAMP2, CD55, APOL1, ATP13A1, CD59, KIAA0922, PTTG1IP, CD79B, TMEM41A, CD200, LRRC8B, CD8B, SLC20A2, AP1AR, HEXB, LRRC8D, CLSTN1, CXCR3, CD151, ASAH1, PDCD1, LNPEP, DGCR2, DNAJC16, CD93, TPP1, RSPRY1, CXCR4, IL4R, CLDND1, IFNGR2, LAG3, DPP4, ICAM1, C10ORF54, SIT1, LY96, ICAM3, PIGS, GZMB, TMEM245, M6PR, IFNAR1, KIAA0100, CD84, TNFRSF10A, TOR2A, TNFRSF9, GRM4, CTSL, IFNAR2, C5ORF15, MTMR14, CLECL1, TNFSF13B, GINM1, IGF2R, EMC1, CHSY1, CTSC, CSF, GPR108, FAM173A, TSPEAR, SPOCK2, CSF1, TPRA1, TMEM259, COLGALT1, TNFRSF1A, STT3A, GNPTAB, C12ORF49, HRH2, NUP210, TSPAN31, TMEM87A, SLC39A6, PCSK7, MR1, APMAP, CD5, CD27, IL18R1, IL2RB, CES2, PTPRE, ATRAID, PTPRA, LRRN3, CTLA4, SUN2, TSPAN17, TMEM2, CLPTM1, P2RY10, GLA, SLC6A6, POFUT1, NCLN |
| Signal | 235 | CDIPT, TMEM19, SEC31A, IL6ST, LHCGR, NELL2, MPV17, SLC52A2, HIBADH, SHKBP1, PGP, IFNG, ERAP1, IZUMO4, TIMMDC1, BSG, CAPNS1, PMCH, TRABD2A, UBR2, PIK3IP1, TMEM131, BTN3A1, NPC2, CD320, HLA-DPA1, FAM177A1, CD226, BTN3A2, SUCO, TMX2, HSD17B11, GLG1, C16ORF91, TMX3, NPIPB4, AKAP10, LIF, C1ORF56, RAC1, HLA-DPB1, EMB, GPR155, LAPTM4A, TM2D1, SLAMF7, BTLA, APOL3, CD55, APOL1, ATP13A1, CD59, KIAA0922, TMEM41A, CD200, METTL17, FAM96A, FAM3C, VPS37B, PDIA4, ASAH1, TMEM109, DNAJC16, IL4R, GPX7, CLDND1, LAG3, ICAM1, C10ORF54, LY96, ICAM3, GZMB, ECSIT, TNFRSF10A, GRM4, MTMR14, FKBP11, CSF2, EXOC7, USP3, CSF1, COLGALT1, DNAJC30, STAU1, NUP214, C12ORF49, NUP210, PCSK7, NENF, CD27, IL18R1, CES2, LRRN3, CTLA4, DNPEP, SDHA, FAM78A, GLA, MCFD2, JMJD8, PHGDH, TAPBPL, OGG1, NCLN, GOLGB1, IL2, RALY, TSPO, ATP6AP2, HBS1L, RGL4, SMIM7, RNF149, DDOST, SPN, TMEM205, STIM1, CECR5, HCST, RALGAPA1, IGSF8, ABHD17B, CHID1, LRP10, KDSR, MFAP3, SMARCA2, UGGT1, PCCB, CCL3, ITGAE, TMEM219, MUM1, CTSA, ITGB1, CCL4, CASD1, FBXW7, C12ORF10, RNF167, SDF2, RYK, C21ORF33, ENDOD1, ABCB7, FURIN, DNASE2, TIGIT, TXNDC12, LAMP1, LAMP2, TXNDC11, DNAJB9, PDE7A, PTTG1IP, CD79B, XCL1, XCL2, IFI6, CD8A, CD8B, YLPM1, HEXB, CLSTN1, DHRSX, LSR, ZZEF1, PDCD1, DGCR2, CD93, RSPRY1, TPP1, CCDC107, TM9SF4, IFNGR2, EBAG9, TM9SF2, ELP2, CCDC88B, SIT1, DYNLT3, M6PR, IFNAR1, DHRS7, KIAA0100, NUCB1, CD84, TOR2A, CTSL, C5ORF15, TNFRSF9, IFNAR2, PANK2, HIPK1, GINM1, IGF2R, CD81, HIPK2, DDT, NUCB2, OXNAD1, CTSC, EMC1, KPNA1, C7ORF73, GPR108, TSPEAR, SPOCK2, CD247, APLP2, TNFRSF1A, NUDT9, TSPAN31, TMED1, SHISA5, TMEM87A, SLC39A6, MR1, CD5, IL2RB, PTPRE, ATRAID, PTPRA, CBL, RAF1, SLC10A3, GORAB, WSB1, ADI1, C3ORF58, TDP2, SLC6A6, POFUT1, RCN2 |
| topological domain:Cytoplasmic | 213 | B3GALT6, ADCY7, VAPB, IL6ST, LHCGR, USE1, TMEM140, ATP2B4, ERAP1, JAGN1, KLRD1, PLD3, GPR137, BSG, TRABD2A, UBE2J1, UBE2J2, PIK3IP1, ERGIC1, MGAT1, MGAT2, CD37, BTN3A1, CD320, ATP2C1, CCR4, LPAR6, HLA-DPA1, AMFR, CD226, BTN3A2, GLG1, TMX2, ORAI1, CLCN3, C16ORF91, TMX3, SLC11A2, SERINC3, SLC29A1, SYPL1, STX17, SERINC1, HLA-DPB1, EMB, STX10, MGAT4A, ST6GAL1, SPTSSA, ATP11A, SLAMF7, CD63, BTLA, ATP13A1, SYNE2, KIAA0922, BET1L, CD200, RTN4, SLC20A2, CD151, HVCN1, LNPEP, DNAJC16, IL4R, SLMAP, LAG3, DPP4, ICAM1, C10ORF54, ZDHHC3, JKAMP, ZDHHC8, ICAM3, TNFRSF10A, GRM4, ZDHHC16, BNIP1, NUS1, LRMP, CHSY1, CSF1, BET1, SFT2D2, STT3A, NUP210, PEX16, PCSK7, ACSL4, ACSL3, C1GALT1, CD27, ACSL5, IL18R1, EPB41L4A-AS1, LRRN3, CTLA4, TMEM5, ITPR2, SAMD8, PLSCR1, P2RY10, TAPBPL, NCLN, GOLGB1, ATP6AP2, UNC50, TSPAN5, SLC7A6, ST3GAL1, GLT8D1, STARD3, MFF, SMIM7, LRRC59, MS4A1, DDOST, SPN, SCAMP3, STIM1, MOGS, HCST, BCAP31, IGSF8, LRP10, VAMP5, KDSR, VAMP2, MFAP3, DERL1, ITGAE, CERS6, ITGB1, PRR7, P2RY8, FIS1, CERS2, ENTPD6, SLC30A5, B3GNT2, LYSMD3, PRAF2, B4GALT3, TMEM222, RYK, SYT11, NIPA2, SREBF2, ATF6, TIGIT, LAMP1, LAMP2, TRAF3IP3, PTTG1IP, RHOT1, RHOT2, CD79B, CD8A, CD8B, ATL3, CLSTN1, PEX3, CXCR3, LSR, PDCD1, DGCR2, CD93, CXCR4, ATP8B2, IFNGR2, EBAG9, TM9SF2, SIT1, PIGS, M6PR, LDLRAD4, IFNAR1, CD84, TNFRSF9, C5ORF15, IFNAR2, TNFSF13B, CLECL1, GINM1, IGF2R, CD81, EMC1, GALNT2, CD247, ALDH3A2, APLP2, NDC1, TNFRSF1A, HRH2, |

TABLE 3-continued

HIV- low cutoff

| Category | Count | Genes |
|---|---|---|
| topological domain:Extracellular | 130 | TSPAN31, TMED1, SHISA5, SEC22B, SLC39A6, MR1, APMAP, SLC39A3, CD5, IL2RB, PTPRE, GIMAP5, ATRAID, PTPRA, TSPAN17, GIMAP1, CLPTM1, LMBR1L, SLC6A6 IL6ST, ATP6AP2, LHCGR, TSPAN5, SLC7A6, TMEM140, STARD3, ATP2B4, SMIM7, KLRD1, SPN, GPR137, BSG, TRABD2A, STIM1, PIK3IP1, HCST, IGSF8, CD37, BTN3A1, CD320, LRP10, LPAR6, CCR4, HLA-DPA1, AMFR, MFAP3, CD226, BTN3A2, GLG1, TMX2, ORAI1, C16ORF91, ITGAE, ITGB1, P2RY8, SERINC3, SLC11A2, SLC29A1, PRR7, SERINC1, SLC30A5, HLA-DPB1, EMB, LYSMD3, PRAF2, TMEM222, RYK, ATP11A, NIPA2, SLAMF7, CD63, BTLA, TIGIT, ATP13A1, KIAA0922, TRAF3IP3, PTTG1IP, CD79B, CD200, CD8A, SLC20A2, CD8B, CLSTN1, CXCR3, CD151, HVCN1, LSR, PDCD1, LNPEP, DGCR2, DNAJC16, CD93, CXCR4, IL4R, SLMAP, ATP8B2, IFNGR2, LAG3, DPP4, EBAG9, ICAM1, C10ORF54, SIT1, ICAM3, LDLRAD4, IFNAR1, CD84, TNFRSF10A, TNFRSF9, GRM4, C5ORF15, IFNAR2, NUS1, TNFSF13B, CLECL1, GINM1, CD81, EMC1, CD247, APLP2, TNFRSF1A, HRH2, TSPAN31, TMED1, SHISA5, SLC39A6, PCSK7, APMAP, MR1, SLC39A3, CD5, CD27, IL18R1, IL2RB, PTPRE, GIMAP5, ATRAID, PTPRA, LRRN3, CTLA4, TMEM5, TSPAN17, GIMAP1, ITPR2, CLPTM1, LMBR1L, PLSCR1, P2RY10, SLC6A6 |

Example 2. A Comprehensive Single Cell Atlas of Non-Human Primate Cells During Homeostasis and Pathogenic Infection Immune systems play an essential role in ensuring our health. From decades of laboratory and clinical work, there has been a basic understanding of immune balance and its importance for a healthy immune system. For example, hyperactivity can lead to allergy, inflammation, tissue damage, autoimmune disease and excessive cellular death. On the other hand, immunodeficiency can lead to outgrowth of cancers and the inability to kill or suppress external invaders. The immune system has evolved multiple modalities and redundancies that balance the system, including but not limited to memory, exhaustion, anergy, and senescence.

As the gene-expression program of a given cell closely reflects both its identity and function (Heinz et al., 2015), a systematic atlas of single-cell RNA profiles can help address many questions about immune regulations, their networks and molecular processes, and the response to pathogenic stimuli. Given the importance of the immune system, a systematic understanding of immune regulations on cell, tissue, and organism levels is crucial for clinicians and researchers to efficiently diagnose and develop treatments for immune system related disease.

Here, using scRNA-seq, this study identified gene signatures involved in SHIV- infection and immune responses, characterized cellular heterogeneity within specific cell-types, and demonstrated how these cell types and states change dynamically at different states of infection. More importantly, this study provides a resourceful pan-tissue database of expression profiles of healthy non-human primates that serves as a detailed reference data set for follow up studies regarding HIV as well as more diseases and pathogenic states. Given the resemblance between HIV and SHIV, and the kinship between human and non-human primates, the atlas disclosed by this study also allows for parallel comparison and identifications of specific sub cell types as well as differentially regulated genes involved in human HIV infection.

Four Rhesus Macaques were sacrificed with full necropsy. Single cells from 12 distinct tissues were collected and single cell RNA-Sequencing was performed on these cells. Three Rhesus Macaques were infected with SHIV for 6 months, anti-retroviral therapy was applied for 6 months, and the animals were then sacrificed with full necropsy. Eight distinct tissues per SHIV+ animal were collected for single cell RNA-Sequencing. Tissues were collected as population controls in multiple forms, including RNALater, paraffin embedded, live cells frozen, lysed post dissociation and saved for control experiments and validations.

Figure 9:
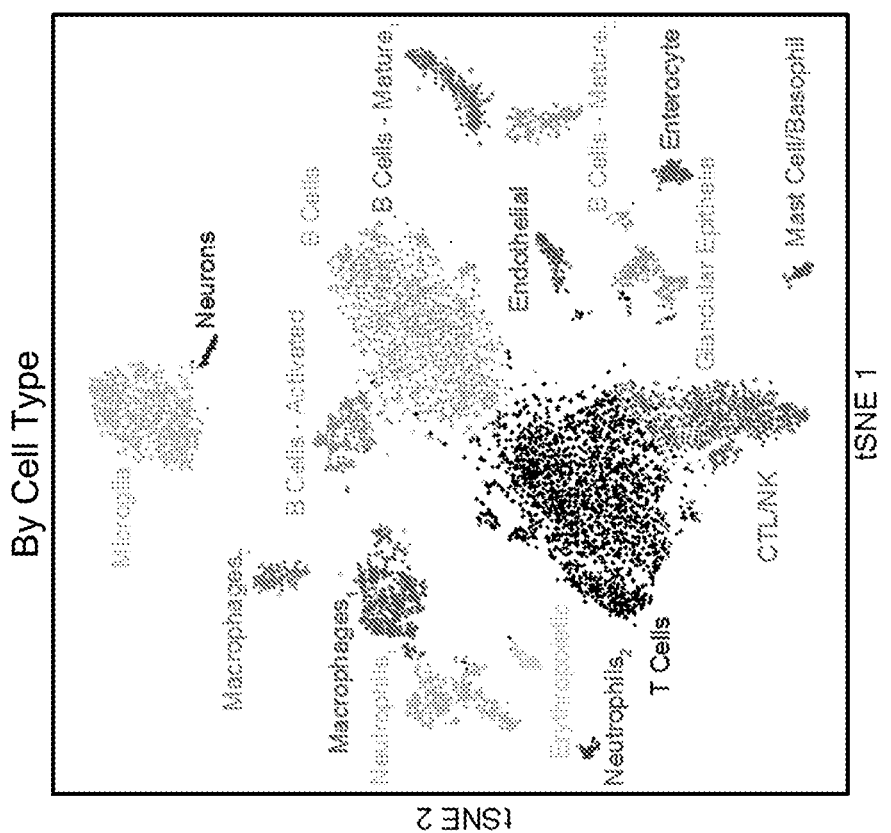
FIG. 9— Single cell profiles define cells by tissue (left) and cell type (right).
Figure 9:
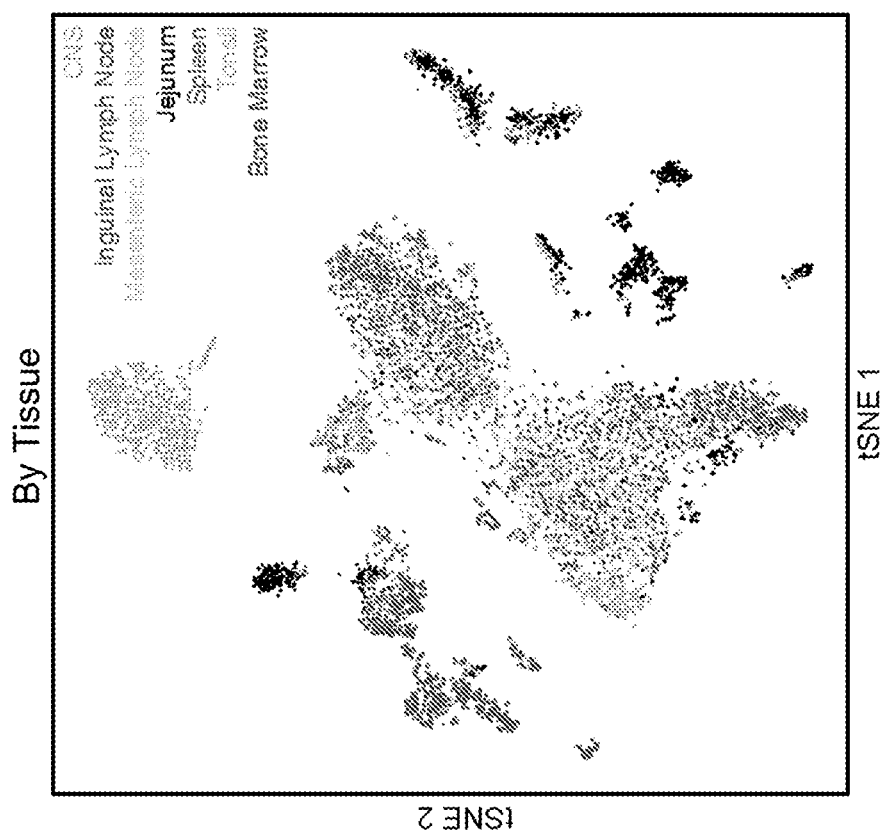
Figure 10:
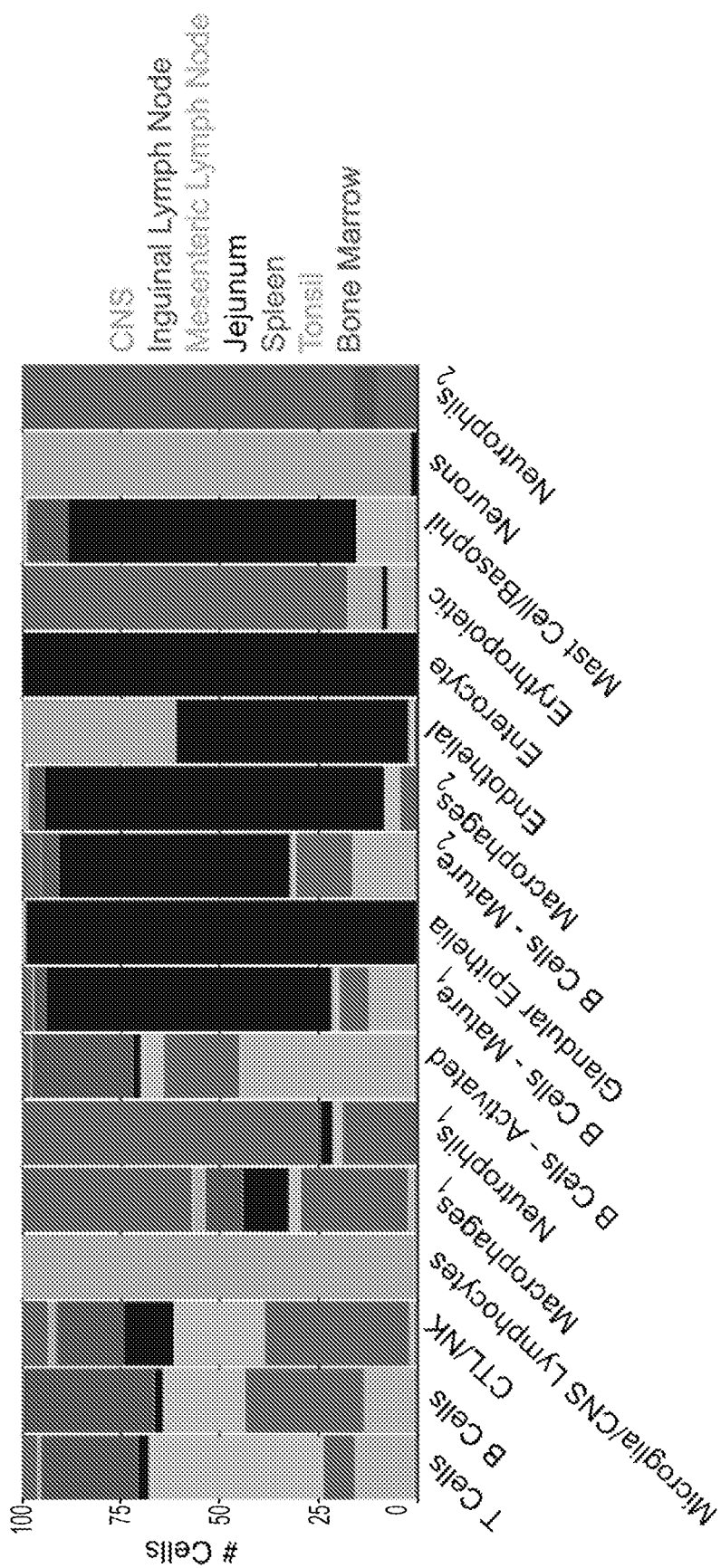
FIG. 10— Single cell transcriptome expression profiles cluster by cell type.
Figure 11:
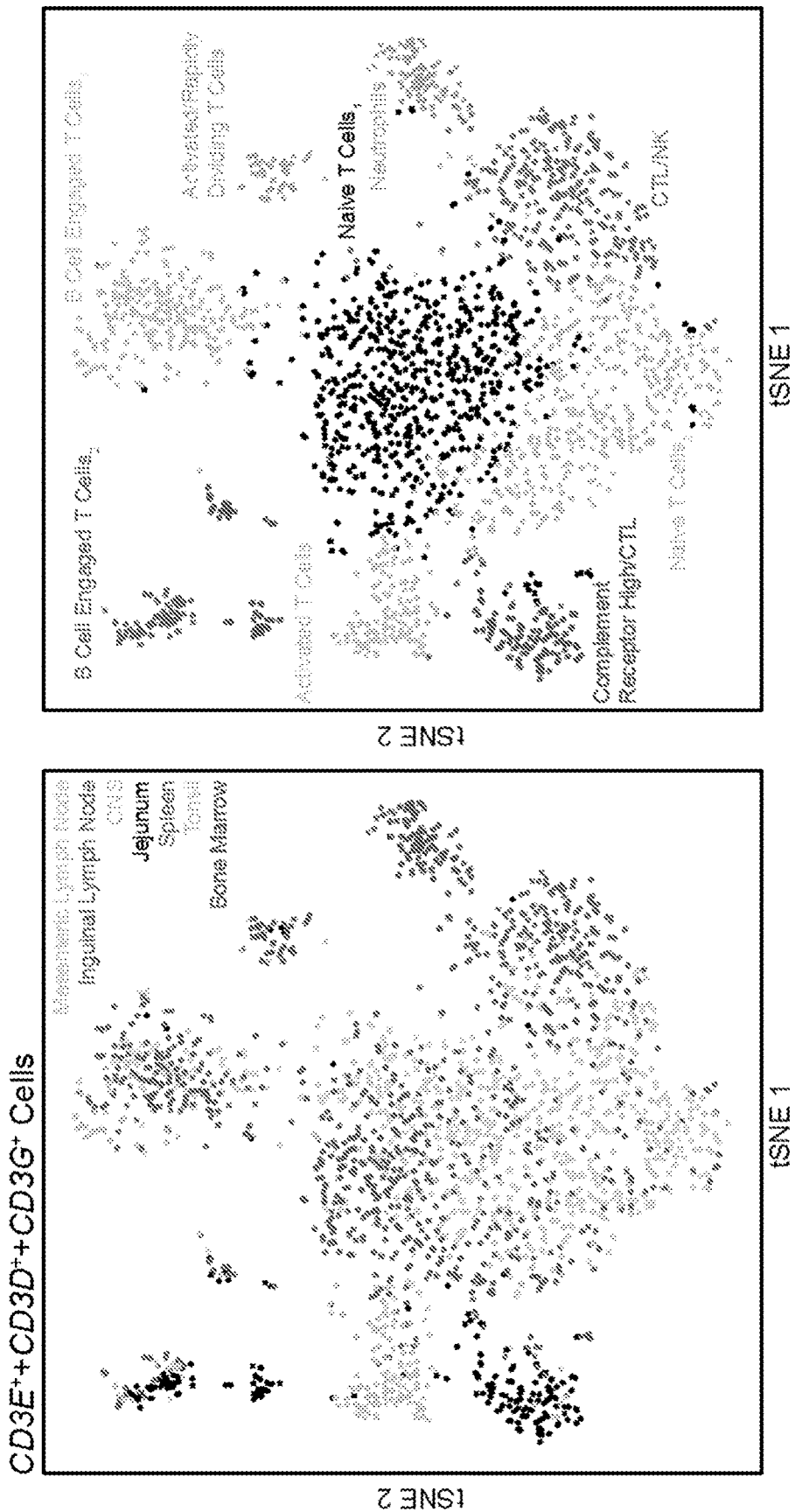
FIG. 11— CD3E++CD3D++CD3G+ cells by tissue and cell type.
Figure 12A:
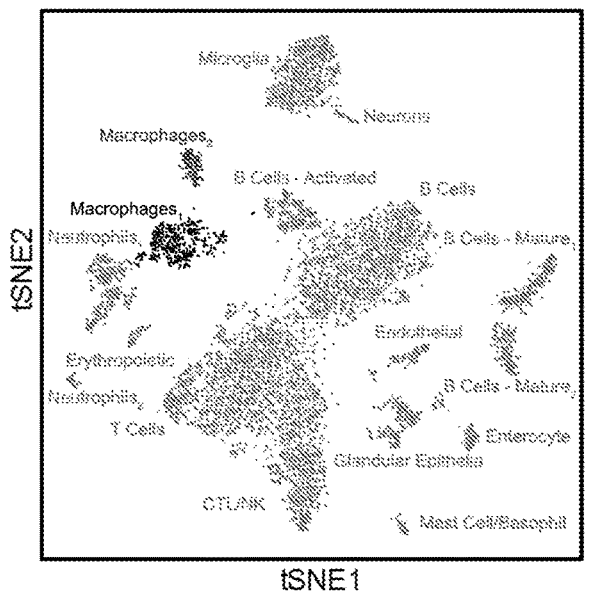
FIG. 12A—Tissue specific behavior of macrophages.
Figure 12B:
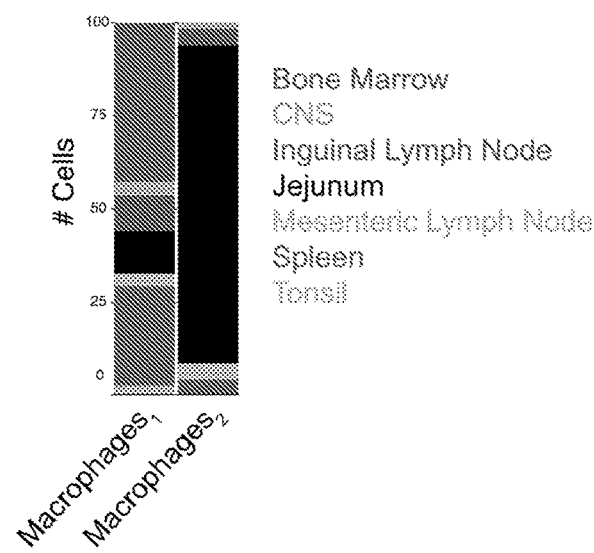
FIG. 12B charts number of tissue specific cells of macrophages.
Figure 12C:
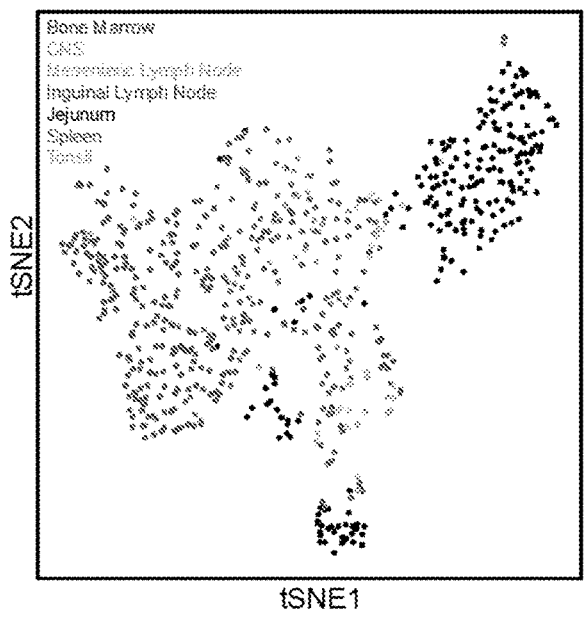
FIG. 12C single cell transcriptomes of macrophages identify genes that define them.
Figure 12D:
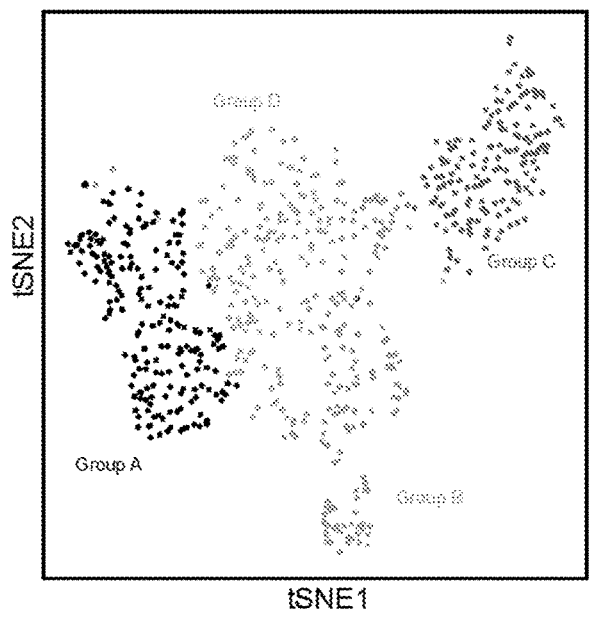
FIG. 12D single cell transcriptomes of macrophages identify tissue specific sub sets.
Figure 13:
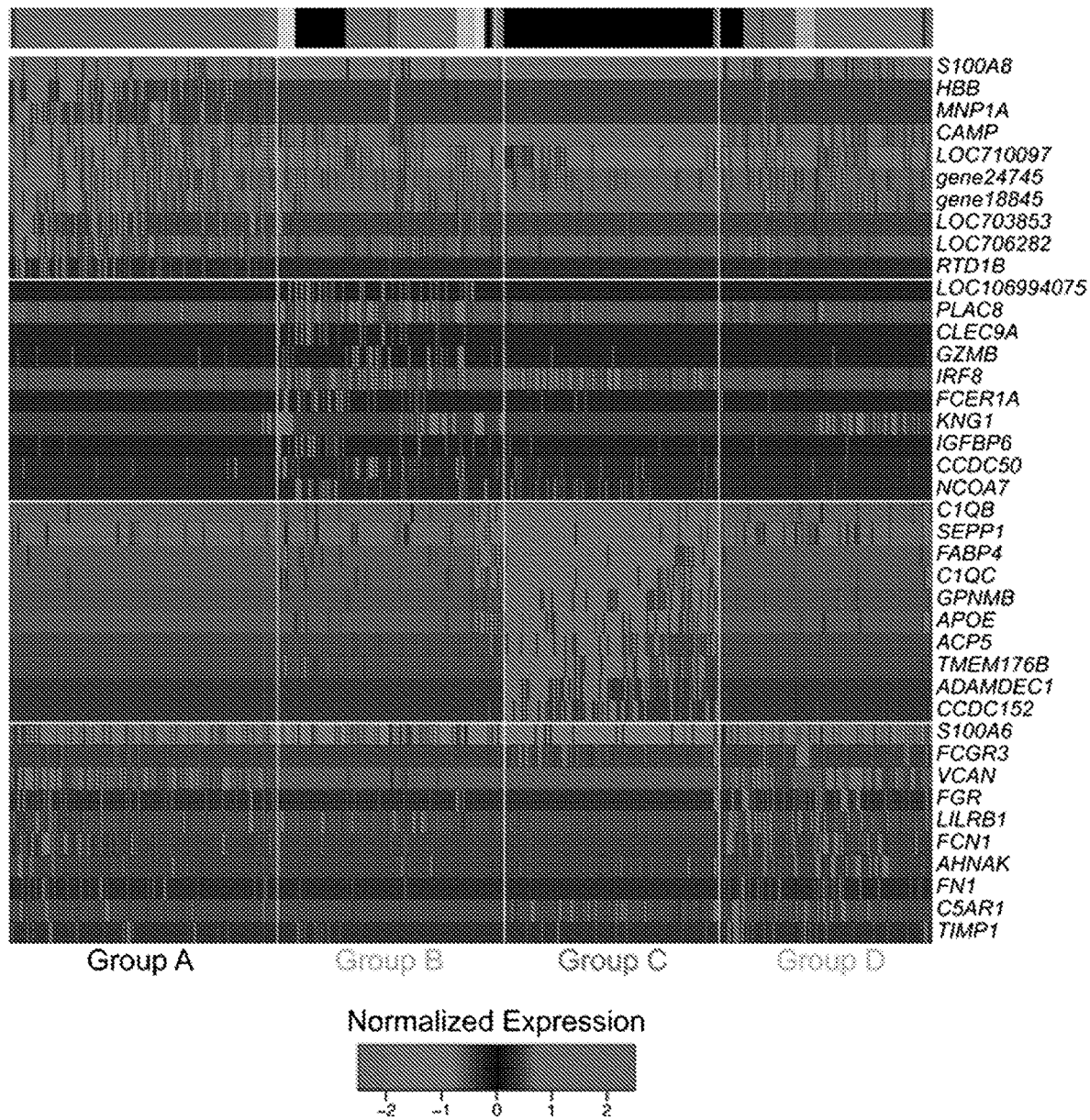
FIG. 13— Macrophage expression profiles correspond with tissues of origin.
Figure 14:
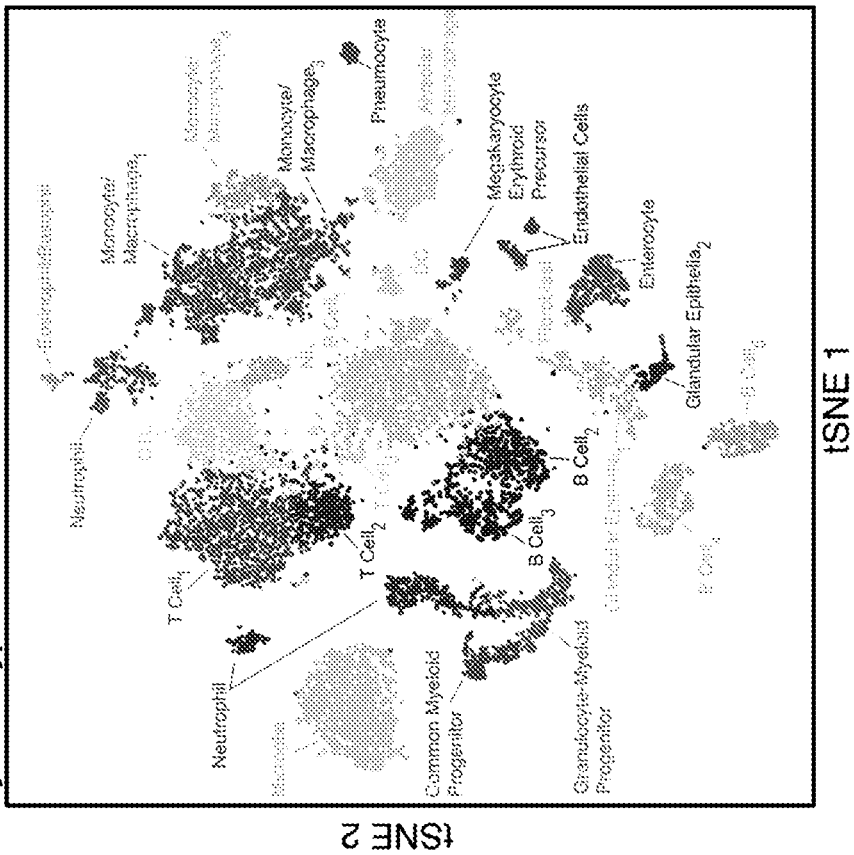
FIG. 14— Single cell profiles define cells by tissue (left) and cell type (right).
Figure 14:
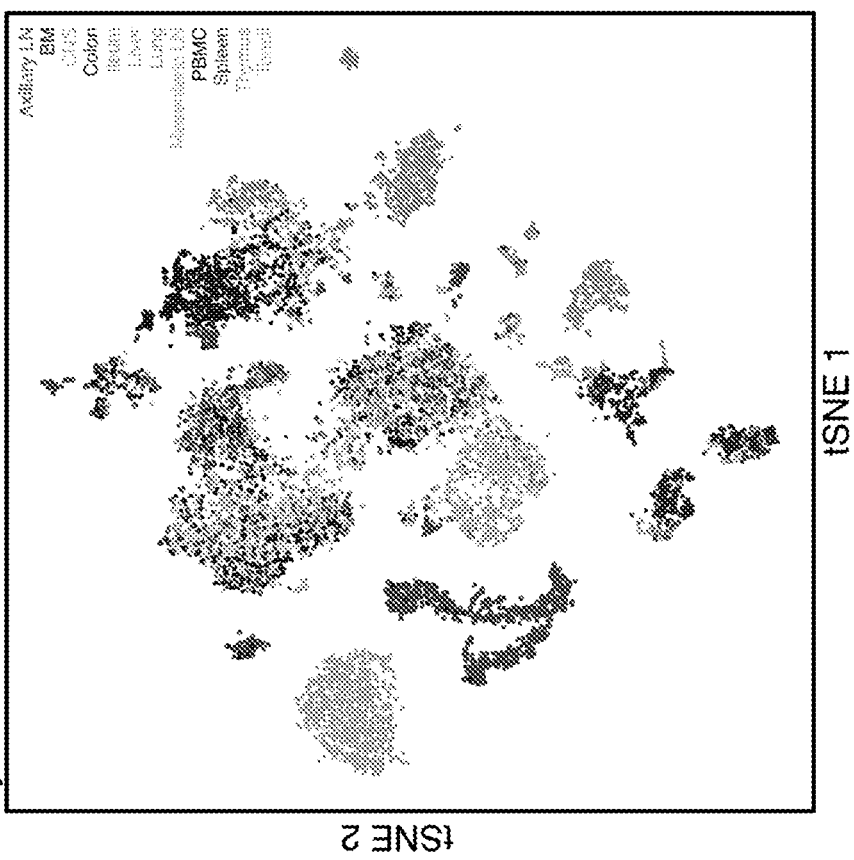
Figure 15A:
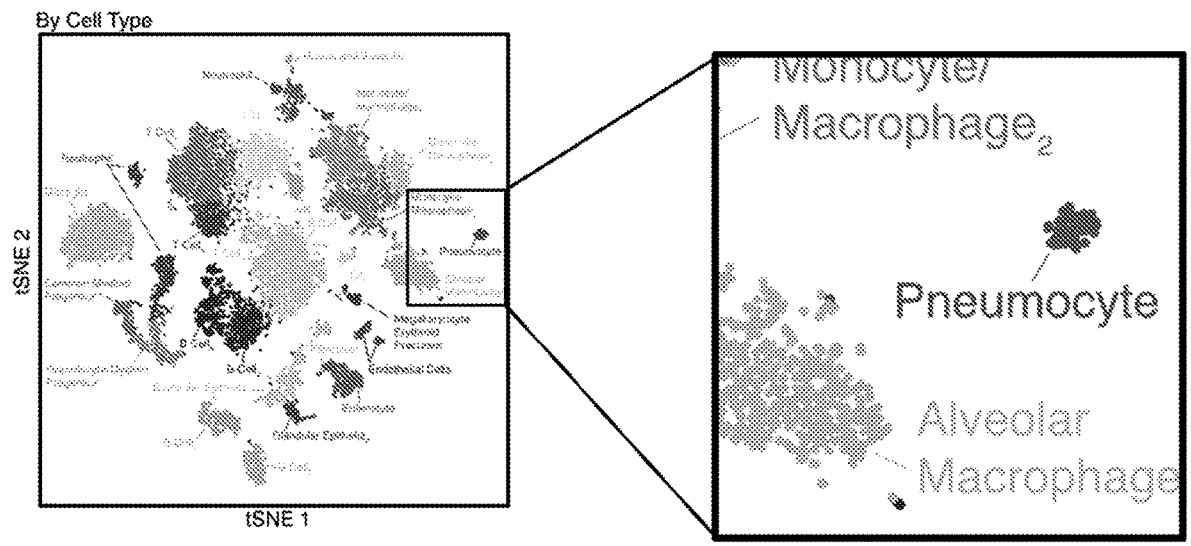
FIG. 15— Identification of pneumocyte (FIG. 15A) and NK (FIG. 15B) cell clusters.
Figure 15B:
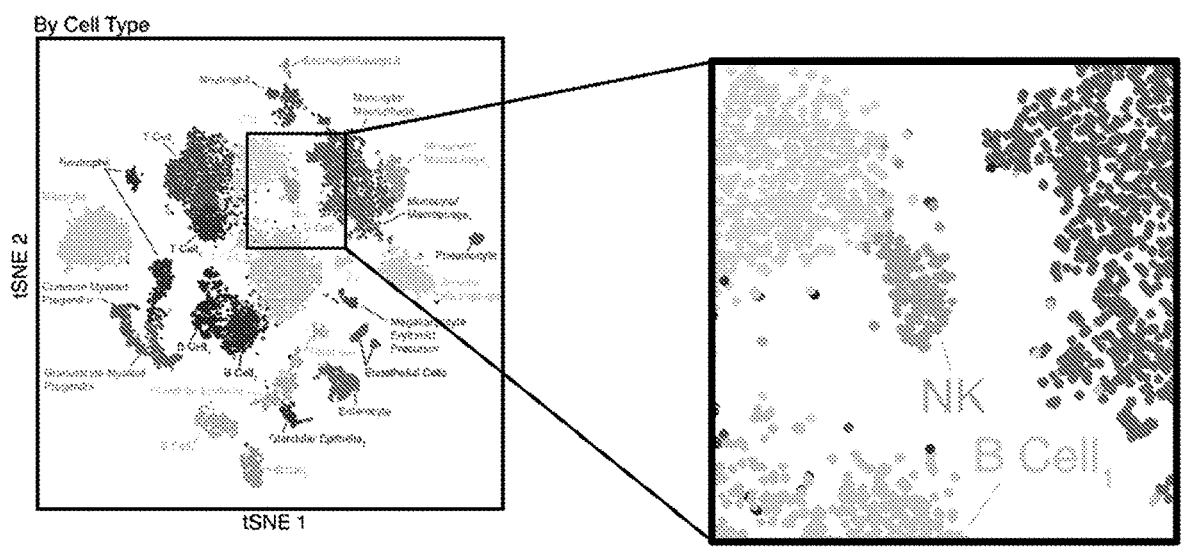
Figure 16:
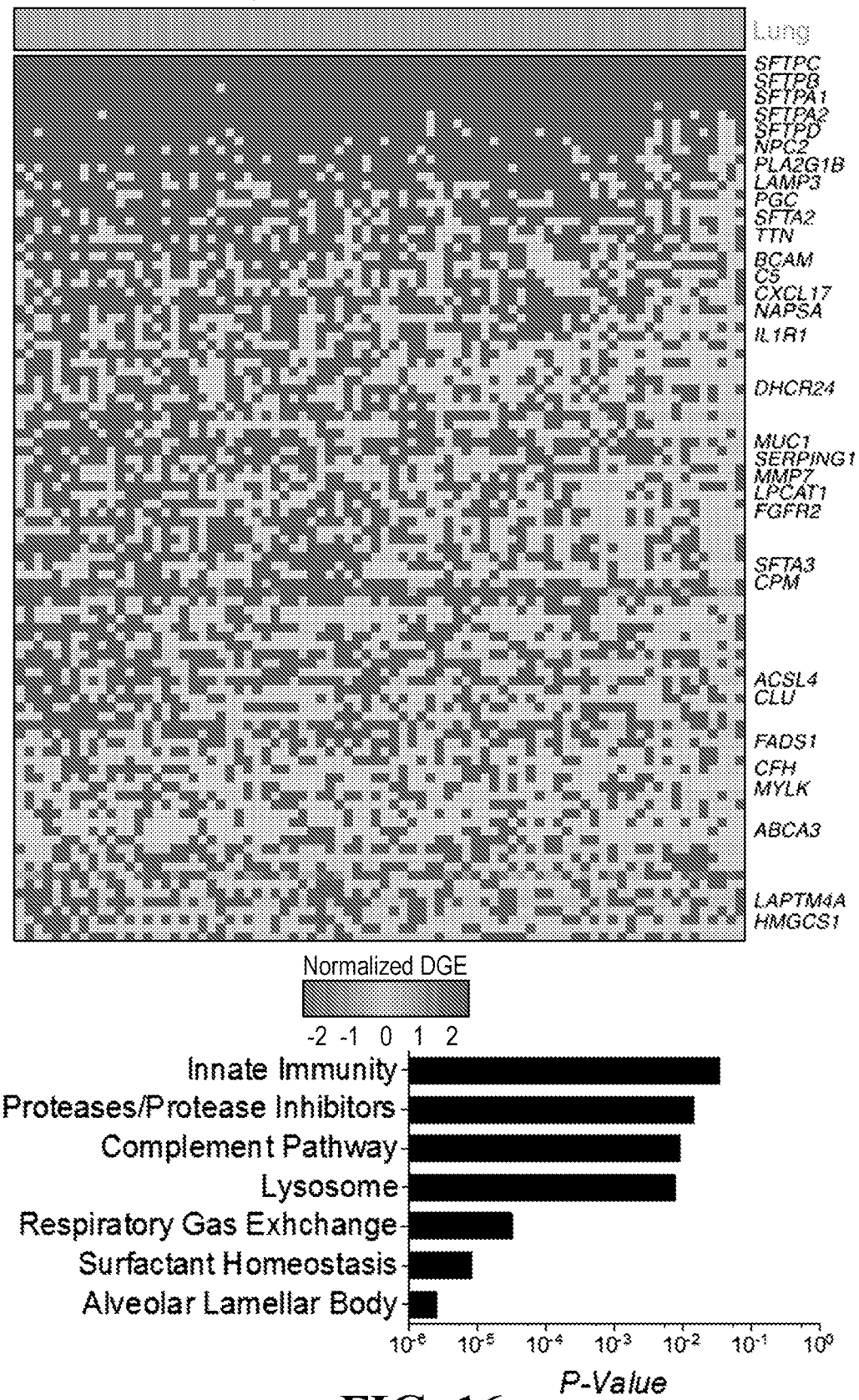
FIG. 16— Gene expression in pneumocytes indicates tissue-dependence.
Figure 17:
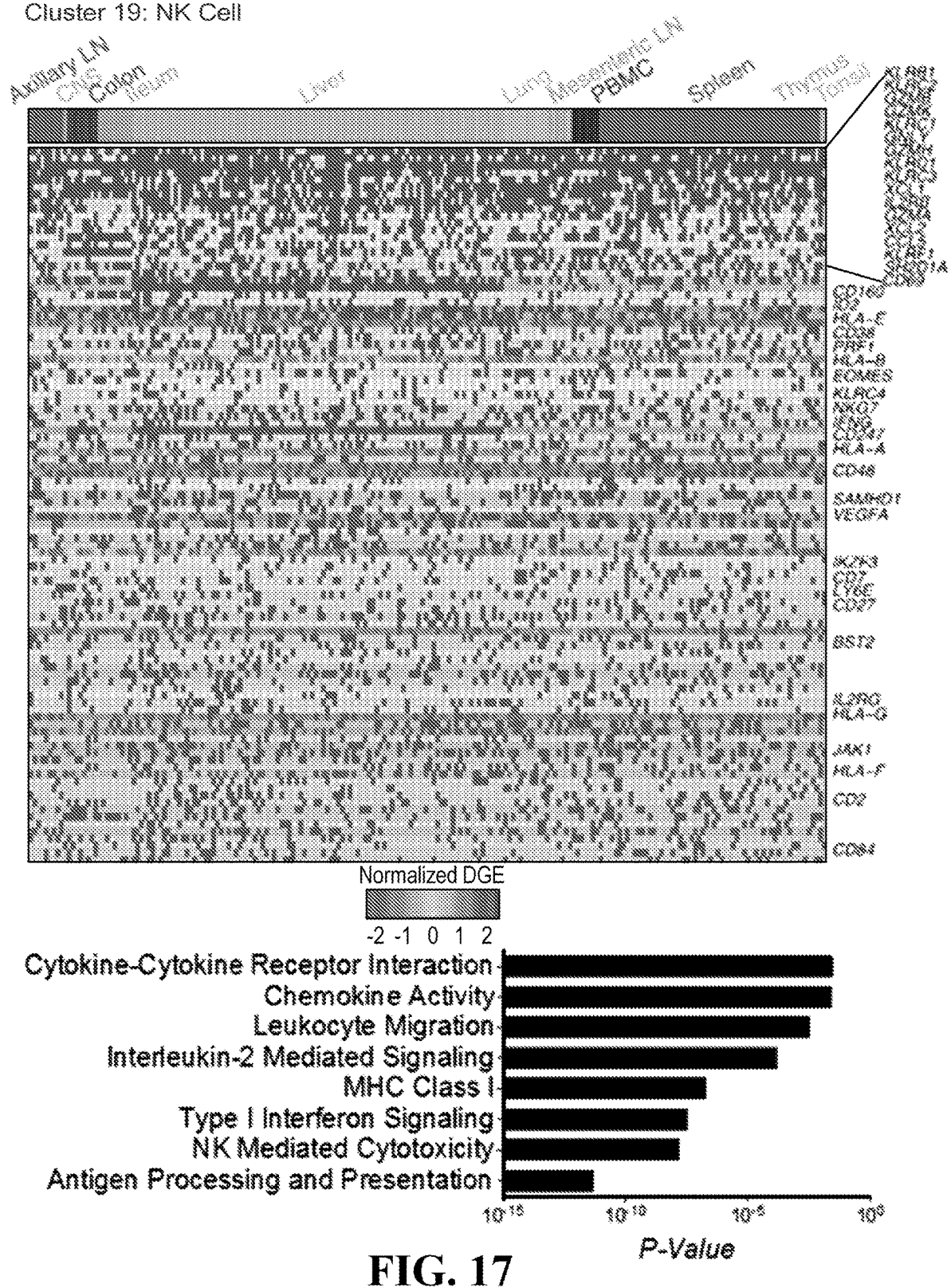
FIG. 17— Gene expression in NK cells indicates common functions and potential differences driven by tissue-of-origin.
Figure 18:
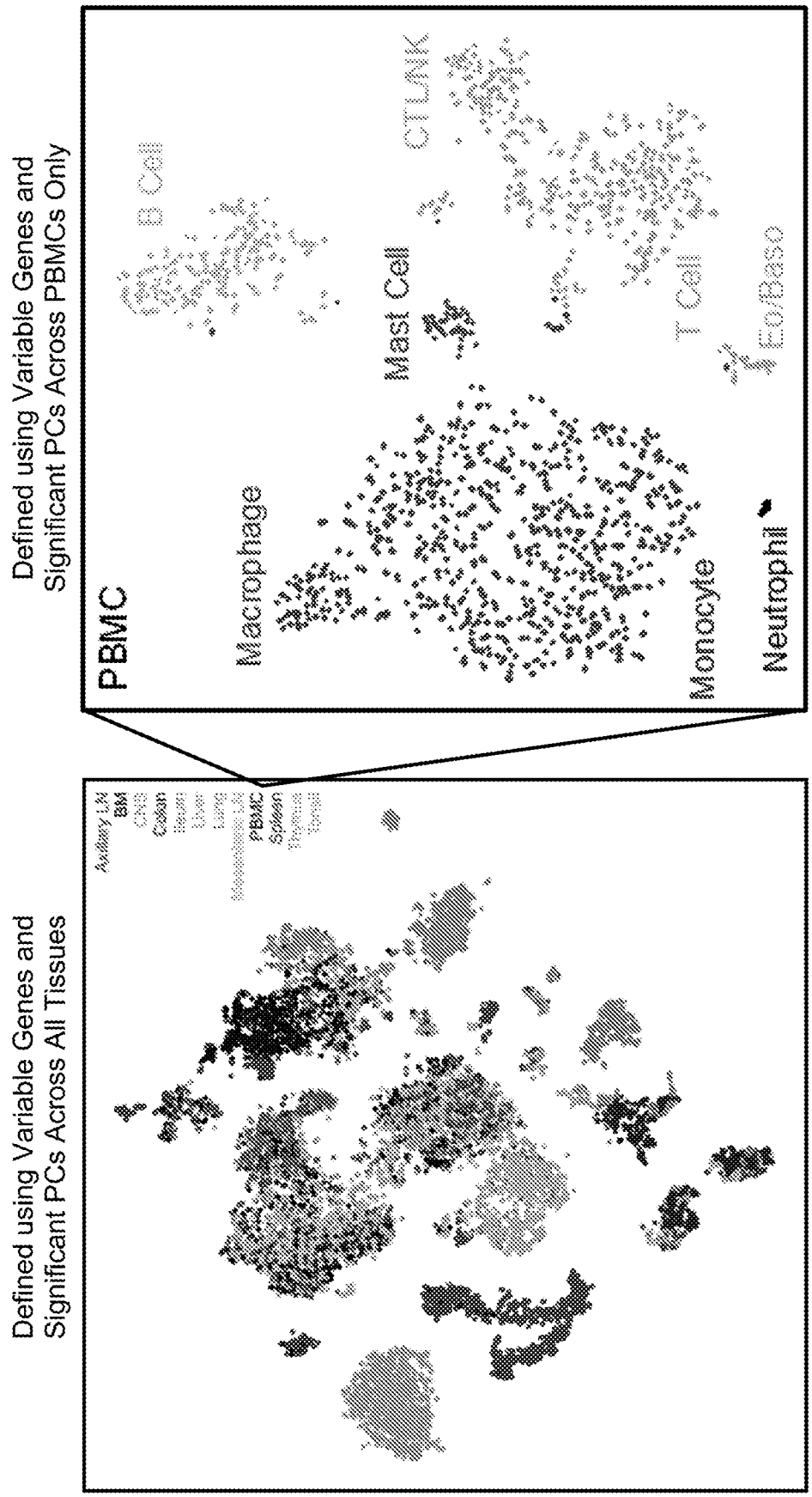
FIG. 18— Cell resolution looking at individual tissues.
Figure 19:
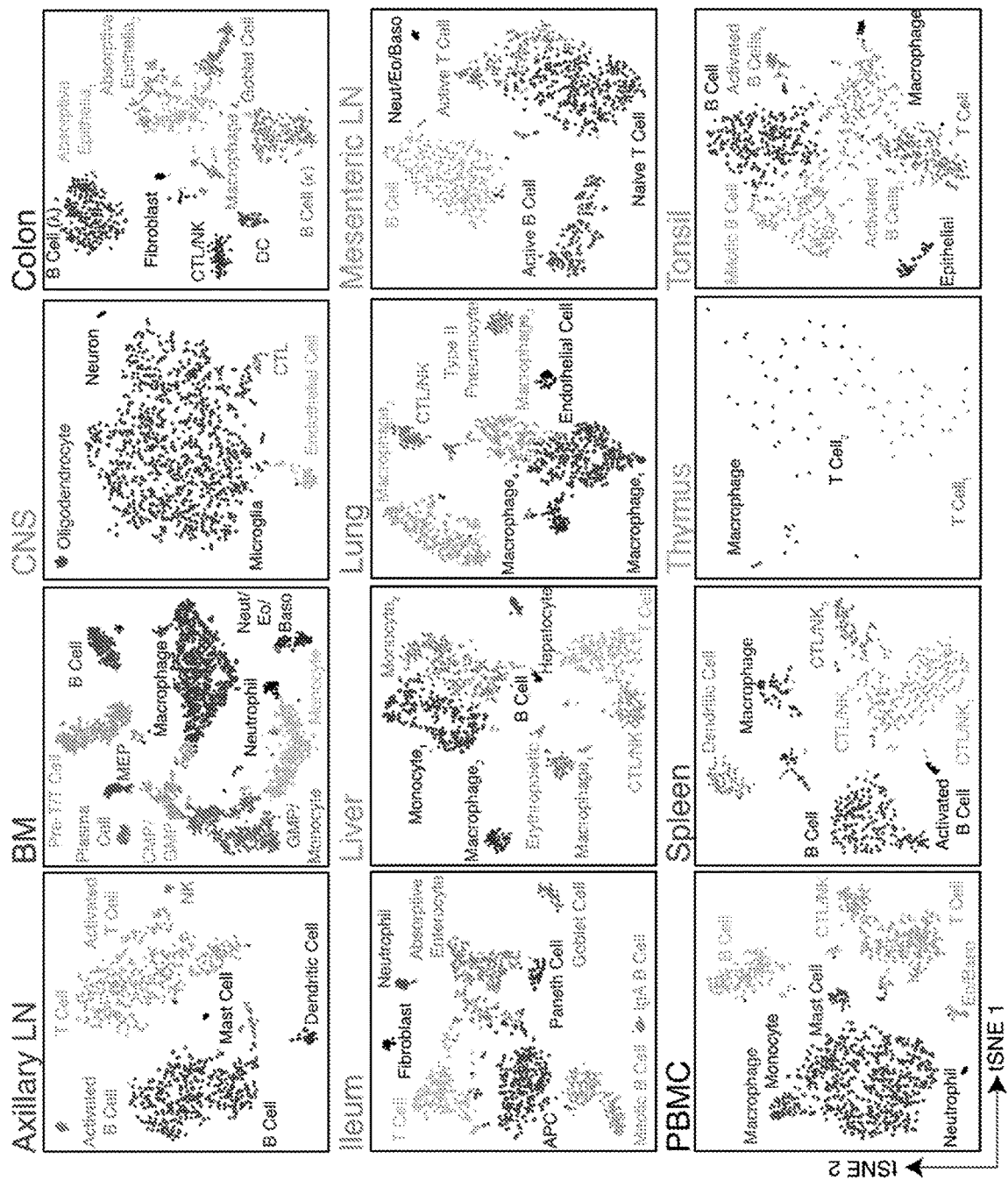
FIG. 19— Cell expression profiles by tissue.
Figure 20:
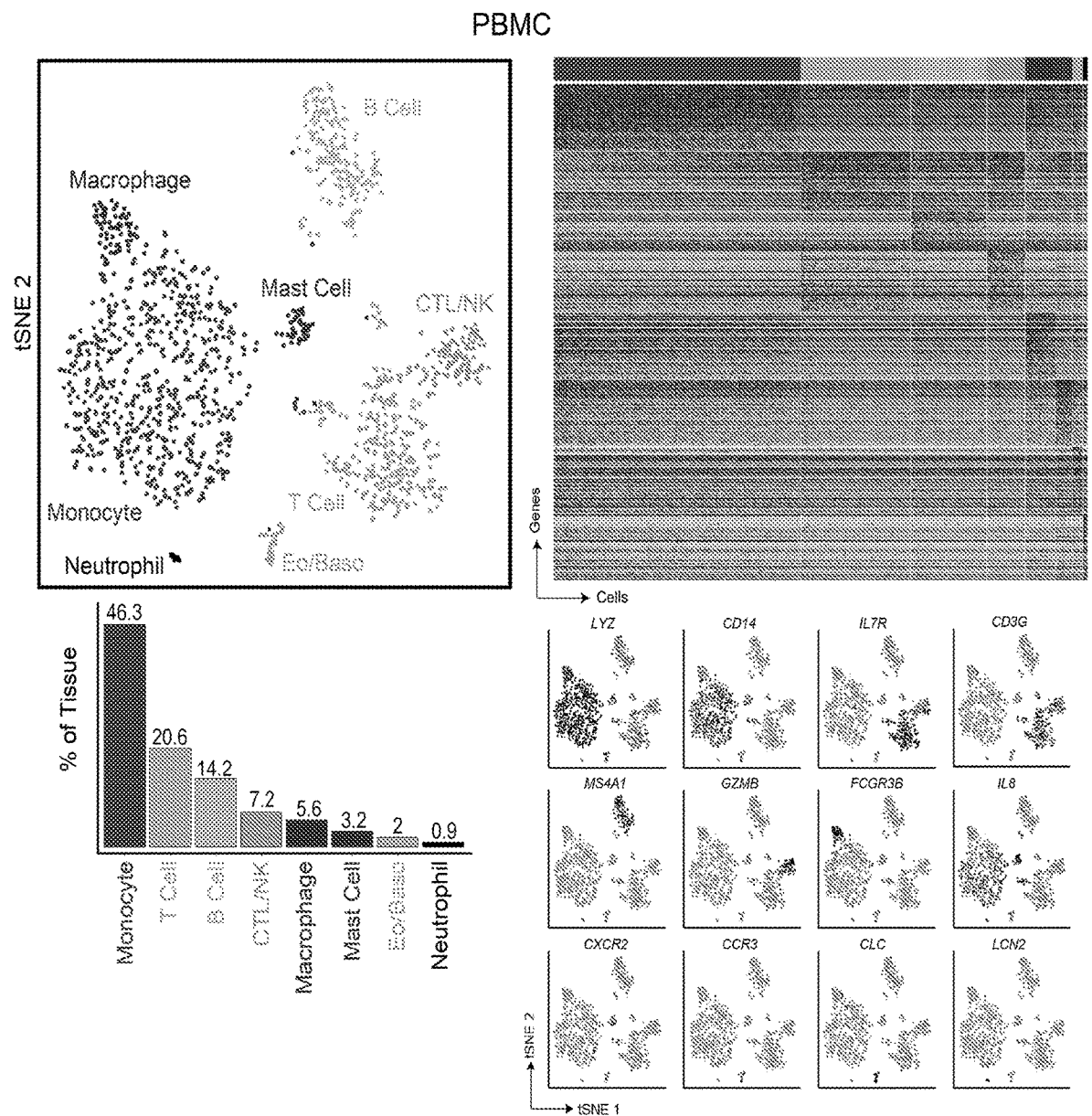
FIG. 20— Gene expression in PBMCs showing individual cell types and correlation with gene groups.
Figure 21:
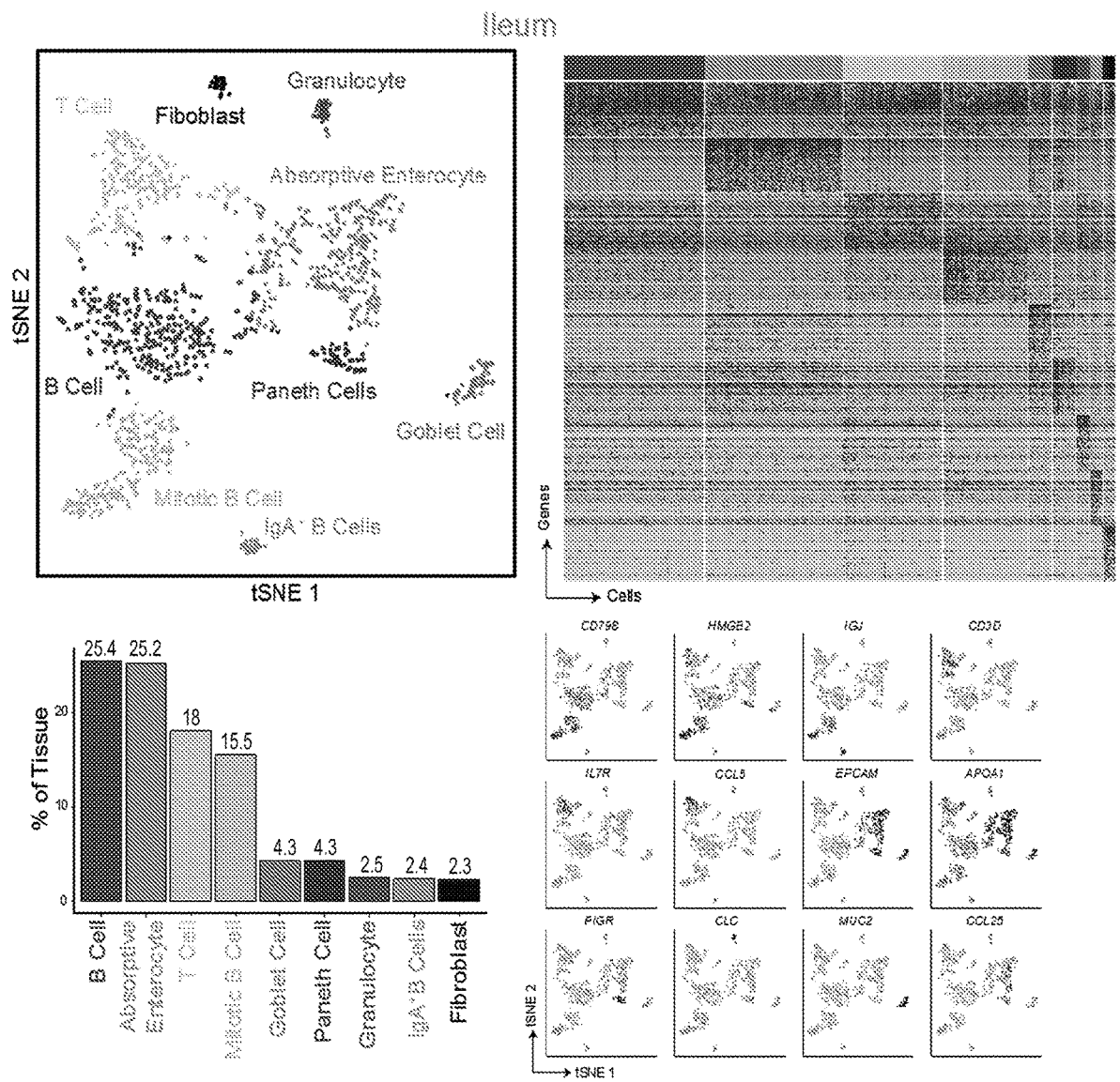
FIG. 21— Gene expression of cells in Ileum showing individual cell types and correlation with gene groups.

Single cell sequencing data were partitioned and annotated with supervised clustering, the results of which were visualized using tSNE (Amir el et al., 2013; Shekhar et al., 2016; van der Maaten and Hinton, 2008a). Based on expression profiles, individual cells are clustered and defined by tissues and cell types (FIGS. 9 and 10). Particularly, this study identifies tissue specific phenotypes and behaviors of T cells (CD3E+, CD3D+, and CD3G+ cells), neutrophils, microglia, B cells, glandular epithelia, enterocytes, fibroblasts, megakaryocytes, erythroid precursor, DC, NK, macrophages, pneumocytes, eosinophil, and basophil cells are differentiated by expression profiles in axillary lymph nodes, central nerve system, colon, ileum, liver, lung, mesenteric lymph nodes, blood, spleen, thymus, and tonsil tissues, as illustrated in FIGS. 11-21. Specifically, in macrophages from different tissues, gene expression (S100A8, HBB, MNP1A, CAMP, LOC710097, gene 24745, gene 18845, LOC703853, LOC706282, RTD1B, LOC106994075, PLACE, CLEC9A, GZMB, IRF8, FCER1A, KNG1, IGFBP6, CCDC50, NCOA7, C1QB, SEPP1, FABP4, C1QC, GPNMB, APOE, ACP5, YMRM176B, ADAMDEC1, CCDC 152, S100A6, FCGR3, VCAN, FGR, LILRB1, FCN1, AHNAK, FN1, C5AR1, TIMP1) distinguishes individual cells by their tissue of origins (FIG. 13).

Figure 22A:
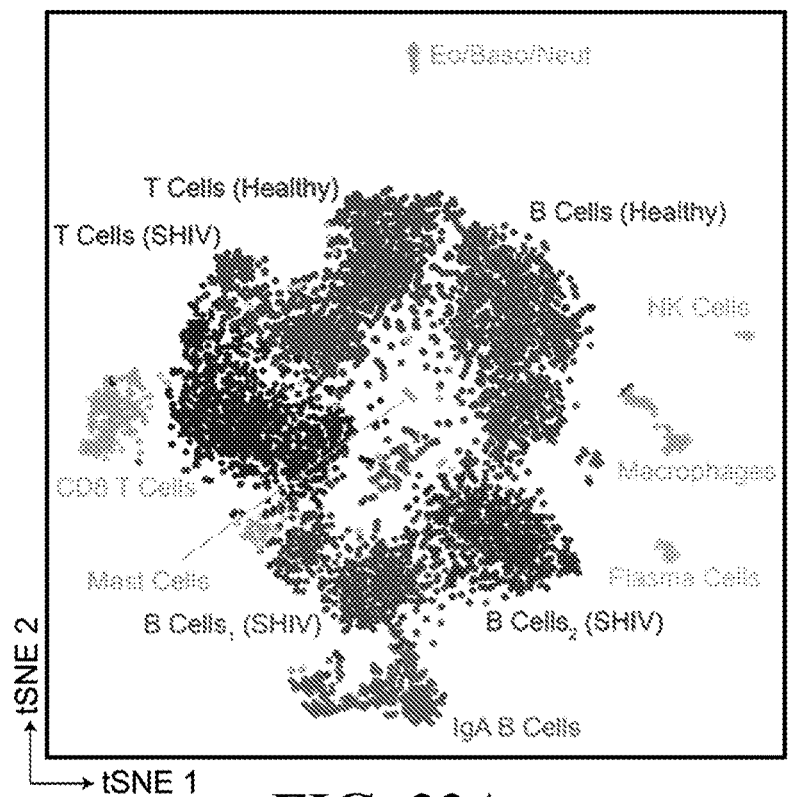
FIG. 22A-22C—Single cell genomics FIG. 22A Single cell genomics of cells from lymphoid tissue from healthy and SHIV-infected Rhesus macaques defines specific cell subsets.
Figure 22B:
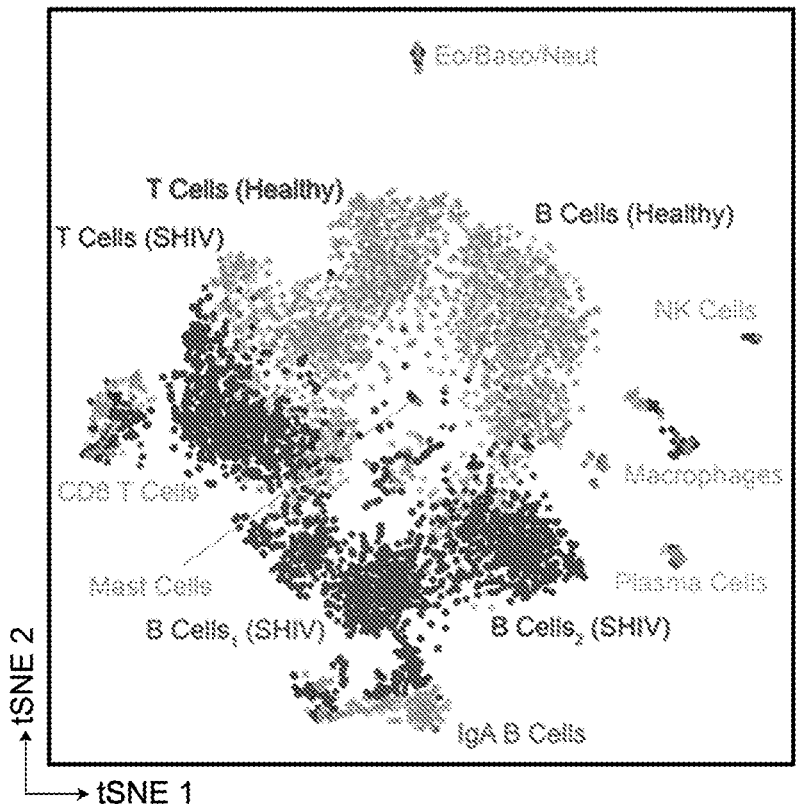
Figure 22C:
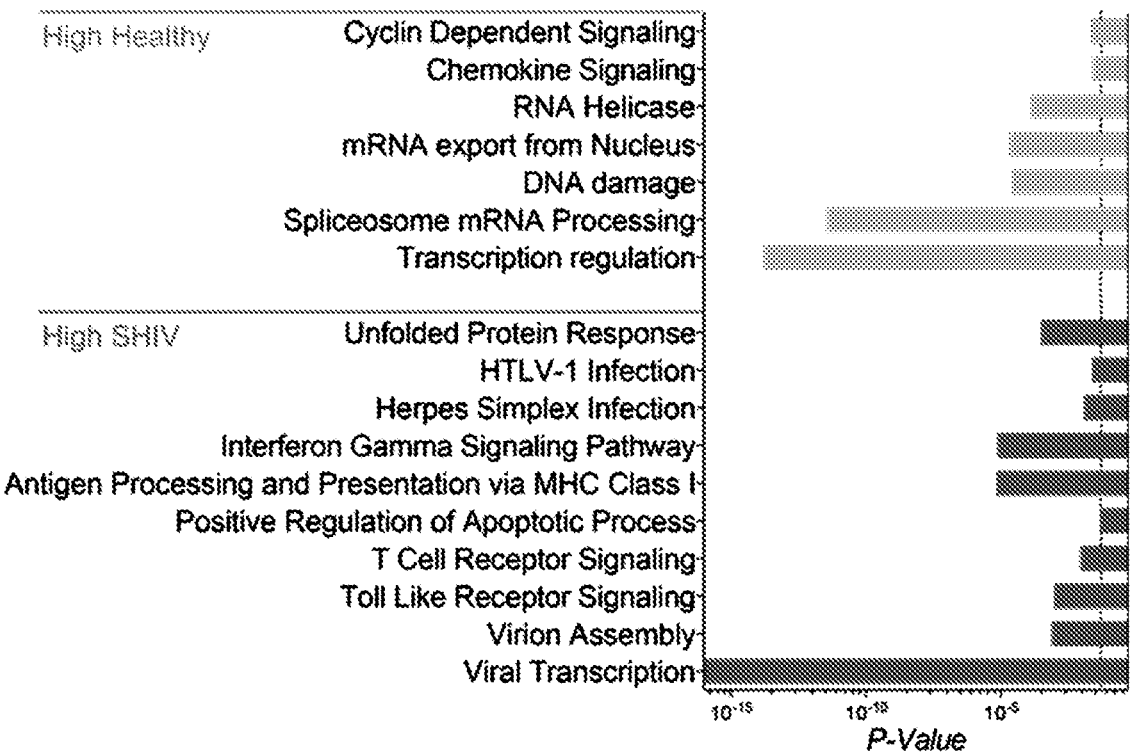
Figure 23:
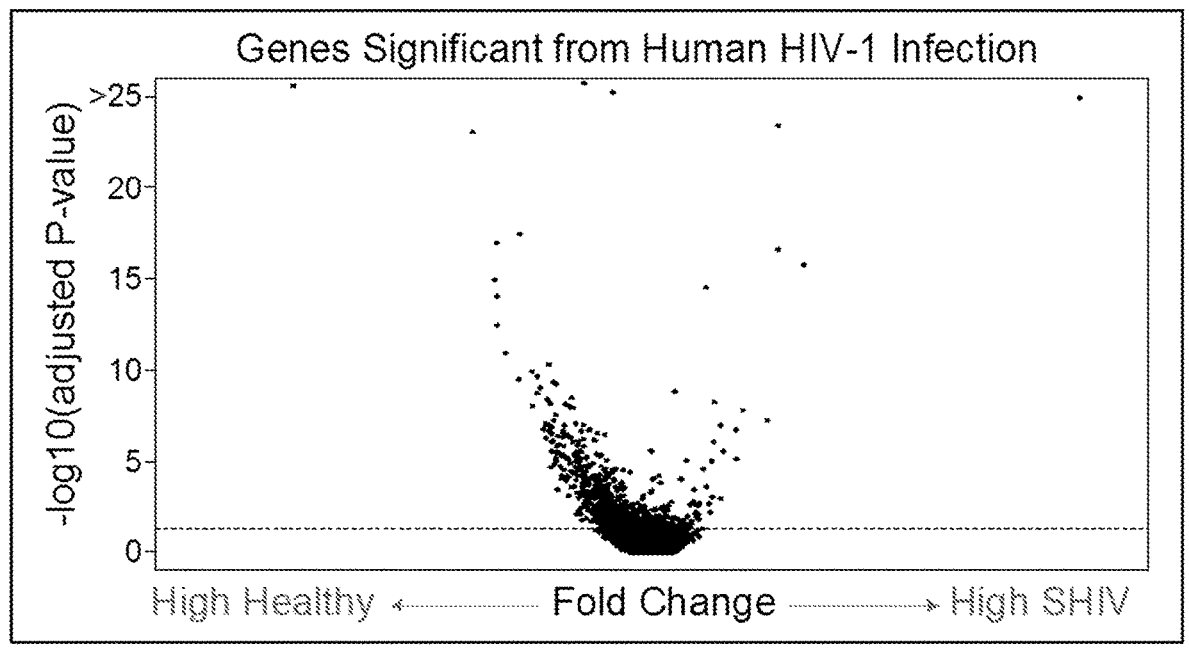
FIG. 23—Comparison of differentially expressed genes between $HIV^+$ and $HIV^-$ T cells in human lymph nodes with $SHIV^+$ and $SHIV^-$ T cells in non-human primates shows significant overlap.
Figure 24A:
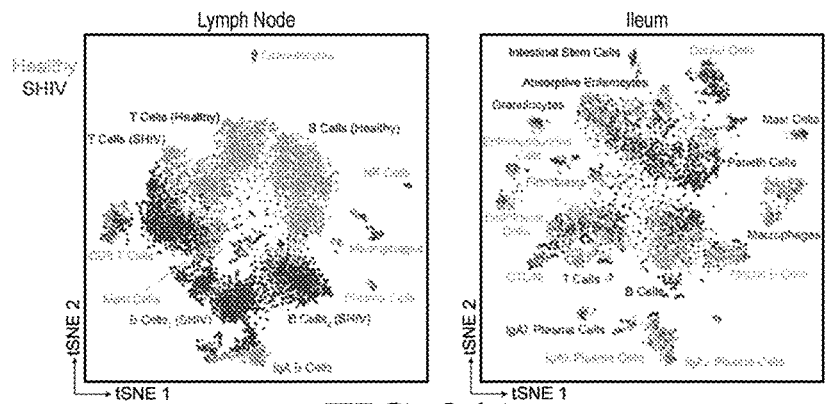
FIG. 24A-24D—Impact of chronic SHIV infection on different tissue niches.
Figure 24B:
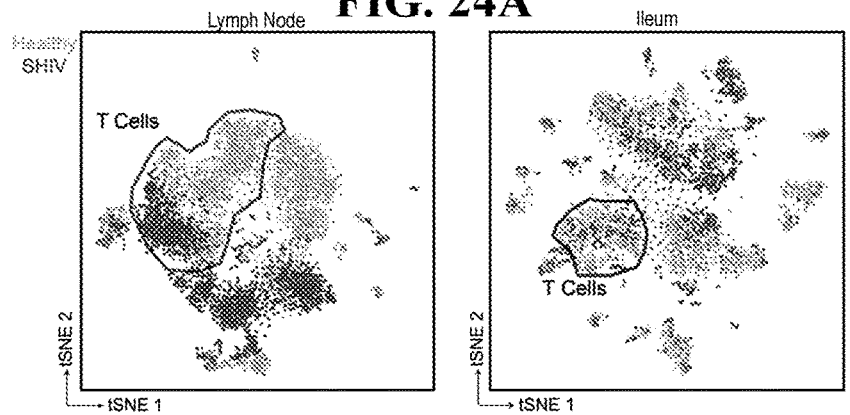
Figure 24C:
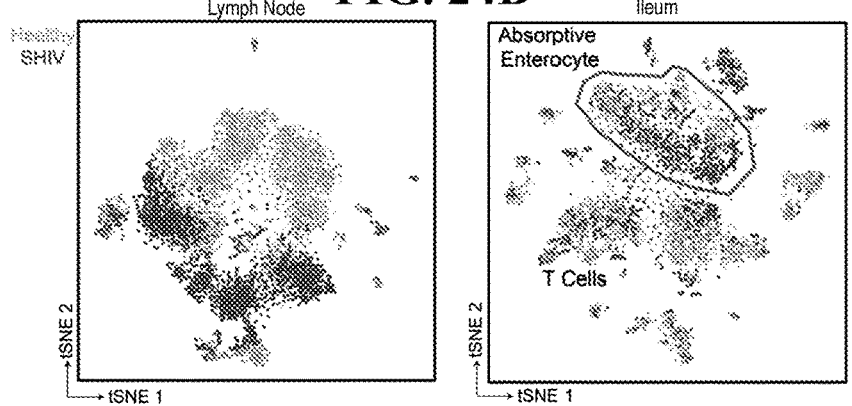
Figure 24D:
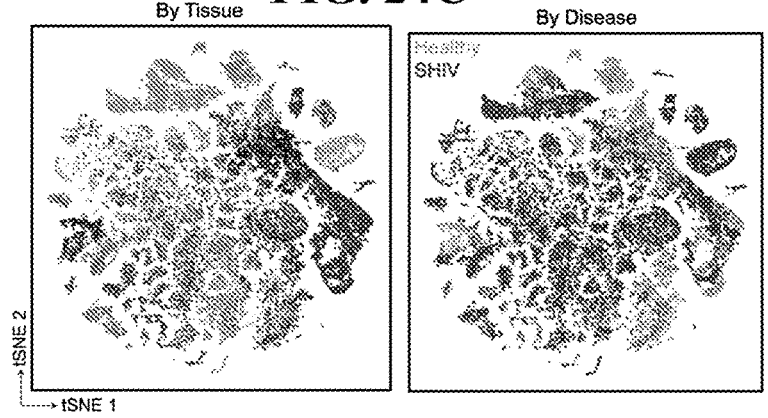

By comparing single cell profiles of healthy subjects with SHIV infected ones, this study identified subsets of cells in specific tissues differentially respond to SHIV infection (FIGS. 22A and 22B). In lymphoid tissue, certain immune cells such as CD8+ T cells and macrophages appear to be equally represented in both healthy and SHIV infected cells, while other cells such as CD4+ T cells and B cells show marked difference between the two states. The comparison further identifies pathways and genes that are differentially expressed in healthy and SHIV infected cells. In CD4+ T cells, genes involved in cyclin dependent signaling, chemokine signaling, RNA helicase, mRNA export from nucleus, DNA damage, spliceosome mRNA processing, and transcription regulation are identified as correlated with healthy cells, and genes involved in unfolded protein response, HTLV-1 infection, herpes simplex infection, interferon gamma signaling pathway, antigen processing and presentation via MHC class I, positive regulation of apoptotic processes, T cell receptor signaling, virion assembly, and viral transcription are associated with HIV infection (FIGS. 22C and 22D). More comprehensively, this study identified gene markers that are differentially expressed in SHIV infected cells. This study also validated the close relationship between SHIV and HIV infection in non-human primate and human cells, by comparing differentially expressed genes between HIV infected and healthy human lymph node cells with SHIV infected and healthy T cells in non-human primates. The significant overlap of the two sets of differentially expressed genes (FIG. 23) confirm that biomarkers identified in this study can further be used in diagnosis, monitoring, and treatment of human HIV related disease.

Figure 25:
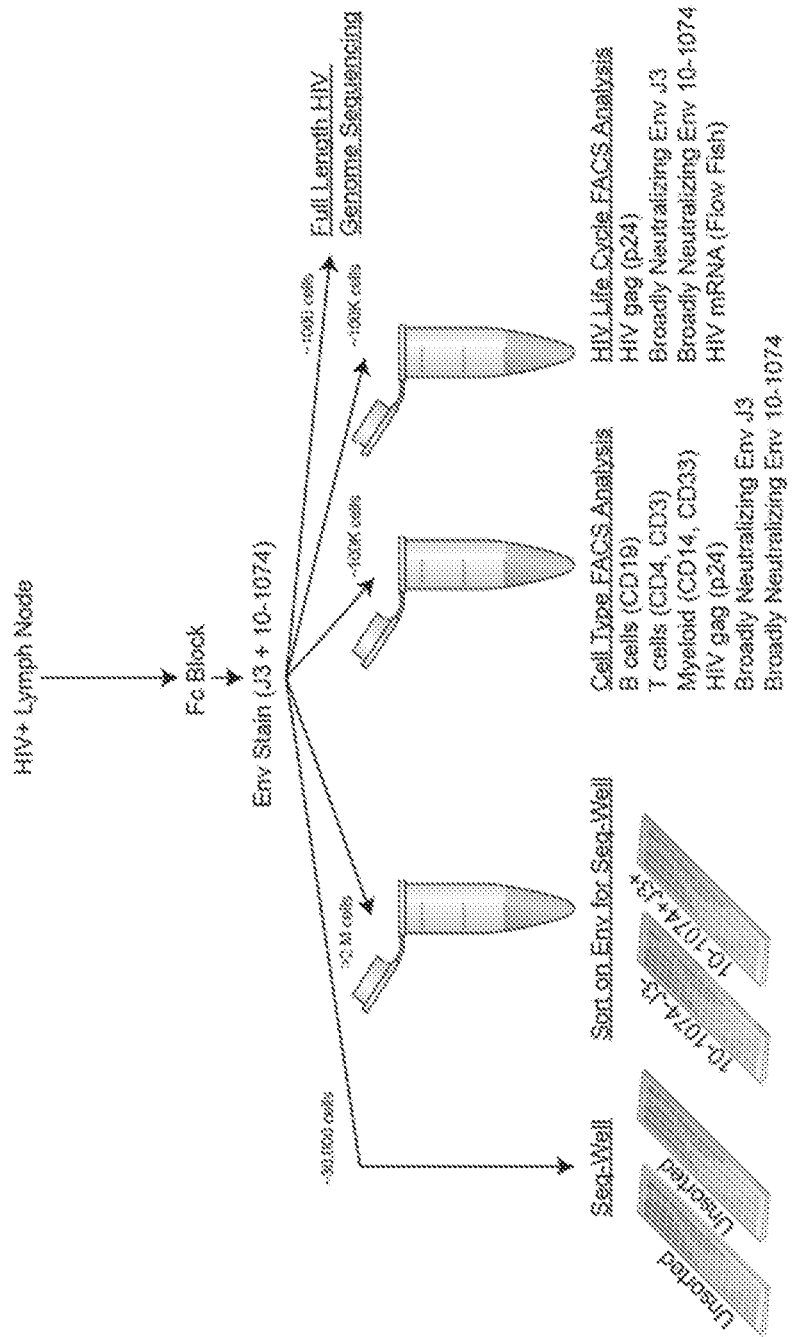
FIG. 25 shows the proposed experimental workflow using a lymph node sample from an $HIV^+$ patient.
Figure 26C:
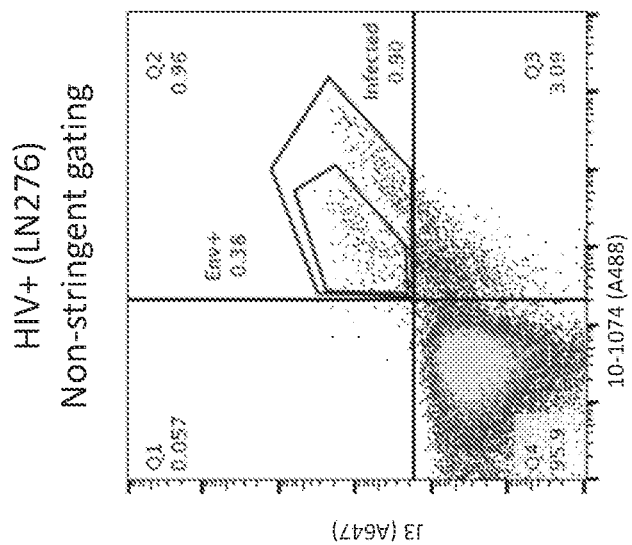
FIGS. 26A-26C show flow cytometry data illustrating that J3 and 10-1074 bnAbs are specific for $HIV^+$ samples.
Figure 26B:
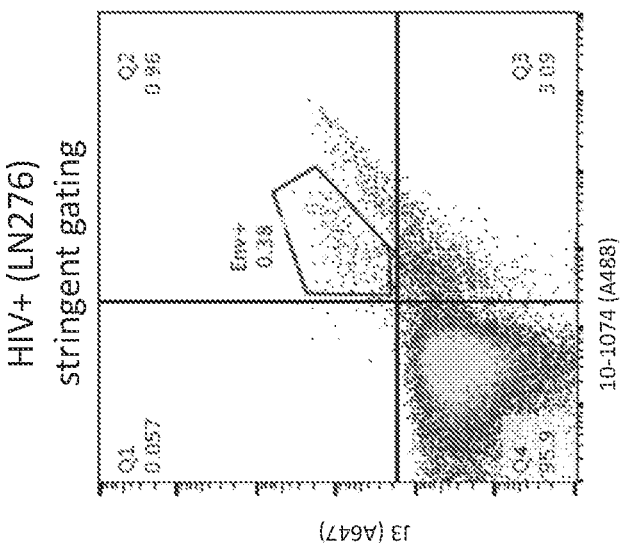
Figure 26A:
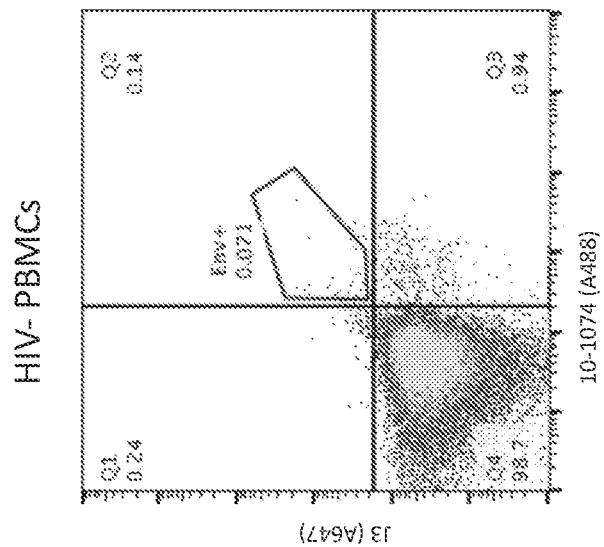
Figure 27B:
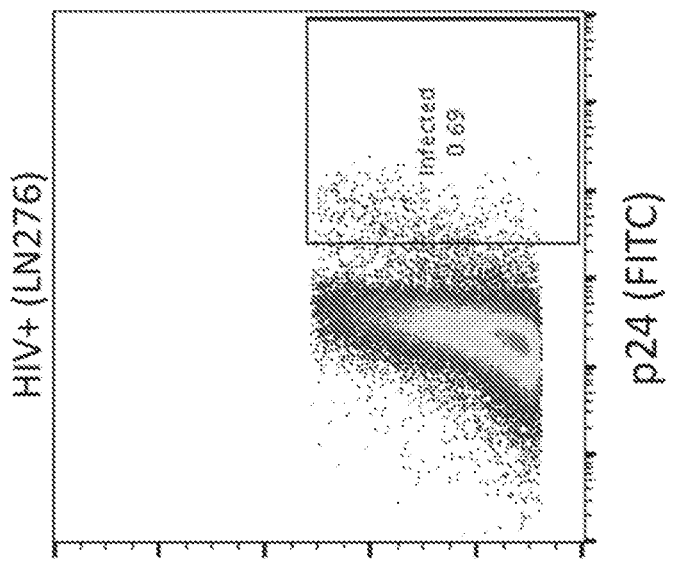
FIGS. 27A and 27B show flow cytometry plots illustrating confirmatory staining with intracellular HIV gag.
Figure 27A:
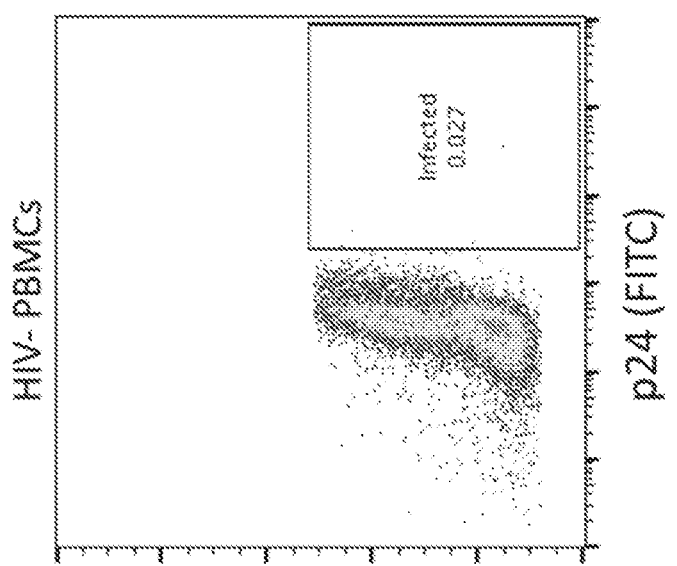

Example 3— Host-Pathogen Interactions Observed in the Lymph Node of a Human HIV+Patient FIG. 25 shows the proposed experimental workflow. The ideal dataset is as follows:
 4 HIV+LN, ARV-treated, suppressed
 2-3 HIV+LN, virologic failure
 2-3 HIV− LN
 ~4 arrays per patient
 Matched uninfected PBMCs as staining controls FIGS. 26A-26C illustrate that J3 and 10-1074 bnAbs are specific for HIV+ samples. Env antibody staining was done using 10-1074 (NIH) and J3 llama nanobody from Kiera Clayton (Walker lab) (originally developed by Robin Weiss at UCL).

Figure 28B:
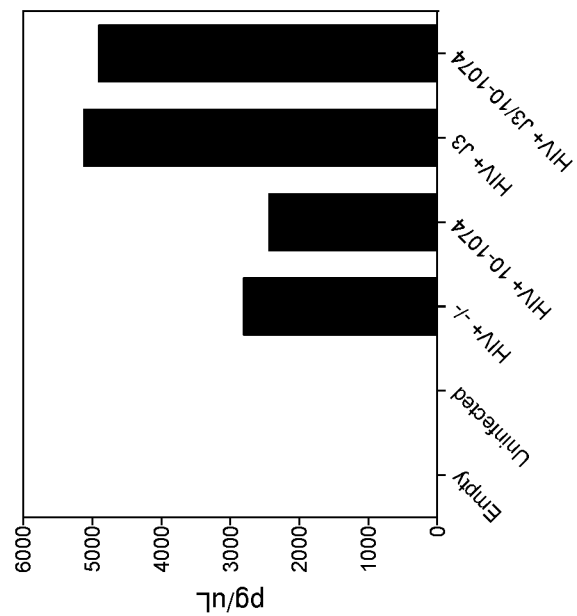
FIGS. 28A and 28B show that J3 and 10-1074 bnAbs successfully enrich for $HIV^+$ cells.
Figure 28A:
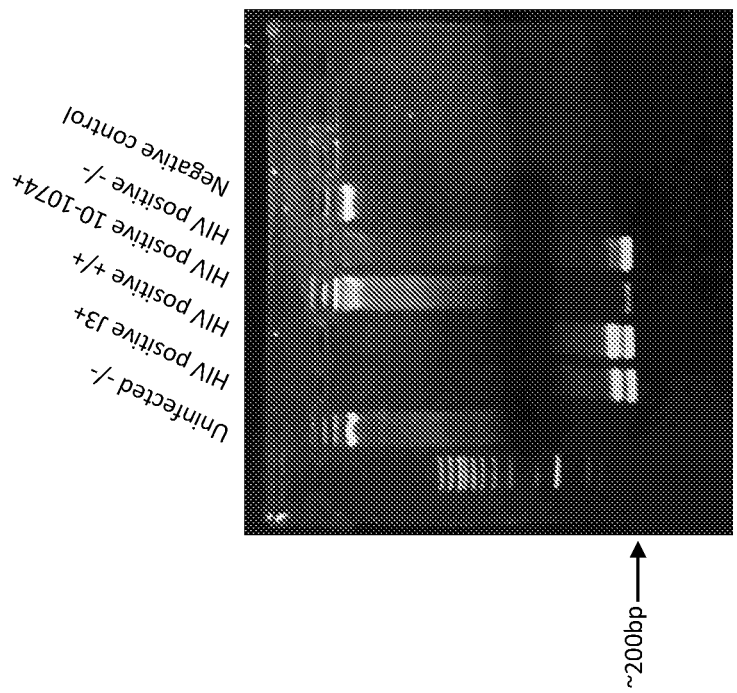
Figure 29:
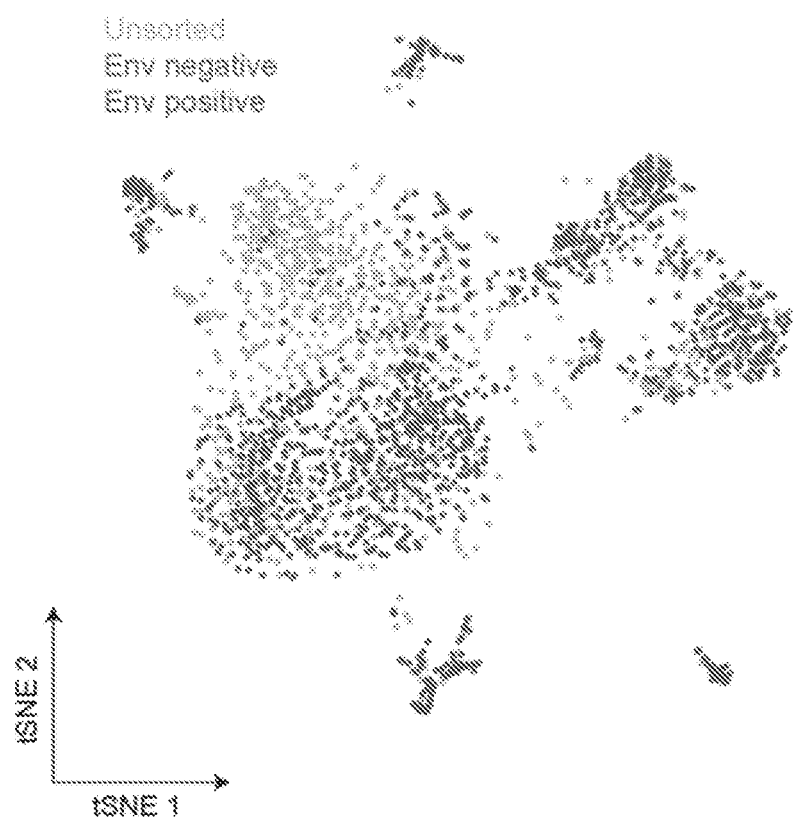
FIG. 29 shows results of Seq-Well on lymph nodes from an $HIV^+$, ARV-treated patient.
Figure 30:
FIG. 30 shows results of Seq-Well on lymph nodes from an $HIV^+$, ARV-treated patient.
Figure 31:
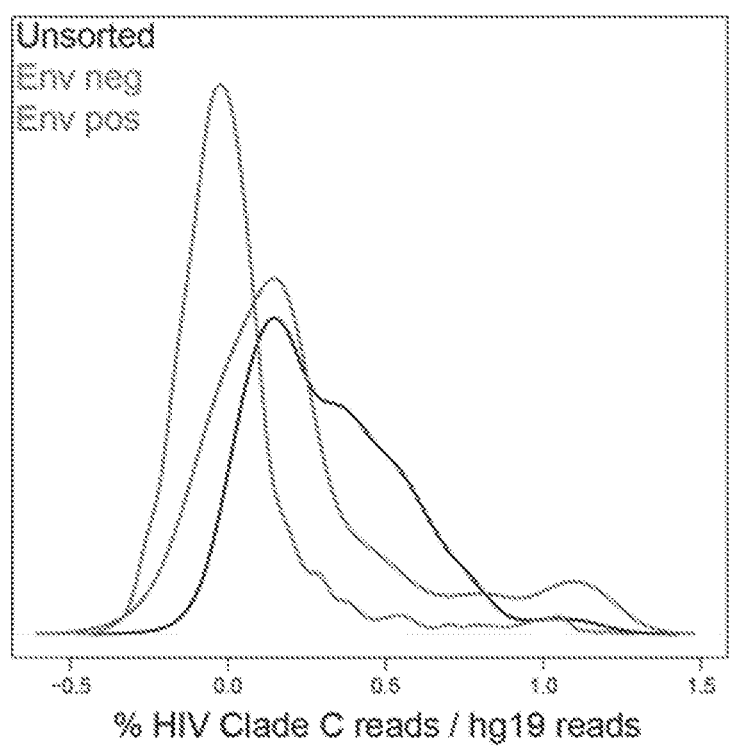
FIG. 31 shows results of Seq-Well on lymph nodes from an $HIV^+$, ARV-treated patient.

FIGS. 28A and 28B illustrate that J3 and 10-1074 bnAbs successfully enrich for HIV+ cells. The protocol was as follows:
 1. Prepare in vitro HIV-1 infected (NL-AD8) and uninfected PBMCs
 2. Stain with J3, 10-1074
 3. Sort 5 populations into RLT+1% BME (1000 cells each)
  1. Uninfected cells
  2. HIV+ J3− 10-1074−
  3. HIV+ J3− 10-1074+
  4. HIV+ J3+ 10-1074−
  5. HIV+ J3+10-1074+
 4. RT, PCR for Clade B rev FIG. 29 shows results of Seq-Well on a lymph node sample from an HIV+, ARV-treated patient. The protocol was as follows:
 1. Thawed LN276 (HIV+) and PBMCs (HIV−)
 2. Saved 15,000 cells from unstained LN276 (HIV+) for Seq-Well
 3. Stained with J3 (A647), 10-1074 (A488)
 4. Sorted Env− (J3− 10-1074−) and Env+ (~5000 J3 or 10-1074 single positive, ~5000 J3/10-1074 double positive)
 5. Ran 3 Seq-Well Arrays (most up-to-date protocol)
  1. Unsorted
  2. Env positive
  3. Env negative FIG. 31 shows results of Seq-Well on a lymph node sample from an HIV+, ARV− treated patient. Applicants concluded that high quality libraries were generated from samples, including live cells and successful Seq-Well data. They also determined the following points:
 Cell type specific depletion Sorted vs. Unsorted samples
 Depletion of gag+env+ subset after sorting—fragility of infected cells?
 Low relative yield single cells from Env+ fraction
 Env− loaded ~20,000: yield ~1500 cells
 Env+ loaded ~10,000: yield ~250 cells
 Env+ cells show modest enrichment for HIV mRNA, are largely CD4+ monocytes/macrophages Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method of diagnosing a latent HIV or anti-retroviral (ART)-resistant HIV infection in a cell or tissue, the method comprising detecting whether eight or more genes from Table 1 or Table 2 are overexpressed compared to a cell that is HIV free; or detecting whether eight or more genes from Table 3 are underexpressed compared to a cell that is HIV free.

2. A method of treating latent HIV or ART-resistant HIV in a patient comprising:

detecting eight or more genes or gene products from Tables 1 or 2;

determining whether the patient has a latent HIV or ART-resistant HIV infection based on the presence of the eight or more genes or gene products from Tables 1 or 2; and administering an anti-HIV therapeutic if the eight or more genes or gene products from Tables 1 or 2 are present.

3. The method of claim 2, wherein the step of detecting comprises detecting the presence of the eight or more gene products using an immunological assay.

4. The method of claim 3, wherein the immunological assay comprises detection of specific binding between an antibody and the marker.

5. The method of claim 4, wherein the marker is a peptide, polypeptide, or protein.

6. The method of claim 2, further comprising monitoring HIV disease progression and/or treatment in the patient, comprising detecting expression of eight or more genes or gene products from Tables 1, 2 and 3 after administration of the anti-HIV therapeutic; and administering an additional or alternative round of anti-HIV therapy if expression of the eight or more genes from Table 1 or 2 has increased or not decreased, or if expression of the eight or more genes in Table 3 has decreased relative to prior to administering the first anti-HIV therapy.

7. The method of claim 6 wherein the additional or alternative round of anti-HIV therapy comprises the same drug or combination of drugs as the first round of anti-HIV therapy.

8. The method of claim 6 wherein the additional or alternative round of anti-HIV therapy comprises a different drug or combination of drugs than the first round of anti-HIV therapy.

9. The method of claim 1, wherein the cell or tissue is from a subject having a latent HIV or anti-viral ART-resistant HIV infection.

10. The method of claim 6, further comprising monitoring treatment of a latent HIV or (ART)-resistant HIV infection in a cell or tissue from the patient by detecting whether eight or more genes from Table 1 or Table 2 are overexpressed compared to a cell that is HIV free.

11. The method of claim 6, further comprising monitoring treatment of a latent HIV or ART-resistant HIV infection in a cell or tissue from the patient by detecting whether eight or more genes from Table 3 are underexpressed compared to a cell that is HIV free.

* * * * *

UNITED STATES PATENT AND TRADEMARK OFFICE
CERTIFICATE OF CORRECTION

| | | |
|---|---|---|
| PATENT NO. | : 11,781,193 B2 | Page 1 of 1 |
| APPLICATION NO. | : 16/756573 | |
| DATED | : October 10, 2023 | |
| INVENTOR(S) | : Shalek et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this
Eighth Day of July, 2025

Coke Morgan Stewart
*Acting Director of the United States Patent and Trademark Office*